(12) United States Patent
Shiomi et al.

(10) Patent No.: US 12,250,883 B2
(45) Date of Patent: Mar. 11, 2025

(54) ORGANIC ELECTROLUMINESCENCE ELEMENT AND ELECTRONIC DEVICE

(71) Applicant: IDEMITSU KOSAN CO.,LTD., Tokyo (JP)

(72) Inventors: Takushi Shiomi, Chiyoda-ku (JP); Toshinari Ogiwara, Chiyoda-ku (JP); Hiromi Nakano, Chiyoda-ku (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 11 days.

(21) Appl. No.: 18/668,609

(22) Filed: May 20, 2024

(65) Prior Publication Data

US 2024/0324455 A1    Sep. 26, 2024

Related U.S. Application Data

(63) Continuation of application No. 18/537,181, filed on Dec. 12, 2023, which is a continuation of application (Continued)

(30) Foreign Application Priority Data

Feb. 17, 2020    (JP) .................................. 2020-024283

(51) Int. Cl.
*H01L 51/50* (2006.01)
*C07D 209/86* (2006.01)
(Continued)

(52) U.S. Cl.
CPC ....... *H10K 85/6572* (2023.02); *C07D 209/86* (2013.01); *C07D 405/10* (2013.01);
(Continued)

(58) Field of Classification Search
None
See application file for complete search history.

(56) References Cited

U.S. PATENT DOCUMENTS

| | | |
|---|---|---|
| 2018/0010040 A1 | 1/2018 | Pan et al. |
| 2019/0058124 A1 | 2/2019 | Hatakeyama et al. |
| 2019/0337397 A1 | 11/2019 | Park |

FOREIGN PATENT DOCUMENTS

| | | |
|---|---|---|
| CN | 108431984 A | 8/2018 |
| EP | 3696167 A1 | 8/2020 |

(Continued)

OTHER PUBLICATIONS

Chinese Office Action issued on Apr. 29, 2024 in Chinese Patent Application No. 202180005591.X, (10 pages).
(Continued)

*Primary Examiner* — Anthony Ho
(74) *Attorney, Agent, or Firm* — Oblon, McClelland, Maier & Neustadt, L.L.P.

(57) ABSTRACT

A compound may include a partial structures of formula (3-1A), (32h), and (3-11B) in one molecule, (3-1A)

(Continued)

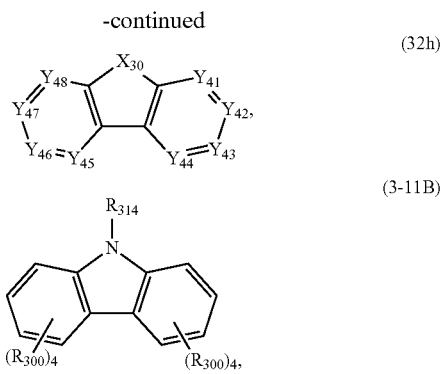

Figure 1:
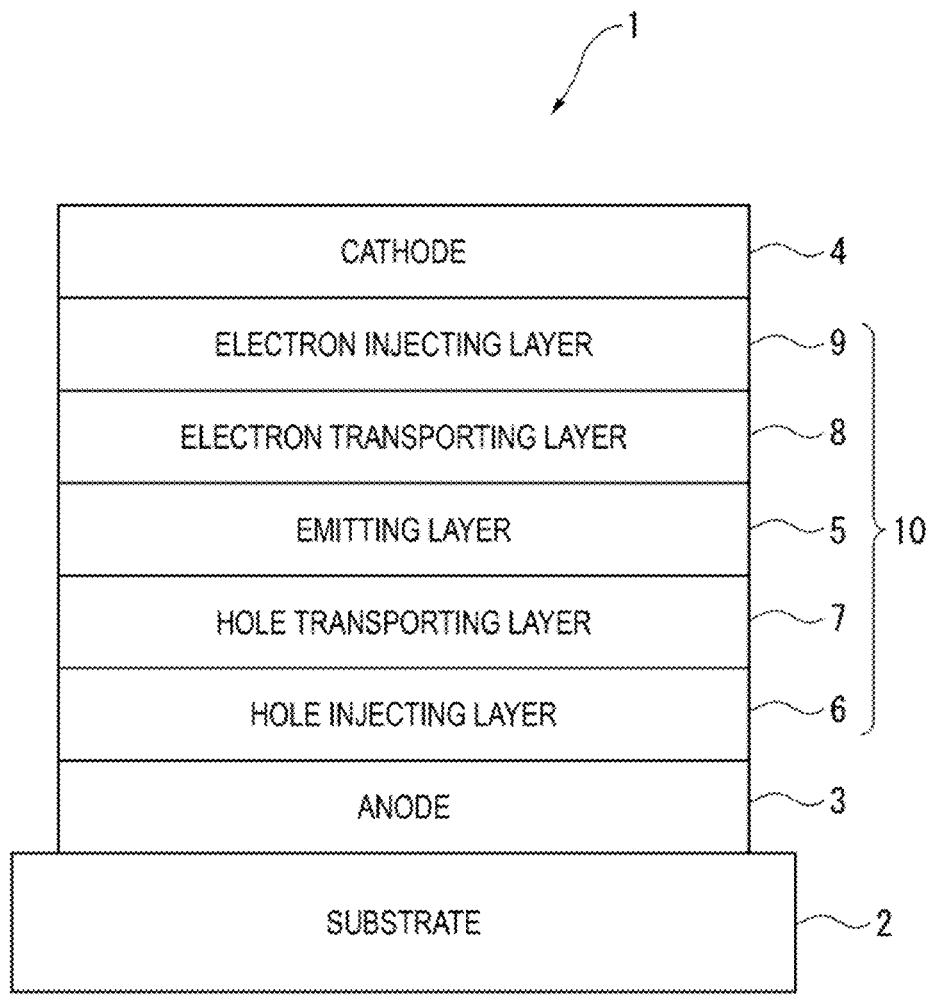

$R_{300}$ to $R_{306}$ being independently H or a substituent, or adjacent pair(s) form a ring, at least one of $R_{301}$ to $R_{306}$ is a single bond to another atom/structure in the molecule, and one of $R_{301}$ to $R_{306}$ is a single bond to the partial structure of formula (32h), $X_{30}$ is N bonded to the partial structure of formula (3-1A), $Y_{41}$ to $Y_{48}$ are independently $CR_{32}$, or C bonded to another atom/structure in the molecule, at least one of $Y_{41}$ to $Y_{48}$ is C bonded to the partial structure of formula (3-11B), $R_{32}$ are independently H or a substituent, or pair(s) of adjacent $R_{32}$ are bonded to form a ring, and at least one $R_{32}$ is independently a single bond to another atom/structure in the molecule.

20 Claims, 5 Drawing Sheets

Related U.S. Application Data

No. 17/764,846, filed as application No. PCT/JP2021/002267 on Jan. 22, 2021.

(51) Int. Cl.

| | | |
|---|---|---|
| C07D 405/10 | (2006.01) | |
| C07D 405/14 | (2006.01) | |
| C07D 491/048 | (2006.01) | |
| C07D 495/04 | (2006.01) | |
| C09K 11/06 | (2006.01) | |
| H10K 85/60 | (2023.01) | |
| H10K 50/11 | (2023.01) | |

(52) U.S. Cl.
CPC ....... *C07D 405/14* (2013.01); *C07D 491/048* (2013.01); *C07D 495/04* (2013.01); *C09K 11/06* (2013.01); *H10K 85/654* (2023.02); *H10K 85/657* (2023.02); *H10K 85/6574* (2023.02); *C07B 2200/05* (2013.01); *C09K 2211/1018* (2013.01); *H10K 50/11* (2023.02)

(56) References Cited

FOREIGN PATENT DOCUMENTS

| JP | 2009-231516 A | 10/2009 |
| JP | 2009-277790 A | 11/2009 |
| WO | WO 2016/086885 A1 | 6/2016 |
| WO | WO 2019/212287 A1 | 11/2019 |
| WO | WO 2020/022378 A1 | 1/2020 |
| WO | WO 2020/022860 A1 | 1/2020 |

OTHER PUBLICATIONS

European Office Action issued on Mar. 4, 2024 in European Patent Application No. 21756750.2, (7 pages) filed on Jan. 22, 2021.
International Search Report issued Mar. 16, 2021 in PCT/JP2021/002267 filed Jan. 22, 2021, 2 pages.
Adachi, C., "Device Physics of Organic Semiconductors", Kodansha, 2012, pp. 1-10 and pp. 261-268, 19 total pages (with English Translation).
Uoyama, H., et al., "Highly efficient organic light-emitting diodes from delayed fluorescence", Nature, vol. 492, 2012, 7 total pages.
International Preliminary Report on Patentability and Written Opinion issued Aug. 23, 2022 in PCT/JP2021/002267 (submitting English translation only), 5 pages.
Chinese Office Action issued on Nov. 16, 2024 in Chinese Patent Application No. 202180005591.X, with English translation (22 pages) citing reference 24.
2012-2013 Report on Advances in Chemistry, Supervised by China Association for Science and Technology, edited/written by Chinese Chemical Society, China Science and Technology Press, Apr. 30, 2014, pp. 142-161.

ORGANIC ELECTROLUMINESCENCE ELEMENT AND ELECTRONIC DEVICE

CROSS-REFERENCE TO RELATED APPLICATIONS

The present application is a continuing application based on U.S. application Ser. No. 18/537,181, filed Dec. 12, 2023, which was a continuing application based on U.S. application Ser. No. 17/764,846, filed Mar. 29, 2022, and published as US 2023/0048761 A1, on Feb. 16, 2023, which was the national stage of international application PCT/JP2021/002267, filed Jan. 22, 2021, claiming the benefit of the filing date of Japanese Appl. No. 2020-024283, filed Feb. 17, 2020, priority to each of which is claimed and the content of each of which is incorporated by reference.

TECHNICAL FIELD

The present invention relates to an organic electroluminescence device and an electronic device.

BACKGROUND ART

When a voltage is applied to an organic electroluminescence device (hereinafter, occasionally referred to as "organic EL device"), holes are injected from an anode and electrons are injected from a cathode into an emitting layer. The injected holes and electrons are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies have been made to improve a performance of the organic EL device.

For instance, the organic EL device is expected to further efficiently emit light using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

A TADF (Thermally Activated Delayed Fluorescence) mechanism uses such a phenomenon that inverse intersystem crossing from triplet excitons to singlet excitons thermally occurs when a material having a small energy difference (∆ST) between singlet energy level and triplet energy level is used. Thermally activated delayed fluorescence is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

For example, Patent Literatures 1 and 2 disclose organic EL devices using the TADF mechanism. Patent Literatures 1 and 2 disclose compounds having deuterium atoms as compounds that can be used in organic EL devices.

CITATION LIST

Patent Literature(s)

Patent Literature 1: International Publication No. 2016/086885

Patent Literature 2: International Publication No. 2019/212287

SUMMARY OF THE INVENTION

Problems to be Solved by the Invention

To improve the performance of electronic devices such as displays, organic EL devices are desired to have a longer lifetime.

Objects of the invention are to provide an organic electroluminescence device that can have an extended lifetime and to provide an electronic device including the organic electroluminescence device.

Means for Solving the Problem(s)

According to an aspect of the invention, there is provided an organic electroluminescence device including an anode, a cathode, and an emitting layer disposed between the anode and the cathode, in which the emitting layer contains a delayed fluorescent compound M2 and a compound M3 having at least one deuterium atom, the compound M3 is not a compound having a partial structure represented by a formula (1C) or (2C) below, and a singlet energy $S_1(M2)$ of the compound M2 and a singlet energy $S_1(M3)$ of the compound M3 satisfy a relationship of a numerical formula (Numerical Formula 1).

$$S_1(M3) > S_1(M2) \qquad \text{(Numerical Formula 1)}$$

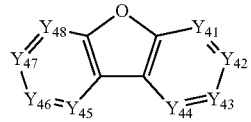

(1C)

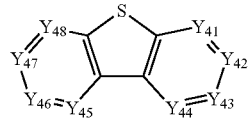

(2C)

In the formulae (1C) and (2C), $Y_{41}$ to $Y_{48}$ are each independently a nitrogen atom, CR, or a carbon atom bonded to another atom or another structure in a molecule of the compound M3, at least one of $Y_{41}$ to $Y_{48}$ is a nitrogen atom, at least one of $Y_{41}$ to $Y_{48}$ is a carbon atom bonded to another atom or another structure in the molecule of the compound M3, each R is independently a hydrogen atom or a substituent, and a plurality of R are mutually the same or different.

According to another aspect of the invention, an electronic device including the organic electroluminescence device according to the above aspect of the invention is provided.

The aspects of the invention can provide an organic electroluminescence device that can have an extended lifetime and can provide an electronic device including the organic electroluminescence device.

BRIEF DESCRIPTION OF DRAWING(S)

FIG. 1 schematically shows an exemplary arrangement of an organic electroluminescence device according to a first exemplary embodiment of the invention.

Figure 2:
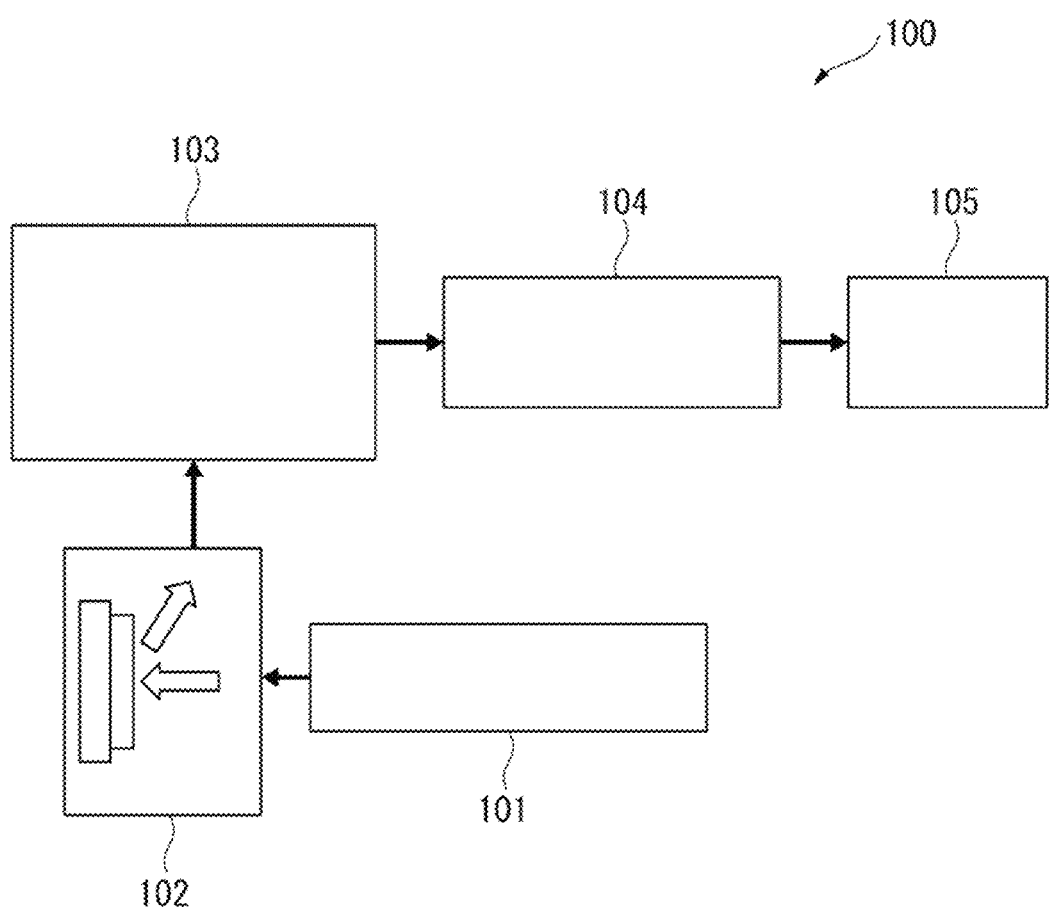

FIG. 2 schematically shows a device of measuring transient PL.

Figure 3:
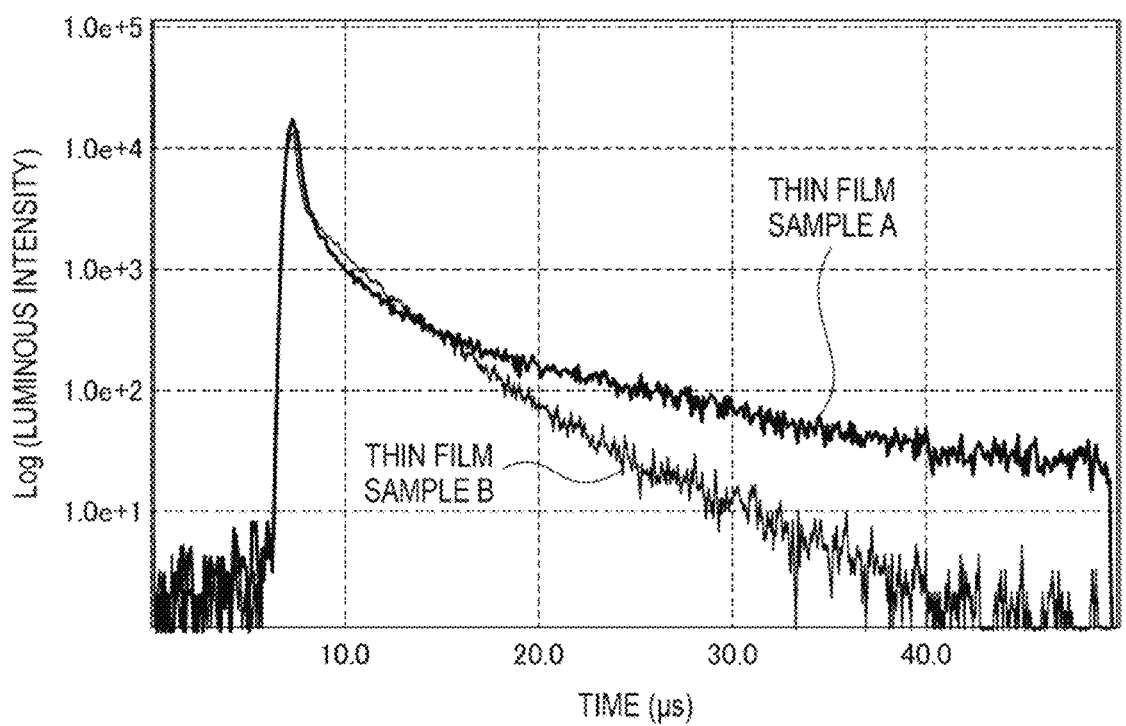

FIG. 3 shows an example of decay curves of the transient PL.

Figure 4:
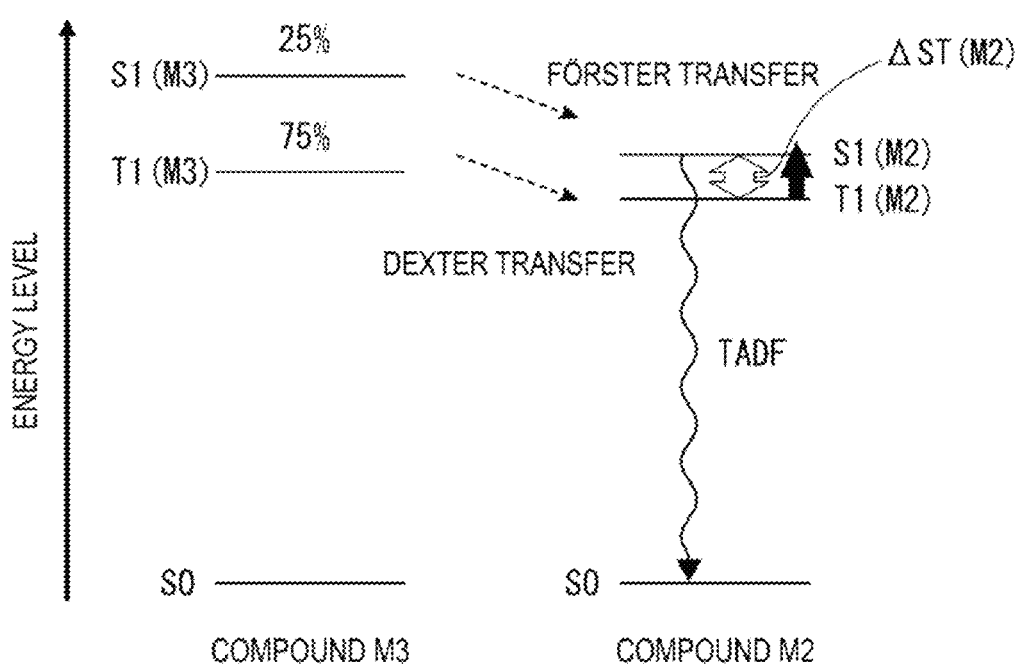

FIG. 4 schematically shows a relationship in energy level and energy transfer between a compound M3 and a compound M2 in an emitting layer in an exemplary arrangement of the organic electroluminescence device according to the first exemplary embodiment of the invention.

Figure 5:
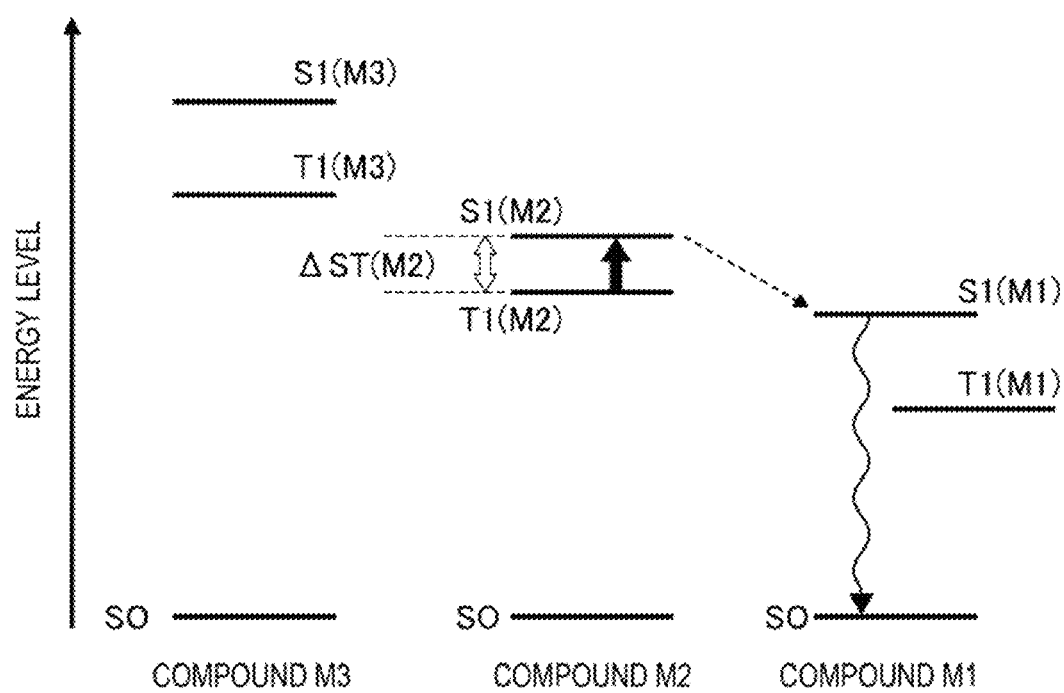

FIG. 5 schematically shows a relationship in energy level and energy transfer between the compound M3, the compound M2, and a compound M1 in an emitting layer in an exemplary arrangement of the organic electroluminescence device according to a second exemplary embodiment of the invention.

DESCRIPTION OF EMBODIMENT(S)

First Exemplary Embodiment

An arrangement of an organic EL device according to a first exemplary embodiment of the invention will be described below.

The organic EL device includes an anode, a cathode, and an organic layer between the anode and the cathode. This organic layer includes at least one layer formed of an organic compound(s). Alternatively, the organic layer includes a plurality of layers formed of an organic compound(s). The organic layer may further include an inorganic compound. In the organic EL device according to the exemplary embodiment, at least one layer of the organic layer is an emitting layer. Accordingly, the organic layer may, for instance, be provided by a single emitting layer, or include a layer(s) usable for an organic EL device. Examples of the layer(s) usable for the organic EL device, which are not particularly limited, include at least one layer selected from the group consisting of a hole injecting layer, hole transporting layer, electron injecting layer, electron transporting layer, and blocking layer.

The organic EL device according to the exemplary embodiment includes an emitting layer between the anode and the cathode.

FIG. 1 schematically shows an exemplary arrangement of an organic EL device according to the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8, and an electron injecting layer 9, which are sequentially laminated on the anode 3.

An organic layer between the cathode 4 and the emitting layer 5 corresponds to an electron transporting zone. The electron transporting zone includes, for example, at least one layer selected from the group consisting of an electron injecting layer, an electron transporting layer, and a hole blocking layer.

In the case of FIG. 1, the electron transporting zone includes the electron transporting layer 8 and the electron injecting layer 9. The electron transporting layer 8 is adjacent to the emitting layer 5.

An organic layer between the anode 3 and the emitting layer 5 corresponds to a hole transporting zone. The hole transporting zone includes, for example, at least one layer selected from the group consisting of a hole injecting layer, a hole transporting layer, and an electron blocking layer.

In the case of FIG. 1, the hole transporting zone includes the hole injecting layer 6 and the hole transporting layer 7. The hole transporting layer 7 is adjacent to the emitting layer 5.

In an exemplary arrangement of the exemplary embodiment, the emitting layer may contain a metal complex.

In an exemplary arrangement of the exemplary embodiment, the emitting layer preferably does not contain a phosphorescent material (dopant material).

In an exemplary arrangement of the exemplary embodiment, the emitting layer preferably does not contain a heavy-metal complex and a phosphorescent rare earth metal complex. Examples of the heavy-metal complex herein include iridium complex, osmium complex, and platinum complex.

In an exemplary arrangement of the exemplary embodiment, the emitting layer also preferably does not contain a metal complex.

In the organic EL device according to the exemplary embodiment, the emitting layer contains a delayed fluorescent compound M2 and a compound M3 having at least one deuterium atom.

However, the compound M3 is not a compound having a partial structure represented by a formula (1C) or (2C) below.

The compound having a partial structure represented by the formula (1C) is a compound having an aza-dibenzofuran ring.

The compound having a partial structure represented by the formula (2C) is a compound having an aza-dibenzothiophene ring.

In the exemplary embodiment, the compound M2 is preferably a dopant material (which may be referred to as a guest material, an emitter, or a luminescent material), and the compound M3 is preferably a host material (which may be referred to as a matrix material).

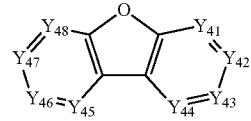

(1C)

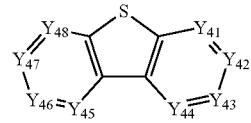

(2C)

In the formulae (1C) and (2C), $Y_{41}$ to $Y_{48}$ are each independently a nitrogen atom, CR, or a carbon atom bonded to another atom or another structure in a molecule of the compound M3, at least one of $Y_{41}$ to $Y_{48}$ is a nitrogen atom, at least one of $Y_{41}$ to $Y_{48}$ is a carbon atom bonded to another atom or another structure in the molecule of the compound M3, each R is independently a hydrogen atom or a substituent, and a plurality of R are mutually the same or different.

When R is a substituent, the substituent may be, for example, the same group as $R_{31}$ in a formula (31). A plurality of R are the same or different.

Patent Literature 1 discloses that an organic EL device in which a deuterated TADF material is contained in an emitting layer has an improved lifetime. TADF materials use the inverse intersystem crossing from a triplet exciton to a singlet exciton and thus is present as an unstable exciton for a long time. Thus, the device lifetime of the organic EL device described in Patent Literature 1 is considered to be improved by replacing a C—H bond in a TADF material with a more stable C-D bond. It should be noted that D represents a deuterium atom.

On the other hand, since a host material contained in the emitting layer together with a TADF material has a large energy gap, the host material is less likely to absorb energy from the TADF material and is less likely to be in an unstable excited state. Therefore, even if the host material used together with the TADF material is deuterated, probably, the deuteration is less likely to contribute to the improvement in the device lifetime, and an example of such an improvement in the device lifetime has also not been reported. However, the inventors of the invention considered that a host material may also have a reduced energy gap and may be in an unstable excited state if the host material is in a radical cation state in which a hole has been injected or in a radical anion state in which an electron has been injected.

In view of this, as a result of intensive studies, the inventors of the invention have found that the device lifetime can be improved by incorporating a deuterated host material in an emitting layer together with a TADF material (deuterated or non-deuterated TADF material), thereby completing an organic EL device according to the present disclosure.

Patent Literature 2 discloses an organic EL device in which a deuterated host material is contained in an emitting layer. However, the deuterated host material described in Patent Literature 2 has an aza-dibenzofuran ring. Such a host material having an aza-dibenzofuran ring cannot sufficiently contribute to an improvement in the device lifetime in some cases when used in combination with a TADF material. This is probably because a C—H bond adjacent to a nitrogen atom in the aza-dibenzofuran ring has higher acidity than a C—H bond adjacent to a carbon atom and thus is more likely to be broken.

For the same reason, a host material having an aza-dibenzothiophene ring also cannot sufficiently contribute to an improvement in the device lifetime in some cases when used in combination with a TADF material.

Accordingly, according to the exemplary embodiment, an organic EL device that can have an extended lifetime is provided by incorporating a delayed fluorescent compound M2 (deuterated or non-deuterated TADF material) and a compound M3 having at least one deuterium atom (deuterated host material (provided that a host material having an aza-dibenzofuran ring or an aza-dibenzothiophene ring is excluded)) in an emitting layer.

Further, according to the exemplary embodiment, a high-performance organic EL device is achievable.

High performance means at least one of luminous efficiency, device lifetime, drive voltage, or luminance is improved.

Thus, according to the exemplary embodiment, in addition to the device lifetime, at least one of luminous efficiency, drive voltage, or luminance intensity is expected to be improved.

Herein, the "compound M3 having at least one deuterium atom" refers to a compound in which the hydrogen atoms in the compound M3 are not composed only of protium atoms.

In the following description, a "compound M3 having at least one deuterium atom" may be referred to as a "deuterated compound M3". A compound in which all hydrogen atoms included in the compound M3 are protium atoms may be referred to as a "non-deuterated compound m3".

In the exemplary embodiment, a content ratio of the non-deuterated compound m3 relative to the total of the deuterated compound M3 and the non-deuterated compound m3 in the emitting layer is 99% by mole or less. The content ratio of the non-deuterated compound m3 is examined by mass spectrometry.

In the organic EL device according to the exemplary embodiment, a content ratio of the deuterated compound M3 relative to the total of the deuterated compound M3 and the non-deuterated compound m3 contained in the emitting layer is preferably 30% by mole or more, 50% by mole or more, 70% by mole or more, 90% by mole or more, 95% by mole or more, 99% by mole or more, or 100% by mole.

In the exemplary embodiment, it is also preferable that deuterium atoms account for 10% or more of the total number of hydrogen atoms included in the compound M3, deuterium atoms account for 20% or more thereof, deuterium atoms account for 30% or more thereof, deuterium atoms account for 40% or more thereof, deuterium atoms account for 50% or more thereof, deuterium atoms account for 60% or more thereof, deuterium atoms account for 70% or more thereof, and deuterium atoms account for 80% or more thereof.

Method for Checking Whether Deuterium Atom Is Included in Compound M3 and Method for Specifying Bonding Position of Deuterium Atom in Compound M3

Whether a deuterium atom is included in the compound M3 is checked by mass spectrometry or 1H-NMR analysis. The bonding position of the deuterium atom in the compound M3 is specified by 1H-NMR analysis.

The details are as follows. Mass spectrometry is performed on a target compound. When a molecular weight of the target compound is increased by one as compared with a related compound in which all the hydrogen atoms in the target compound are replaced by protium atoms, it is determined that the target compound includes one deuterium atom. Further, since a signal of a deuterium atom does not appear in 1H-NMR spectrometry, the number of deuterium atoms in the molecule is determined by an integral value obtained by performing 1H-NMR spectrometry on the target compound. Furthermore, the bonding position of the deuterium atom is determined by conducting 1H-NMR spectrometry on the target compound to perform signal assignment.

Emitting Layer

Compound M3 (Deuterated Compound M3)

The compound M3 may be a thermally activated delayed fluorescent compound or a compound exhibiting no thermally activated delayed fluorescence. However, the compound M3 is preferably a compound exhibiting no thermally activated delayed fluorescence.

Partial Structures Represented by Formulae (31) to (48)

In the exemplary embodiment, the compound M3 preferably includes, in one molecule thereof, at least one of partial structures represented by formulae (31) to (48) below.

However, when the compound M3 has a plurality of partial structures represented by the formula (31), a plurality of partial structures represented by the formula (32), a plurality of partial structures represented by the formula (33), and a plurality of partial structures represented by the formula (34) below, the plurality of partial structures represented by the formula (31) are the same or different, the plurality of partial structures represented by the formula (32) are the same or different, the plurality of partial structures represented by the formula (33) are the same or different, and the plurality of partial structures represented by the formula (34) are the same or different.

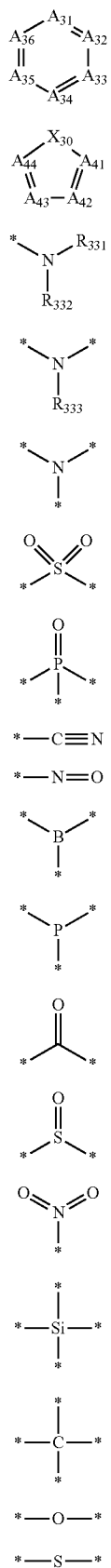

In the formula (31), $A_{31}$ to $A_{36}$ are each independently a nitrogen atom, $CR_{31}$, or a carbon atom bonded to another atom or another structure in the molecule of the compound M3, at least one of $A_{31}$ to $A_{36}$ is a carbon atom bonded to another atom or another structure in the molecule of the compound M3, and each $R_{31}$ is independently a hydrogen atom or a substituent, or at least one pair of pairs of adjacent ones of $R_{31}$ are mutually bonded to form a ring.

In the formula (32), $A_{41}$ to $A_{44}$ are each independently a nitrogen atom, $CR_{32}$, or a carbon atom bonded to another atom or another structure in the molecule of the compound M3, each $R_{32}$ is independently a hydrogen atom or a substituent, or at least one pair of pairs of adjacent ones of $R_{32}$ are mutually bonded to form a ring, $X_{30}$ is $NR_{33}$, $CR_{34}R_{35}$, $SiR_{36}R_{37}$, an oxygen atom, a sulfur atom, a nitrogen atom bonded to another atom or another structure in the molecule of the compound M3, a carbon atom bonded to $R_{38}$ and another atom or another structure in the molecule of the compound M3, or a silicon atom bonded to $R_{39}$ and another atom or another structure in the molecule of the compound M3, at least one of carbon atoms in $A_{41}$ to $A_{44}$, a nitrogen atom in $X_{30}$, a carbon atom in $X_{30}$, or a silicon atom in $X_{30}$ is bonded to another atom or another structure in the molecule of the compound M3, and $R_{33}$ to $R_{39}$ are each independently a hydrogen atom or a substituent, or at least one pair of a pair of adjacent $R_{34}$ and $R_{35}$ or a pair of adjacent $R_{36}$ and $R_{37}$ are mutually bonded to form a ring.

In the formulae (33) and (34), $R_{331}$ to $R_{333}$ are each independently a hydrogen atom or a substituent, or a pair of adjacent $R_{331}$ and $R_{332}$ are mutually bonded to form a ring.

In the formulae (31) to (34), $R_{31}$ to $R_{39}$ and $R_{331}$ to $R_{333}$ serving as a substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, a substituted or unsubstituted arylthio group having 6 to 30 ring carbon atoms, a substituted or unsubstituted aralkyl group having 7 to 30 carbon atoms, a substituted germanium group, a substituted phosphine oxide group, a nitro group, a substituted or unsubstituted carbonyl group, or a substituted boryl group, a plurality of $R_{31}$ are mutually the same or different, a plurality of $R_{32}$ are mutually the same or different; and * is a bonding portion to another atom or another structure in the molecule of the compound M3.

In the formula (32), when $X_{30}$ is "a nitrogen atom bonded to another atom or another structure in the molecule of the compound M3", the formula (32) is represented by a formula (32-1) below.

In the formula (32), when $X_{30}$ is "a carbon atom bonded to $R_{38}$ and another atom or another structure in the molecule of the compound M3", the formula (32) is represented by a formula (32-2) below.

In the formula (32), when $X_{30}$ is "a silicon atom bonded to $R_{39}$ and another atom or another structure in the molecule of the compound M3", the formula (32) is represented by a formula (32-3) below.

In the formulae (32-1) to (32-3), $A_{41}$ to $A_{44}$ each independently represent the same as $A_{41}$ to $A_{44}$ in the formula (32), $R_{38}$ and $R_{39}$ each independently represent the same as $R_{32}$ in the formula (32), and * is a bonding portion to another atom or another structure in the molecule of the compound M3.

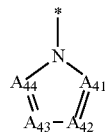

(32-1)

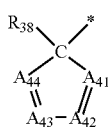

(32-2)

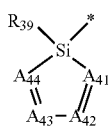

(32-3)

In the exemplary embodiment, the partial structure represented by the formula (31) is preferably represented by any of groups represented by formulae (31a) to (31f) below, and monovalent or higher-valent residues derived from compounds represented by formulae (31g) to (31k), (31m), (31n), (31p), and (31q) below.

(31a)–(31m) [chemical structure diagrams]

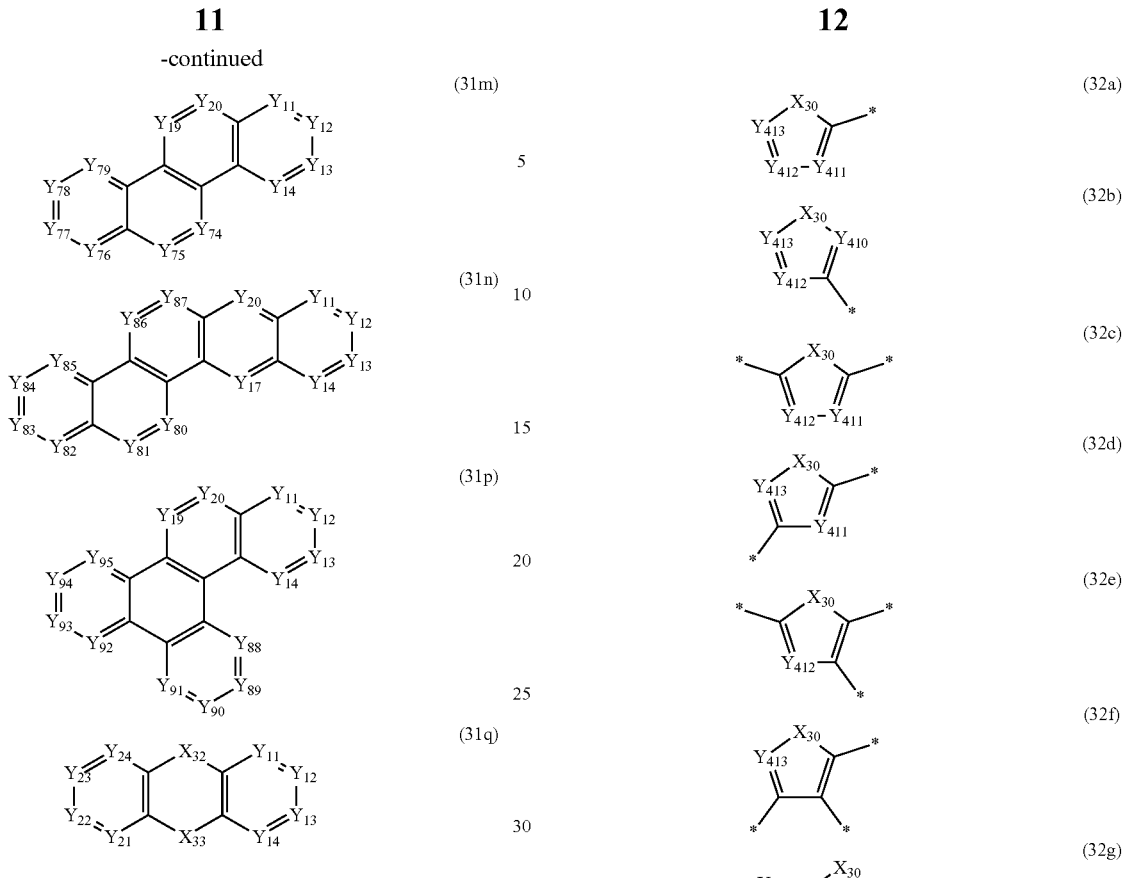

In the formulae (31a) to (31f), $Y_{12}$ to $Y_{16}$ are each independently a nitrogen atom or $CR_{31}$, each $R_{31}$ independently represents the same as $R_{31}$ in the formula (31), and * is a bonding portion to another atom or another structure in the molecule of the compound M3.

In the formulae (31g) to (31k), (31m), (31n), and (31p), $Y_{11}$ to $Y_{14}$, $Y_{17}$ to $Y_{39}$, and $Y_{70}$ to $Y_{95}$ are each independently a nitrogen atom, $CR_{31}$, or a carbon atom bonded to another atom or another structure in the molecule of the compound M3, each $R_{31}$ independently represents the same as $R_{31}$ in the formula (31), and at least one of $Y_{11}$ to $Y_{14}$, $Y_{17}$ to $Y_{39}$, or $Y_{70}$ to $Y_{95}$ is a carbon atom bonded to another atom or another structure in the molecule of the compound M3.

In the formula (31q), $Y_{11}$ to $Y_{14}$ and $Y_{21}$ to $Y_{24}$ are each independently a nitrogen atom, $CR_{31}$, or a carbon atom bonded to another atom or another structure in the molecule of the compound M3, each $R_{31}$ independently represents the same as $R_{31}$ in the formula (31), $X_{32}$ and $X_{33}$ each independently represent the same as $X_{30}$ in the formula (32), and at least one of carbon atoms in $Y_{11}$ to $Y_{14}$, carbon atoms in $Y_{21}$ to $Y_{24}$, nitrogen atoms in $X_{32}$ and $X_{33}$, carbon atoms in $X_{32}$ and $X_{33}$, or silicon atoms in $X_{32}$ and $X_{33}$ is bonded to another atom or another structure in the molecule of the compound M3; and * is a bonding portion to another atom or another structure in the molecule of the compound M3.

In the formulae (31a) to (31k), (31m), (31n), (31p), and (31q), at least one of $R_{31}$ in $CR_{31}$ is preferably a deuterium atom.

In the exemplary embodiment, the partial structure represented by the formula (32) is preferably represented by any of groups represented by formulae (32a) to (32f) below, and monovalent or higher-valent residues derived from compounds represented by formulae (32g) to (32k), (32m), (32n), and (32p) below.

In the formulae (32a) to (32f), $Y_{410}$ to $Y_{413}$ are each independently a nitrogen atom or $CR_{32}$, each $R_{32}$ independently represents the same as $R_{32}$ in the formula (32), $X_{30}$ represents the same as $X_{30}$ in the formula (32), and * is a bonding portion to another atom or another structure in the molecule of the compound M3.

In the formula (32g), $Y_{410}$ to $Y_{411}$ and $Y_{45}$ to $Y_{48}$ are each independently a nitrogen atom, $CR_{32}$, or a carbon atom bonded to another atom or another structure in the molecule of the compound M3, each $R_{32}$ independently represents the same as $R_{32}$ in the formula (32), $X_{30}$ represents the same as $X_{30}$ in the formula (32), and at least one of carbon atoms in $Y_{410}$ to $Y_{411}$ and $Y_{45}$ to $Y_{48}$, a nitrogen atom in $X_{30}$, a carbon atom in $X_{30}$, or a silicon atom in $X_{30}$ is bonded to another atom or another structure in the molecule of the compound M3.

In the formula (32h), $Y_{41}$ to $Y_{48}$ are each independently a nitrogen atom, $CR_{32}$, or a carbon atom bonded to another atom or another structure in the molecule of the compound M3, each $R_{32}$ independently represents the same as $R_{32}$ in the formula (32), $X_{30}$ represents the same as $X_{30}$ in the formula (32), and when $X_{30}$ is an oxygen atom or a sulfur atom, $Y_{41}$ to $Y_{48}$ are each $CR_{32}$, and at least one of carbon atoms in $Y_{41}$ to $Y_{48}$, a nitrogen atom in $X_{30}$, a carbon atom in $X_{30}$, or a silicon atom in $X_{30}$ is bonded to another atom or another structure in the molecule of the compound M3; and * is a bonding portion to another atom or another structure in the molecule of the compound M3.

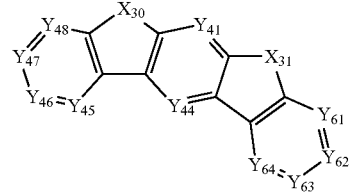

(32i)

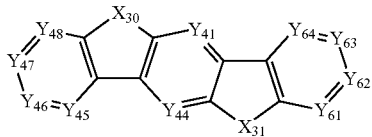

(32j)

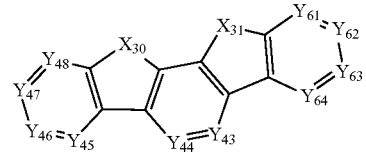

(32k)

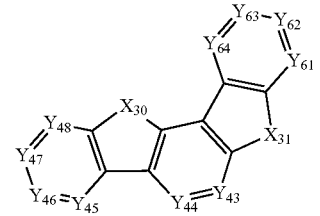

(32m)

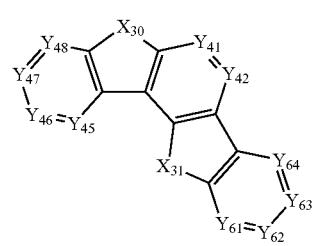

(32n)

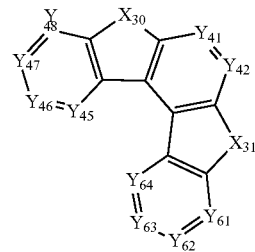

(32p)

In the formulae (32i) to (32k), (32m), (32n), and (32p), $Y_{41}$ to $Y_{48}$ and $Y_{61}$ to $Y_{64}$ are each independently a nitrogen atom, $CR_{32}$, or a carbon atom bonded to another atom or another structure in the molecule of the compound M3, each $R_{32}$ independently represents the same as $R_{32}$ in the formula (32), and $X_{30}$ and $X_{31}$ each independently represent the same as $X_{30}$ in the formula (32), and at least one of carbon atoms in $Y_{41}$ to $Y_{48}$ and $Y_{61}$ to $Y_{64}$, nitrogen atoms in $X_{30}$ and $X_{31}$, carbon atoms in $X_{30}$ and $X_{31}$, or silicon atoms in $X_{30}$ and $X_{31}$ is bonded to another atom or another structure in the molecule of the compound M3.

In the formulae (32a) to (32k), (32m), (32n), and (32p), at least one of $R_{32}$ in $CR_{32}$ is preferably a deuterium atom.

In the formulae (32a) to (32k), (32m), (32n), and (32p), when at least one of $R_{32}$ in $CR_{32}$ is a substituent and the substituent has one or more hydrogen atoms, it is preferable that at least one of the hydrogen atoms is a deuterium atom or all the hydrogen atoms are deuterium atoms.

In the compound M3 of the exemplary embodiment, $R_{31}$, $R_{32}$, and $R_{331}$ to $R_{333}$ are preferably each independently a hydrogen atom, a halogen atom, a cyano group, an unsubstituted aryl group having 6 to 30 ring carbon atoms, an unsubstituted heterocyclic group having 5 to 30 ring atoms, an unsubstituted alkyl group having 1 to 30 carbon atoms, an unsubstituted alkyl halide group having 1 to 30 carbon atoms, an unsubstituted alkylsilyl group having 3 to 30 carbon atoms, an unsubstituted arylsilyl group having 6 to 60 ring carbon atoms, an unsubstituted arylphosphoryl group having 6 to 60 ring carbon atoms, an unsubstituted alkoxy group having 1 to 30 carbon atoms, an unsubstituted aryloxy group having 6 to 30 ring carbon atoms, an amino group, an unsubstituted alkylamino group having 2 to 30 carbon atoms, an unsubstituted arylamino group having 6 to 60 ring carbon atoms, a thiol group, an unsubstituted alkylthio group having 1 to 30 carbon atoms, or an unsubstituted arylthio group having 6 to 30 ring carbon atoms, more preferably a hydrogen atom, a halogen atom, a cyano group, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 6 carbon atoms, an unsubstituted alkylsilyl group having 3 to 6 carbon atoms, an unsubstituted arylsilyl group having 6 to 60 ring carbon atoms, an unsubstituted arylphosphoryl group having 6 to 60 ring carbon atoms, an unsubstituted alkoxy group having 1 to 6 carbon atoms, an unsubstituted aryloxy group having 6 to 14 ring carbon atoms, an amino group, an unsubstituted alkylamino group having 2 to 12 carbon atoms, an unsubstituted arylamino group having 6 to 60 ring carbon atoms, a thiol group, an unsubstituted alkylthio group having 1 to 6 carbon atoms, or an unsubstituted arylthio group having 6 to 14 ring carbon atoms, and still more preferably a hydrogen atom.

In the compound M3 of the exemplary embodiment, $R_{33}$ to $R_{39}$ in $X_{30}$ and $R_{33}$ to $R_{39}$ in $X_{31}$ (which represent the same as $R_{33}$ to $R_{39}$ in $X_{30}$) are preferably each independently a hydrogen atom, an unsubstituted aryl group having 6 to 30 ring carbon atoms, an unsubstituted heterocyclic group having 5 to 30 ring atoms, an unsubstituted alkyl group having 1 to 30 carbon atoms, or an unsubstituted alkyl halide group having 1 to 30 carbon atoms, more preferably a hydrogen atom, an unsubstituted aryl group having 6 to 14 ring carbon atoms, an unsubstituted heterocyclic group having 5 to 14 ring atoms, an unsubstituted alkyl group having 1 to 6 carbon atoms, or an unsubstituted alkyl halide group having 1 to 6 carbon atoms, and still more preferably an unsubstituted aryl group having 6 to 14 ring carbon atoms or an unsubstituted alkyl group having 1 to 6 carbon atoms.

In the compound M3 of the exemplary embodiment, when any one or more of $R_{31}$, $R_{32}$, $R_{331}$ to $R_{333}$, $R_{33}$ to $R_{39}$ in $X_{30}$, and $R_{33}$ to $R_{39}$ in $X_{31}$ (which represent the same as $R_{33}$ to $R_{39}$ in $X_{30}$) are hydrogen atoms, it is preferable that at least one of the hydrogen atoms is a deuterium atom or all the hydrogen atoms are deuterium.

In the compound M3 of the exemplary embodiment, when any one or more of $R_{31}$, $R_{32}$, $R_{331}$ to $R_{333}$, $R_{33}$ to $R_{39}$ in $X_{30}$, and $R_{33}$ to $R_{39}$ in $X_{31}$ (which represent the same as $R_{33}$ to $R_{39}$ in $X_{30}$) are substituents and the substituents have one or more hydrogen atoms, it is preferable that at least one of the hydrogen atoms is a deuterium atom or all the hydrogen atoms are deuterium atoms.

Examples of partial structures represented by any of the formulae (31) to (48) include partial structures represented by formulae (3-1A) to (3-25A) and (3-1B) to (3-25B) below.

It is also preferable that the compound M3 includes, in one molecule thereof, at least any of partial structures represented by formulae (3-1A) to (3-25A) and (3-1B) to (3-25B) below.

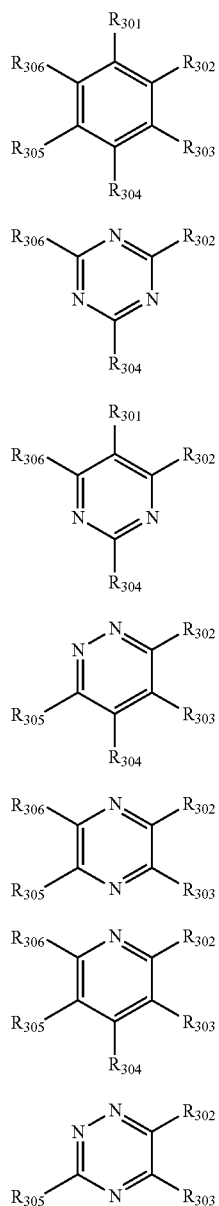

In the formulae (3-1A) to (3-7A), $R_{301}$ to $R_{306}$ each independently represent the same as $R_{31}$ in the formula (31), and at least one of $R_{301}$ to $R_{306}$ is a single bond bonded to another atom or another structure in the molecule of the compound M3.

In the formulae (3-1A) to (3-7A), at least one pair of the following are mutually bonded to form a ring or not bonded to form no ring: a pair of adjacent $R_{301}$ and $R_{302}$, a pair of adjacent $R_{302}$ and $R_{303}$, a pair of adjacent $R_{303}$ and $R_{304}$, a pair of adjacent $R_{304}$ and $R_{305}$, a pair of adjacent $R_{305}$ and $R_{306}$, or a pair of adjacent $R_{306}$ and $R_{301}$.

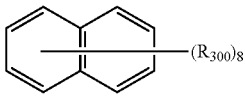

(3-8A)

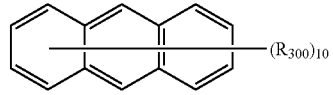

(3-9A)

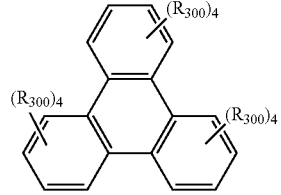

(3-10A)

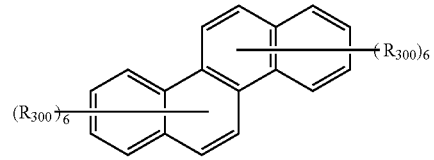

(3-11A)

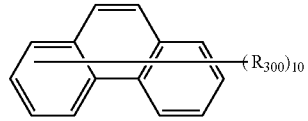

(3-12A)

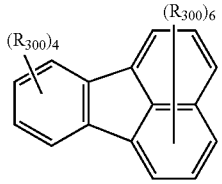

(3-13A)

In the formulae (3-8A) to (3-13A), $R_{300}$ each independently represent the same as $R_{31}$ in the formula (31), at least one of $R_{300}$ is a single bond bonded to another atom or another structure in the molecule of the compound M3, and a plurality of $R_{300}$ are mutually the same or different.

In the formulae (3-8A) to (3-13A), at least one pair of pairs of adjacent ones of Ram are mutually bonded to form a ring or not bonded to form no ring.

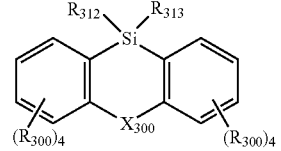

(3-14A)

(3-15A)
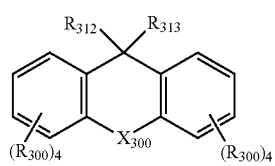

(3-16A)
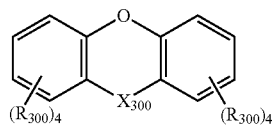

(3-17A)
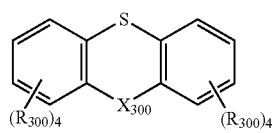

(3-18A)
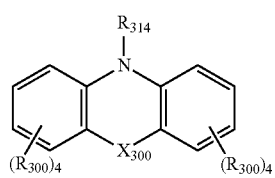

In the formulae (3-14A) to (3-18A), $R_{300}$ and $R_{312}$ to $R_{314}$ each independently represent the same as $R_{31}$ in the formula (31), each $X_{300}$ independently represents the same as $X_{30}$ in the formula (32), at least one of $R_{300}$ or $R_{312}$ to $R_{314}$ is a single bond bonded to another atom or another structure in the molecule of the compound M3, or at least one of a nitrogen atom, a carbon atom, or a silicon atom in $X_{300}$ is bonded to another atom or another structure in the molecule of the compound M3, and a plurality of $R_{300}$ are mutually the same or different.

In the formulae (3-14A) to (3-18A), at least one pair of the following are mutually bonded to form a ring or not bonded to form no ring: pairs of adjacent ones of $R_{300}$, a pair of $R_{312}$ and $R_{313}$, a pair of $R_{34}$ and $R_{35}$ in $X_{300}$ (which represent the same as a pair of $R_{34}$ and $R_{35}$ in $X_{30}$), or a pair of $R_{36}$ and $R_{37}$ in $X_{300}$ (which represent the same as a pair of $R_{36}$ and $R_{37}$ in $X_{30}$).

(3-19A)
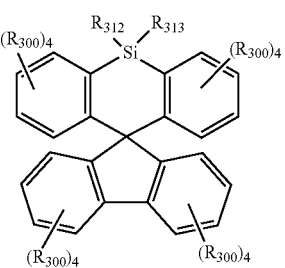

(3-20A)
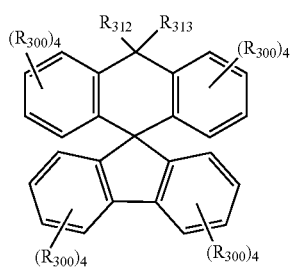

(3-21A)
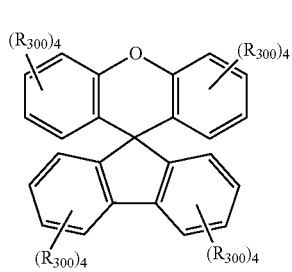

(3-22A)
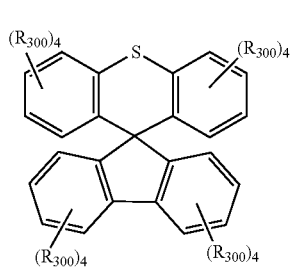

(3-23A)
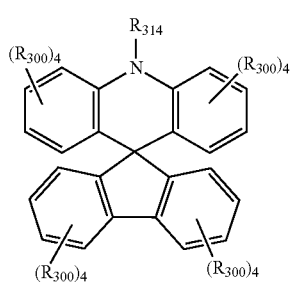

In the formulae (3-19A) to (3-23A), $R_{300}$ and $R_{312}$ to $R_{314}$ each independently represent the same as $R_{31}$ in the formula (31), at least one of $R_{300}$ or $R_{312}$ to $R_{314}$ is a single bond bonded to another atom or another structure in the molecule of the compound M3, and a plurality of $R_{300}$ are mutually the same or different.

In the formulae (3-19A) to (3-23A), at least one pair of the following are mutually bonded to form a ring or not bonded to form no ring: pairs of adjacent ones of $R_{300}$ or a pair of $R_{312}$ and $R_{313}$.

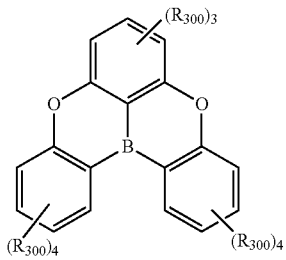
(3-24A)

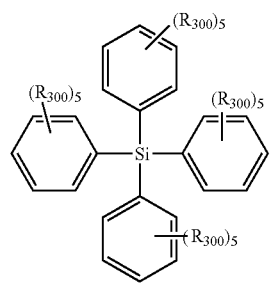
(3-25A)

In the formulae (3-24A) and (3-25A), $R_{300}$ each independently represent the same as $R_{31}$ in the formula (31), at least one of $R_{300}$ is a single bond bonded to another atom or another structure in the molecule of the compound M3, and a plurality of $R_{300}$ are mutually the same or different.

In the formulae (3-24A) and (3-25A), at least one pair of pairs of adjacent ones of $R_{300}$ are mutually bonded to form a ring or not bonded to form no ring.

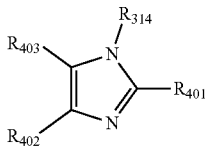
(3-1B)

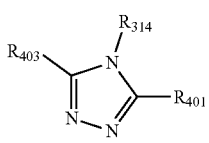
(3-2B)

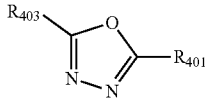
(3-3B)

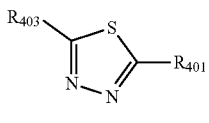
(3-4B)

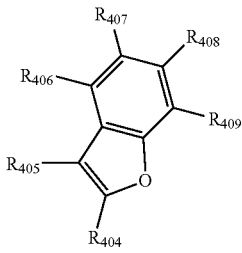
(3-5B)

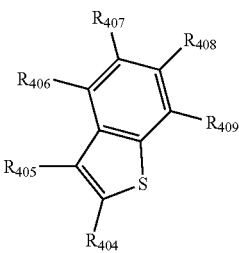
(3-6B)

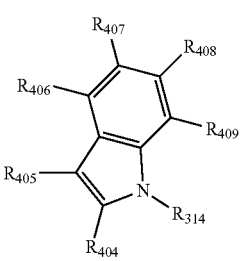
(3-7B)

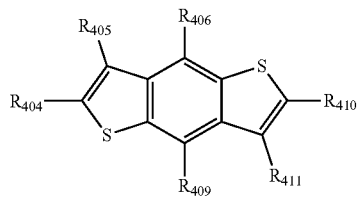
(3-8B)

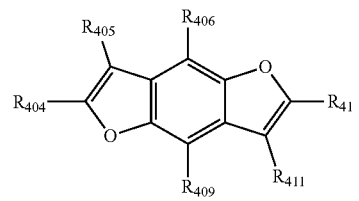
(3-9B)

In the formulae (3-1B) to (3-9B), $R_{314}$ and $R_{401}$ to $R_{411}$ each independently represent the same as $R_{32}$ in the formula (32), and at least one of $R_{314}$ or $R_{401}$ to $R_{411}$ is a single bond bonded to another atom or another structure in the molecule of the compound M3.

In the formulae (3-1B) and (3-2B), at least one pair of the following are mutually bonded to form a ring or not bonded to form no ring: a pair of $R_{402}$ and $R_{403}$, a pair of $R_{403}$ and $R_{314}$, or a pair of $R_{314}$ and $R_{401}$.

In the formulae (3-5B) and (3-6B), at least one pair of the following are mutually bonded to form a ring or not bonded to form no ring: a pair of $R_{404}$ and $R_{405}$, a pair of $R_{405}$ and $R_{406}$, a pair of $R_{406}$ and $R_{407}$, a pair of $R_{407}$ and $R_{408}$, or a pair of $R_{408}$ and $R_{409}$.

In the formula (3-7B), at least one pair of the following are mutually bonded to form a ring or not bonded to form no ring: a pair of $R_{404}$ and $R_{405}$, a pair of $R_{405}$ and $R_{406}$, a pair of $R_{406}$ and $R_{407}$, a pair of $R_{407}$ and $R_{408}$, a pair of $R_{408}$ and $R_{409}$, a pair of $R_{409}$ and $R_{314}$, or a pair of $R_{314}$ and $R_{404}$.

In the formulae (3-8B) and (3-9B), at least one pair of the following are mutually bonded to form a ring or not bonded to form no ring: a pair of $R_{404}$ and $R_{405}$, a pair of $R_{405}$ and $R_{406}$, a pair of $R_{410}$ and $R_{411}$, or a pair of $R_{411}$ and $R_{409}$.

(3-10B) 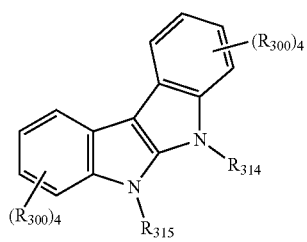

(3-11B) 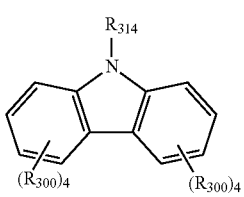

(3-12B) 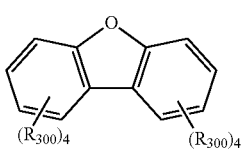

(3-13B) 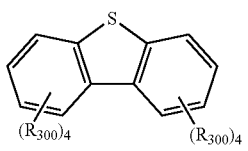

(3-14B) 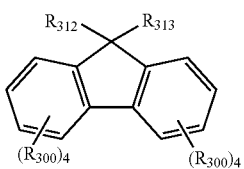

(3-15B) 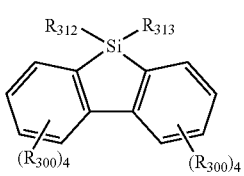

(3-16B) 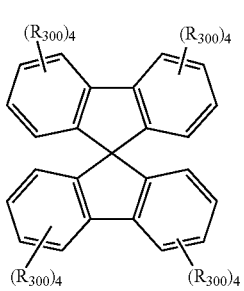

(3-17B) 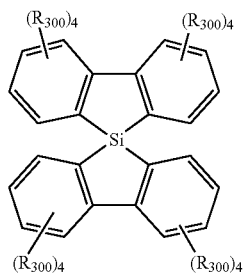

In the formulae (3-10B) to (3-17B), $R_{300}$ and $R_{312}$ to $R_{315}$ each independently represent the same as $R_{32}$ in the formula (32), at least one of $R_{300}$ or $R_{312}$ to $R_{315}$ is a single bond bonded to another atom or another structure in the molecule of the compound M3, and a plurality of $R_{300}$ are mutually the same or different.

In the formulae (3-10B) to (3-17B), at least one pair of the following are mutually bonded to form a ring or not bonded to form no ring: pairs of adjacent ones of $R_{300}$ or a pair of $R_{312}$ and $R_{313}$.

(3-18B) 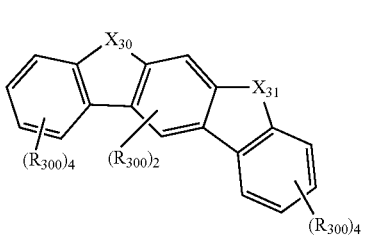

(3-19B) 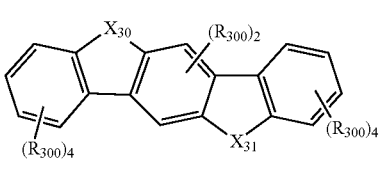

(3-20B) 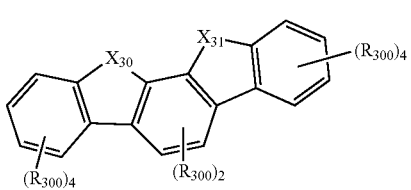

(3-21B) 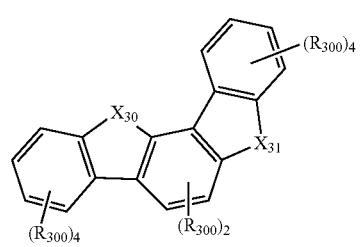

(3-22B)

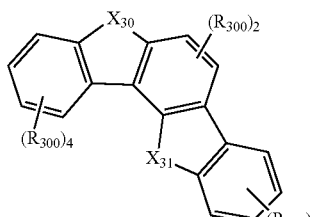

(3-23B)

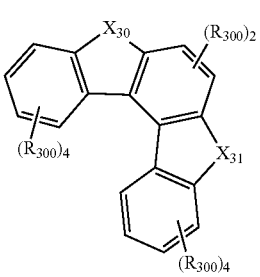

In the formulae (3-18B) to (3-23B), $R_{300}$ each independently represent the same as $R_{32}$ in the formula (32), $X_{30}$ and $X_{31}$ each independently represent the same as $X_{30}$ in the formula (32), at least one of $R_{300}$ is a single bond bonded to another atom or another structure in the molecule of the compound M3, or at least one of a nitrogen atom, a carbon atom, or a silicon atom in $X_{30}$ to $X_{31}$ is bonded to another atom or another structure in the molecule of the compound M3, and a plurality of $R_{300}$ are mutually the same or different.

In the formulae (3-18B) to (3-23B), at least one pair of the following are mutually bonded to form a ring or not bonded to form no ring: pairs of adjacent ones of $R_{300}$, a pair of $R_{34}$ and $R_{35}$ in $X_{30}$, a pair of $R_{36}$ and $R_{37}$ in $X_{30}$, a pair of $R_{34}$ and $R_{35}$ in $X_{31}$ (which represent the same as a pair of $R_{34}$ and $R_{35}$ in $X_{30}$), or a pair of $R_{36}$ and $R_{37}$ in $X_{31}$ (which represent the same as a pair of $R_{36}$ and $R_{37}$ in $X_{30}$).

(3-24B)

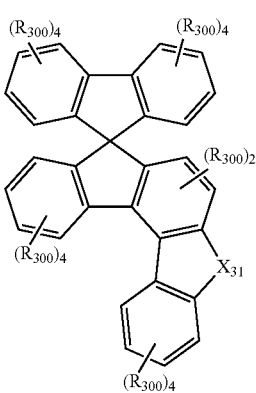

(3-25B)

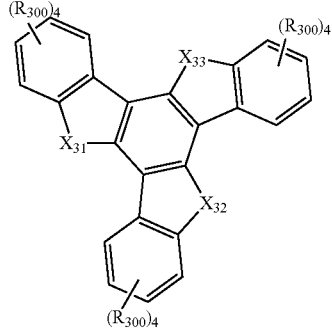

In the formulae (3-24B) and (3-25B), $R_{300}$ each independently represent the same as $R_{32}$ in the formula (32), $X_{31}$ to $X_{33}$ each independently represent the same as $X_{30}$ in the formula (32), at least one of $R_{300}$ is a single bond bonded to another atom or another structure in the molecule of the compound M3, Or at least one of a nitrogen atom, a carbon atom, or a silicon atom in $X_{31}$ to $X_{33}$ is bonded to another atom or another structure in the molecule of the compound M3, and a plurality of $R_{300}$ are mutually the same or different.

In the formulae (3-24B) and (3-25B), at least one pair of the following are mutually bonded to form a ring or not bonded to form no ring: pairs of adjacent ones of $R_{300}$, a pair of $R_{34}$ and $R_{35}$ in $X_{31}$ to $X_{33}$ (which represent the same as a pair of $R_{34}$ and $R_{35}$ in $X_{30}$), or a pair of $R_{36}$ and $R_{37}$ in $X_{31}$ to $X_{33}$ (which represent the same as a pair of $R_{34}$ and $R_{35}$ in $X_{30}$).

In the formulae (3-1A) to (3-25A) and (3-1B) to (3-25B), $R_{300}$, $R_{301}$ to $R_{306}$, $R_{312}$ to $R_{315}$, and $R_{401}$ to $R_{411}$ are preferably each independently a hydrogen atom, an unsubstituted aryl group having 6 to 30 ring carbon atoms, an unsubstituted heterocyclic group having 5 to 30 ring atoms, an unsubstituted alkyl group having 1 to 30 carbon atoms, or an unsubstituted alkyl halide group having 1 to 30 carbon atoms, more preferably a hydrogen atom, an unsubstituted aryl group having 6 to 14 ring carbon atoms, an unsubstituted heterocyclic group having 5 to 14 ring atoms, an unsubstituted alkyl group having 1 to 6 carbon atoms, or an unsubstituted alkyl halide group having 1 to 6 carbon atoms, and still more preferably an unsubstituted aryl group having 6 to 14 ring carbon atoms or an unsubstituted alkyl group having 1 to 6 carbon atoms.

In the formulae (3-1A) to (3-25A) and (3-1B) to (3-25B), $R_{33}$ to $R_{39}$ in $X_{31}$ to $X_{33}$ and $X_{300}$ (which represent the same as $R_{33}$ to $R_{39}$ in $X_{30}$) are preferably each independently a hydrogen atom, an unsubstituted aryl group having 6 to 30 ring carbon atoms, an unsubstituted heterocyclic group having 5 to 30 ring atoms, an unsubstituted alkyl group having 1 to 30 carbon atoms, or an unsubstituted alkyl halide group having 1 to 30 carbon atoms, more preferably a hydrogen atom, an unsubstituted aryl group having 6 to 14 ring carbon atoms, an unsubstituted heterocyclic group having 5 to 14 ring atoms, an unsubstituted alkyl group having 1 to 6 carbon atoms, or an unsubstituted alkyl halide group having 1 to 6 carbon atoms, and still more preferably an unsubstituted aryl group having 6 to 14 ring carbon atoms or an unsubstituted alkyl group having 1 to 6 carbon atoms.

In the formulae (3-1A) to (3-25A) and (3-1B) to (3-25B), when any one or more of $R_{300}$, $R_{301}$ to $R_{306}$, $R_{312}$ to $R_{315}$, $R_{401}$ to $R_{411}$, and $R_{33}$ to $R_{39}$ in $X_{31}$ to $X_{33}$ and $X_{300}$ (which represent the same as $R_{33}$ to $R_{39}$ in $X_{30}$) are hydrogen atoms, it is preferable that at least one of the hydrogen atoms is a deuterium atom or all the hydrogen atoms are deuterium.

In the formulae (3-1A) to (3-25A) and (3-1B) to (3-25B), when any one or more of $R_{300}$, $R_{301}$ to $R_{306}$, $R_{312}$ to $R_{315}$, $R_{401}$ to $R_{411}$, and $R_{33}$ to $R_{39}$ in $X_{31}$ to $X_{33}$ and $X_{300}$ (which represent the same as $R_{33}$ to $R_{39}$ in $X_{30}$) are substituents and the substituents have one or more hydrogen atoms, it is preferable that at least one of the hydrogen atoms is a deuterium atom or all the hydrogen atoms are deuterium atoms.

In the exemplary embodiment, the compound M3 preferably has at least one group of a cyano group, an amino group, a substituted or unsubstituted alkylamino group having 2 to 30 carbon atoms, or a substituted or unsubstituted arylamino group having 6 to 60 ring carbon atoms, or preferably has at least one monovalent or higher-valent residue derived from any of a substituted or unsubstituted benzene, a substituted or unsubstituted naphthalene, a substituted or unsubstituted indole, a substituted or unsubstituted carbazole, a substituted or unsubstituted dibenzofuran, a substituted or unsubstituted dibenzothiophene, a substituted or unsubstituted fluorene, a compound represented by a formula (36a) below, a substituted or unsubstituted triazine, a substituted or unsubstituted pyrimidine, a substituted or unsubstituted pyridine, a substituted or unsubstituted pyridazine, a substituted or unsubstituted pyrazine, a substituted or unsubstituted imidazole, a substituted or unsubstituted benzimidazole, a substituted or unsubstituted phenanthrene, a substituted or unsubstituted anthracene, a substituted or unsubstituted triphenylene, a substituted or unsubstituted chrysene, a substituted or unsubstituted fluoranthene, and a substituted or unsubstituted benzochrysene.

(36a)

In the formula (36a), $R_{36}$ to $R_{38}$ are each independently a hydrogen atom or a substituent, or at least one pair of pairs of adjacent ones of $R_{38}$ or a pair of $R_{36}$ and $R_{37}$ are mutually bonded to form a ring, $R_{36}$ to $R_{38}$ serving as a substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, a substituted or unsubstituted arylthio group having 6 to 30 ring carbon atoms, a substituted or unsubstituted aralkyl group having 7 to 30 carbon atoms, a substituted germanium group, a substituted phosphine oxide group, a nitro group, or a substituted or unsubstituted carbonyl group, and a plurality of $R_{38}$ are mutually the same or different.

In the exemplary embodiment, the compound M3 more preferably has a cyano group, or more preferably has at least one monovalent or higher-valent residue derived from any of a substituted or unsubstituted carbazole, a substituted or unsubstituted dibenzofuran, a substituted or unsubstituted dibenzothiophene, a substituted or unsubstituted fluorene, a compound represented by the formula (36a), a substituted or unsubstituted triazine, a substituted or unsubstituted pyrimidine, a substituted or unsubstituted pyridine, and a substituted or unsubstituted triphenylene.

In the exemplary embodiment, the compound M3 still more preferably has a cyano group, or still more preferably has at least one monovalent or higher-valent residue derived from any of a substituted or unsubstituted carbazole, a substituted or unsubstituted dibenzofuran, a substituted or unsubstituted dibenzothiophene, a substituted or unsubstituted triazine, and a substituted or unsubstituted pyrimidine.

In the exemplary embodiment, the compound M3 still more preferably has a monovalent or higher-valent residue derived from a substituted or unsubstituted carbazole.

In the exemplary embodiment, the compound M3 still more preferably has a monovalent or higher-valent residue derived from a structure represented by a formula (3-10) below.

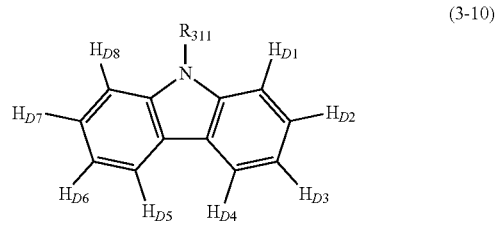

(3-10)

In the formula (3-10), $H_{D1}$ to $H_{D8}$ are hydrogen atoms, at least one of $H_{D1}$ to $HD_8$ is a deuterium atom, $R_{311}$ is a substituent, and at least one of $D_1$ to $D_8$ or $R_{311}$ is a single bond bonded to another atom or another structure in the molecule of the compound M3, and $R_{311}$ serving as a substituent is a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, a substituted or unsubstituted arylthio group having 6 to 30 ring carbon atoms, a substituted or unsubstituted aralkyl group having 7 to 30 carbon atoms, a substituted germanium group, a substituted phosphine oxide group, a nitro group, a substituted or unsubstituted carbonyl group, or a substituted boryl group.

In the exemplary embodiment, the compound M3 still more preferably has a monovalent or higher-valent residue derived from a structure represented by a formula (3-100) below.

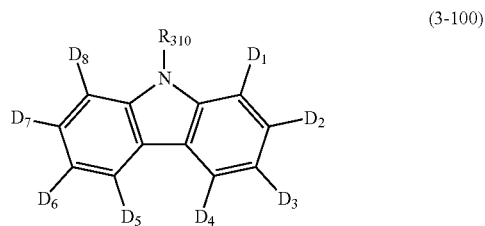

(3-100)

In the formula (3-100), $D_1$ to $D_8$ are deuterium atoms, $R_{310}$ is a substituent, and at least one of $D_1$ to $D_8$ or $R_{310}$ is a single bond bonded to another atom or another structure in the molecule of the compound M3, and $R_{310}$ serving as a substituent represents the same as $R_{311}$ in the formula (3-10).

In the formulae (3-10) and (3-100), $R_{310}$ and $R_{311}$ are preferably each independently a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, or a substituted or unsubstituted alkyl halide group having 1 to 30 carbon atoms, more preferably a substituted or unsubstituted aryl group having 6 to 30 ring carbon atoms or a substituted or unsubstituted alkyl group having 1 to 30 carbon atoms, and still more preferably a substituted or unsubstituted aryl group having 6 to 30 ring carbon atoms.

In the formulae (3-10) and (3-100), when $R_{310}$ and $R_{311}$ are hydrogen atoms, $R_{310}$ and $R_{311}$ are preferably deuterium atoms.

Compound M3 Represented by Formula (301) or (302)

In the exemplary embodiment, the compound M3 is also preferably a compound represented by a formula (301) or (302) below.

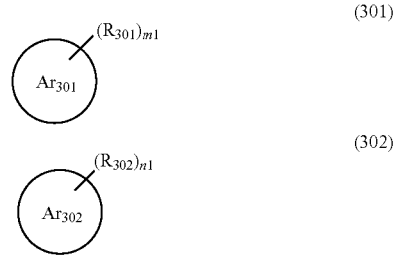

(301)

(302)

In the formula (301), $Ar_{301}$ is a substituted or unsubstituted aromatic hydrocarbon ring having 6 to 30 ring carbon atoms, or a substituted or unsubstituted heterocycle having 5 to 30 ring atoms; m1 is 1, 2, 3, 4, 5, or 6; each $R_{301}$ is an electron-donating group, and each $R_{301}$ is bonded to an element forming $Ar_{301}$; when m1 is 2 or more, a plurality of $R_{301}$ are mutually the same or different; and $Ar_{301}$ is not an electron-accepting aromatic hydrocarbon ring or heterocycle, and when $Ar_{301}$ has a substituent, the substituent is not an electron-accepting group.

In the formula (302), $Ar_{302}$ is a substituted or unsubstituted aromatic hydrocarbon ring having 6 to 30 ring carbon atoms, or a substituted or unsubstituted heterocycle having 5 to 30 ring atoms; n1 is 1, 2, 3, 4, 5, or 6; each $R_{302}$ is an electron-accepting group, and each $R_{302}$ is bonded to an element forming $Ar_{302}$; when n1 is 2 or more, a plurality of $R_{302}$ are mutually the same or different; and $Ar_{302}$ is not an electron-donating aromatic hydrocarbon ring or heterocycle, and when $Ar_{302}$ has a substituent, the substituent is not an electron-donating group.

In the formulae (301) and (302), $Ar_{301}$ and $Ar_{302}$ are preferably each independently a monovalent or higher-valent residue derived from any of compounds represented by formulae (A1) to (A3) below.

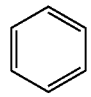

(A1)

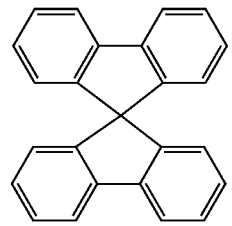

(A2)

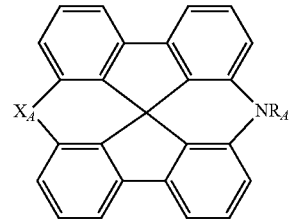

(A3)

In the formulae (A1) to (A3), $X_A$ is an oxygen atom or a sulfur atom, and RA is a hydrogen atom or a substituent.

In the formula (A3), when $R_A$ is a substituent, the substituent may be, for example, the same group as $R_{31}$ in the formula (31).

In the formula (301), each $R_{301}$ serving as an electron-donating group is preferably independently a monovalent or higher-valent residue derived from any of compounds represented by formulae (D1) to (D6) and (D8) to (D10) below, or a group represented by a formula (D7) below.

In the formula (302), each $R_{302}$ serving as an electron-accepting group is preferably independently a monovalent or higher-valent residue derived from any of compounds represented by formulae (A4) to (A18), (A22) and (A23) below, or any of groups represented by formulae (A1) to (A3), (A19) to (A21), and (A24) below.

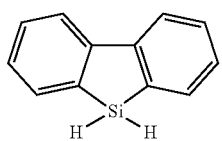 (D1)
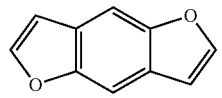 (D2)
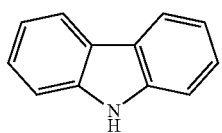 (D3)
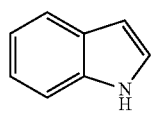 (D4)
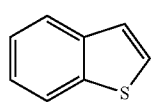 (D5)
 (D6)
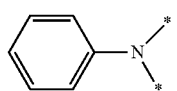 (D7)
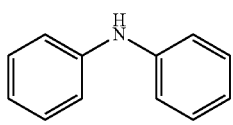 (D8)
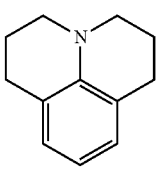 (D9)
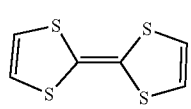 (D10)
In the formula (D7), each * represents a bonding portion to an element forming $Ar_{301}$.
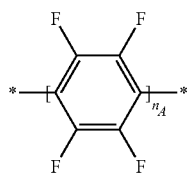 (A1)
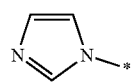 (A2)
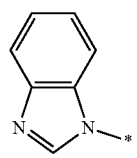 (A3)
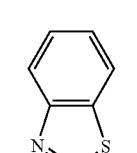 (A4)
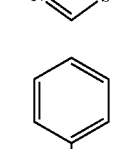 (A5)
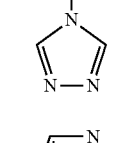 (A6)
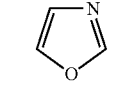 (A7)
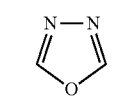 (A8)
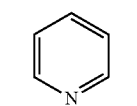 (A9)
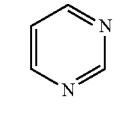 (A10)
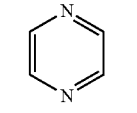 (A11)
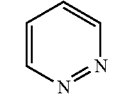 (A12)
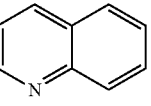 (A13)

(A14) 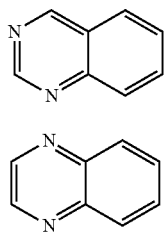

(A15) 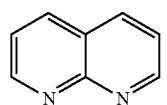

(A16) 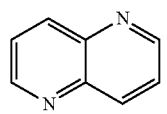

(A17) 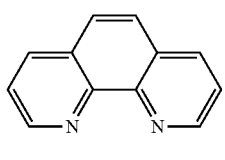

(A18) 

(A19) 

(A20) 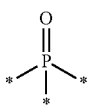

(A21) 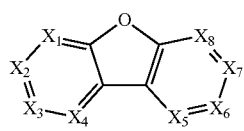

(A22) 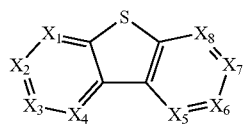

(A23)

(A24) 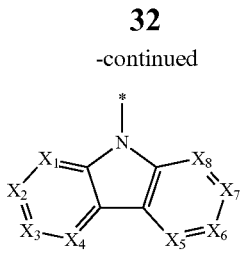

In the formula (A1), $n_A$ is 1, 2, or 3.

In the formulae (A22) and (A23), $X_1$ to $X_8$ are each independently $CR_{320}$ or a carbon atom bonded to another atom or another structure in the molecule of the compound M3, each $R_{320}$ is independently a hydrogen atom or a substituent, or at least one pair of pairs of adjacent ones of $R_{320}$ are mutually bonded to form a ring, and at least one of carbon atoms in $X_1$ to $X_8$ is bonded to an element forming $Ar_{302}$.

In the formula (A24), $X_1$ to $X_8$ are each independently a nitrogen atom, $CR_{320}$, or a carbon atom bonded to an element forming $Ar_{302}$, and each $R_{320}$ is independently a hydrogen atom or a substituent, or at least one pair of pairs of adjacent ones of $R_{320}$ are mutually bonded to form a ring.

In the formulae (A1) to (A3), (A19) to (A21), and (A24), each * represents a bonding portion to an element forming $Ar_{302}$.

$R_{320}$ in the formulae (A1) to (A3) represents the same as $R_{31}$ in the formula (31).

Manufacturing Method of Compound M3 (Deuterated Compound M3) According to Exemplary Embodiment The compound M3 can be manufactured by a publicly known method.

The compound M3 can be manufactured by, for example, the following method.

A compound (non-deuterated compound m3) in which all hydrogen atoms included in the compound M3 are protium atoms is first prepared by well-known coupling and substitution reactions. Subsequently, a deuterated precursor substance is used, or more generally, the non-deuterated compound m3 is treated with a deuterated solvent (such as d6-benzene) in the presence of a Lewis acid H/D exchange catalyst (such as aluminum trichloride or ethyl aluminum chloride).

The compound M3 can also be manufactured in accordance with the reactions described in Examples below using known alternative reactions and raw materials according to the target compound.

Specific Examples of Compound M3

Specific examples of the compound M3 of the exemplary embodiment include compounds below. It should however be noted that the invention is not limited to the specific examples of the compound.

In some of the specific examples of the compound M3, hydrogen atoms are omitted.

Specific examples of the compound M3 in which hydrogen atoms are omitted will be described.

For example, in the case where a specific example of the compound M3 is a compound represented by (M3-1) below, the compound is represented by a formula (M3-11) below when shown without omitting hydrogen atoms.

In the formula (M3-11) below, "HD" each represent a protium atom or a deuterium atom, and at least one of the plurality of "HD" is a deuterium atom.

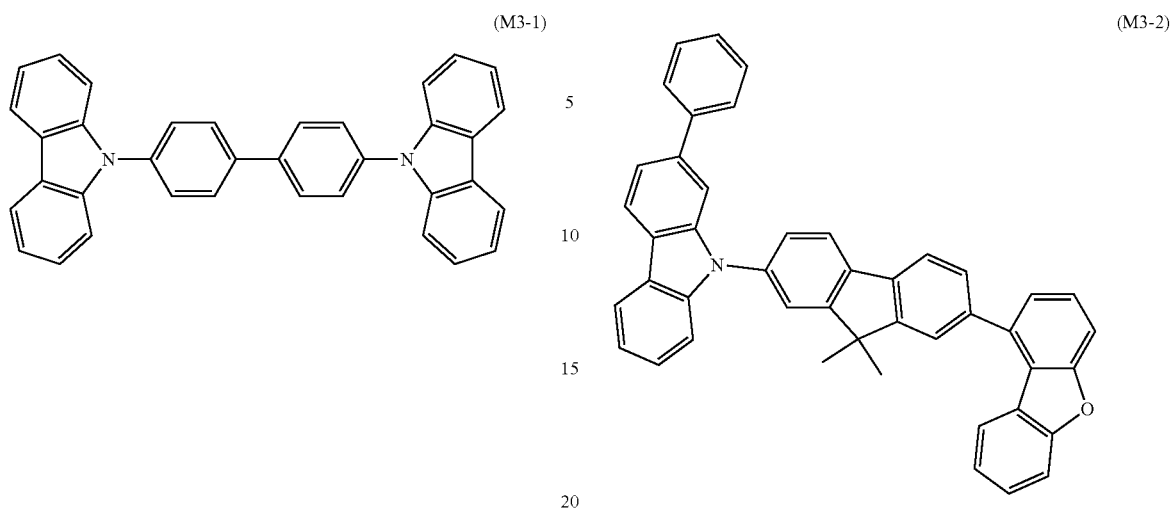

(M3-1) (M3-2)

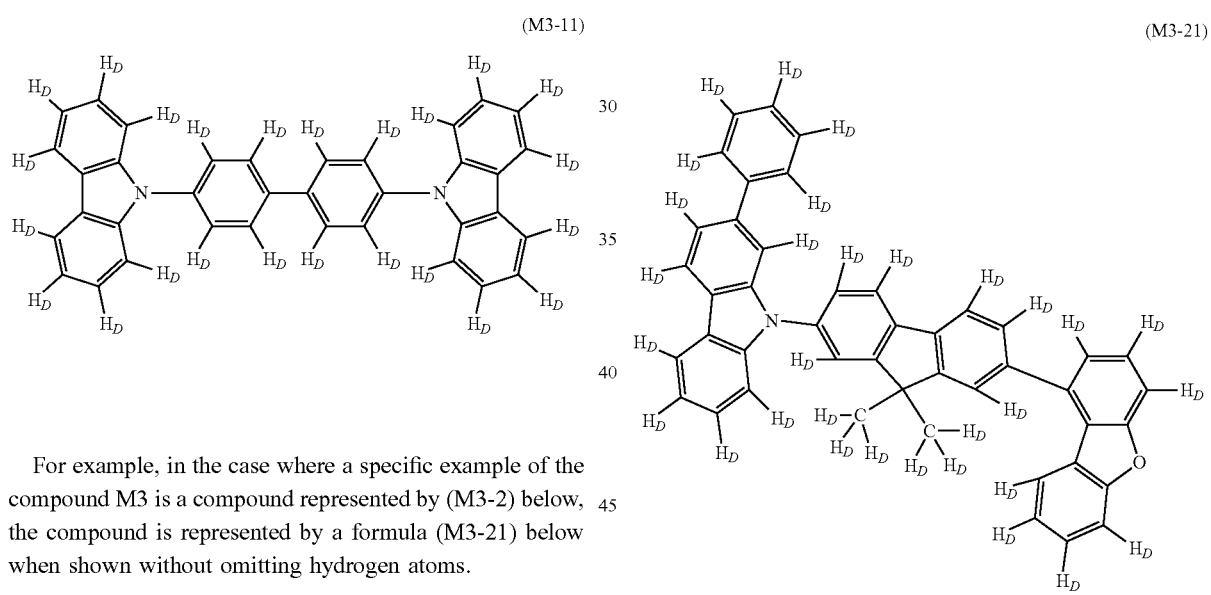

(M3-11) (M3-21)

For example, in the case where a specific example of the compound M3 is a compound represented by (M3-2) below, the compound is represented by a formula (M3-21) below when shown without omitting hydrogen atoms.

In the formula (M3-21) below, "HD" each represent a protium atom or a deuterium atom, and at least one of the plurality of "HD" is a deuterium atom.

The following specific examples of the compound M3 are specific examples in which hydrogen atoms are omitted.

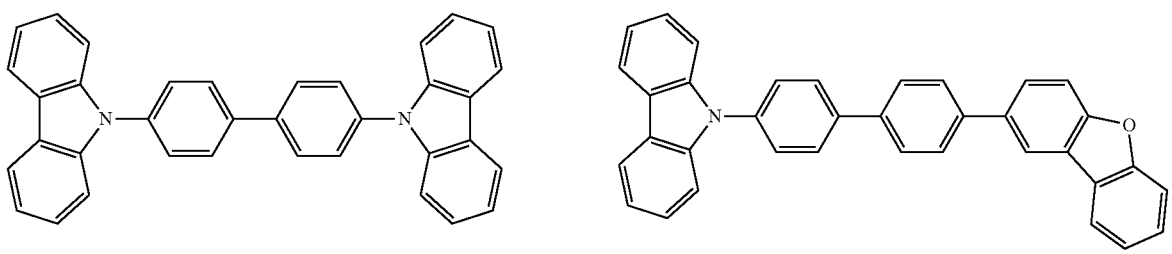

-continued
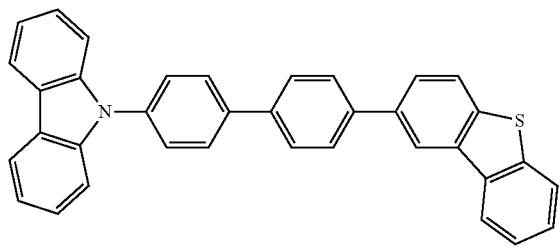
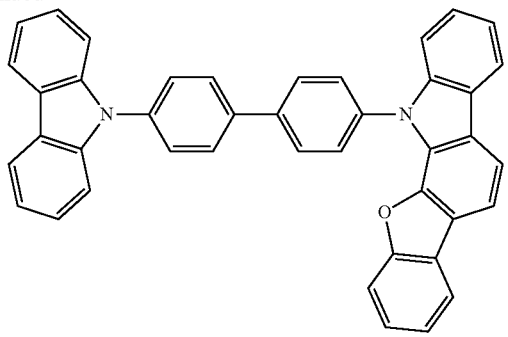
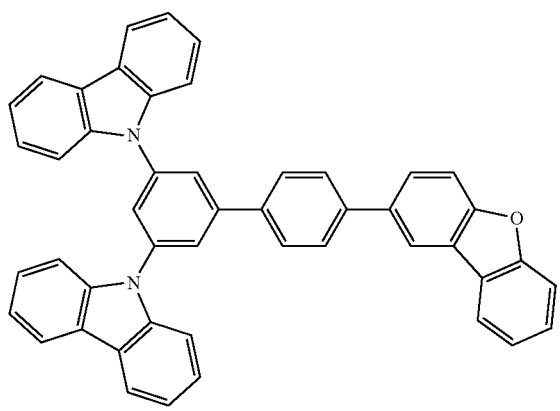
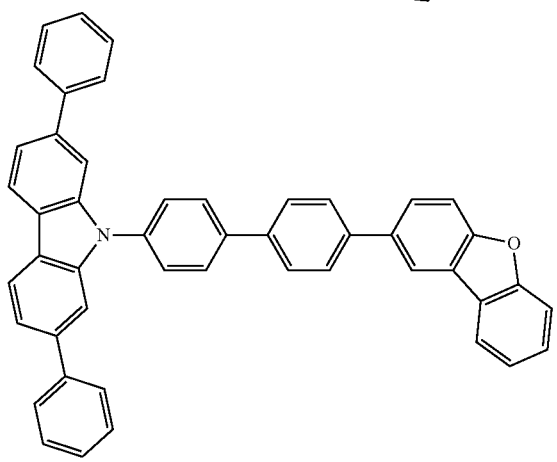
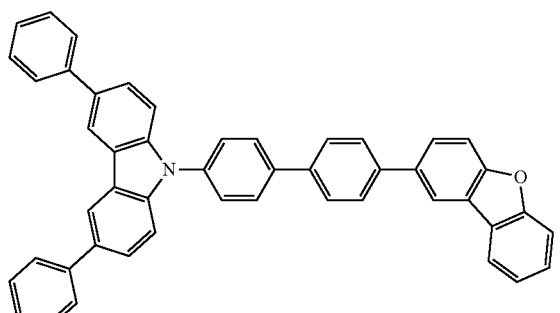
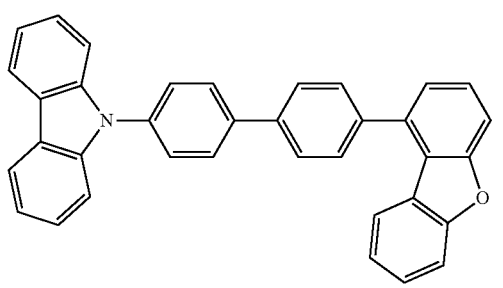
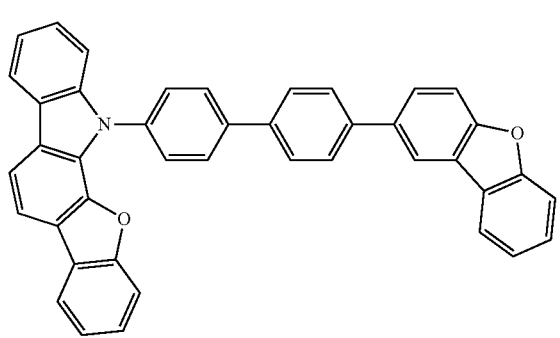
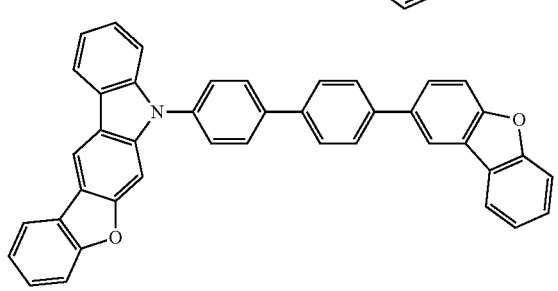

-continued
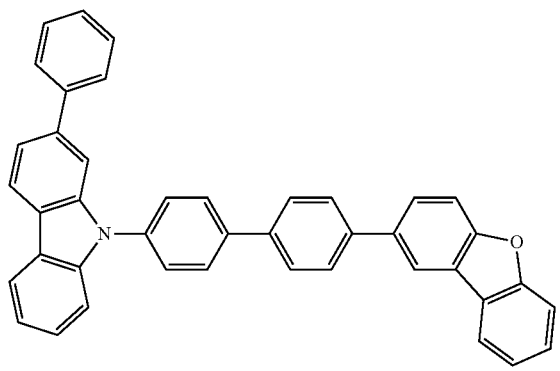
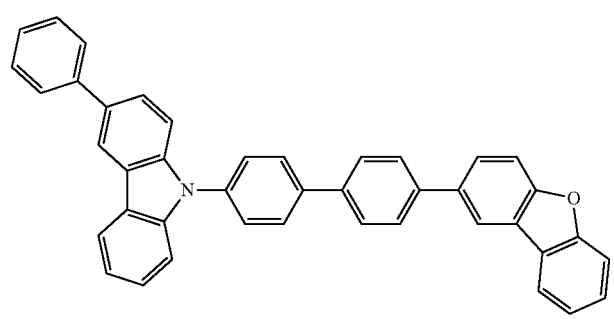
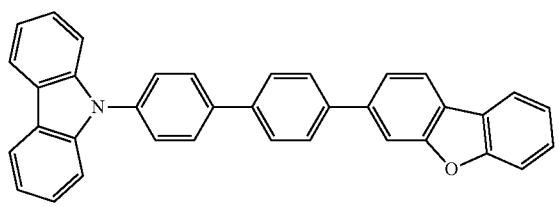
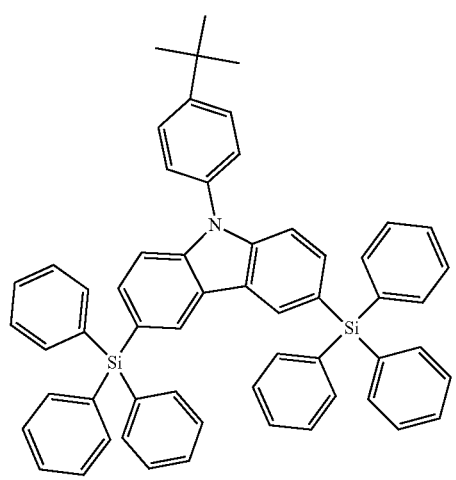
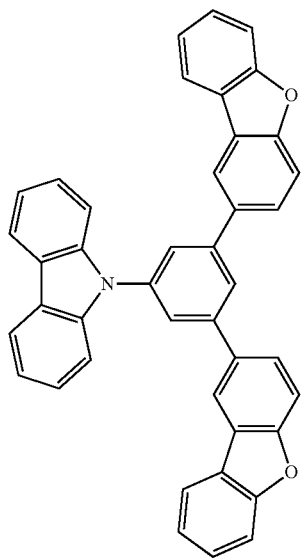
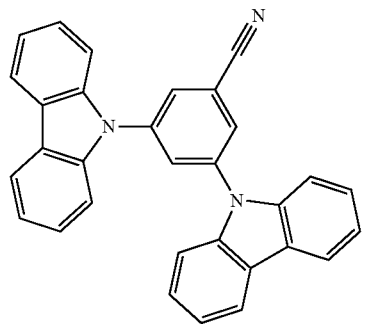

-continued
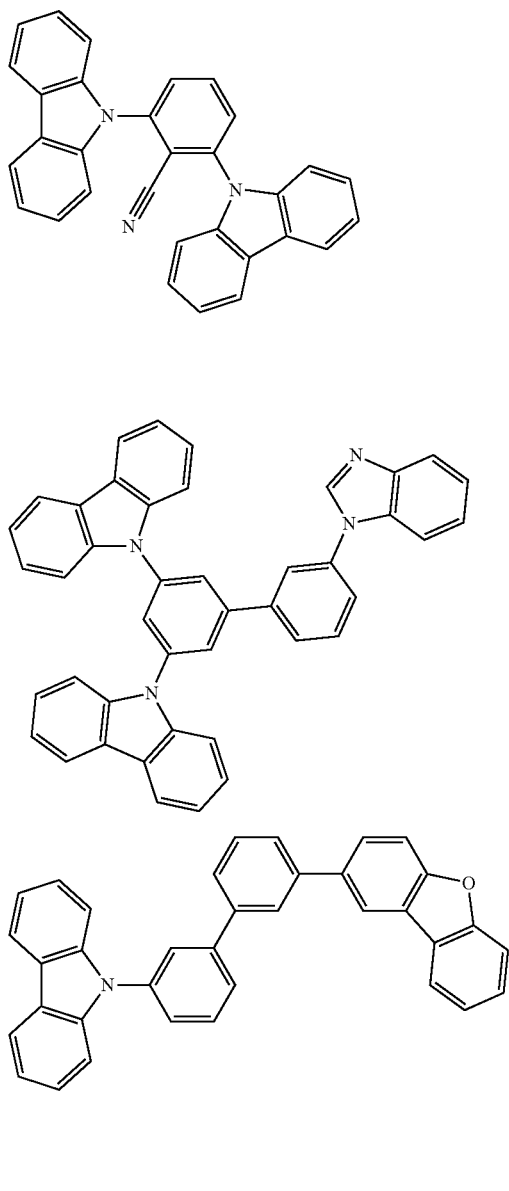
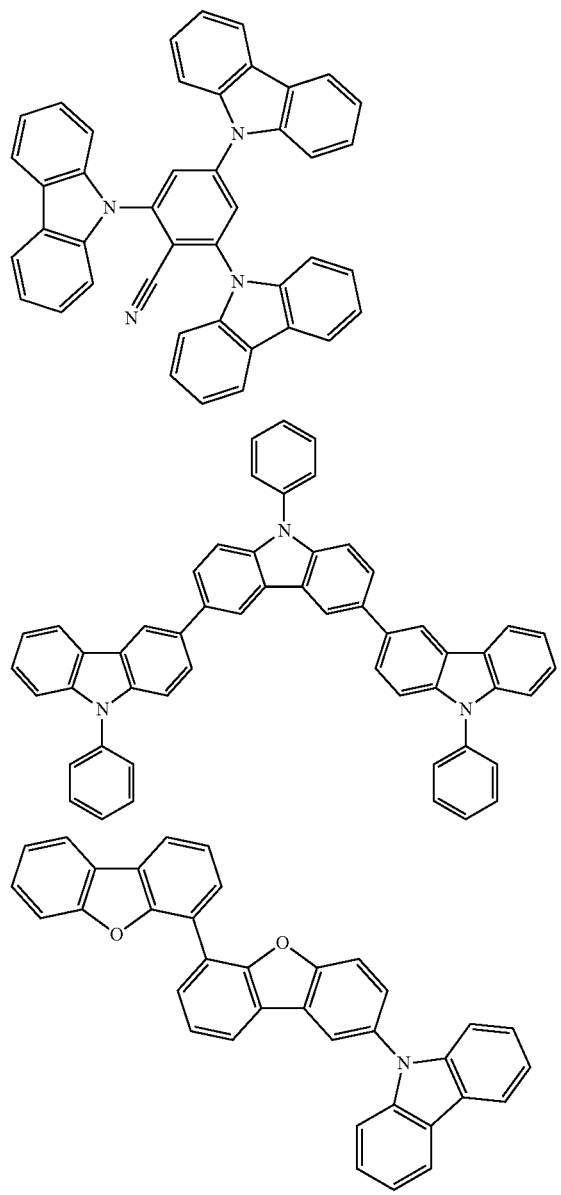
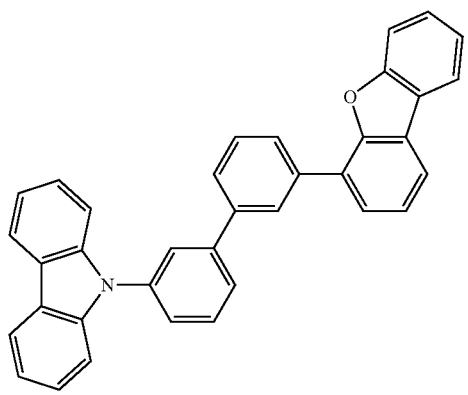
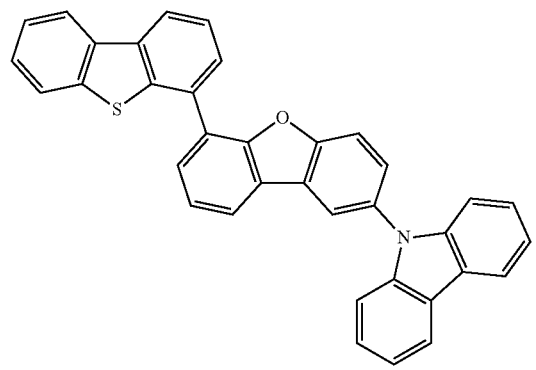

-continued
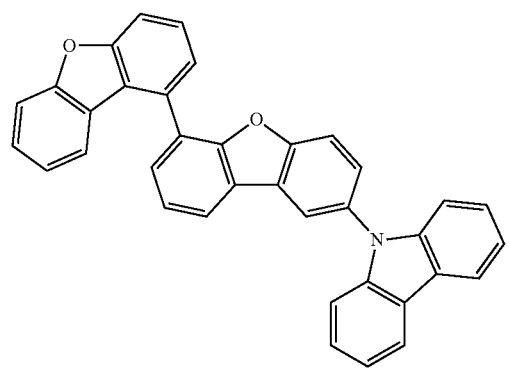
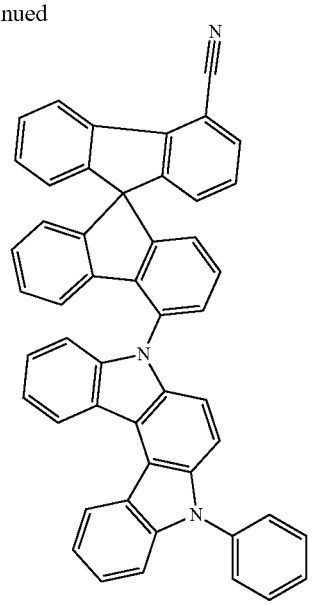
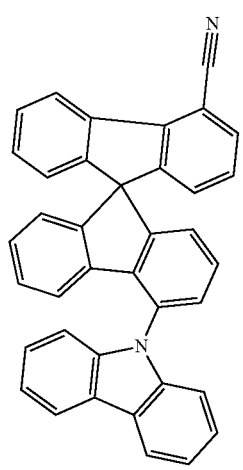
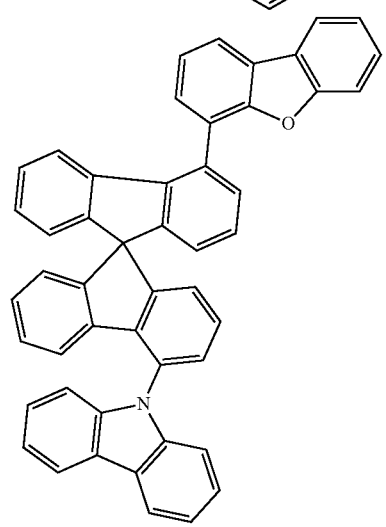
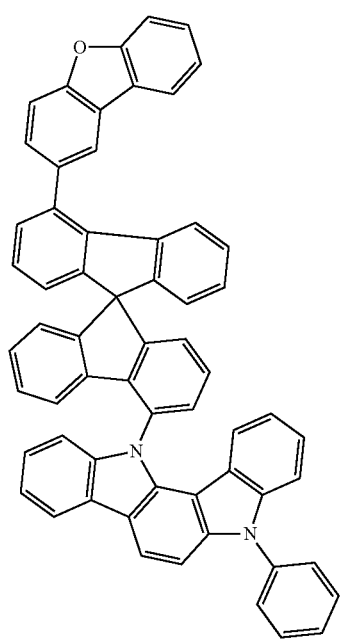
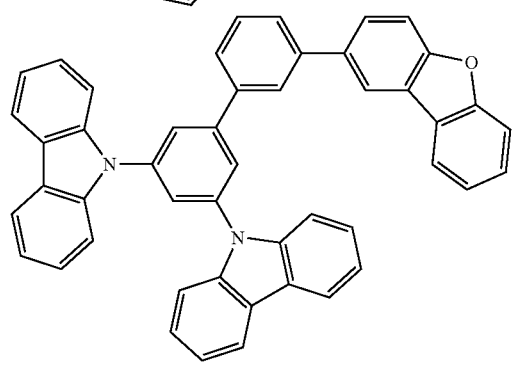

-continued
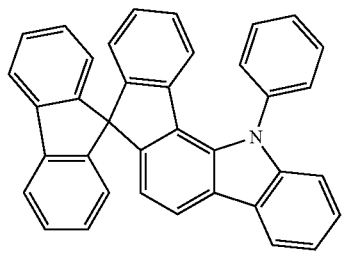
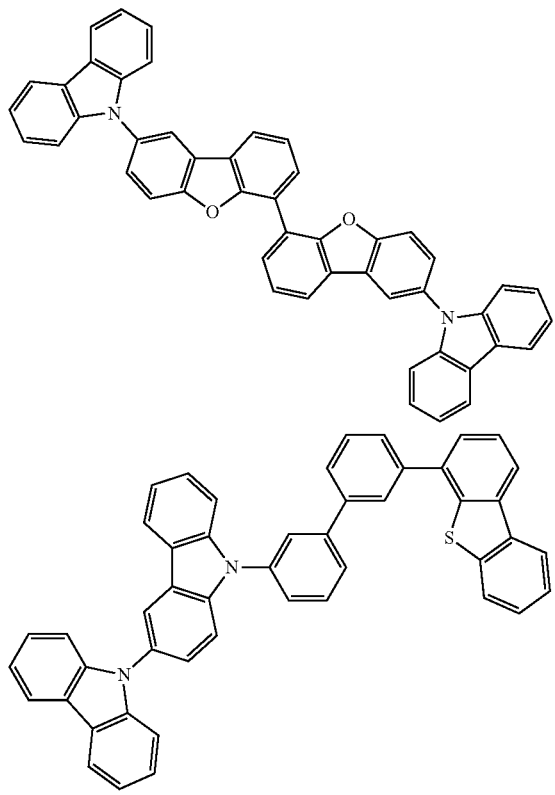
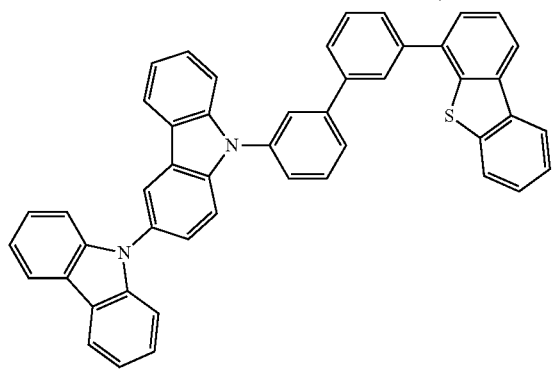
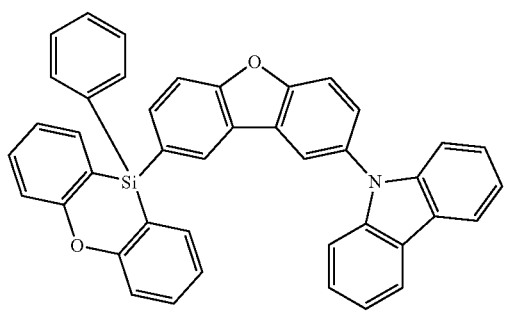
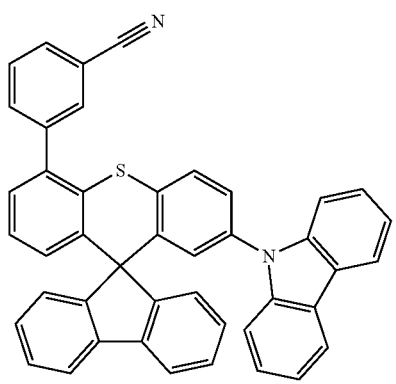
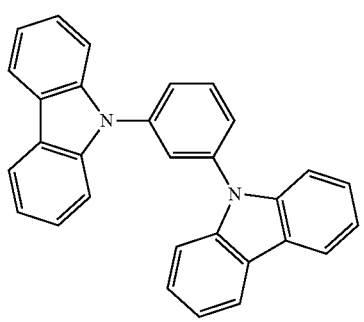
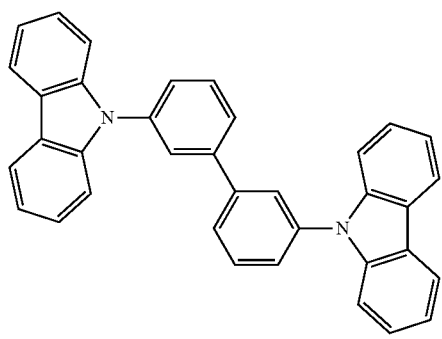
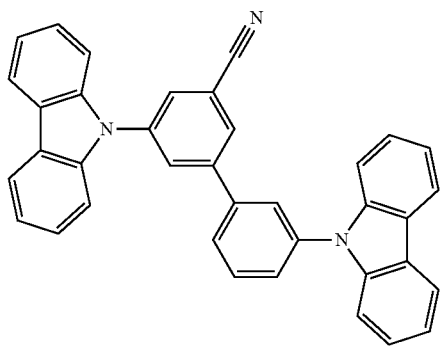

-continued
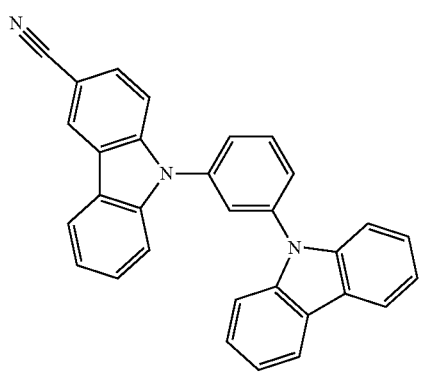
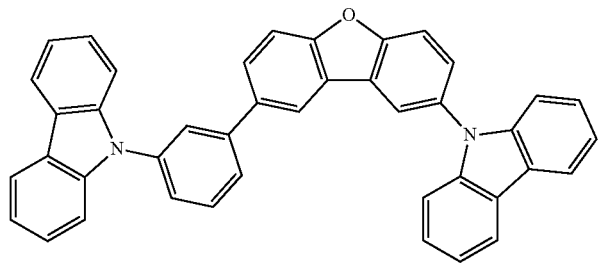
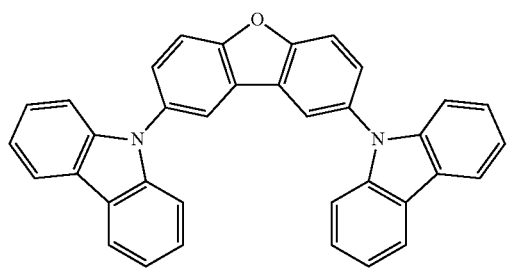
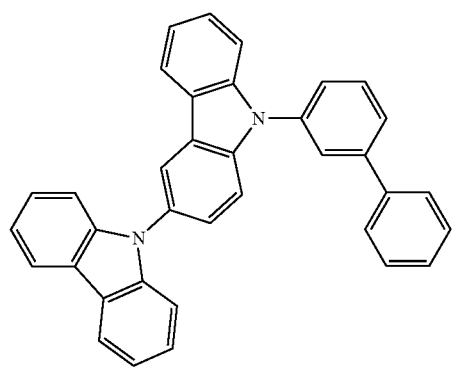
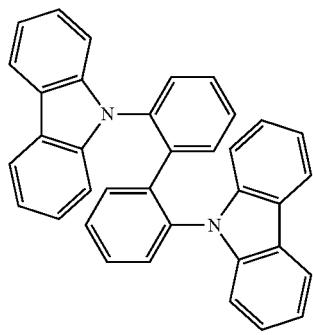
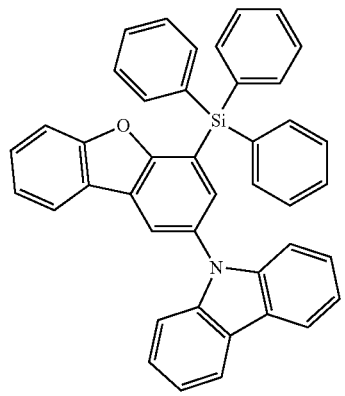
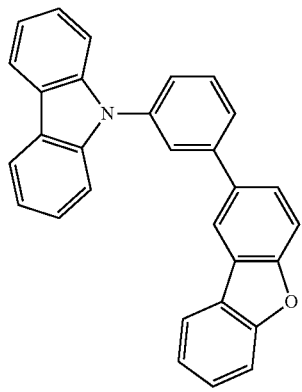
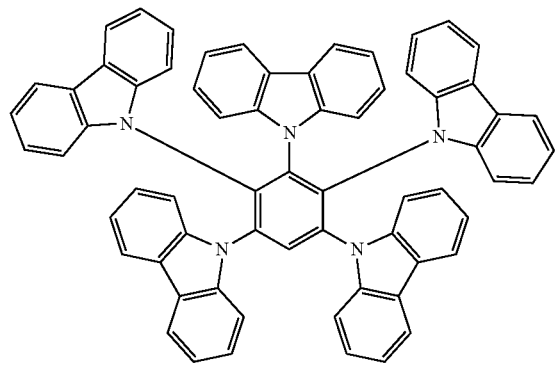

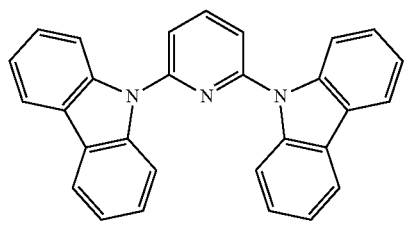
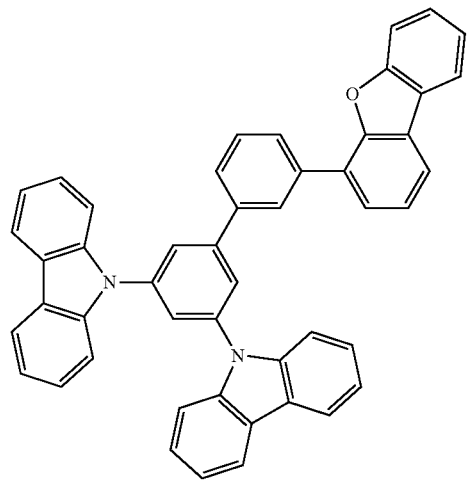
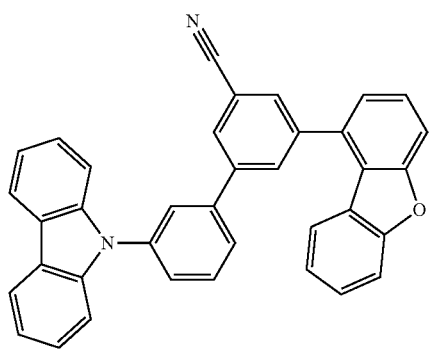
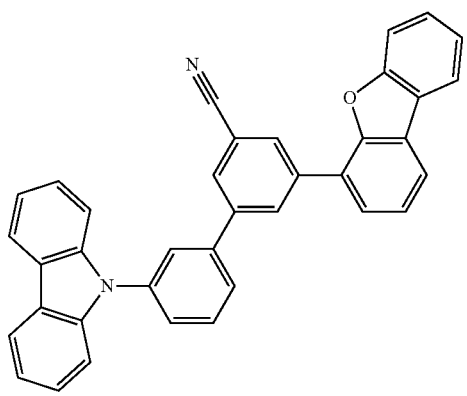
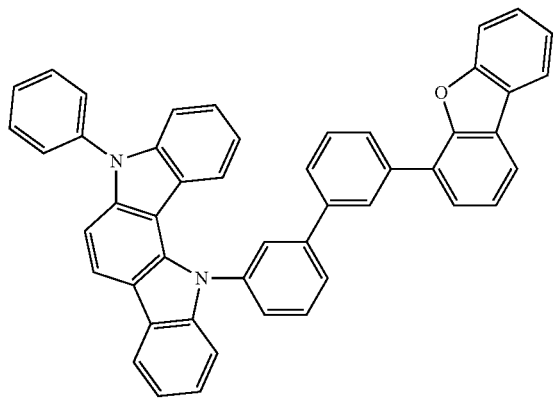
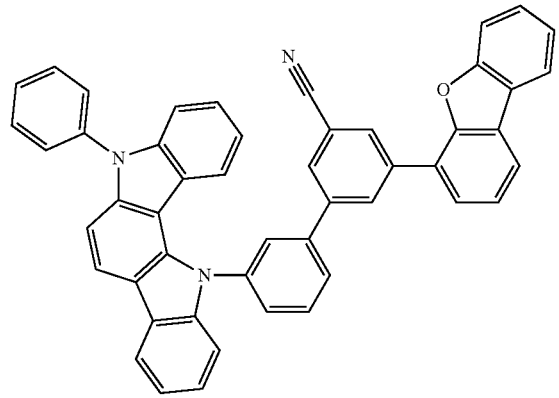
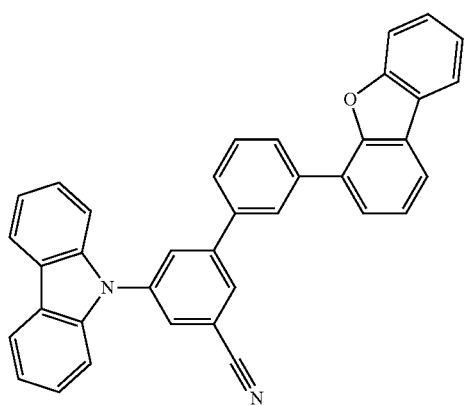
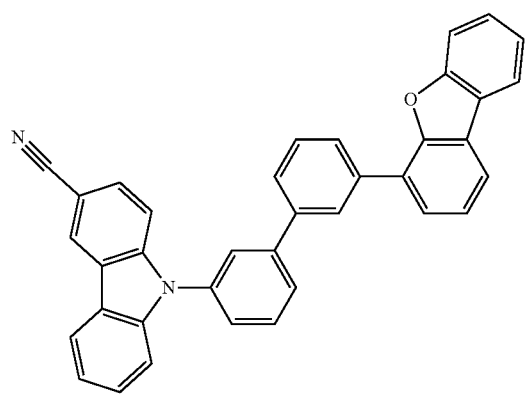

-continued
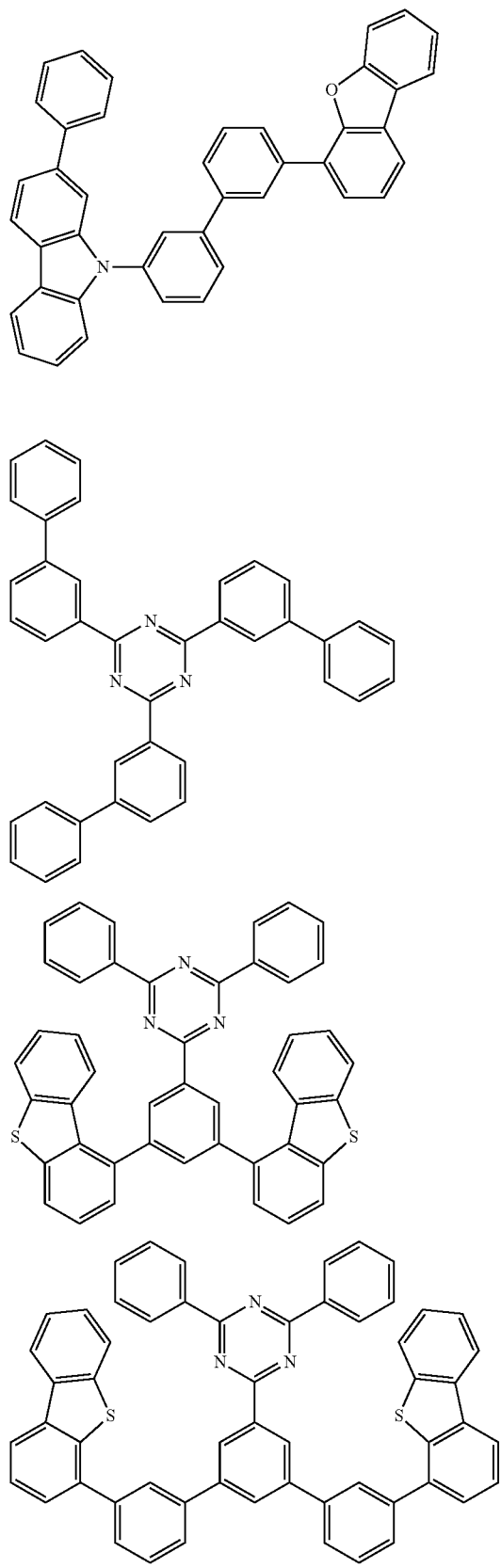
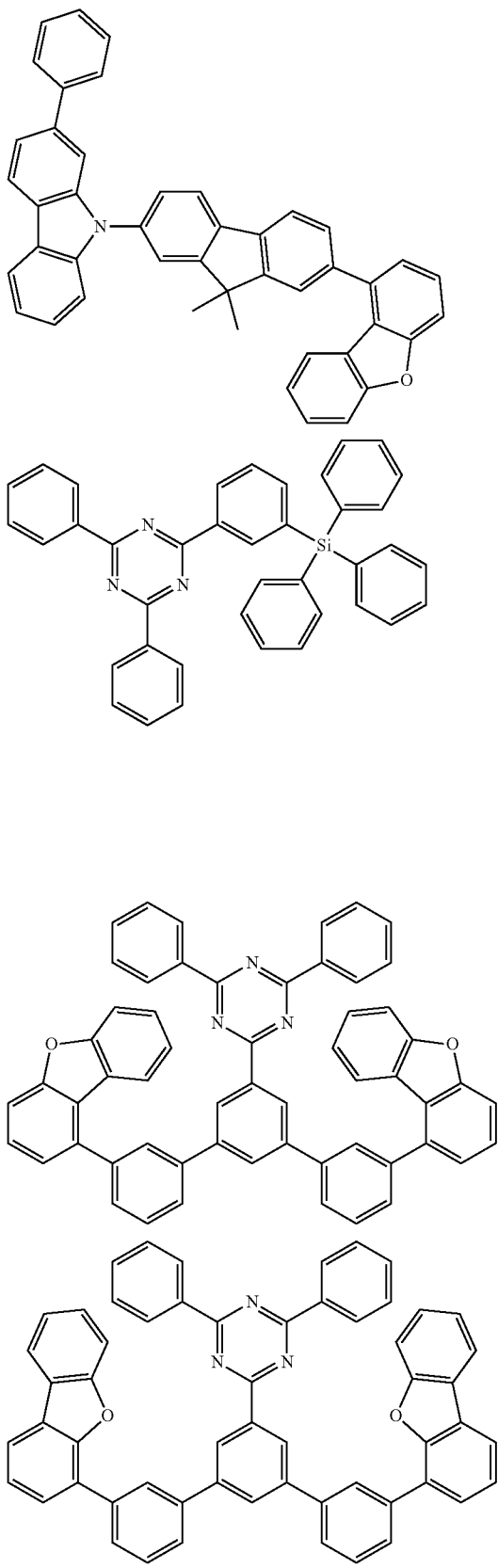

51
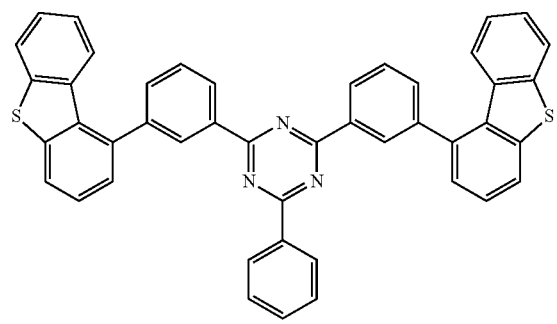
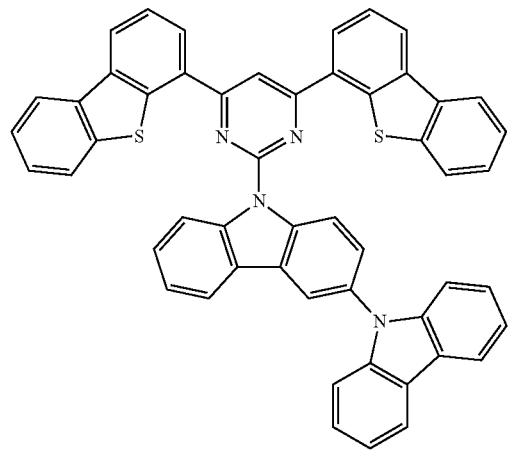
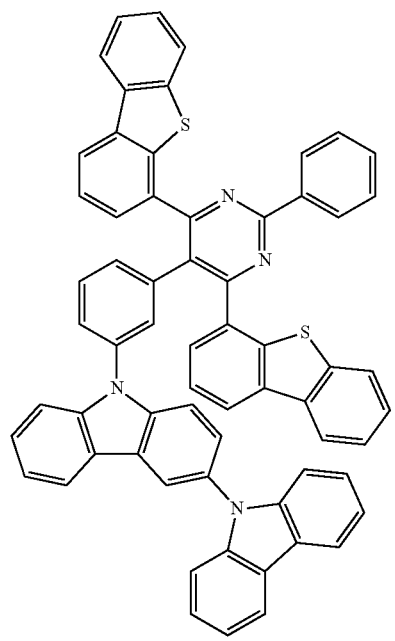
52
-continued
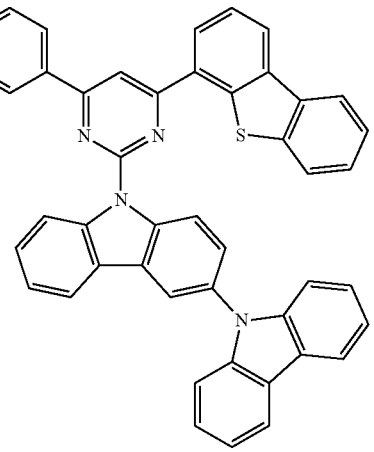
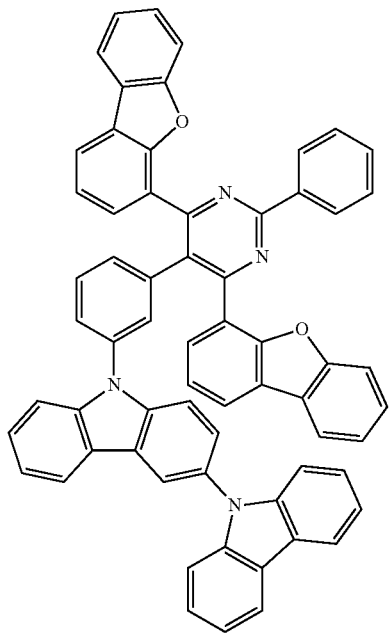
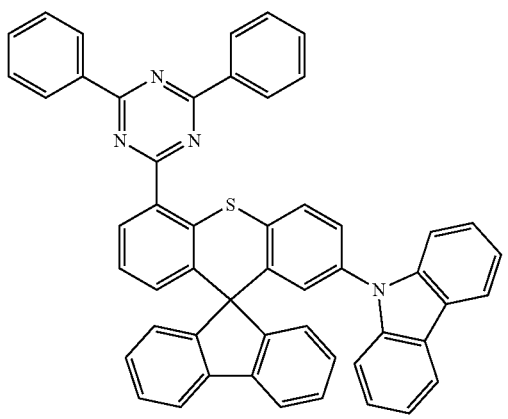

-continued
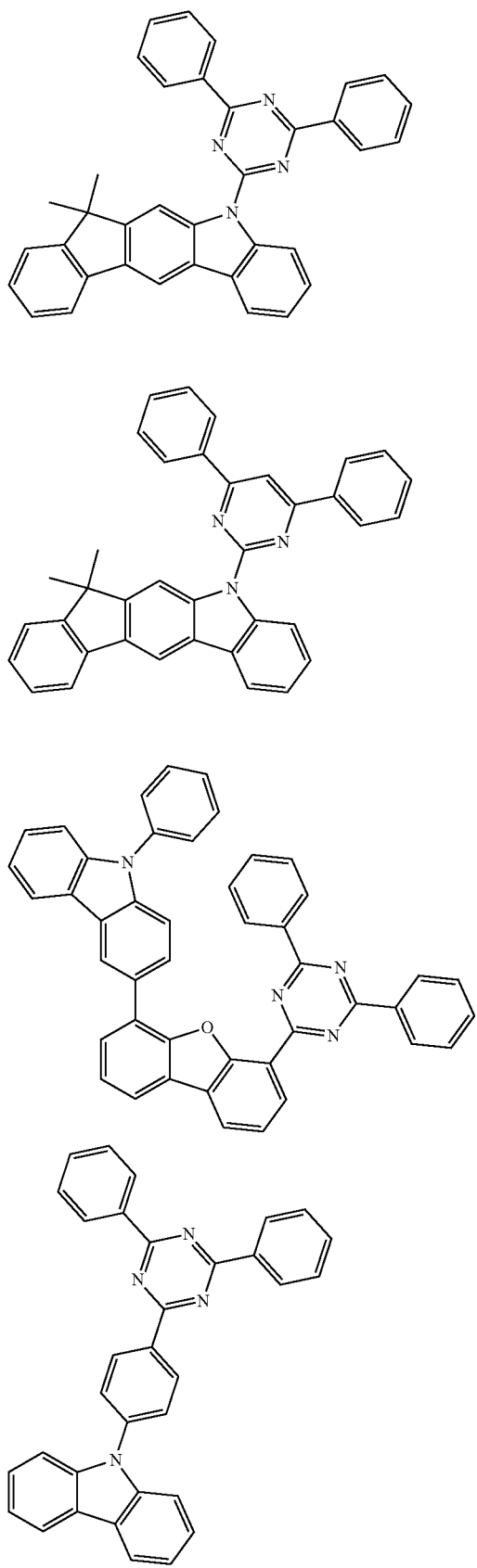
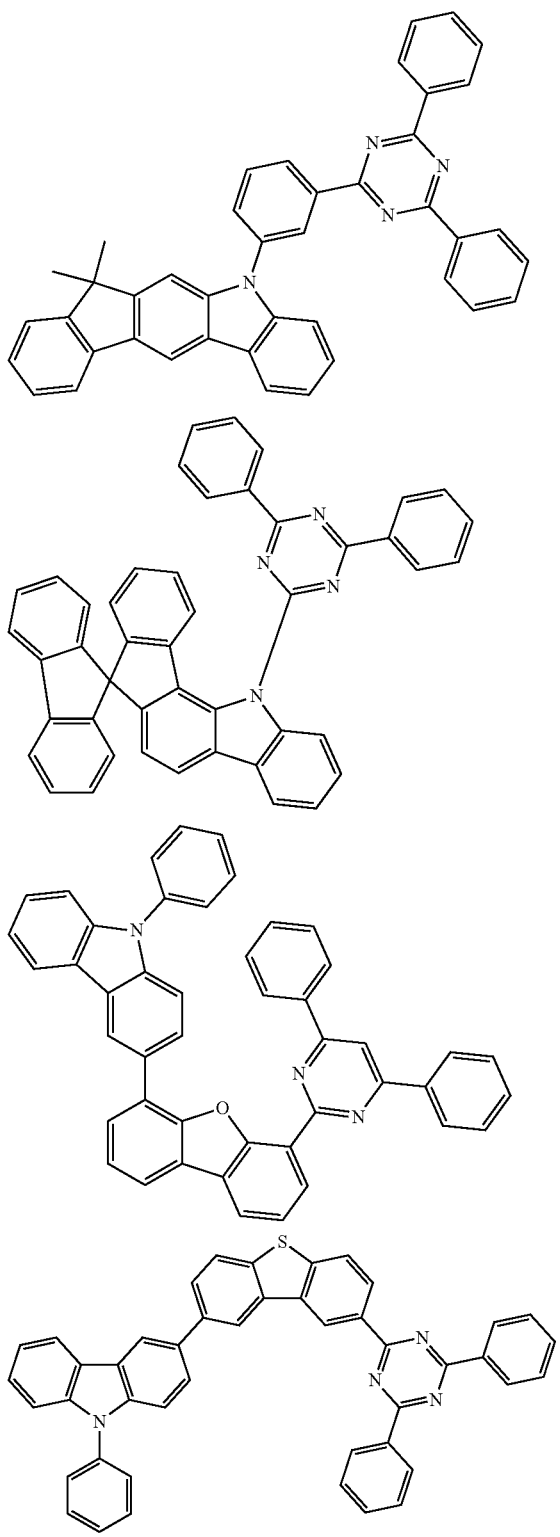

-continued
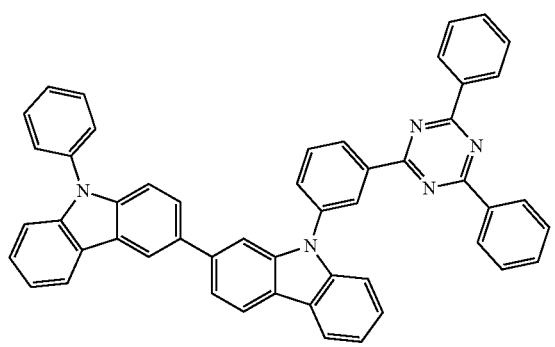
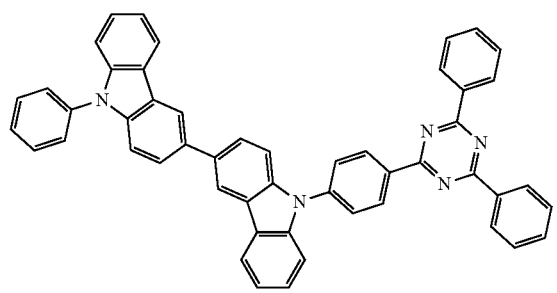
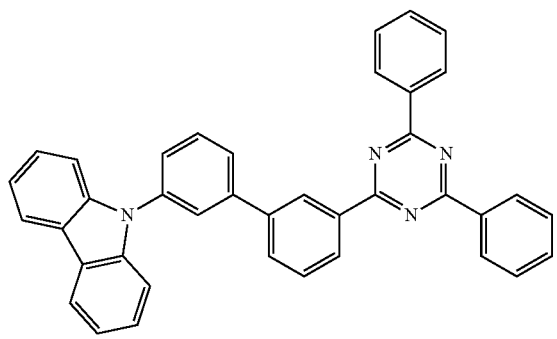
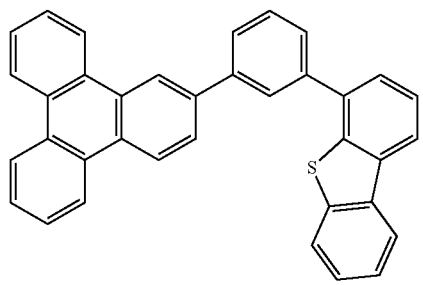
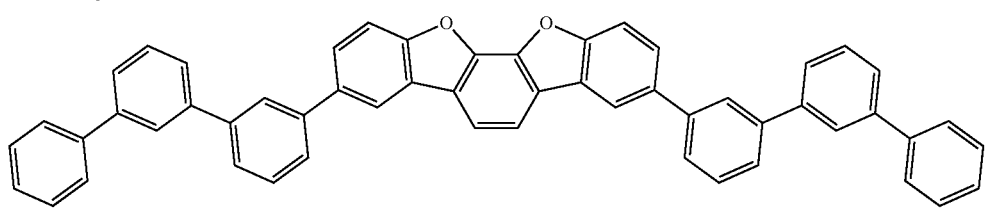
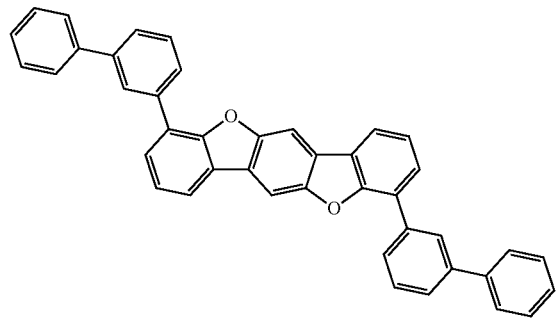
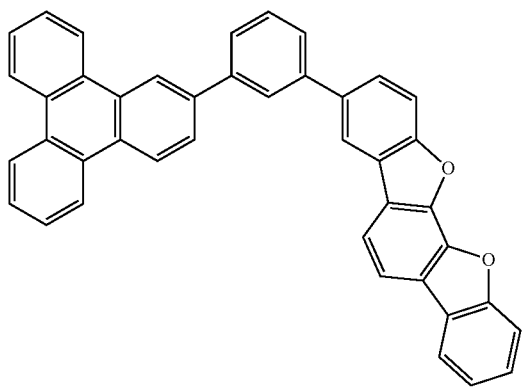
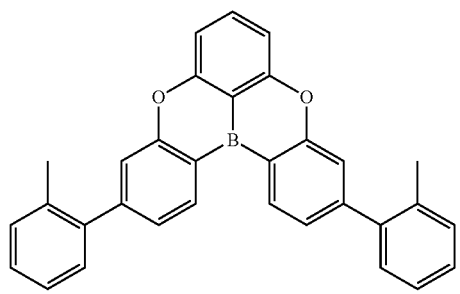

-continued
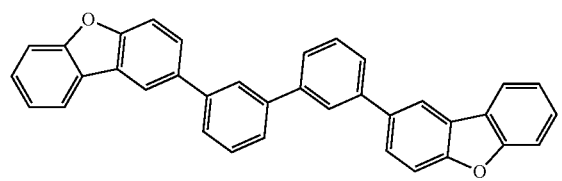
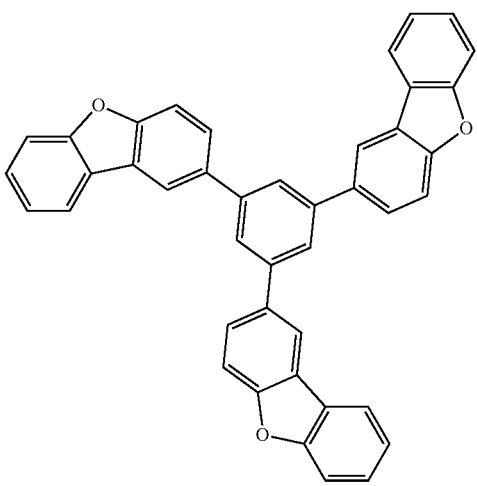
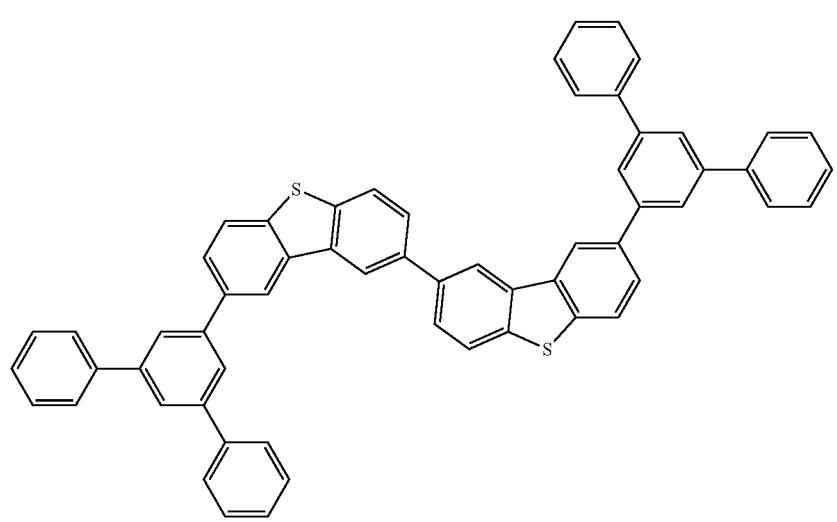
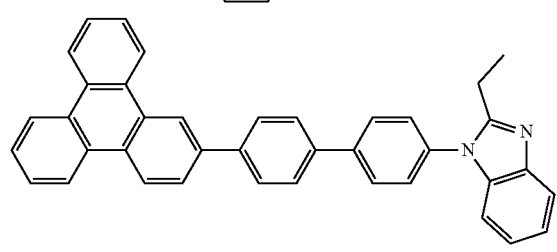
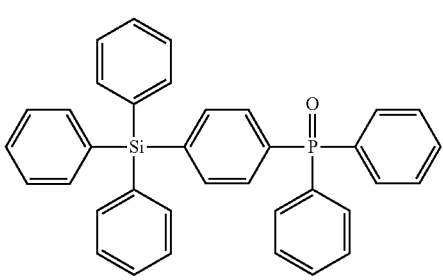
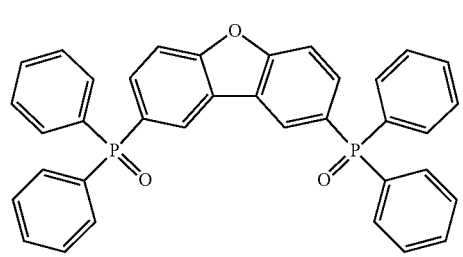
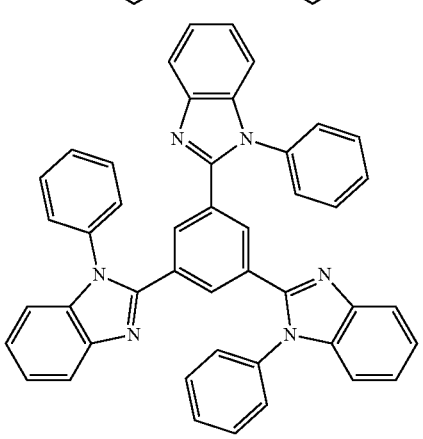

-continued
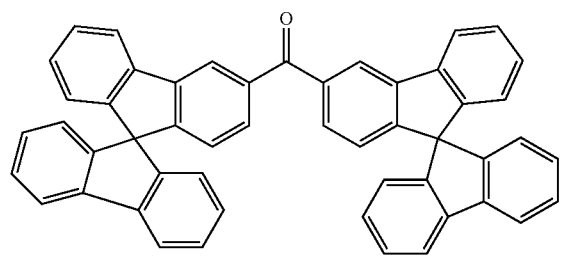
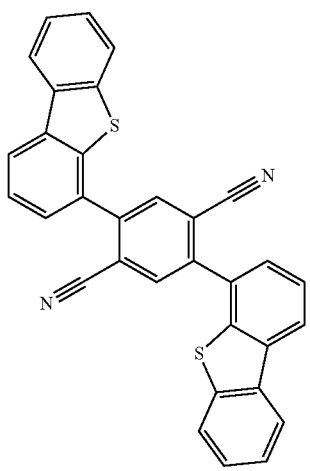
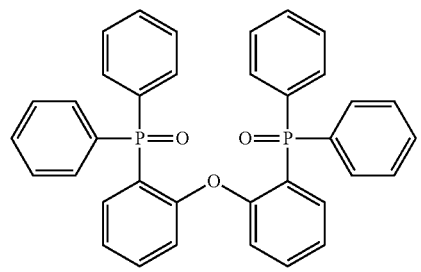
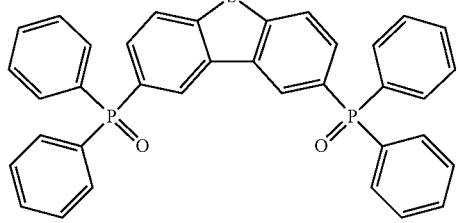
H-1      H-2
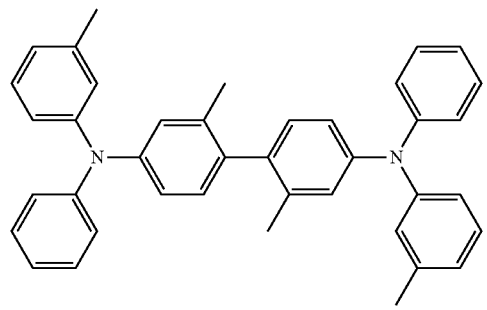
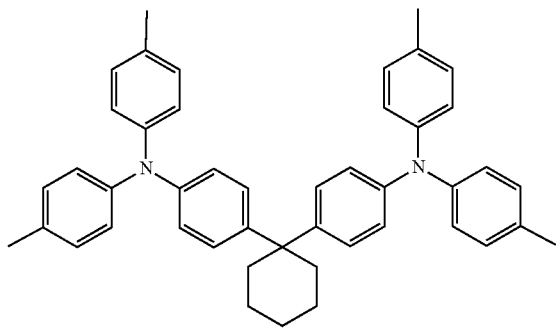
H-3      H-4
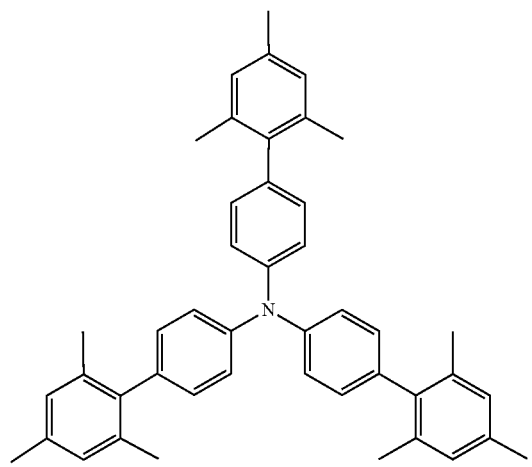
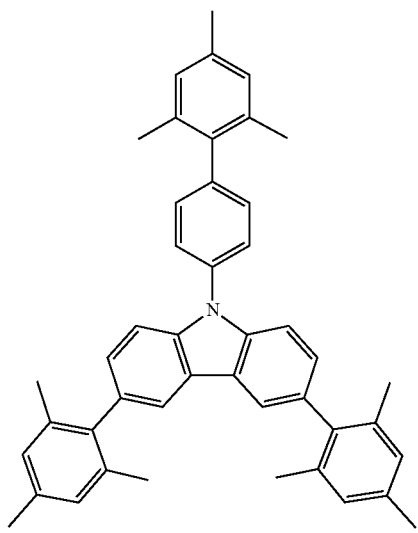

-continued
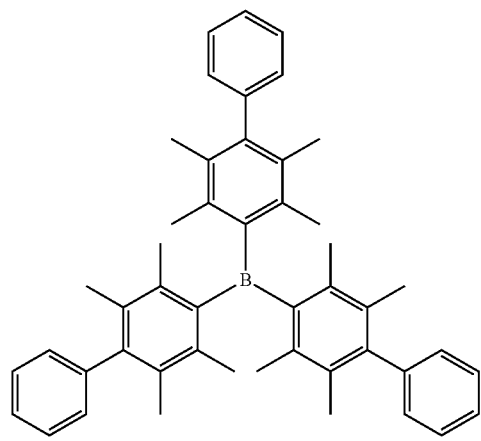
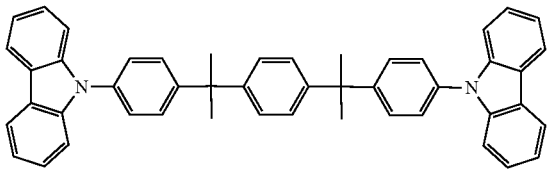
H-5
H-6
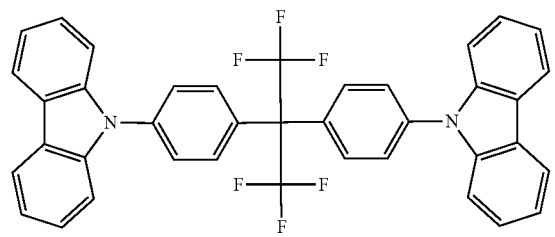
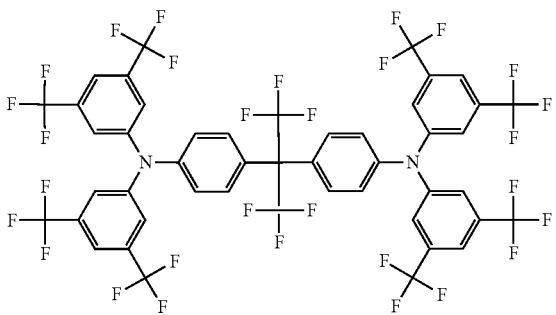
H-7
H-8
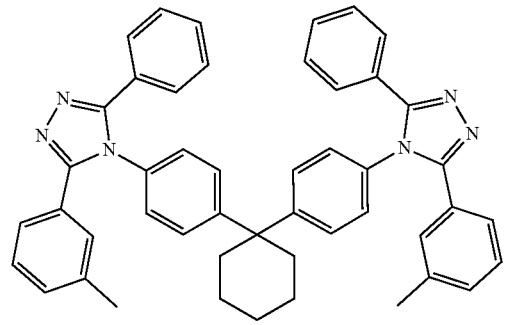
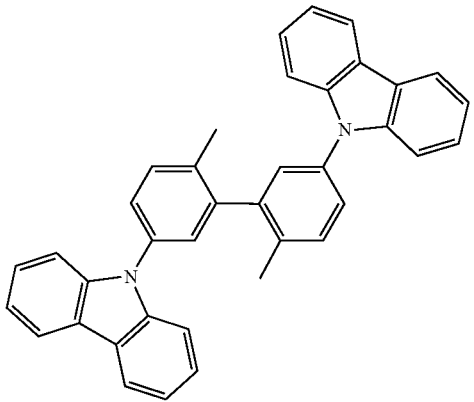
H-9
H-10
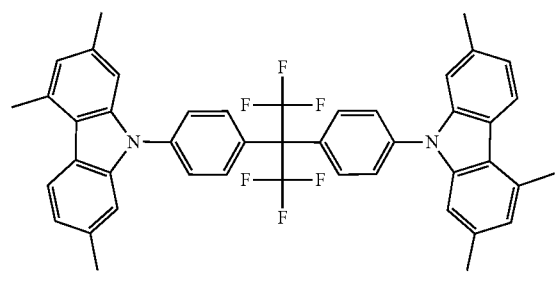
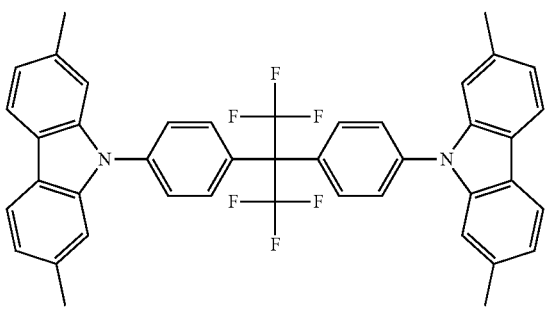
H-11
H-12

-continued
H-13
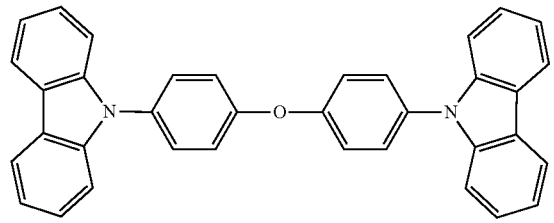
H-14
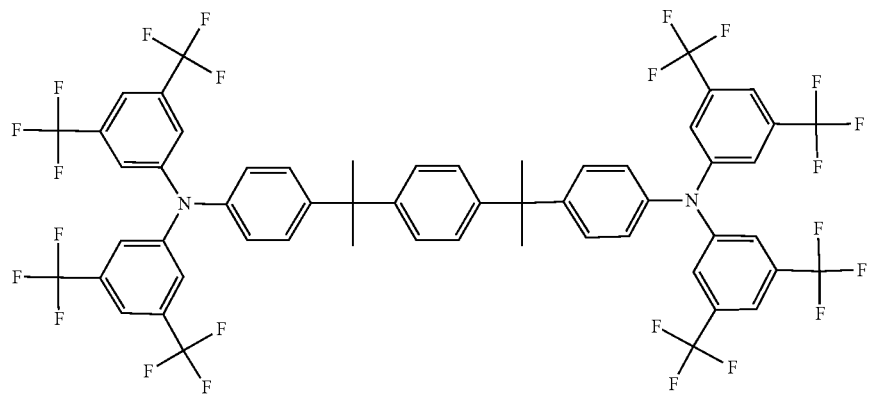
H-15
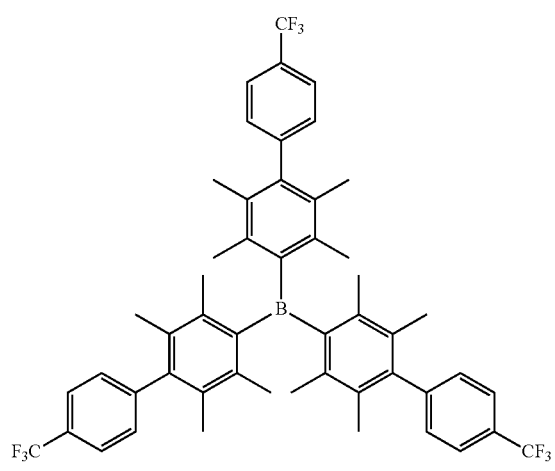
H-16
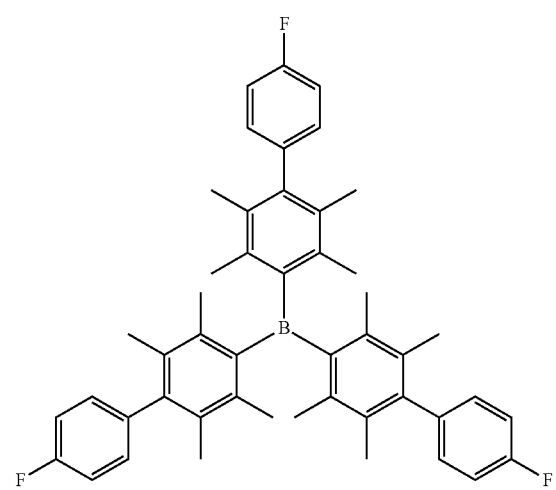
H-17
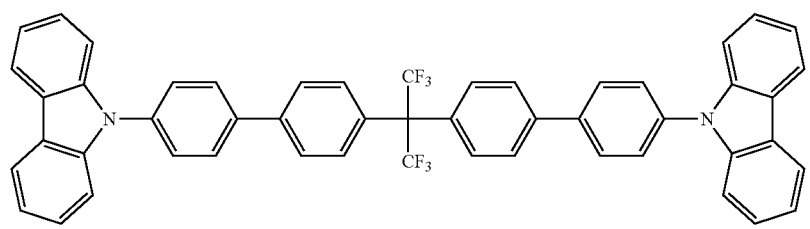

-continued
H-18
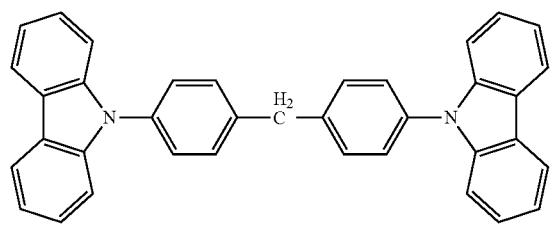
H-19
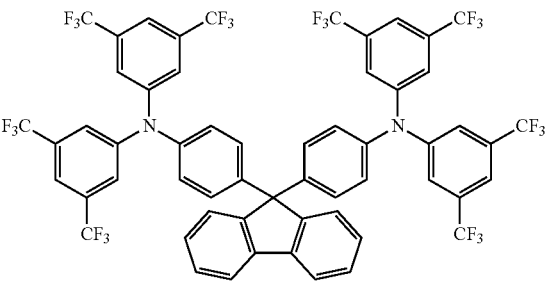
H-20
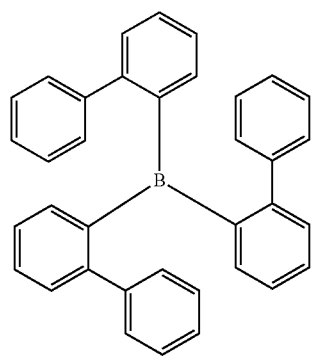
H-23
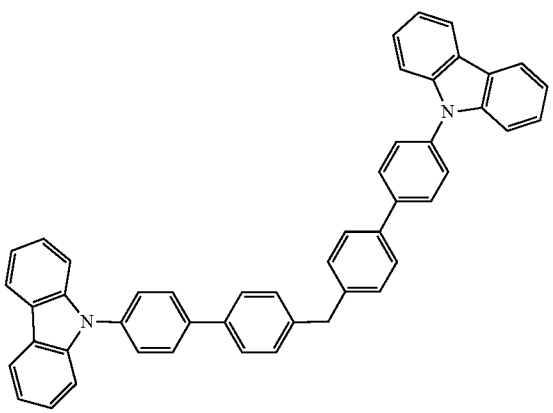
H-26
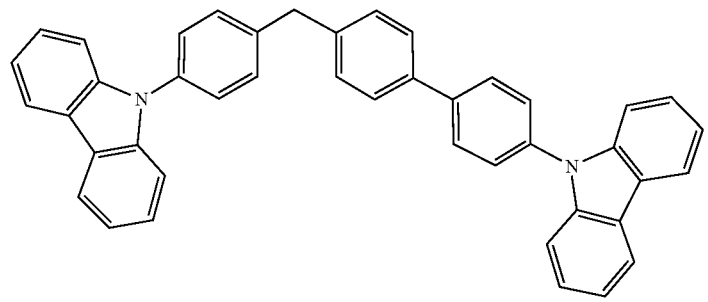
H-24
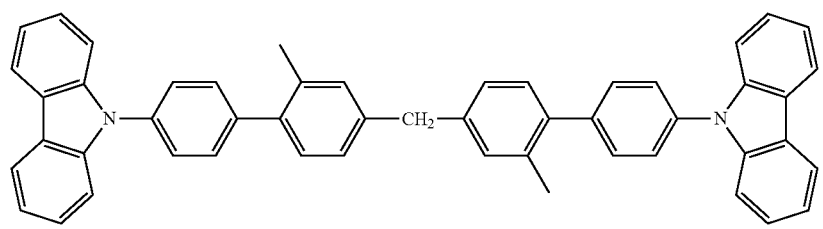

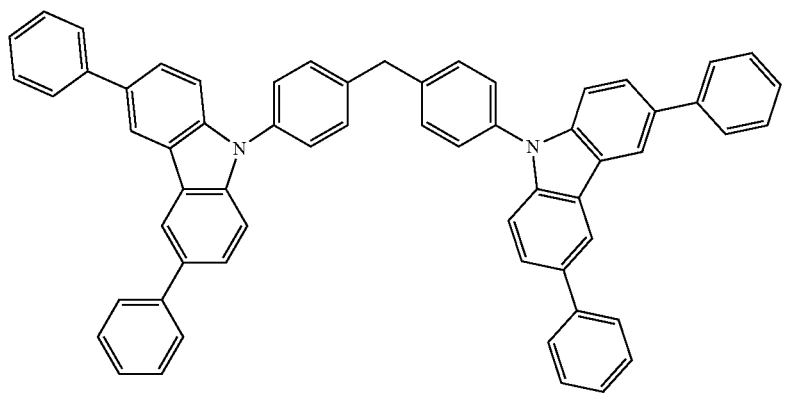
H-31
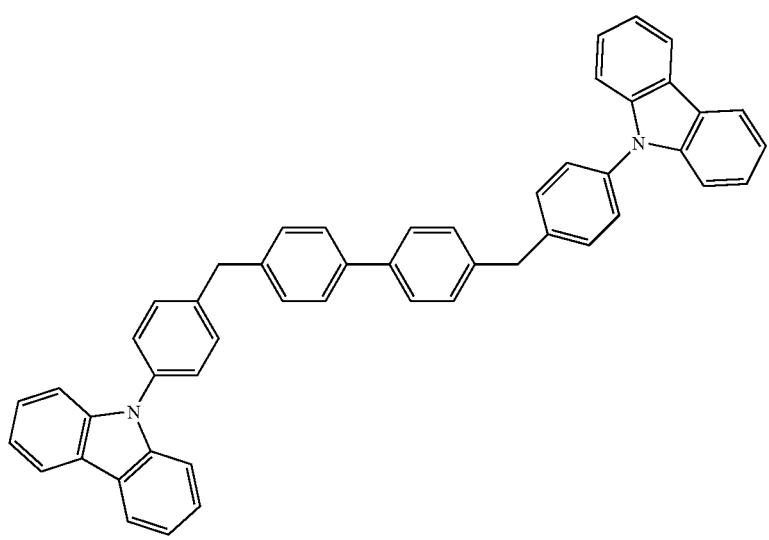
H-34
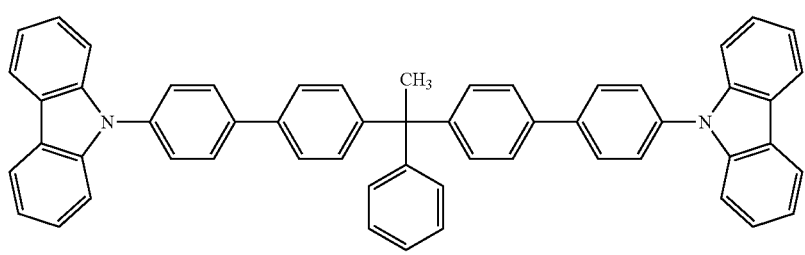
H-35

-continued
H-61
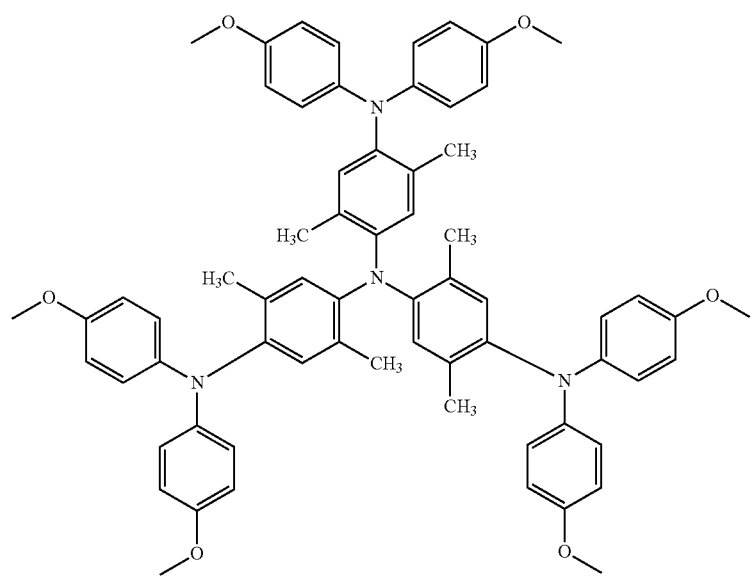
H-38
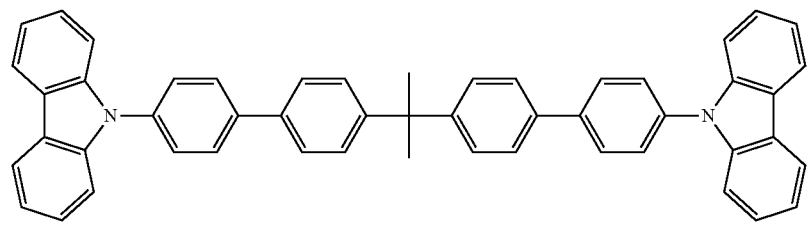
H-36
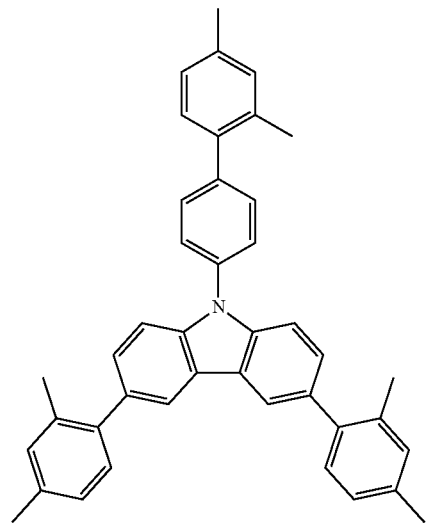
H-62
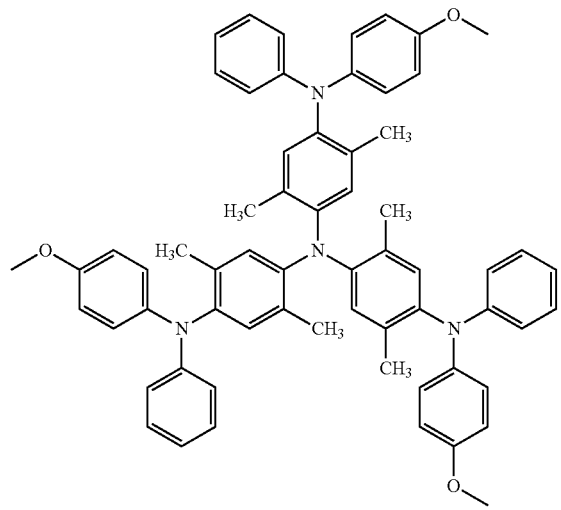
H-63
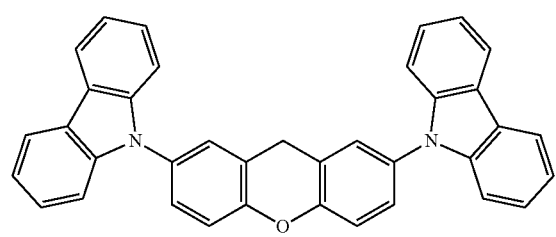
H-64
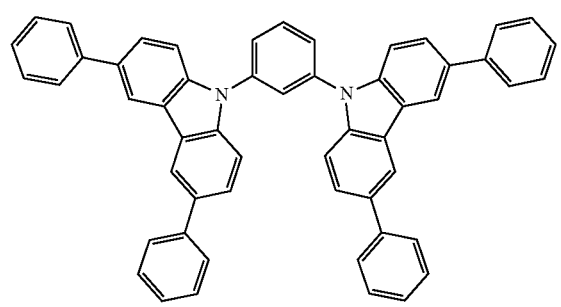

-continued
H-65
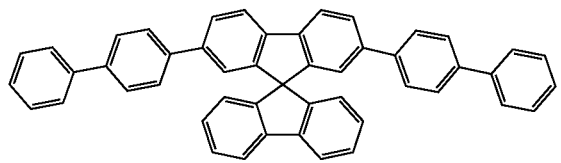
H-66
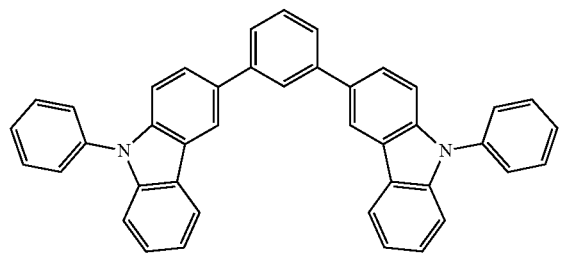
H-67
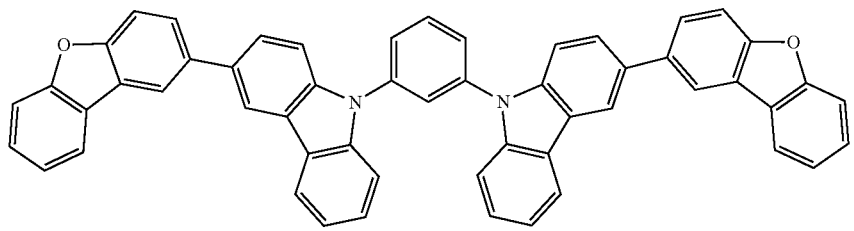
H-68
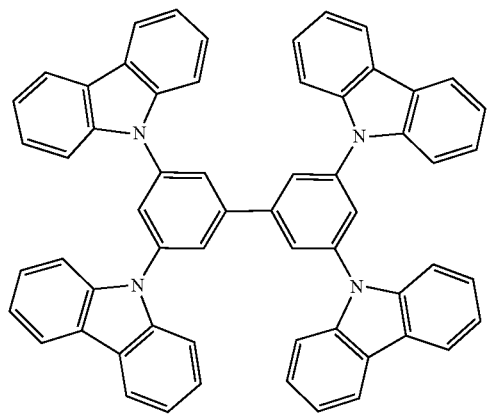
H-69
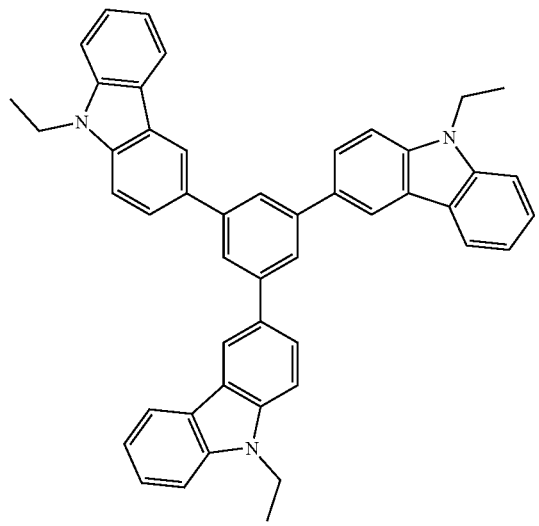
H-70
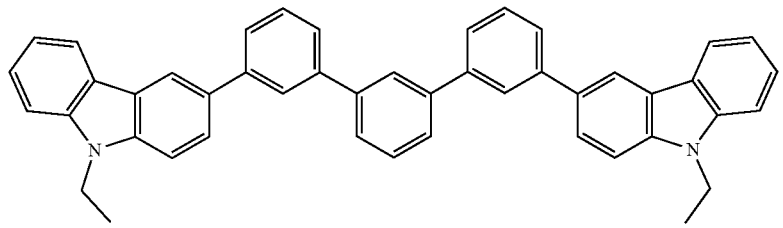
H-73
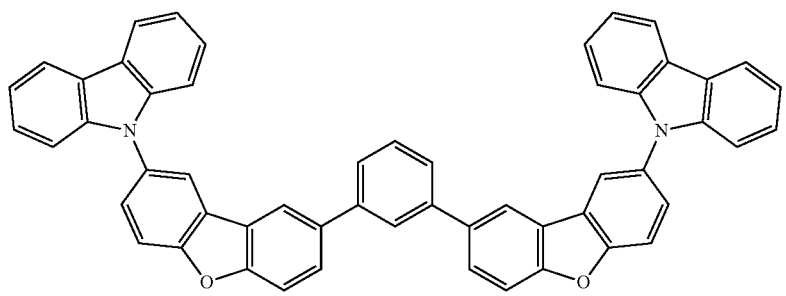

-continued
H-76
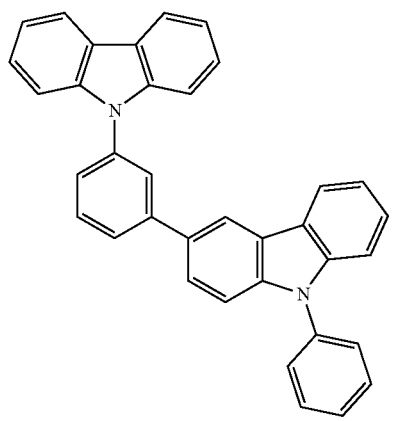
H-77
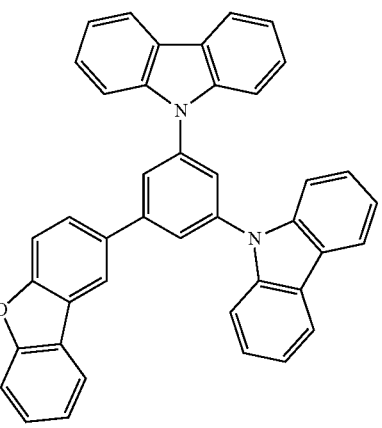
H-78
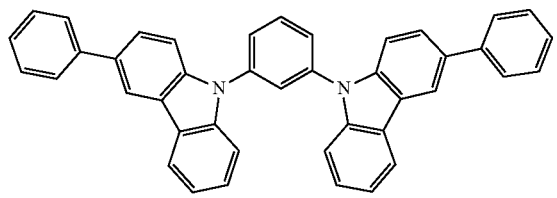
H-79
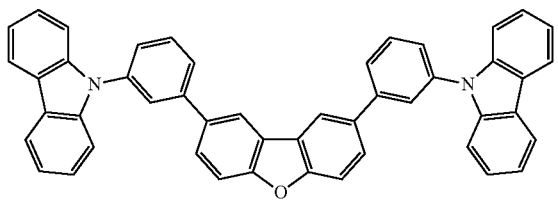
H-80
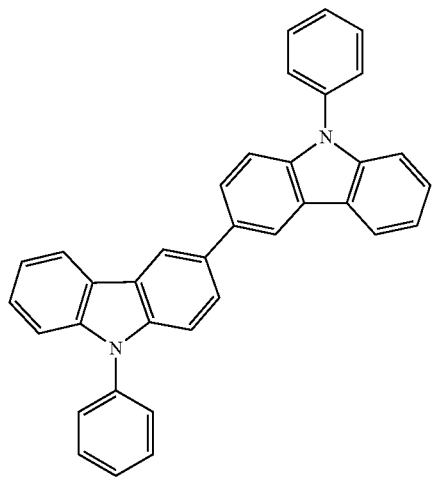
H-83
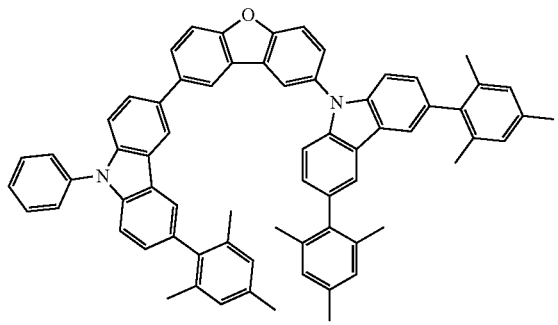
H-71
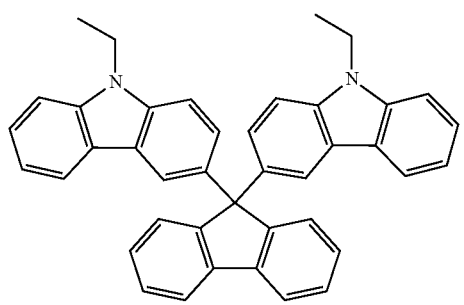

H-94
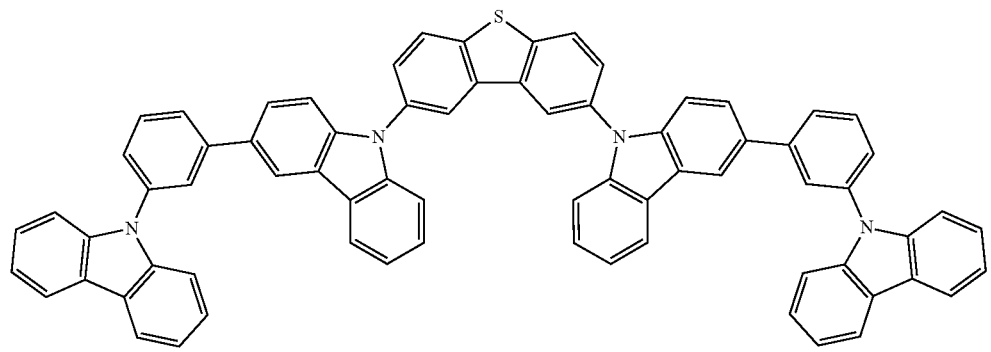
H-96
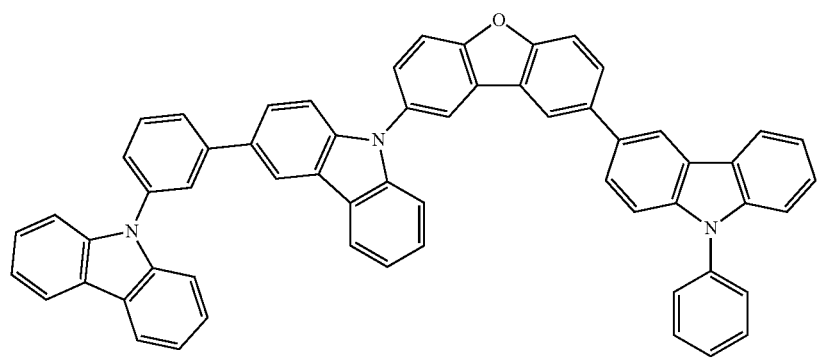
H-97
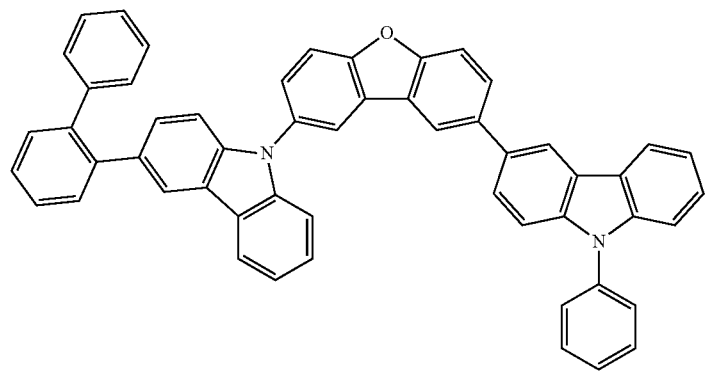
H-99
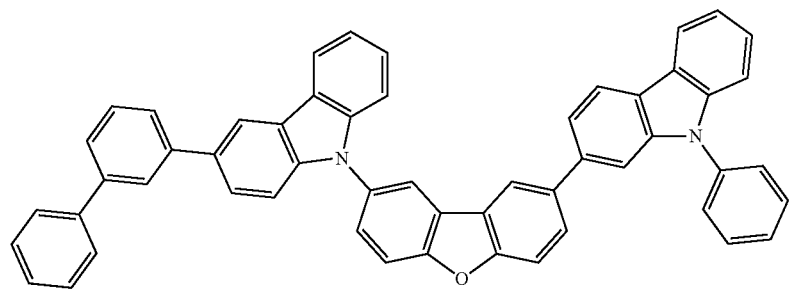

-continued
H-100
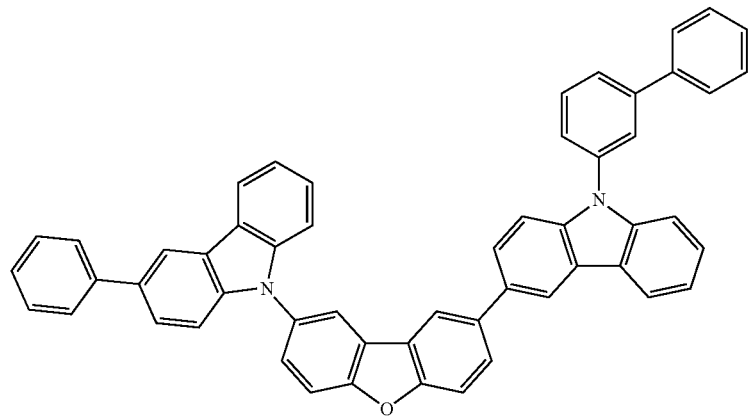
H-101
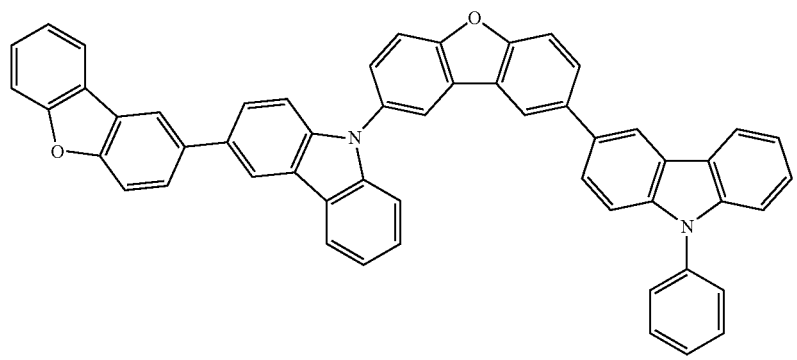
H-103
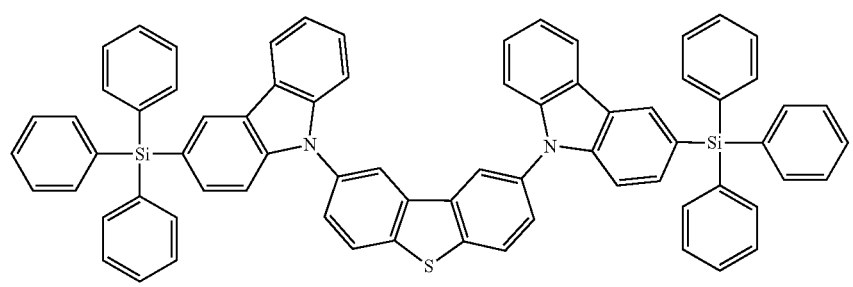
H-108
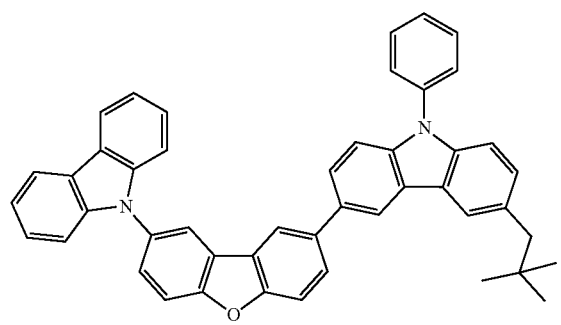
H-109
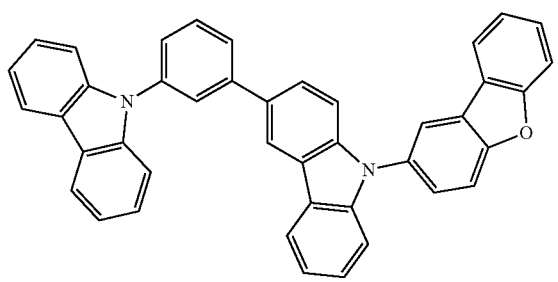

-continued
H-110
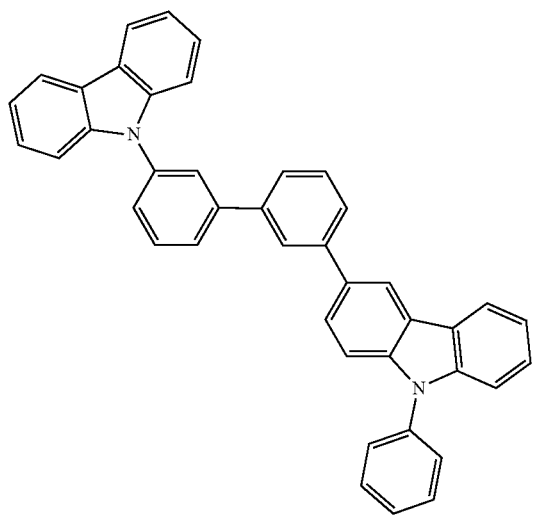
H-104
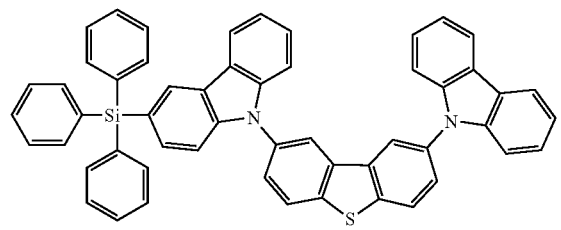
H-111
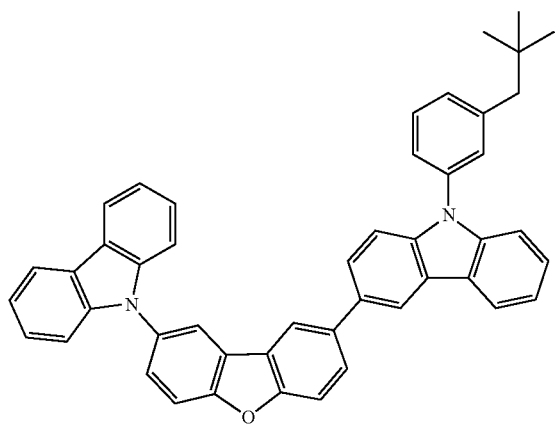
H-112
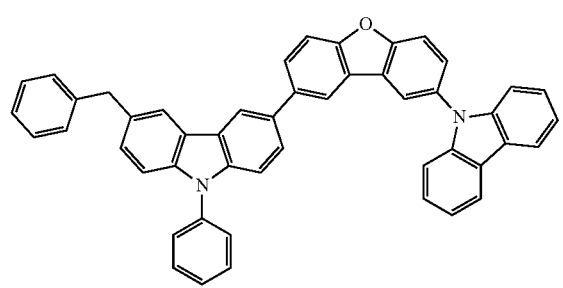
H-113
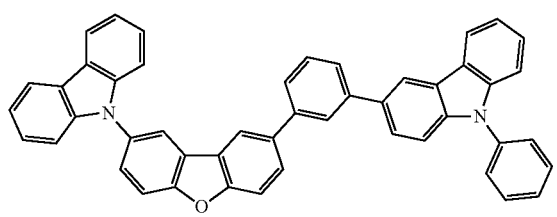
H-114
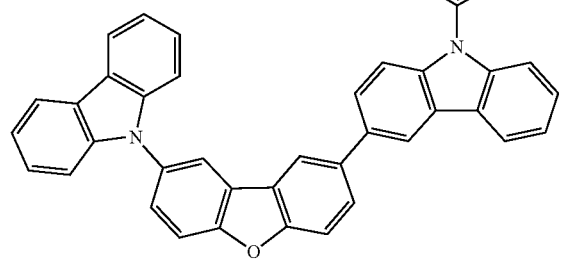

-continued
H-115
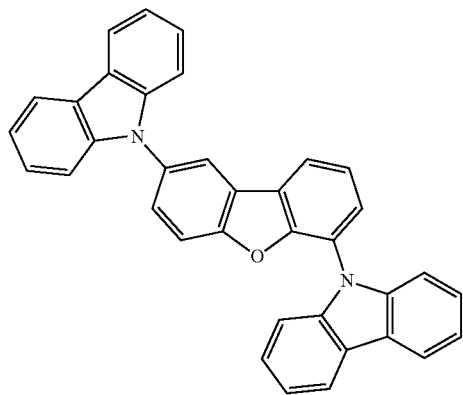
H-116
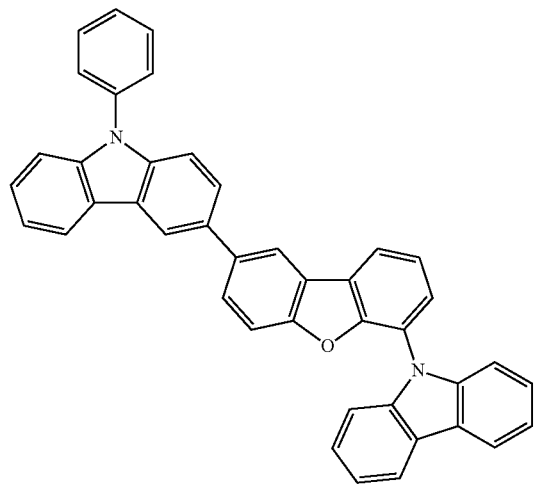
H-117
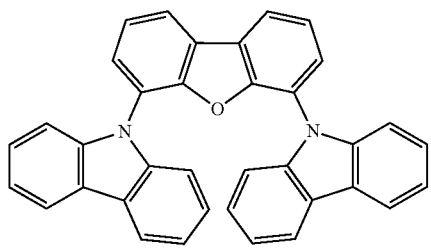
H-118
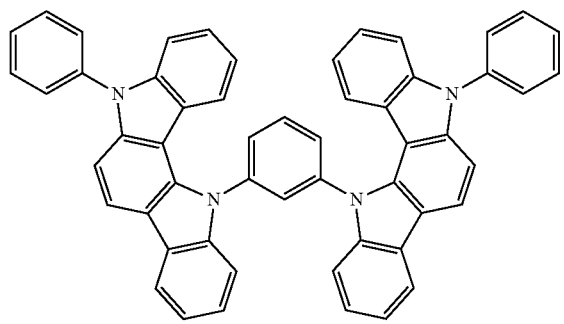
H-122
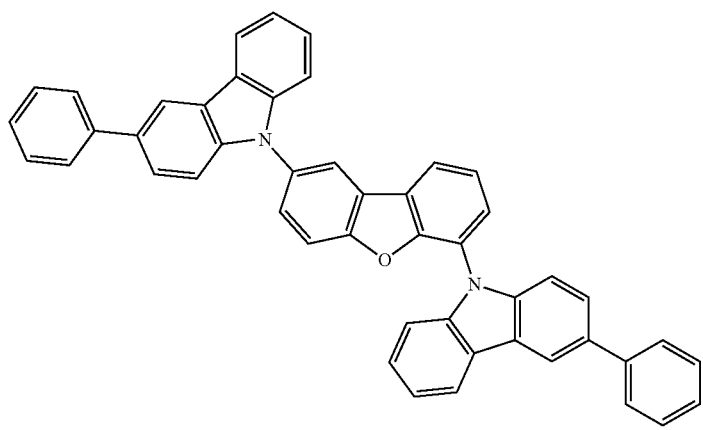

-continued
H-123
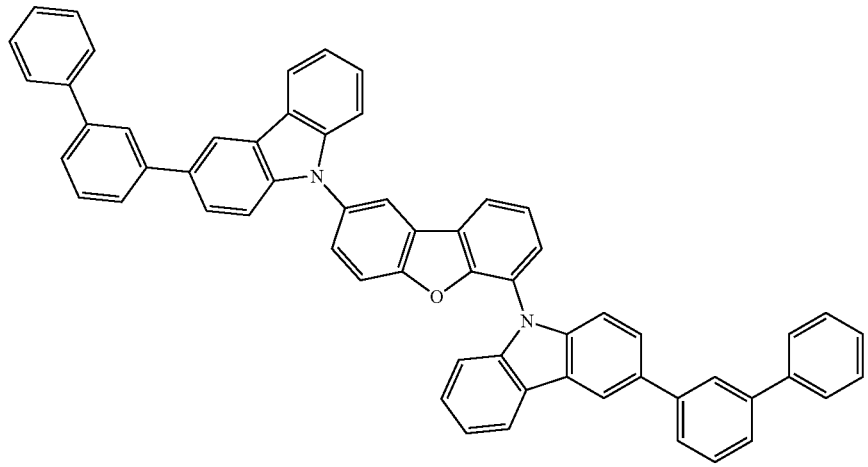
H-124
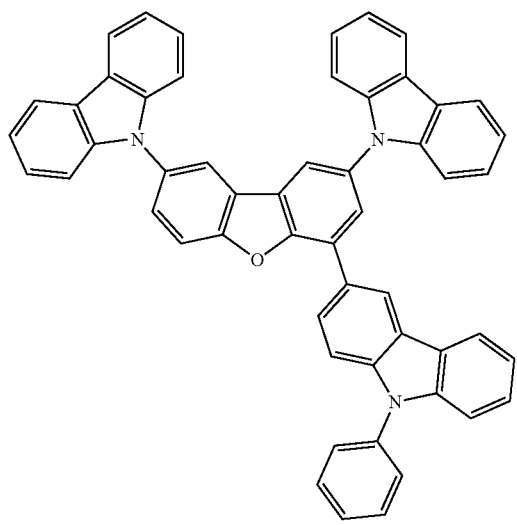
H-125
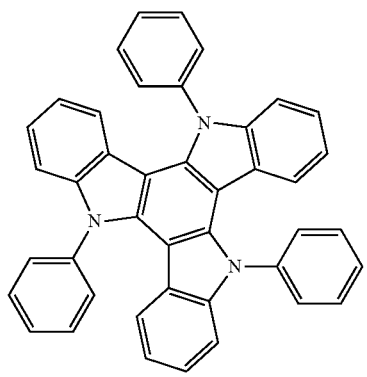
H-126
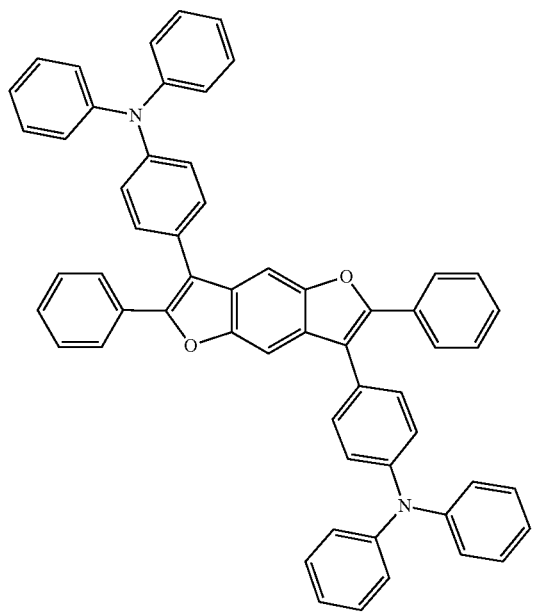
H-127
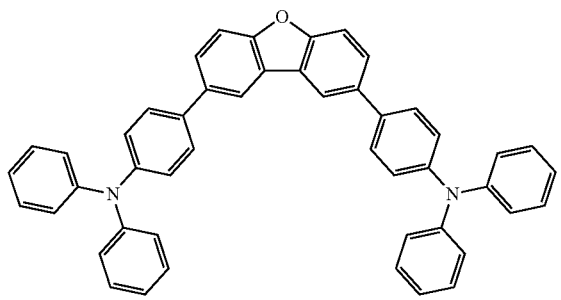

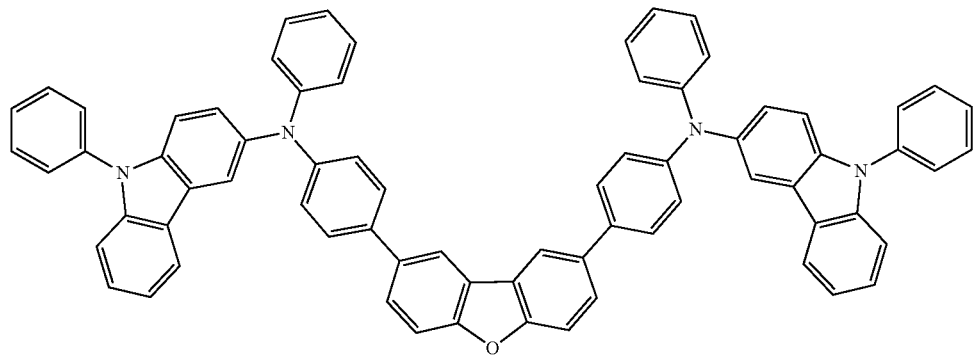
H-128
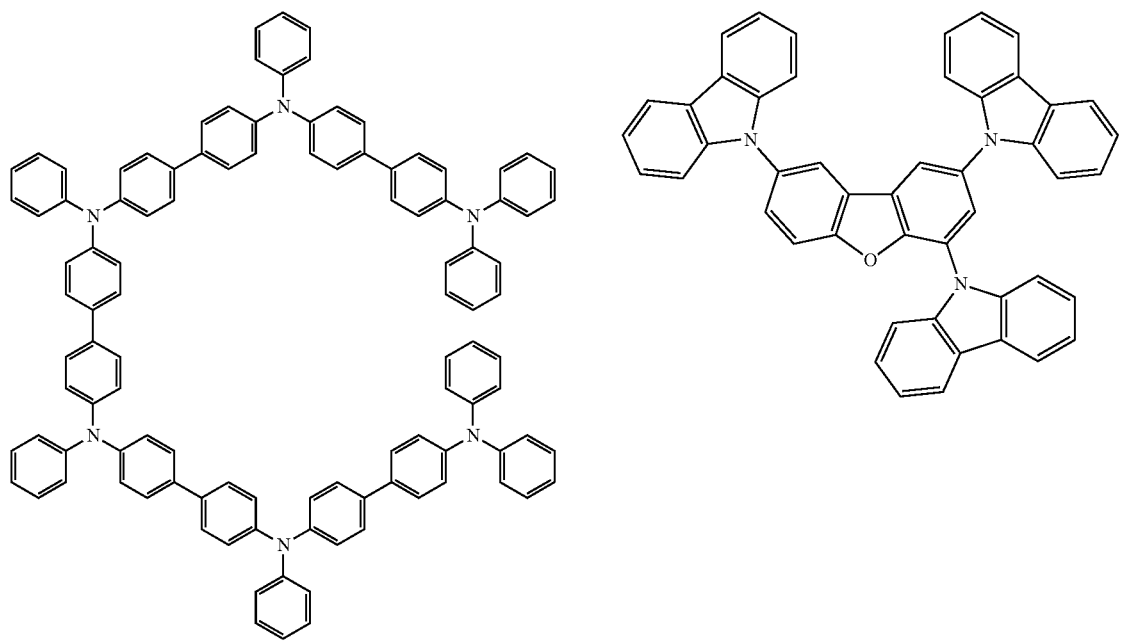
H-129
H-130
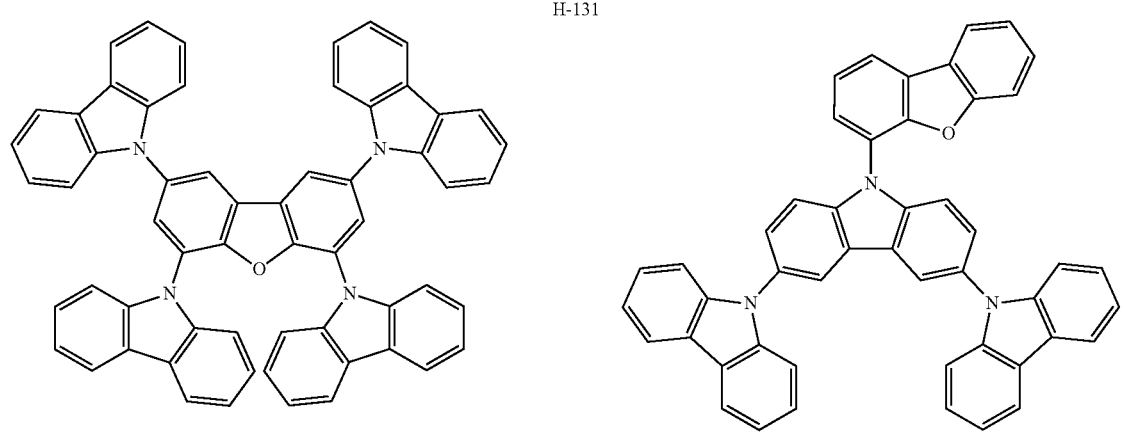
H-131
H-132

-continued
H-133
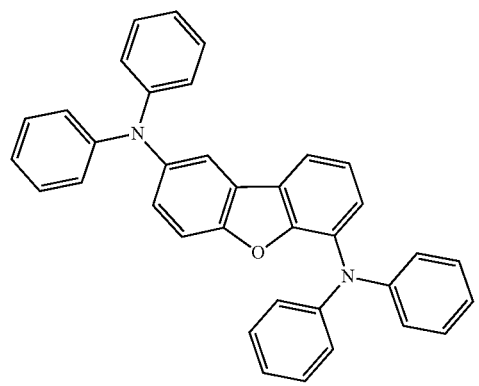
H-134
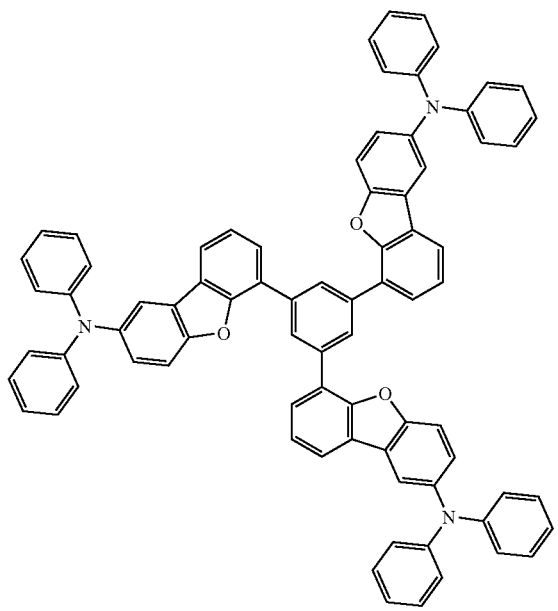
H-135
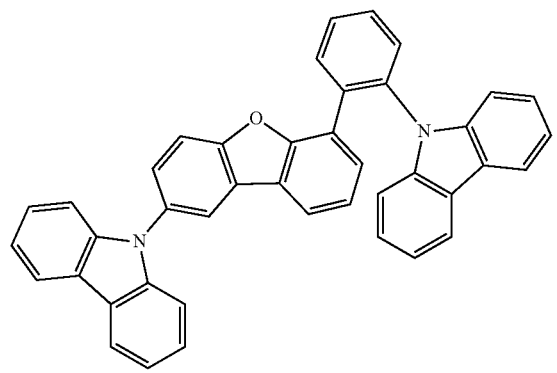
H-136
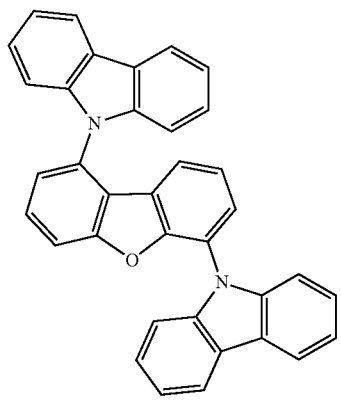
H-137
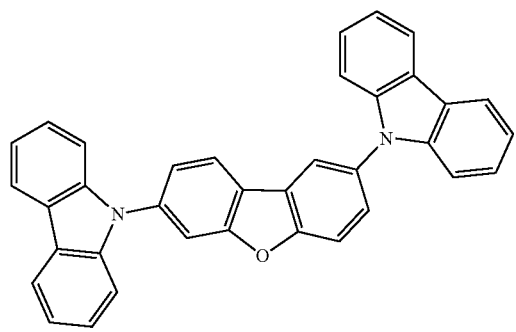
H-138
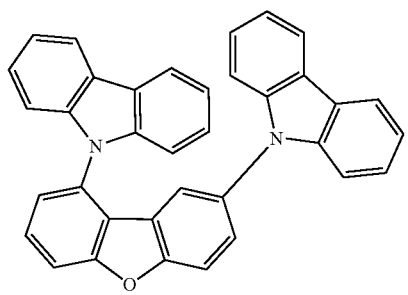

-continued
H-139
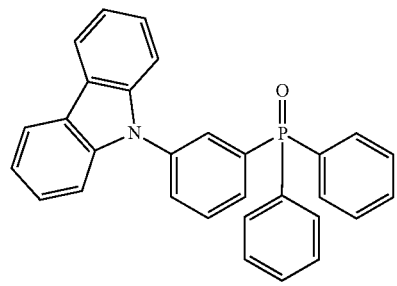
H-140
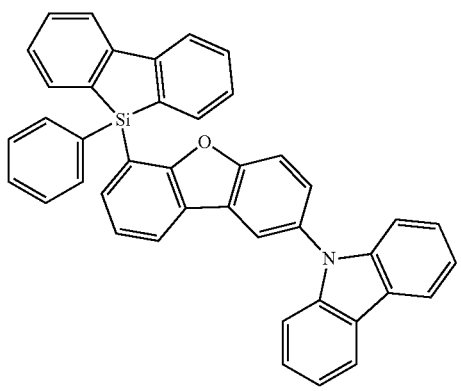
H-148
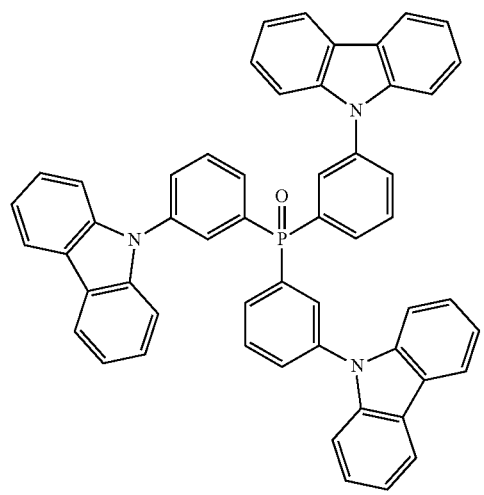
H-142
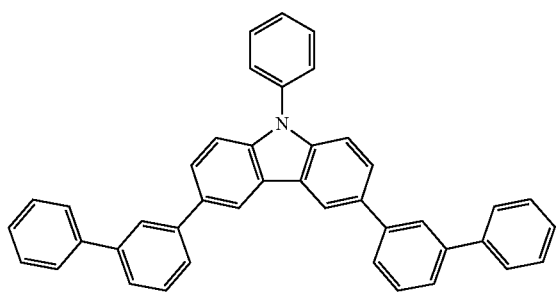
H-153
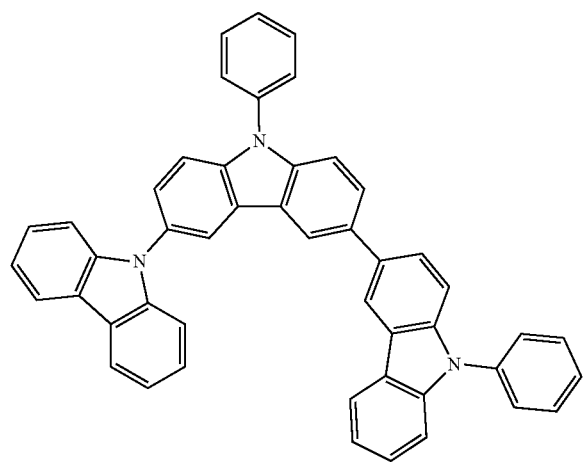
H-154
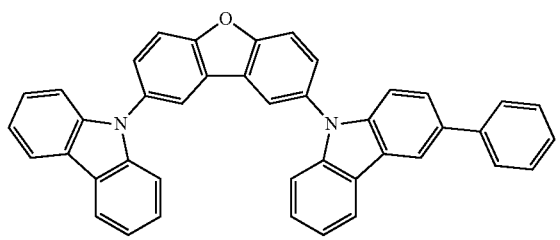
H-155
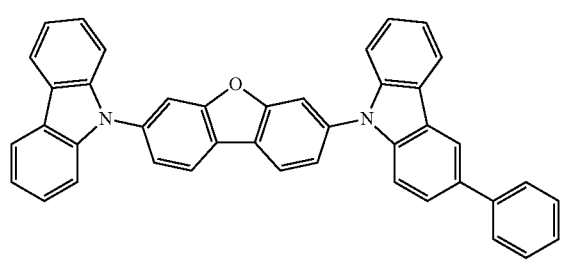
H-156
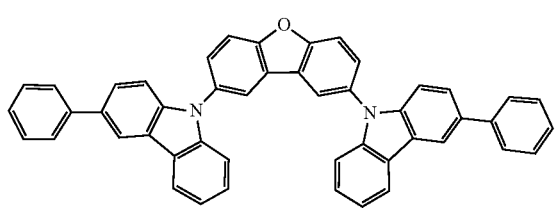

-continued
H-160
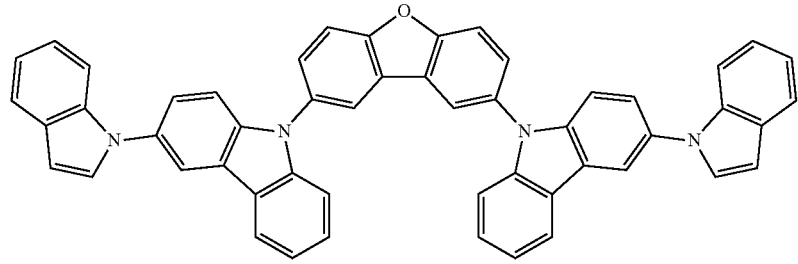
H-161
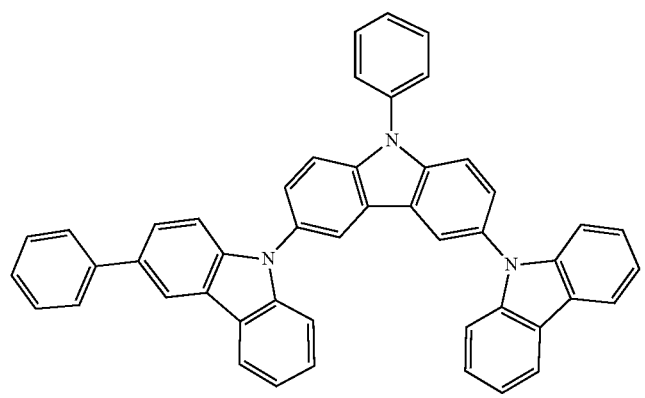
H-165
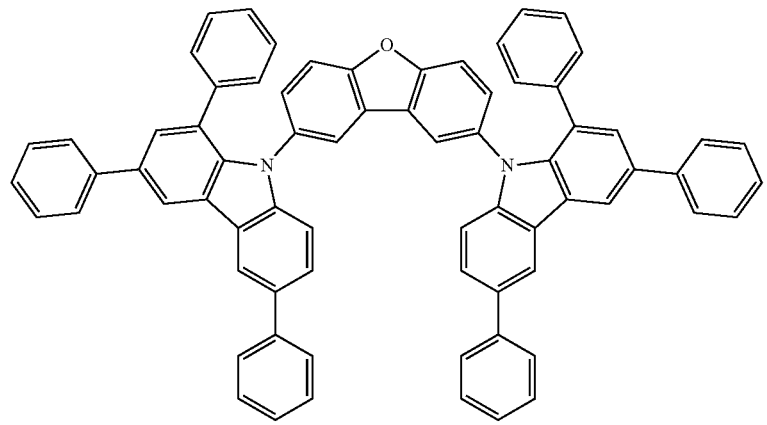
H-152
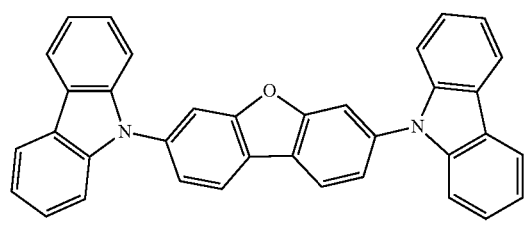
H-166
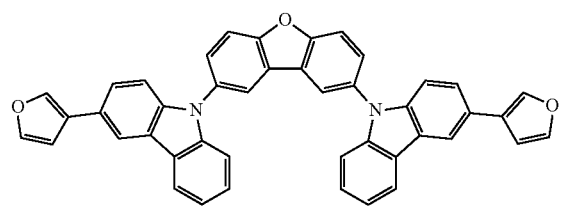

-continued
H-159
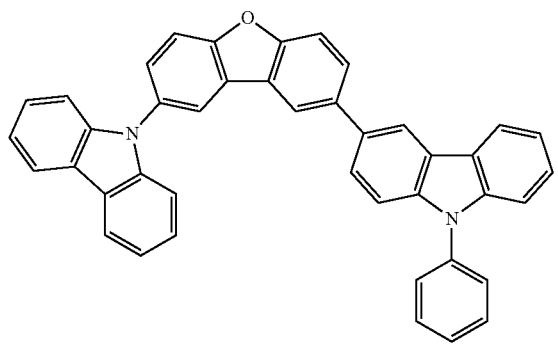
H-167
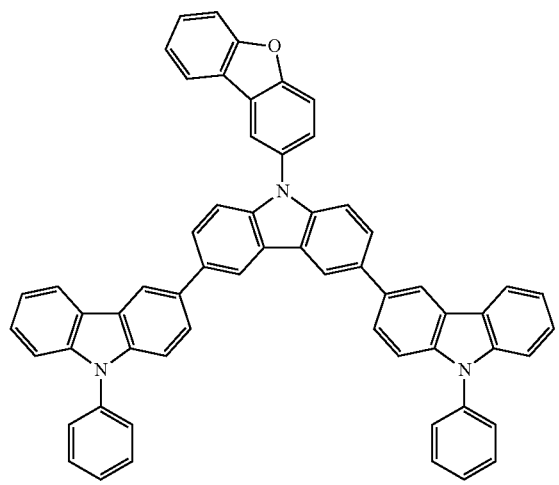
H-168
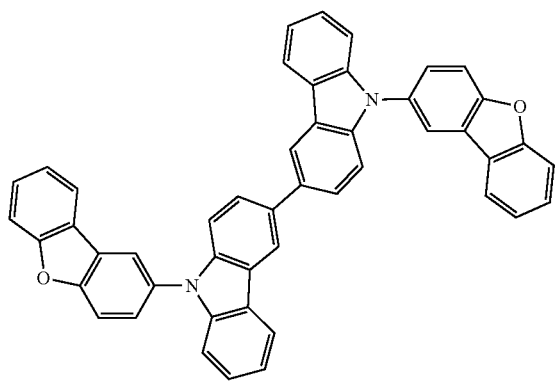
H-169
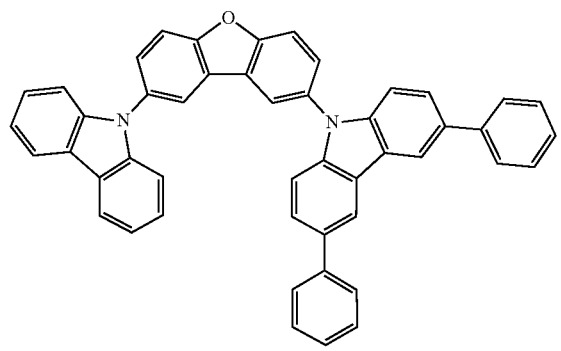
H-171
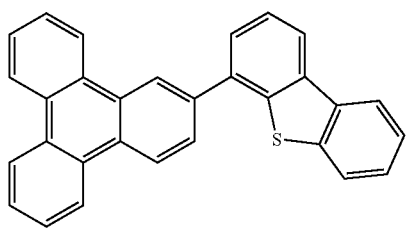
H-172
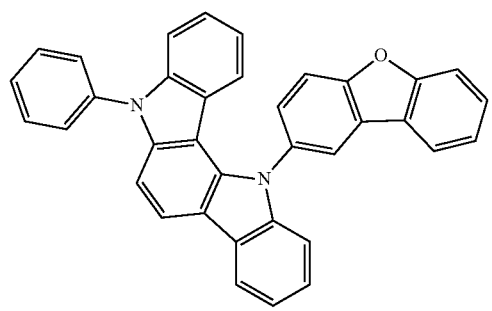

-continued
H-174
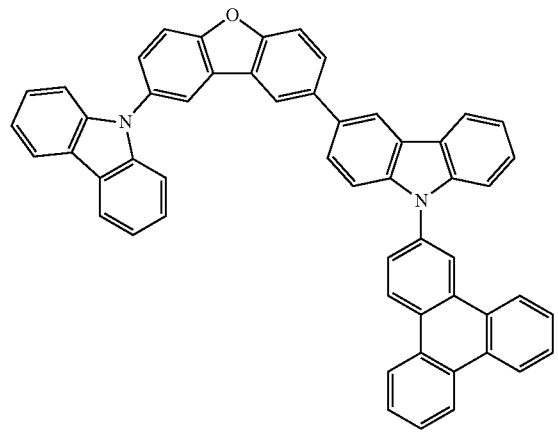
H-175
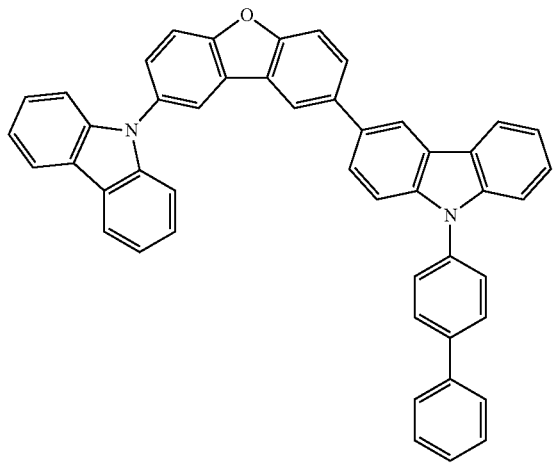
H-176
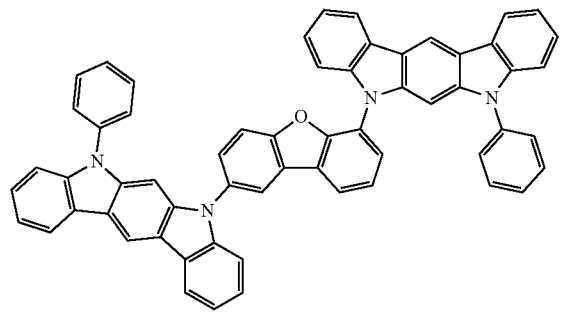
H-178
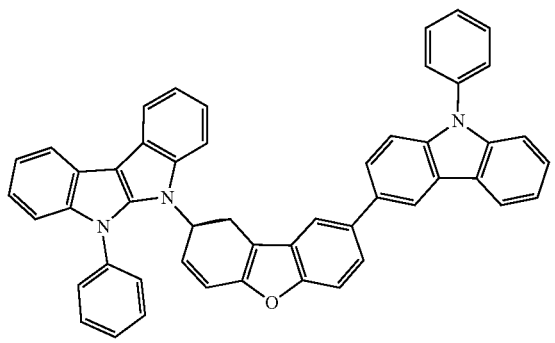
H-179
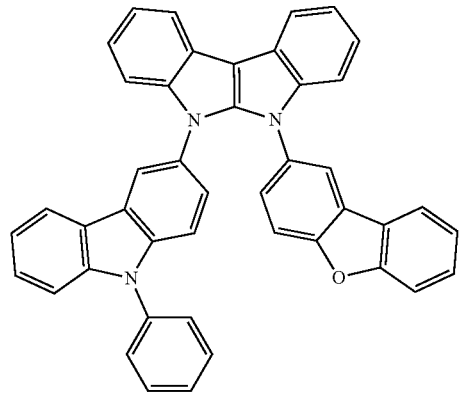
H-180
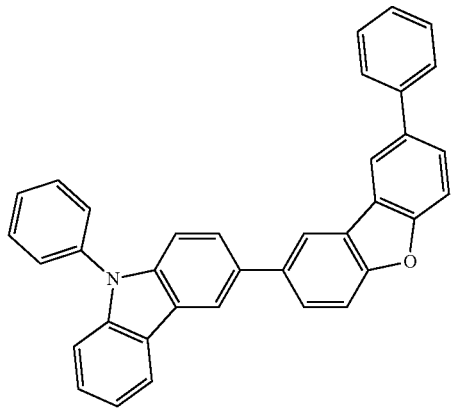
H-182
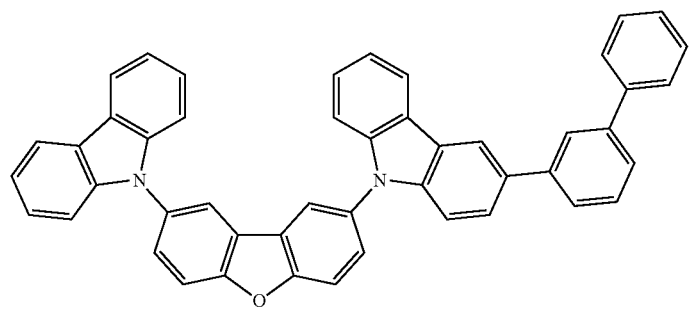

H-183
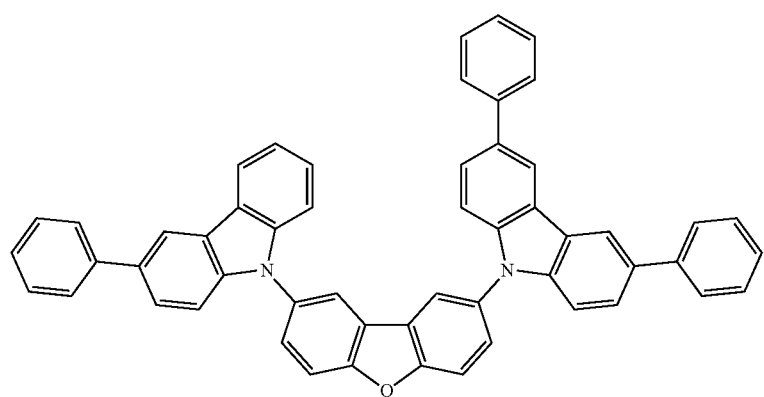
H-184
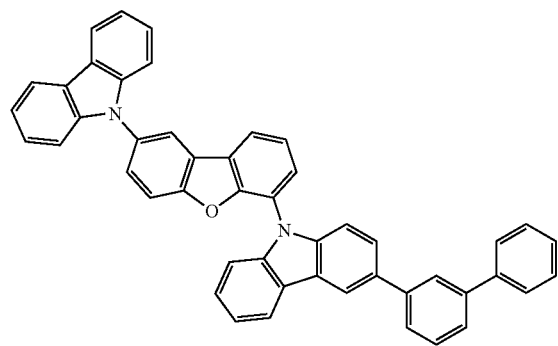
H-185
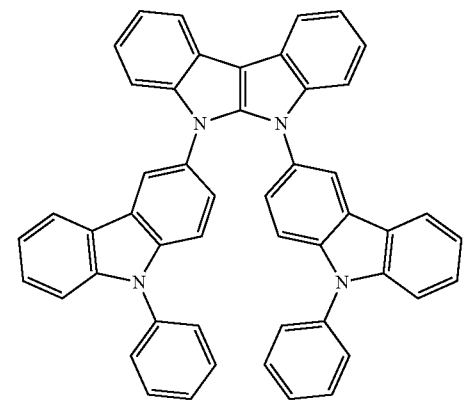
H-186
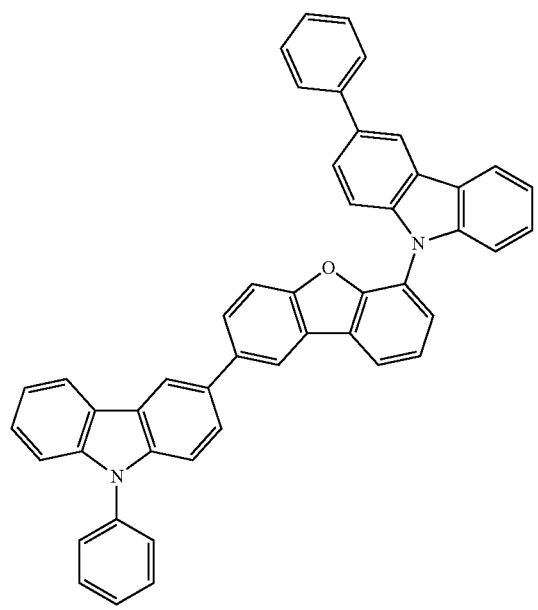
H-187
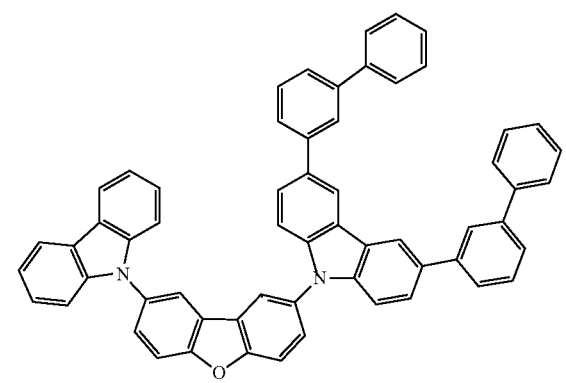

-continued
H-188
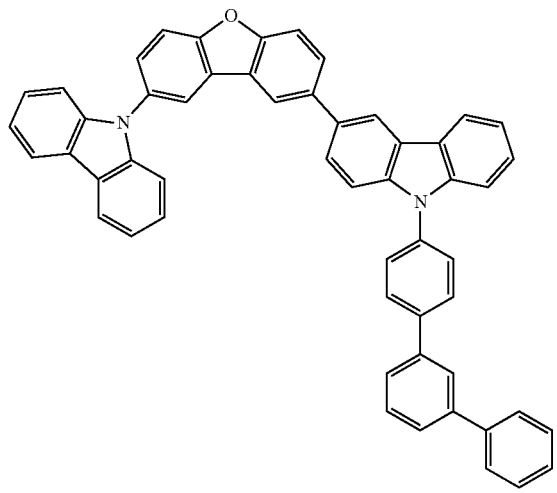
H-189
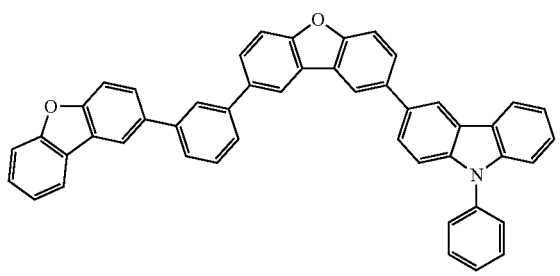
H-190
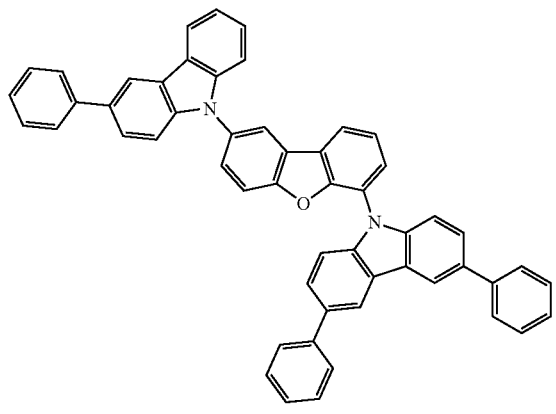
H-191
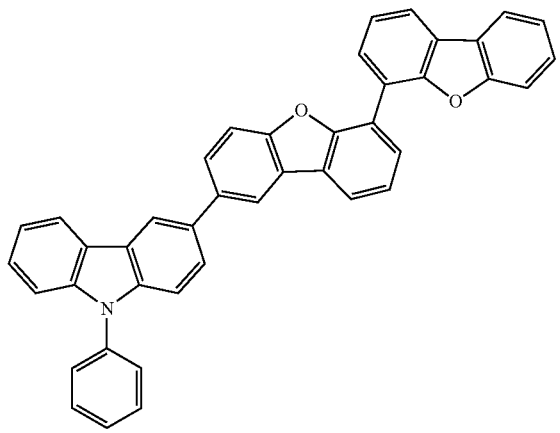
H-192
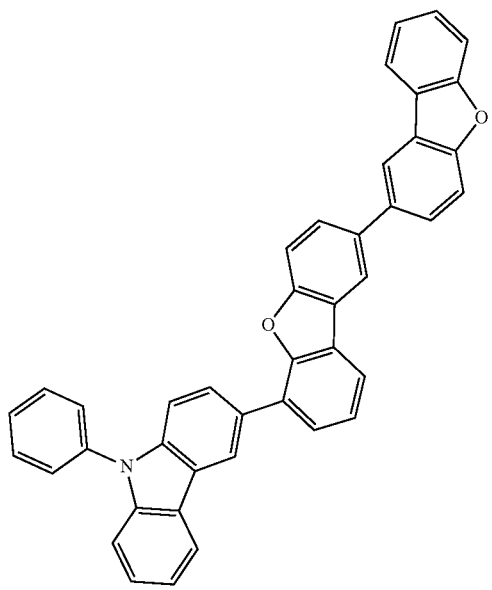
H-193
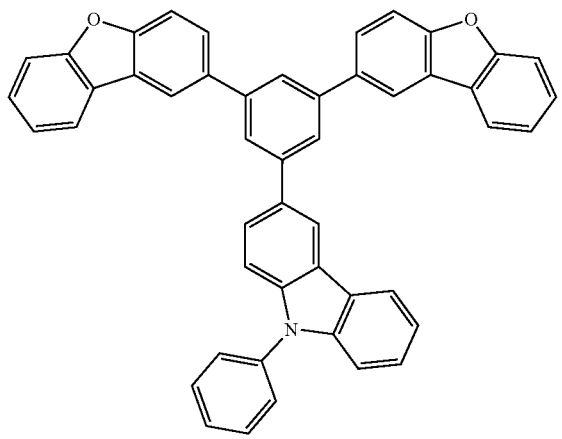

-continued
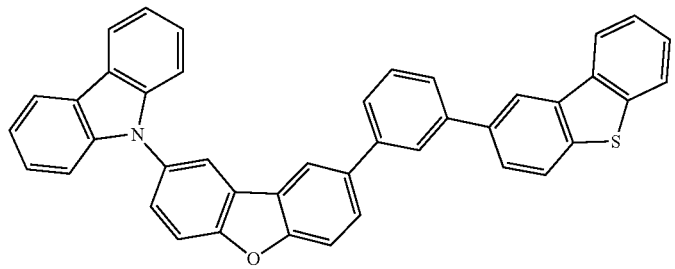
H-194
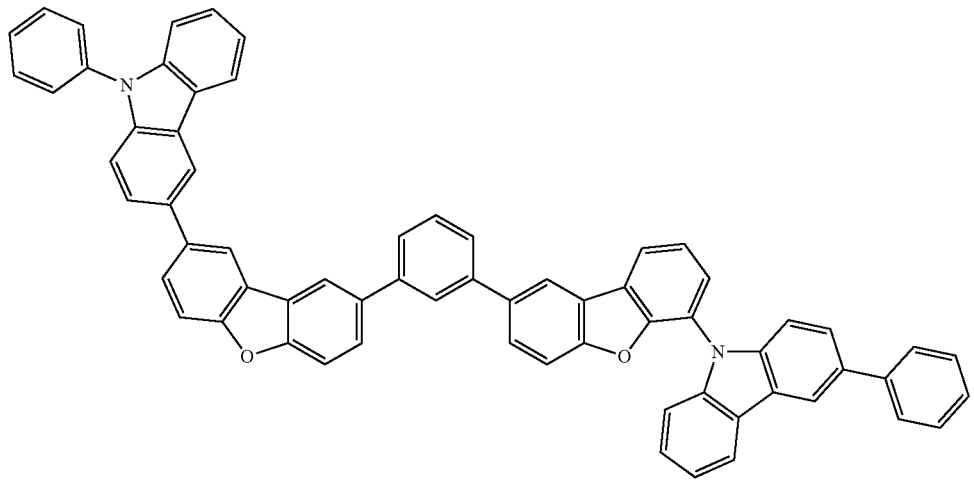
H-195
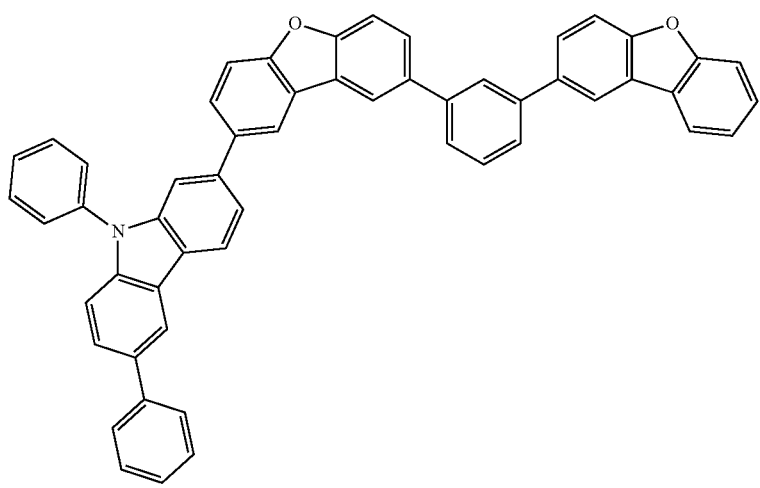
H-196
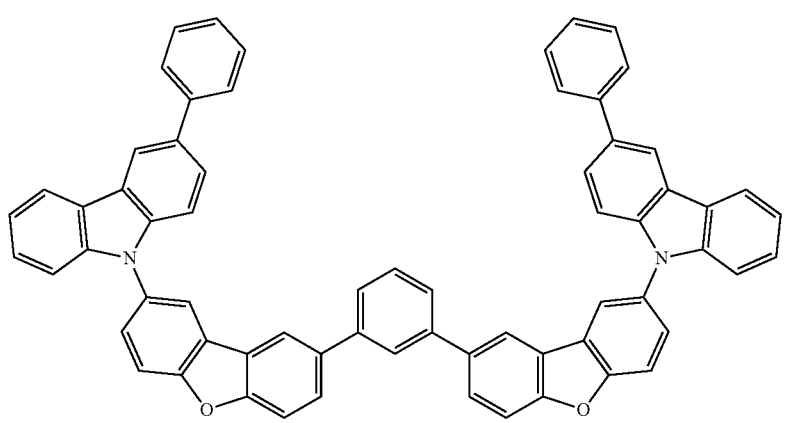
H-197

-continued
H-198
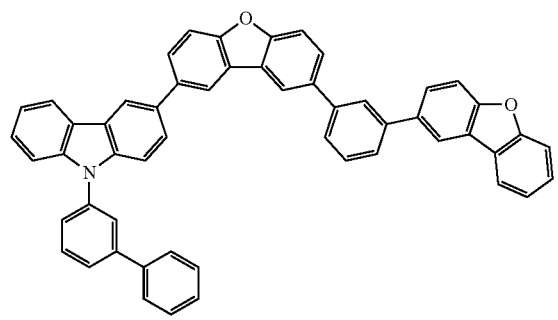
H-199
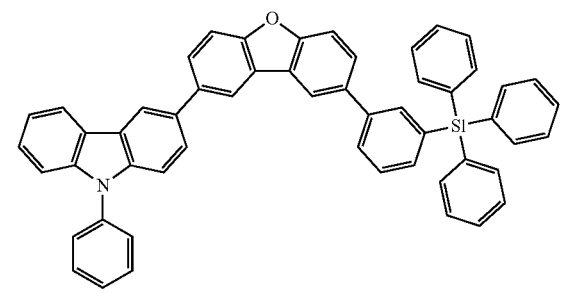
H-200
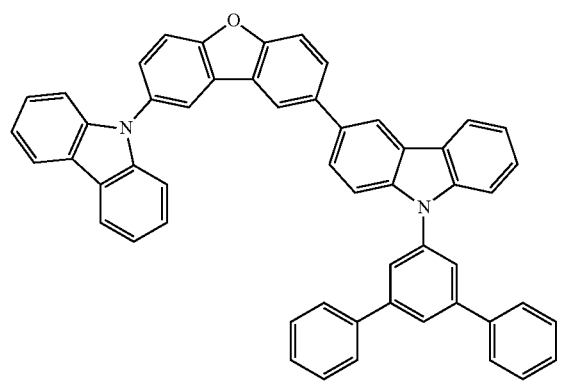
H-201
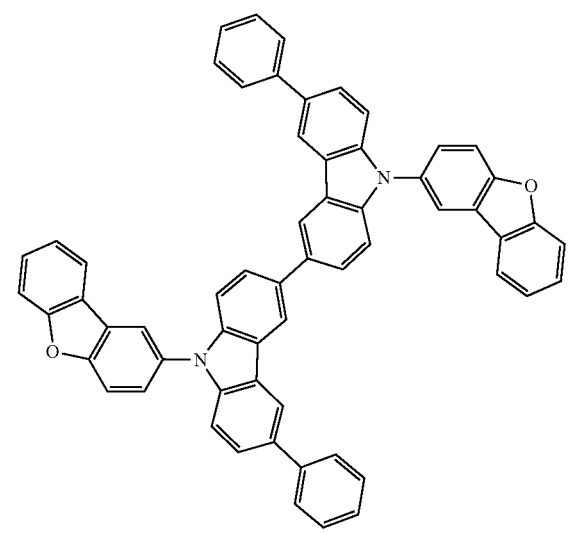
H-202
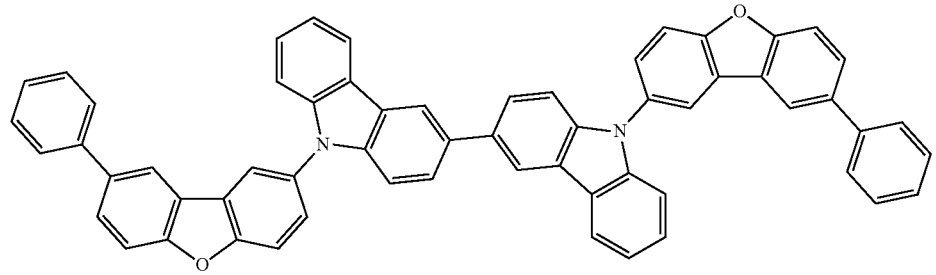
H-203
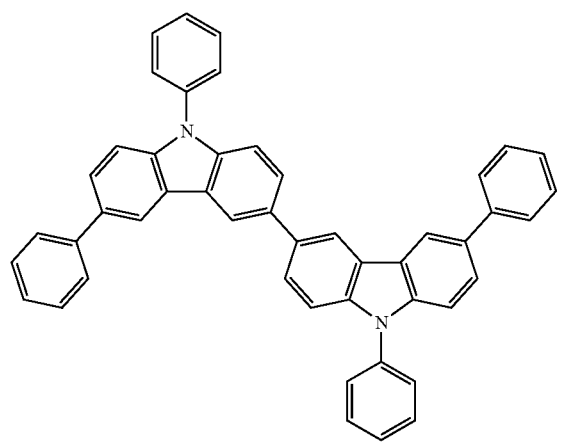
H-204
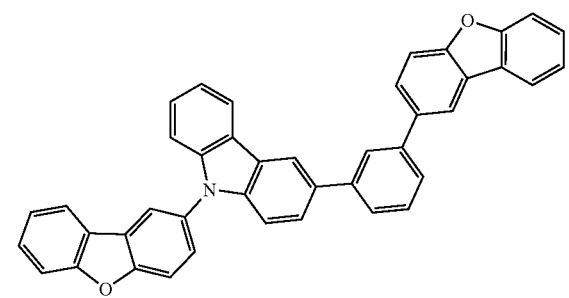

-continued
H-205
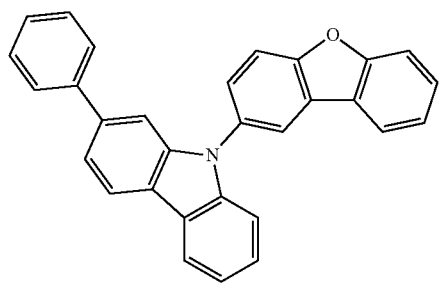
H-206
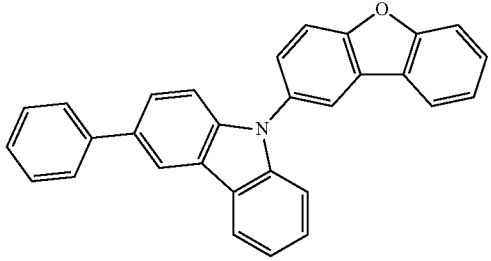
H-207
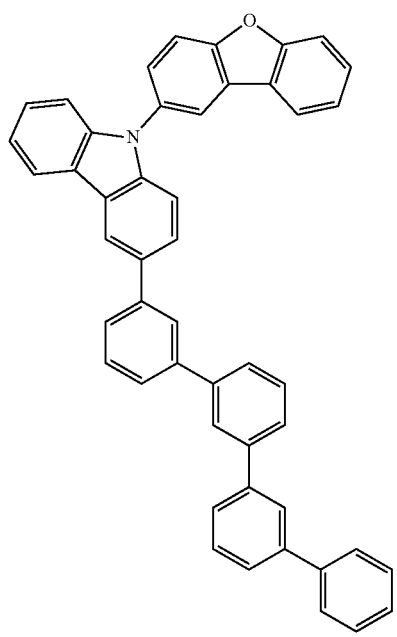
H-208
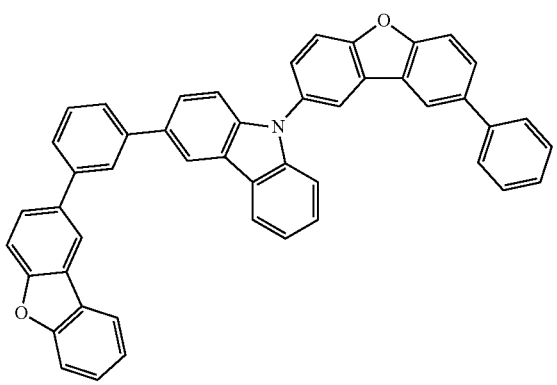
H-209
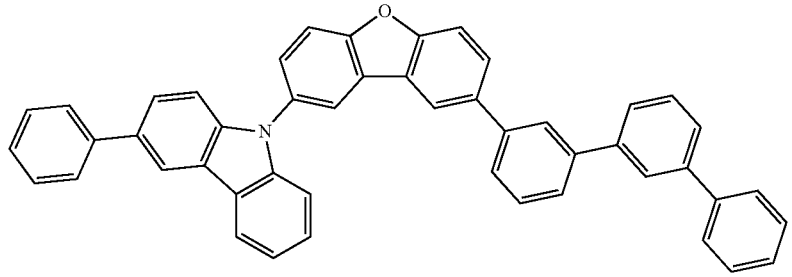
H-210
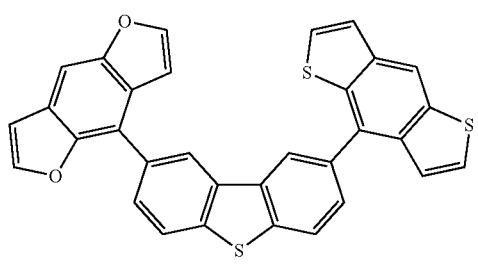
H-211
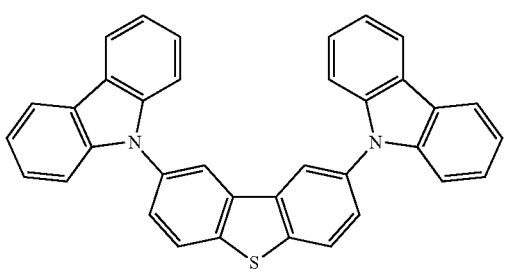

-continued
H-212
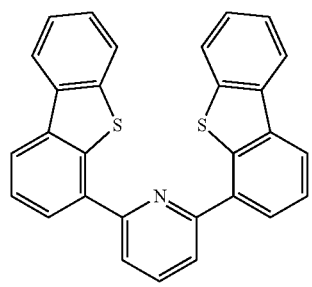
H-213
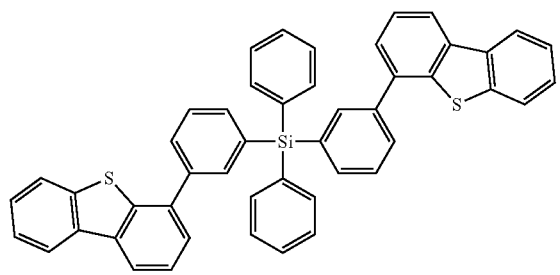
H-216
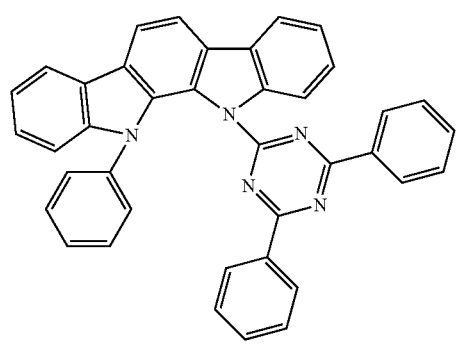
H-217
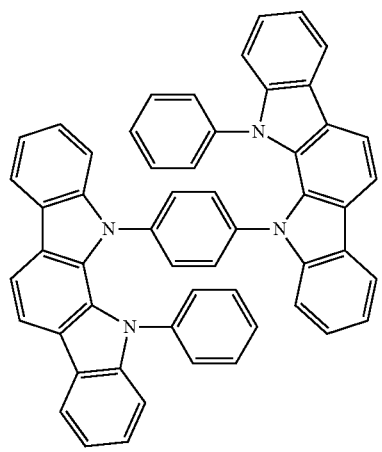
H-218
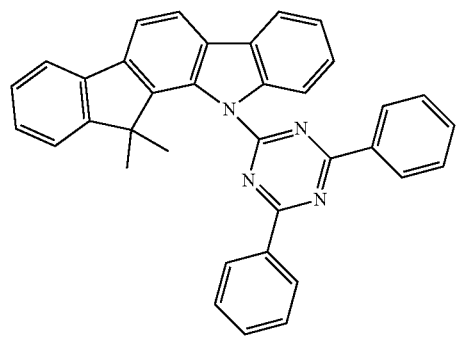
H-219
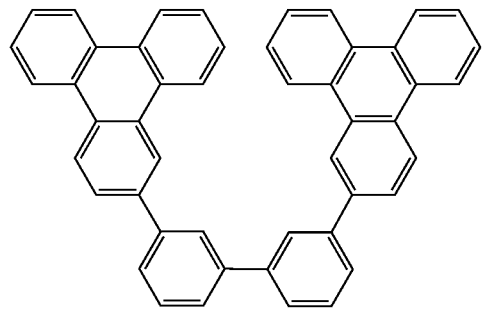
H-220
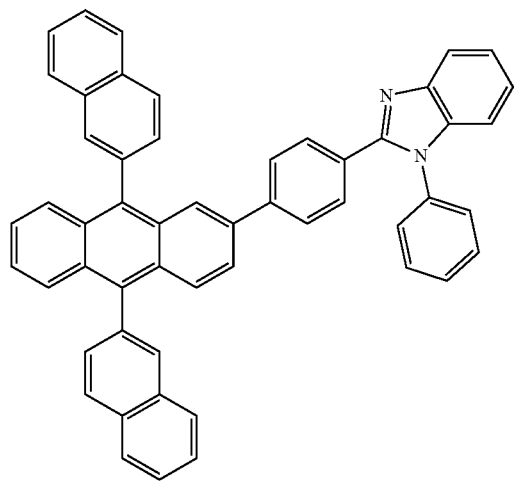
H-221

-continued
H-222
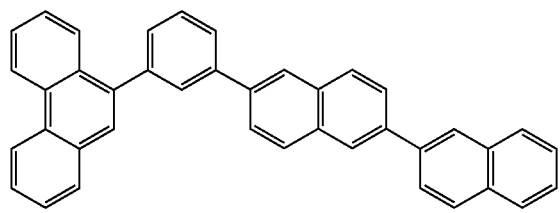
H-223
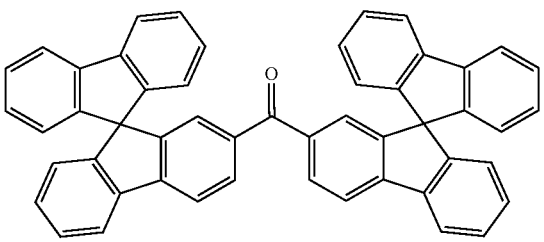
H-224
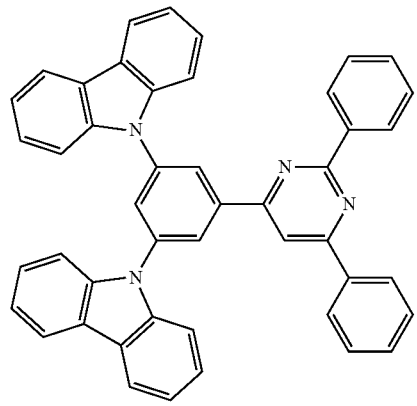
H-225
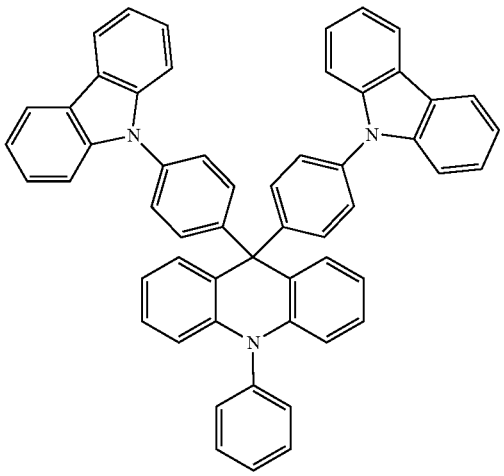
H-226
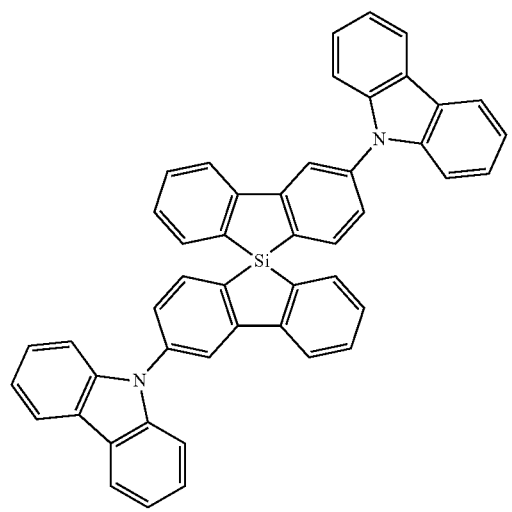
H-227
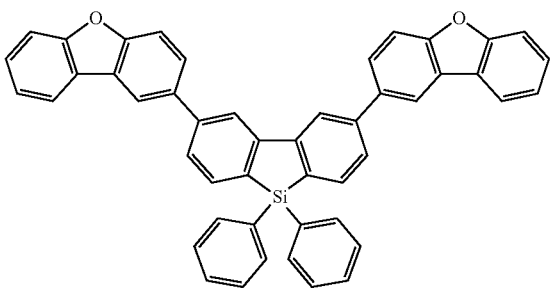
H-228
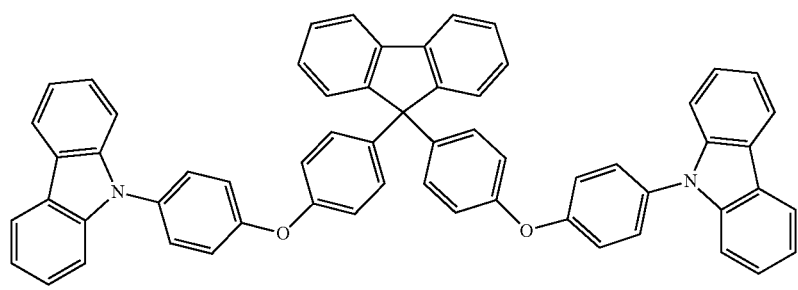

H-229
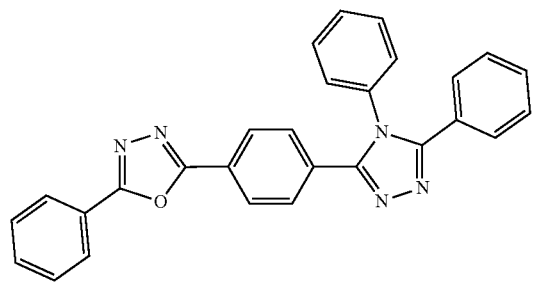
H-230
15
The following specific examples of the compound M3 are specific examples in which hydrogen atoms are not omitted.
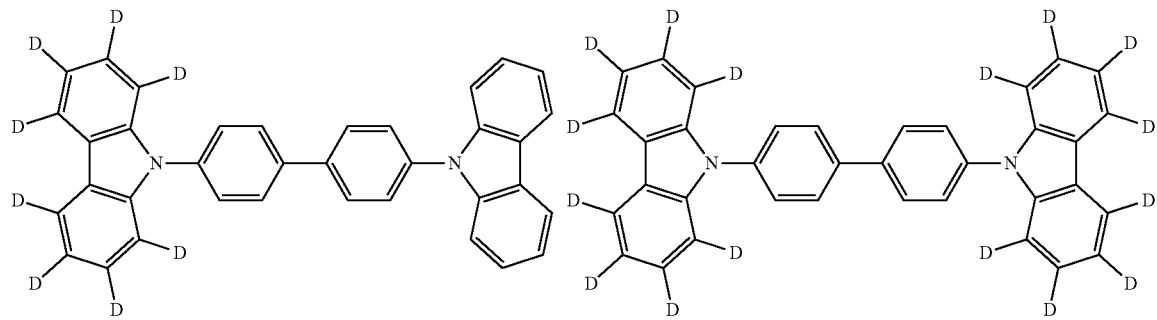
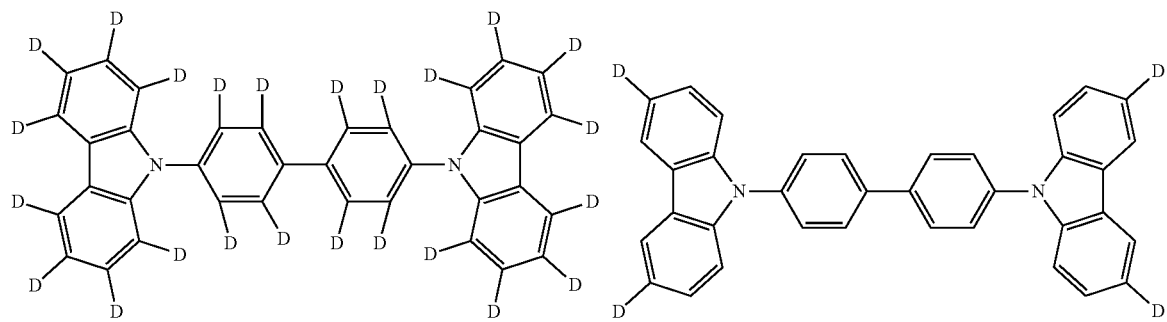
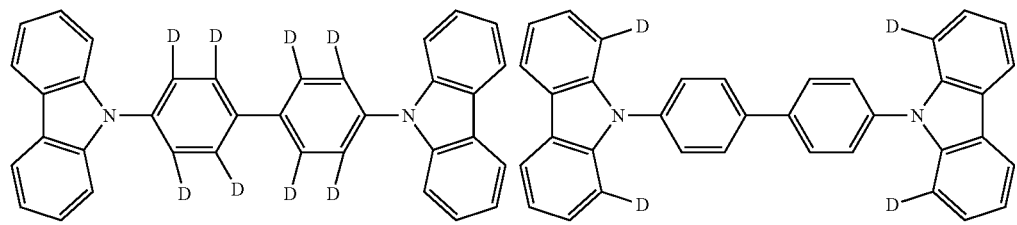

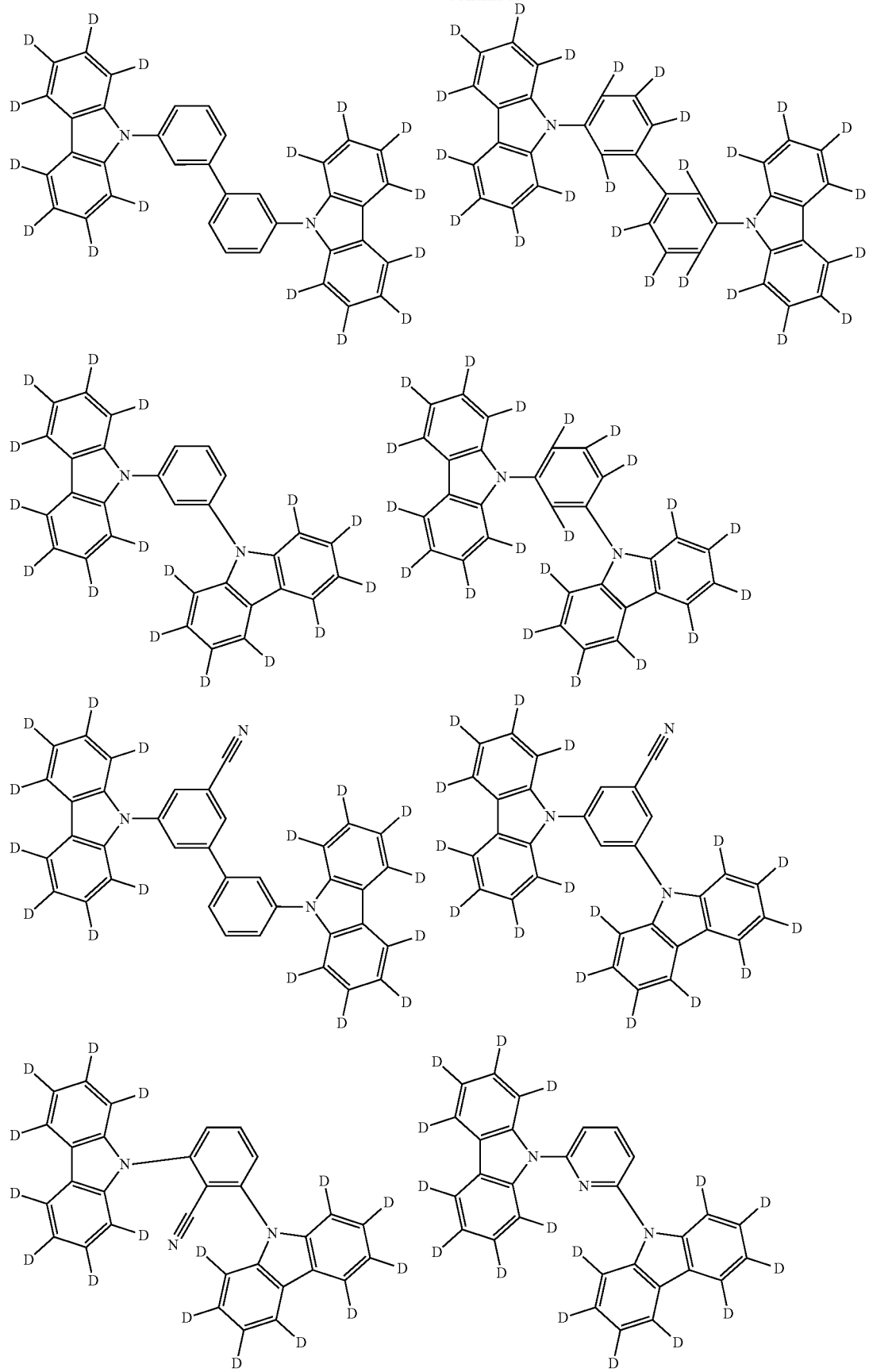

-continued
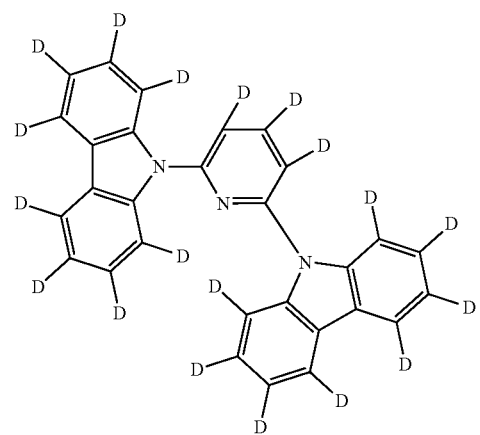
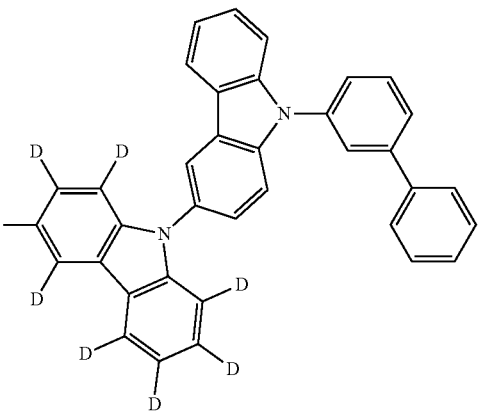
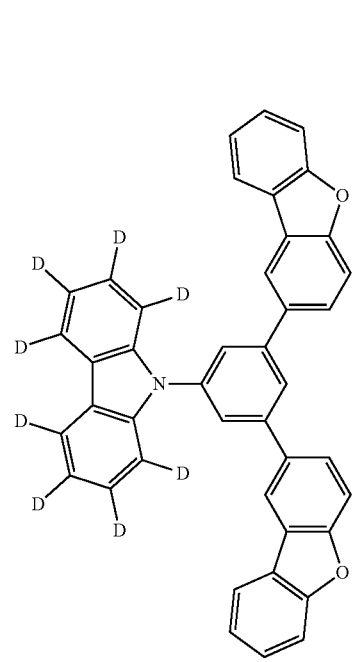
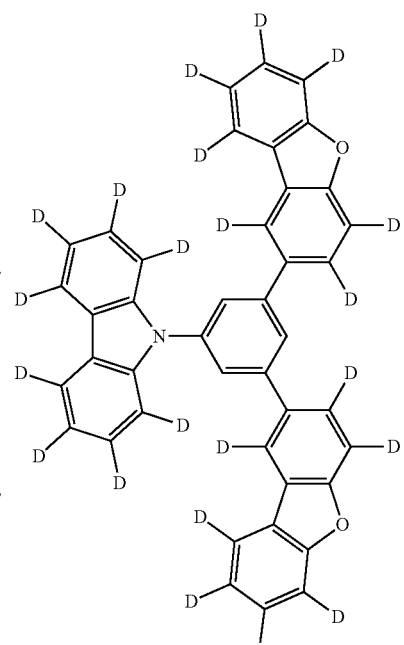
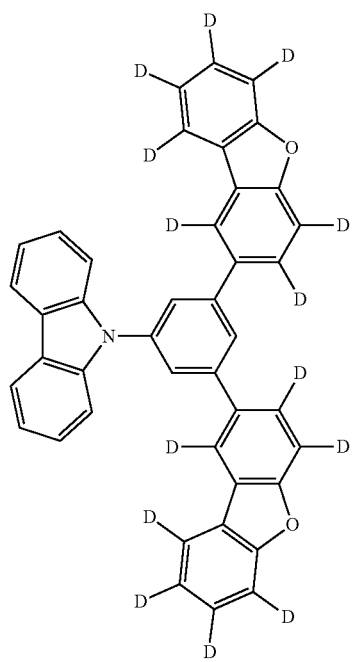
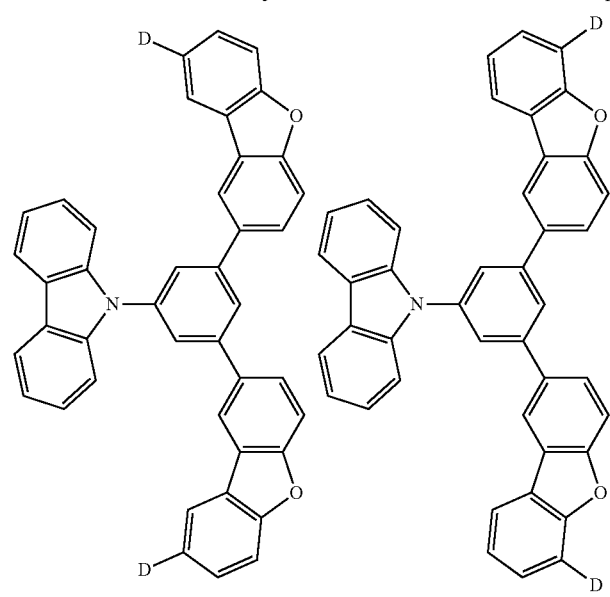

-continued
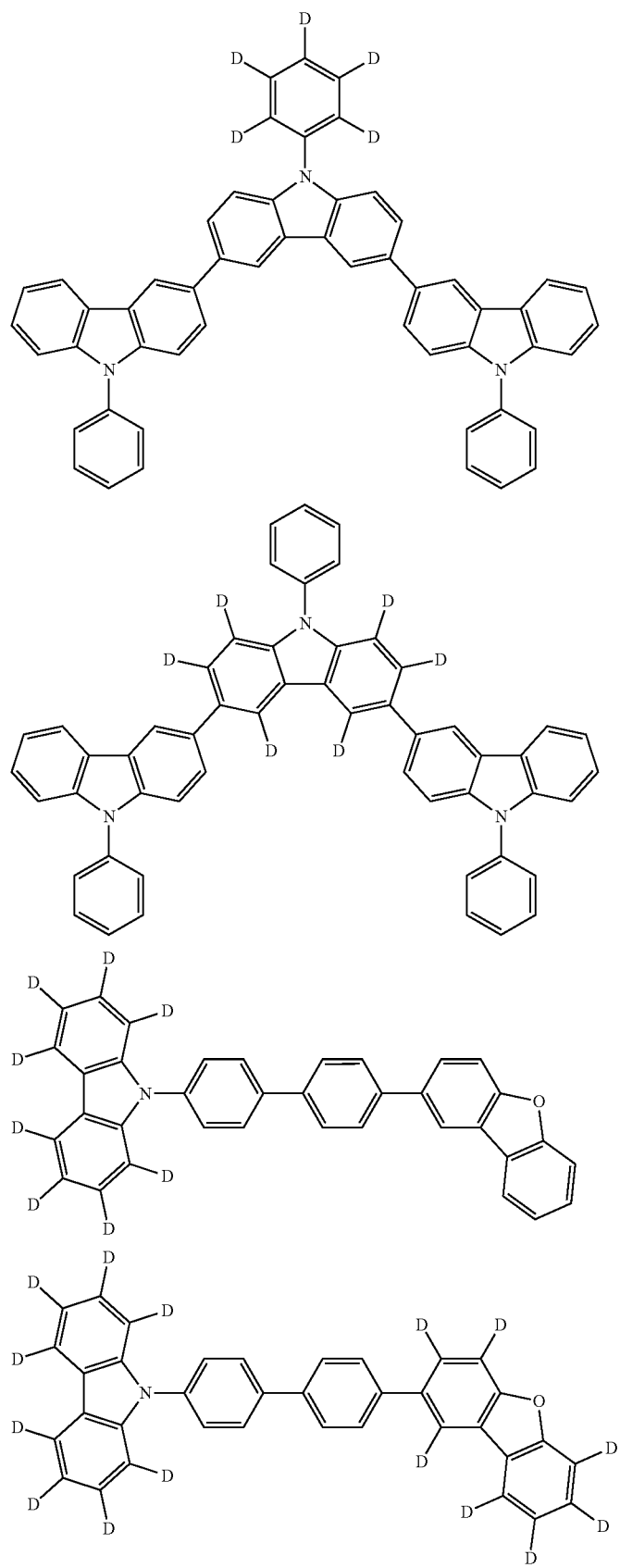

-continued
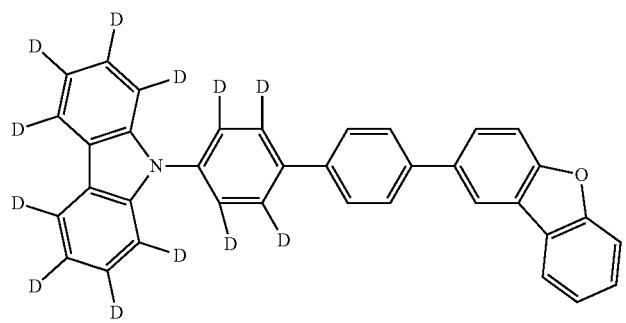
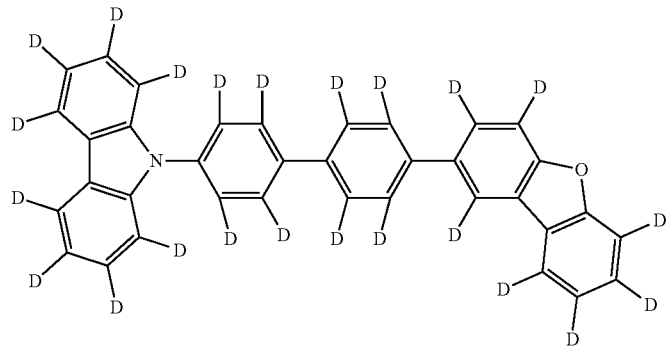
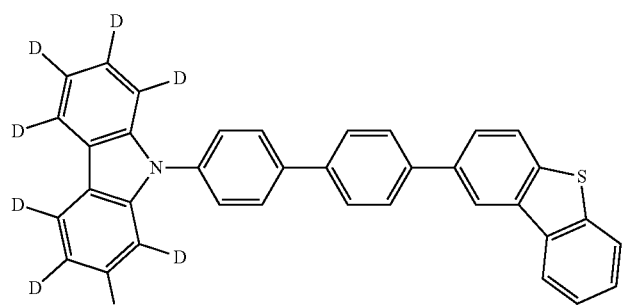
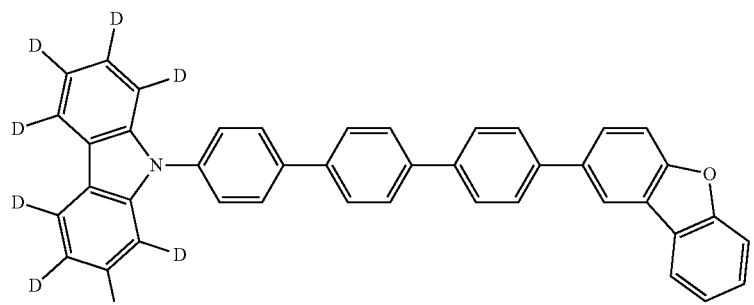
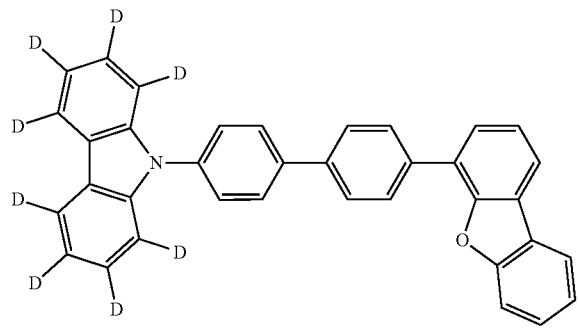
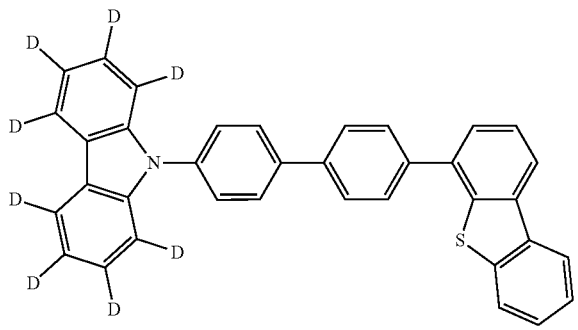

-continued
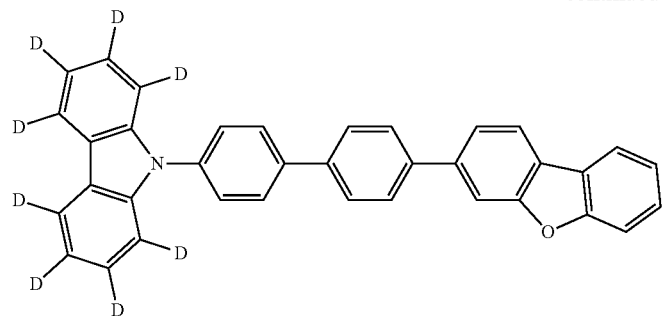
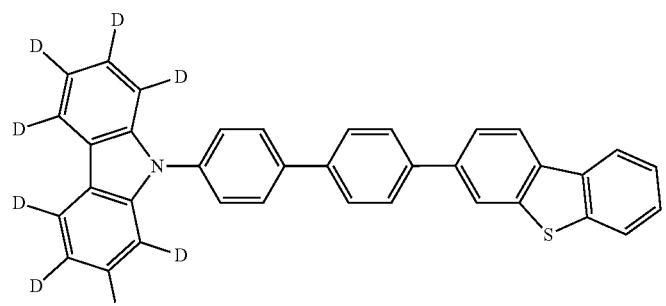
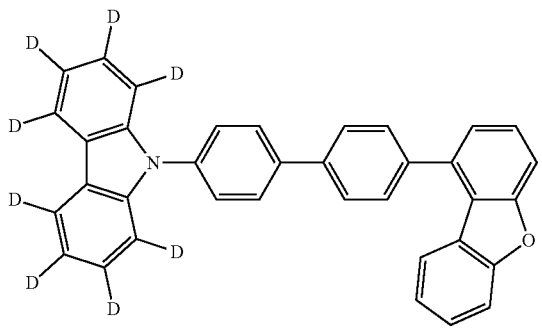
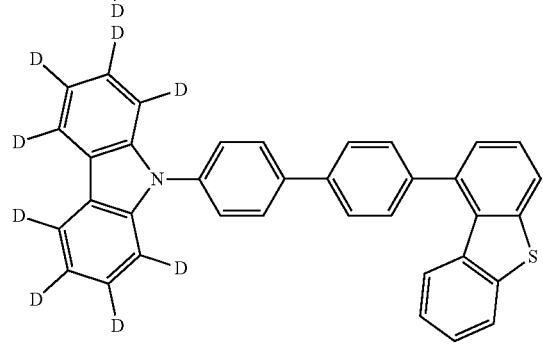
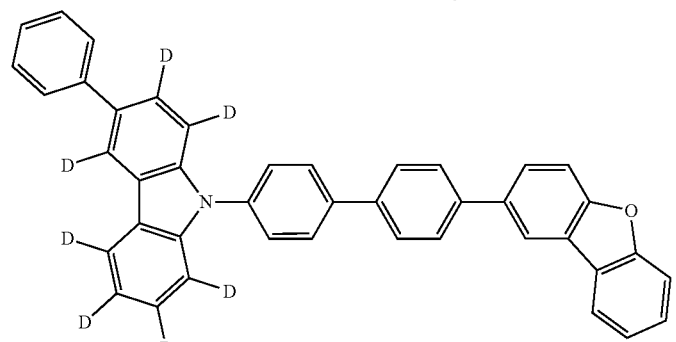
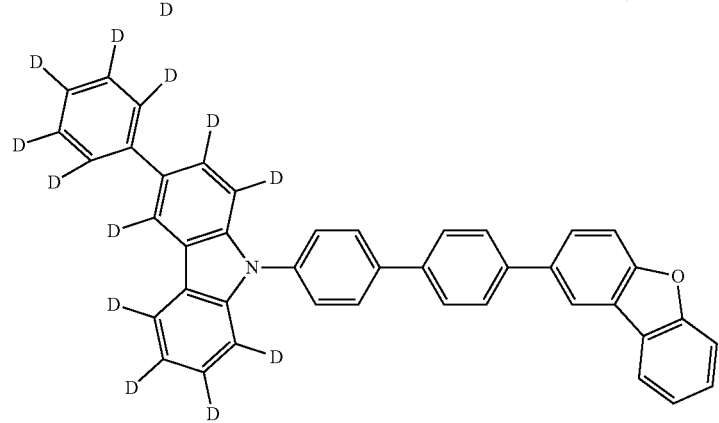

-continued
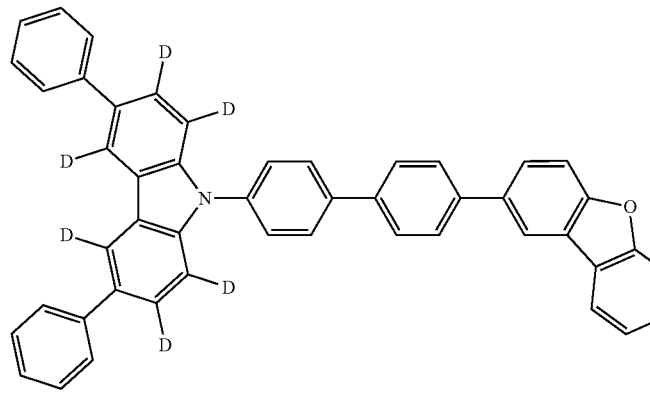
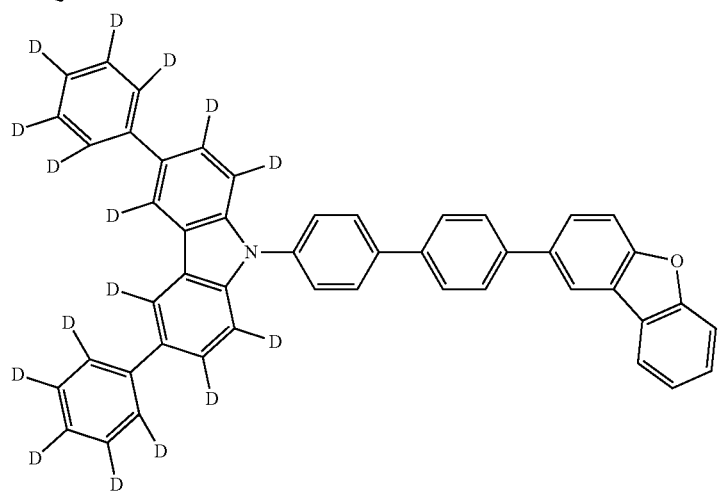
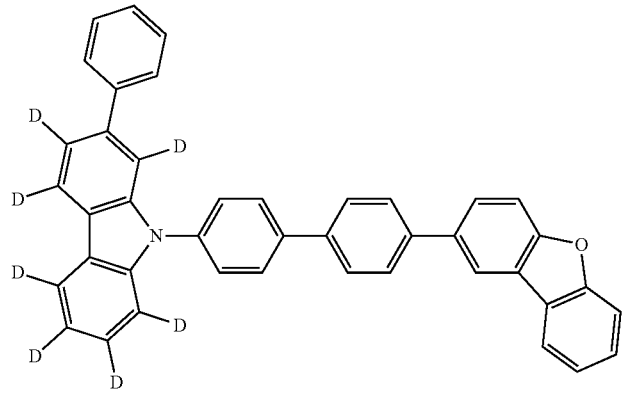
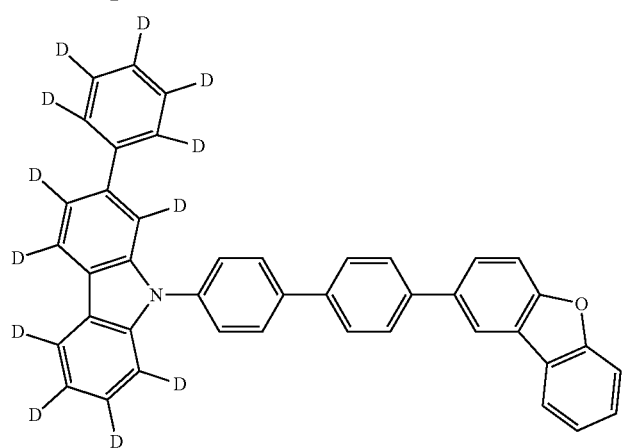

-continued
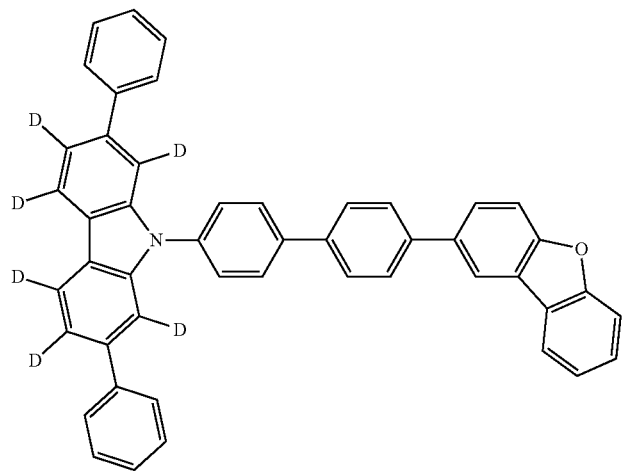
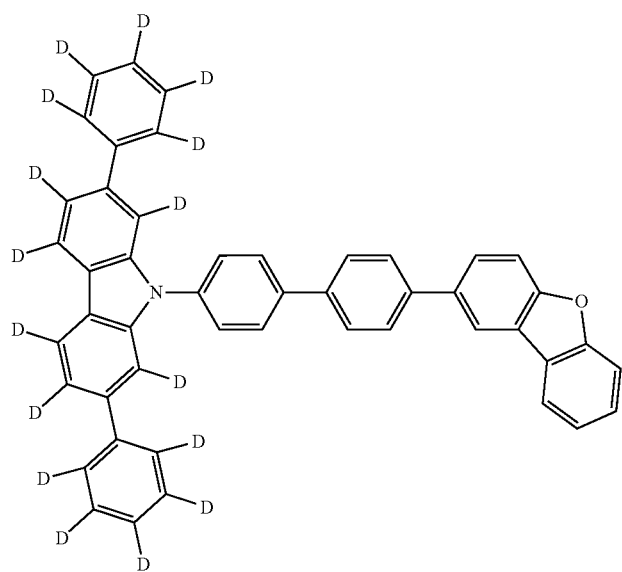
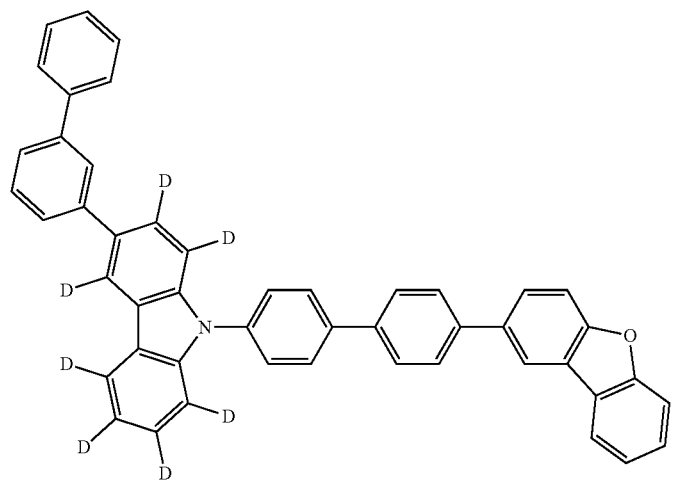

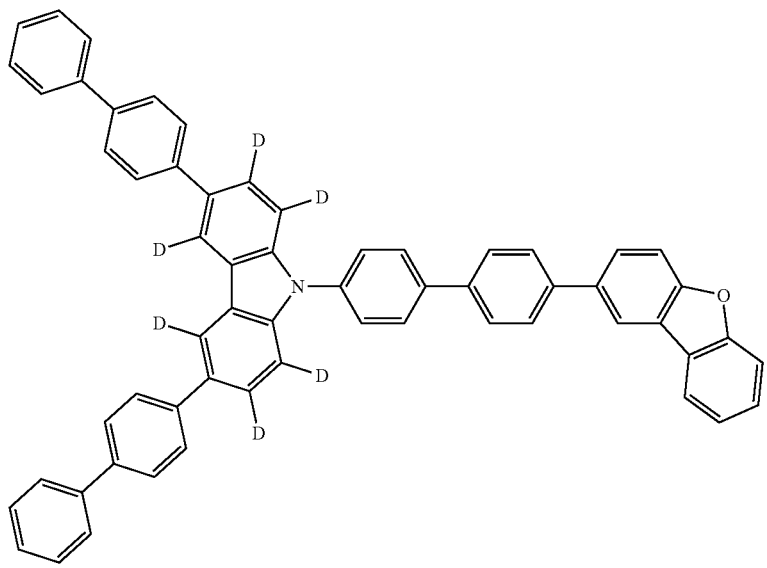
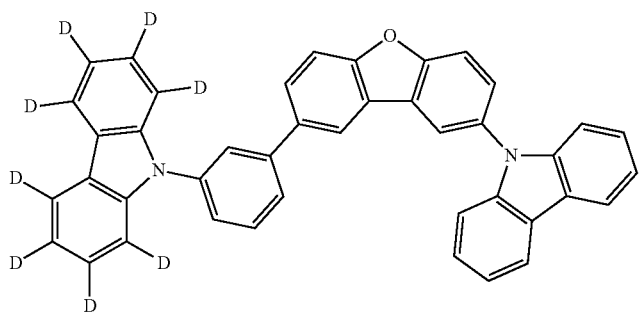
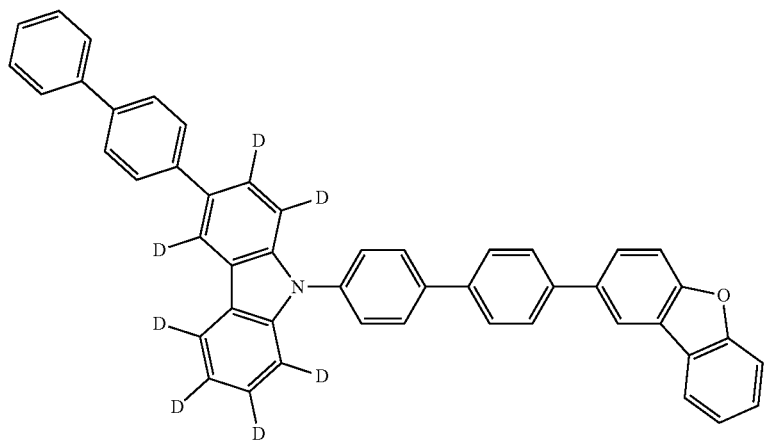

-continued
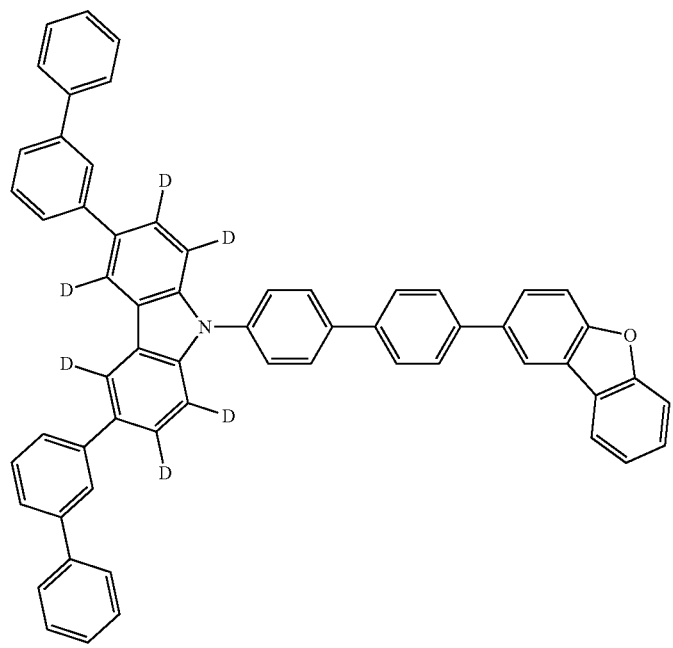
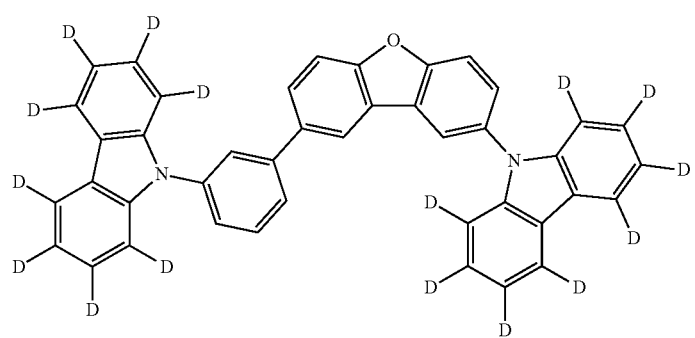
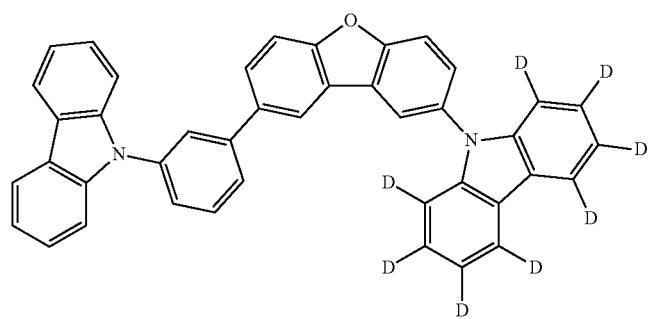

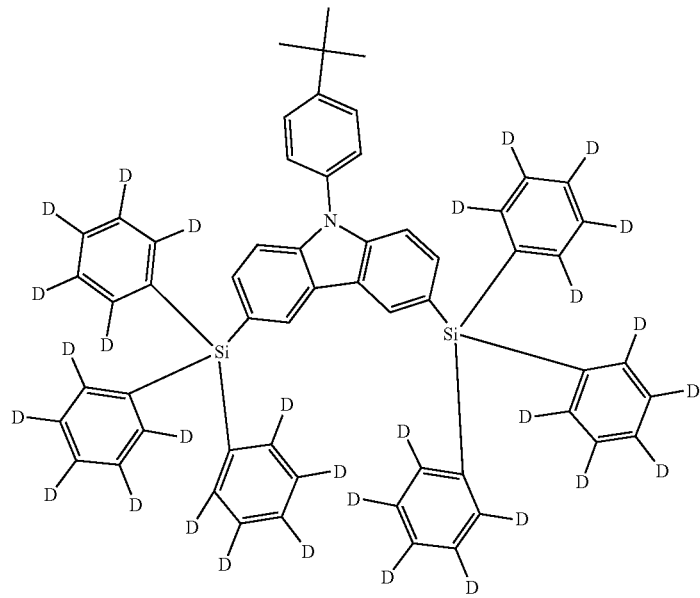
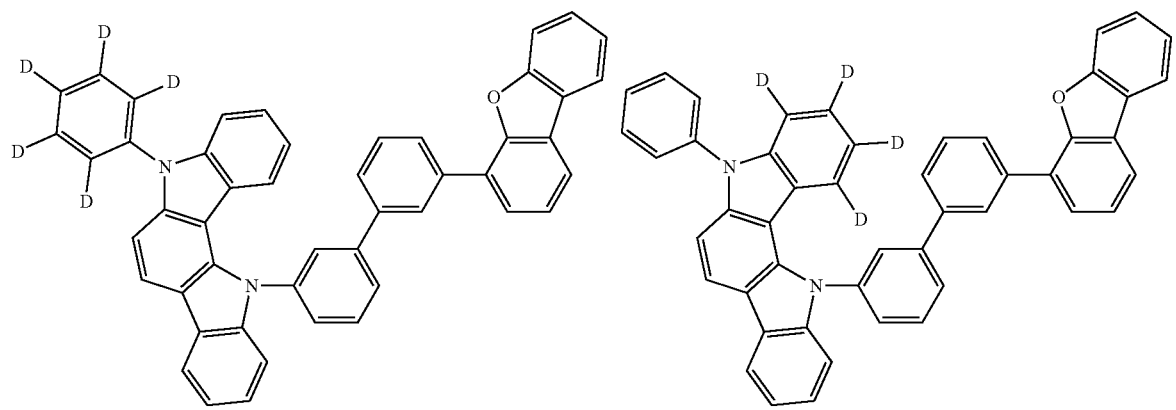
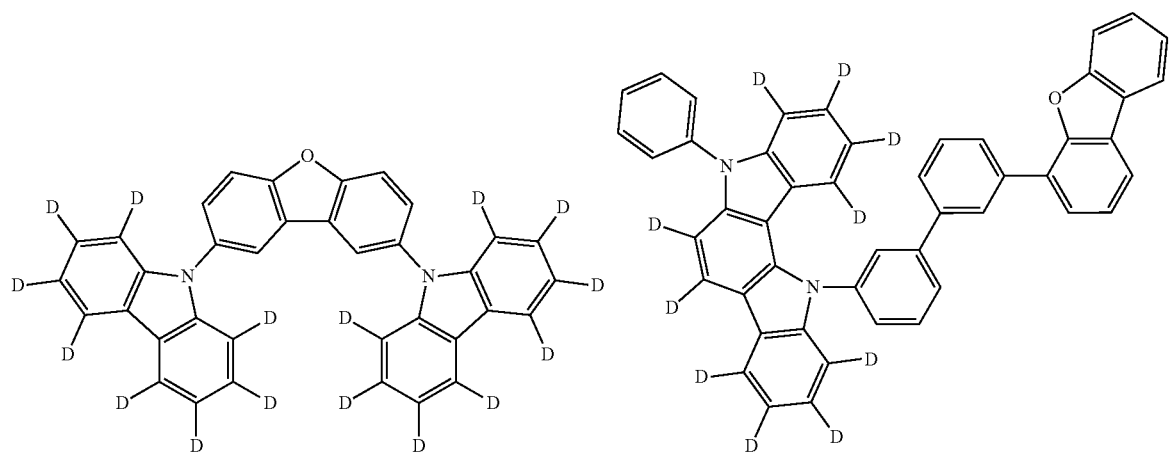

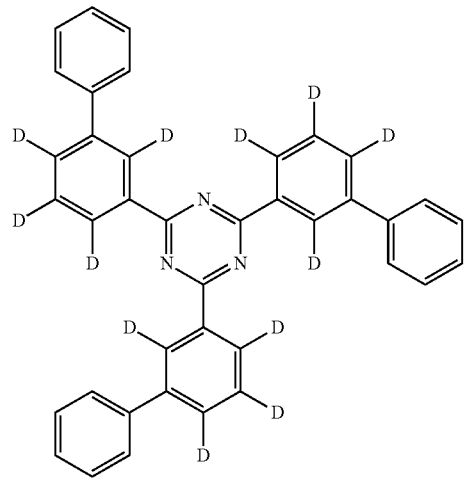
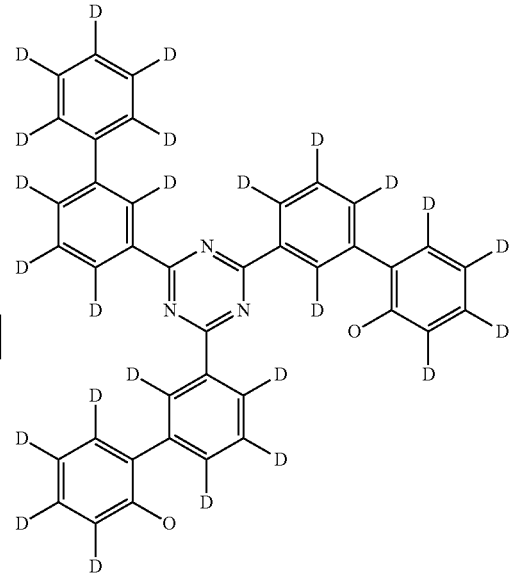
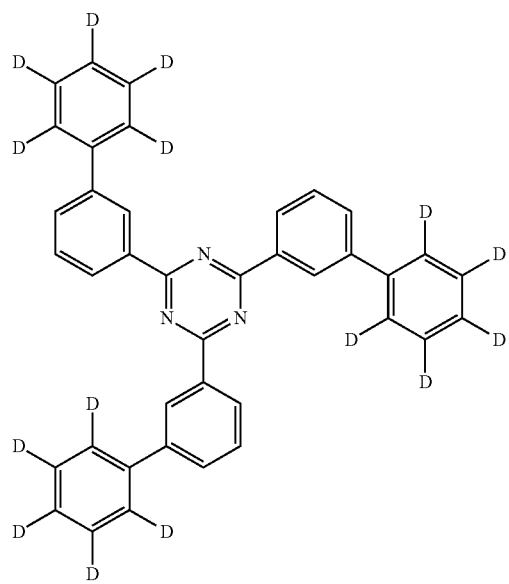
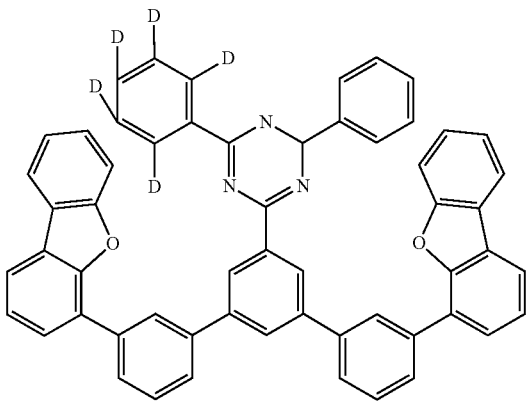
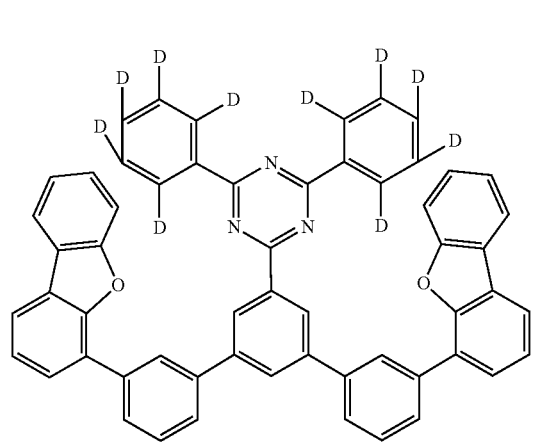
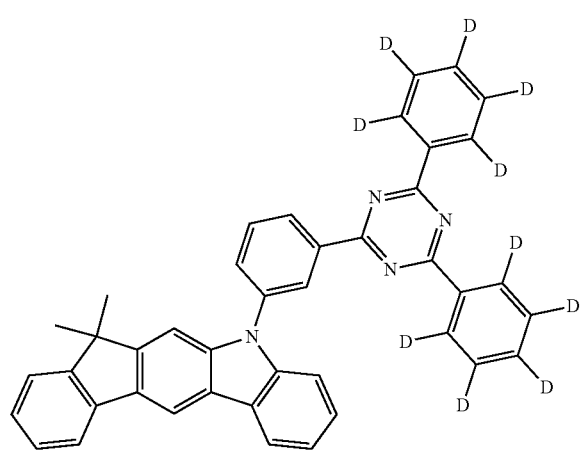

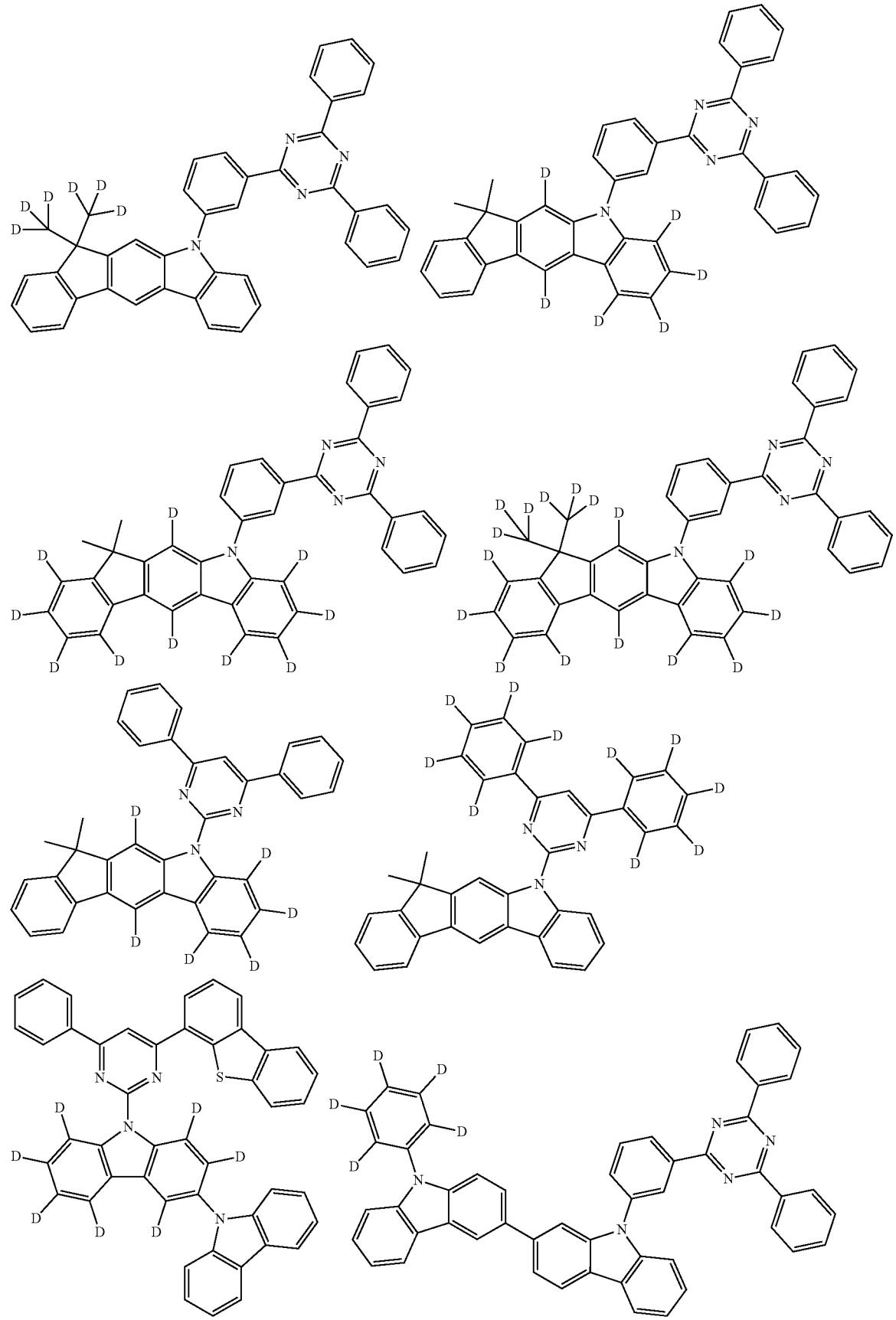

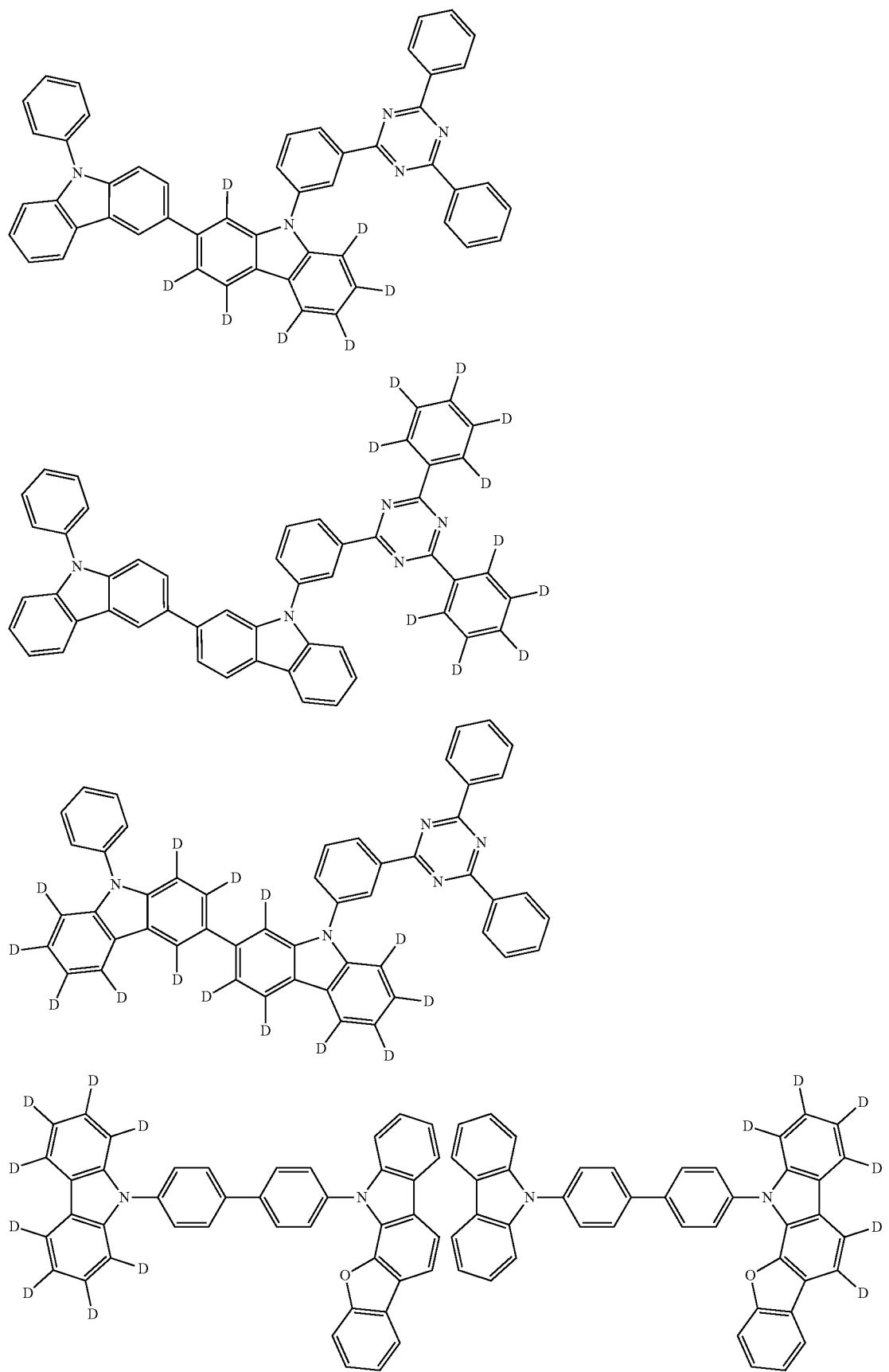

-continued
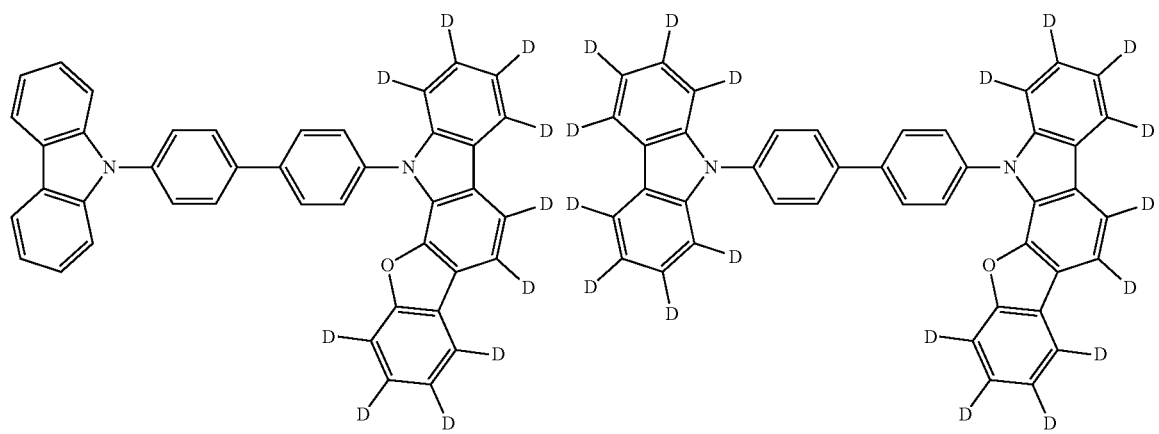
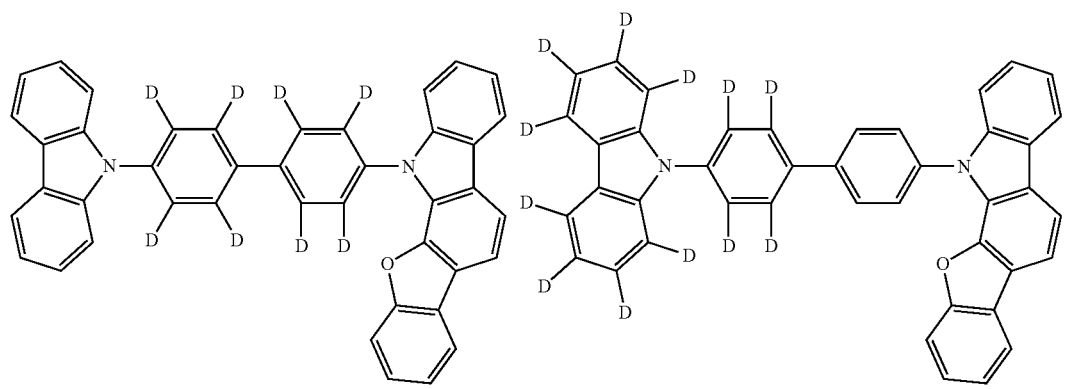
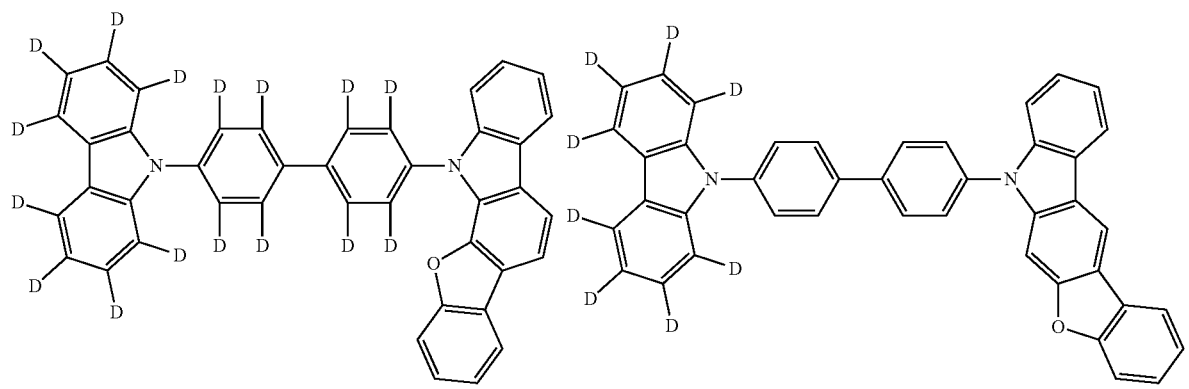
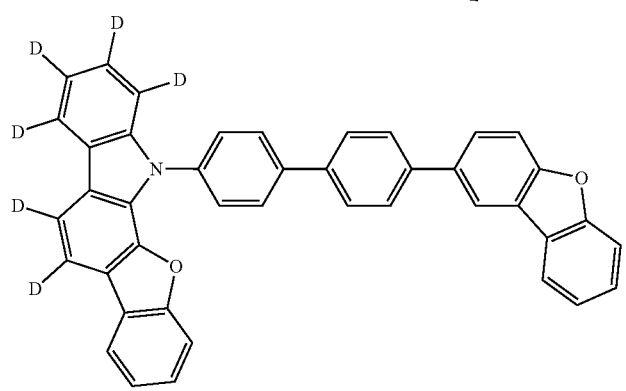

-continued
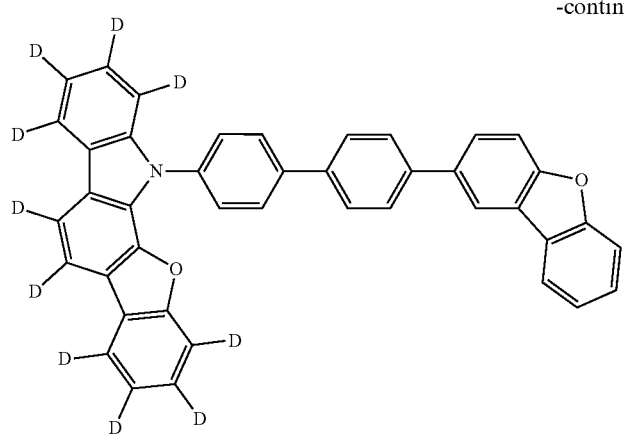
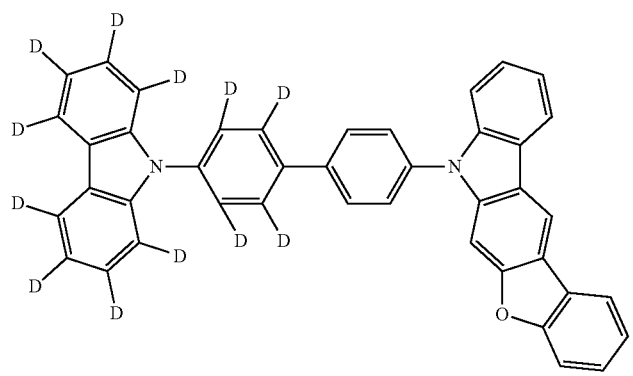
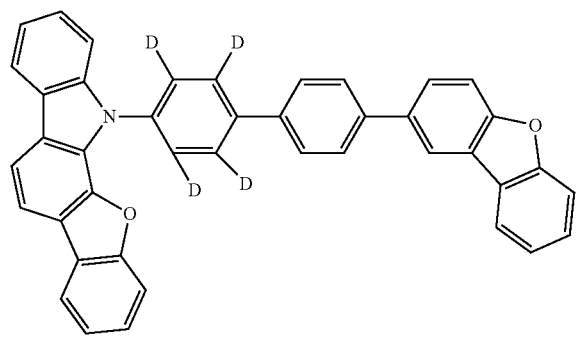
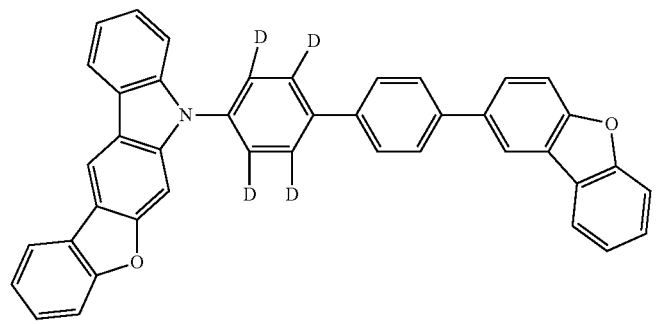

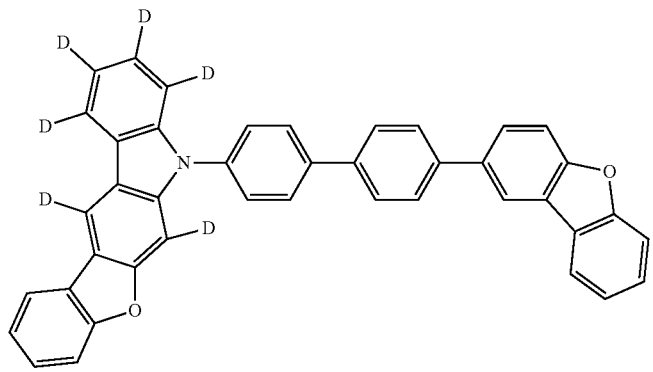
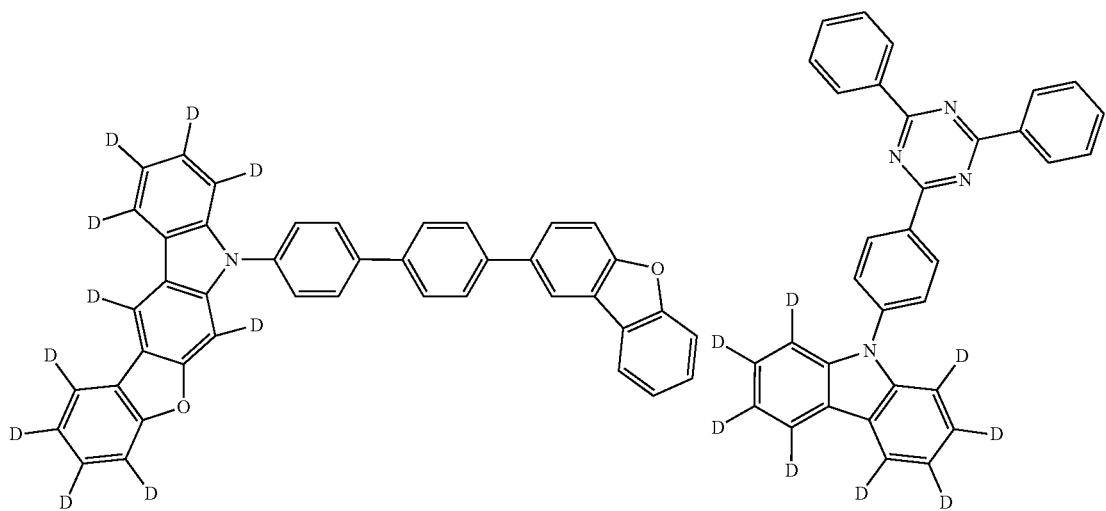
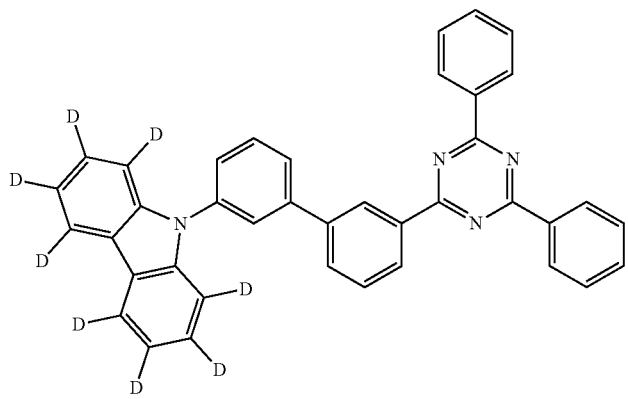

-continued
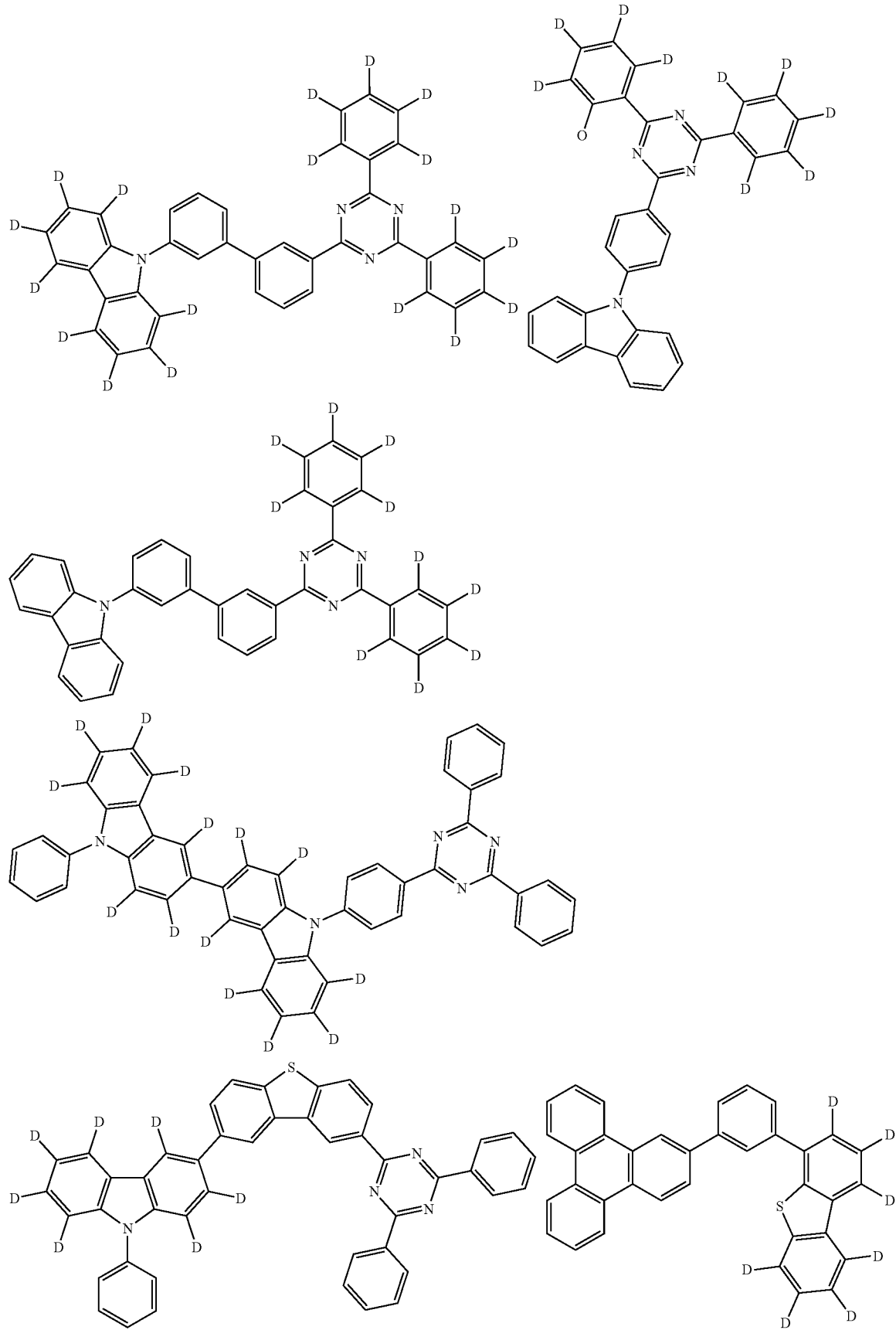

-continued
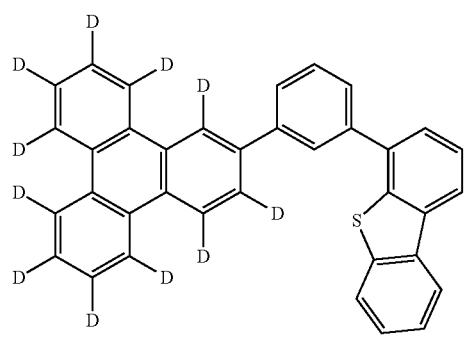
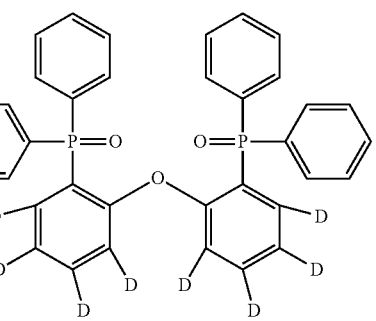
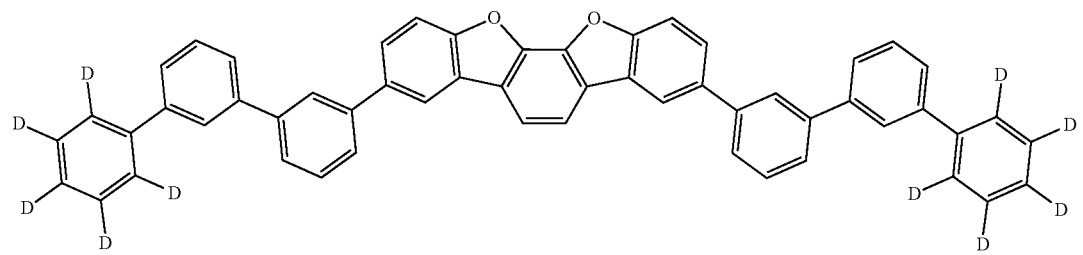
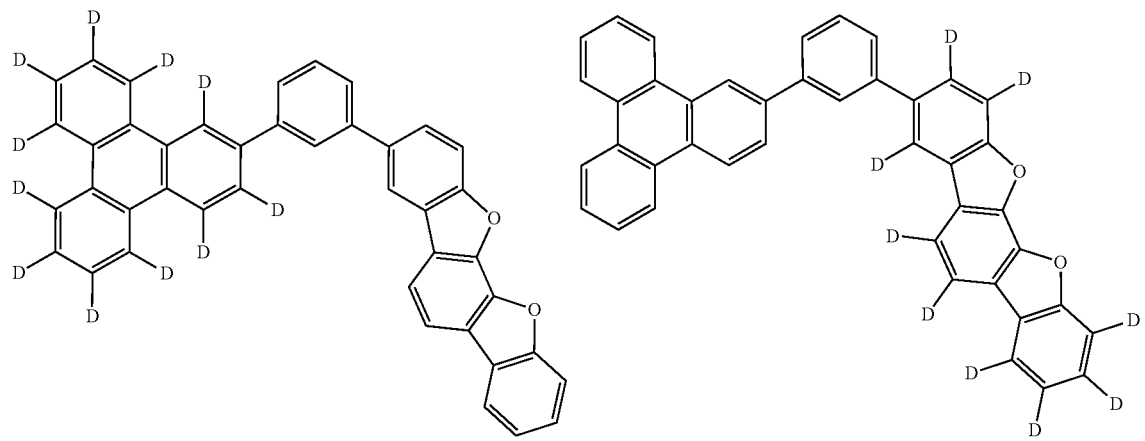
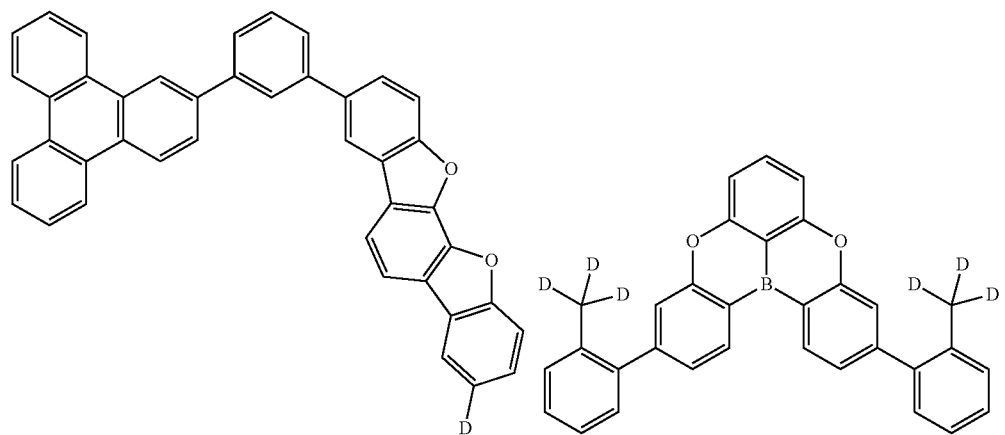

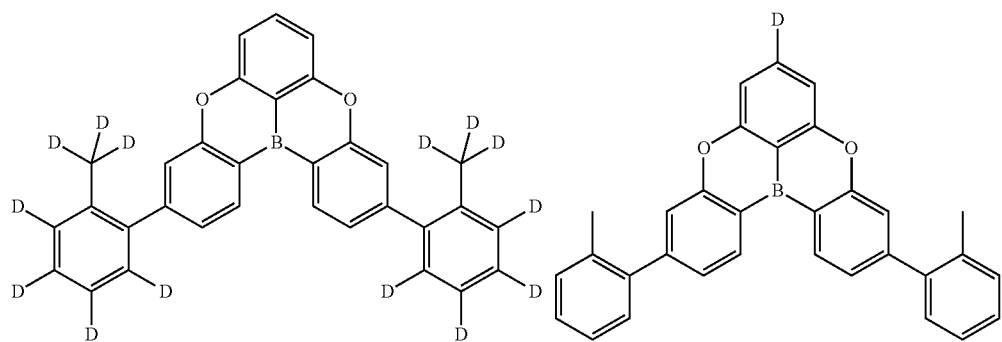
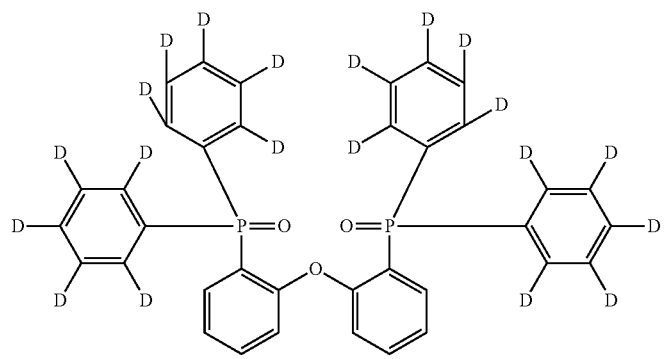
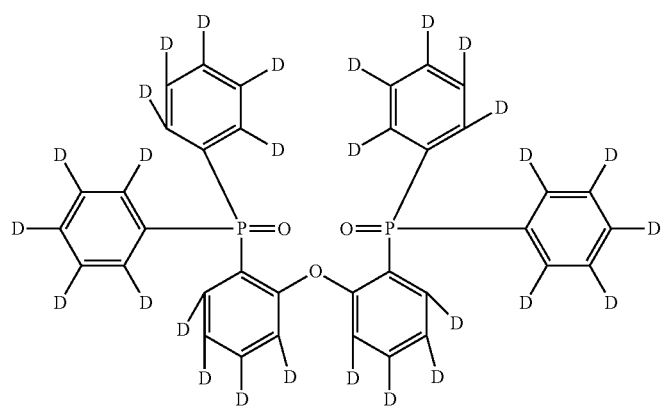
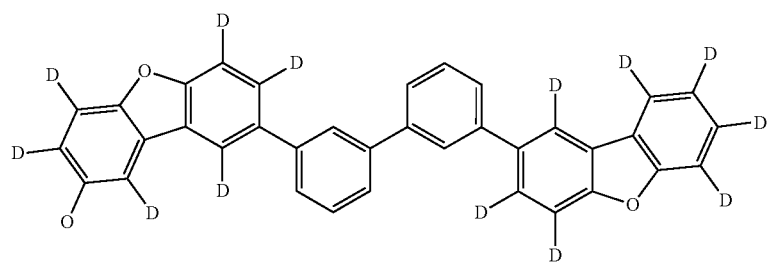

-continued
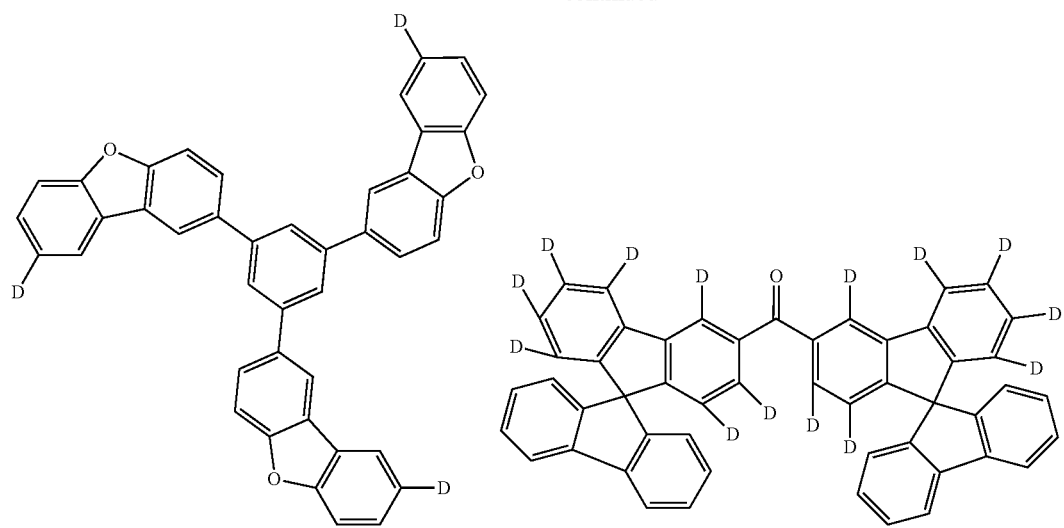
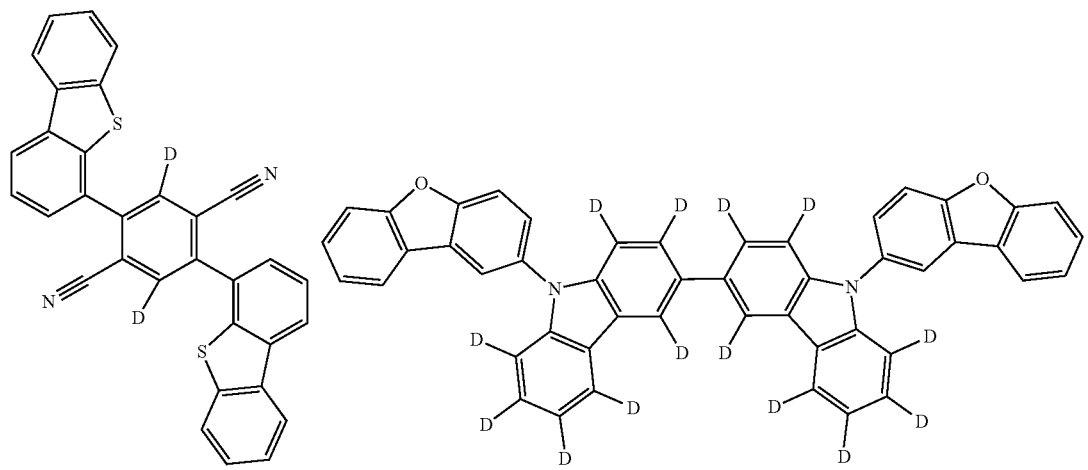
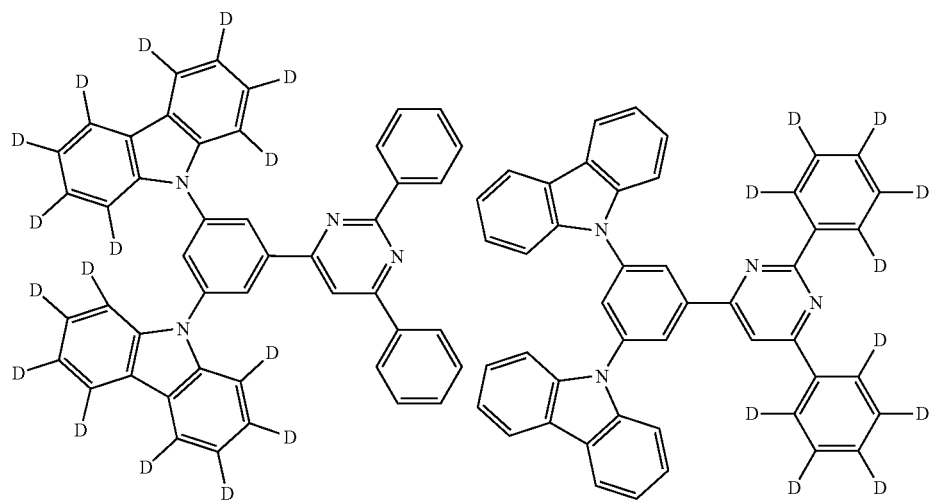

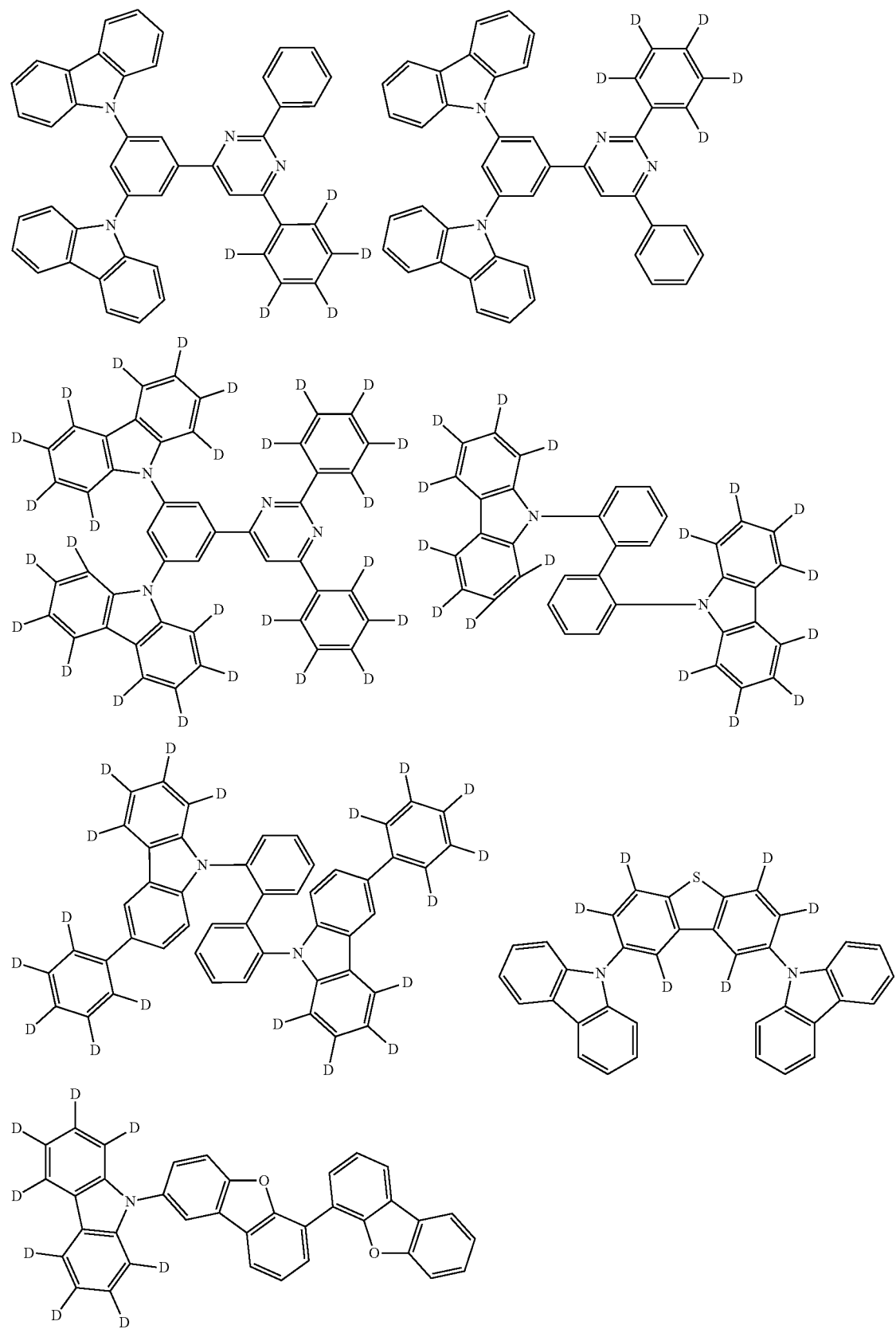

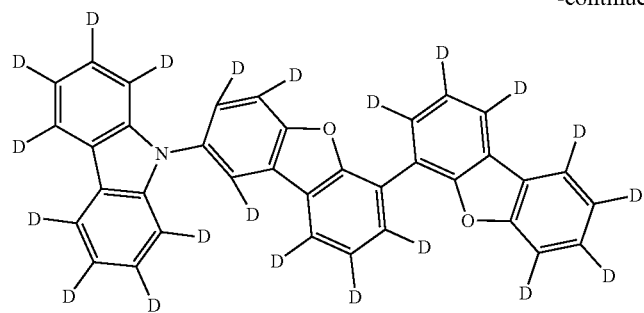
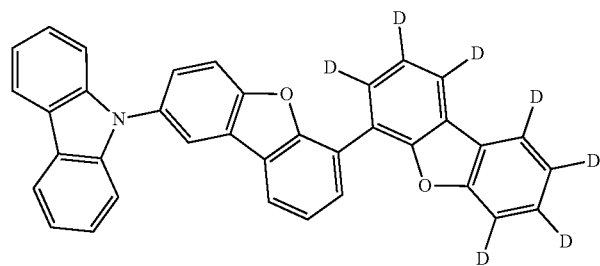
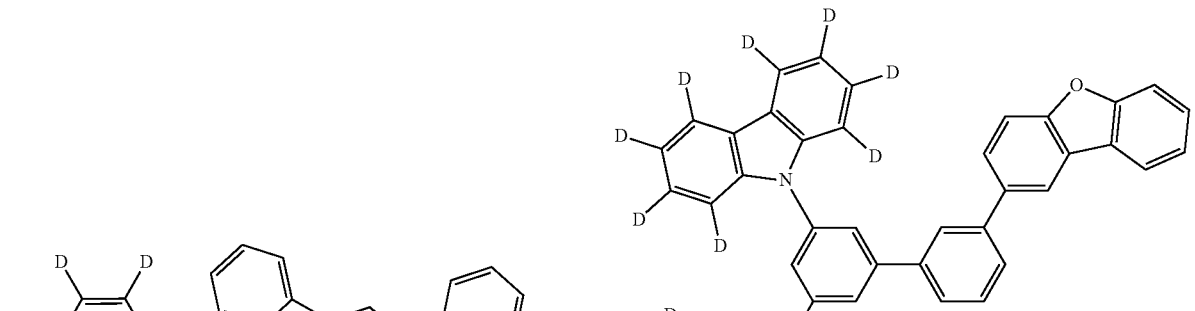
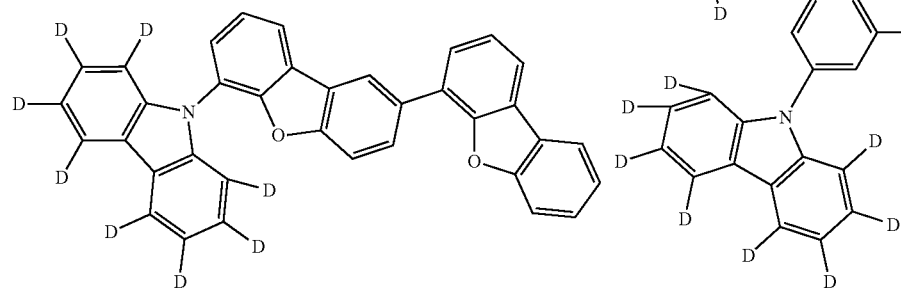
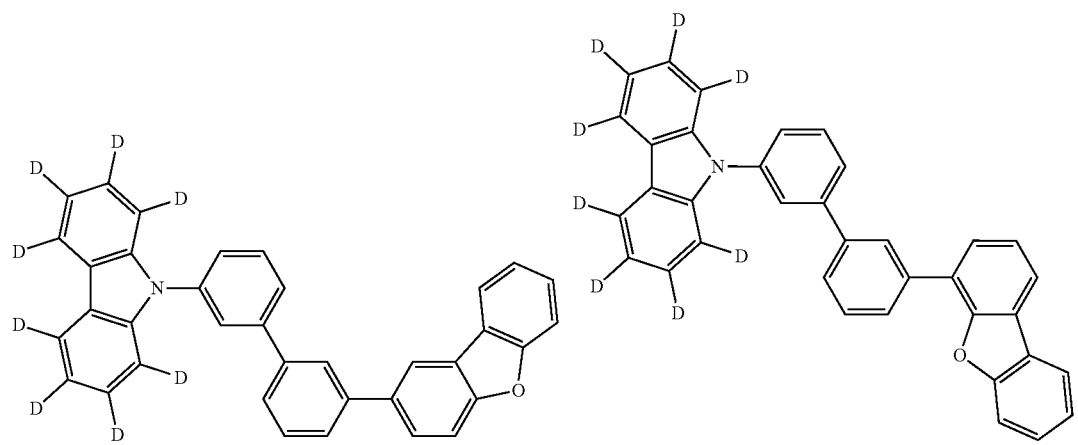

-continued
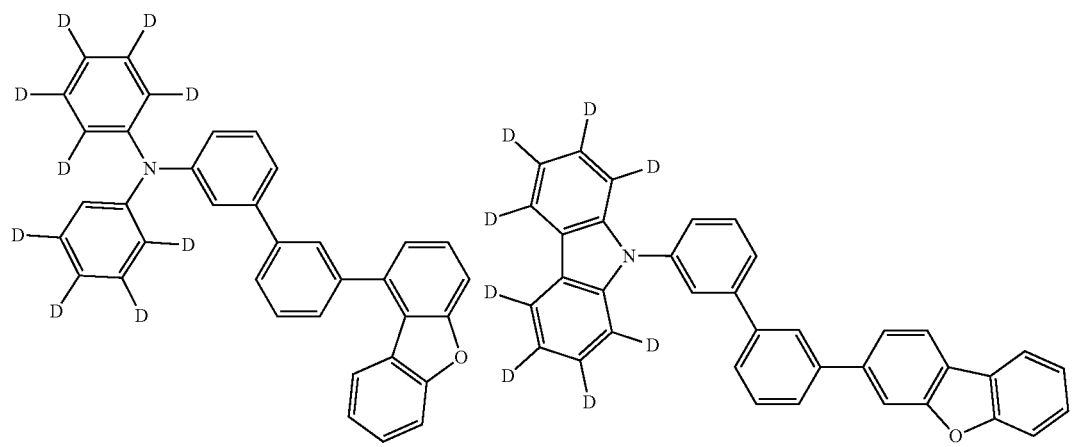
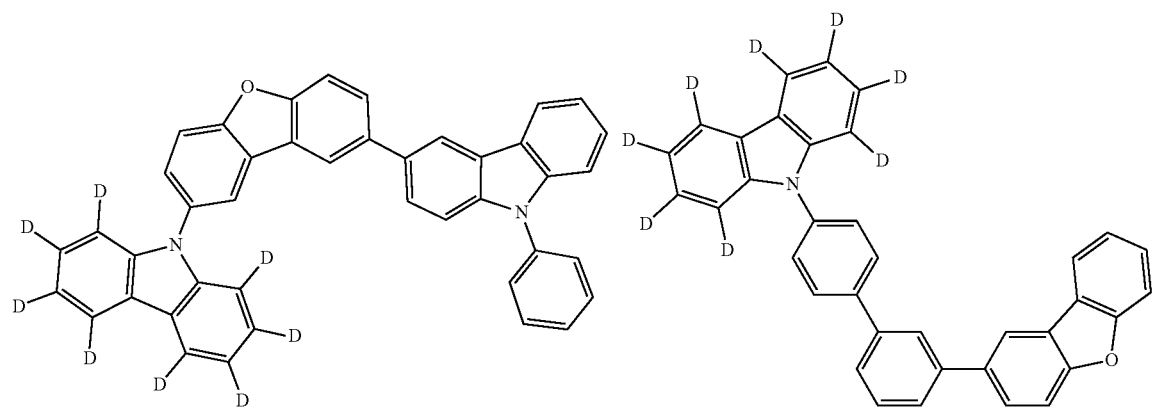
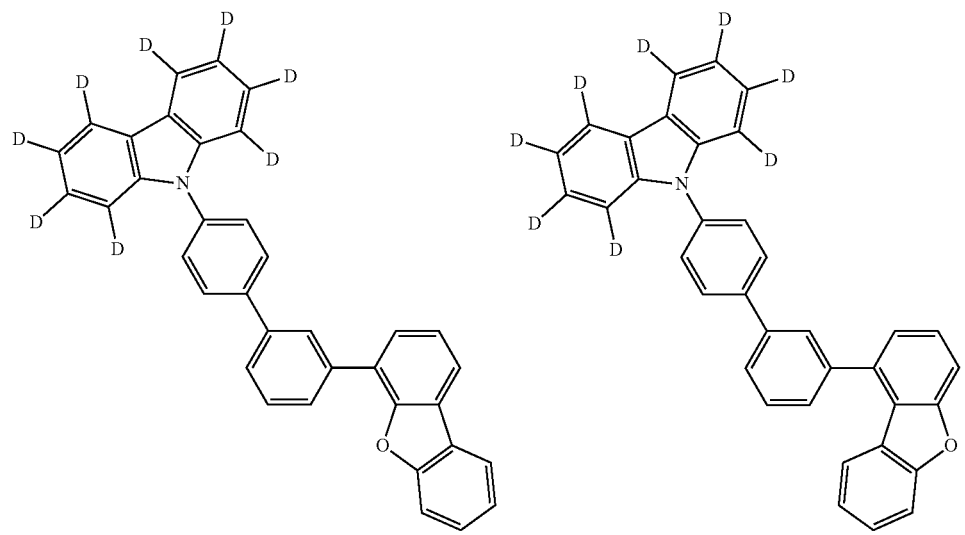

-continued
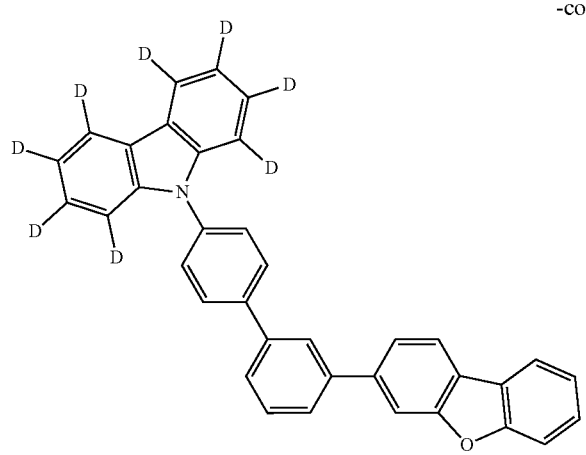
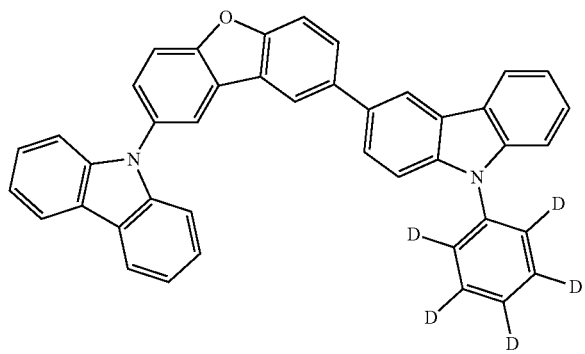
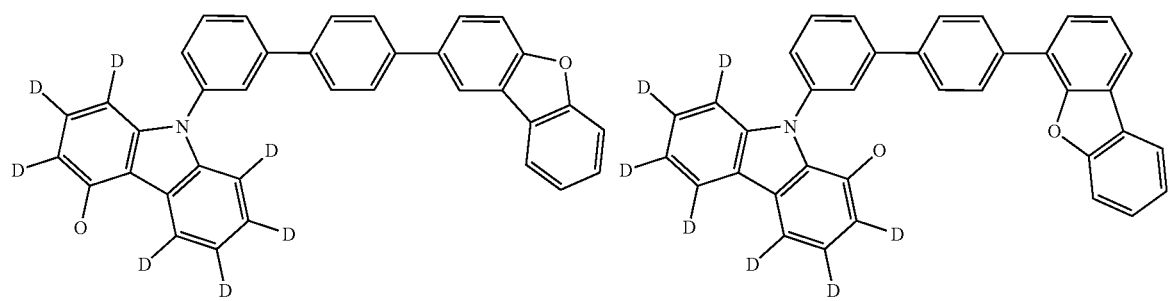
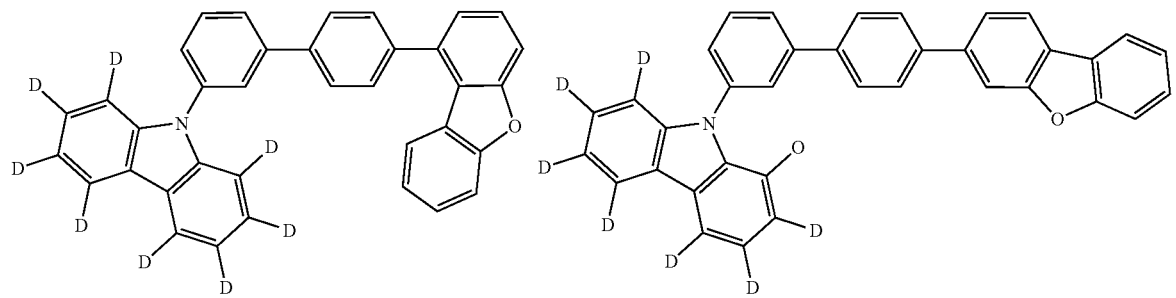
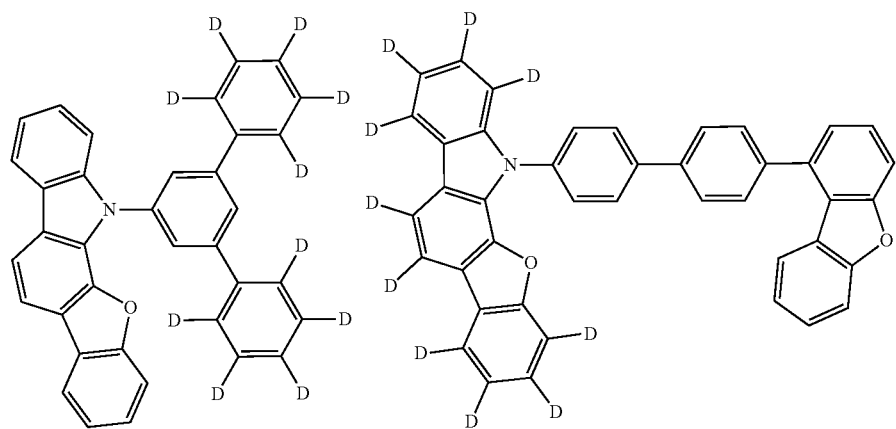

-continued
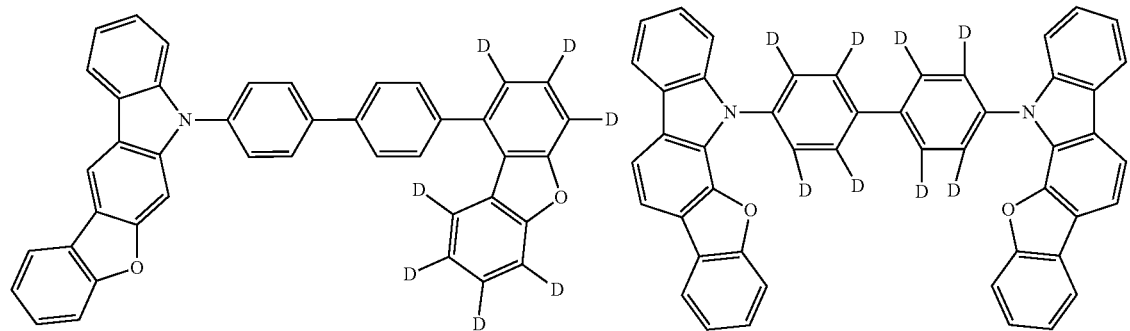
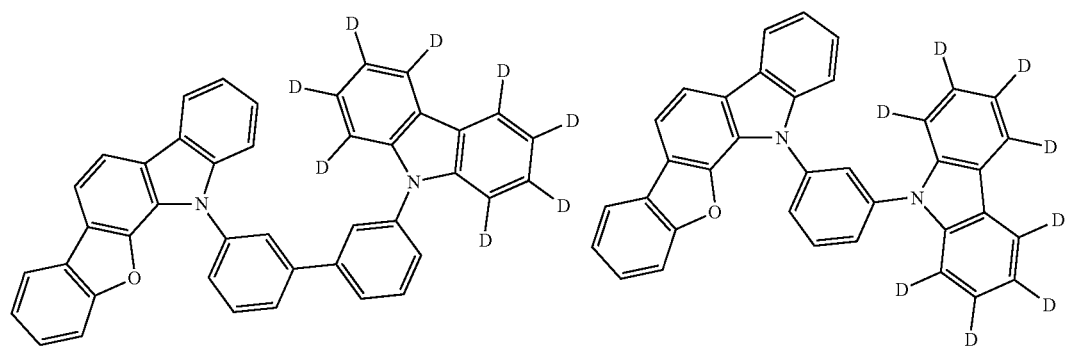
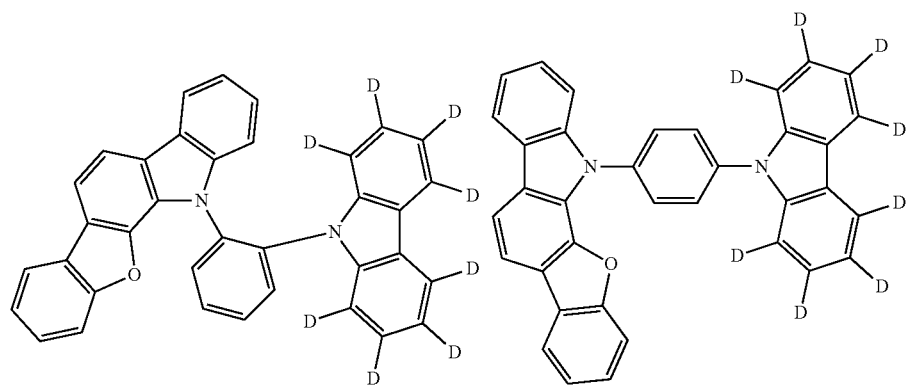
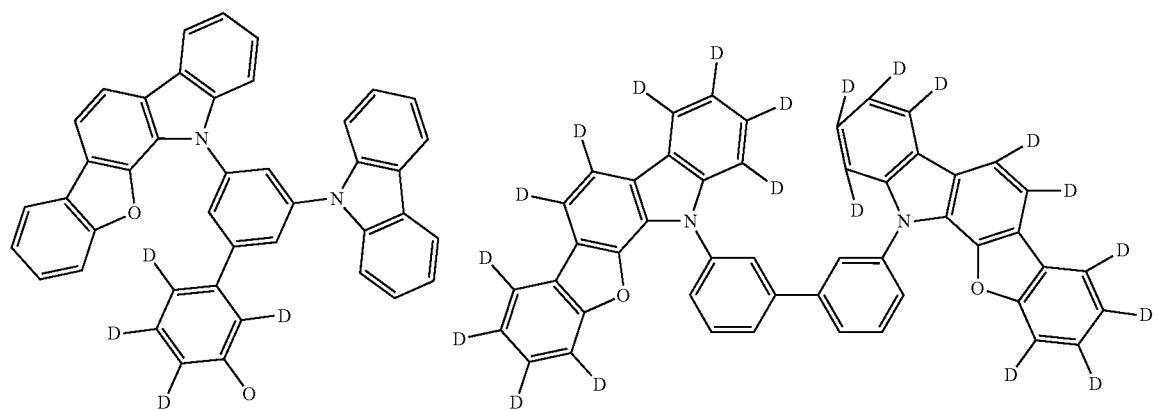

-continued
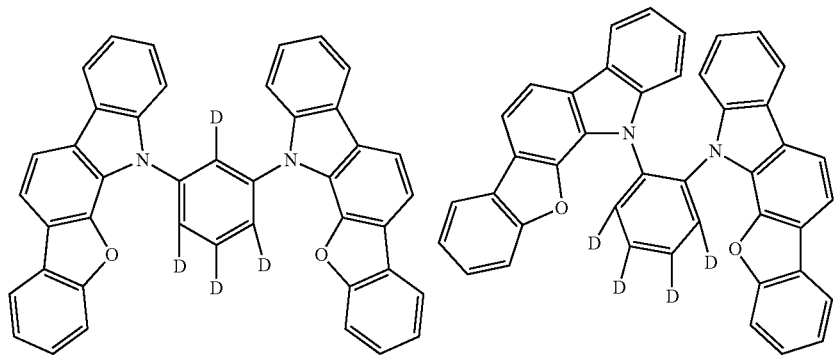
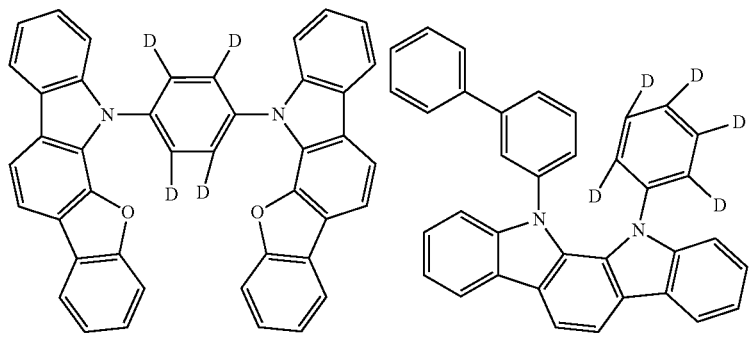
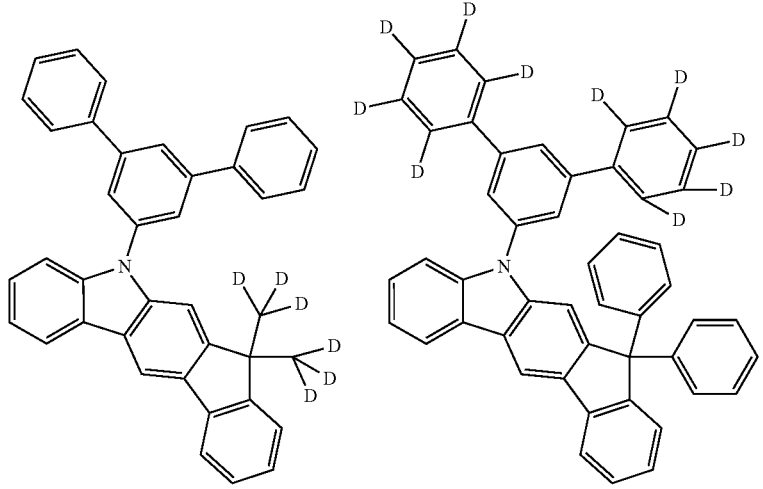
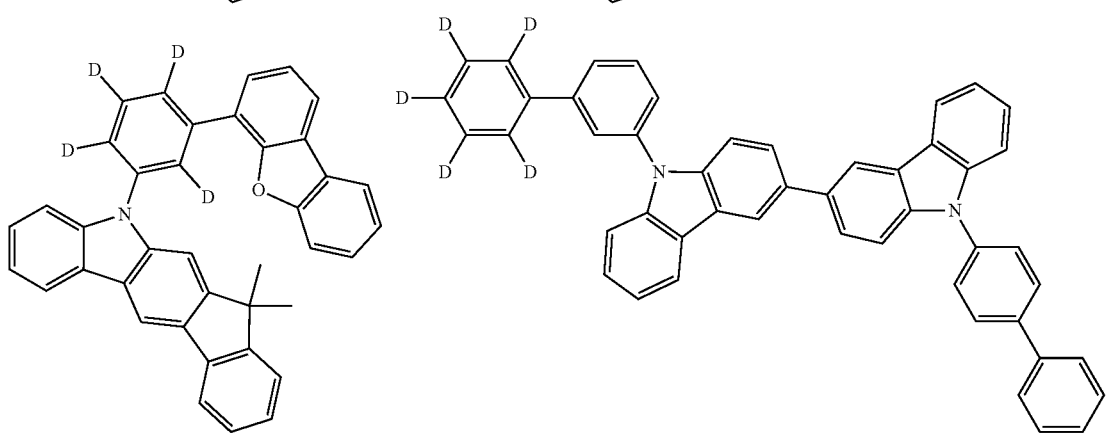

-continued
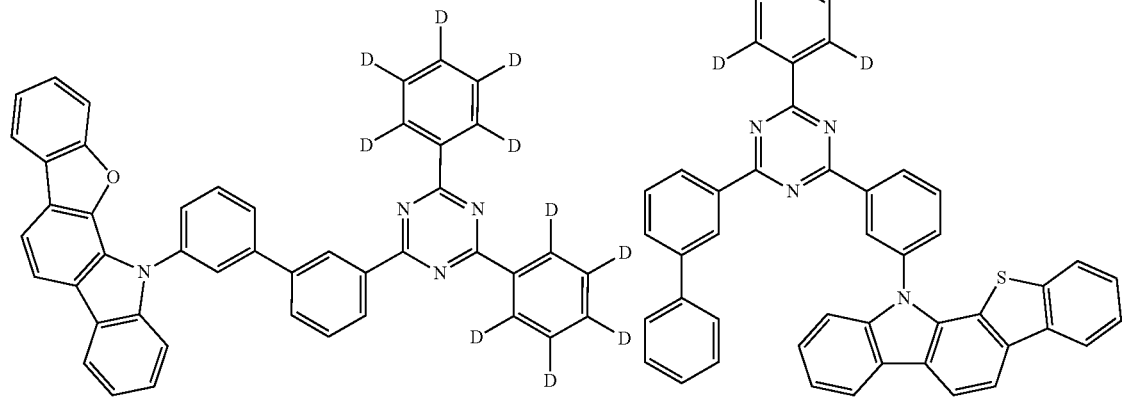
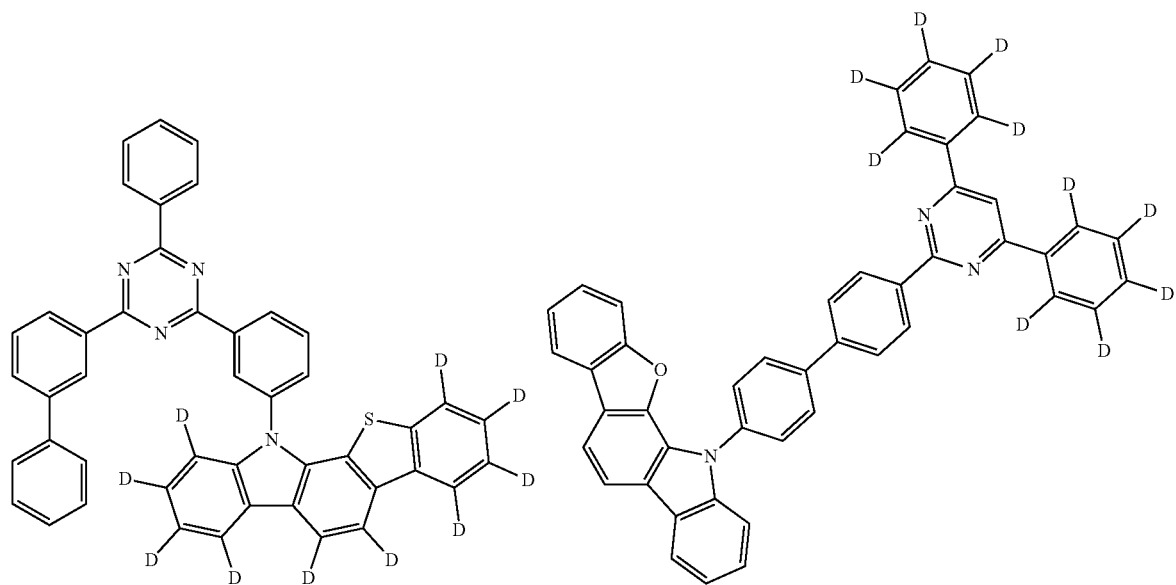
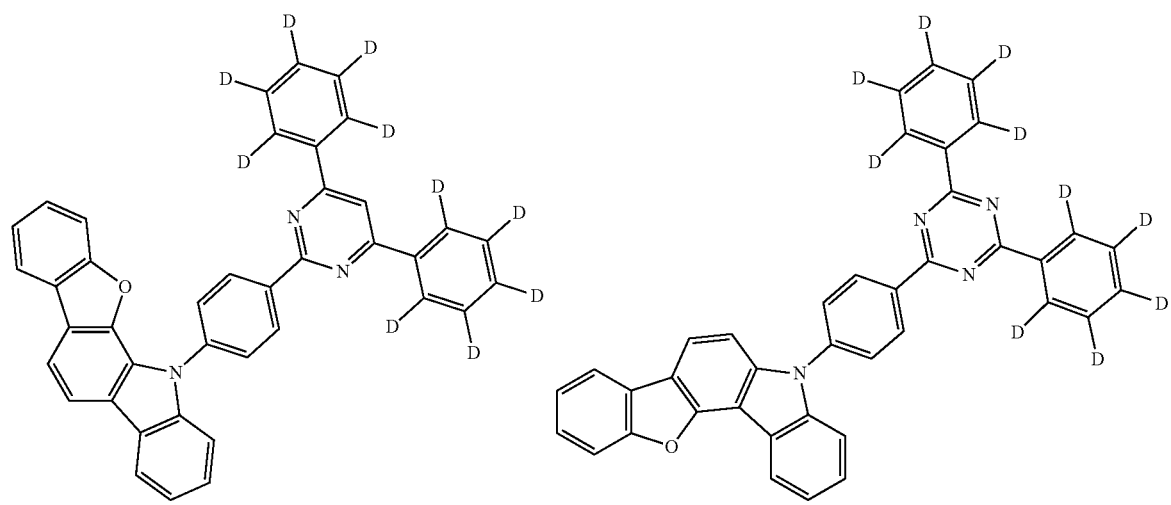

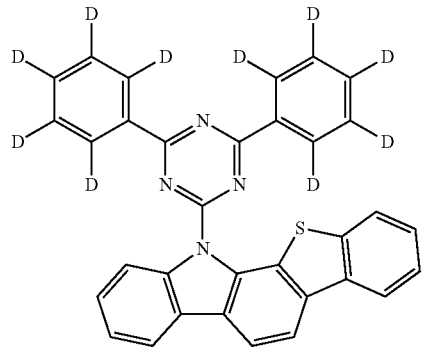
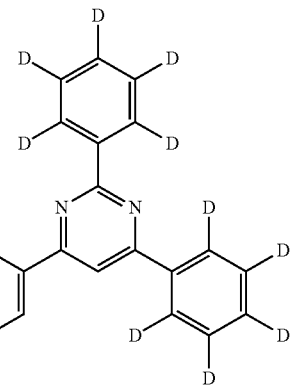
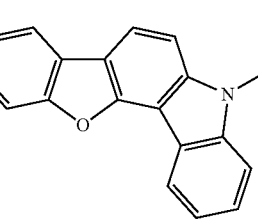
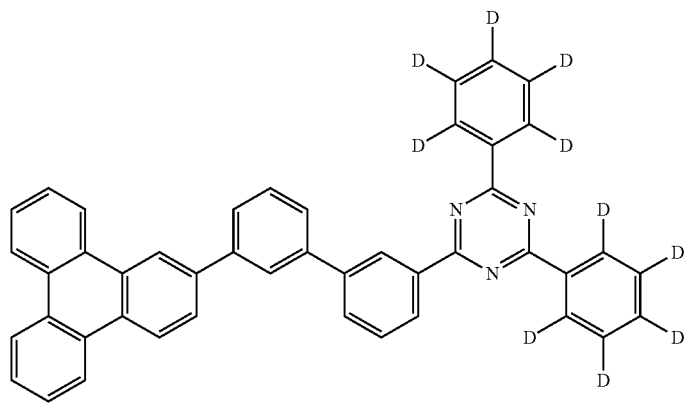
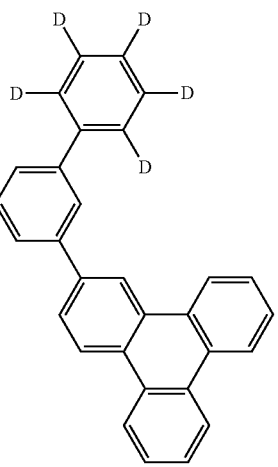
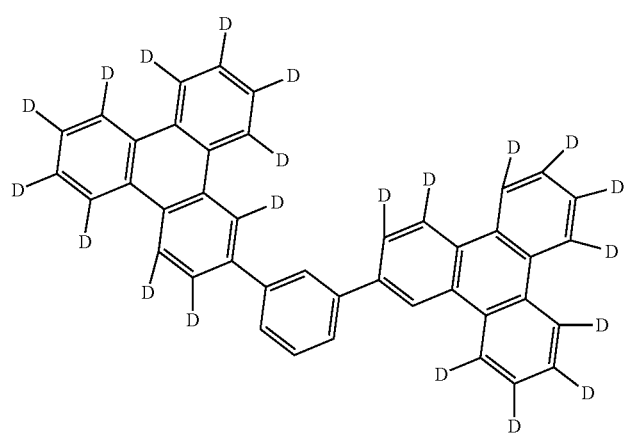

-continued
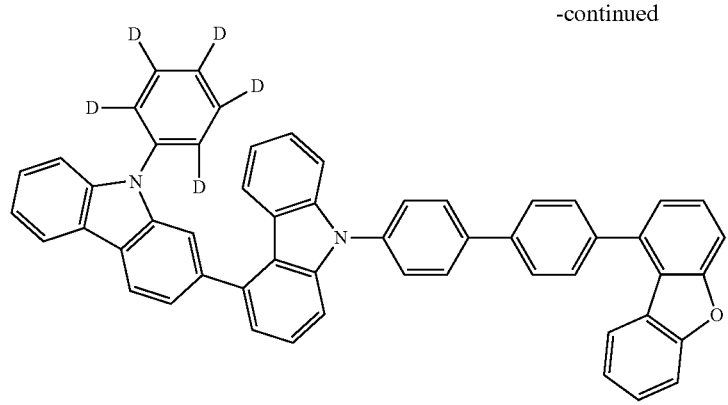
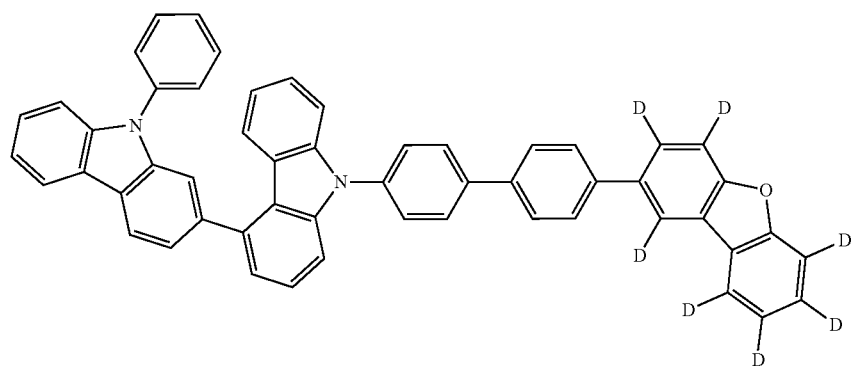
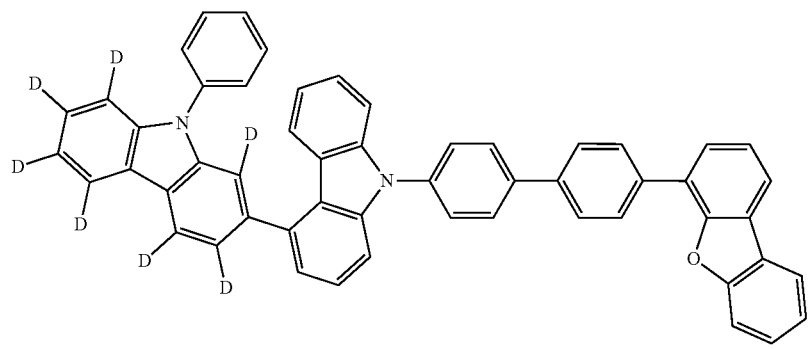
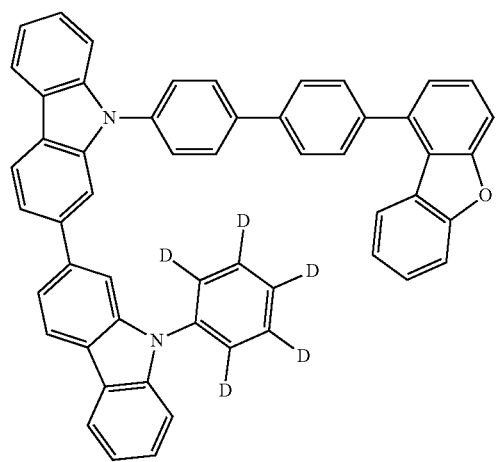

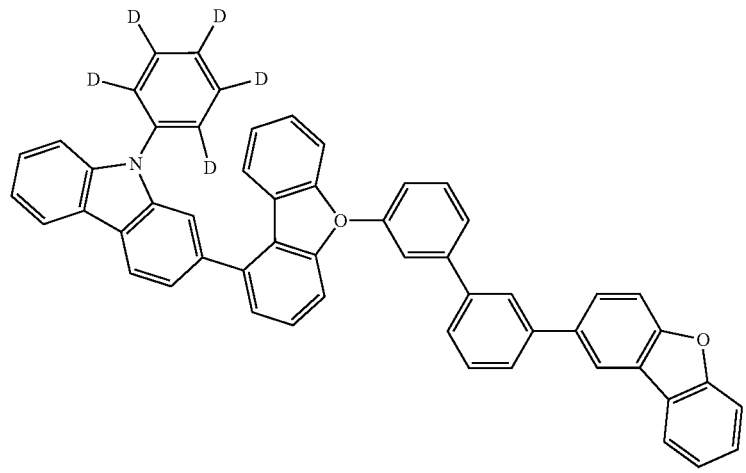
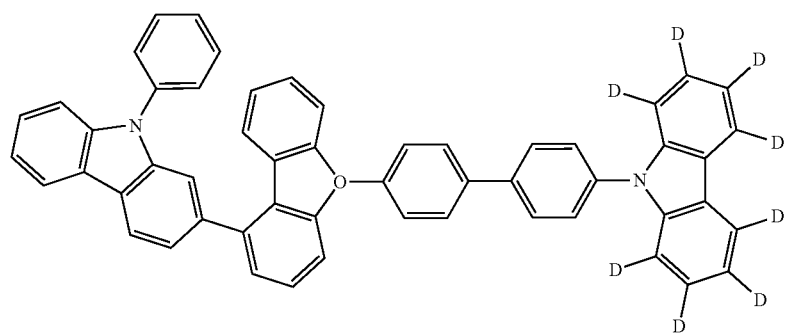
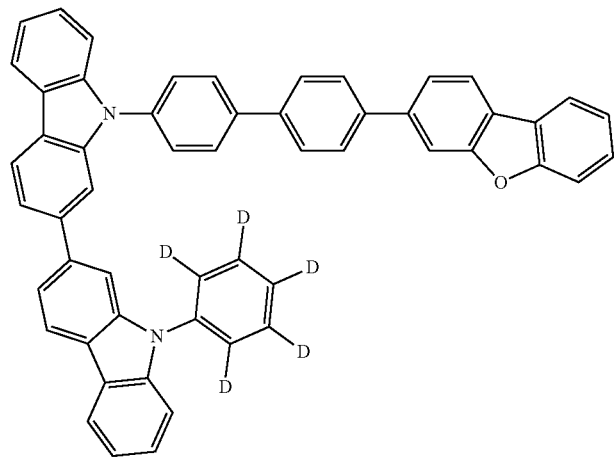
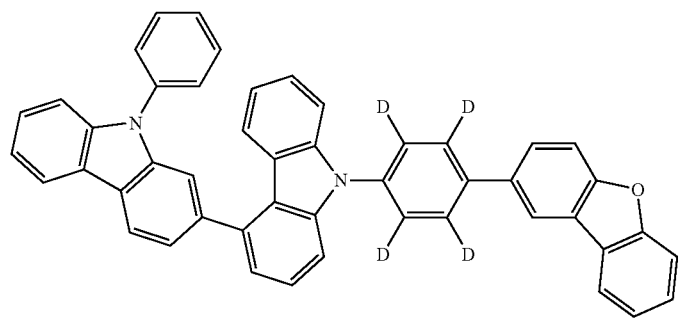

-continued
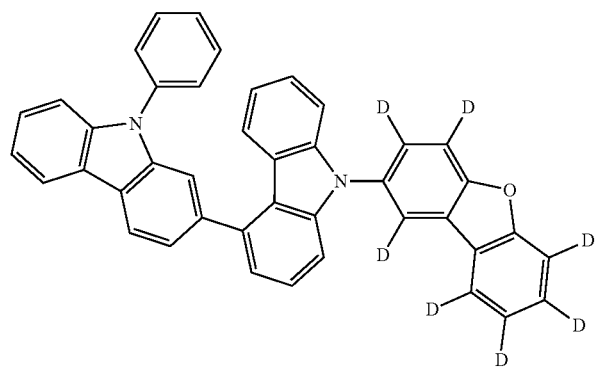
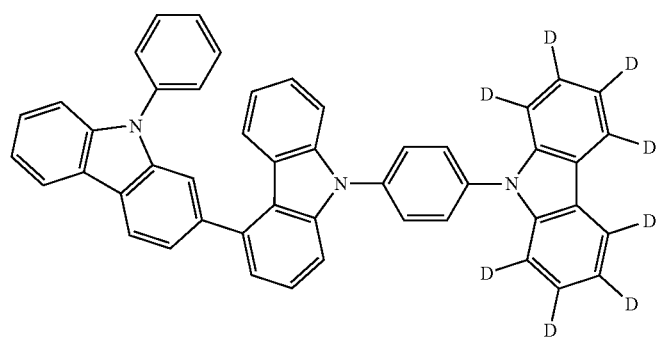
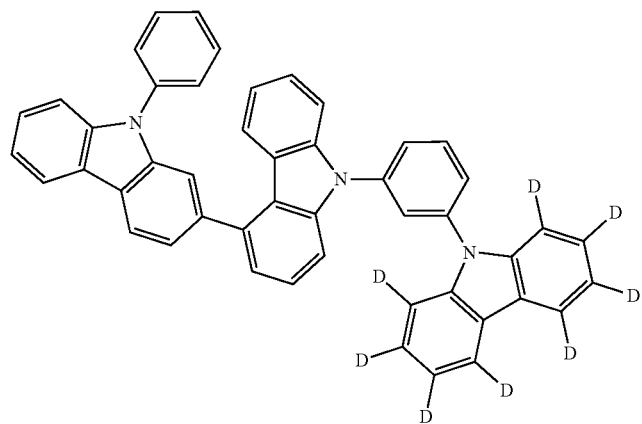
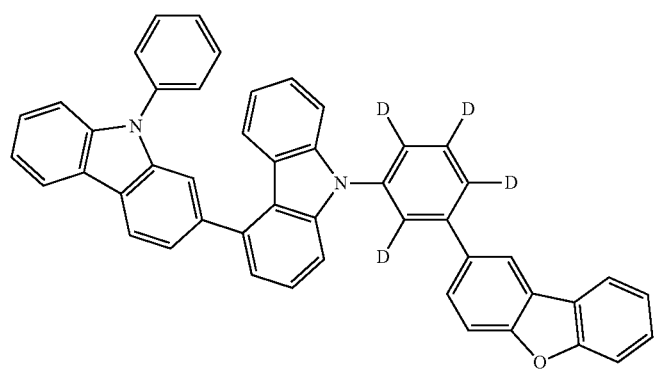

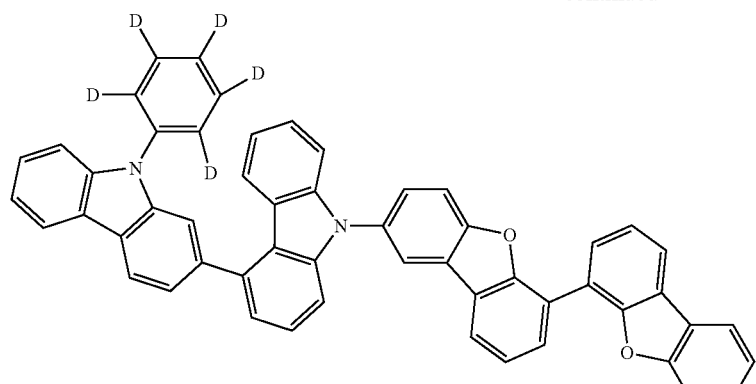
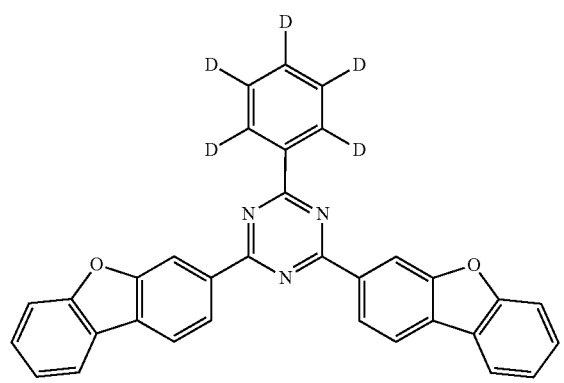
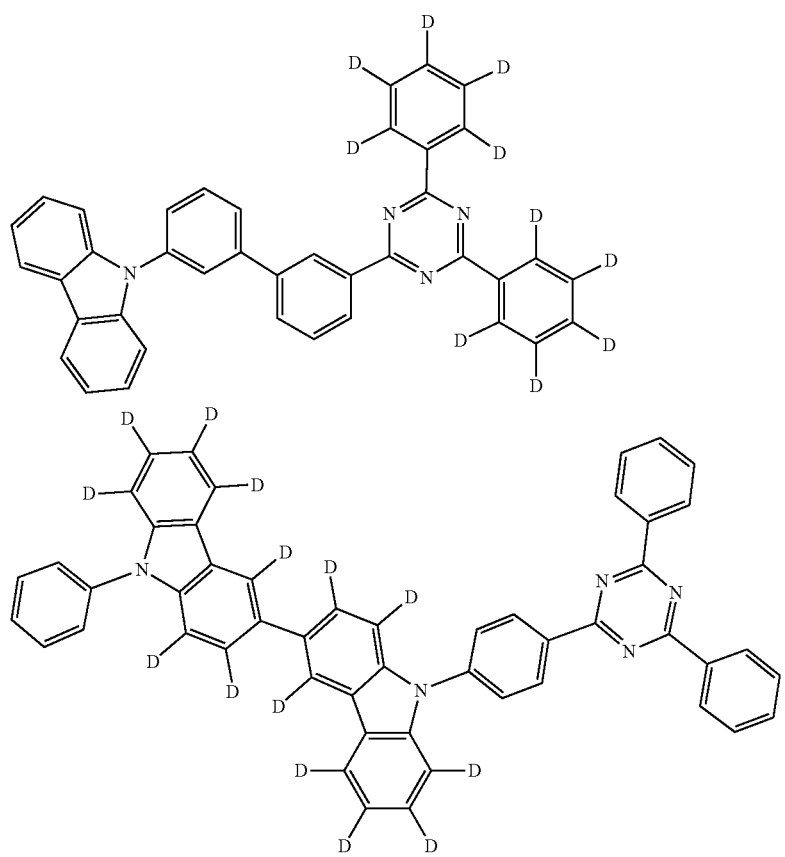

177
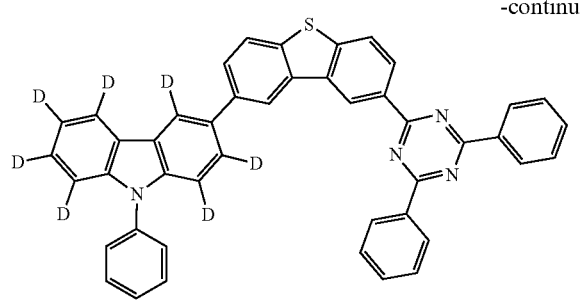
178
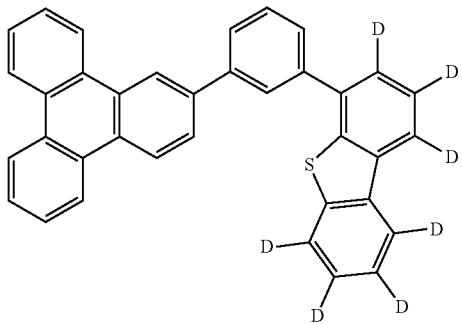
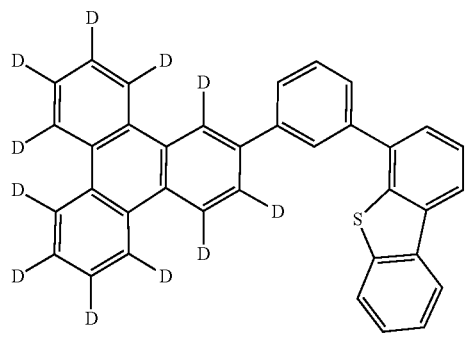
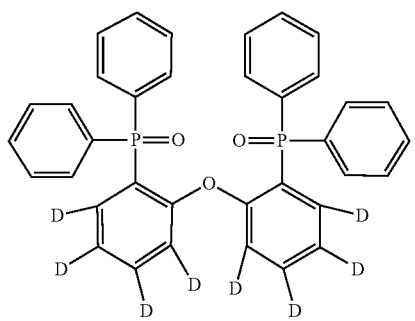
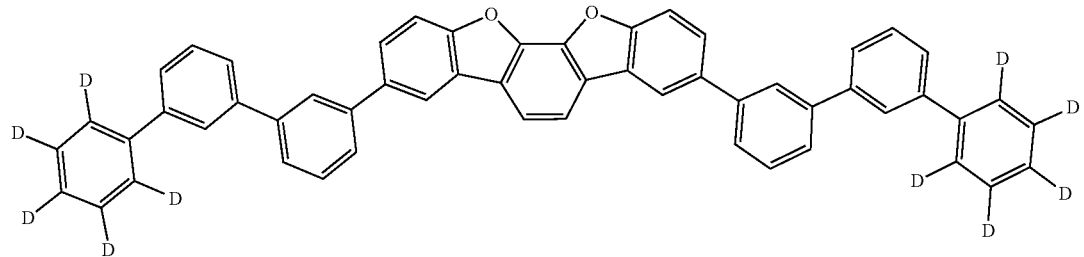
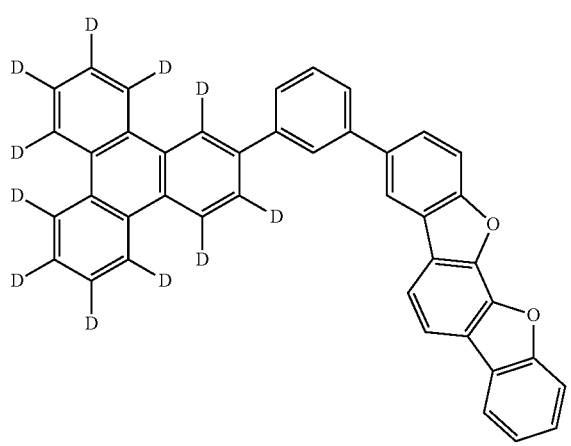
-continued
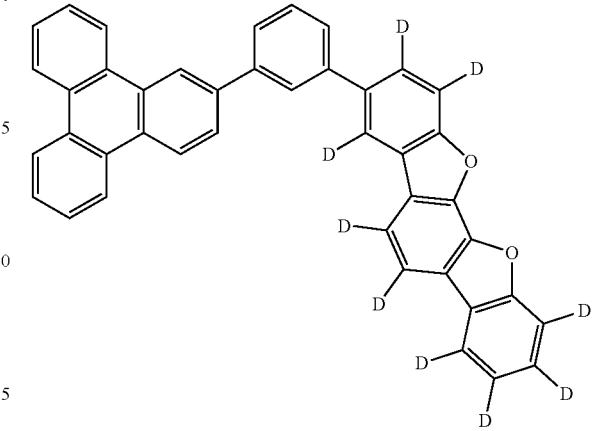

179
-continued
180
-continued
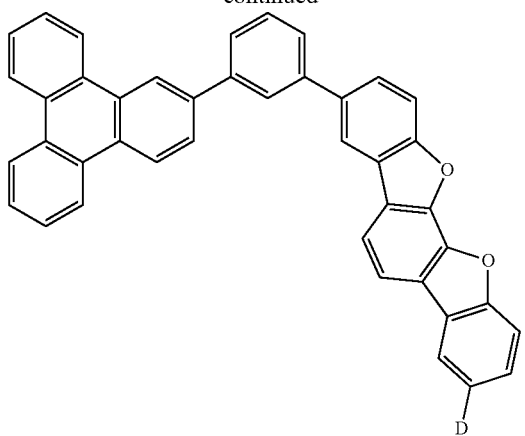
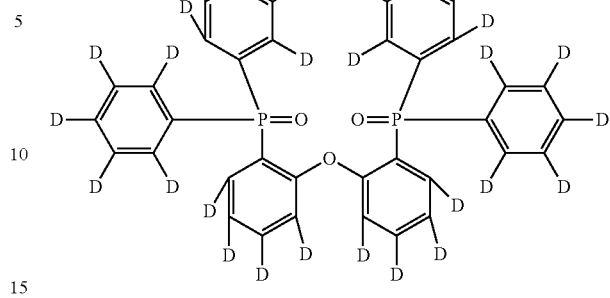
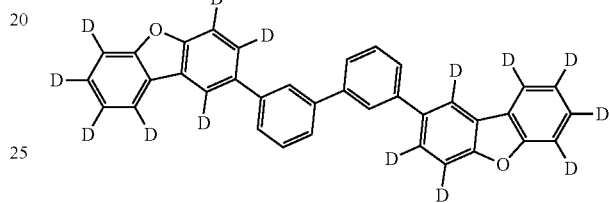
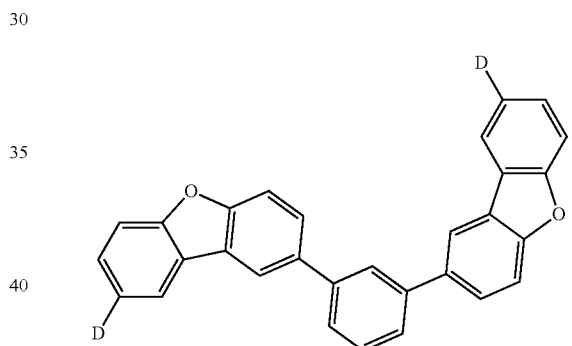
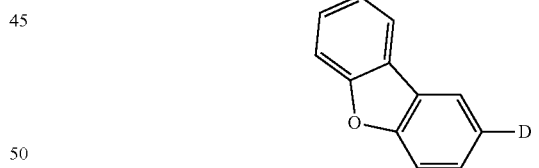
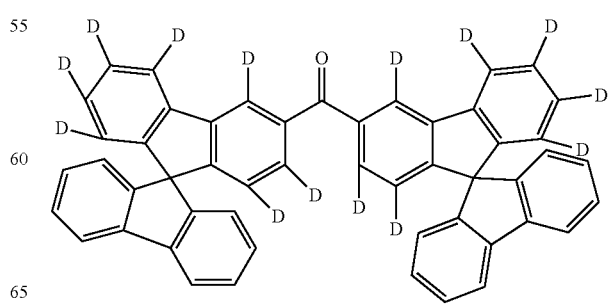

-continued
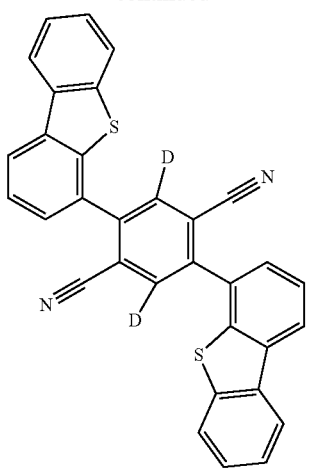
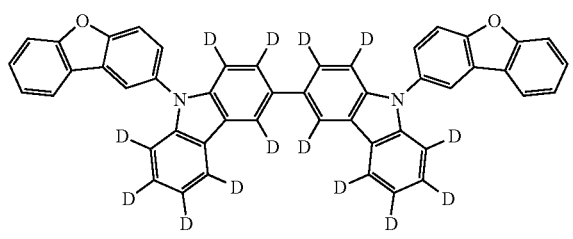
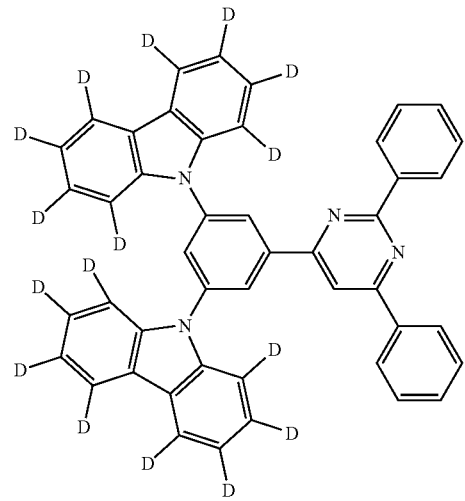
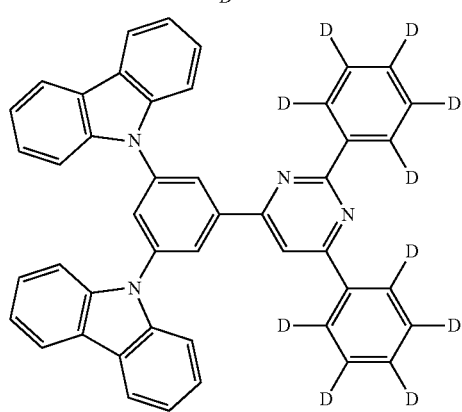
-continued
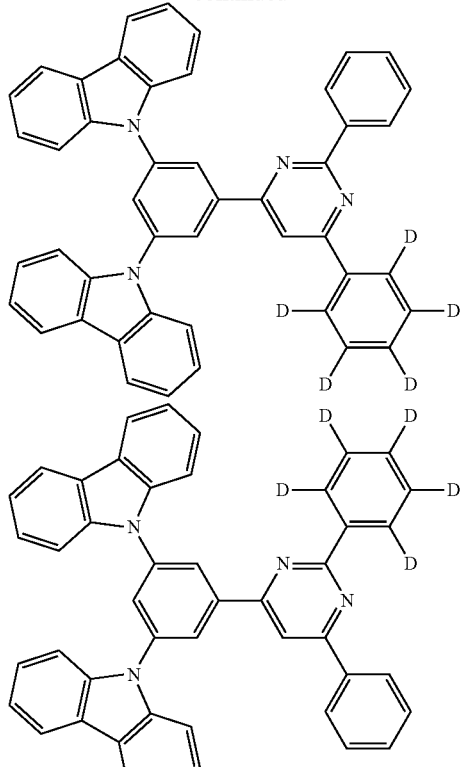
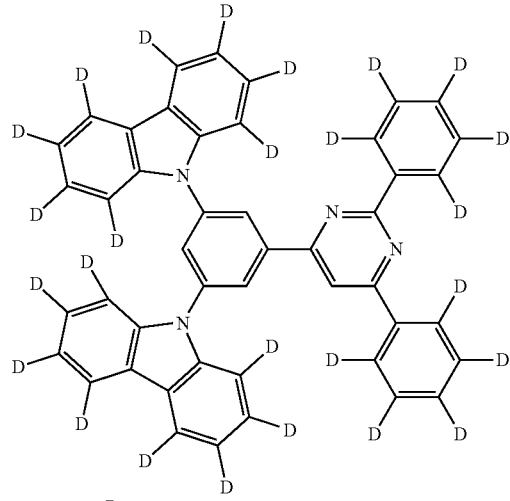
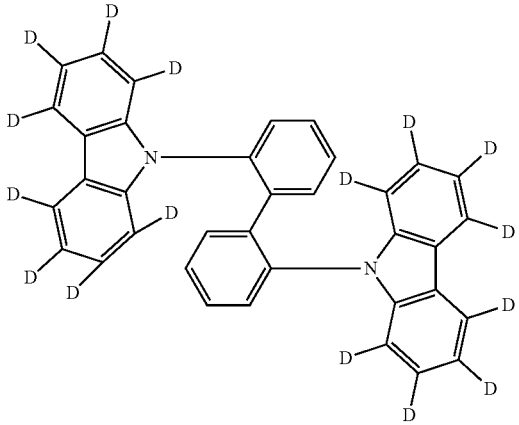

183
-continued
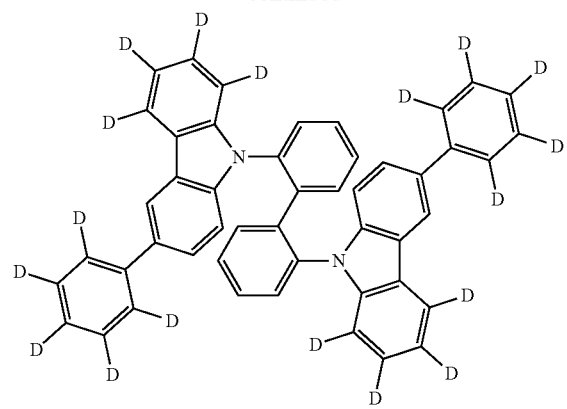
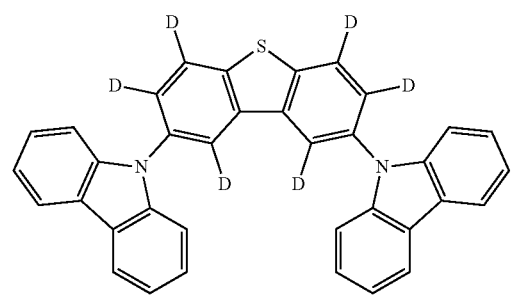
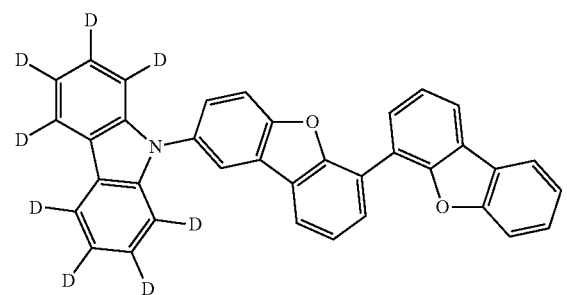
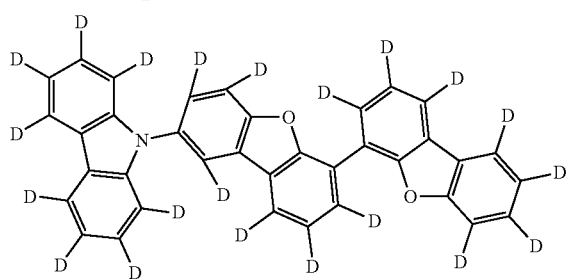
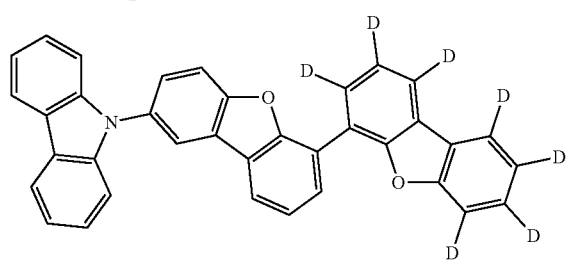
184
-continued
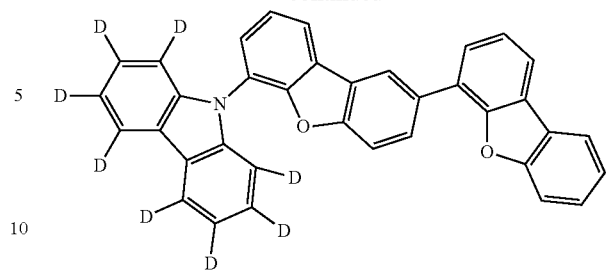
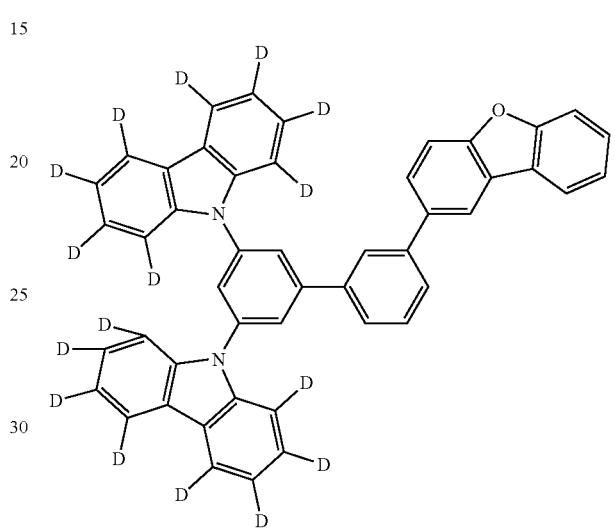
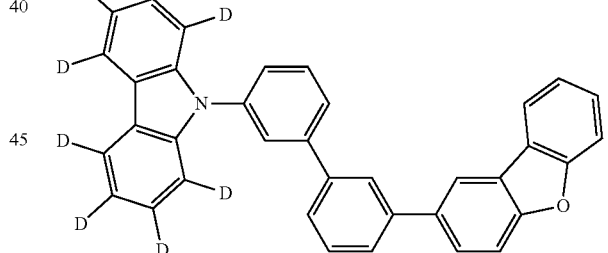
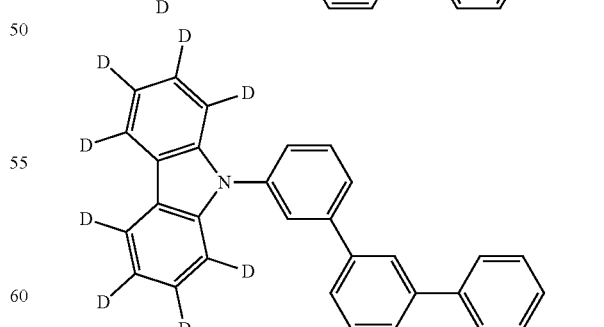
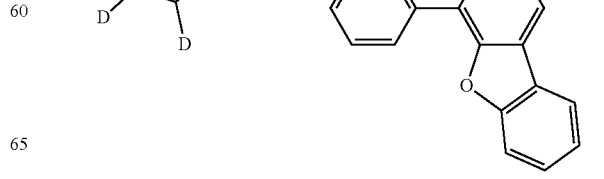

185
-continued
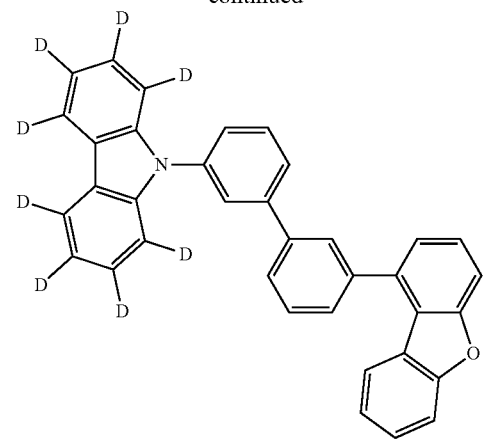
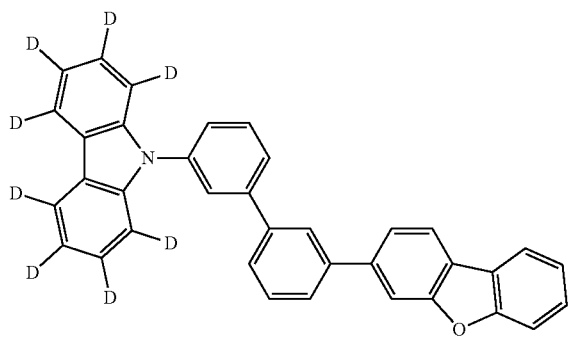
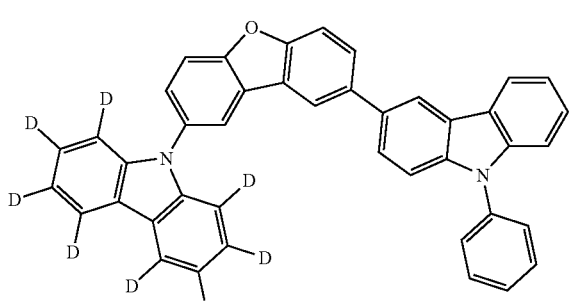
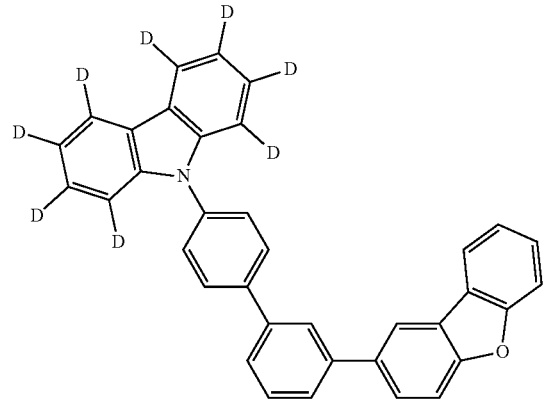
186
-continued
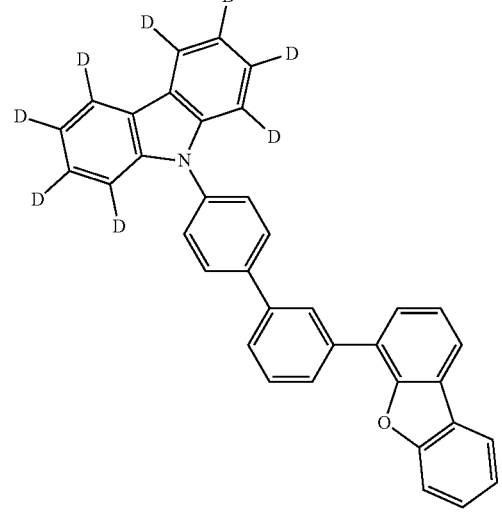
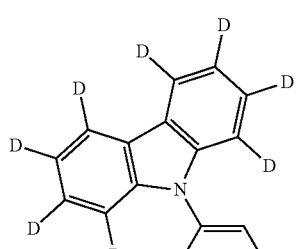
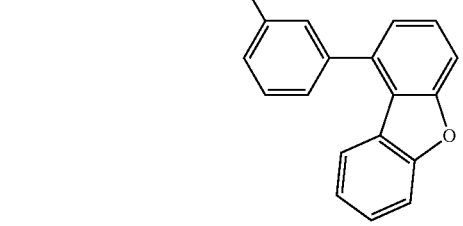
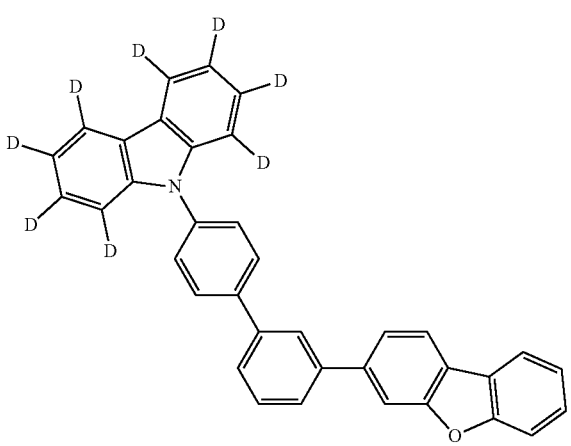

187
-continued
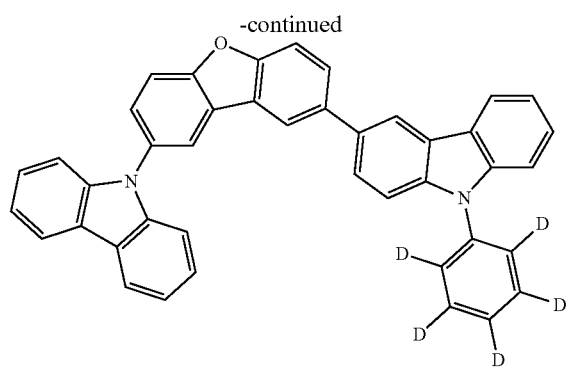
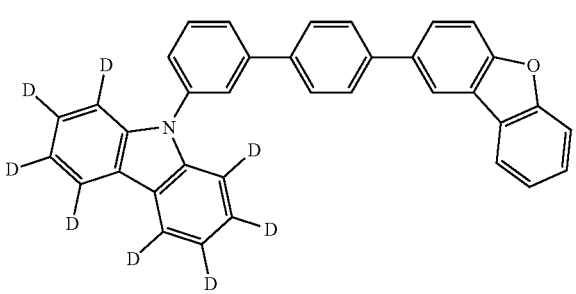
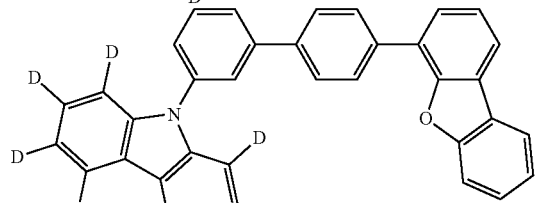
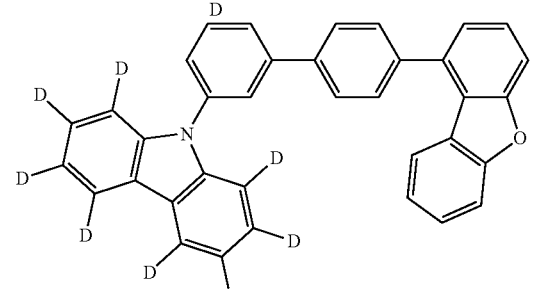
188
-continued
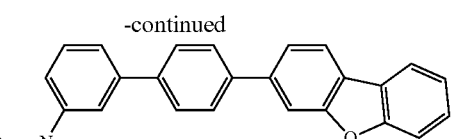
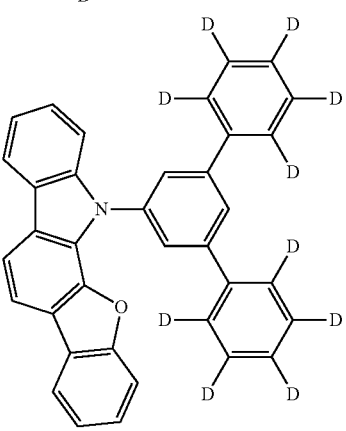
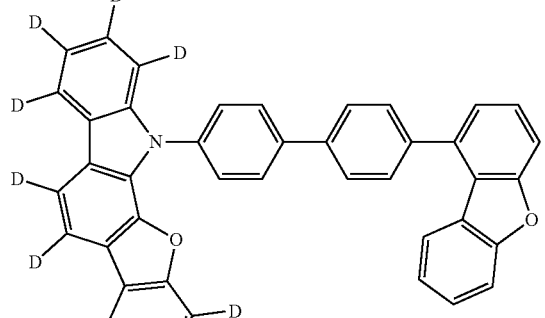
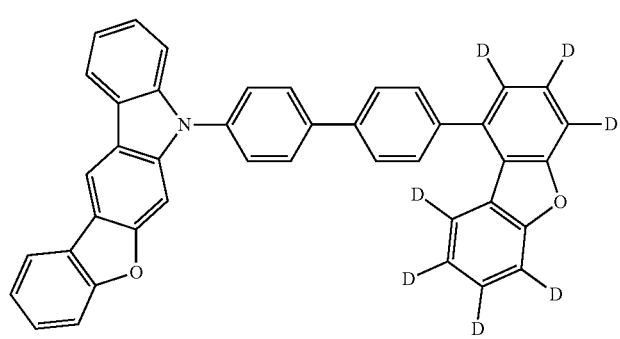
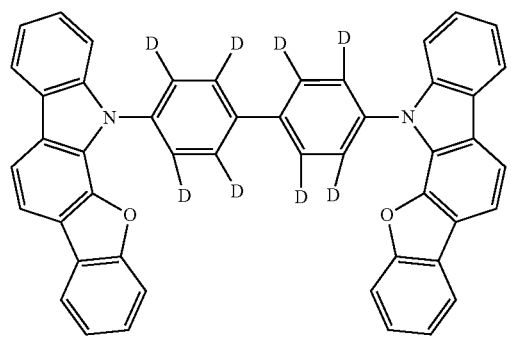

-continued
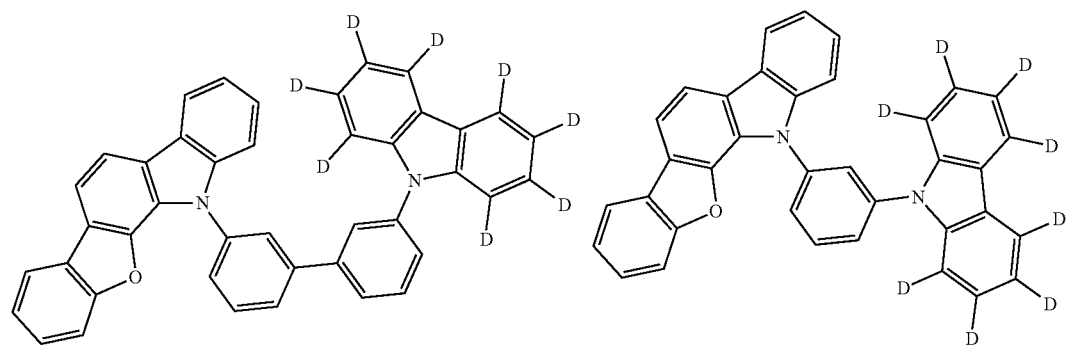
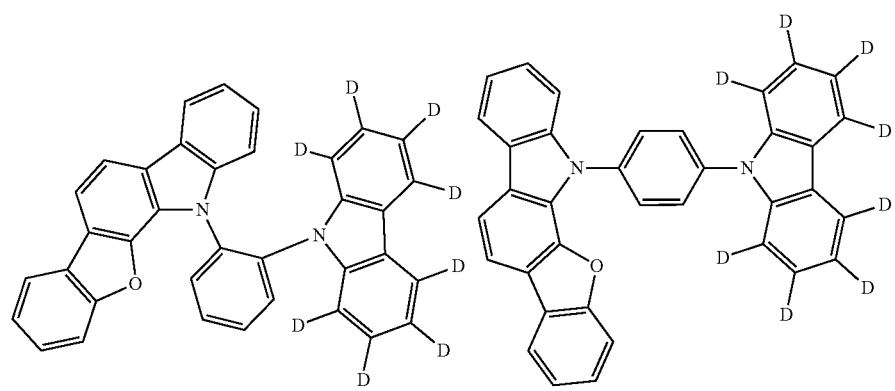
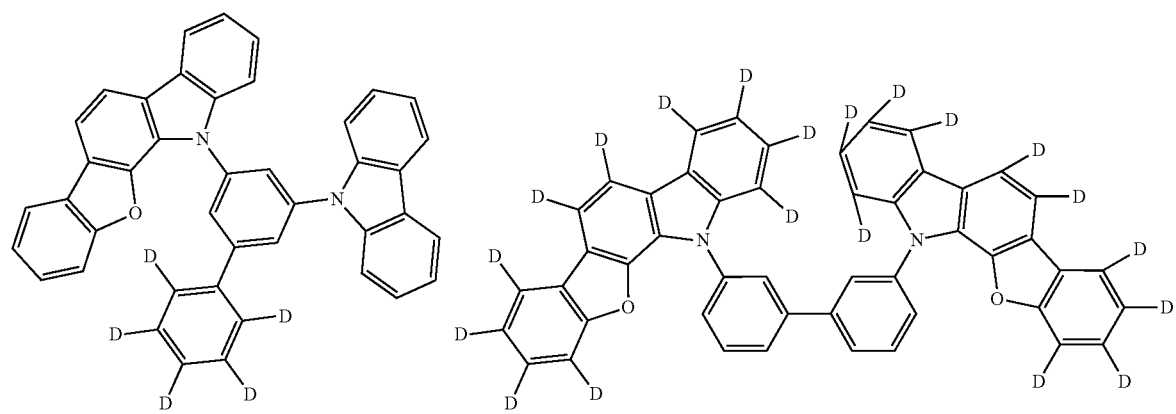
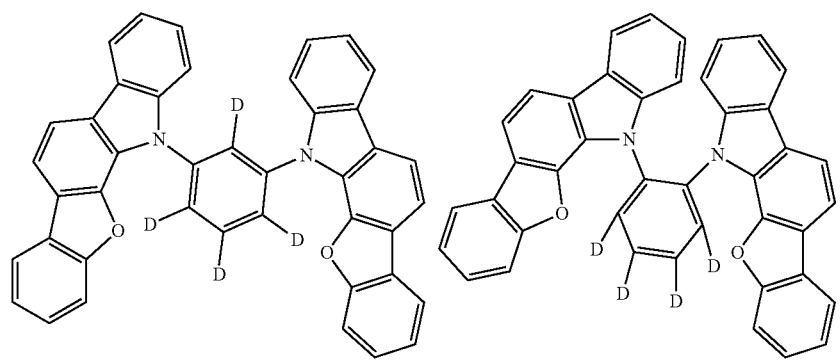

191
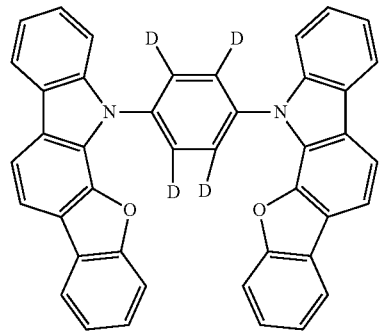 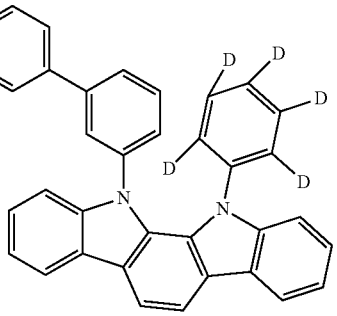 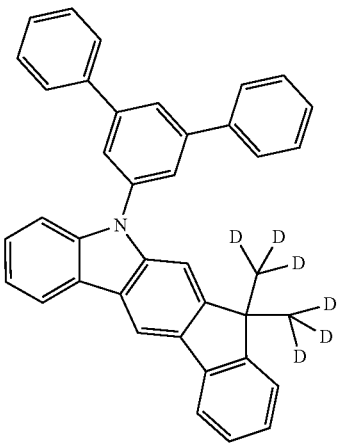
192
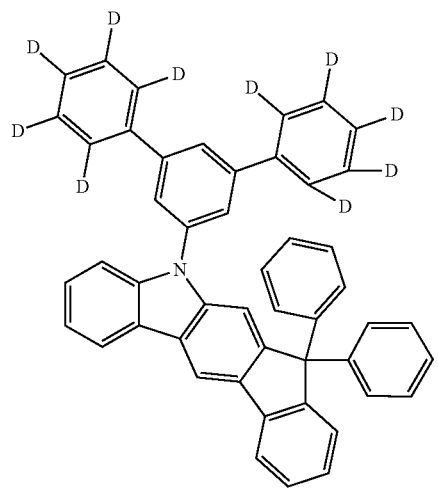 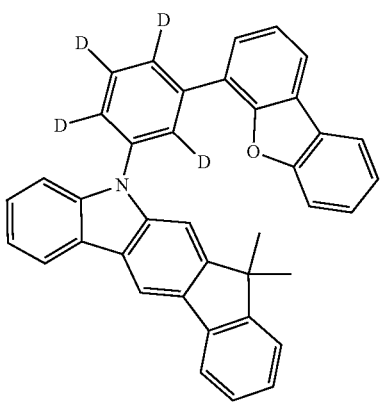
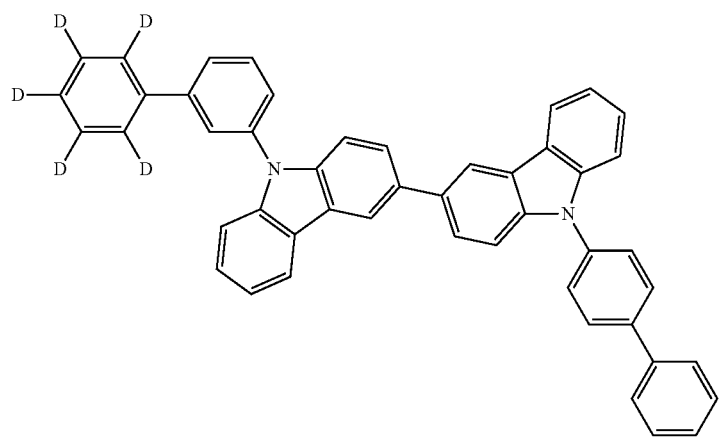

193 194
-continued
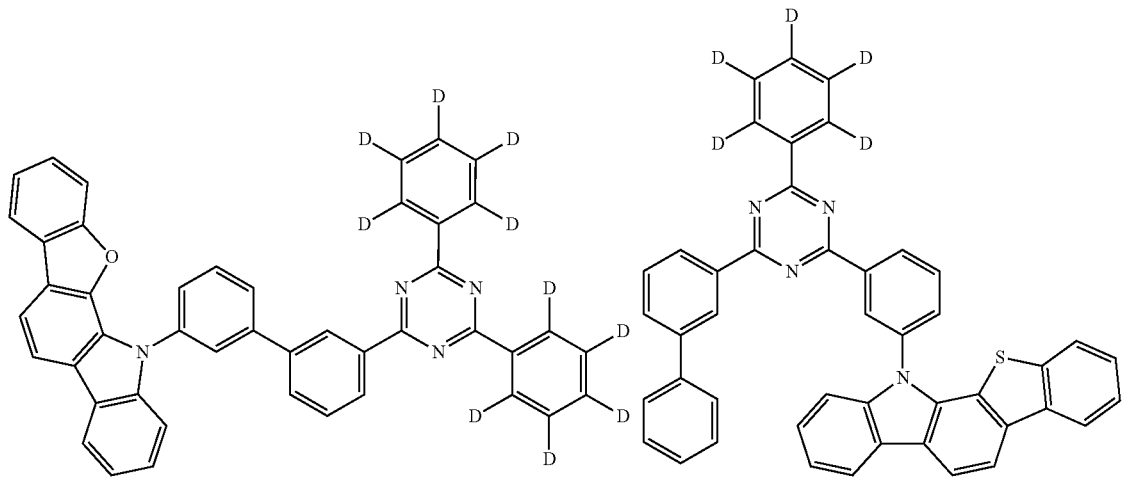
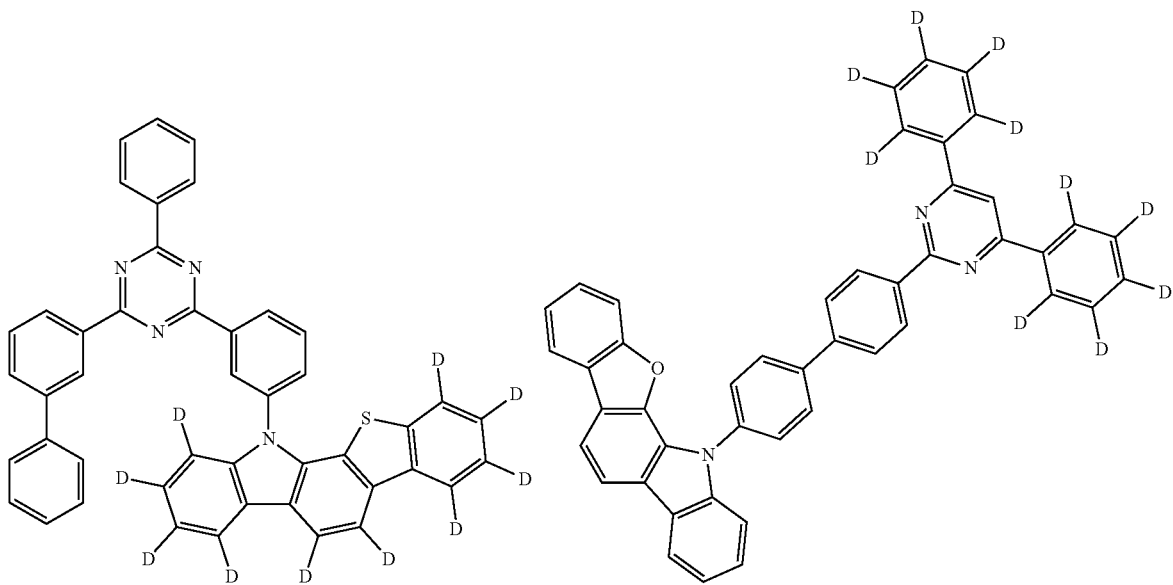
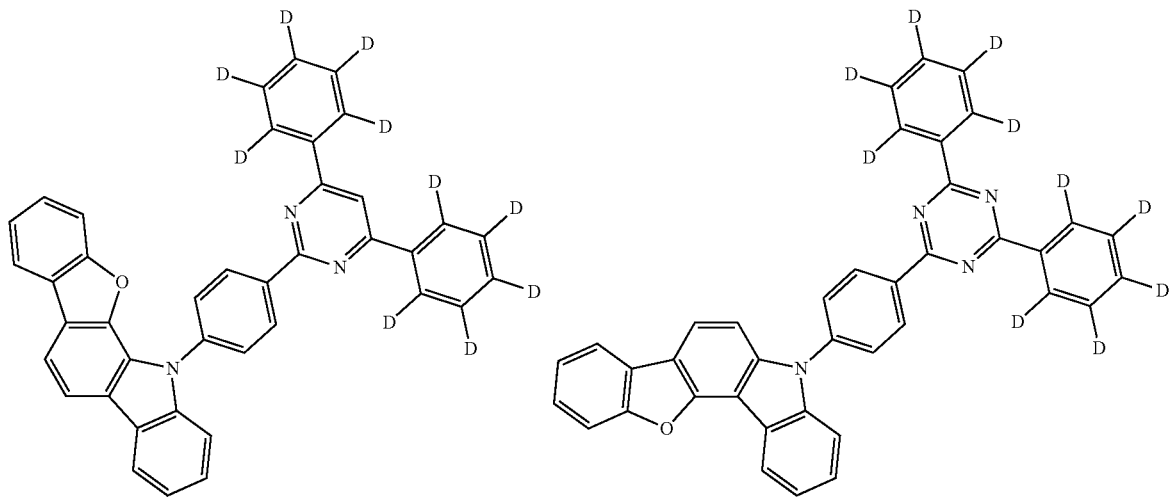

195 196
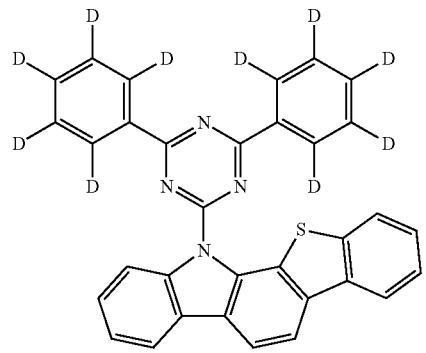
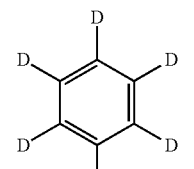
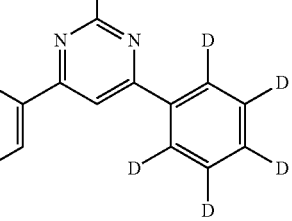
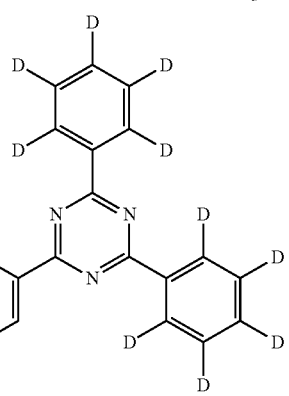
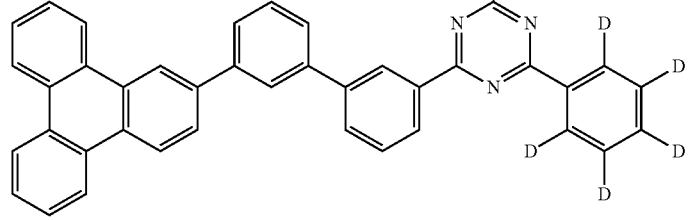
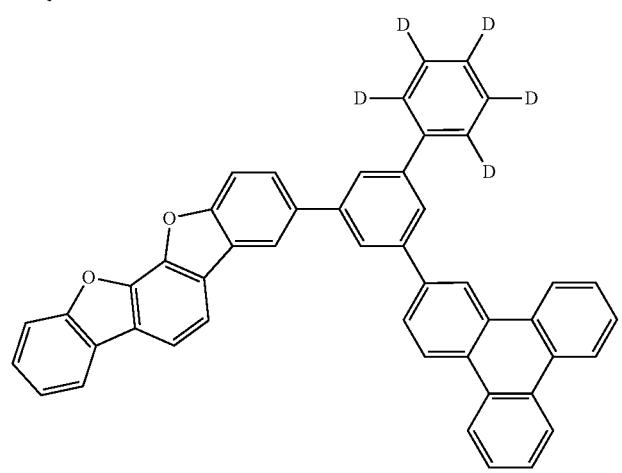
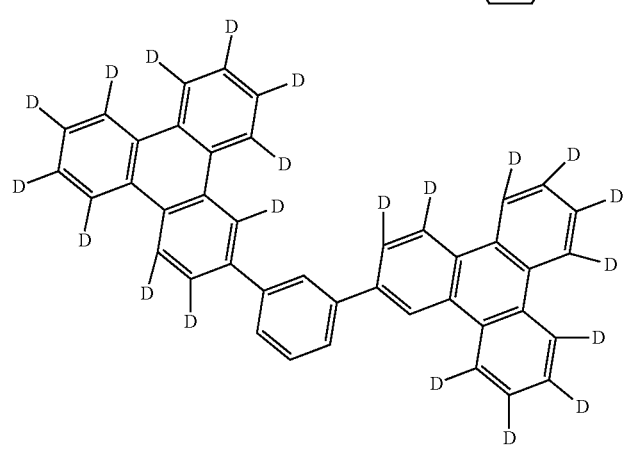

-continued
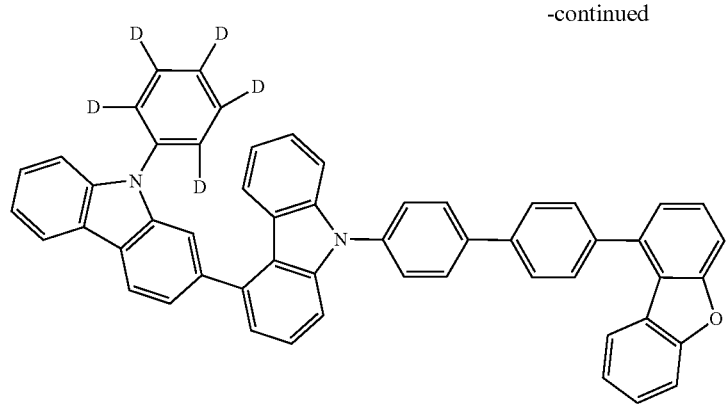
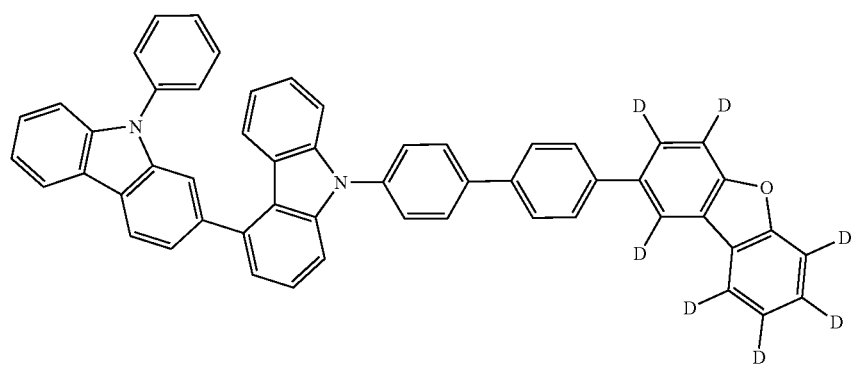
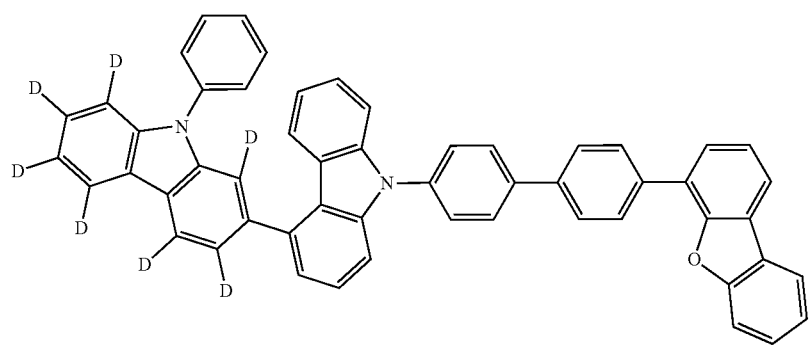
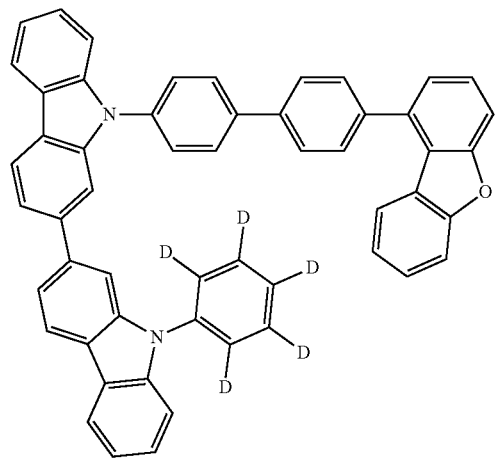

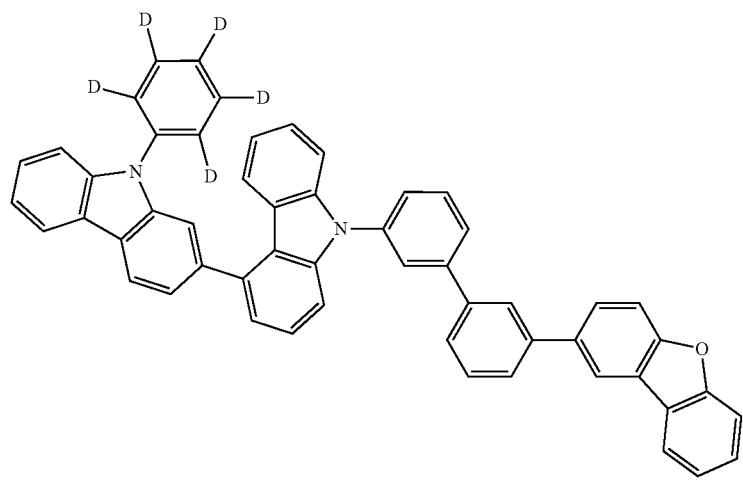
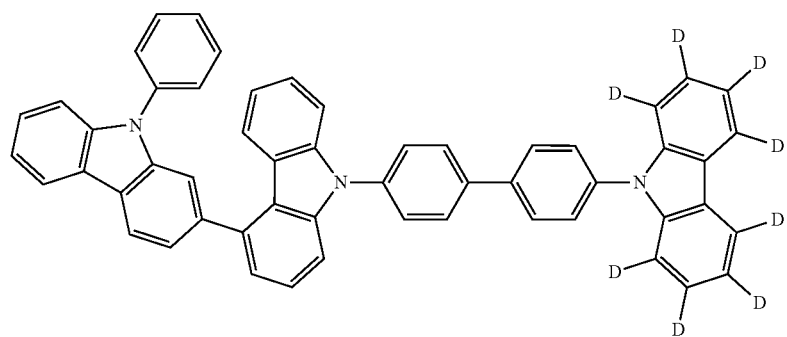
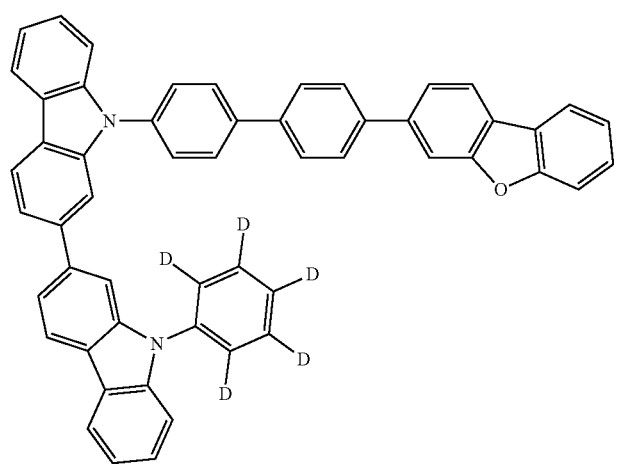
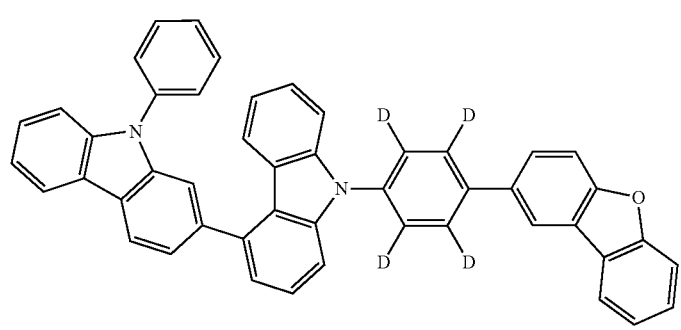

-continued
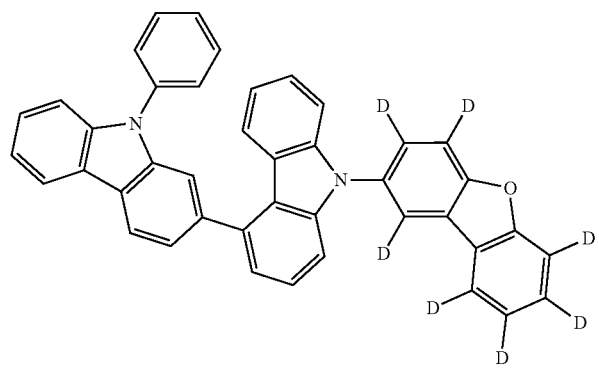
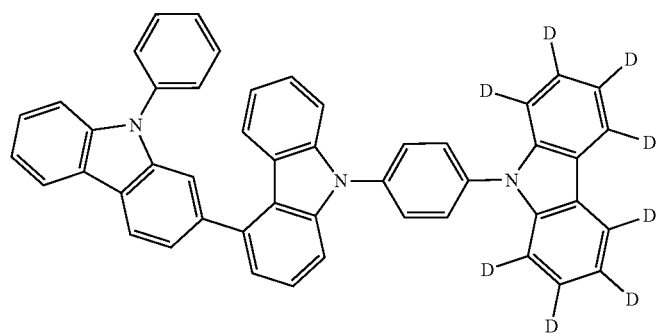
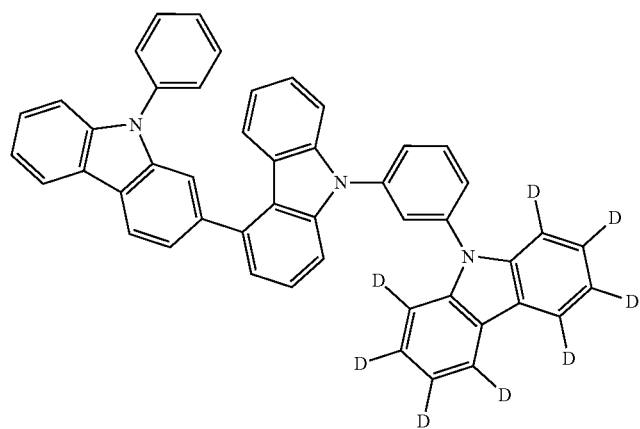
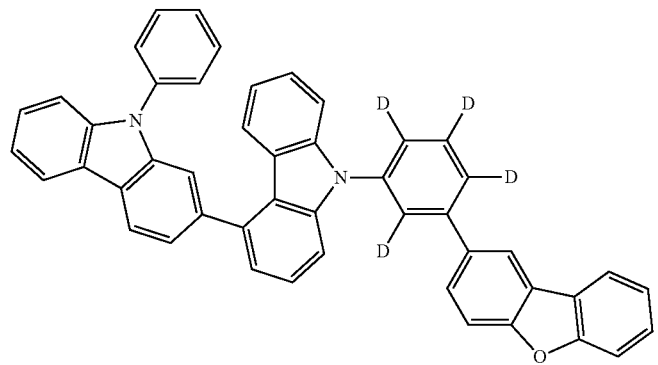

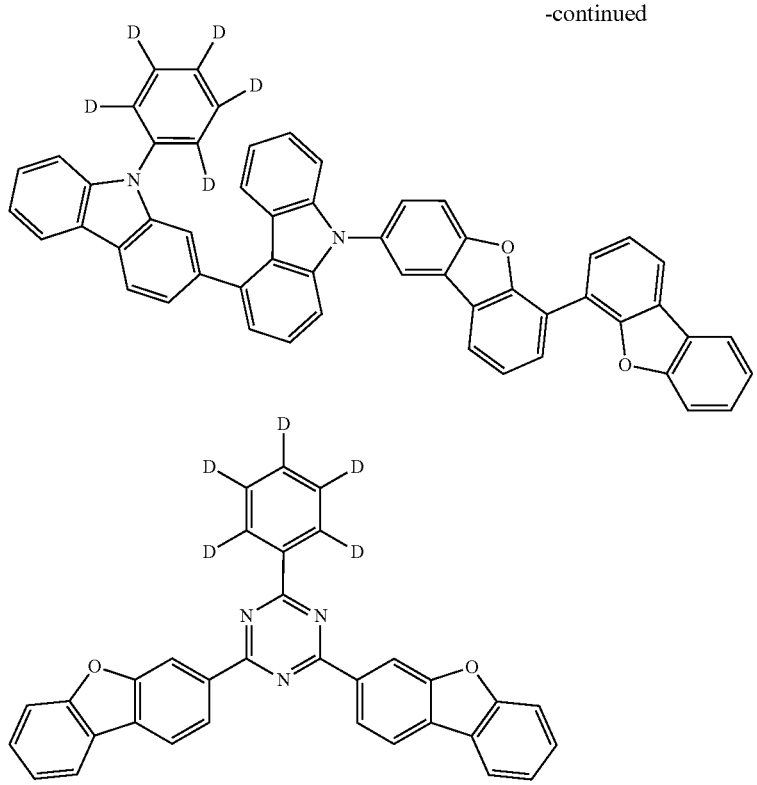

Compound M2

The compound M2 of the exemplary embodiment is a delayed fluorescent compound. The delayed fluorescent compound is not particularly limited.

The compound M2 of the exemplary embodiment is preferably a compound having at least one deuterium atom.

Herein, a "compound having at least one deuterium atom" among compounds M2 refers to a compound in which hydrogen atoms included in the compound M2 are not composed only of protium atoms.

In the following description, a "compound having at least one deuterium atom" among compounds M2 may be referred to as a "deuterated compound DM2". A compound in which all hydrogen atoms included in the compound M2 are protium atoms may be referred to as a "non-deuterated compound m2". In the exemplary embodiment, when the compound M2 is the deuterated compound DM2, a content ratio of the non-deuterated compound m2 relative to the total of the deuterated compound DM2 and the non-deuterated compound m2 in the emitting layer is 99% by mole or less. The content ratio of the non-deuterated compound m2 can be examined by mass spectrometry.

In the exemplary embodiment, when the compound M2 is the deuterated compound DM2, a content ratio of the deuterated compound DM2 relative to the total of the deuterated compound DM2 and the non-deuterated compound m2 contained in the emitting layer is preferably 30% by mole or more, 50% by mole or more, 70% by mole or more, 90% by mole or more, 95% by mole or more, 99% by mole or more, or 100% by mole.

In the exemplary embodiment, when the compound M2 is the deuterated compound DM2, it is also preferable that deuterium atoms account for 10% or more of the total number of hydrogen atoms included in the compound M2, deuterium atoms account for 20% or more thereof, deuterium atoms account for 30% or more thereof, deuterium atoms account for 40% or more thereof, deuterium atoms account for 50% or more thereof, deuterium atoms account for 60% or more thereof, deuterium atoms account for 70% or more thereof, and deuterium atoms account for 80% or more thereof.

Whether a deuterium atom is included in the compound M2 is checked by the same method as the "Method for Checking Whether Deuterium Atom Is Included in Compound M3" described above.

The bonding position of a deuterium atom in the compound M2 is specified by the same method as the "Method for Specifying Bonding Position of Deuterium Atom in Compound M3" described above.

Delayed Fluorescence

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy difference $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The compound M2 of the exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

FIG. 2 shows a schematic diagram of an exemplary device for measuring the transient PL. An example of a method of measuring a transient PL using FIG. 2 and an example of behavior analysis of delayed fluorescence will be described.

A transient PL measuring device 100 in FIG. 2 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a matrix material with a doping material at a concentration of 12 mass % and forming a thin film on a quartz substrate.

The thin film sample housed in the sample chamber 102 is irradiated with a pulse laser from the pulse laser 101 to excite the doping material. Emission is extracted in a direction of 90 degrees with respect to an irradiation direction of the excitation light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound H1 as the matrix material and a reference compound D1 as the doping material and was measured in terms of the transient PL.

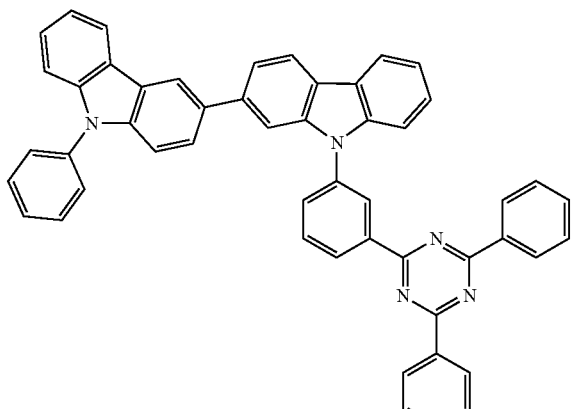

(Reference compound H1)

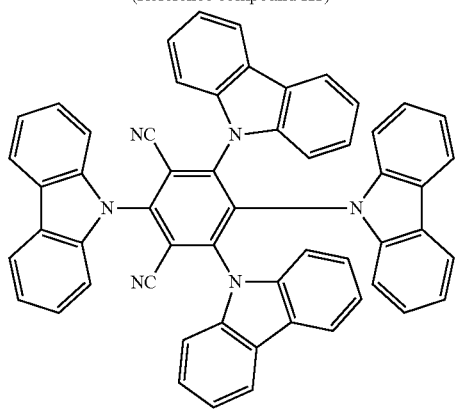

(Reference compound D1)

Herein, the decay curve was analyzed using the above-described thin film sample A and a thin film sample B. The thin film sample B was manufactured in the same manner as described above from a reference compound H2 as the matrix material and the reference compound D1 as the doping material.

FIG. 3 shows a decay curve obtained from the measured transitional PL of the thin film sample A and the thin film sample B.

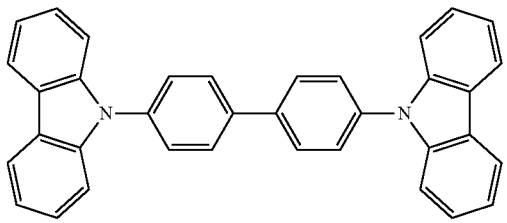

(Reference compound H2)

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

Herein, a sample manufactured by a method shown below is used for measuring delayed fluorescence of the compound M2. For instance, the compound M2 is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969. An amount of Prompt emission, an amount of Delay emission, and a ratio between the amounts thereof can be obtained according to the method as described in Reference Document 1. The amount of Prompt emission and the amount of Delay emission may be calculated using a device different from one described in Reference Document 1 or one shown in FIG. 2.

In the exemplary embodiment, provided that an amount of Prompt emission of a measurement target compound (compound M2) is denoted by XP and the amount of Delay emission is denoted by $X_D$, a value of $X_D/X_P$ is preferably 0.05 or more.

The amounts of Prompt emission and Delay emission and a ratio of the amounts thereof in compounds other than the compound M2 herein are measured in the same manner as those of the compound M2.

The compound M2 is preferably a compound represented by a formula (2) or (22) below.

Compound Represented by Formula (2)

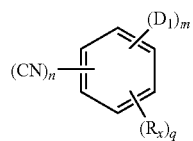

(2)

In the formula (2): n is 1, 2, 3 or 4; m is 1, 2, 3 or 4; q is 0, 1, 2, 3 or 4; m+n+q=6 is satisfied; CN is a cyano group; $D_1$ is a group represented by a formula (2a), (2b) or (2c) below, and when a plurality of $D_1$ are present, the plurality of $D_1$ are mutually the same or different; Rx is a hydrogen atom or a substituent, or a pair of adjacent ones of Rx are mutually bonded to form a ring, and when a plurality of Rx are present, the plurality of Rx are mutually the same or different; each Rx serving as a substituent is independently a halogen atom, a substituted or unsubstituted aryl group having 6 to 30 ring carbon atoms, a substituted or unsubstituted heterocyclic group having 5 to 30 ring atoms, a substituted or unsubstituted amino group, a substituted or unsubstituted carbonyl group, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 30 carbon atoms, or a substituted or unsubstituted arylsilyl group having 6 to 60 ring carbon atoms; and CN, $D_1$ and Rx are bonded to respective carbon atoms of a six-membered ring.

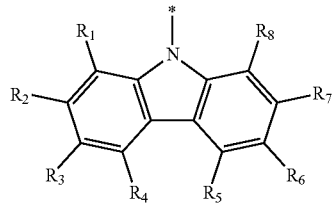

(2a)

In the formula (2a): $R_1$ to $R_8$ are each independently a hydrogen atom or a substituent, or at least one pair of a pair of $R_1$ and $R_2$, a pair of $R_2$ and $R_3$, a pair of $R_3$ and $R_4$, a pair of $R_5$ and $R_6$, a pair of $R_6$ and $R_7$, or a pair of $R_7$ and $R_8$ are mutually bonded to form a ring; $R_1$ to $R_8$ serving as a substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 6 to 60 ring carbon atoms, a hydroxy group, a substituted or unsubstituted alkoxy group having 1 to 30 carbon atoms, a substituted or unsubstituted alkoxy halide group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms; and * represents a bonding portion to a carbon atom of a benzene ring in the formula (2).

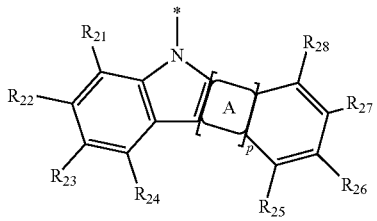

(2b)

In the formula (2b): $R_{21}$ to $R_{28}$ are each independently a hydrogen atom or a substituent, or at least one pair of a pair of $R_{21}$ and $R_{22}$, a pair of $R_{22}$ and $R_{23}$, a pair of $R_{23}$ and $R_{24}$, a pair of $R_{25}$ and $R_{26}$, a pair of $R_{26}$ and $R_{27}$, or a pair of $R_{27}$ and $R_{28}$ are mutually bonded to form a ring; $R_{21}$ to $R_{28}$ serving as a substituent each independently represent the same as $R_1$ to $R_8$ in the formula (2a); A represents a cyclic structure represented by a formula (211) or (212) below, and the cyclic structure A is fused with adjacent cyclic structure(s) at any position(s); p is 1, 2, 3 or 4; when p is 2, 3 or 4, a plurality of cyclic structures A are mutually the same or different; and * represents a bonding portion to a carbon atom of a benzene ring in the formula (2).

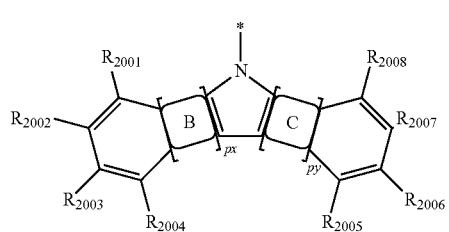

(2c)

In the formula (2c): $R_{2001}$ to $R_{2008}$ are each independently a hydrogen atom or a substituent, or at least one pair of a pair of $R_{2001}$ and $R_{2002}$, a pair of $R_{2002}$ and $R_{2003}$, a pair of $R_{2003}$ and $R_{2004}$, a pair of $R_{2005}$ and $R_{2006}$, a pair of $R_{2006}$ and $R_{2007}$, or a pair of $R_{2007}$ and $R_{2008}$ are mutually bonded to form a ring; $R_{2001}$ to $R_{2008}$ serving as a substituent each independently represent the same as $R_1$ to $R_8$ serving as a substituent in the formula (2a); B represents a cyclic structure represented by the formula (211) or (212), and the cyclic structure B is fused with adjacent cyclic structure(s) at any position(s); px is 1, 2, 3 or 4; when px is 2, 3 or 4, a plurality of cyclic structures B are mutually the same or different; C represents a cyclic structure represented by the formula (211) or (212), and the cyclic structure C is fused with adjacent cyclic structure(s) at any position(s); py is 1, 2, 3 or 4; when py is 2, 3 or 4, a plurality of cyclic structures C are mutually the same or different; and * represents a bonding portion to a carbon atom of a benzene ring in the formula (2).

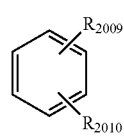

(211)

(212)

In the formula (211), $R_{2009}$ and $R_{2010}$ are each independently a hydrogen atom or a substituent, or bonded to a part of an adjacent cyclic structure, or a pair of $R_{2009}$ and $R_{2010}$ are mutually bonded to form a ring.

In the formula (212), $X_{201}$ is $CR_{2011}R_{2012}$, $NR_{2013}$, a sulfur atom, or an oxygen atom, and $R_{2011}$, $R_{2012}$ and $R_{2013}$ are each independently a hydrogen atom or a substituent, or $R_{2011}$ and $R_{2012}$ are mutually bonded to form a ring; and $R_{2009}$, $R_{2010}$, $R_{2011}$, $R_{2012}$ and $R_{2013}$ serving as a substituent each independently represent the same as $R_1$ to $R_8$ serving as a substituent in the formula (2a).

In the formula (211), $R_{2009}$ and $R_{2010}$ are each independently bonded to a part of an adjacent cyclic structure, which specifically means any of (I) to (IV) below.

In the formula (211), a pair of $R_{2009}$ and $R_{2010}$ are mutually bonded to form a ring, which specifically means (V) below.

When the cyclic structures represented by the formula (211) are adjacent to each other, between the two adjacent rings, at least one pair of the following are mutually bonded to form a ring: $R_{2009}$ of one of the rings and $R_{2009}$ of the other of the rings; $R_{2009}$ of one of the rings and $R_{2010}$ of the other of the rings; or $R_{2010}$ of one of the rings and $R_{2010}$ of the other of the rings.

When the cyclic structure represented by the formula (211) and the benzene ring having $R_{25}$ to $R_{28}$ in the formula (2b) are adjacent to each other, between the two adjacent rings, at least one pair of the following are mutually bonded to form a ring: $R_{209}$ of one of the rings and $R_{25}$ of the other of the rings; $R_{209}$ of one of the rings and $R_{28}$ of the other of the rings; $R_{210}$ of one of the rings and $R_{25}$ of the other of the rings; or $R_{210}$ of one of the rings and $R_{28}$ of the other of the rings.

When the cyclic structure represented by the formula (211) and the benzene ring having $R_{2001}$ to $R_{2004}$ in the formula (2c) are adjacent to each other, between the two adjacent rings, at least one pair of the following are mutually bonded to form a ring: $R_{2009}$ of one of the rings and $R_{2001}$ of the other of the rings; $R_{2009}$ of one of the rings and $R_{2004}$ of the other of the rings; $R_{2010}$ of one of the rings and $R_{2001}$ of the other of the rings; or $R_{2010}$ of one of the rings and $R_{2004}$ of the other of the rings.

When the cyclic structure represented by the formula (211) and the benzene ring having $R_{2005}$ to $R_{2008}$ in the formula (2c) are adjacent to each other, between the two adjacent rings, at least one pair of the following are mutually bonded to form a ring: $R_{2009}$ of one of the rings and $R_{2005}$ of the other of the rings; $R_{2009}$ of one of the rings and $R_{2008}$ of the other of the rings; $R_{2010}$ of one of the rings and $R_{2005}$ of the other of the rings; or $R_{2010}$ of one of the rings and $R_{2008}$ of the other of the rings.

The pair of $R_{2009}$ and $R_{2010}$ of the cyclic structure represented by the formula (211) are mutually bonded to form a ring. In other words, (V) means that the pair of $R_{2009}$ and $R_{2010}$, which are bonded to the same ring, are mutually bonded to form a ring.

In the compound M2 of the exemplary embodiment, it is preferable that Rx is each independently a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms; and when Rx is an unsubstituted heterocyclic group having 5 to 30 ring atoms, Rx as the unsubstituted heterocyclic group having 5 to 30 ring atoms is a pyridyl group, pyrimidinyl group, triazinyl group, dibenzofuranyl group, or dibenzothienyl group.

Herein, the triazinyl group refers to a group obtained by excluding one hydrogen atom from 1,3,5-triazine, 1,2,4-triazine, or 1,2,3-triazine.

The triazinyl group is preferably a group obtained by excluding one hydrogen atom from 1,3,5-triazine.

In the compound M2 of the exemplary embodiment, it is more preferable that Rx is each independently a hydrogen atom, an unsubstituted aryl group having 6 to 30 ring carbon atoms, an unsubstituted dibenzofuranyl group, or an unsubstituted dibenzothienyl group.

In the compound M2 of the exemplary embodiment, Rx is further preferably a hydrogen atom.

In the compound M2 of the exemplary embodiment, when any one or more Rx are hydrogen atoms, it is preferable that all the hydrogen atoms are protium atoms, at least one of the hydrogen atoms is a deuterium atom, or all the hydrogen atoms are deuterium.

In the compound M2 of the exemplary embodiment, when any one or more Rx are substituents and the substituents have one or more hydrogen atoms, it is preferable that all the hydrogen atoms are protium atoms, at least one of the hydrogen atoms is a deuterium atom, or all the hydrogen atoms are deuterium atoms.

In the compound M2 of the exemplary embodiment, it is preferable that $R_1$ to $R_8$, $R_{21}$ to $R_{28}$, $R_{2001}$ to $R_{2008}$, $R_{2009}$ to $R_{2010}$ and $R_{2011}$ to $R_{2013}$ serving as a substituent are each independently an unsubstituted aryl group having 6 to 30 ring carbon atoms, an unsubstituted heterocyclic group having 5 to 30 ring atoms, or an unsubstituted alkyl group having 1 to 30 carbon atoms.

It is preferable that $R_{101}$ to $R_{150}$ and $R_{61}$ to $R_{70}$ serving as a substituent in the compound M2 of the exemplary embodiment are each independently an unsubstituted aryl group having 6 to 14 ring carbon atoms, an unsubstituted heterocyclic group having 5 to 14 ring atoms, or an unsubstituted alkyl group having 1 to 6 carbon atoms, and $R_{X21}$ to $R_{X26}$ serving as a substituent are each independently an unsubstituted aryl group having 6 to 14 ring carbon atoms or an unsubstituted heterocyclic group having 5 to 14 ring atoms.

It is also preferable that $R_{101}$ to $R_{150}$ and $R_{61}$ to $R_{70}$ in the compound M2 of the exemplary embodiment are hydrogen atoms, and $R_{X21}$ to $R_{X26}$ serving as a substituent are each independently an unsubstituted aryl group having 6 to 14 ring carbon atoms or an unsubstituted heterocyclic group having 5 to 14 ring atoms.

It is preferable that $R_{201}$ to $R_{260}$ serving as a substituent in the compound M2 of the exemplary embodiment are each independently a halogen atom, an unsubstituted aryl group having 6 to 14 ring carbon atoms, an unsubstituted heterocyclic group having 5 to 14 ring atoms, or an unsubstituted alkyl group having 1 to 6 carbon atoms; and $R_{X27}$ and $R_{X28}$ serving as a substituent are each independently an unsubstituted aryl group having 6 to 14 ring carbon atoms or an unsubstituted alkyl group having 1 to 6 carbon atoms.

It is more preferable that $R_{201}$ to $R_{260}$ serving as a substituent in the compound M2 of the exemplary embodiment are each independently an unsubstituted aryl group having 6 to 14 ring carbon atoms, an unsubstituted heterocyclic group having 5 to 14 ring atoms, or an unsubstituted alkyl group having 1 to 6 carbon atoms; and $R_{X27}$ and $R_{X28}$ serving as a substituent are each independently an unsubstituted aryl group having 6 to 14 ring carbon atoms or an unsubstituted alkyl group having 1 to 6 carbon atoms.

It is also preferable that $R_{201}$ to $R_{260}$ in the compound M2 of the exemplary embodiment are hydrogen atoms, and $R_{X27}$ and $R_{X28}$ serving as a substituent are each independently an unsubstituted aryl group having 6 to 14 ring carbon atoms or an unsubstituted alkyl group having 1 to 6 carbon atoms.

In the compound M2 of the exemplary embodiment, when any one or more of $R_{101}$ to $R_{150}$, $R_{61}$ to $R_{70}$, and $R_{201}$ to $R_{260}$ are hydrogen atoms, it is preferable that all the hydrogen atoms are protium atoms, at least one of the hydrogen atoms is a deuterium atom, or all the hydrogen atoms are deuterium.

In the compound M2 of the exemplary embodiment, when any one or more of $R_{101}$ to $R_{150}$, $R_{61}$ to $R_{70}$, and $R_{201}$ to $R_{260}$ are substituents and the substituents have one or more hydrogen atoms, it is preferable that all the hydrogen atoms are protium atoms, at least one of the hydrogen atoms is a deuterium atom, or all the hydrogen atoms are deuterium atoms.

In the compound M2 of the exemplary embodiment, $D_1$ is preferably any one of groups represented by formulae (D-21) to (D-37) below.

Groups Represented by Formulae (D-21) to (D-25)

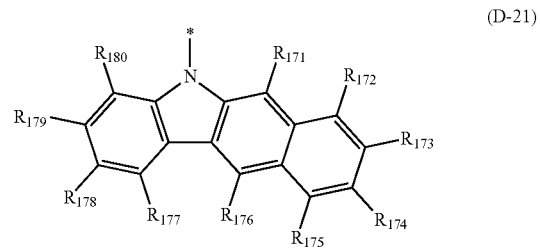

(D-21)

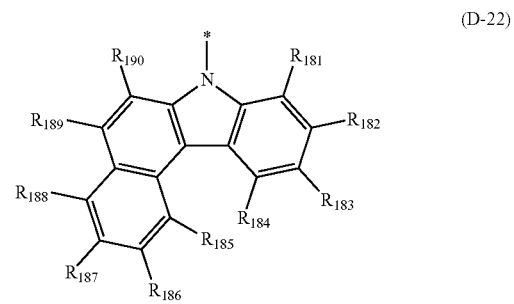

(D-22)

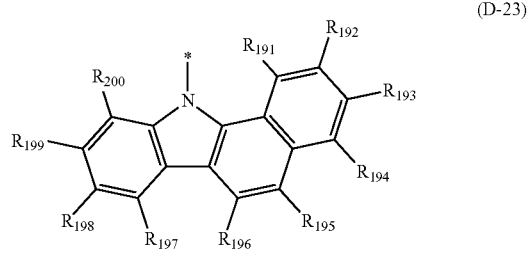

(D-23)

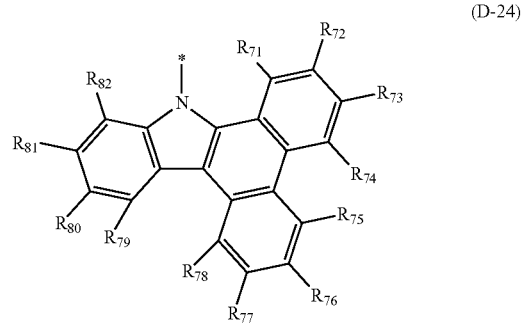

(D-24)

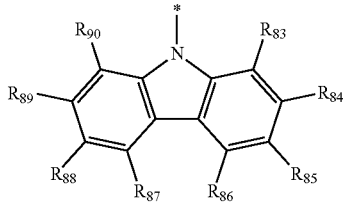
(D-25)

In the formulae (D-21) to (D-25), $R_{171}$ to $R_{200}$ and $R_{71}$ to $R_{90}$ are each independently a hydrogen atom or a substituent, or at least one pair of the following are mutually bonded to form a ring: a pair of $R_{171}$ and $R_{172}$, a pair of $R_{172}$ and $R_{173}$, a pair of $R_{173}$ and $R_{174}$, a pair of $R_{174}$ and $R_{175}$, a pair of $R_{175}$ and $R_{176}$, a pair of $R_{177}$ and $R_{178}$, a pair of $R_{178}$ and $R_{179}$, a pair of $R_{179}$ and $R_{180}$, a pair of $R_{181}$ and $R_{182}$, a pair of $R_{182}$ and $R_{183}$, a pair of $R_{183}$ and $R_{184}$, a pair of $R_{185}$ and $R_{186}$, a pair of $R_{186}$ and $R_{187}$, a pair of $R_{187}$ and $R_{188}$, a pair of $R_{188}$ and $R_{189}$, a pair of $R_{189}$ and $R_{190}$, a pair of $R_{191}$ and $R_{192}$, a pair of $R_{192}$ and $R_{193}$, a pair of $R_{193}$ and $R_{194}$, a pair of $R_{194}$ and $R_{195}$, a pair of $R_{195}$ and $R_{196}$, a pair of $R_{197}$ and $R_{198}$, a pair of $R_{198}$ and $R_{199}$, a pair of $R_{199}$ and $R_{200}$, a pair of $R_{71}$ and $R_{72}$, a pair of $R_{72}$ and $R_{73}$, a pair of $R_{73}$ and $R_{74}$, a pair of $R_{75}$ and $R_{76}$, a pair of $R_{76}$ and $R_{77}$, a pair of $R_{77}$ and $R_{78}$, a pair of $R_{79}$ and $R_{80}$, a pair of $R_{80}$ and $R_{81}$, or a pair of $R_{81}$ and $R_{82}$; $R_{171}$ to $R_{200}$ and $R_{71}$ to $R_{90}$ serving as a substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; and * represents a bonding portion to a carbon atom of a benzene ring in the formula (2).

In the compound M2 of the exemplary embodiment, $R_{171}$ to $R_{200}$ and $R_{71}$ to $R_{90}$ serving as a substituent are preferably each independently an unsubstituted aryl group having 6 to 14 ring carbon atoms, an unsubstituted heterocyclic group having 5 to 14 ring atoms, or an unsubstituted alkyl group having 1 to 6 carbon atoms.

In the compound M2 of the exemplary embodiment, $R_{171}$ to $R_{200}$ and $R_{71}$ to $R_{90}$ are also preferably hydrogen atoms.

In the compound M2 of the exemplary embodiment, when any one or more of $R_{171}$ to $R_{200}$ and $R_{71}$ to $R_{90}$ are hydrogen atoms, it is preferable that all the hydrogen atoms are protium atoms, at least one of the hydrogen atoms is a deuterium atom, or all the hydrogen atoms are deuterium.

In the compound M2 of the exemplary embodiment, when any one or more of $R_{171}$ to $R_{200}$ and $R_{71}$ to $R_{90}$ are substituents and the substituents have one or more hydrogen atoms, it is preferable that all the hydrogen atoms are protium atoms, at least one of the hydrogen atoms is a deuterium atom, or all the hydrogen atoms are deuterium atoms.

The groups represented by the formulae (D-21) to (D-25) are each preferably any one of groups represented by formulae (2-5) to (2-17) below.

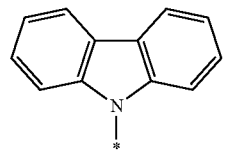
(2-5)

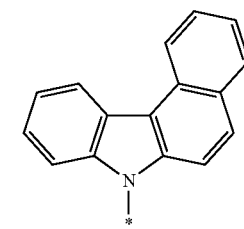
(2-6)

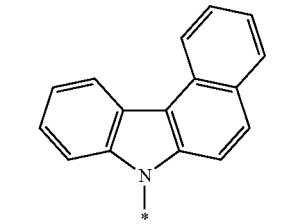
(2-7)

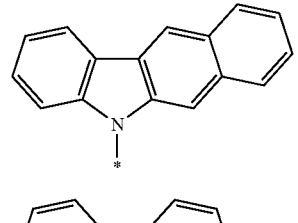
(2-8)

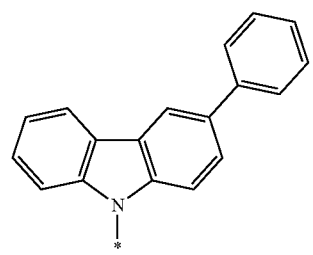
(2-9)

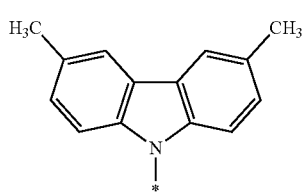
(2-10)

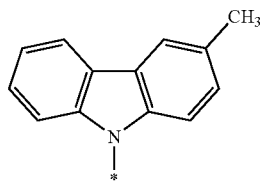
(2-11)

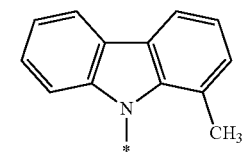
(2-12)

-continued (2-13)
(2-14)
(2-15)
(2-16)
(2-17)

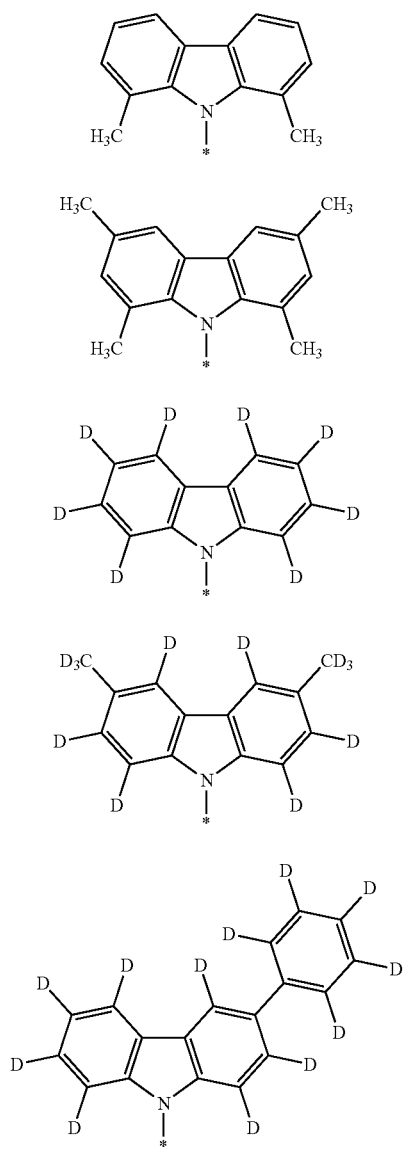

In the formulae (2-5) to (2-17), * represents a bonding portion to a carbon atom of a benzene ring in the formula (2), and D represents a deuterium atom. Groups Represented by Formulae (D-26) to (D-31)

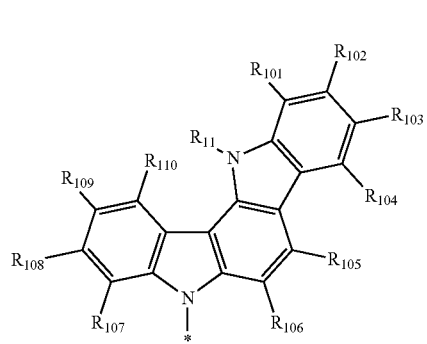
(D-26)

-continued

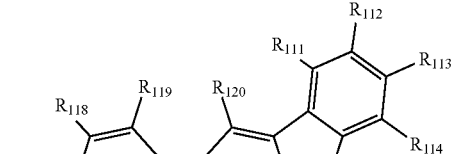
(D-27)

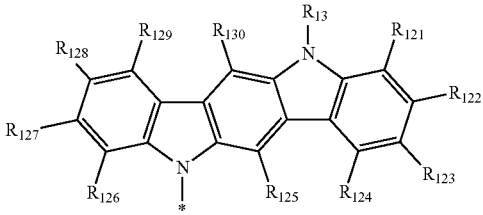
(D-28)

(D-29)

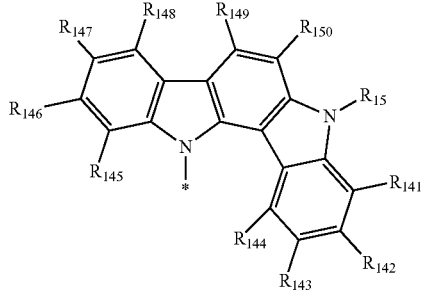
(D-30)

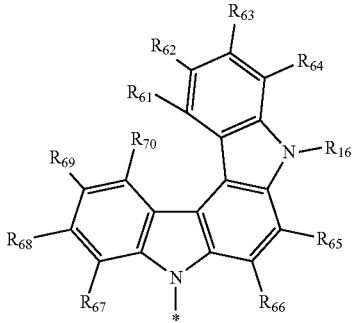
(D-31)

In the formulae (D-26) to (D-31), $R_{11}$ to $R_{16}$ are substituents, $R_{101}$ to $R_{150}$ and $R_{61}$ to $R_{70}$ are each independently a hydrogen atom or a substituent, or at least one pair of the following are mutually bonded to form a ring: a pair of $R_{101}$ and $R_{102}$, a pair of $R_{102}$ and $R_{103}$, a pair of $R_{103}$ and $R_{104}$, a pair of $R_{105}$ and $R_{106}$, a pair of $R_{107}$ and $R_{108}$, a pair of $R_{108}$ and $R_{109}$, a pair of $R_{109}$ and $R_{110}$, a pair of $R_{111}$ and $R_{112}$, a pair of $R_{112}$ and $R_{113}$, a pair of $R_{113}$ and $R_{114}$, a pair of $R_{116}$ and $R_{117}$, a pair of $R_{117}$ and $R_{118}$, a pair of $R_{118}$ and $R_{119}$, a pair of $R_{121}$ and $R_{122}$, a pair of $R_{122}$ and $R_{123}$, a pair of $R_{123}$ and $R_{124}$, a pair of $R_{126}$ and $R_{127}$, a pair of $R_{127}$ and $R_{128}$, a pair of $R_{128}$ and $R_{129}$, a pair of $R_{131}$ and $R_{132}$, a pair of $R_{132}$ and $R_{133}$, a pair of $R_{133}$ and $R_{134}$, a pair of $R_{135}$ and $R_{136}$, a pair of $R_{136}$ and $R_{137}$, a pair of $R_{137}$ and $R_{138}$, a pair of $R_{139}$ and $R_{140}$, a pair of $R_{141}$ and $R_{142}$, a pair of $R_{142}$ and $R_{143}$, a pair of $R_{143}$ and $R_{144}$, a pair of $R_{145}$ and $R_{146}$, a pair of $R_{146}$ and $R_{147}$, a pair of $R_{147}$ and $R_{148}$, a pair of $R_{149}$ and $R_{150}$, a pair of $R_{61}$ and $R_{62}$, a pair of $R_{62}$ and $R_{63}$, a pair of $R_{63}$ and $R_{64}$, a pair of $R_{65}$ and $R_{66}$, a pair of $R_{67}$ and $R_{68}$, a pair of $R_{68}$ and $R_{69}$, or a pair of $R_{69}$ and $R_{70}$; $R_{101}$ to $R_{150}$ and $R_{61}$ to $R_{70}$ serving as a substituent are each independently a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; $R_{11}$ to $R_{16}$ serving as a substituent are each independently a substituted or unsubstituted alkyl group having 1 to 6 carbon atoms, a substituted or unsubstituted aryl group having 6 to 14 ring carbon atoms, a substituted or unsubstituted heterocyclic group having 5 to 14 ring atoms, a substituted or unsubstituted alkylsilyl group having 3 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms; and * represents a bonding portion to a carbon atom of a benzene ring in the formula (2).

In the compound M2 of the exemplary embodiment, $R_{101}$ to $R_{150}$ and $R_{61}$ to $R_{70}$ serving as a substituent are preferably each independently an unsubstituted aryl group having 6 to 14 ring carbon atoms, an unsubstituted heterocyclic group having 5 to 14 ring atoms, or an unsubstituted alkyl group having 1 to 6 carbon atoms, and $R_{11}$ to $R_{16}$ serving as a substituent are preferably each independently an unsubstituted aryl group having 6 to 14 ring carbon atoms or an unsubstituted heterocyclic group having 5 to 14 ring atoms.

In the compound M2 of the exemplary embodiment, it is also preferable that $R_{101}$ to $R_{150}$ and $R_{61}$ to $R_{70}$ are hydrogen atoms, and $R_{11}$ to $R_{16}$ serving as a substituent are each independently an unsubstituted aryl group having 6 to 14 ring carbon atoms or an unsubstituted heterocyclic group having 5 to 14 ring atoms.

In the compound M2 of the exemplary embodiment, when any one or more of $R_{101}$ to $R_{150}$ and $R_{61}$ to $R_{70}$ are hydrogen atoms, it is preferable that all the hydrogen atoms are protium atoms, at least one of the hydrogen atoms is a deuterium atom, or all the hydrogen atoms are deuterium atoms.

In the compound M2 of the exemplary embodiment, when any one or more of $R_{11}$ to $R_{16}$, $R_{101}$ to $R_{150}$, and $R_{61}$ to $R_{70}$ are substituents and the substituents have one or more hydrogen atoms, it is preferable that all the hydrogen atoms are protium atoms, at least one of the hydrogen atoms is a deuterium atom, or all the hydrogen atoms are deuterium atoms.

Groups Represented by Formulae (D-32) to (D-37)

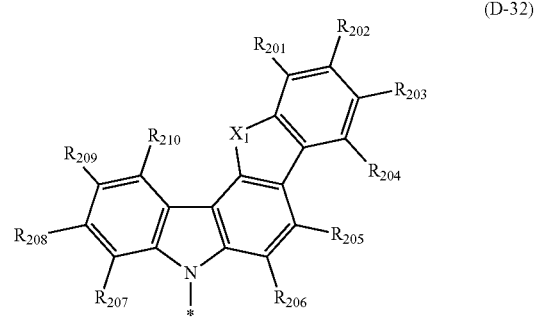

(D-32)

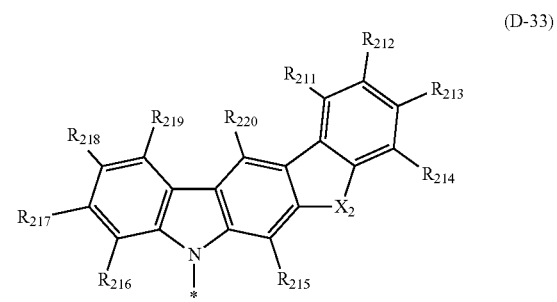

(D-33)

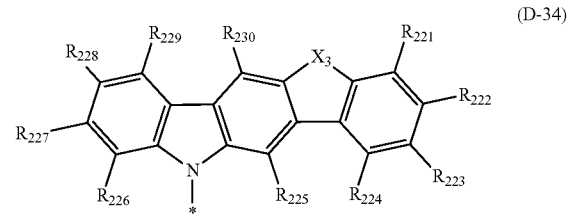

(D-34)

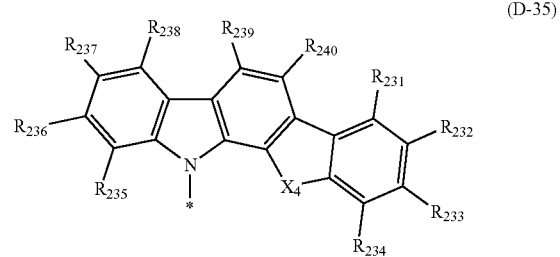

(D-35)

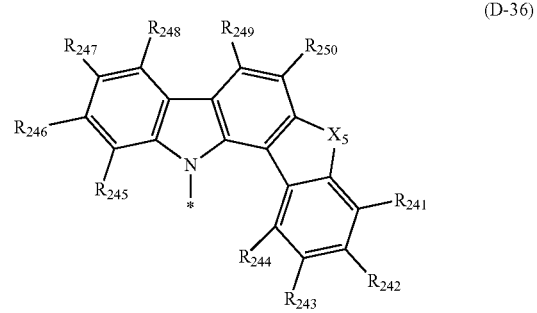

(D-36)

-continued

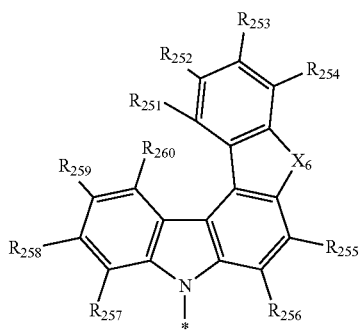

(D-37)

In the formulae (D-32) to (D-37), $X_1$ to $X_6$ are each independently an oxygen atom, a sulfur atom, or $CR_{151}R_{152}$; $R_{151}$ and $R_{152}$ are each independently a hydrogen atom or a substituent, or $R_{151}$ and $R_{152}$ are bonded to each other to form a ring; $R_{201}$ to $R_{260}$ are each independently a hydrogen atom or a substituent, or at least one pair of a pair of $R_{201}$ and $R_{202}$, a pair of $R_{202}$ and $R_{203}$, a pair of $R_{203}$ and $R_{204}$, a pair of $R_{205}$ and $R_{206}$, a pair of $R_{207}$ and $R_{208}$, a pair of $R_{208}$ and $R_{209}$, a pair of $R_{209}$ and $R_{210}$, a pair of $R_{211}$ and $R_{212}$, a pair of $R_{212}$ and $R_{213}$, a pair of $R_{213}$ and $R_{214}$, a pair of $R_{216}$ and $R_{217}$, a pair of $R_{217}$ and $R_{218}$, a pair of $R_{218}$ and $R_{219}$, a pair of $R_{221}$ and $R_{222}$, a pair of $R_{222}$ and $R_{223}$, a pair of $R_{223}$ and $R_{224}$, a pair of $R_{226}$ and $R_{227}$, a pair of $R_{227}$ and $R_{228}$, a pair of $R_{228}$ and $R_{229}$, a pair of $R_{231}$ and $R_{232}$, a pair of $R_{232}$ and $R_{233}$, a pair of $R_{233}$ and $R_{234}$, a pair of $R_{235}$ and $R_{236}$, a pair of $R_{236}$ and $R_{237}$, a pair of $R_{237}$ and $R_{238}$, a pair of $R_{238}$ and $R_{239}$ and $R_{240}$, a pair of $R_{241}$ and $R_{242}$, a pair of $R_{242}$ and $R_{243}$, a pair of $R_{243}$ and $R_{244}$, a pair of $R_{245}$ and $R_{246}$, a pair of $R_{246}$ and $R_{247}$, a pair of $R_{247}$ and $R_{248}$, a pair of $R_{249}$ and $R_{250}$, a pair of $R_{251}$ and $R_{252}$, a pair of $R_{252}$ and $R_{253}$, a pair of $R_{253}$ and $R_{254}$, a pair of $R_{255}$ and $R_{256}$, a pair of $R_{257}$ and $R_{258}$, a pair of $R_{258}$ and $R_{259}$, or a pair of $R_{259}$ and $R_{260}$ are bonded to each other to form a ring; $R_{151}$, $R_{152}$, and $R_{201}$ to $R_{260}$ serving as a substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted cycloalkyl group having 3 to 30 ring carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; and * represents a bonding portion to a carbon atom of a benzene ring in the formula (2).

In the compound M2 of the exemplary embodiment, $R_{201}$ to $R_{260}$ serving as a substituent are preferably each independently a halogen atom, an unsubstituted aryl group having 6 to 14 ring carbon atoms, an unsubstituted heterocyclic group having 5 to 14 ring atoms, or an unsubstituted alkyl group having 1 to 6 carbon atoms, and $R_{151}$ and $R_{152}$ serving as a substituent are preferably each independently an unsubstituted aryl group having 6 to 14 ring carbon atoms or an unsubstituted alkyl group having 1 to 6 carbon atoms.

In the compound M2 of the exemplary embodiment, it is more preferable that $R_{201}$ to $R_{260}$ serving as a substituent are each independently an unsubstituted aryl group having 6 to 14 ring carbon atoms, an unsubstituted heterocyclic group having 5 to 14 ring atoms, or an unsubstituted alkyl group having 1 to 6 carbon atoms, and $R_{151}$ and $R_{152}$ serving as a substituent are each independently an unsubstituted aryl group having 6 to 14 ring carbon atoms or an unsubstituted alkyl group having 1 to 6 carbon atoms.

It is also preferable that $R_{201}$ to $R_{260}$ in the compound M2 of the exemplary embodiment are hydrogen atoms, and $R_{151}$ and $R_{152}$ serving as a substituent are each independently an unsubstituted aryl group having 6 to 14 ring carbon atoms or an unsubstituted alkyl group having 1 to 6 carbon atoms.

In the compound M2 of the exemplary embodiment, when any one or more of $R_{151}$, $R_{152}$, and $R_{201}$ to $R_{260}$ are hydrogen atoms, it is preferable that all the hydrogen atoms are protium atoms, at least one of the hydrogen atoms is a deuterium atom, or all the hydrogen atoms are deuterium.

In the compound M2 of the exemplary embodiment, when any one or more of $R_{151}$, $R_{152}$, and $R_{201}$ to $R_{260}$ are substituents and the substituents have one or more hydrogen atoms, it is preferable that all the hydrogen atoms are protium atoms, at least one of the hydrogen atoms is a deuterium atom, or all the hydrogen atoms are deuterium atoms.

Compound Represented by Formula (22)

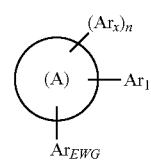

(22)

In the formula (22), $Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1j) below; $Ar_{EWG}$ is a substituted or unsubstituted heteroaryl group having 5 to 30 ring atoms and including one or more nitrogen atoms in a ring, or an aryl group having 6 to 30 ring carbon atoms and substituted with one or more cyano groups; $Ar_x$ is each independently a hydrogen atom or a substituent, and $Ar_x$ serving as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by the formulae (1a) to (1j) below; n is 0, 1, 2, 3, 4, or 5 and when n is 2, 3, 4, or 5, a plurality of $Ar_x$ are mutually the same or different; a ring (A) is a substituted or unsubstituted aromatic hydrocarbon ring or a substituted or unsubstituted heterocycle, the ring (A) is a five-membered ring, a six-membered ring, or a seven-membered ring, $Ar_{EWG}$, $Ar_1$ and $Ar_x$ are bonded to respective ones of elements forming the ring (A); and at least one of $Ar_1$ or $Ar_x$ is a group selected from the group consisting of groups represented by the formulae (1a) to (1j).

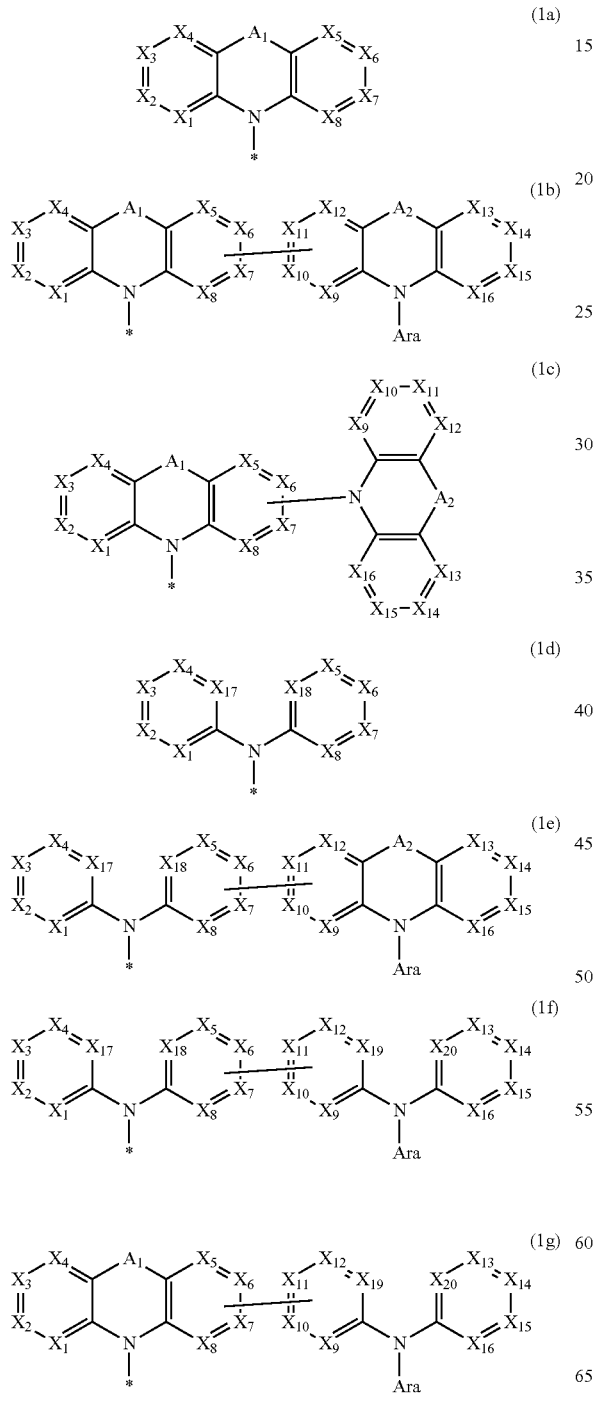

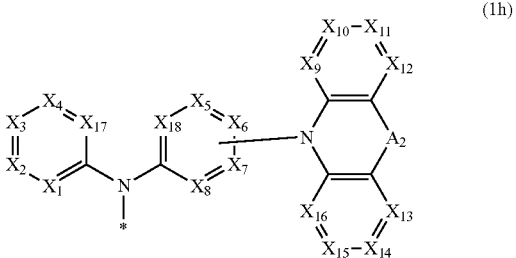

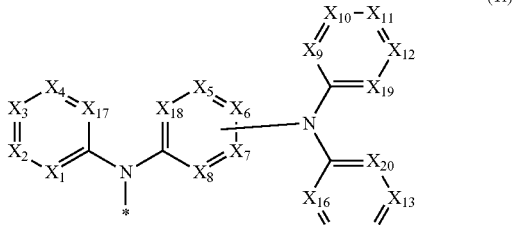

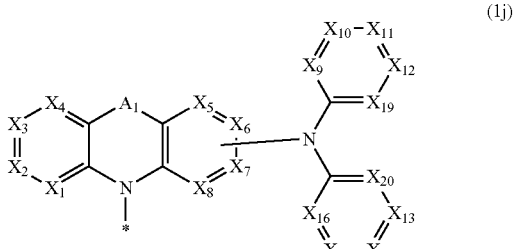

In the formulae (1a) to (1j), $X_1$ to $X_{20}$ are each independently a nitrogen atom (N) or a carbon atom bonded with $R_{A1}$ (C-$R_{A1}$).

In the formula (1b), one of $X_5$ to $X_8$ is a carbon atom bonded to one of $X_9$ to $X_{12}$, and one of $X_9$ to $X_{12}$ is a carbon atom bonded to one of $X_5$ to $X_8$.

In the formula (1c), one of $X_5$ to $X_8$ is a carbon atom bonded to a nitrogen atom in a ring including A2.

In the formula (1e), one of $X_5$ to $X_8$ and $X_{18}$ is a carbon atom bonded to one of $X_9$ to $X_{12}$, and one of $X_9$ to $X_{12}$ is a carbon atom bonded to one of $X_5$ to $X_8$ and $X_{18}$.

In the formula (1f), one of $X_5$ to $X_8$ and $X_{18}$ is a carbon atom bonded to one of $X_9$ to $X_{12}$ and $X_{19}$, and one of $X_9$ to $X_{12}$ and $X_{19}$ is a carbon atom bonded to one of $X_5$ to $X_8$ and $X_{18}$.

In the formula (1g), one of $X_5$ to $X_8$ is a carbon atom bonded to one of $X_9$ to $X_{12}$ and $X_{19}$, and one of $X_9$ to $X_{12}$ and $X_{19}$ is a carbon atom bonded to one of $X_5$ to $X_8$.

In the formula (1h), one of $X_5$ to $X_8$ and $X_{18}$ is a carbon atom bonded to a nitrogen atom in a ring including A2.

In the formula (1i), one of $X_5$ to $X_8$ and $X_{18}$ is a carbon atom bonded to a nitrogen atom linking a ring including $X_9$ to $X_{12}$ and $X_{19}$ with a ring including $X_{13}$ to $X_{16}$ and $X_{20}$.

In the formula (1j), one of $X_5$ to $X_8$ is a carbon atom bonded to a nitrogen atom linking a ring including $X_9$ to $X_{12}$ and $X_{19}$ with a ring including $X_{13}$ to $X_{16}$ and $X_{20}$.

$R_{A1}$ is each independently a hydrogen atom or a substituent, or at least one pair of pairs among a plurality of $R_{A1}$ are mutually directly bonded to form a ring or bonded via a hetero atom to form a ring; and $R_{A1}$ serving as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

When a plurality of $R_{A1}$ serving as a substituent are present, the plurality of $R_{A1}$ are mutually the same or different.

In the formula (1a), when $X_1$ to $X_8$ are a carbon atom bonded with $R_{A1}$ (C-$R_{A1}$), a plurality of $R_{A1}$ preferably form no ring.

When any one or more of $R_{A1}$ are hydrogen atoms, it is preferable that all the hydrogen atoms are protium atoms, at least one of the hydrogen atoms is a deuterium atom, or all the hydrogen atoms are deuterium.

When any one or more of $R_{A1}$ are substituents and the substituents have one or more hydrogen atoms, it is preferable that all the hydrogen atoms are protium atoms, at least one of the hydrogen atoms is a deuterium atom, or all the hydrogen atoms are deuterium atoms.

In the formulae (1a) to (1j), * represents a bonding portion to the ring (A).

In the formulae (1a) to (1j), $A_1$ and $A_2$ are each independently a single bond, an oxygen atom (O), a sulfur atom (S), $C(R_{2021})(R_{2022})$, $Si(R_{2023})(R_{2024})$, $C(=O)$, $S(=O)$, $SO_2$ or $N(R_{2025})$. $R_{2021}$ to $R_{2025}$ are each independently a hydrogen atom or a substituent, and $R_{2021}$ to $R_{2025}$ serving as a substituent are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

In the formulae (1a) to (1j), Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

Ara is preferably a substituted or unsubstituted aryl group having 6 to 30 ring carbon atoms or a substituted or unsubstituted heteroaryl group having 5 to 30 ring atoms.

The formula (1a) is represented by a formula (1aa) below when A1 is a single bond, represented by a formula (1ab) below when A1 is O, represented by a formula (1ac) below when A1 is S, represented by a formula (1ad) below when A1 is $C(R_{2021})(R_{2022})$, represented by a formula (1ae) below when A1 is $Si(R_{2023})(R_{2024})$, represented by a formula (1af) below when A1 is $C(=O)$, represented by a formula (1ag) below when A1 is $S(=O)$, represented by a formula (1ah) below when A1 is $SO_2$, and represented by a formula (1ai) below when A1 is $N(R_{2025})$. In the formulae (1aa) to (1ai), $X_1$ to $X_8$ and $R_{2021}$ to $R_{2025}$ represent the same as described above. Linkages between rings via A1 and A2 in the formulae (1b), (1c), (1e) and (1g) to (1j) are the same as those in the formulae (1aa) to (1ai). In the formula (1aa), when $X_1$ to $X_8$ are a carbon atom bonded with $R_{A1}$ (C-$R_{A1}$), a plurality of $R_{A1}$ serving as a substituent preferably form no ring.

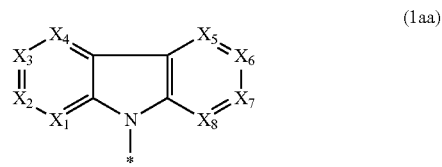

(1aa)

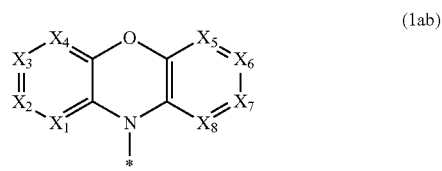

(1ab)

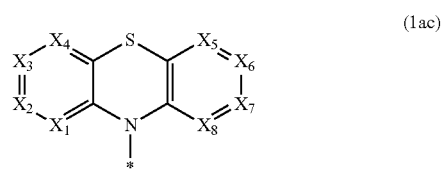

(1ac)

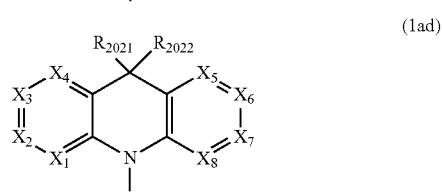

(1ad)

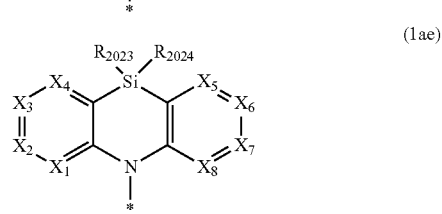

(1ae)

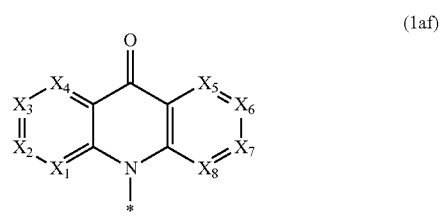

(1af)

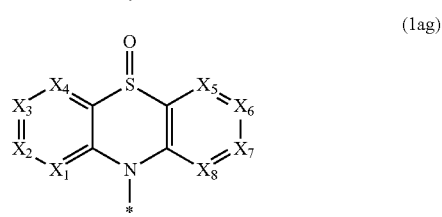

(1ag)

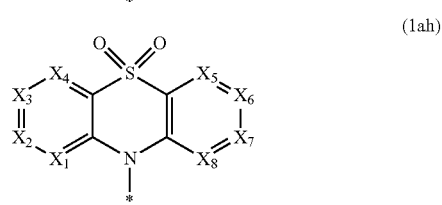

(1ah)

-continued

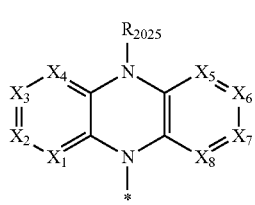
(1ai)

The compound M2 is also preferably represented by a formula (221) below.

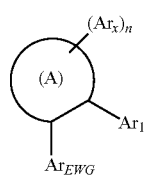
(221)

$Ar_1$, $Ar_{EWG}$, $Ar_x$, n and a ring (A) in the formula (221) respectively represent the same as $Ar_1$, $Ar_{EWG}$, $Ar_x$, n and the ring (A) in the formula (22).

The compound M2 is also preferably represented by a formula (222) below.

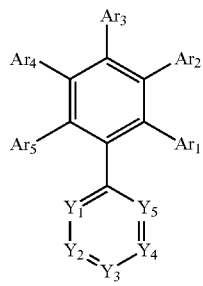
(222)

In the formula (222), $Y_1$ to $Y_5$ are each independently a nitrogen atom (N), a carbon atom bonded with a cyano group (C—CN), or a carbon atom bonded with $R_{A2}$ (C-$R_{A2}$), and at least one of $Y_1$ to $Y_5$ is N or C—CN. A plurality of $R_{A2}$ are mutually the same or different. $R_{A2}$ is each independently a hydrogen atom or a substituent, and $R_{A2}$ serving as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and a plurality of $R_{A2}$ are mutually the same or different.

In the formula (222), $Ar_1$ represents the same as $Ar_1$ in the formula (22).

In the formula (222), $Ar_2$ to $Ar_5$ are each independently a hydrogen atom or a substituent, and $Ar_2$ to $Ar_5$ serving as a substituent are each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by the formulae (1a) to (1c).

In the formula (222), when any one or more of $Ar_2$ to $Ar_5$ are hydrogen atoms, it is preferable that all the hydrogen atoms are protium atoms, at least one of the hydrogen atoms is a deuterium atom, or all the hydrogen atoms are deuterium.

In the formula (222), when any one or more of $Ar_2$ to $Ar_5$ are substituents and the substituents have one or more hydrogen atoms, it is preferable that all the hydrogen atoms are protium atoms, at least one of the hydrogen atoms is a deuterium atom, or all the hydrogen atoms are deuterium atoms In the formula (222), at least one of $Ar_1$ to $Ar_5$ is a group selected from the group consisting of groups represented by the formulae (1a) to (1c).

The compound M2 is also preferably a compound represented by a formula (11aa), (11bb) or (11cc) below.

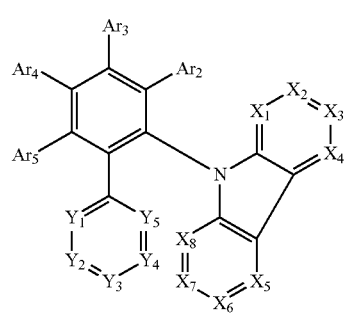
(11aa)

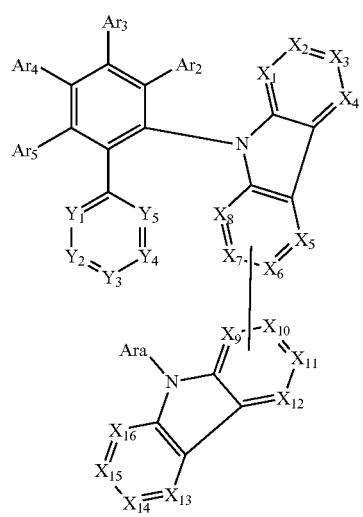
(11bb)

-continued

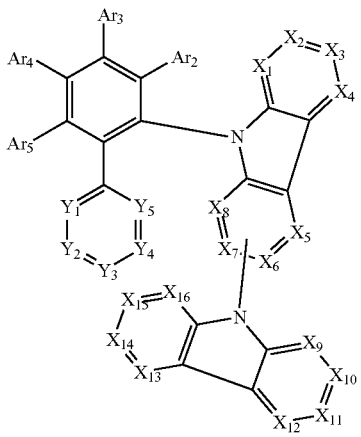
(11cc)

In the formulae (11aa), (11bb) and (11cc), $Y_1$ to $Y_5$, $R_{42}$, $Ar_2$ to $Ar_5$, $X_1$ to $X_{16}$, $R_{41}$ and Ara respectively represent the same as the above-described $Y_1$ to $Y_5$, $R_{42}$, $Ar_2$ to $Ar_5$, $X_1$ to $X_{16}$, $R_{41}$ and Ara.

The compound M2 is exemplified by a compound represented by a formula (23) below.

(23)

In the formula (23): Az is a cyclic structure selected from the group consisting of a substituted or unsubstituted pyridine ring, a substituted or unsubstituted pyrimidine ring, a substituted or unsubstituted triazine ring, and a substituted or unsubstituted pyrazine ring; c is 0, 1, 2, 3, 4 or 5; when c is 0, Cz and Az are bonded by a single bond; when c is 1, 2, 3, 4 or 5, $L_{23}$ is a linking group selected from the group consisting of a substituted or unsubstituted arylene group having 6 to 30 ring carbon atoms, and a substituted or unsubstituted heteroarylene group having 5 to 30 ring atoms; when c is 2, 3, 4 or 5, a plurality of $L_{23}$ are mutually the same or different; the plurality of $L_{23}$ are mutually bonded to form a ring or not bonded to form no ring; and Cz is represented by a formula (23a) below.

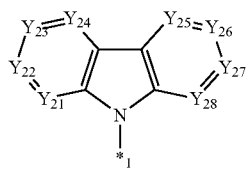
(23a)

In the formula (23a): $Y_{21}$ to $Y_{28}$ are each independently a nitrogen atom or $CR_{43}$; $R_{43}$ is each independently a hydrogen atom or a substituent, or at least one pair of pairs among a plurality of RAS are mutually bonded to form a ring; $R_{43}$ serving as a substituent is each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; a plurality of $R_{43}$ are mutually the same or different; and *1 represents a bonding portion to a carbon atom in a structure of a linking group represented by $L_{23}$, or a bonding portion to a carbon atom in a cyclic structure represented by Az.

$Y_{21}$ to $Y_{28}$ are also preferably $CR_{43}$.

c in the formula (23) is preferably 0 or 1.

Cz is also preferably represented by a formula (23b), (23c) or (23d) below.

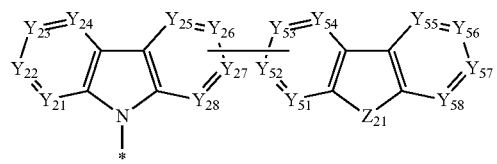
(23b)

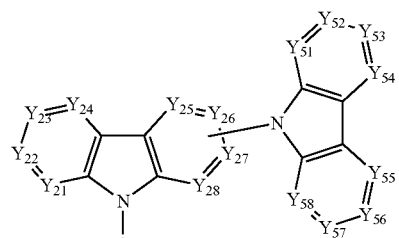
(23c)

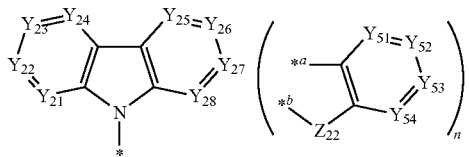
(23d)

In the formulae (23b), (23c) and (23d), $Y_{21}$ to $Y_{28}$ and $Y_{51}$ to $Y_{58}$ are each independently a nitrogen atom or $CR_{44}$; in the formula (23b), at least one of $Y_{25}$ to $Y_{28}$ is a carbon atom bonded to one of $Y_{51}$ to $Y_{54}$, and at least one of $Y_{51}$ to $Y_{54}$ is a carbon atom bonded to one of $Y_{25}$ to $Y_{28}$; in the formula (23c), at least one of $Y_{25}$ to $Y_{28}$ is a carbon atom bonded to a nitrogen atom in a five-membered ring of a nitrogen-containing fused ring including $Y_{51}$ to $Y_{58}$; in the formula (23d), *a and *b each represent a bonding portion to one of $Y_{21}$ to $Y_{28}$, at least one of $Y_{25}$ to $Y_{28}$ is the bonding portion represented by *a, and at least one of $Y_{25}$ to $Y_{28}$ is the bonding position represented by *b; n is 1, 2, 3 or 4; $R_{44}$ is each independently a hydrogen atom or a substituent, or at least one pair of pairs of a plurality of $R_{44}$ are mutually bonded to form a ring; $R_{44}$ serving as a substituent is each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; a plurality of $R_{44}$ are mutually the same or different; $Z_{21}$ and $Z_{22}$ are each independently one selected from the group consisting of an oxygen atom, a sulfur atom, $NR_{45}$, and $CR_{46}R_{47}$; $R_{45}$ is a hydrogen atom or a substituent; $R_{46}$ and $R_{47}$ are each independently a hydrogen atom or a substituent, or a pair of $R_{46}$ and $R_{47}$ are mutually bonded to form a ring; $R_{45}$, $R_{46}$ and $R_{47}$ serving as a substituent are each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; a plurality of $R_{45}$ are mutually the same or different; a plurality of $R_{46}$ are mutually the same or different; a plurality of $R_{47}$ are mutually the same or different; and * represents a bonding portion to a carbon atom in a structure of a linking group represented by $L_{23}$, or a bonding portion to a carbon atom in a cyclic structure represented by Az.

$Z_{21}$ is preferably $NR_{45}$. When $Z_{21}$ is $NR_{45}$, $R_{45}$ is preferably a substituted or unsubstituted aryl group having 6 to 30 ring carbon atoms.

$Z_{22}$ is preferably $NR_{45}$. When $Z_{22}$ is $NR_{45}$, $R_{45}$ is preferably a substituted or unsubstituted aryl group having 6 to 30 ring carbon atoms.

$Y_{51}$ to $Y_{58}$ are preferably $CR_{44}$, provided that at least one of $Y_{51}$ to $Y_{58}$ is a carbon atom bonded to a cyclic structure represented by the formula (23a).

It is also preferable that Cz is represented by the formula (23d) and n is 1.

Az is preferably a cyclic structure selected from the group consisting of a substituted or unsubstituted pyrimidine group and a substituted or unsubstituted triazine group.

Az is a cyclic structure selected from the group consisting of a substituted pyrimidine ring and a substituted triazine ring, in which a substituent of each of the substituted pyrimidine ring and the substituted triazine ring is more preferably a group selected from the group consisting of a substituted or unsubstituted aryl group having 6 to 30 ring carbon atoms and a substituted or unsubstituted heteroaryl group having 5 to 30 ring atoms, further preferably a substituted or unsubstituted aryl group having 6 to 30 ring carbon atoms.

When the pyrimidine ring and the triazine ring as Az have a substituted or unsubstituted aryl group serving as a substituent, the aryl group preferably has 6 to 20 ring carbon atoms, more preferably 6 to 14 ring carbon atoms, further preferably 6 to 12 ring carbon atoms.

When Az has a substituted or unsubstituted aryl group serving as a substituent, the substituent is preferably a group selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably a group selected from the group consisting of a substituted or unsubstituted phenyl group, a substituted or unsubstituted biphenyl group, and a substituted or unsubstituted naphthyl group.

When Az has a substituted or unsubstituted heteroaryl group serving as a substituent, the substituent is preferably a substituent selected from the group consisting of a substituted or unsubstituted carbazolyl group, a substituted or unsubstituted dibenzofuranyl group, and a substituted or unsubstituted dibenzothiophenyl group.

$R_{44}$ is each independently a hydrogen atom or a substituent. $R_{44}$ serving as a substituent is preferably a substituent selected from the group consisting of a substituted or unsubstituted aryl group having 6 to 30 ring carbon atoms and a substituted or unsubstituted heteroaryl group having 5 to 30 ring atoms.

When $R_{44}$ serving as a substituent is a substituted or unsubstituted aryl group having 6 to 30 ring carbon atoms, $R_{44}$ serving as a substituent is preferably a substituent selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably a substituent selected from the group consisting of a substituted or unsubstituted phenyl group, a substituted or unsubstituted biphenyl group, and a substituted or unsubstituted naphthyl group.

When $R_{44}$ serving as a substituent is a substituted or unsubstituted heteroaryl group having 5 to 30 ring atoms, $R_{44}$ serving as a substituent is preferably a substituent selected from the group consisting of a substituted or unsubstituted carbazolyl group, a substituted or unsubstituted dibenzofuranyl group, and a substituted or unsubstituted dibenzothiophenyl group.

$R_{45}$, $R_{46}$ and $R_{47}$ serving as a substituent are preferably each independently a substituent selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms.

In the compound M2 of the exemplary embodiment, when any one or more of $R_{43}$, $R_{44}$, $R_{45}$ to $R_{46}$, and $R_{47}$ are hydrogen atoms, it is preferable that all the hydrogen atoms are protium atoms, at least one of the hydrogen atoms is a deuterium atom, or all the hydrogen atoms are deuterium.

In the compound M2 of the exemplary embodiment, when any one or more of $R_{43}$, $R_{44}$, $R_{45}$ to $R_{46}$, and $R_{47}$ are substituents and the substituents have one or more hydrogen atoms, it is preferable that all the hydrogen atoms are protium atoms, at least one of the hydrogen atoms is a deuterium atom, or all the hydrogen atoms are deuterium atoms.

Manufacturing Method of Compound M2 According to Exemplary Embodiment

The compound M2 can be manufactured by a publicly known method.

For example, when the compound M2 is a non-deuterated compound m2, the compound M2 can be manufactured by a method described in Examples below.

For example, when the compound M2 is a compound having at least one deuterium atom (deuterated compound DM2), the compound M2 can be manufactured by a method described in Examples below.

The compound M2 can also be manufactured in accordance with the reactions described in Examples below using known alternative reactions and raw materials according to the target compound.

Specific examples of the compound M2 of the exemplary embodiment include compounds below. It should however be noted that the invention is not limited to the specific examples of the compound.

In some of the specific examples of the compound M2, hydrogen atoms are omitted.

A specific example of the compound M2 in which hydrogen atoms are omitted will be described.

For example, in the case where a specific example of the compound M2 is a compound represented by (M2-1) below, the compound is represented by a formula (M2-11) below when shown without omitting hydrogen atoms.

In the formula (M2-11) below, "HD" each represent a protium atom or a deuterium atom.

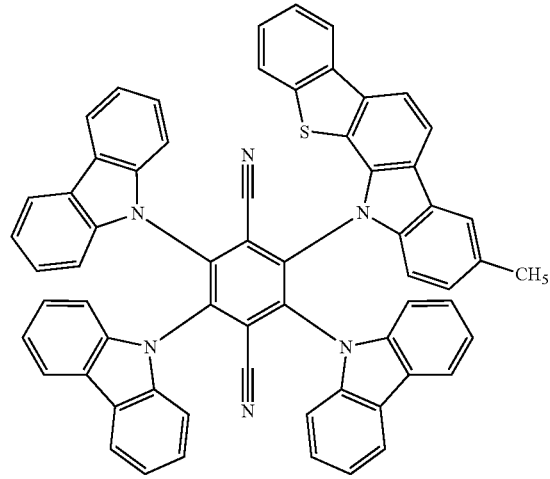

(M2-1)

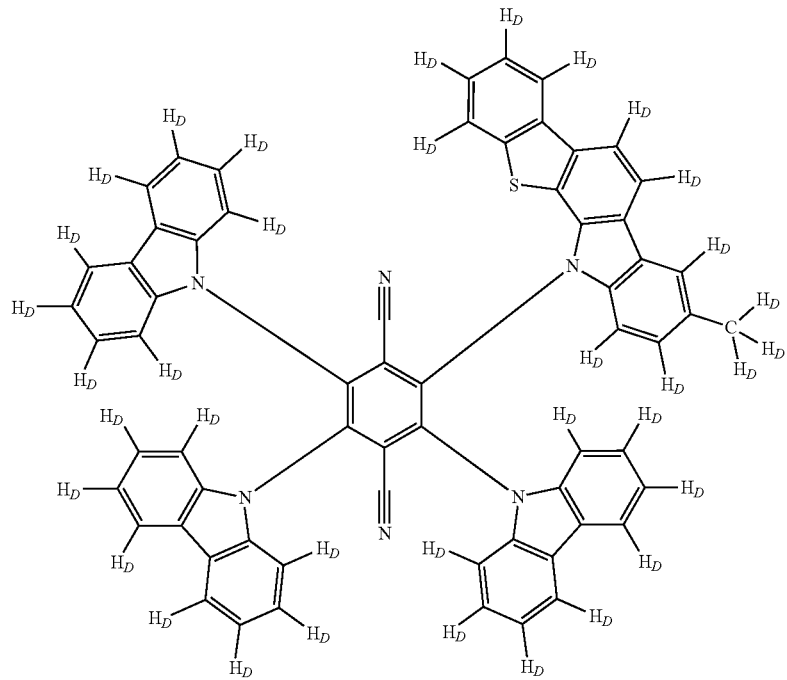

(M2-11)

The following specific examples of the compound M2 are specific examples in which hydrogen atoms are omitted.

233
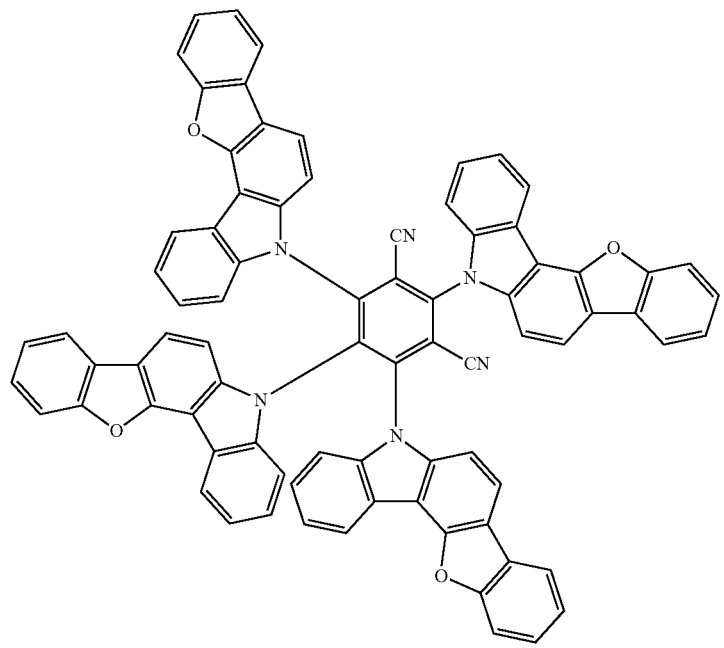
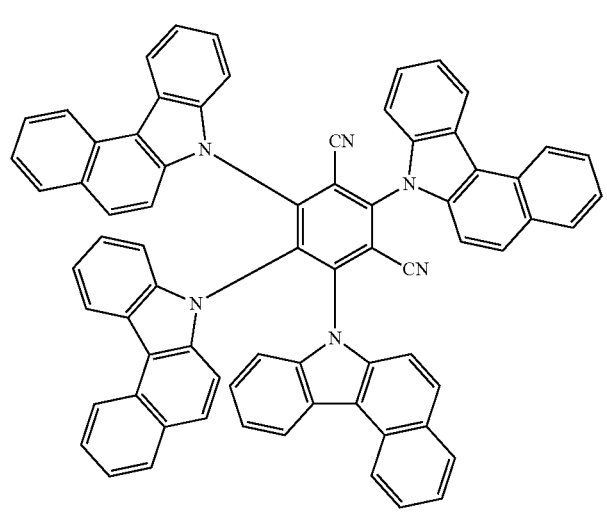
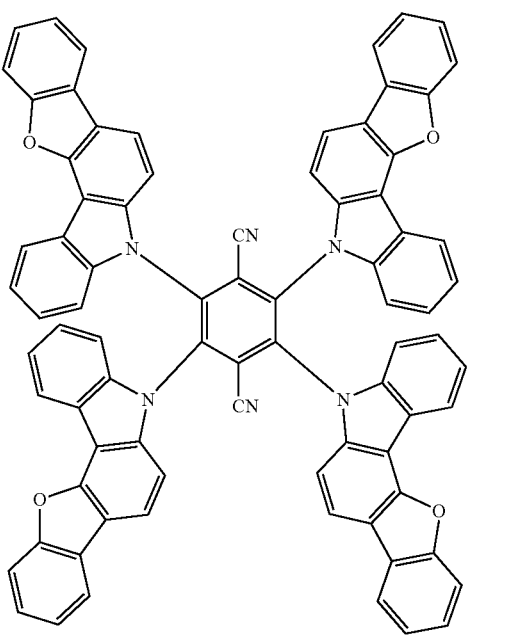
234
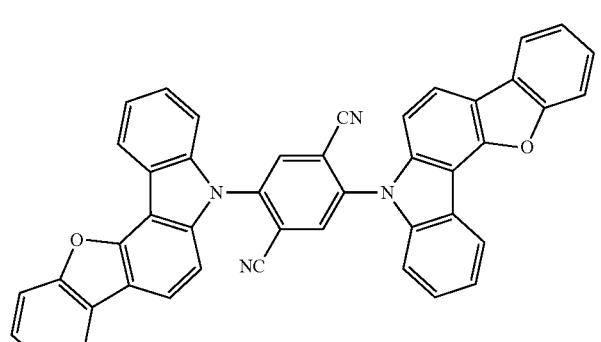
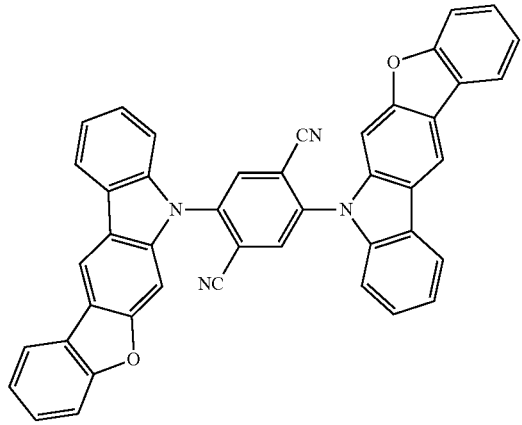

-continued
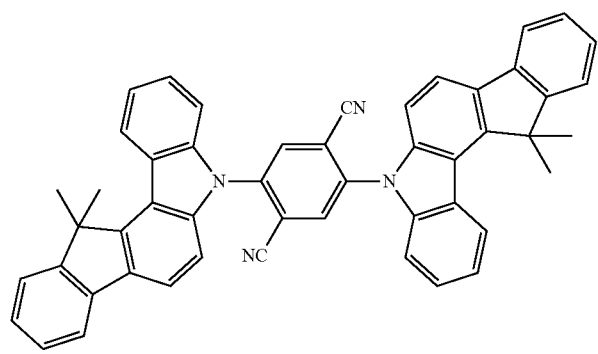
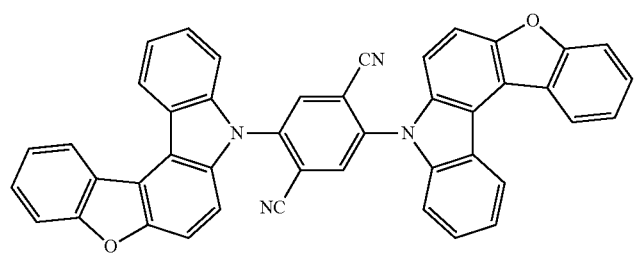
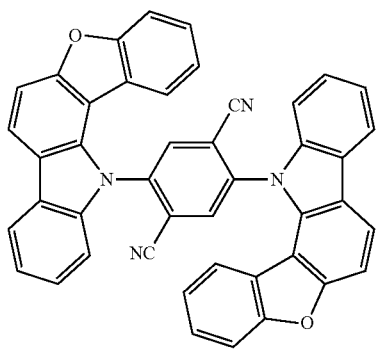
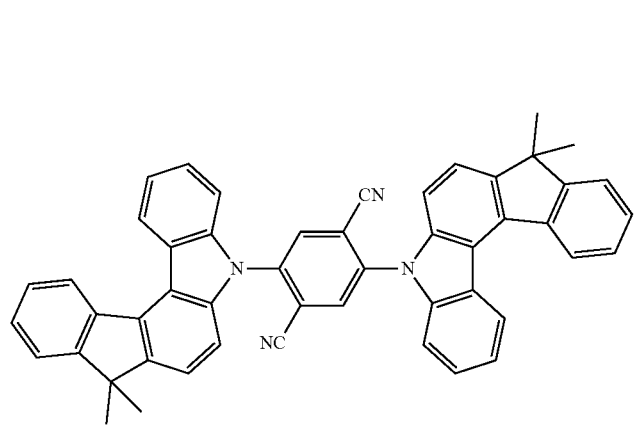
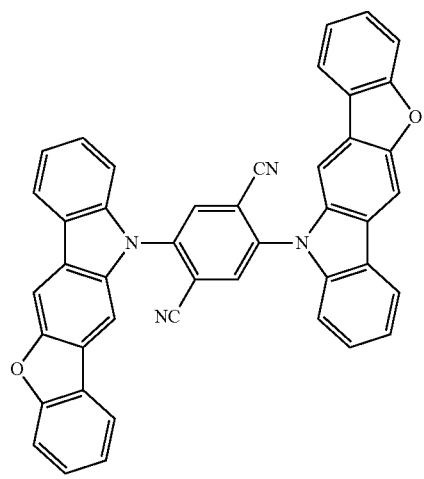
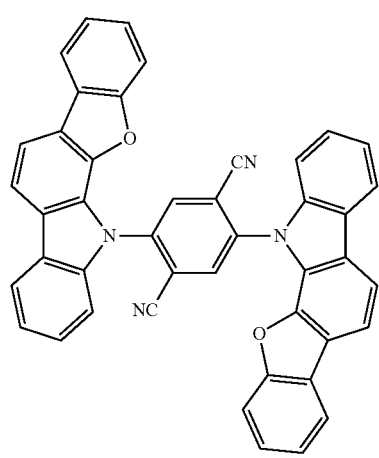
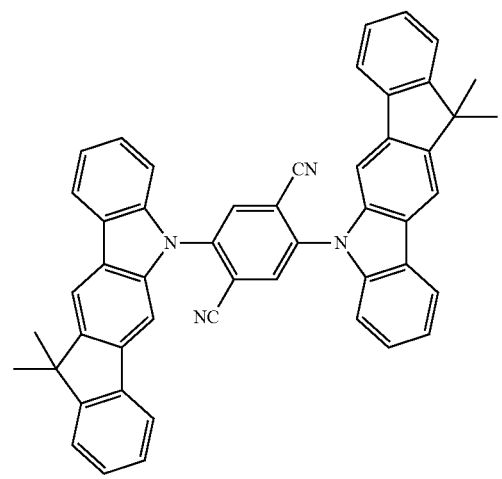

-continued
237
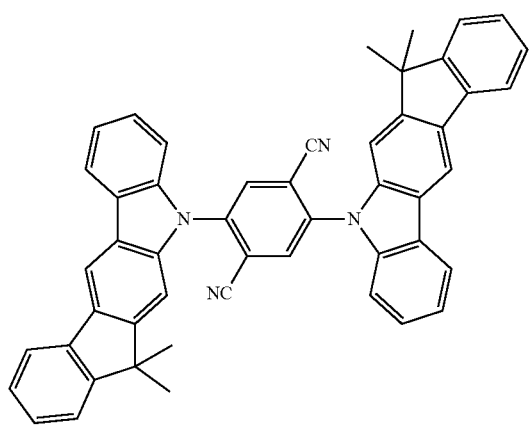
238
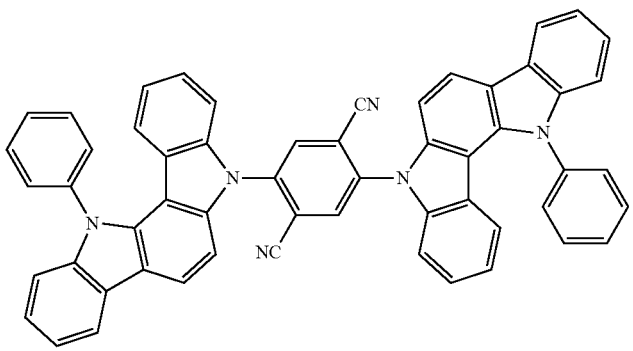
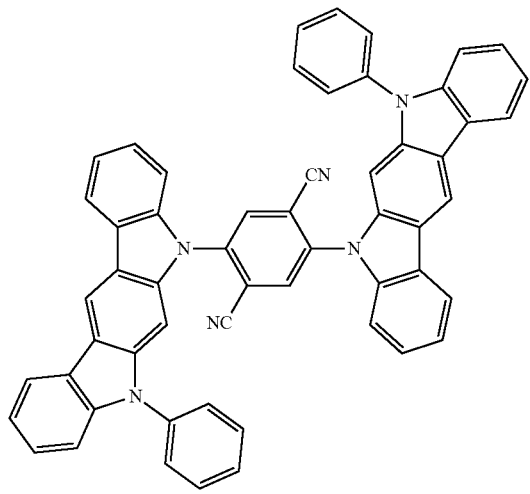
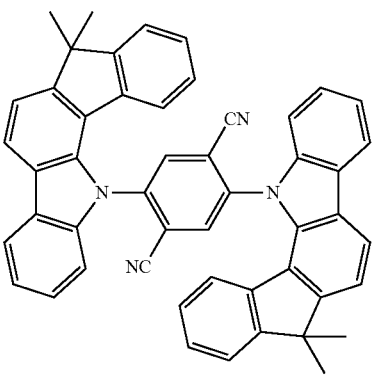
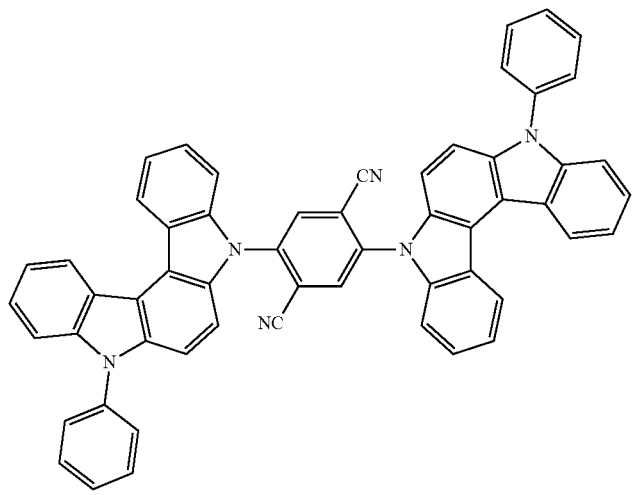

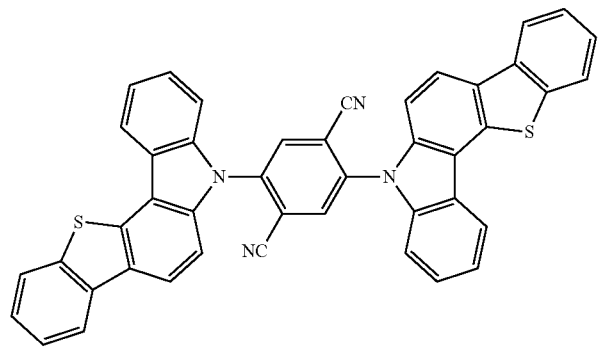
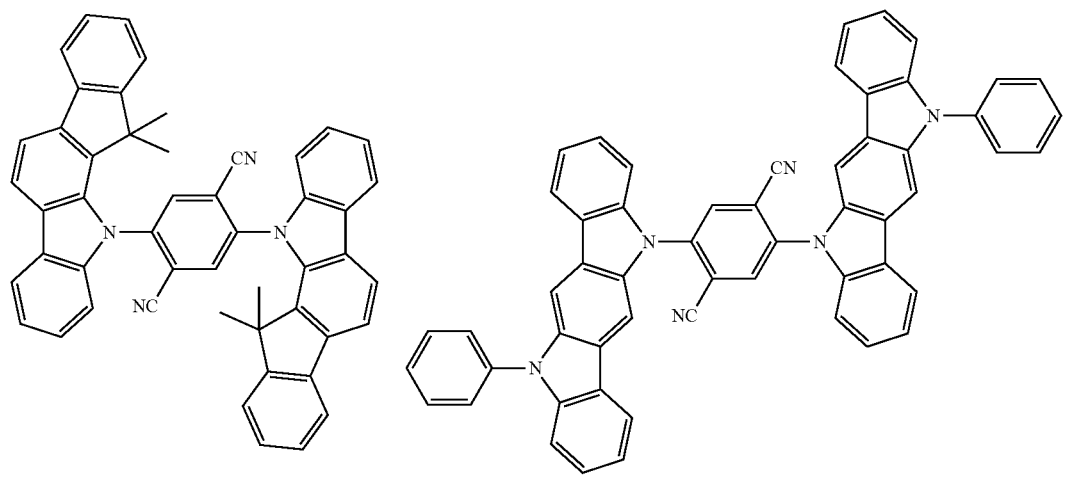
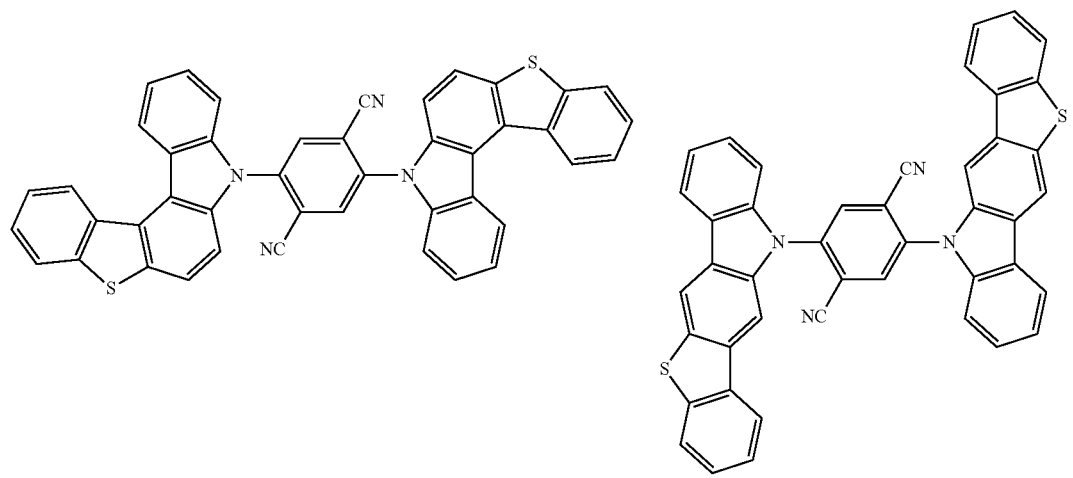

-continued
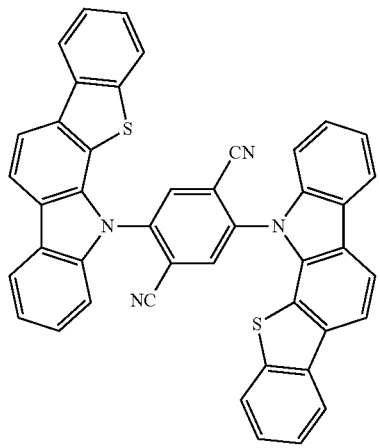
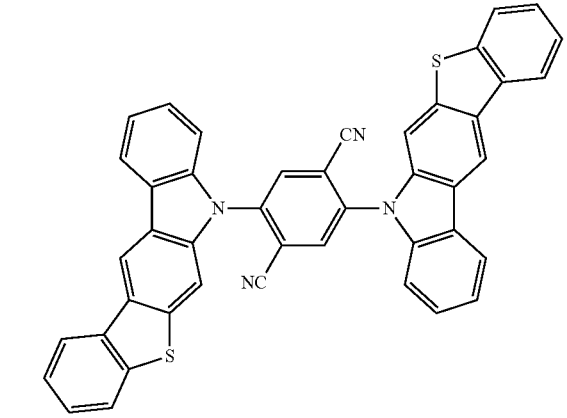
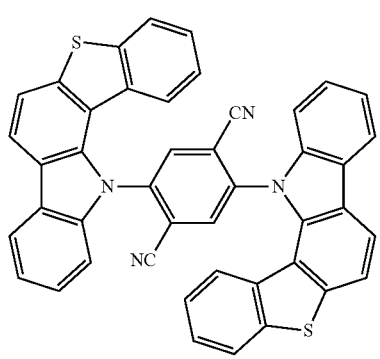
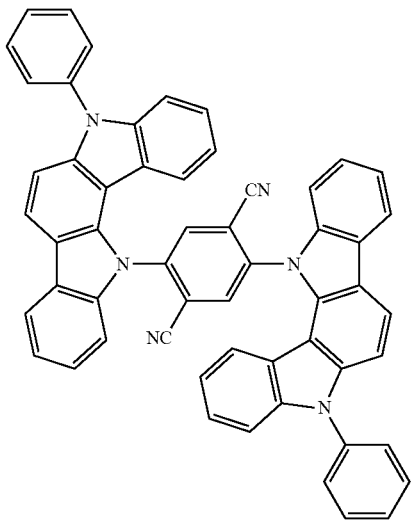
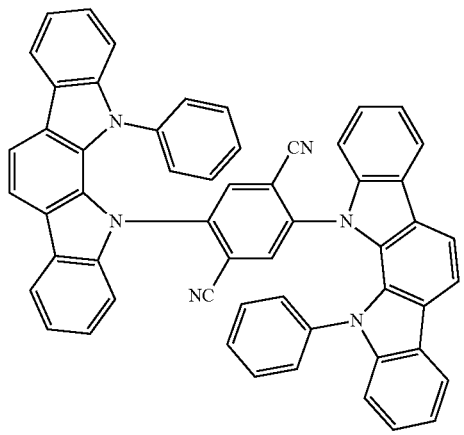
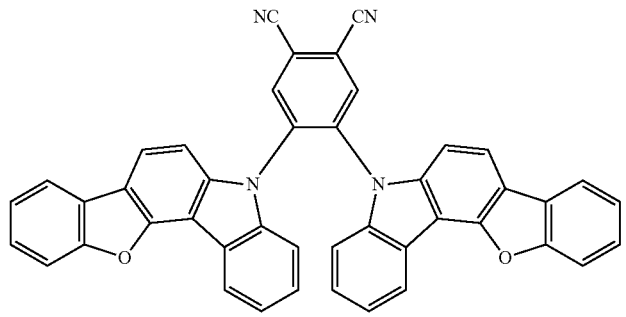
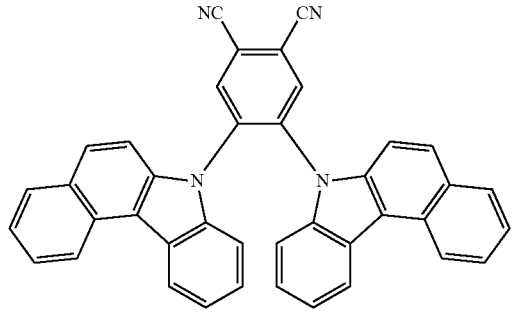
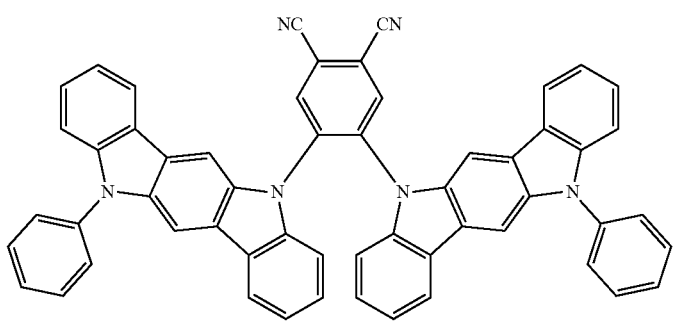

-continued
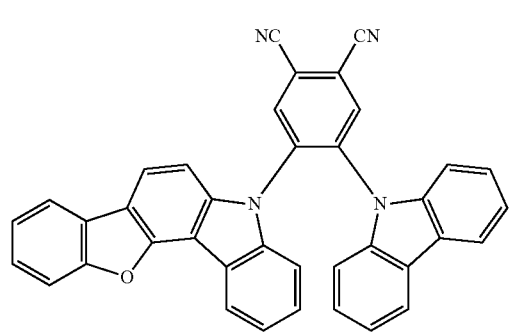
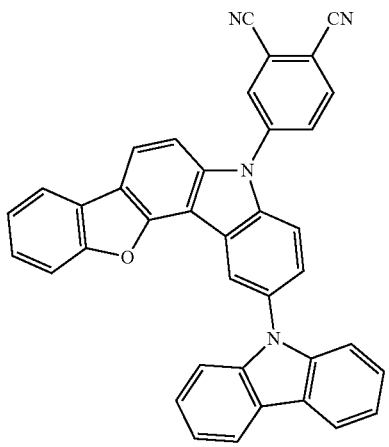
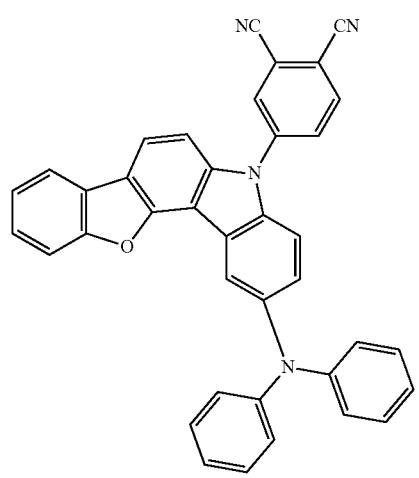
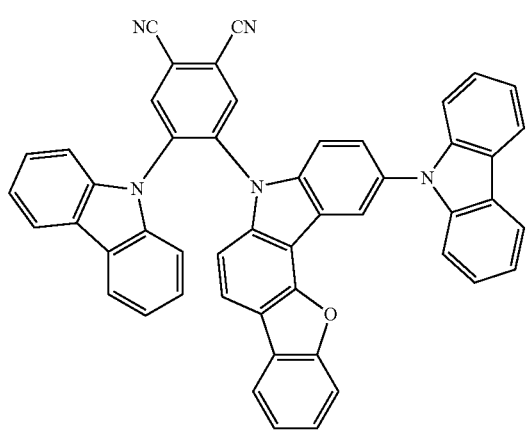
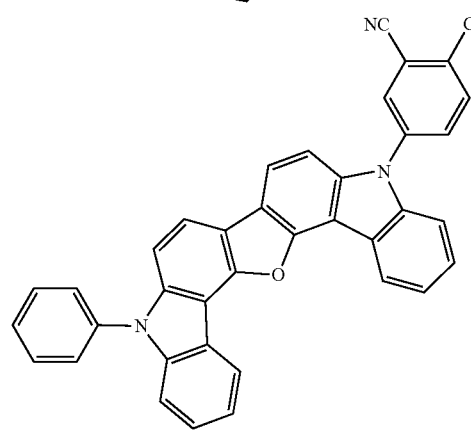
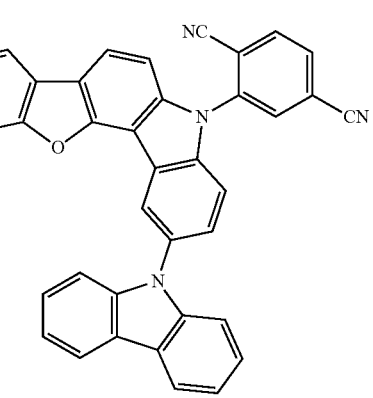
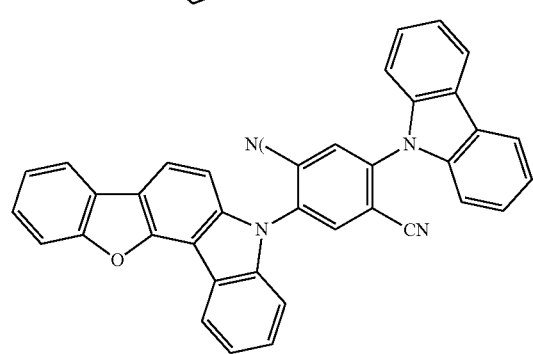
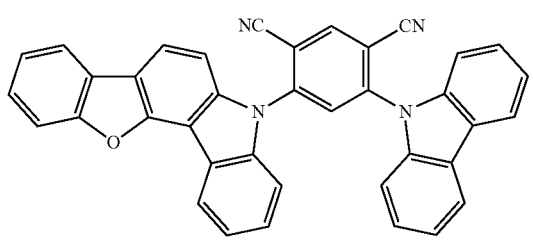

-continued
245
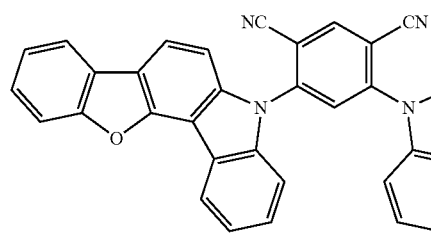
246
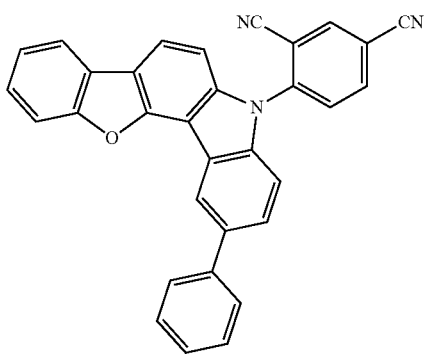
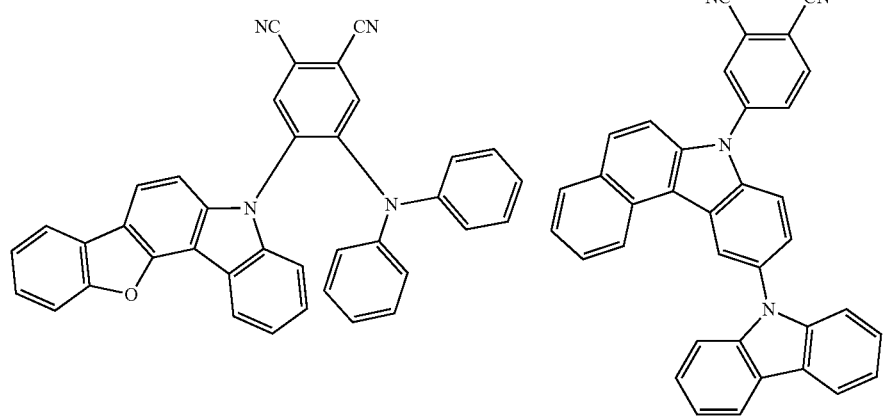
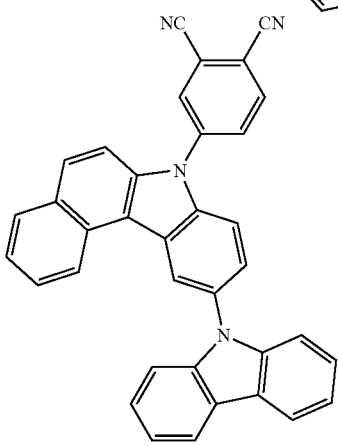
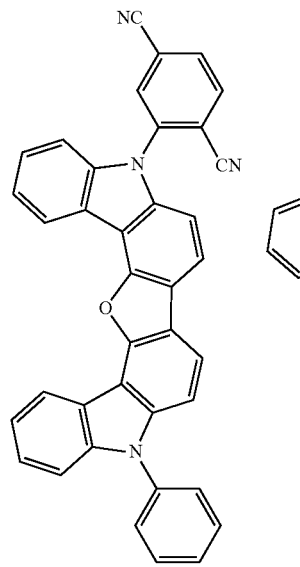
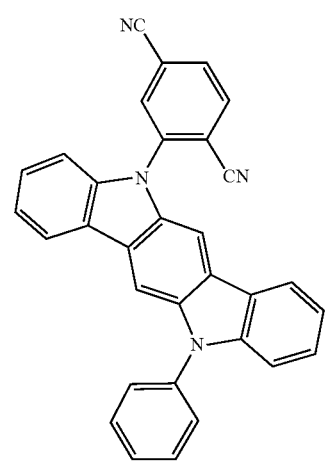
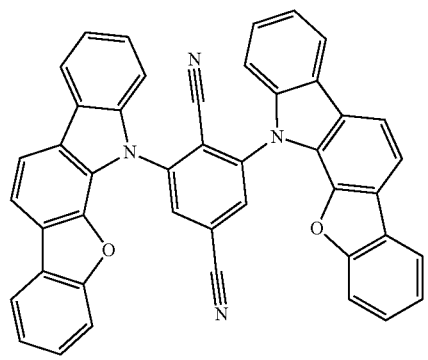
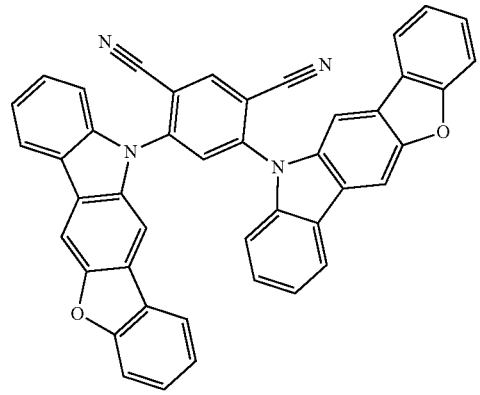

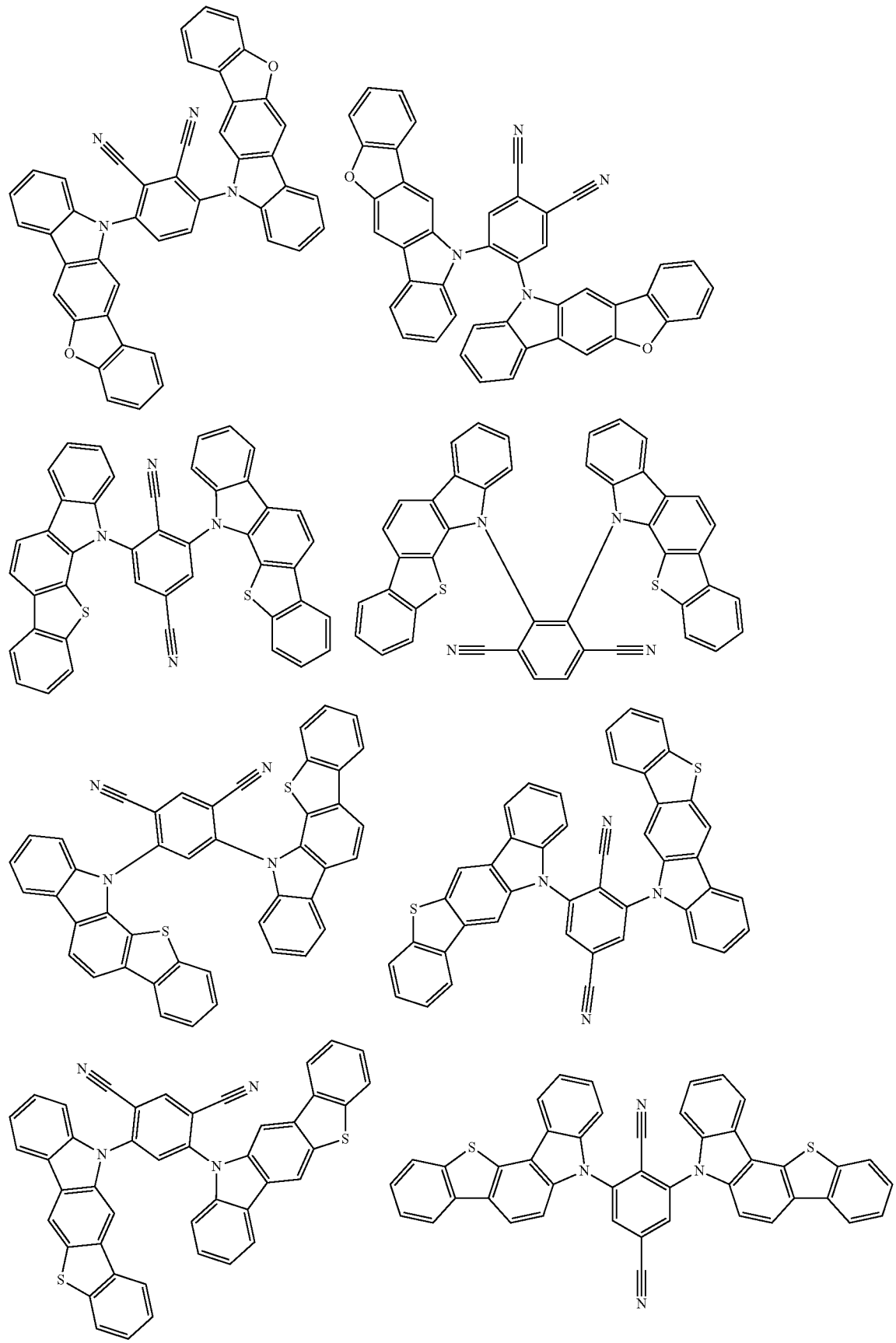

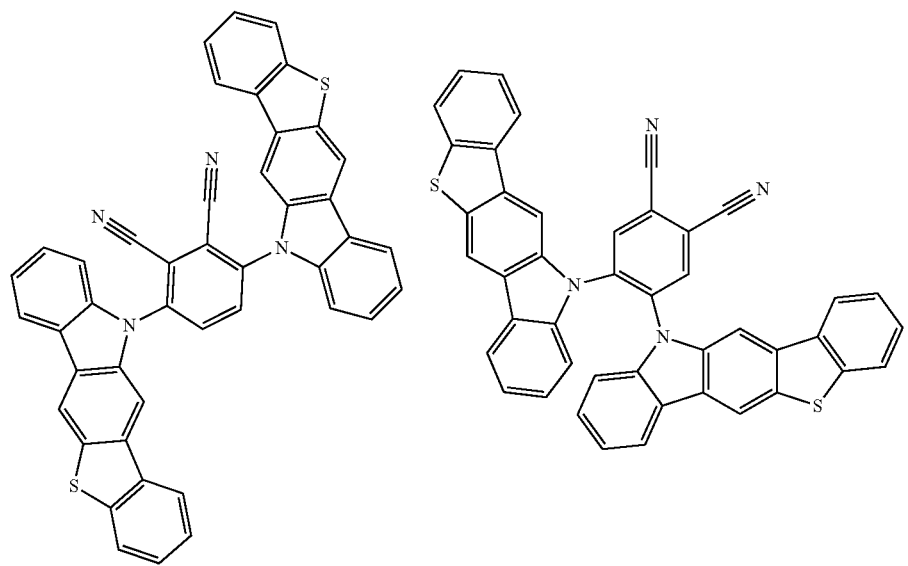
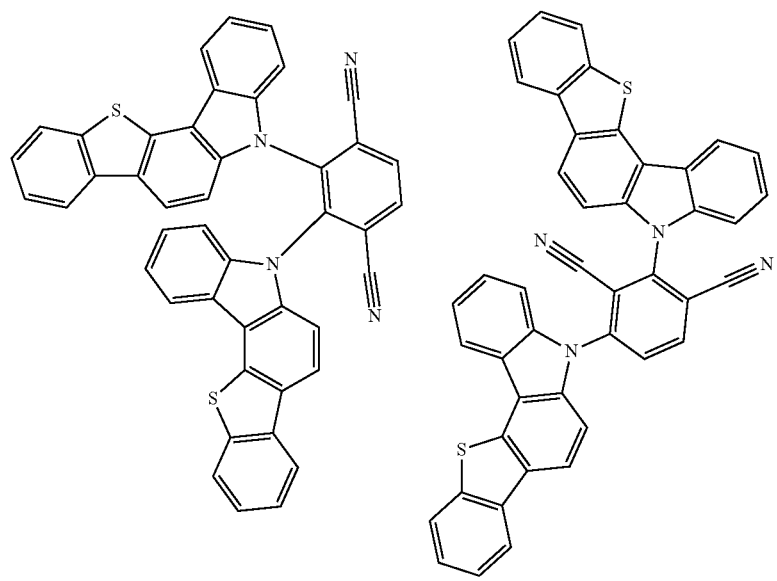
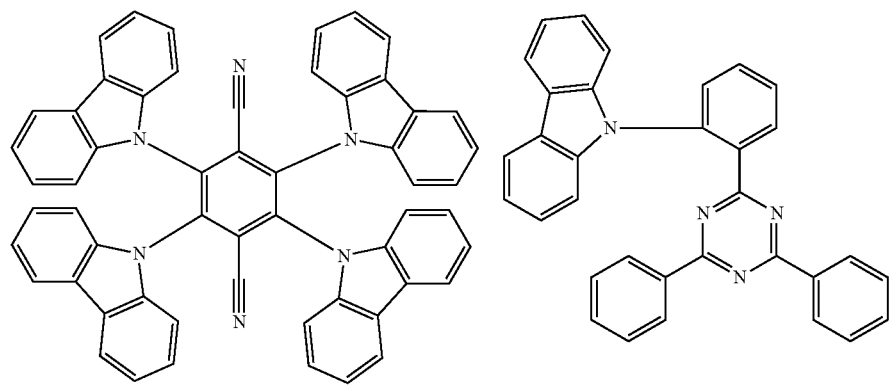

-continued
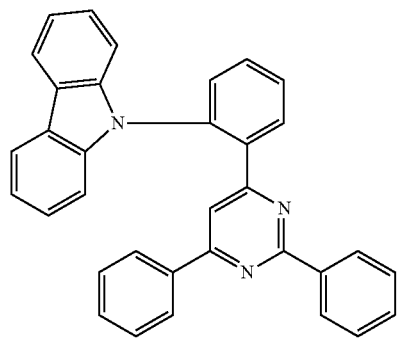
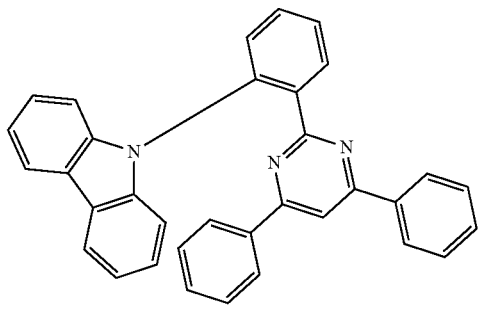
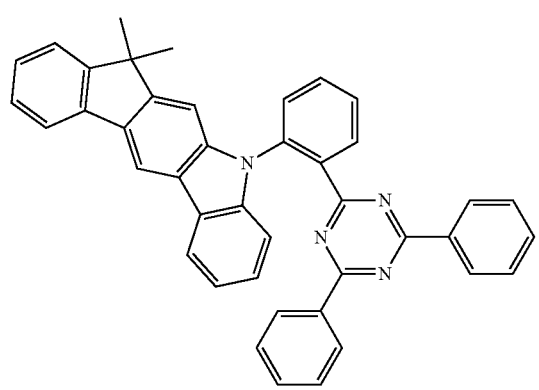
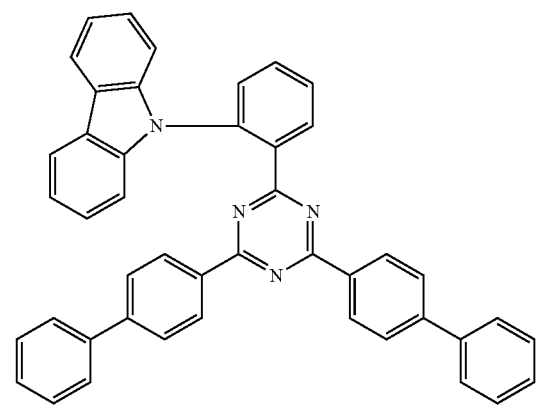
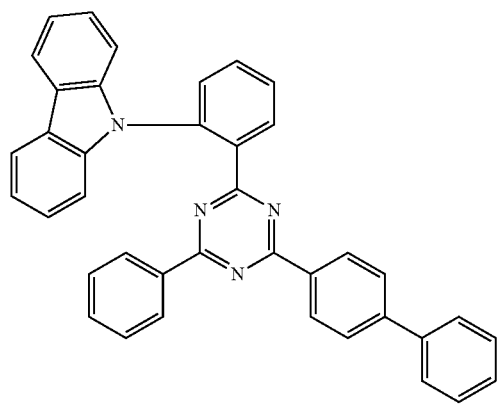
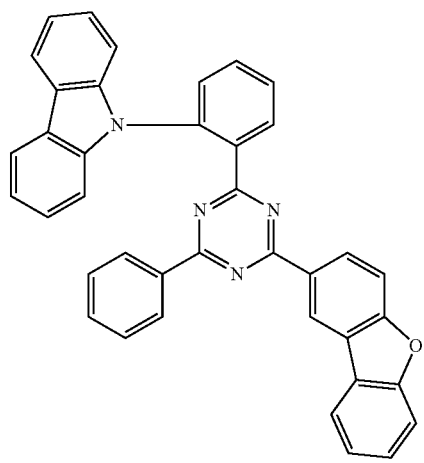
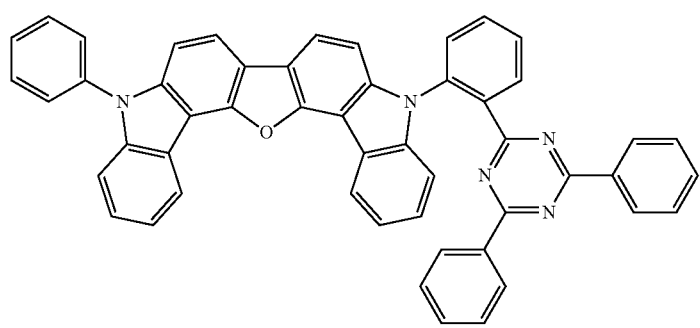

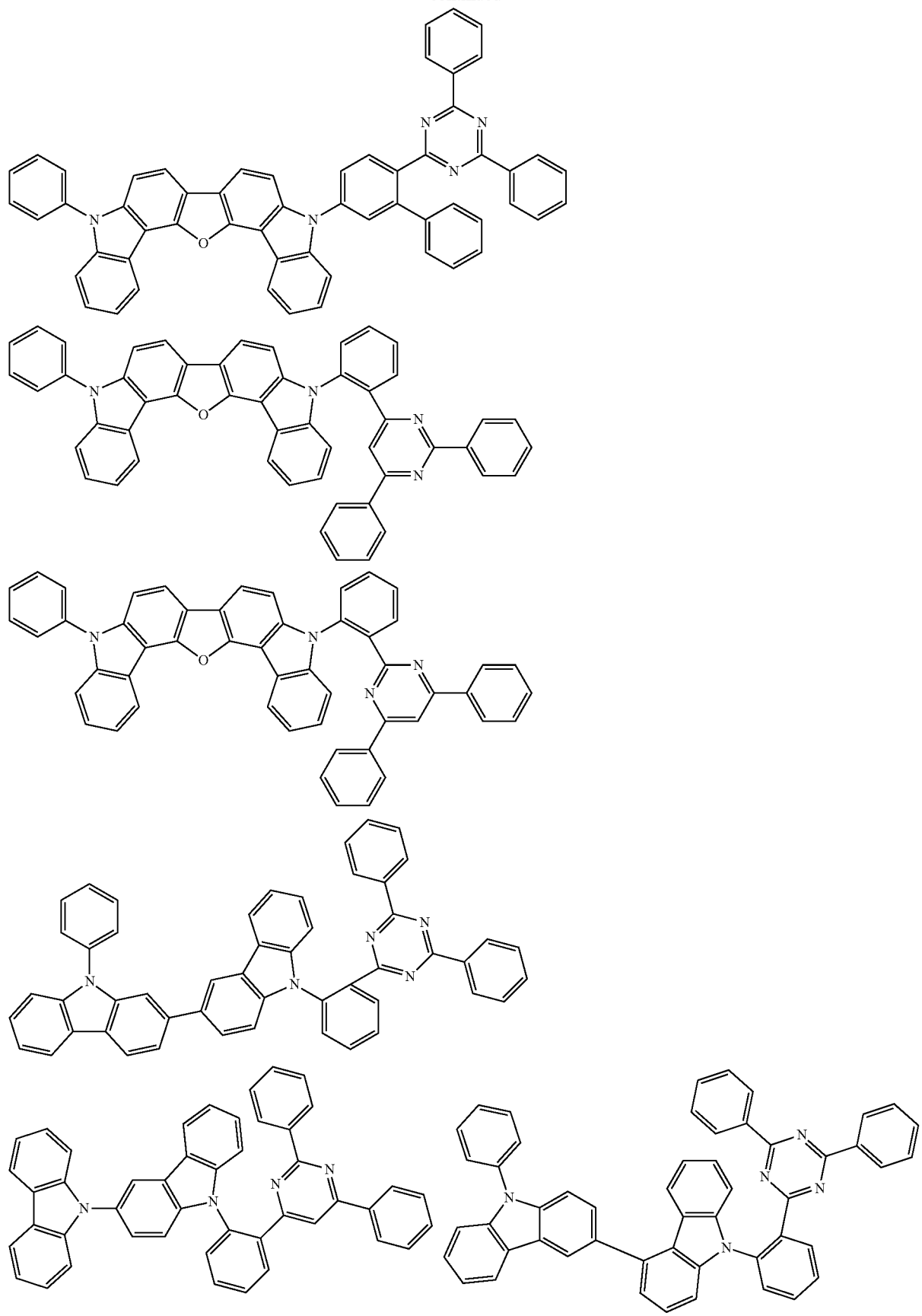

-continued
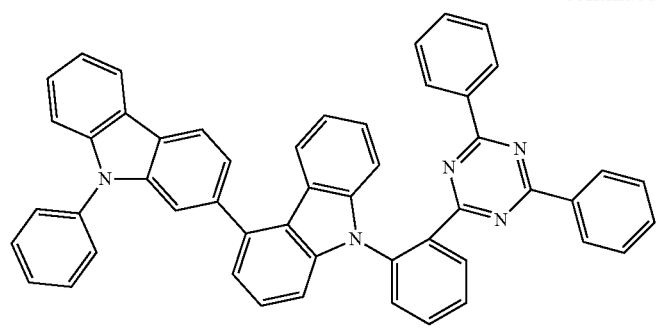
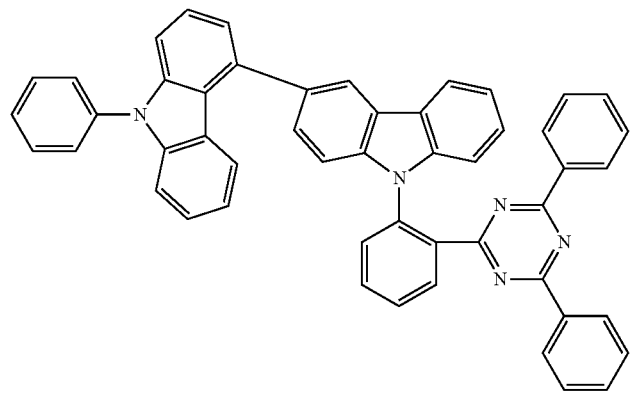
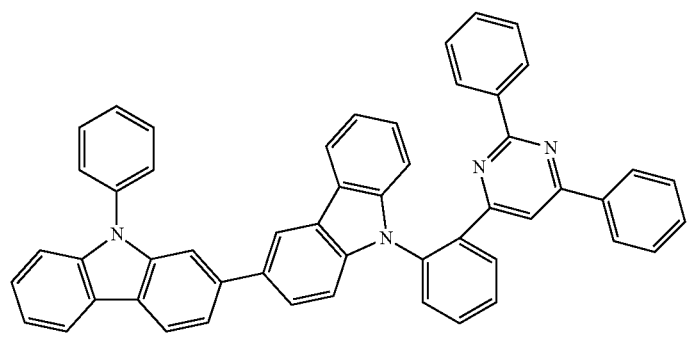
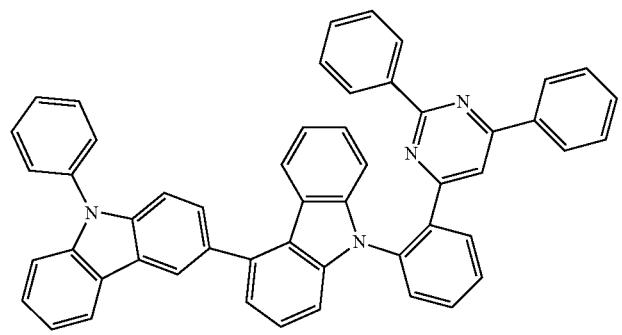
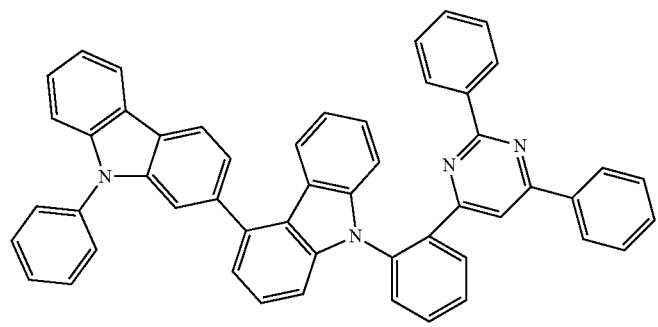

-continued
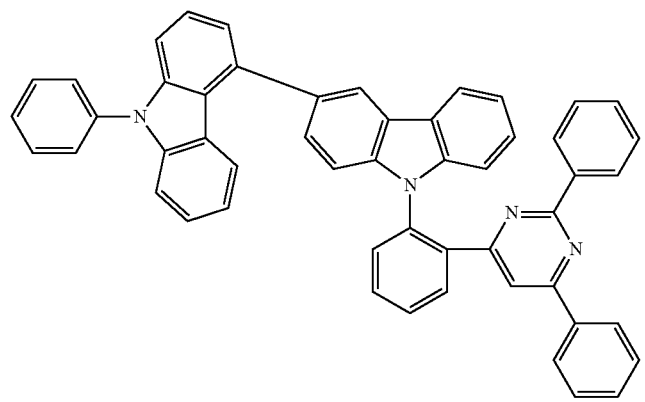
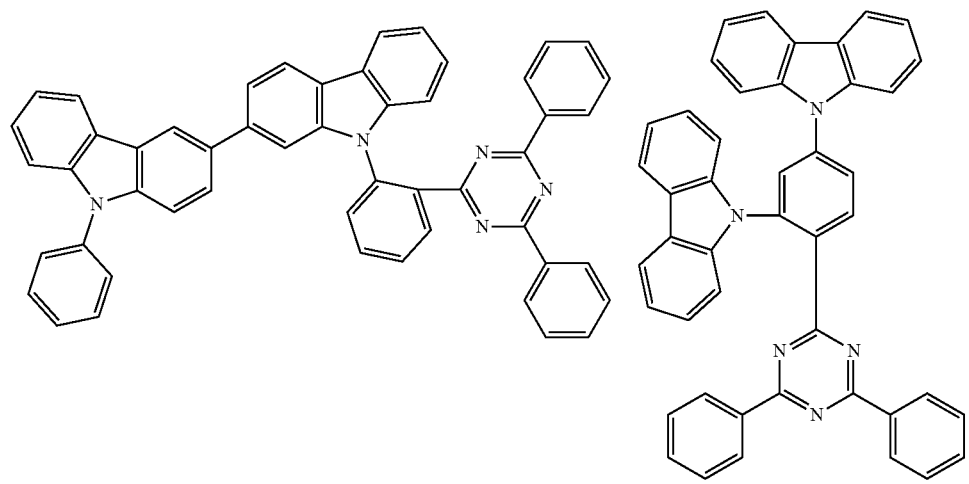
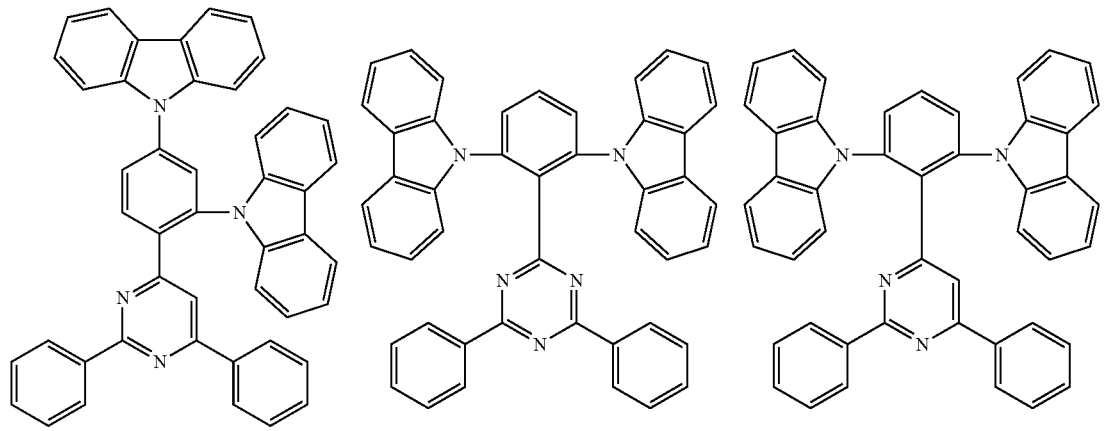

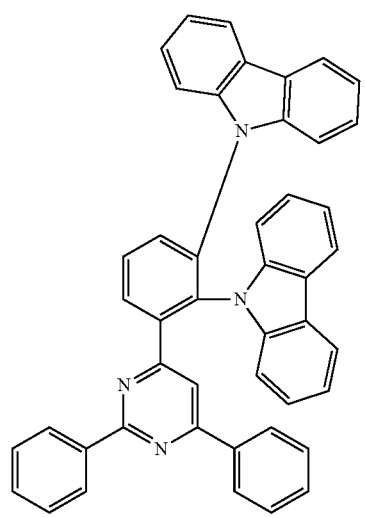
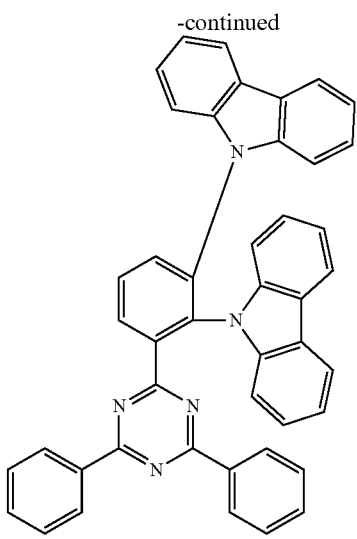
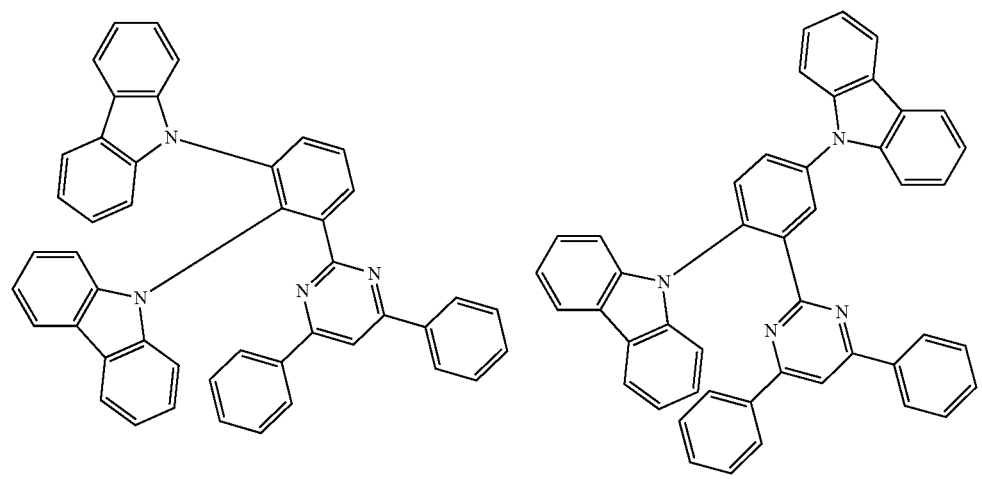
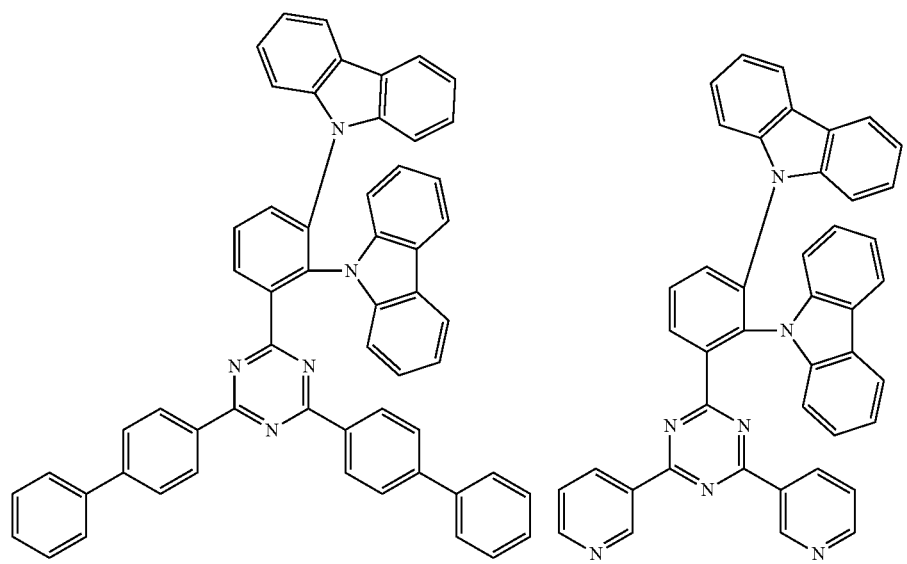

261
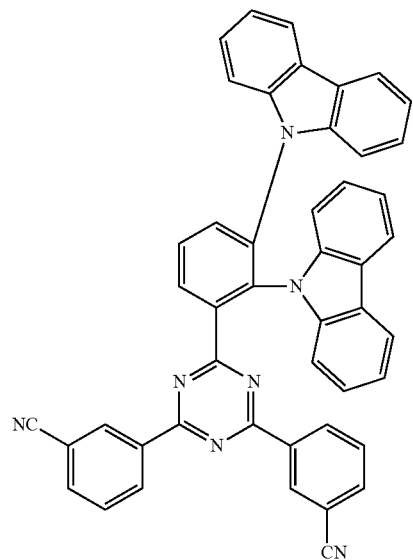
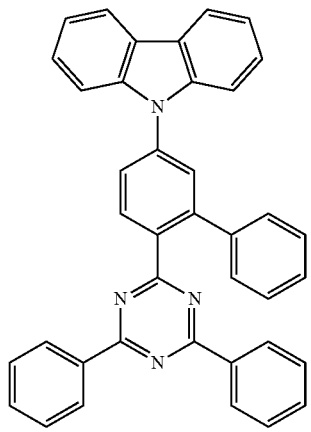
-continued
262
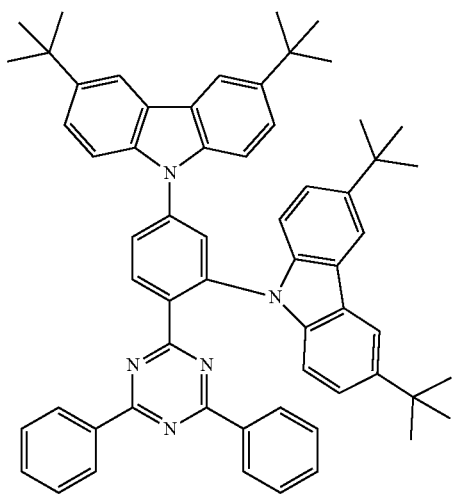
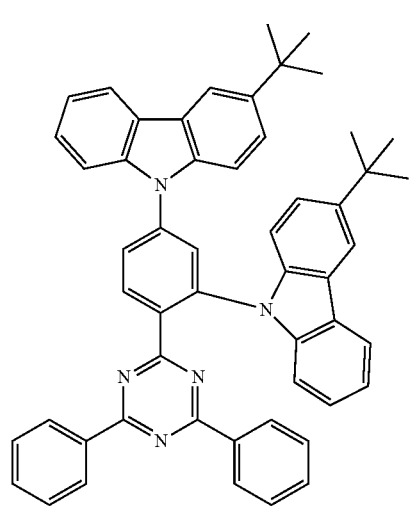
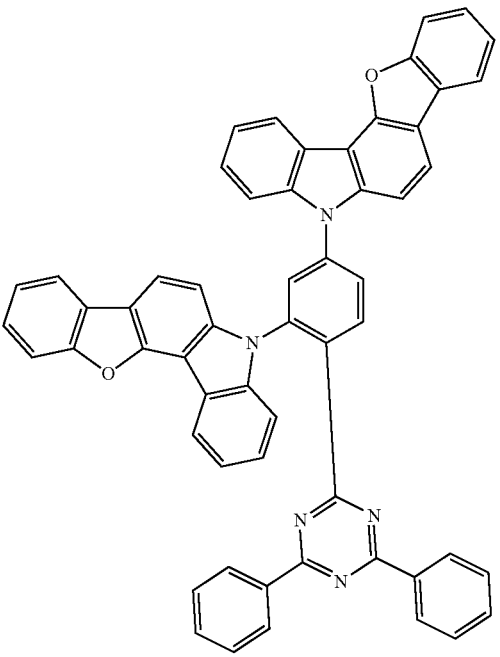

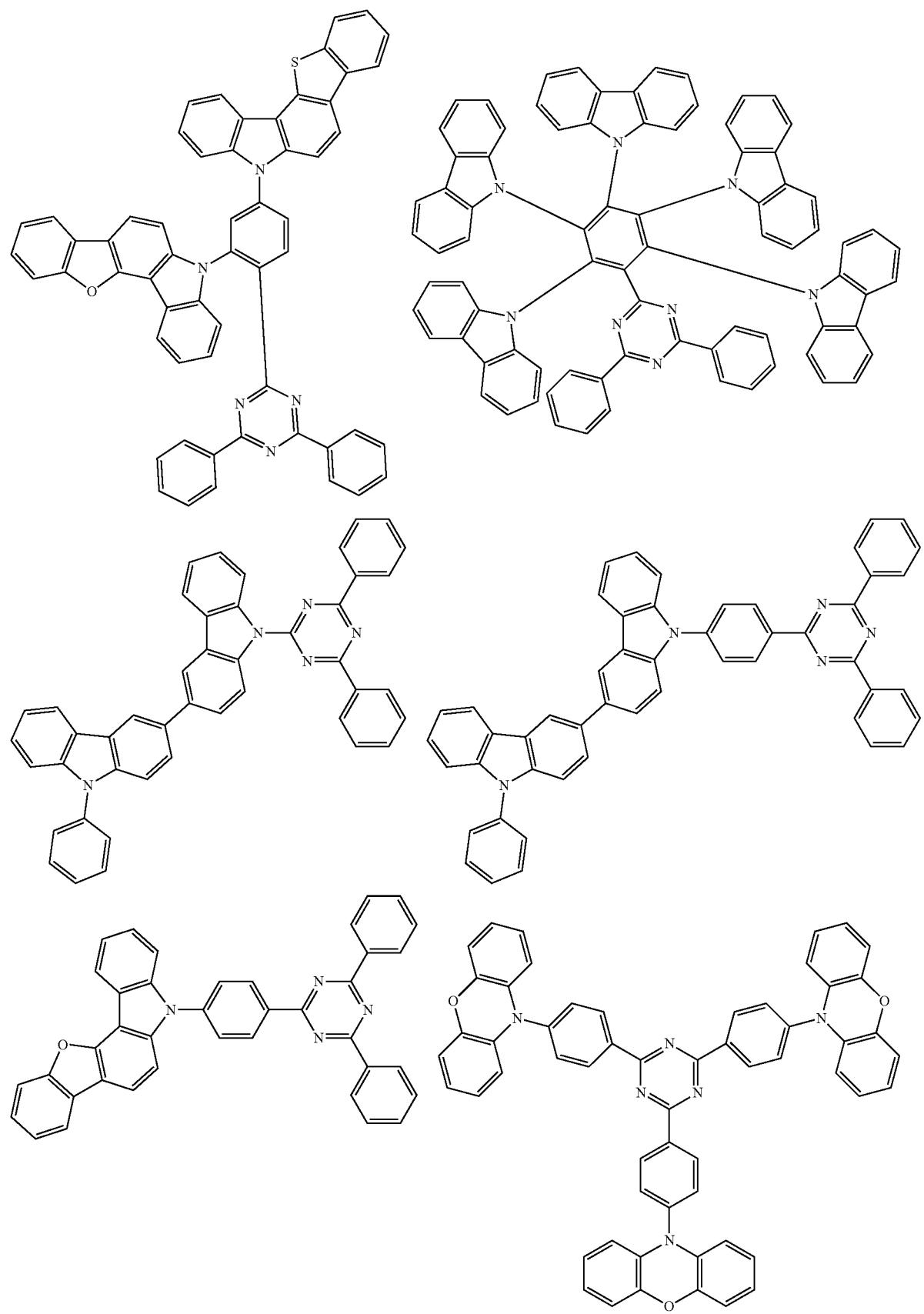

-continued
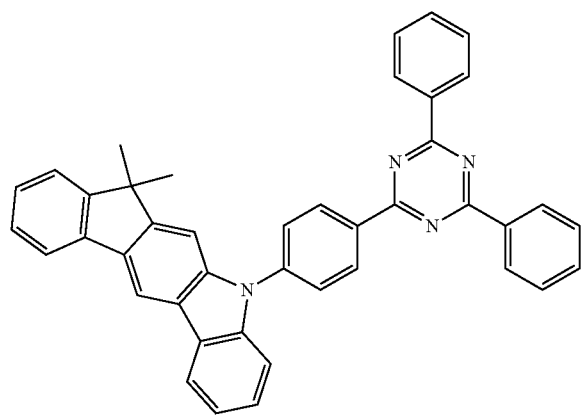
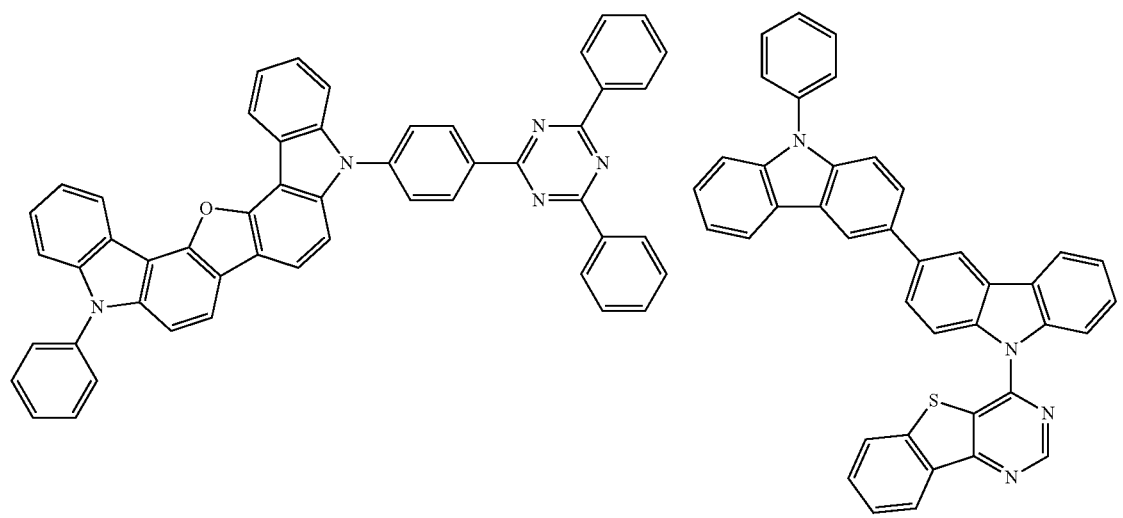
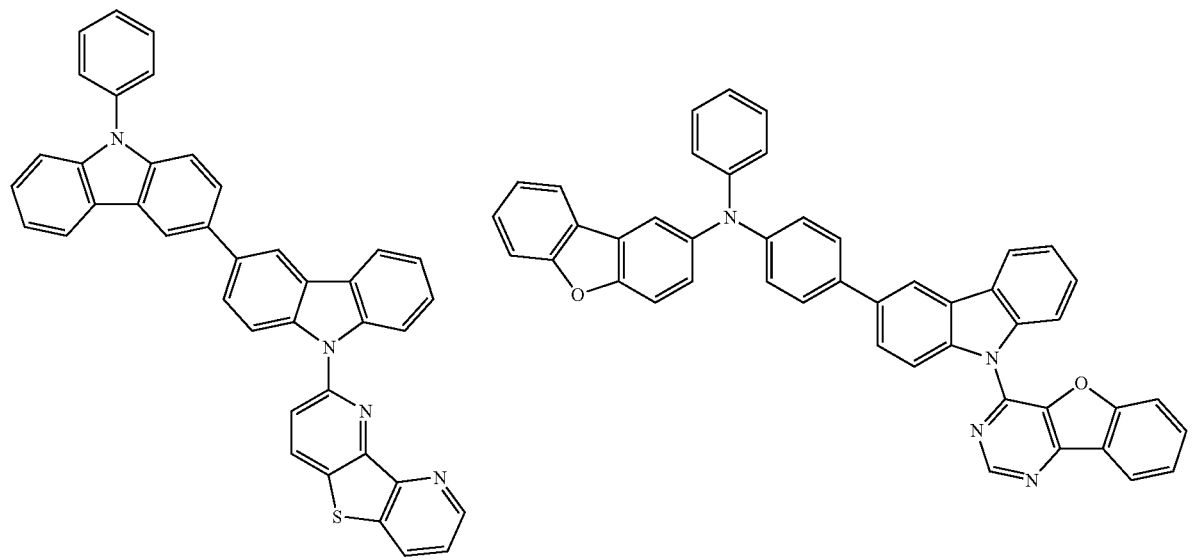

267
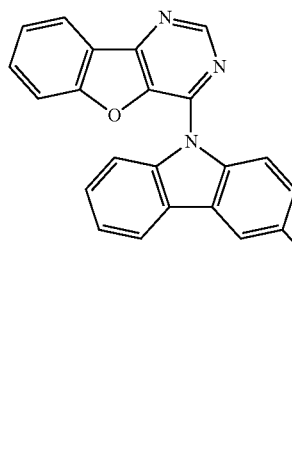
268
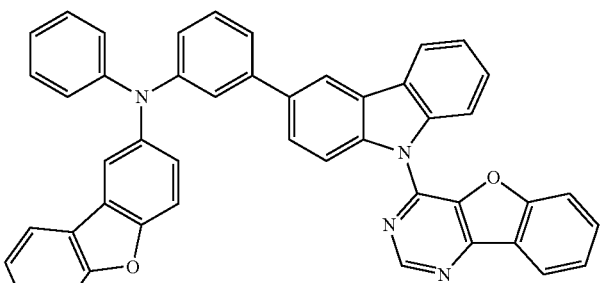
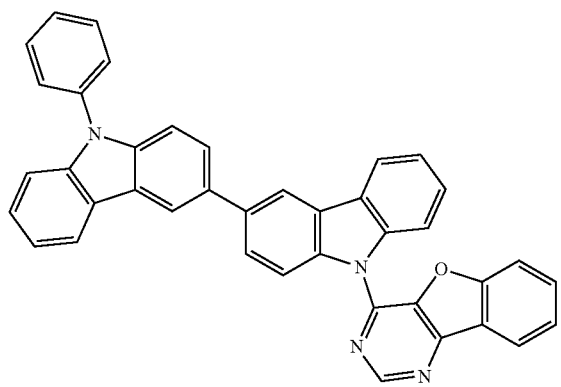
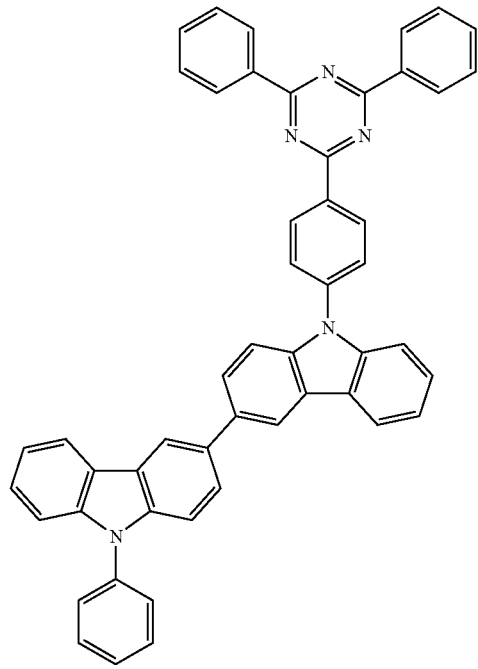

269
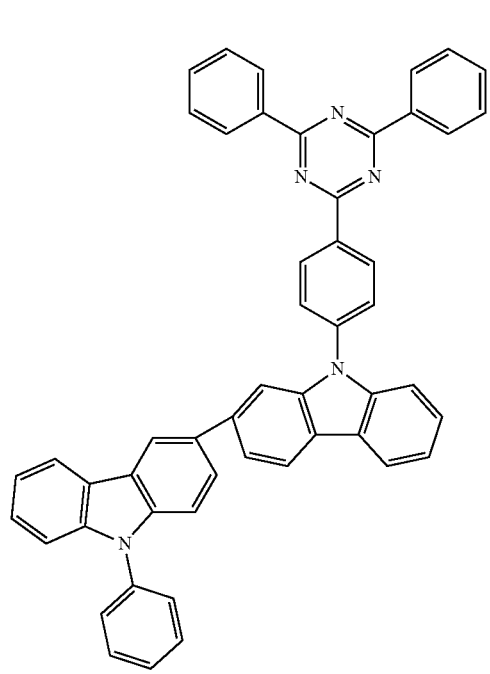
-continued
270
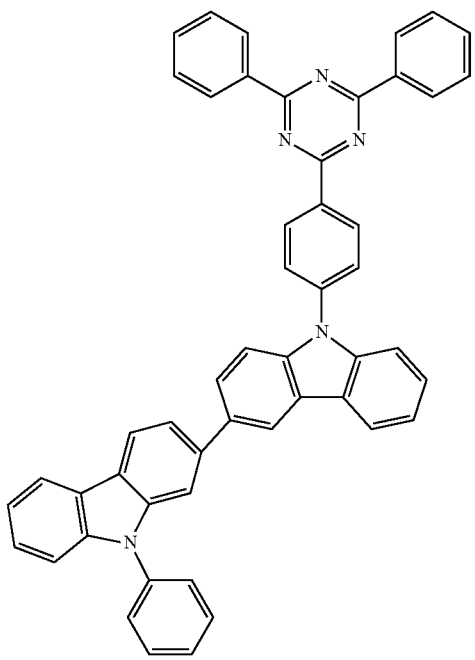
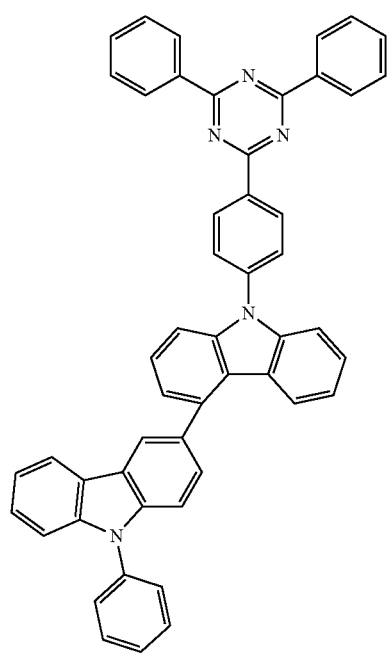
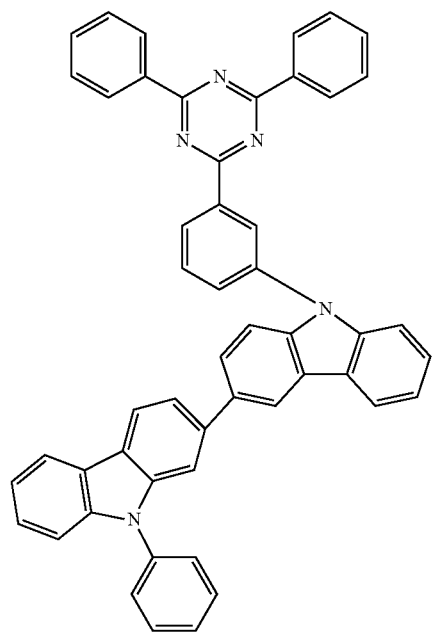

-continued
271
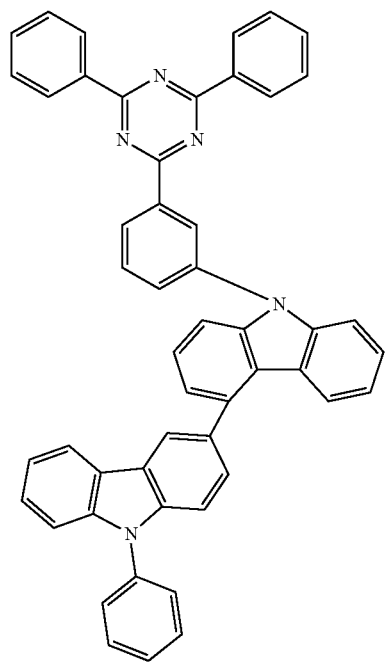
272
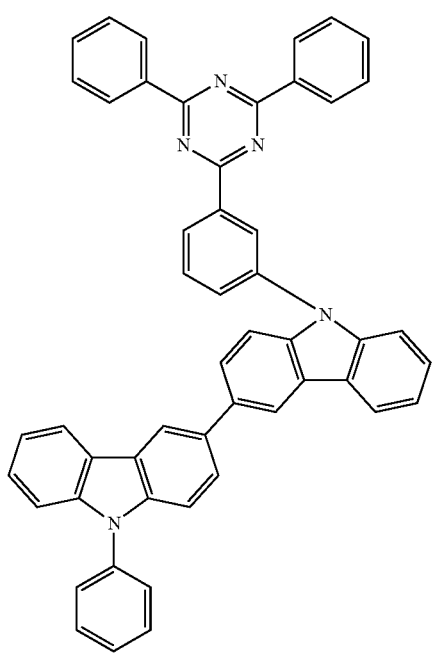
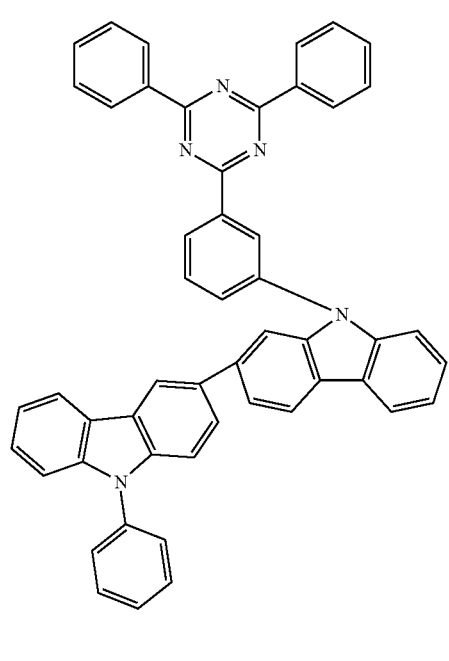
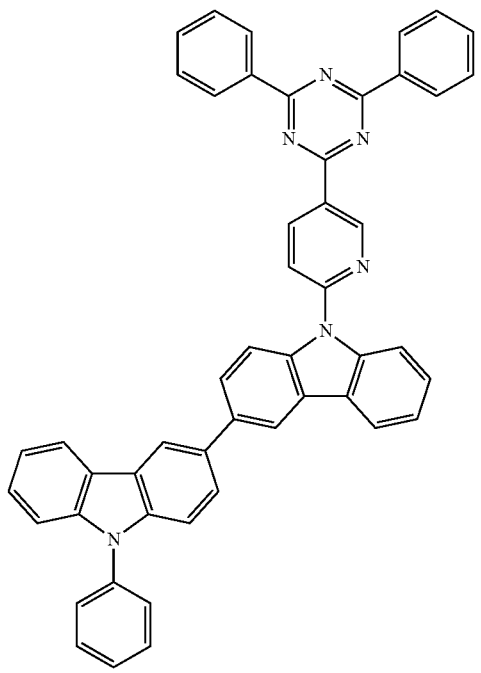

273
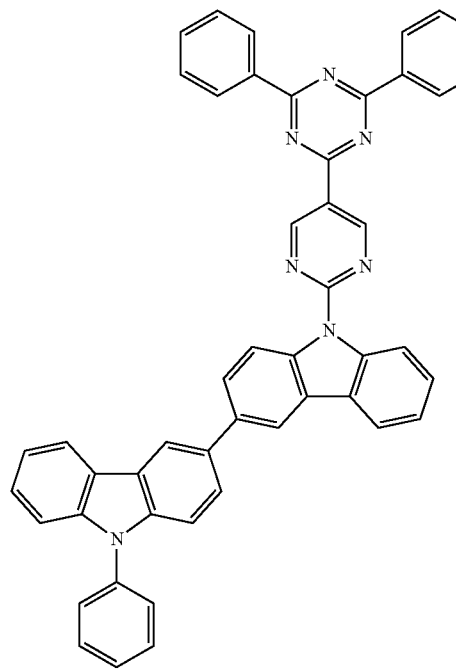
-continued
274
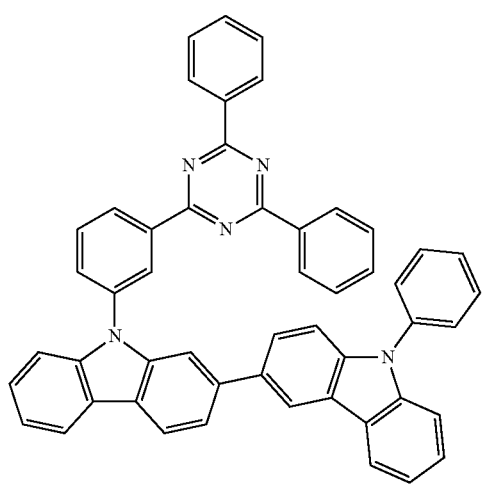
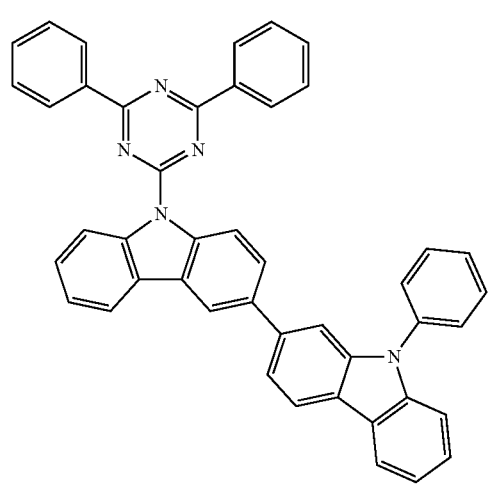
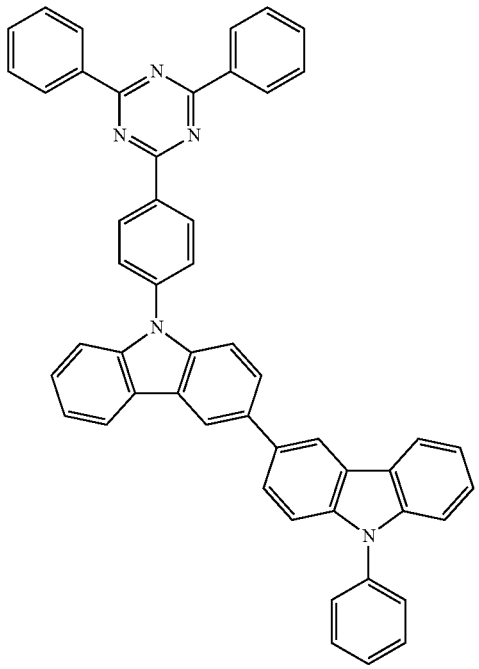

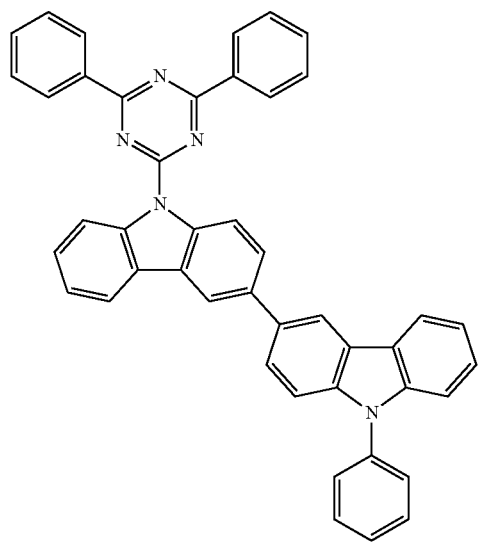
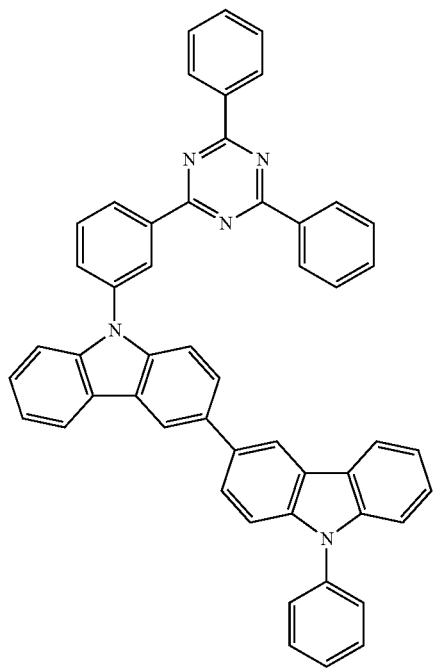
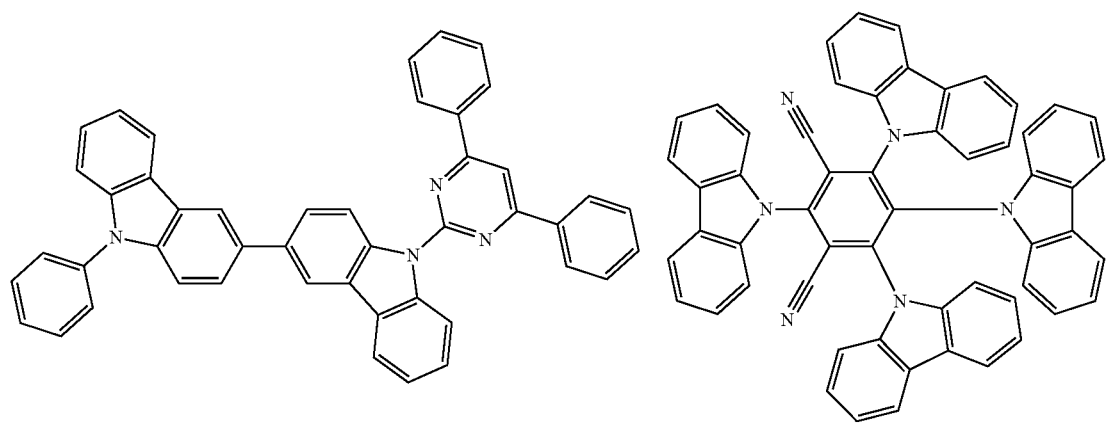
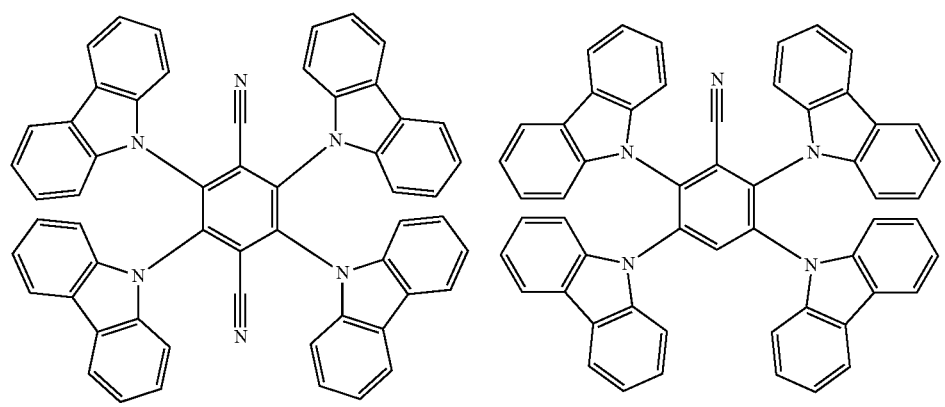

-continued
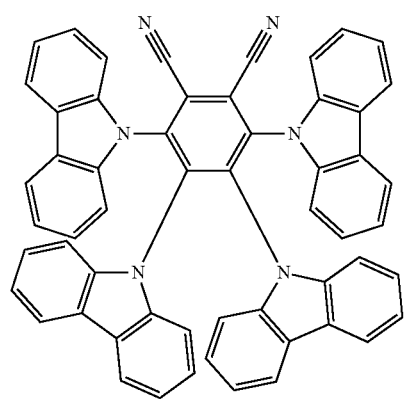
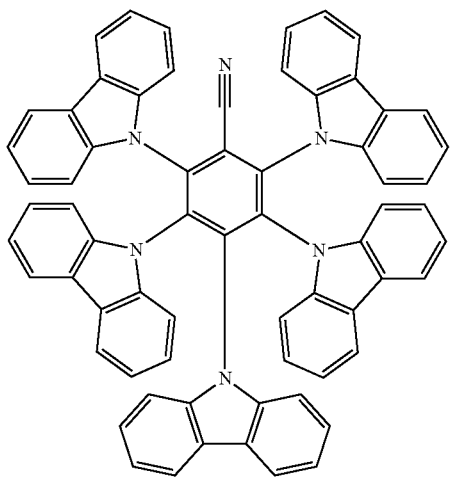
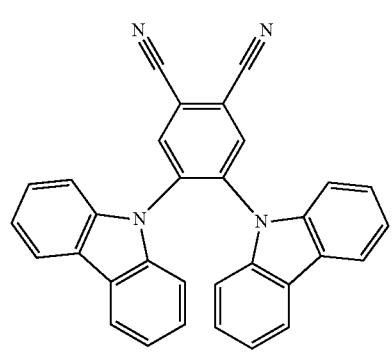
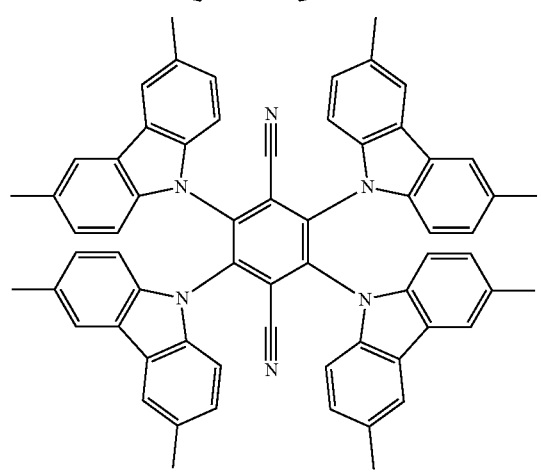
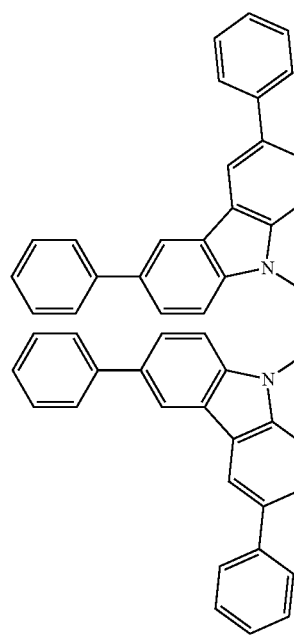
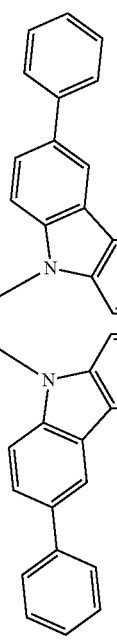
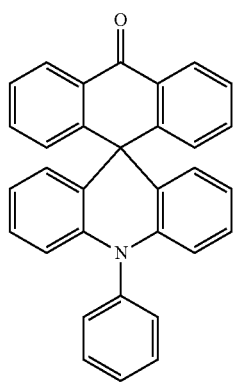

279    280
-continued
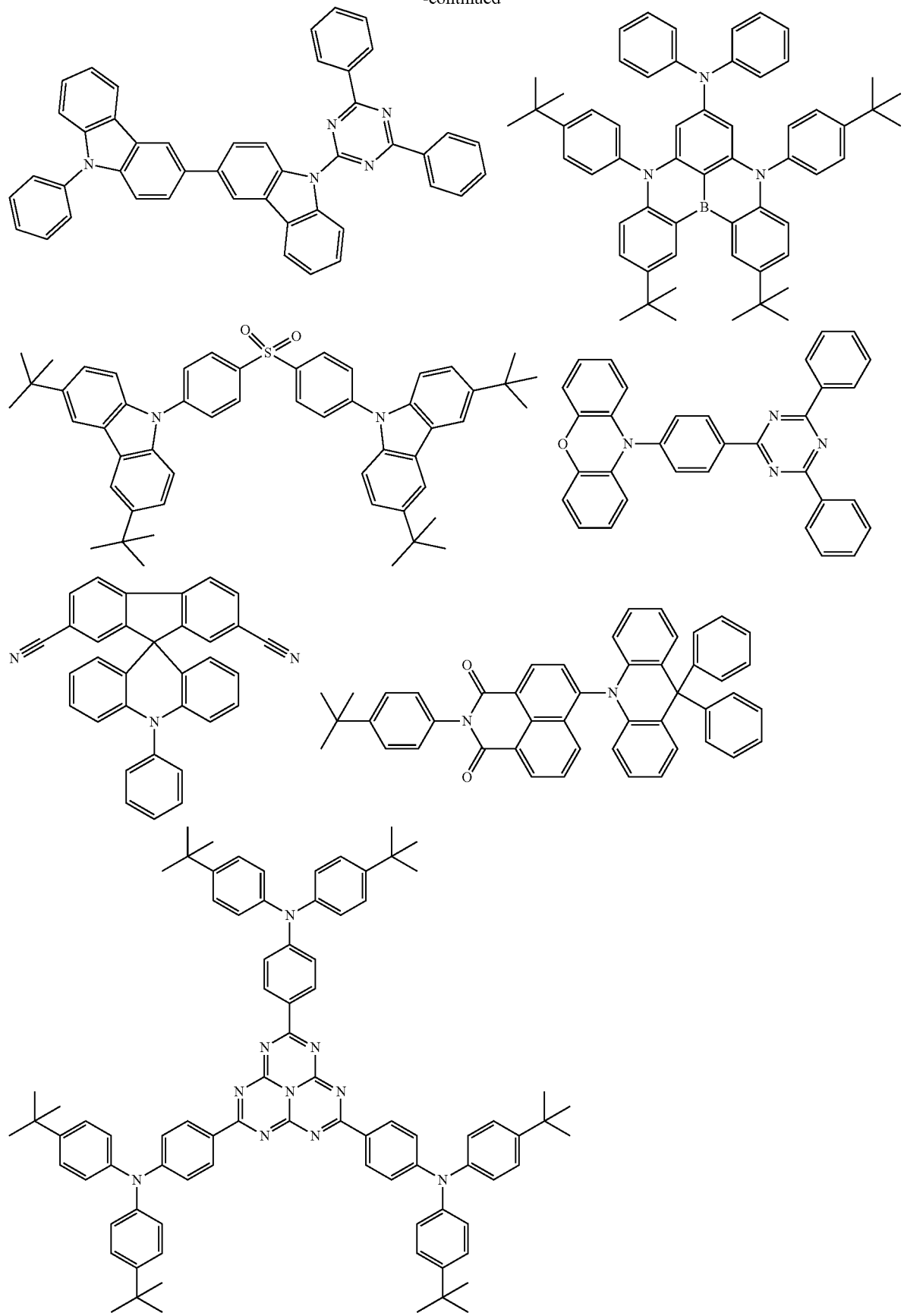

-continued
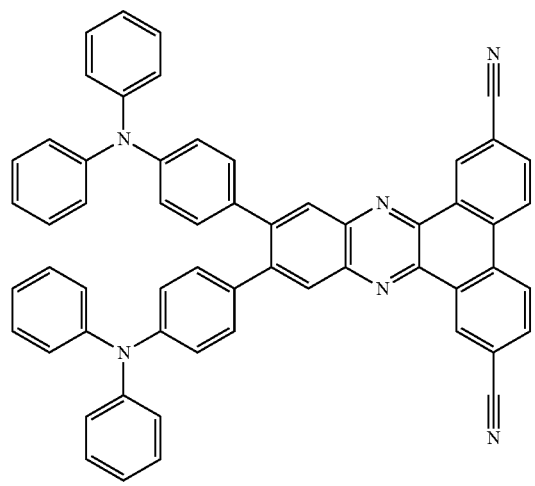
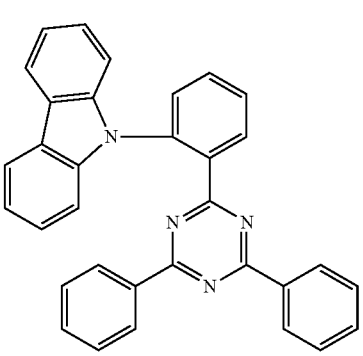
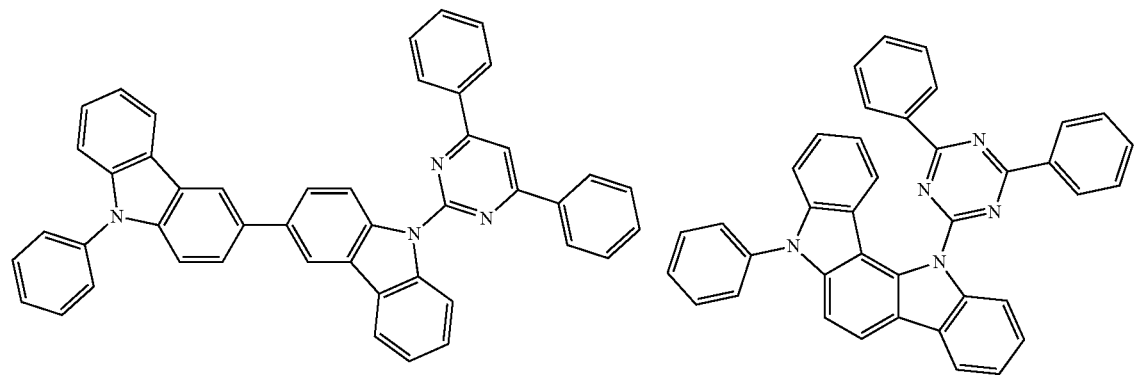
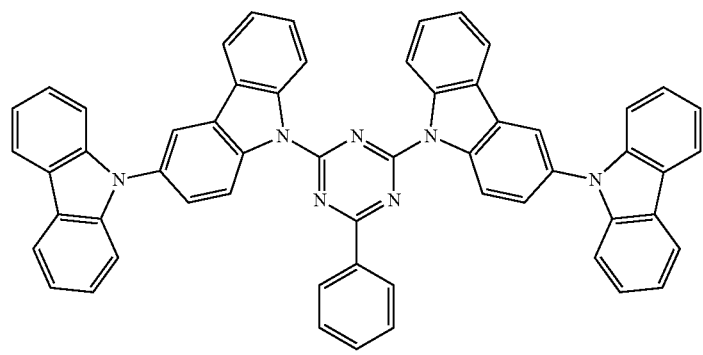
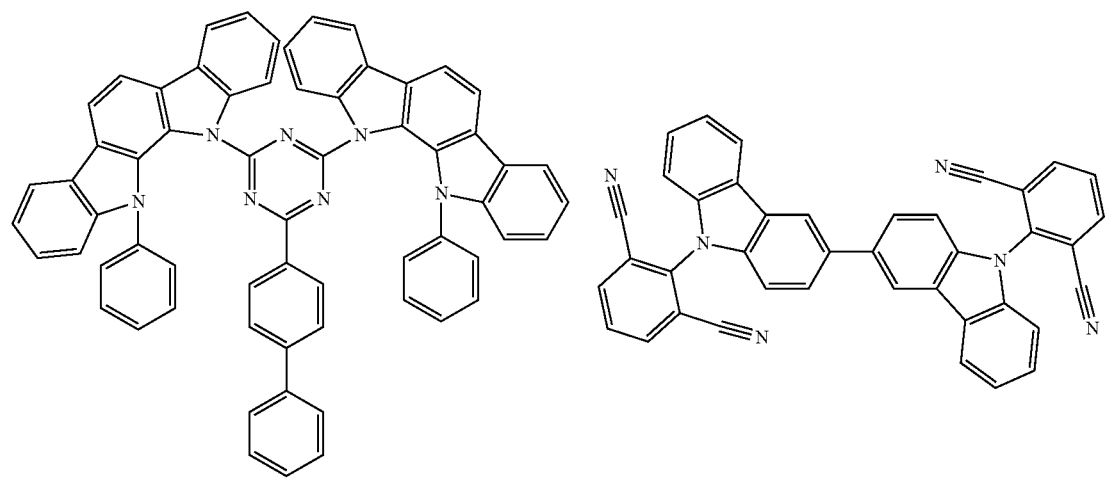

283
-continued
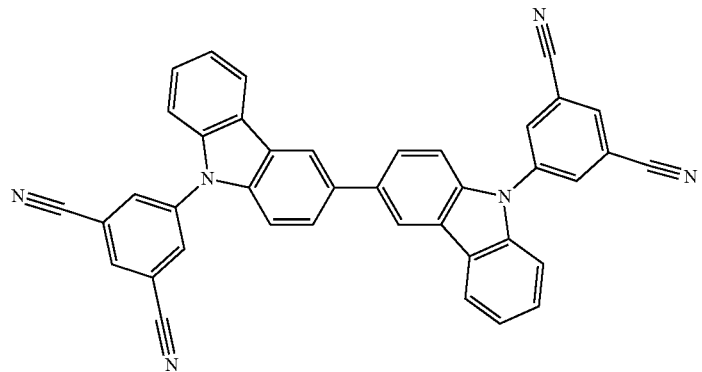
284
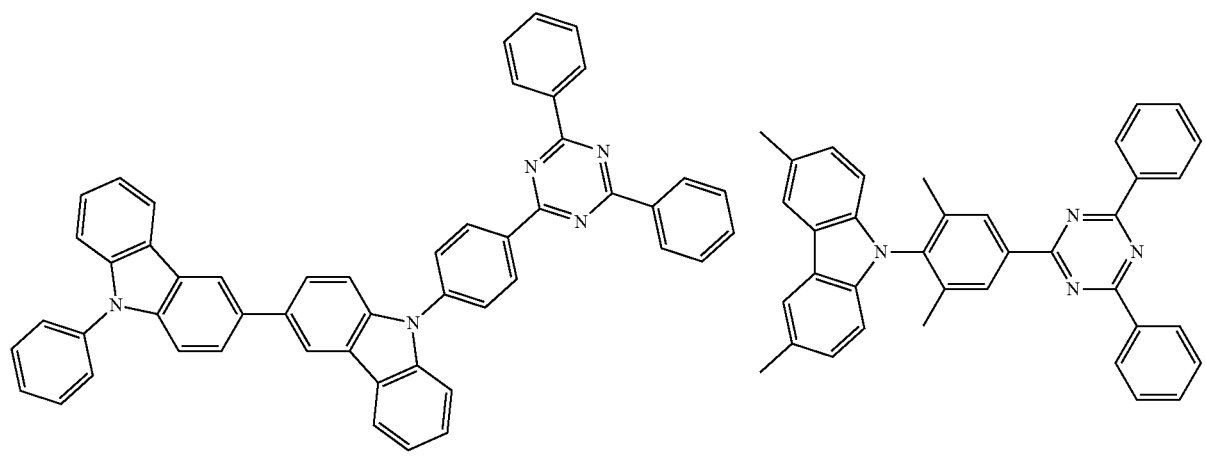
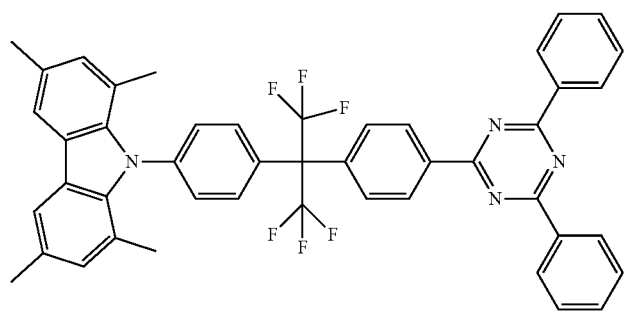

285 286
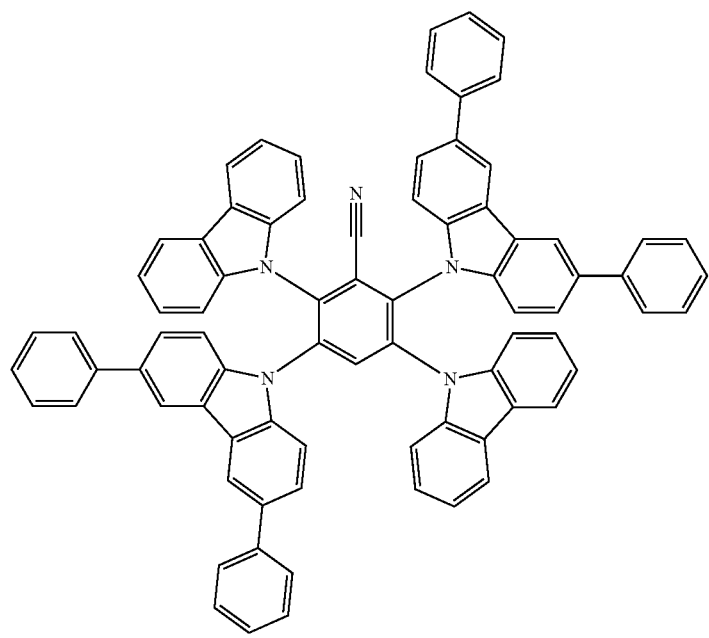
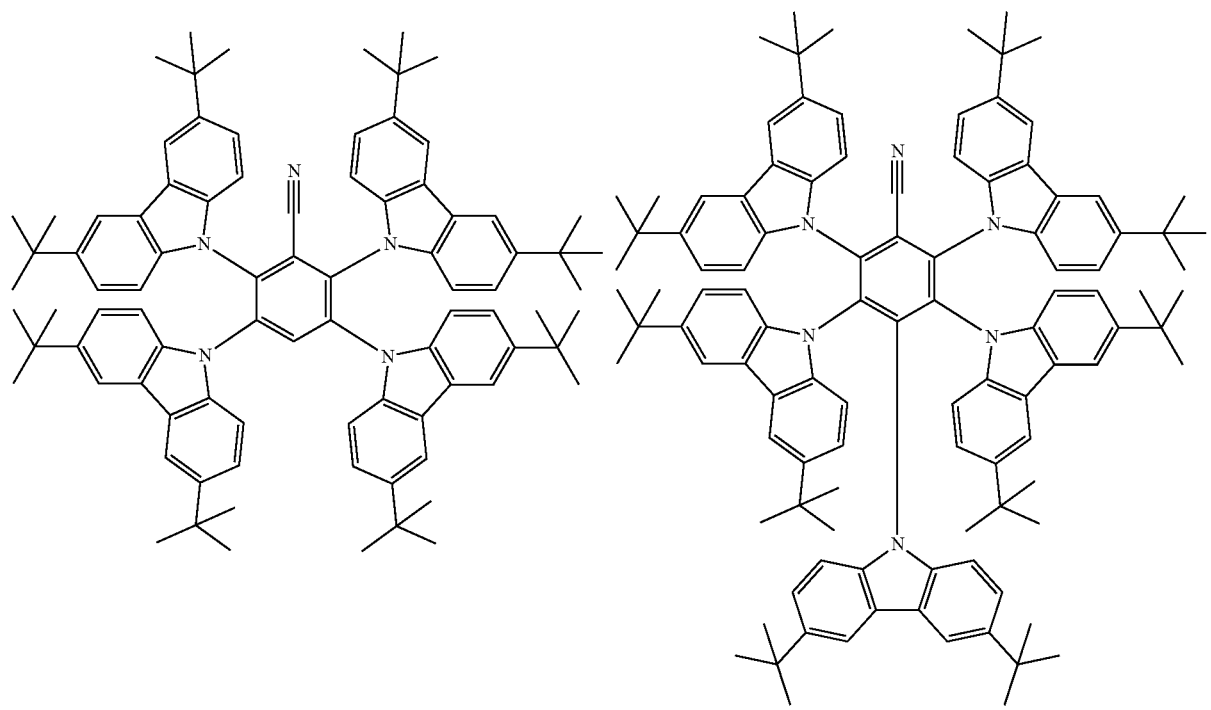

-continued
287
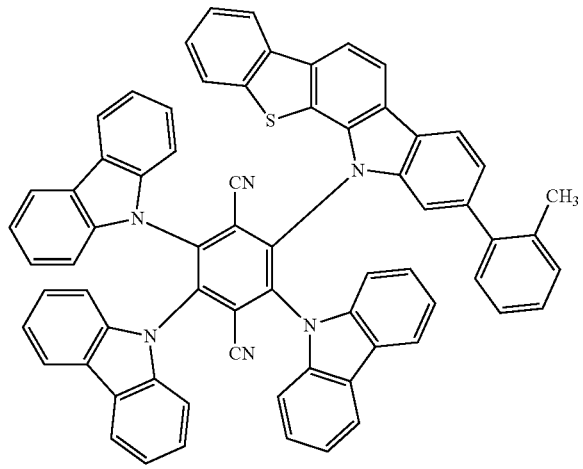
288
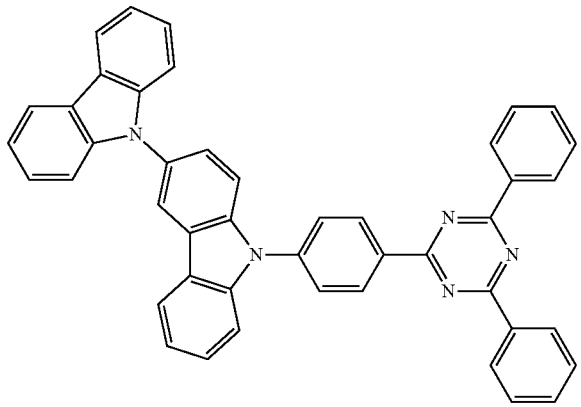
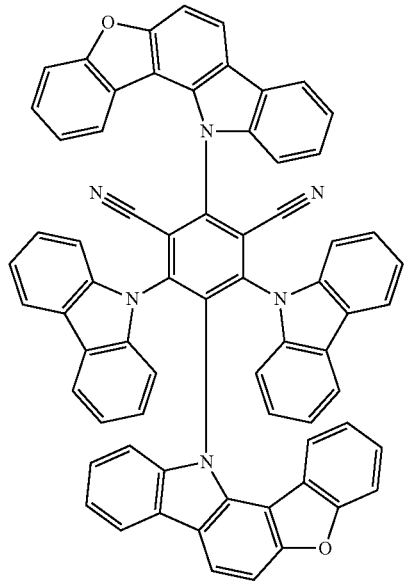
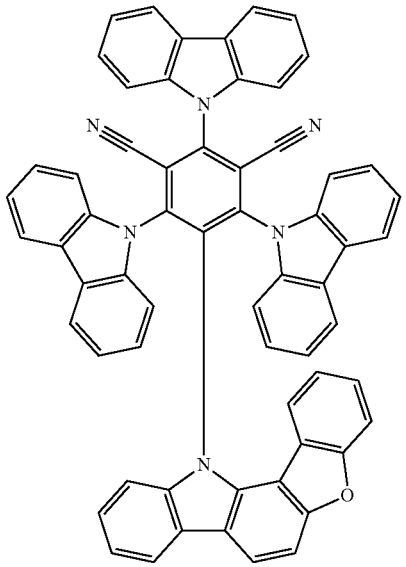
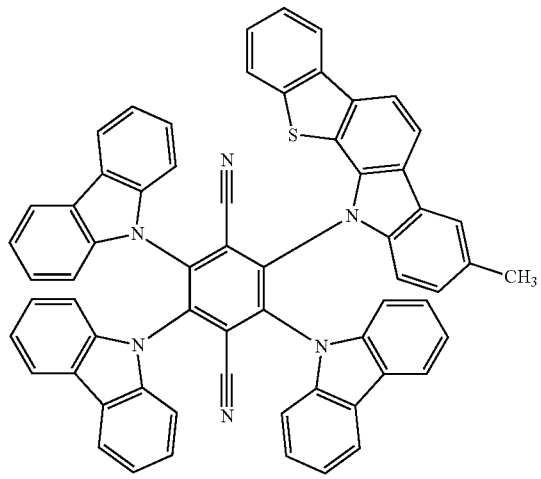
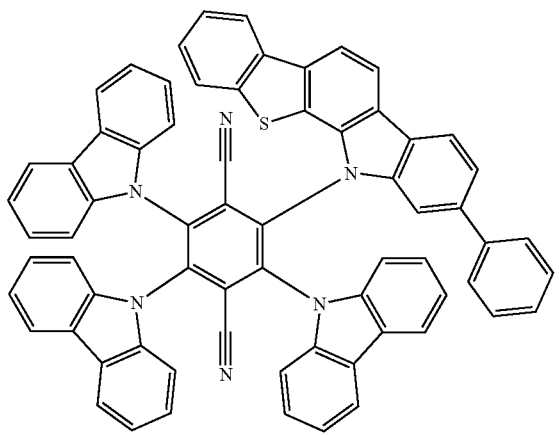

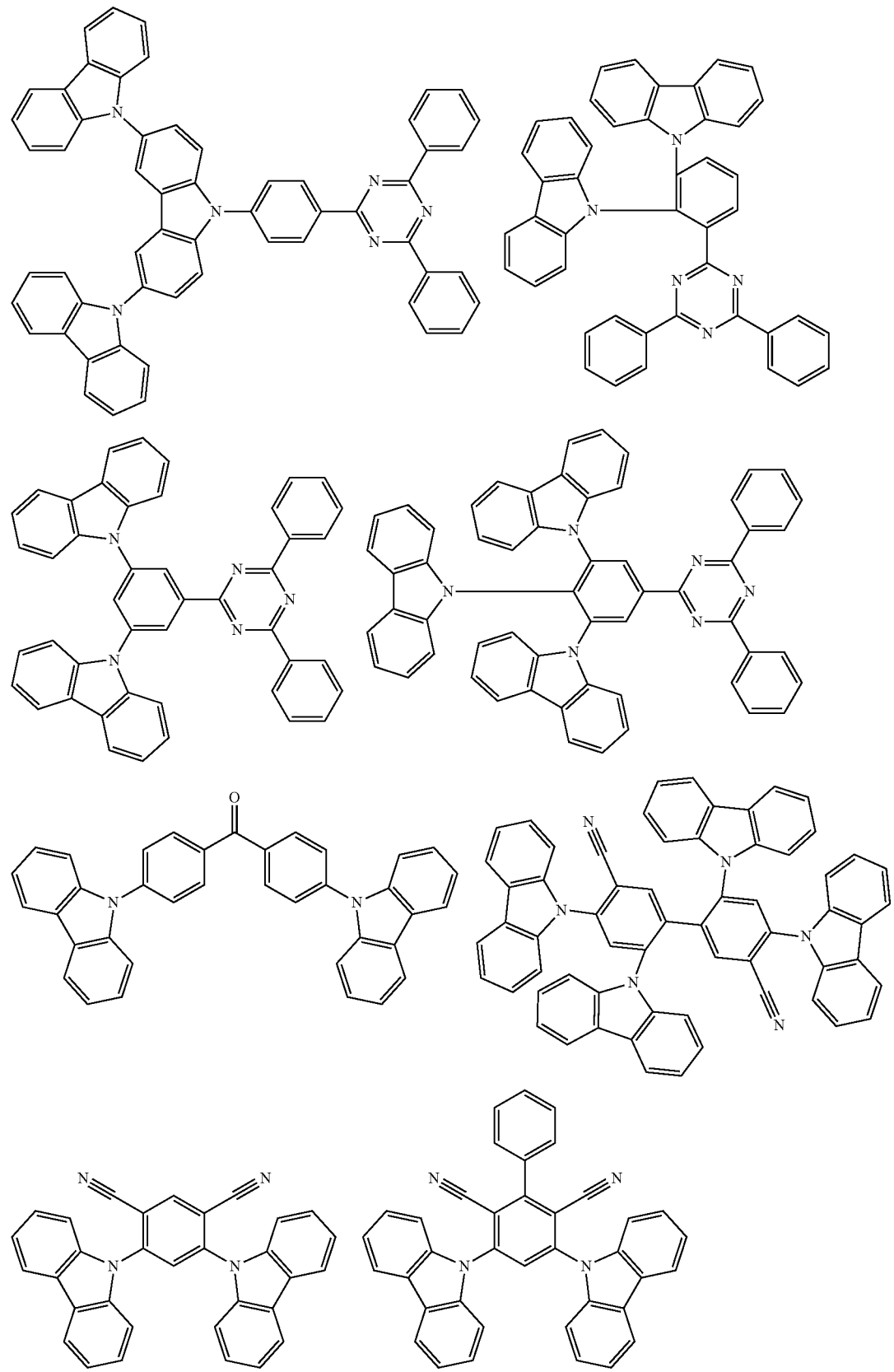

291 292
-continued
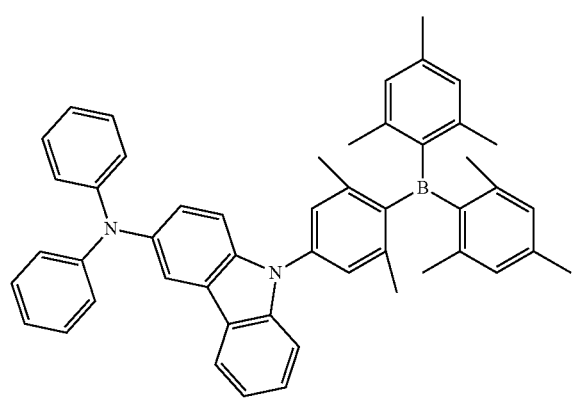
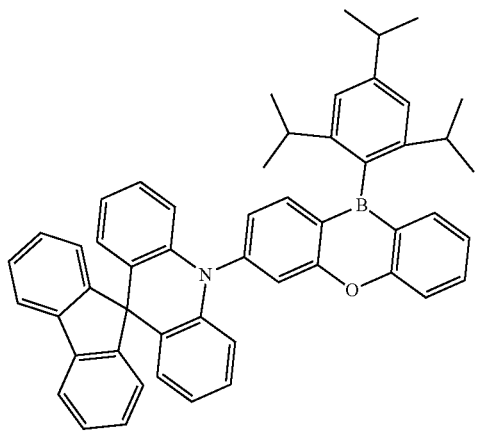
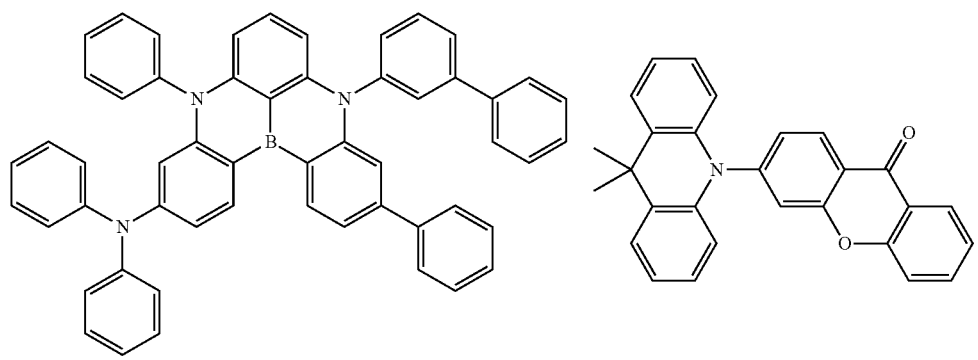
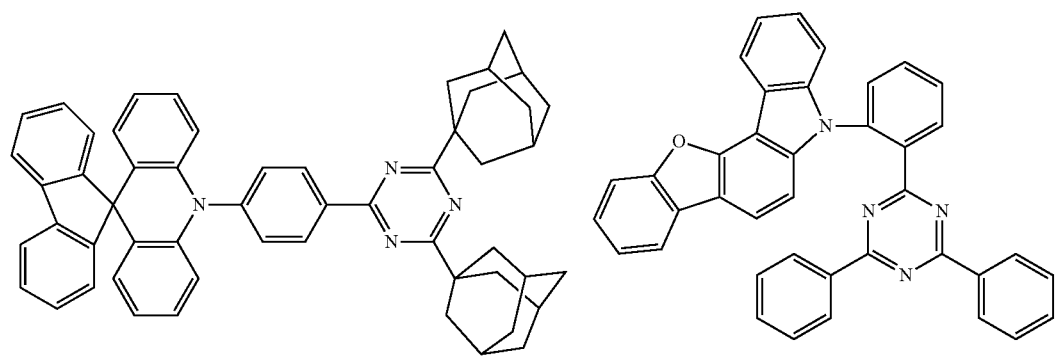
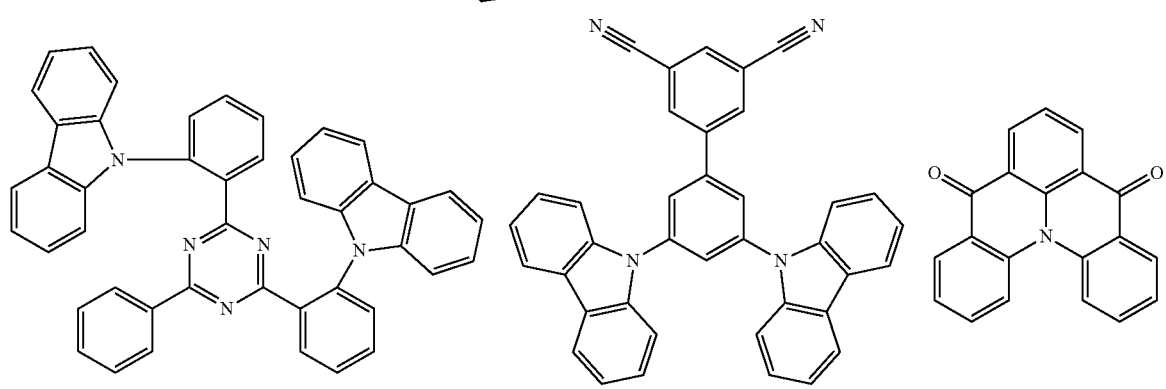

293
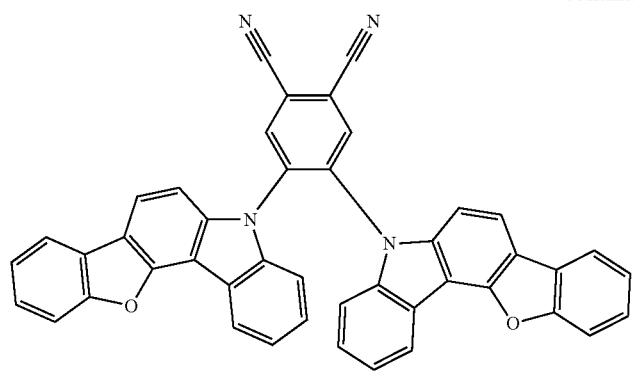
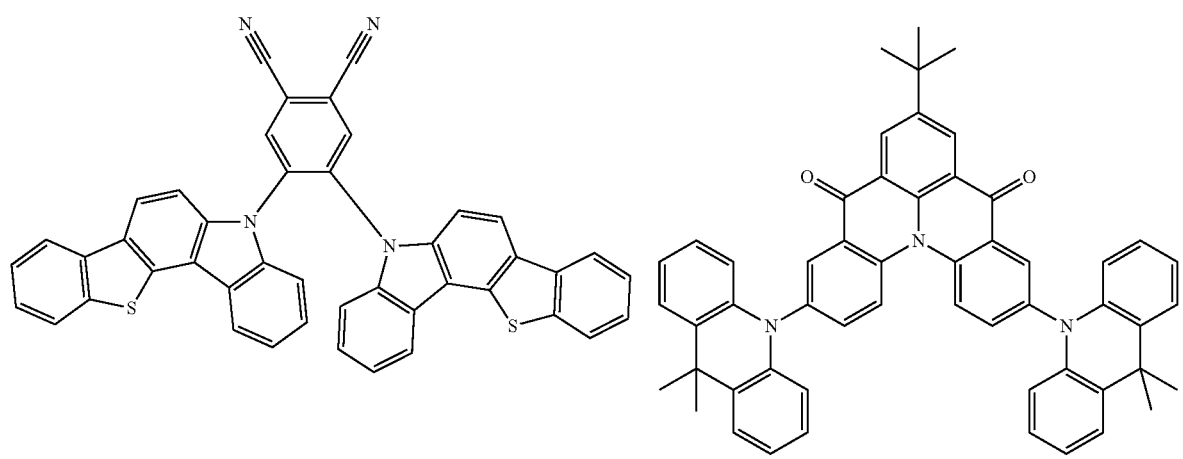
294
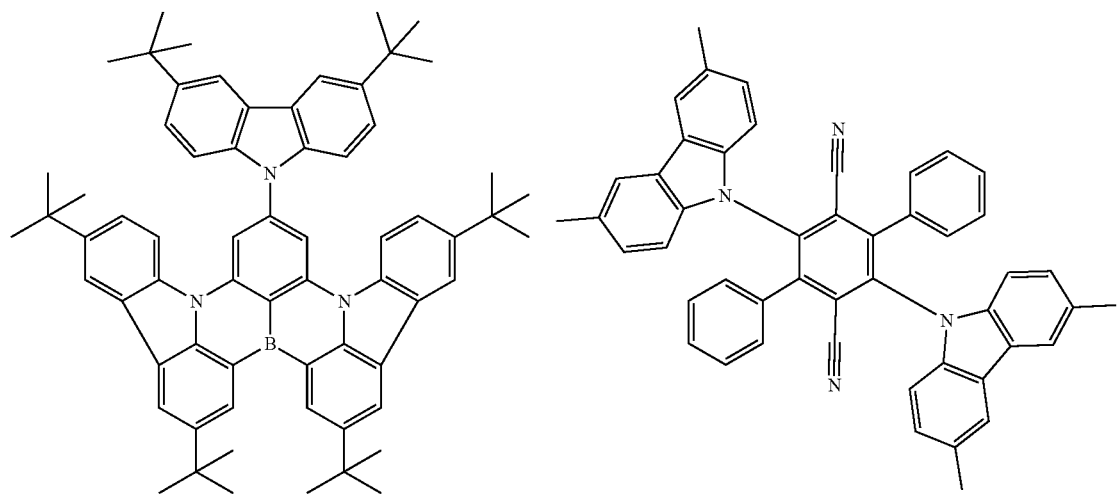

295
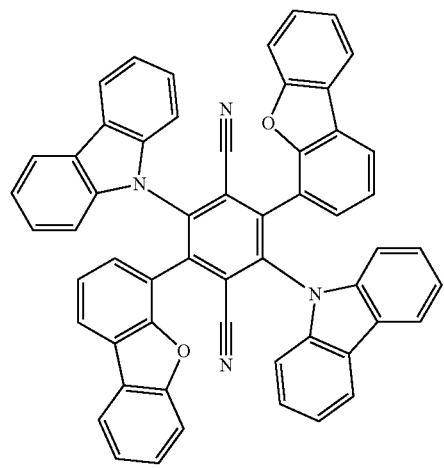
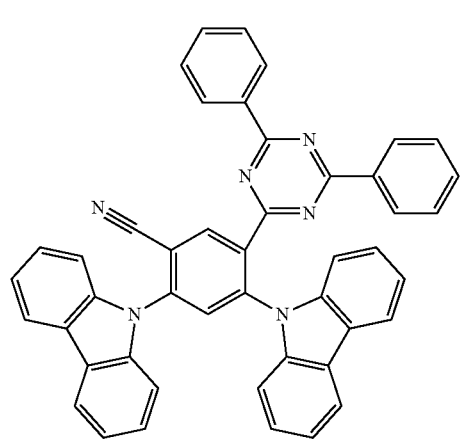
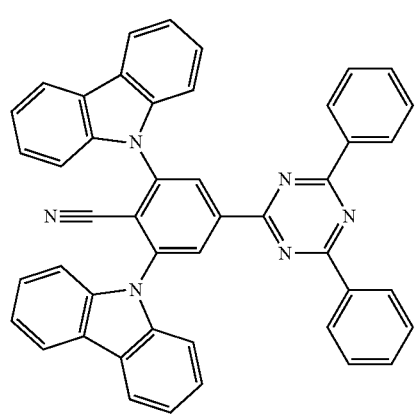
296
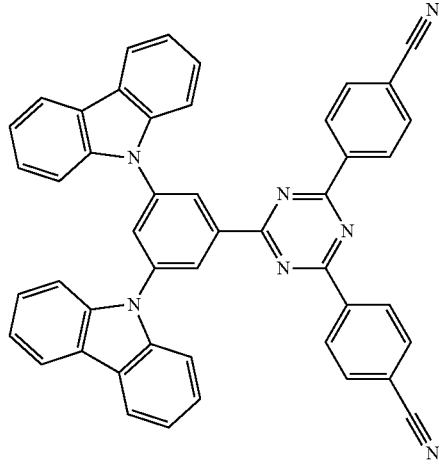
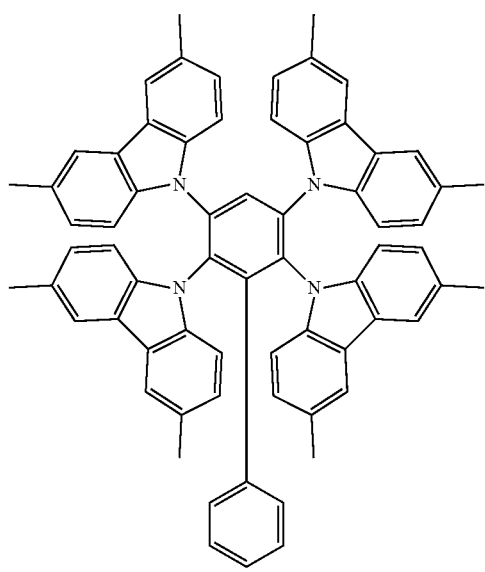
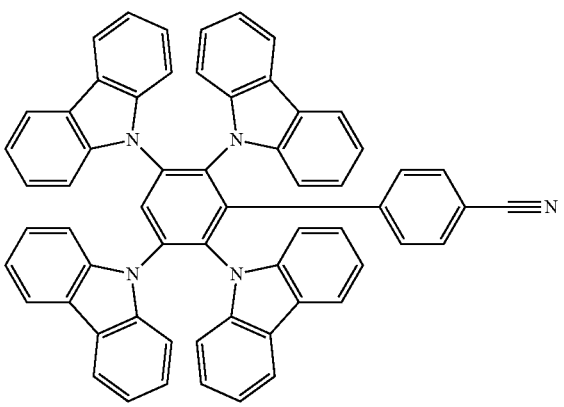

297 298
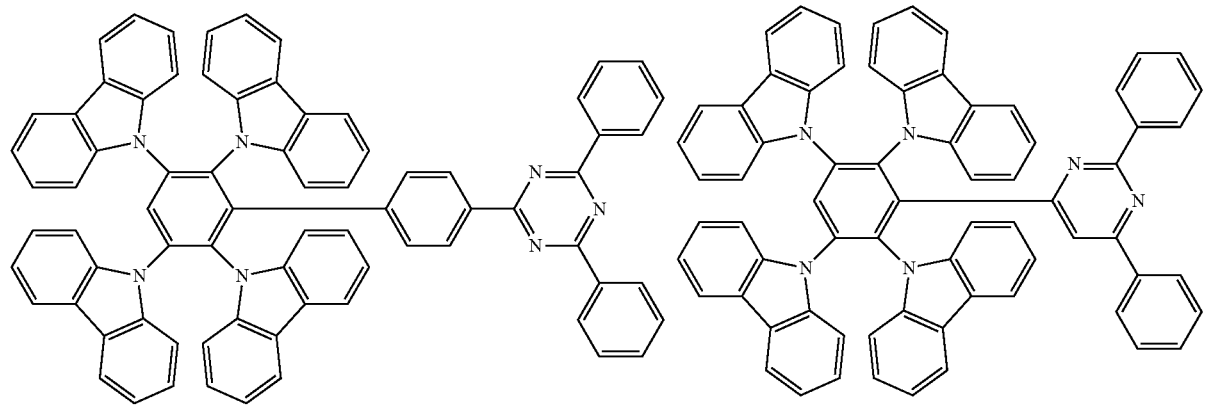
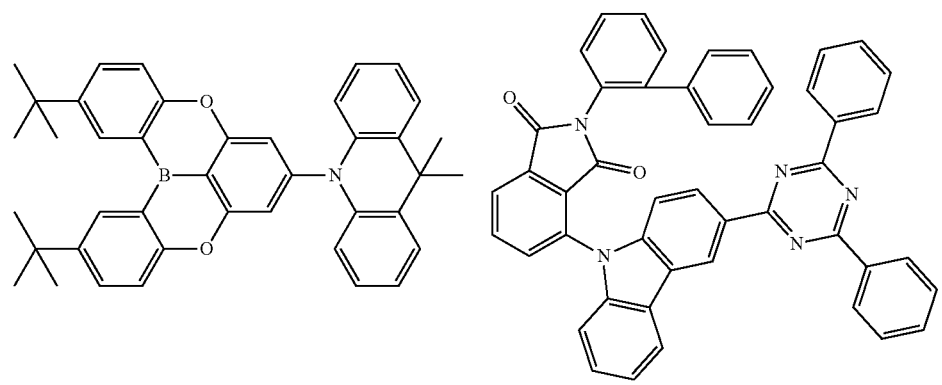
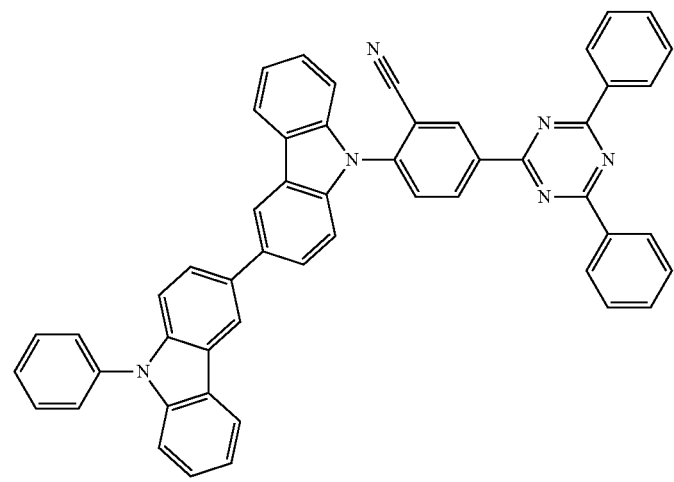

The following specific examples of the compound M2 are specific examples in which hydrogen atoms are not omitted.
In the following specific examples, "D" represents a deuterium atom.
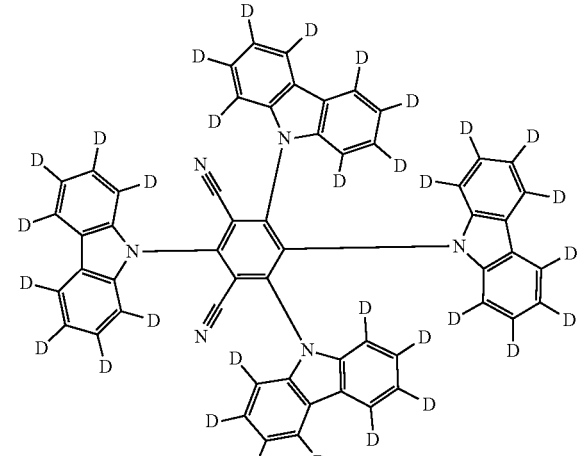
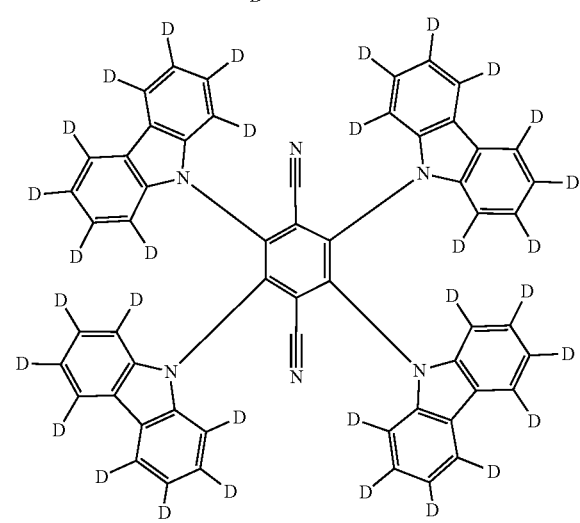
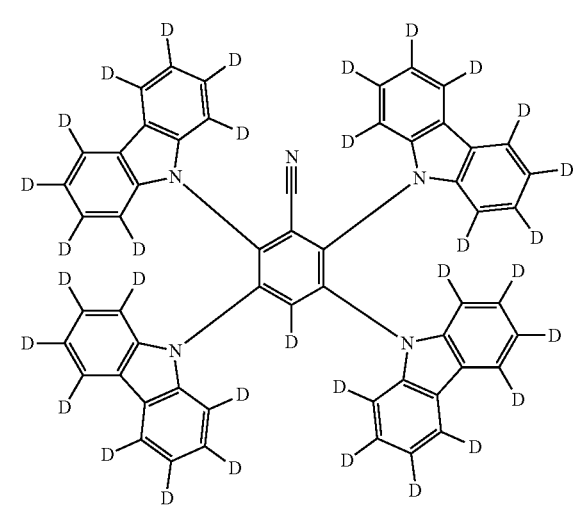
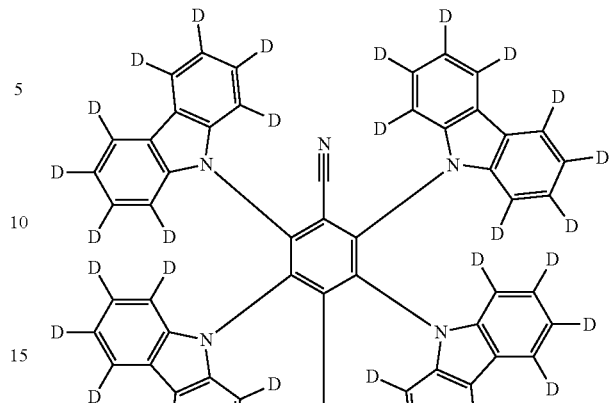
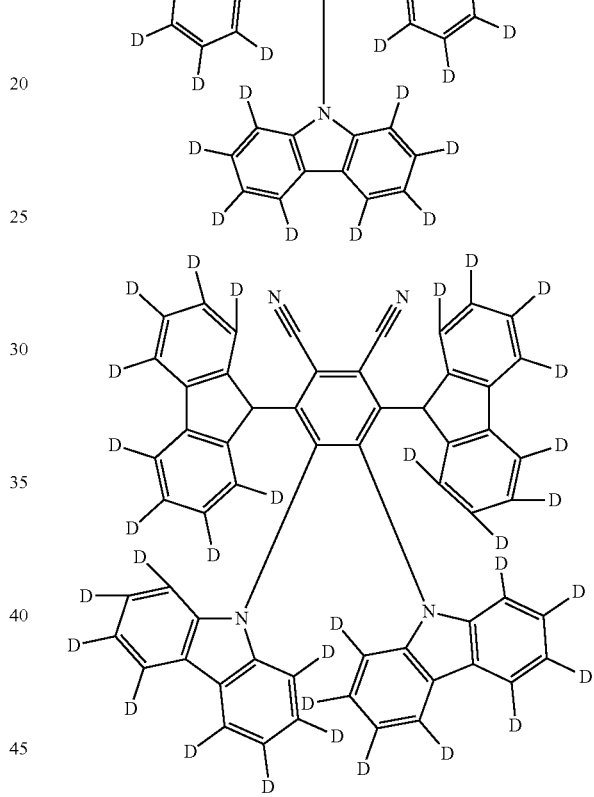
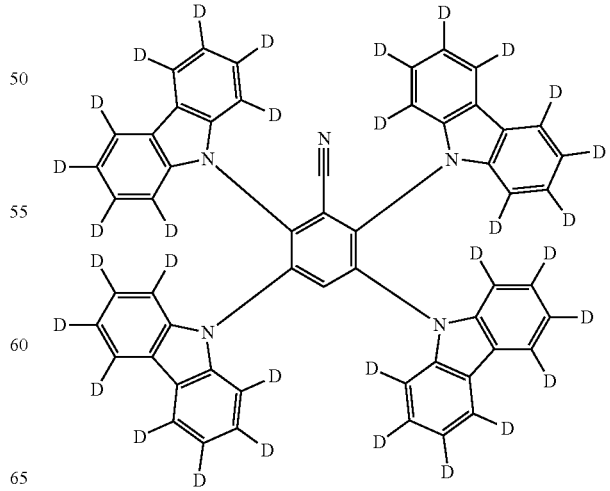

301
-continued
302
-continued
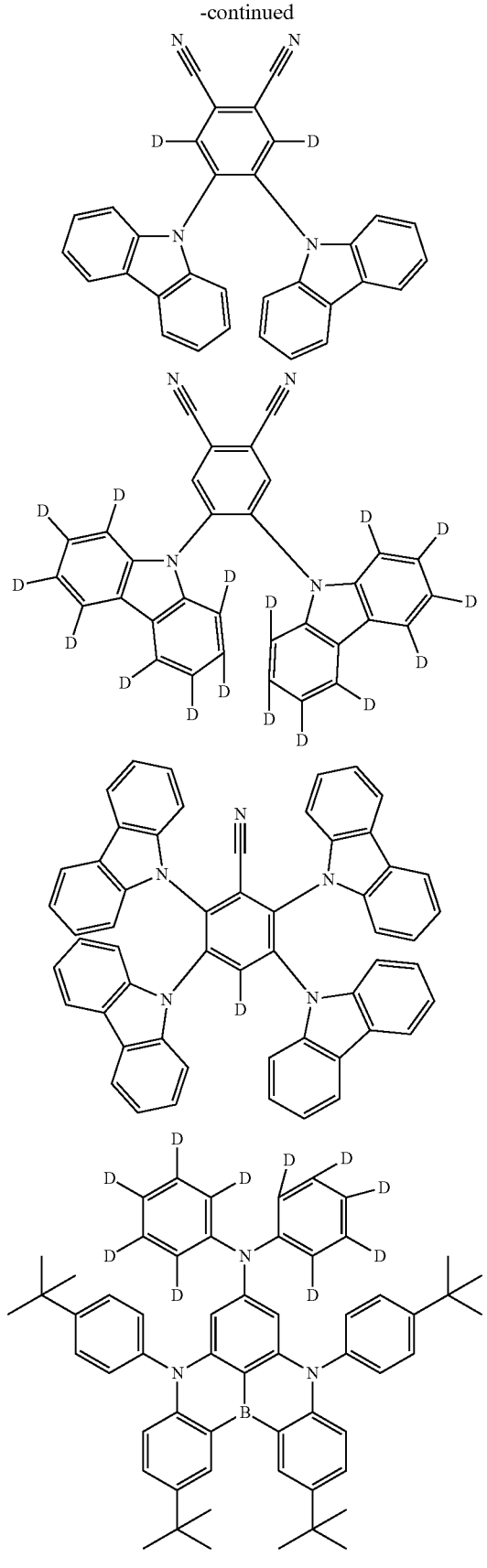
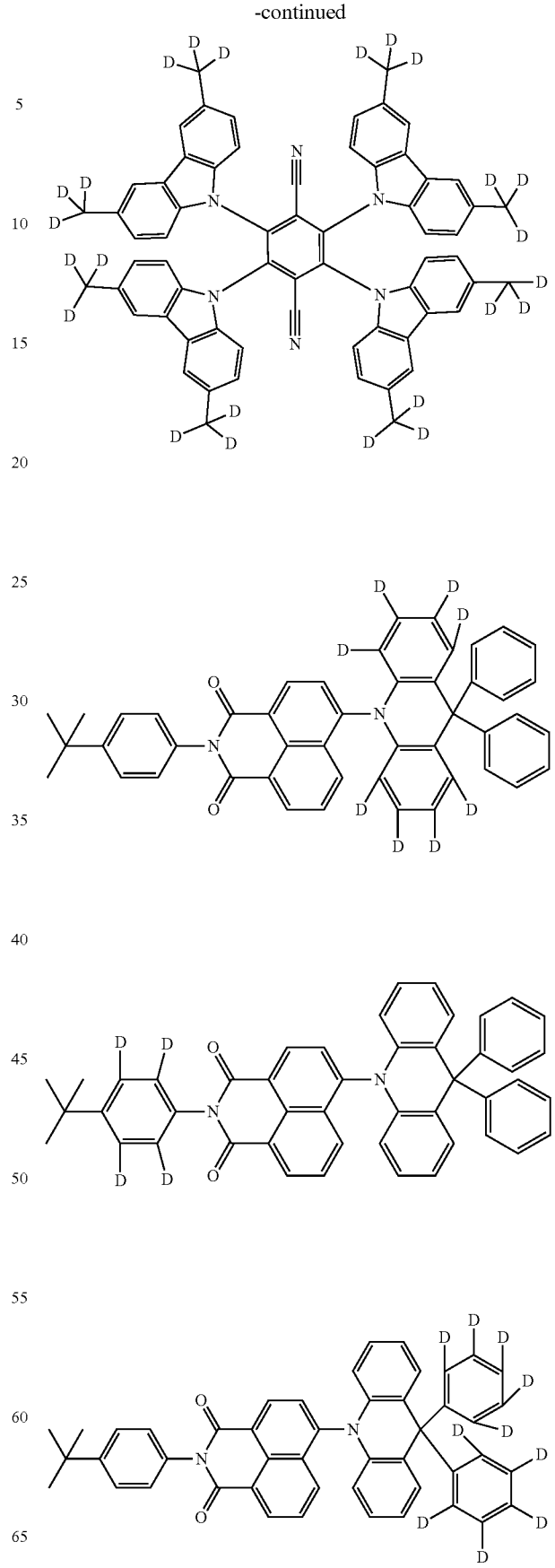

303
-continued
304
-continued
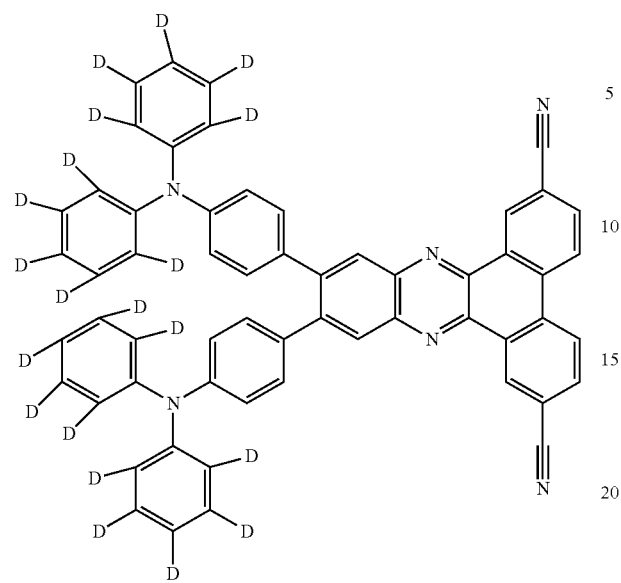
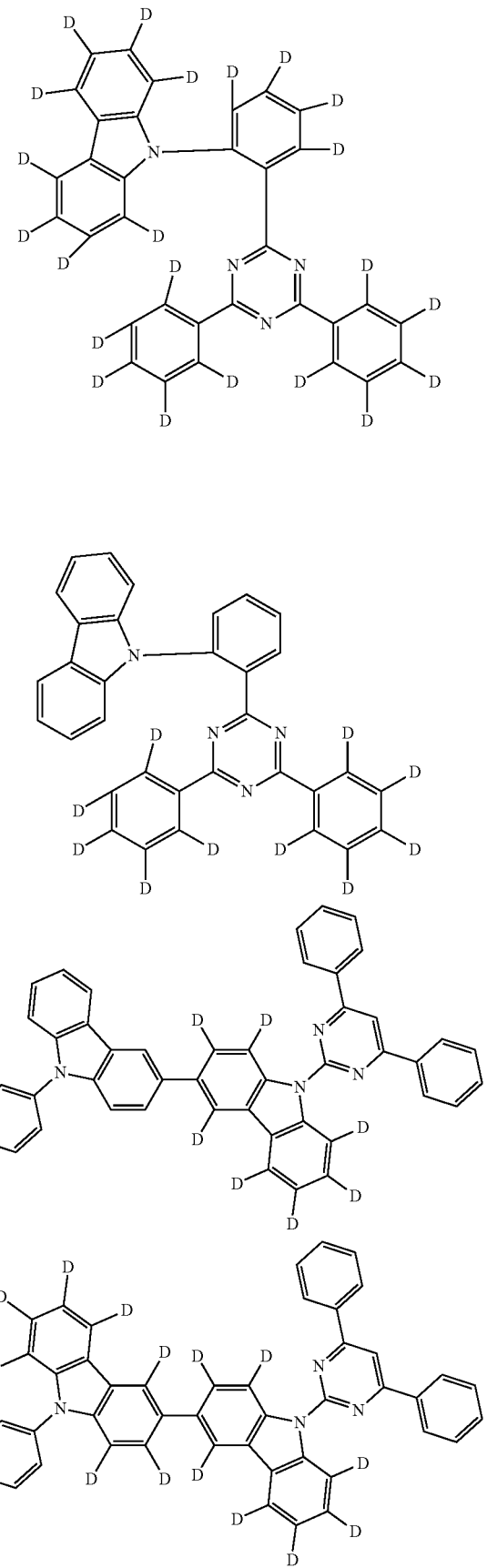

305
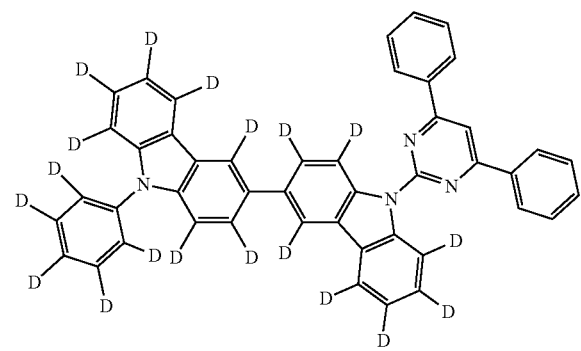
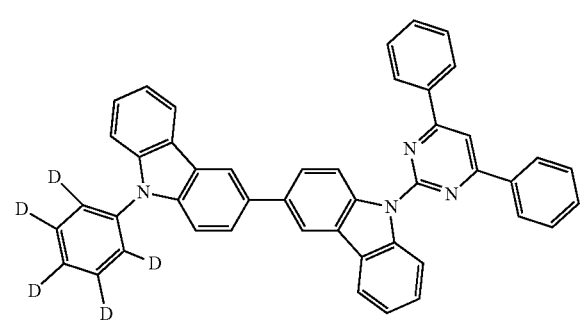
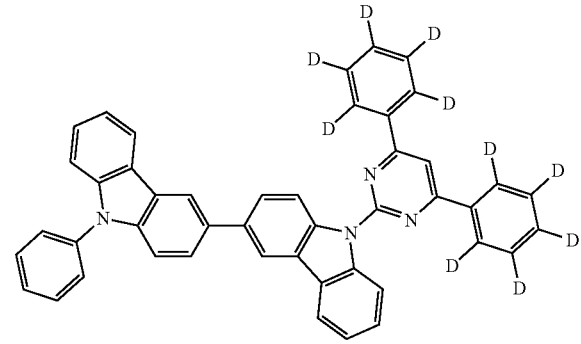
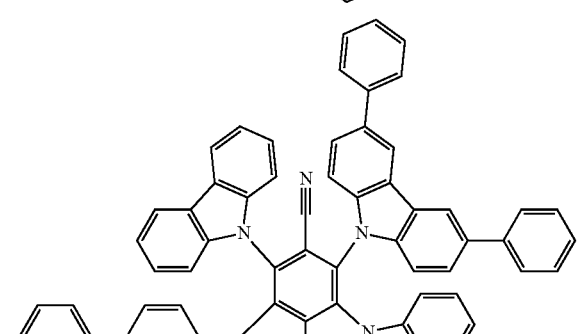
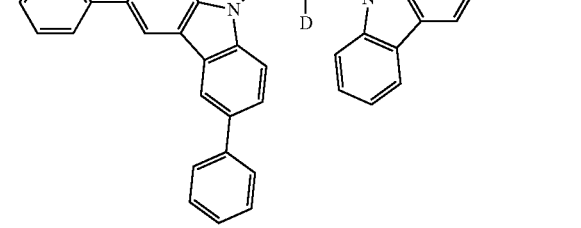
306
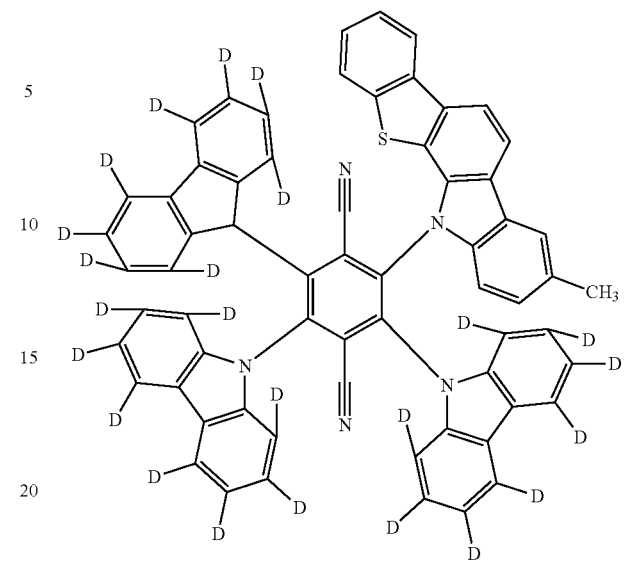
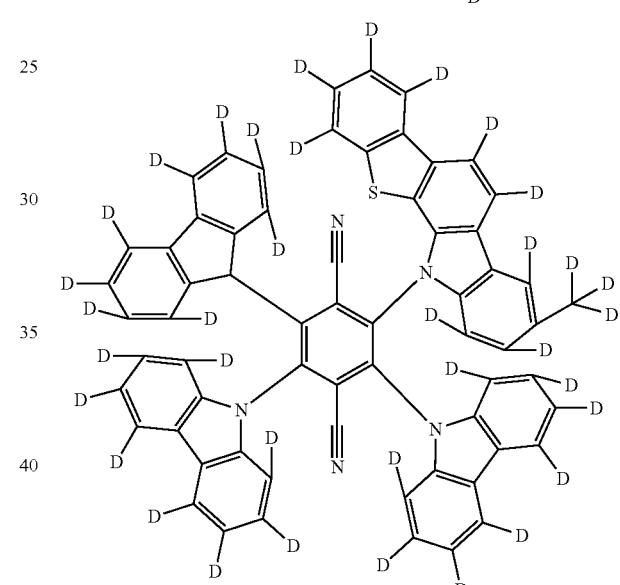
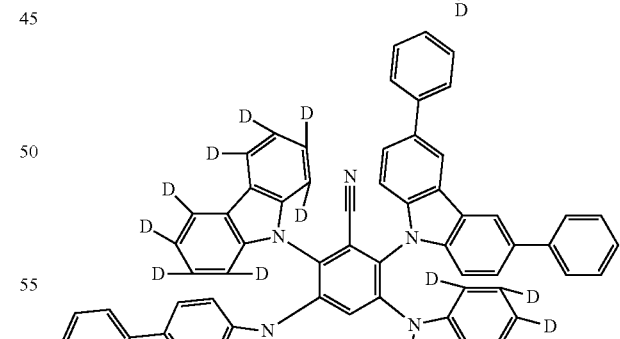
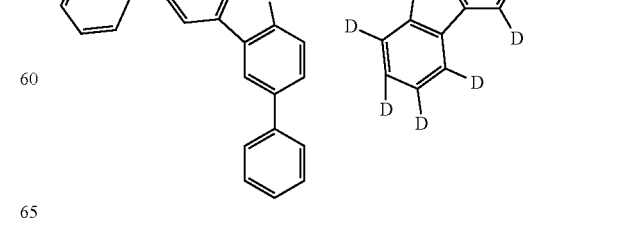

307
-continued
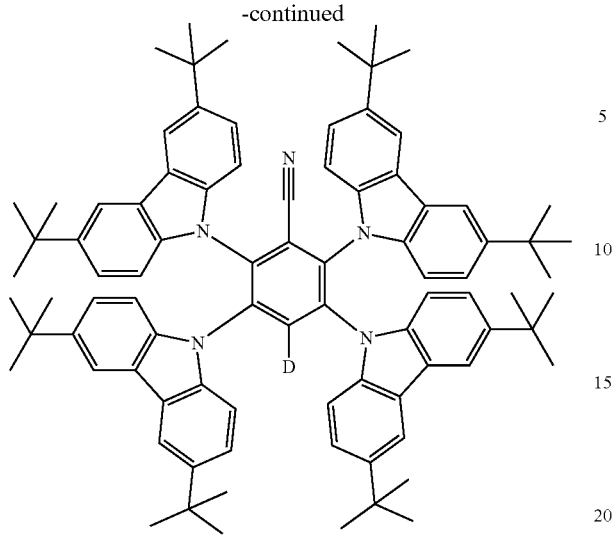
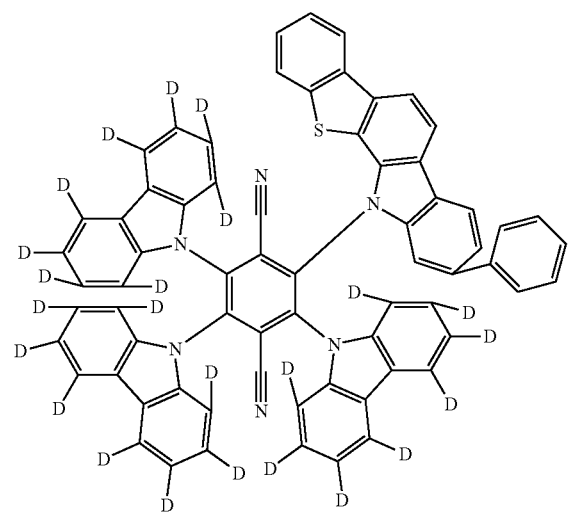
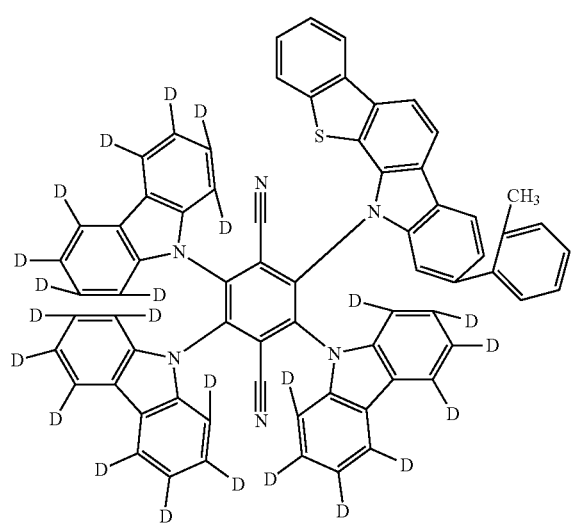
308
-continued
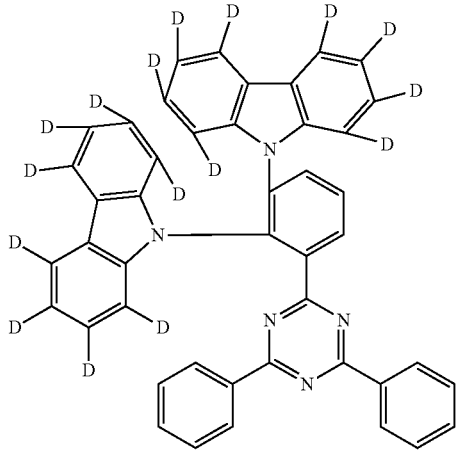
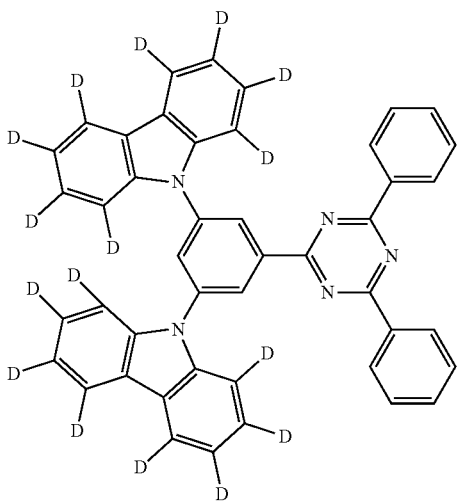
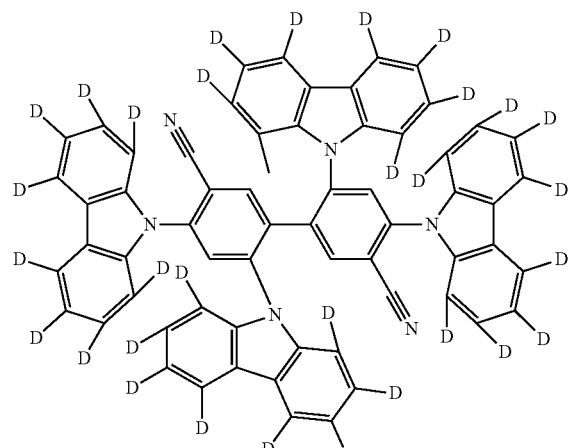

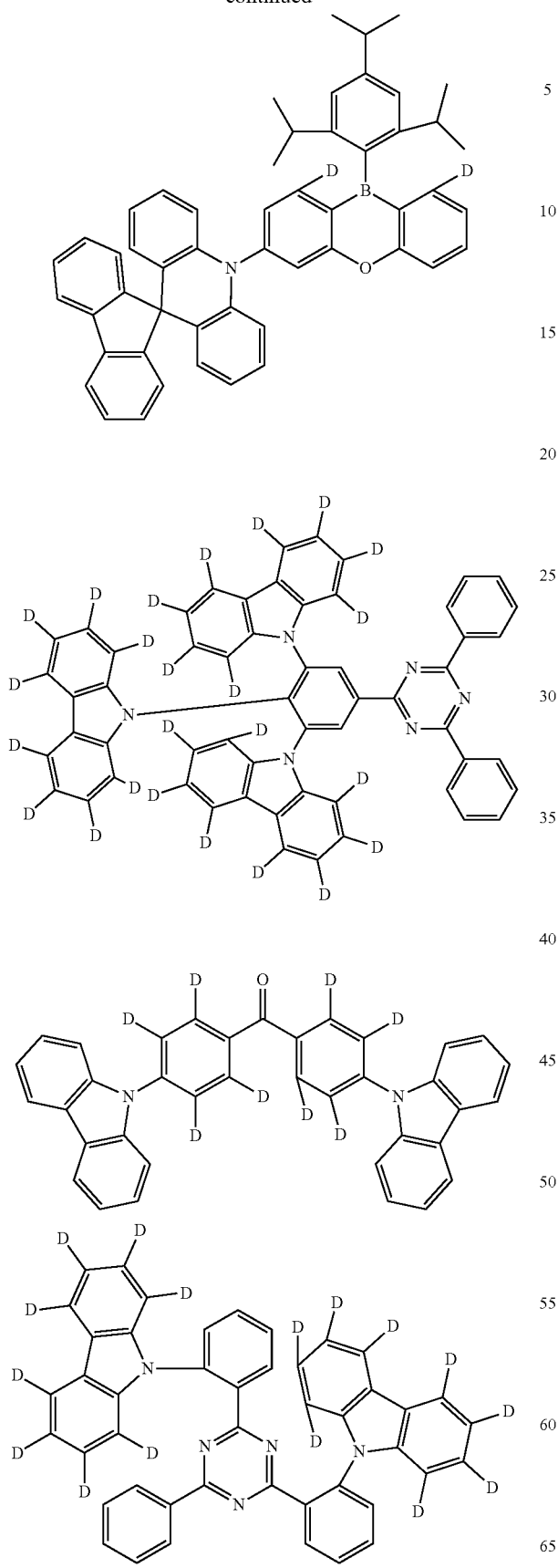
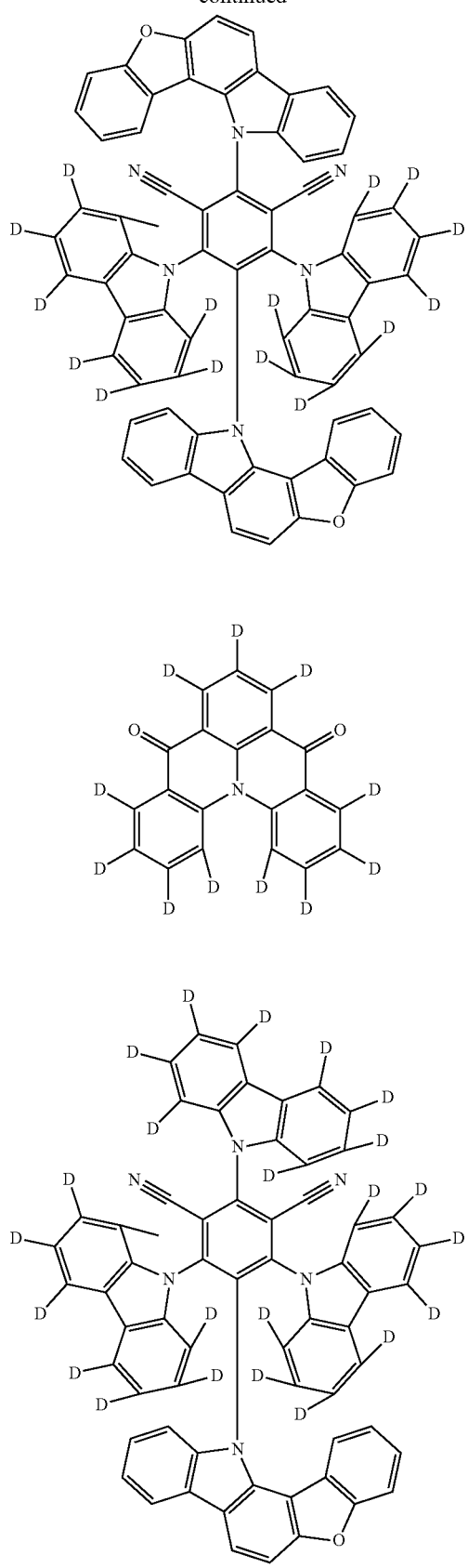

311
-continued
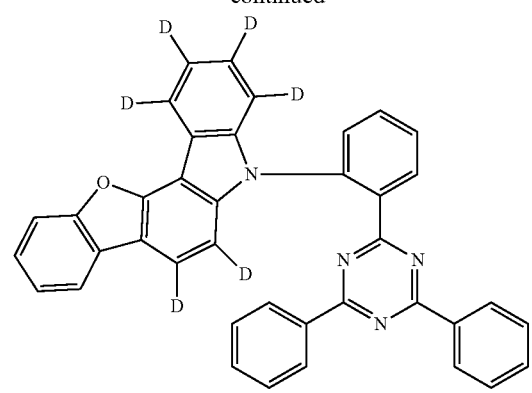
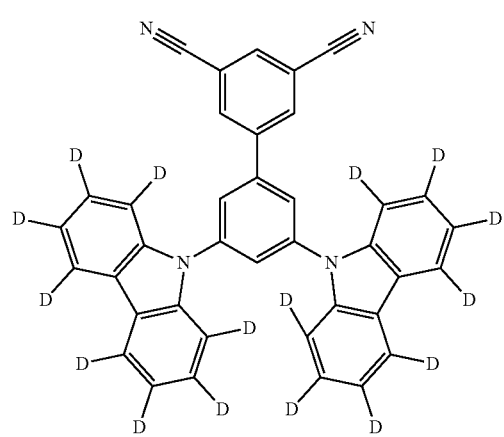
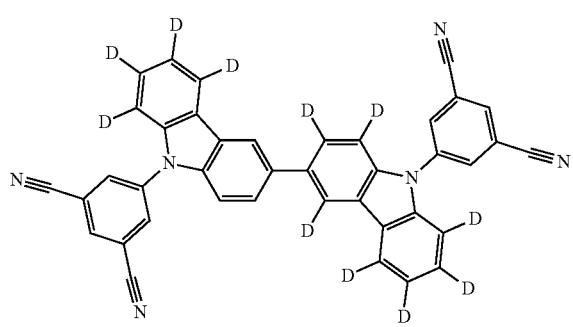
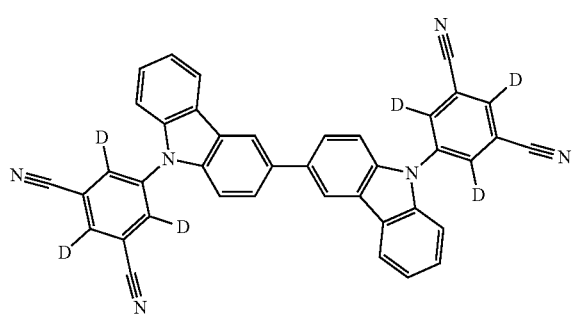
312
-continued
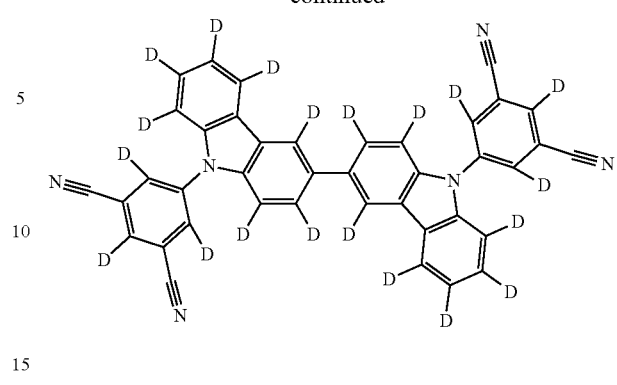
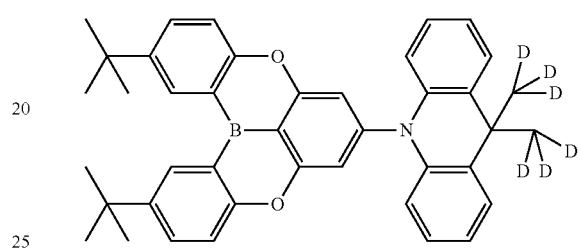
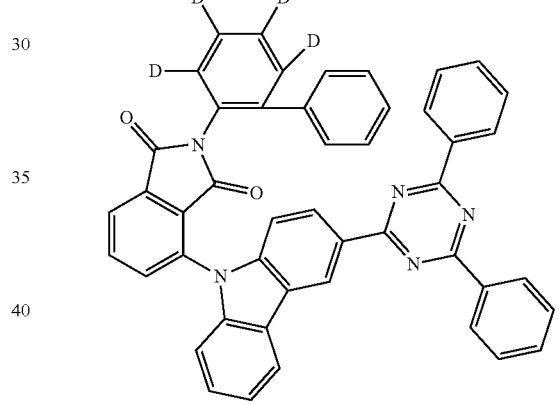
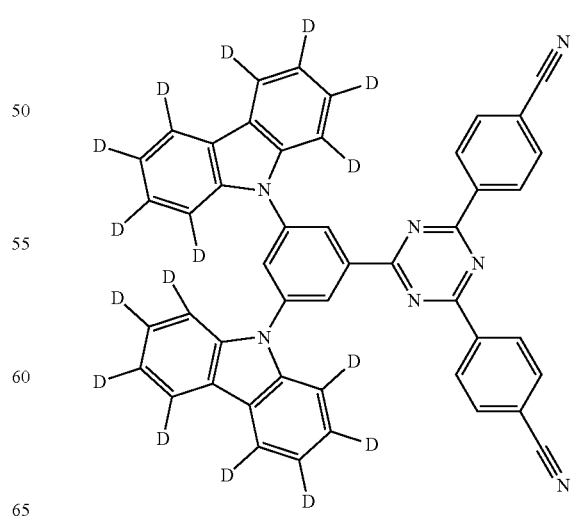

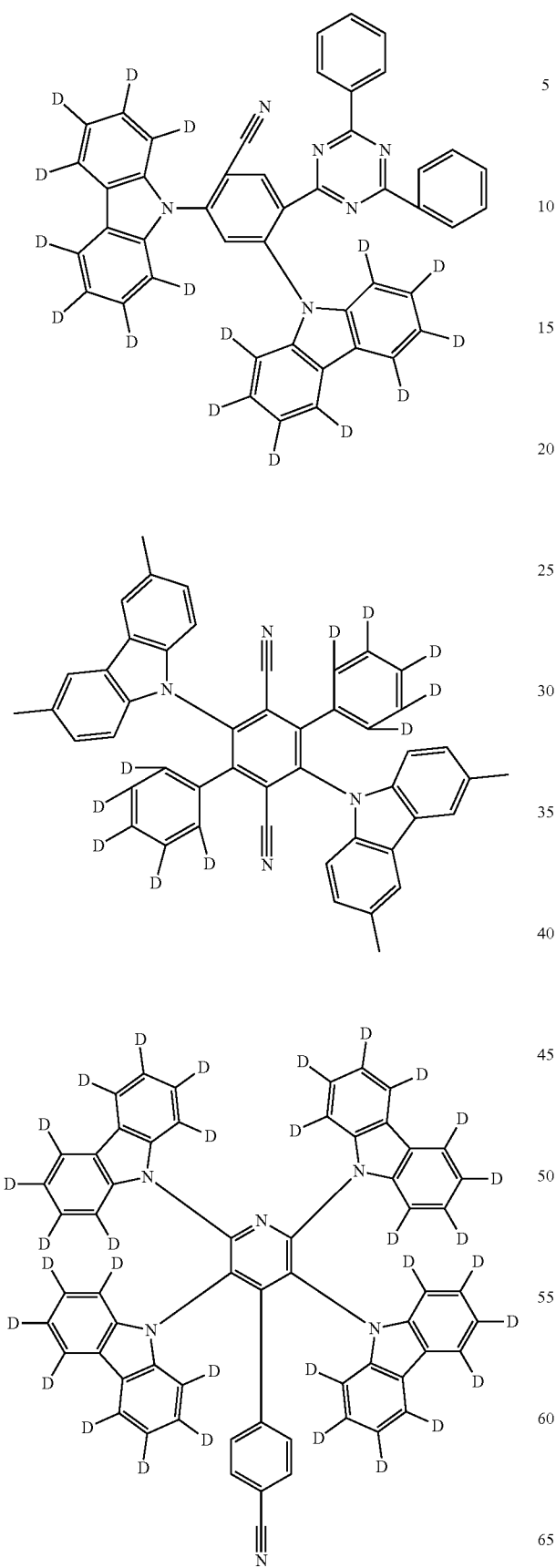
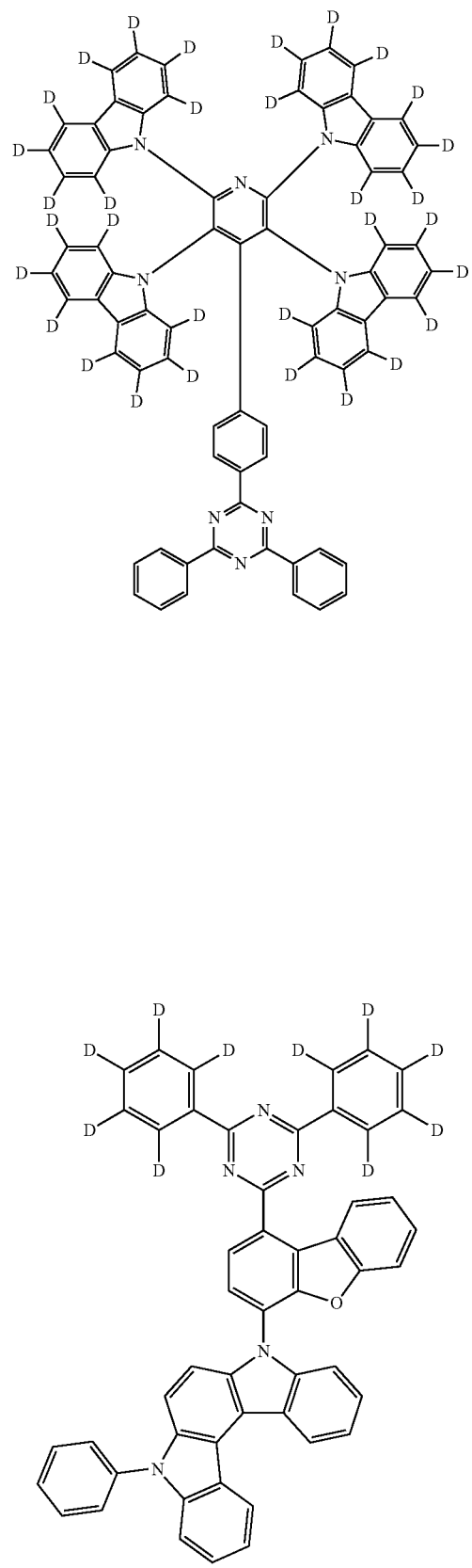

315
-continued
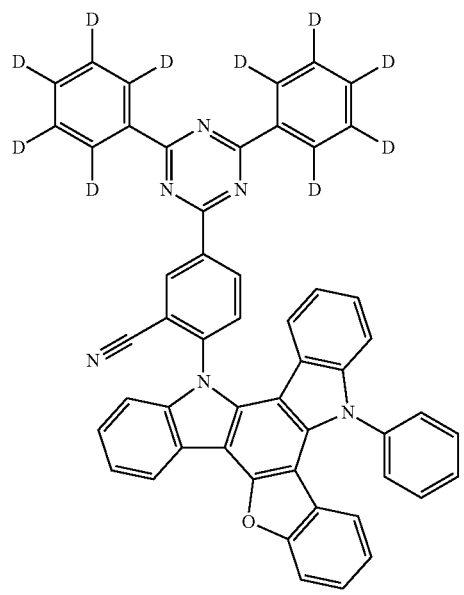
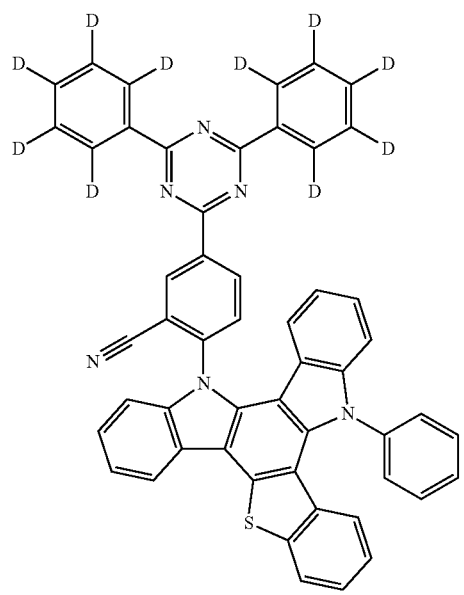
316
-continued
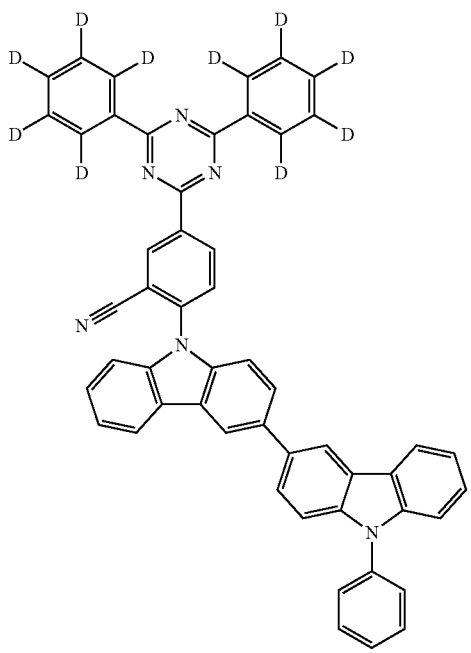
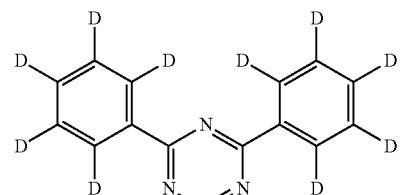
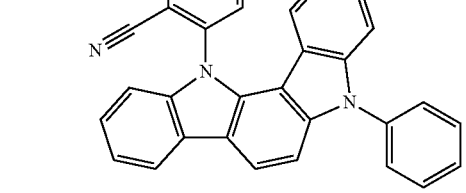
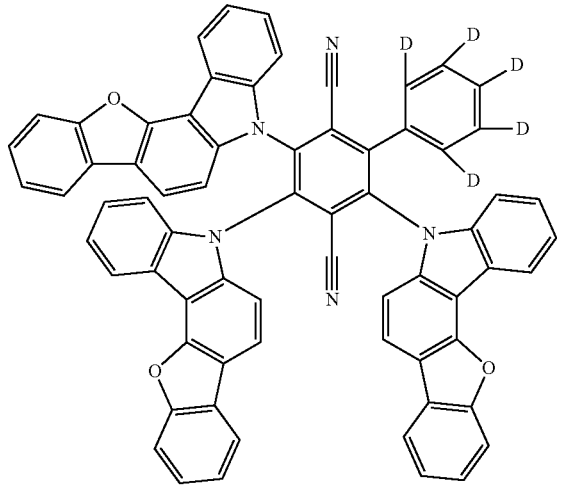

317
-continued
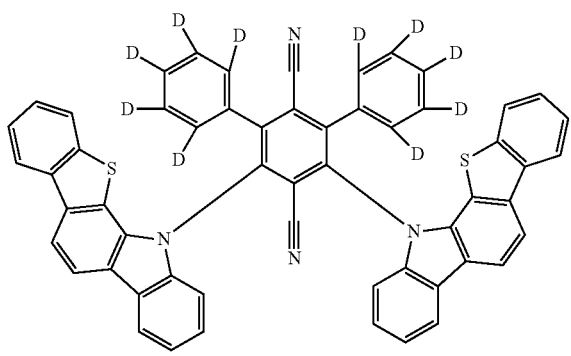
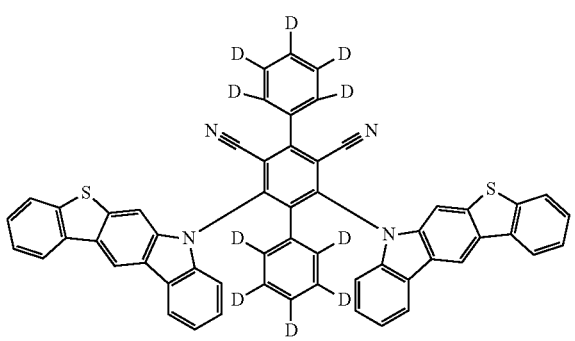
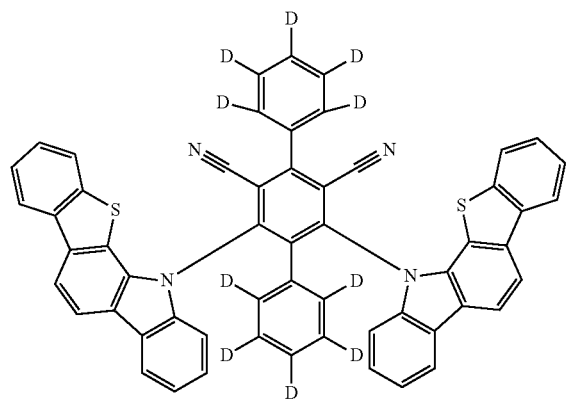
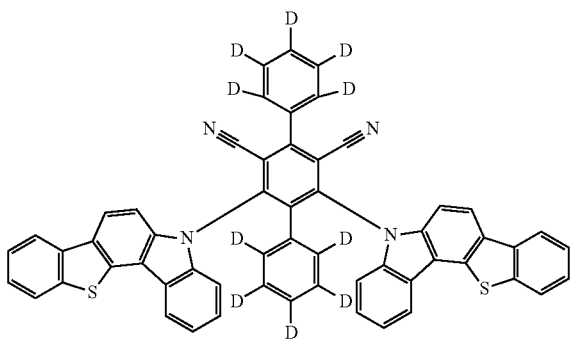
318
-continued
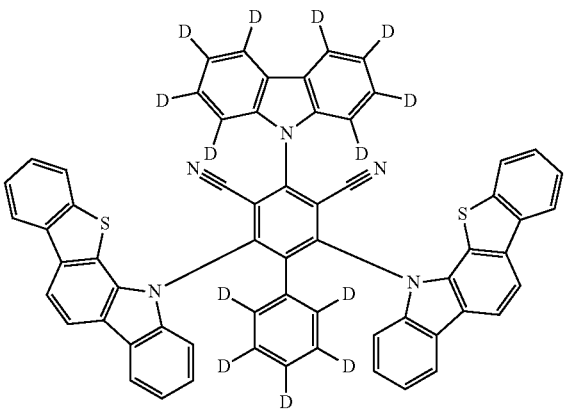
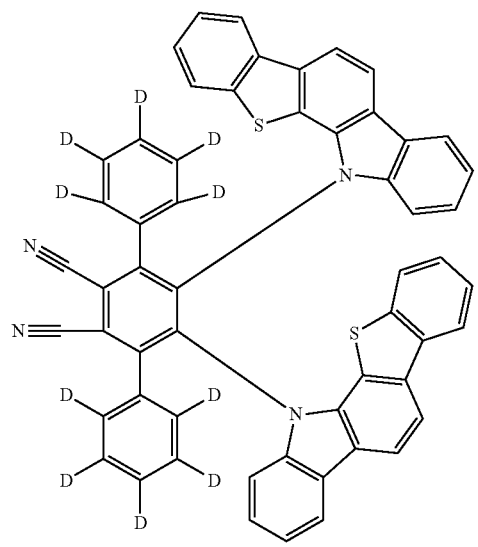
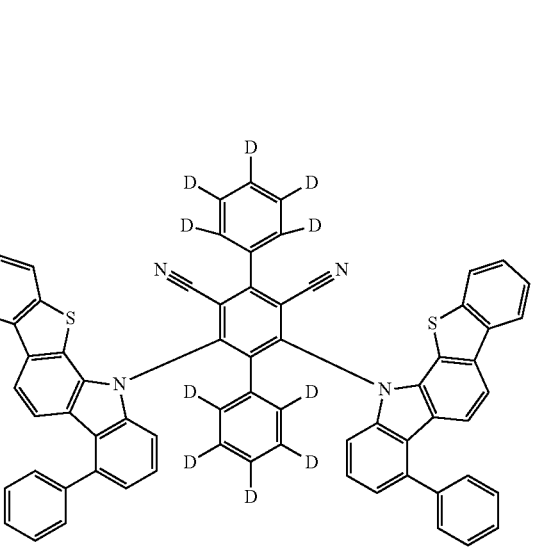

319
-continued

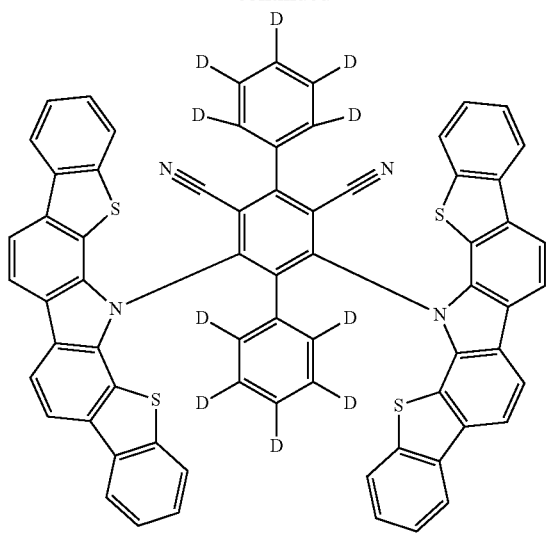

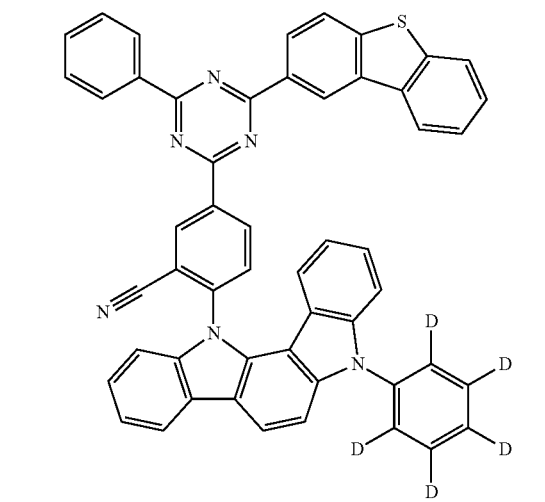

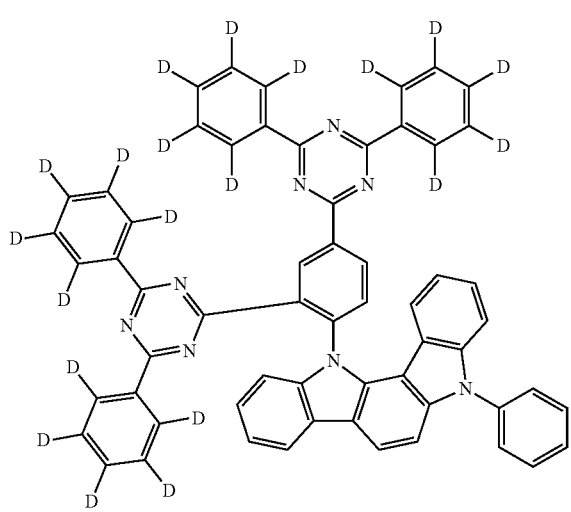

320
-continued

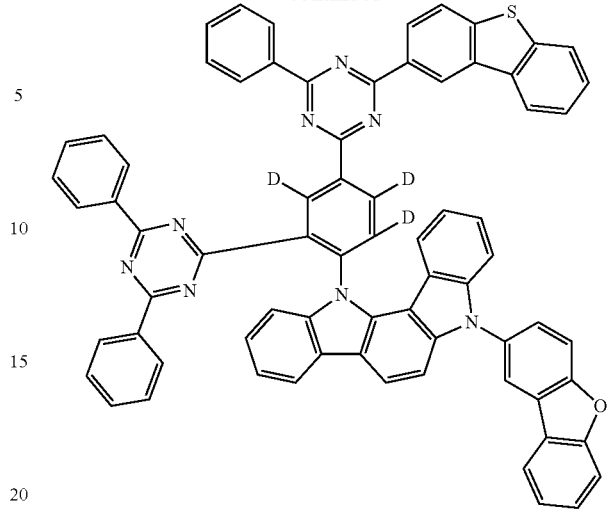

Relationship between Compound M3 and Compound M2 in Emitting Layer

In the organic EL device according to the exemplary embodiment, a singlet energy $S_1(M2)$ of the compound M2 and a singlet energy $S_1(M3)$ of the compound M3 satisfy a relationship of a numerical formula (Numerical Formula 1) below.

$$S_1(M3) > S_1(M2) \qquad \text{(Numerical Formula 1)}$$

An energy gap $T_{77K}(M3)$ at 77K of the compound M3 is preferably larger than an energy gap $T_{77K}(M2)$ at 77K of the compound M2. In other words, a relationship of the following numerical formula (Numerical Formula 11) is preferably satisfied.

$$T_{77K}(M3) > T_{77K}(M2) \qquad \text{(Numerical Formula 11)}$$

When the organic EL device according to the exemplary embodiment emits light, it is preferable that the compound M3 does not mainly emit light in the emitting layer.

Relationship between Triplet Energy and Energy Gap at 77K

Here, a relationship between a triplet energy and an energy gap at 77K will be described. In the exemplary embodiment, the energy gap at 77K is different from a typical triplet energy in some aspects.

The triplet energy is measured as follows. Firstly, a solution in which a compound (measurement target) is dissolved in an appropriate solvent is encapsulated in a quartz glass tube to prepare a sample. A phosphorescence spectrum (ordinate axis: phosphorescent luminous intensity, abscissa axis: wavelength) of the sample is measured at a low temperature (77K). A tangent is drawn to the rise of the phosphorescence spectrum close to the short-wavelength region. The triplet energy is calculated by a predetermined equation on a basis of a wavelength value at an intersection of the tangent and the abscissa axis.

Here, the thermally activated delayed fluorescent compound M2 among the compounds of the exemplary embodiment is preferably a compound having a small $\Delta ST$. When $\Delta ST$ is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescence spectrum (ordinate axis: phosphorescent luminous intensity, abscissa axis: wavelength) of the measurement sample is measured at a low temperature (77K). A tangent is drawn to the rise of the phosphorescence spectrum close to the short-wavelength region. An energy amount is calculated by a conversion equation (F1) below on a basis of a wavelength value λedge [nm] at an intersection of the tangent and the abscissa axis. The calculated energy amount is defined as an energy gap $T_{77K}$ at 77K.

Conversion Equation (F1): $T_{77K}$ [eV]=1239.85/λedge

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Singlet Energy $S_1$

A method of measuring the singlet energy Si with use of a solution (occasionally referred to as a solution method) is exemplified by a method below.

A toluene solution of a measurement target compound at a concentration of 10 μmol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate singlet energy.

Conversion Equation (F2): $S_1$ [eV]=1239.85/λedge

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

In the exemplary embodiment, a difference ($S_1$-$T_{77K}$) between the singlet energy $S_1$ and the energy gap $T_{77K}$ at 77K is defined as ΔST.

In the exemplary embodiment, a difference ΔST(M3) between the singlet energy $S_1$(M3) of the compound M3 and the energy gap $T_{77K}$(M3) at 77K of the compound M3 preferably satisfies a relationship of a numerical formula (Numerical Formula 3) below.

$$\Delta ST(M3)=S_1(M3)-T_{77K}(M3)>0.35 \text{ eV} \quad \text{(Numerical Formula 3)}$$

In the exemplary embodiment, a difference ΔST(M2) between the singlet energy $S_1$(M2) of the compound M2 and the energy gap $T_{77K}$(M2) at 77K of the compound M2 preferably satisfies a relationship of a numerical formula (Numerical Formula 1A) below, more preferably satisfies a relationship of a numerical formula (Numerical Formula 1B) below, still more preferably satisfies a relationship of a numerical formula (Numerical Formula 1C) below, and even still more preferably satisfies a relationship of a numerical formula (Numerical Formula 1D) below.

$$\Delta ST(M2)=S_1(M2)-T_{77K}(M2)<0.3 \text{ eV} \quad \text{(Numerical Formula 1A)}$$

$$\Delta ST(M2)=S_1(M2)-T_{77K}(M2)<0.2 \text{ eV} \quad \text{(Numerical Formula 1B)}$$

$$\Delta ST(M2)=S_1(M2)-T_{77K}(M2)<0.1 \text{ eV} \quad \text{(Numerical Formula 1C)}$$

$$\Delta ST(M2)=S_1(M2)-T_{77K}(M2)<0.01 \text{ eV} \quad \text{(Numerical Formula 1D)}$$

Film Thickness of Emitting Layer

A film thickness of the emitting layer of the organic EL device in the exemplary embodiment is preferably in a range from 5 nm to 50 nm, more preferably in a range from 7 nm to 50 nm, most preferably in a range from 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratios of Compounds in Emitting Layer

Content ratios of the compounds M2 and M3 in the emitting layer preferably fall, for instance, within a range below.

The content ratio of the compound M2 is preferably in a range from 10 mass % to 80 mass %, more preferably in a range from 10 mass % to 60 mass %, further preferably in a range from 20 mass % to 60 mass %.

The content ratio of the compound M3 is preferably in a range from 20 mass % to 90 mass %, more preferably in a range from 40 mass % to 90 mass %, further preferably in a range from 40 mass % to 80 mass %.

It should be noted that the emitting layer of the exemplary embodiment may further contain material(s) other than the compounds M2 and M3.

The emitting layer may include a single type of the compound M2 or may include two or more types of the compound M2. The emitting layer may include a single type of the compound M3 or may include two or more types of the compound M3.

FIG. 4 shows a relationship in energy level and energy transfer between the compound M3 and the compound M2 in the emitting layer.

In FIG. 4, S0 represents a ground state. $S_1(M2)$ represents the lowest singlet state of the compound M2. $T1(M2)$ represents the lowest triplet state of the compound M2. $S_1(M3)$ represents the lowest singlet state of the compound M3. $T1(M3)$ represents the lowest triplet state of the compound M3.

Dashed arrows in FIG. 4 show energy transfer between the excited states. An energy transfer occurs by Forster transfer from the lowest singlet state $S_1$ of the compound M3 to the lowest singlet state $S_1$ of the compound M2 or an energy transfer occurs by Dexter transfer from the lowest triplet state T1 of the compound M3 to the lowest triplet state T1 of the compound M2.

Further, when a material having a small $\Delta ST(M2)$ is used as the compound M2, inverse intersystem crossing can be caused by a heat energy from the lowest triplet state T1 to the lowest singlet state $S_1$ in the compound M2. Consequently, fluorescence from the lowest singlet state $S_1$ of the compound M2 can be observed. It is inferred that the internal quantum efficiency can be theoretically raised up to 100% also by using delayed fluorescence by the TADF mechanism.

The organic EL device according to the exemplary embodiment contains the delayed fluorescent compound M2 and the compound M3 having the singlet energy larger than that of the compound M2 in the emitting layer.

According to the exemplary embodiment, an organic EL device that emits light with a long lifetime can be achieved.

The organic EL device according to the exemplary embodiment is applicable to an electronic device such as a display device and a light-emitting device.

An arrangement of an organic EL device will be further described below. Substrate The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the EL layers formed on the anode, since the hole injecting layer adjacent to the anode is formed of a composite material into which holes are easily injectable irrespective of the work function of the anode, a material usable as an electrode material (e.g., metal, an alloy, an electrically conductive compound, a mixture thereof, and the elements belonging to the group 1 or 2 of the periodic table) is also usable for the anode.

The elements belonging to the group 1 or 2 of the periodic table, which are a material having a small work function, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal are usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of materials for the cathode include elements belonging to the group 1 or 2 of the periodic table, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4', 4"-tris(N, N-diphenylamino) triphenylamine (abbreviation: TDATA), 4,4',4"-tris[N-(3-methylphenyl)-N-phenylamino] triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3, 6,7, 10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N, N'-bis(4-butylphenyl)-N, N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

The hole injecting layer may be an inorganic layer or an organic layer.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N, N'-bis(3-methylphenyl)-N, N'-diphenyl-[1,1'-biphenyl]-4,4'-diamine (abbreviation: TPD), 4-phenyl-4'-(9-phenylfluoren-9-yl) triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N, N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have an electron mobility of $10^{-6}$ cm$^2$/(V.s) or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

When the hole transporting layer includes two or more layers, one of the layers with a larger energy gap is preferably provided closer to the emitting layer. An example of the material with a larger energy gap is HT-2 used in later-described Examples.

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: Almq3), bis(10-hydroxybenzo[h]quinolinato)beryllium (abbreviation: BeBq2), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ cm$^2$/Vs or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Further, a high polymer compound is usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable. Electron Injecting Layer The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF$_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

The electron injecting layer may be an inorganic layer or an organic layer. A layer formed of, for example, lithium (Li), cesium (Cs), calcium (Ca), lithium fluoride (LiF), cesium fluoride (CsF), calcium fluoride (CaF$_2$), or a lithium oxide (LiOx) corresponds to the inorganic layer. A layer formed of, for example, Liq ((8-quinolinolato)lithium) corresponds to the organic layer.

The organic EL device 1 of the exemplary embodiment includes, between the cathode 4 and the emitting layer 5, an electron transporting zone including one or more organic layers. In the case of FIG. 1, the electron transporting zone is formed of the electron transporting layer 8 and the electron injecting layer 9.

The electron transporting zone preferably includes a plurality of organic layers. The organic layers included in the electron transporting zone are preferably formed of two layers or more and four layers or less, and more preferably two layers or more and three layers or less.

The organic EL device 1 of the exemplary embodiment includes, between the anode 3 and the emitting layer 5, a hole transporting zone including one or more organic layers. In the case of FIG. 1, the hole transporting zone is formed of the hole injecting layer 6 and the hole transporting layer 7.

The hole transporting zone preferably includes a plurality of organic layers. The organic layers included in the hole transporting zone are preferably formed of two layers or more and four layers or less, and more preferably two layers or more and three layers or less.

At least one layer of the organic layers included in the electron transporting zone preferably contains a compound represented by a formula (E1) below.

The organic layers included in the electron transporting zone preferably include a first layer adjacent to the emitting layer, and the first layer preferably contains a compound represented by the formula (E1).

In the case of FIG. 1, the electron transporting layer 8 adjacent to the emitting layer 5 corresponds to the first layer.

A device arrangement that exhibits a practical performance included in a commercially available electronic device often includes a hole transporting zone and an electron transporting zone each of which is formed of a plurality of organic layers to improve, for example, the power consumption. In a device arrangement that exhibits such a practical performance, the load on the TADF material and the load on the host material can be further reduced by considering the behavior of the charge injection into the emitting layer compared with an organic EL device having a simple device arrangement (in which, for example, a hole transporting layer and an electron transporting layer are each formed of a single organic layer).

Presumably, for example, when the electron transporting zone is configured to include at least two organic layers, and, of the organic layers included in the electron transporting zone, at least one layer (preferably, the first layer adjacent to the emitting layer) contains a compound represented by the formula (E1) below, a deuterated host material can easily contribute to the improvement in the device lifetime. It is considered that, consequently, the device lifetime can be improved more significantly than that of the organic EL device of Patent Literature 1, which discloses a simple device arrangement.

(E1)

In the formula (E1), $X_{51}$ to $X_{56}$ are each independently a nitrogen atom or $CR_{50}$, or at least one pair of pairs of adjacent ones of $R_{50}$ are mutually bonded to form a ring; two or three of $X_{51}$ to $X_{56}$ are nitrogen atoms; each $R_{50}$ is independently a hydrogen atom or a substituent; each $R_{50}$ serving as a substituent is independently a halogen atom, a cyano group, a substituted or unsubstituted aryl group having 6 to 30 ring carbon atoms, a substituted or unsubstituted heterocyclic group having 5 to 50 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, a substituted or unsubstituted arylthio group having 6 to 30 ring carbon atoms, a substituted or unsubstituted aralkyl group having 7 to 30 carbon atoms, a substituted germanium group, a substituted phosphine oxide group, a nitro group, a substituted or unsubstituted carbonyl group, or a substituted boryl group; and a plurality of $R_{50}$ are mutually the same or different.

The compound represented by the formula (E1) is preferably a compound represented by a formula (E2) below.

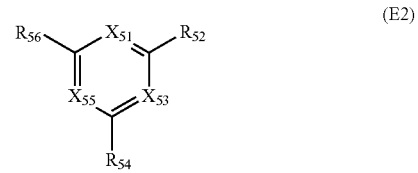
(E2)

In the formula (E2), $X_{51}$, $X_{53}$, and $X_{55}$ each independently represent the same as $X_{51}$, $X_{53}$, and $X_{55}$ in the formula (E1), $R_{52}$, $R_{54}$, and $R_{56}$ each independently represent the same as $R_{50}$ in $CR_{50}$ in the formula (E1), and two or three of $X_{51}$, $X_{53}$, and $X_{55}$ are nitrogen atoms.

In the formula (E2), it is preferable that $R_{52}$ is a group represented by a formula (E21) below, and $R_{54}$ and $R_{56}$ are each independently a group represented by a formula (E21) below, a substituted or unsubstituted aryl group having 6 to 30 ring carbon atoms, or a substituted or unsubstituted heterocyclic group having 5 to 50 ring atoms.

(E21)

In the formula (E21), HAr is a group represented by a formula (E22) below, and a is an integer of 1 or more and 5 or less.

When a is 1, $L_3$ is a single bond or a divalent linking group.

When a is 2 or more and 5 or less, $L_3$ is a trivalent or higher and hexavalent or lower linking group, and HAr are the same or different.

In the formula (E21), $L_3$ serving as a linking group is a group derived from a substituted or unsubstituted aryl group having 6 to 30 ring carbon atoms, a group derived from a substituted or unsubstituted heterocyclic group having 5 to 30 ring atoms, or a group formed by bonding together two or three groups selected from the group consisting of groups derived from a substituted or unsubstituted aryl group having 6 to 30 ring carbon atoms and groups derived from a substituted or unsubstituted heterocyclic group having 5 to 30 ring atoms, and the groups bonded together are mutually the same or different. * represents a bonding position to a benzene ring in the formula (E2).

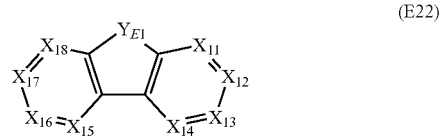

(E22)

In the formula (E22), $X_{11}$ to $X_{18}$ are each independently a nitrogen atom, $CR_{E3}$, or a carbon atom bonded to $L_3$ through a single bond.

In the formula (E22), $Y_{E1}$ is $CR_{E1}R_{E2}$, $SIR_{E4}R_{E5}$, an oxygen atom, a sulfur atom, a carbon atom bonded to $R_{E6}$ and $L_3$, or a silicon atom bonded to $R_{E7}$ and $L_3$, one of carbon atoms in $X_{11}$ to $X_{18}$, a carbon atom in $Y_{E1}$, and a silicon atom in $Y_{E1}$ is bonded to $L_3$, and $R_{E1}$ to $R_{E7}$ are each independently a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms. A plurality of $R_{E3}$ are mutually the same or different. Adjacent $R_{E3}$ may be mutually bonded to form a ring.

In the formula (E22), $X_{13}$ or $X_{16}$ is preferably a carbon atom bonded to $L_3$ through a single bond.

In the formula (E22), $X_{11}$ or $X_{18}$ is also preferably a carbon atom bonded to $L_3$ through a single bond.

In the formula (E22), $X_{12}$ or $X_{17}$ is also preferably a carbon atom bonded to $L_3$ through a single bond.

In the formula (E22), $X_{14}$ or $X_{15}$ is also preferably a carbon atom bonded to $L_3$ through a single bond.

In the formula (E21), a is an integer of 1 or more and 5 or less, more preferably 1 or more and 3 or less, and still more preferably 1 or 2.

In the formula (E21), when a is 1, $L_3$ is a divalent linking group, and the formula (E21) is represented by a formula (E211) below.

In the formula (E21), when a is 2 or more and 5 or less, $L_3$ is a trivalent or higher and hexavalent or lower linking group. When a is 2, $L_3$ is a trivalent linking group, and the formula (E21) is represented by a formula (E212) below.

(E211)

(E212)

In the formulae (E211) and (E212), $L_3$ and HAr each independently represent the same as $L_3$ and HAr in the formula (E21), and * represents a bonding position to a benzene ring in the formula (E2). A plurality of HAr are the same or different.

The compound represented by the formula (E1) is also preferably a compound represented by a formula (E11) or (E12) below.

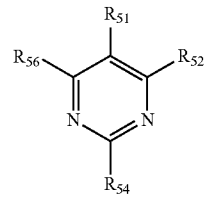

(E11)

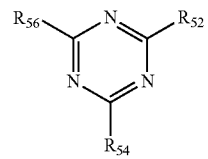

(E12)

In the formula (E11), $R_{51}$, $R_{52}$, $R_{54}$, and $R_{56}$ each independently represent the same as $R_{50}$ in $CR_{50}$ in the formula (E1); and in the formula (E12), $R_{52}$, $R_{54}$, and $R_{56}$ each independently represent the same as $R_{50}$ in $CR_{50}$ in the formula (E1).

In the formula (E11), it is preferable that $R_{51}$, $R_{52}$, $R_{54}$, and $R_{56}$ are each independently a group represented by the formula (E21), a substituted or unsubstituted aryl group having 6 to 30 ring carbon atoms, or a substituted or unsubstituted heterocyclic group having 5 to 30 ring atoms, and one of $R_{51}$, $R_{52}$, $R_{54}$, and $R_{56}$ is a group represented by the formula (E21).

In the formula (E11), it is more preferable that $R_{52}$ is a group represented by the formula (E21), and $R_{51}$, $R_{54}$, and $R_{56}$ are each independently a substituted or unsubstituted aryl group having 6 to 30 ring carbon atoms or a substituted or unsubstituted heterocyclic group having 5 to 30 ring atoms.

In the formula (E12), it is preferable that $R_{52}$, $R_{54}$, and $R_{56}$ are each independently a group represented by the formula (E21), a substituted or unsubstituted aryl group having 6 to 30 ring carbon atoms, or a substituted or unsubstituted heterocyclic group having 5 to 30 ring atoms, and one of $R_{52}$, $R_{54}$, and $R_{56}$ is a group represented by the formula (E21).

In the formula (E12), it is more preferable that $R_{52}$ is a group represented by the formula (E21), and $R_{54}$ and $R_{56}$ are each independently a substituted or unsubstituted aryl group having 6 to 30 ring carbon atoms or a substituted or unsubstituted heterocyclic group having 5 to 30 ring atoms.

In the formulae (E21), (E211), and (E212), $L_3$ is preferably a substituted or unsubstituted aryl group having 6 to 30 ring carbon atoms or a substituted or unsubstituted heterocyclic group having 5 to 30 ring atoms.

In the formulae (E21), (E211), and (E212), $L_3$ is preferably a divalent or trivalent residue derived from any of benzene, biphenyl, terphenyl, naphthalene, and phenanthrene.

In the formula (E21), it is more preferable that a is 1, and $L_3$ is a divalent residue of a substituted or unsubstituted aryl group having 6 to 30 ring carbon atoms or a divalent residue of a substituted or unsubstituted heterocyclic group having 5 to 30 ring atoms.

In the formula (E21), it is more preferable that a is 2, $L_3$ is a linking group, and the linking group is a trivalent residue of a substituted or unsubstituted aryl group having 6 to 30 ring carbon atoms or a trivalent residue of a substituted or unsubstituted heterocyclic group having 5 to 30 ring atoms.

In the formula (E22), $Y_{E1}$ is preferably an oxygen atom.
In the formula (E22), $Y_{E1}$ is also preferably a sulfur atom.
In the formula (E22), $Y_{E1}$ is also preferably $CR_{E1}R_{E2}$.
In the formula (E22), it is preferable that $Y_{E1}$ is an oxygen atom or a sulfur atom, $X_{12}$ and $X_{17}$ are $CR_{E3}$, one of $X_{11}$, $X_{13}$ to $X_{16}$, and $X_{18}$ is a carbon atom bonded to $L_3$ through a single bond, and the others are $CR_{E3}$.

In the formula (E22), it is preferable that $Y_{E1}$ is $CR_{E1}R_{E2}$, $X_{11}$ and $X_{18}$ are $CR_{E3}$, one of $X_{13}$ to $X_{17}$ is a carbon atom bonded to $L_3$ through a single bond, and the others are $CR_{E3}$.

Specific examples of the compound represented by the formula (E1) are shown below. It should however be noted that the invention is not limited to the specific examples of the compound.

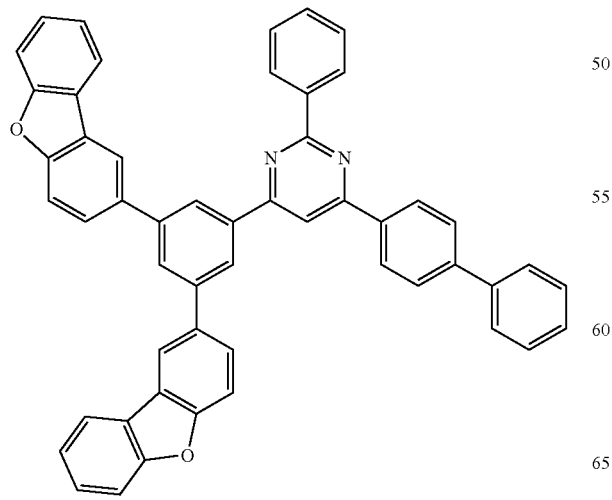

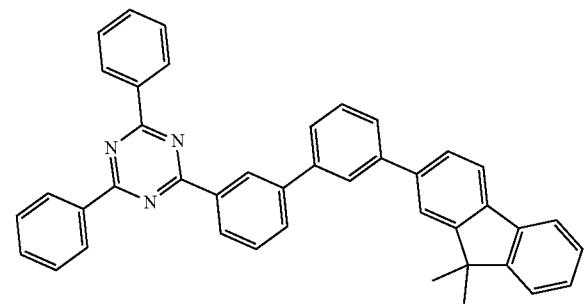

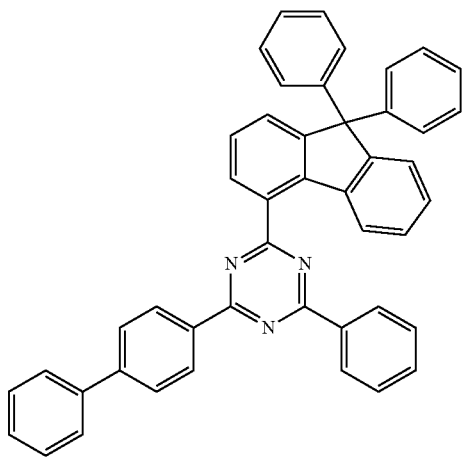

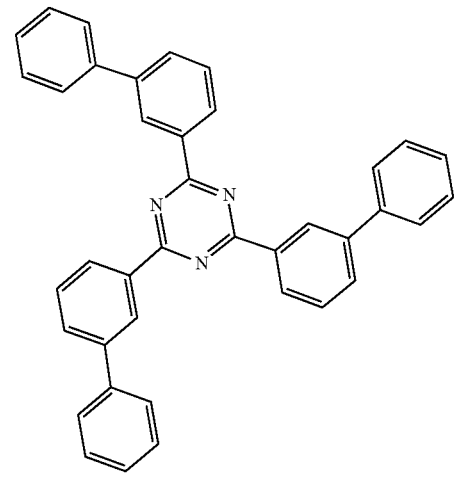

-continued

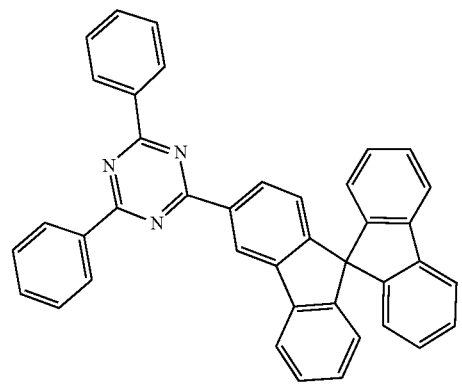

333
-continued
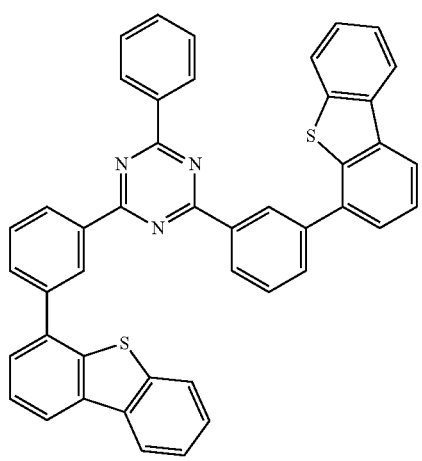
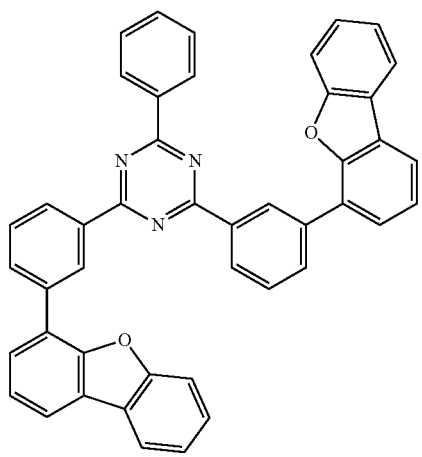
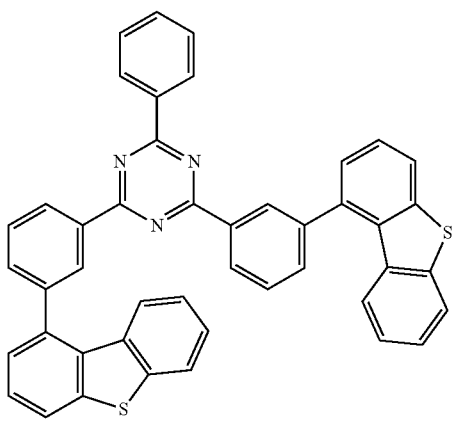
334
-continued
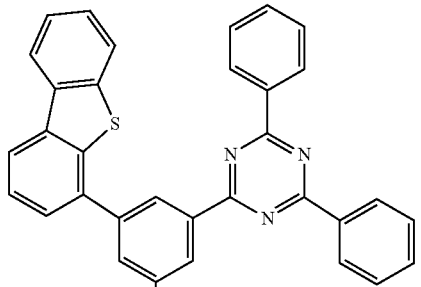
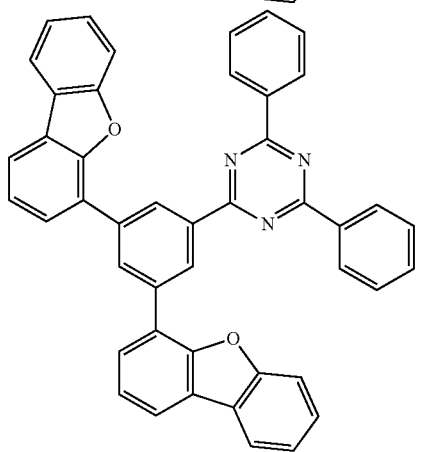
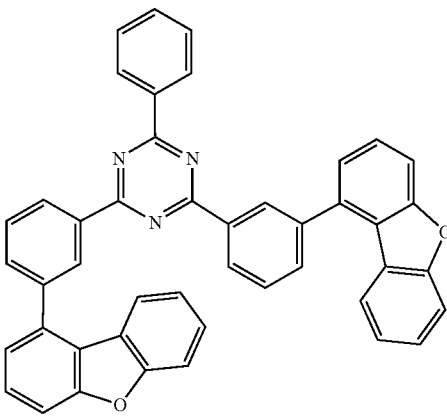
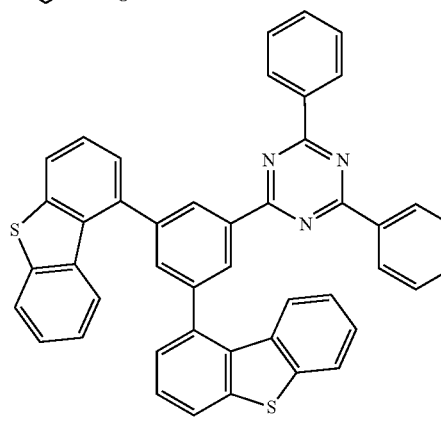

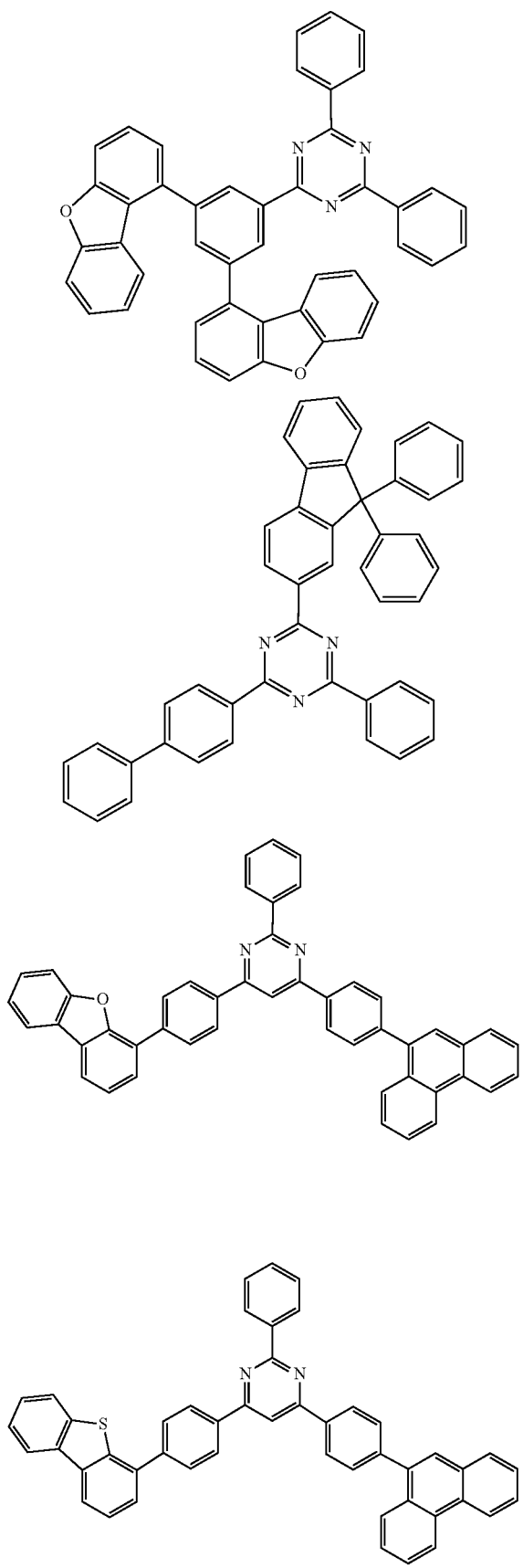

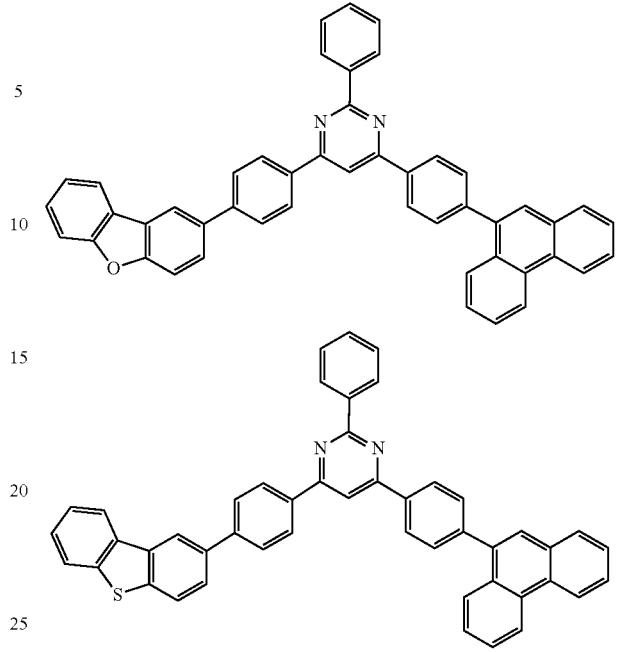

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

A thickness of each of the organic layers in the organic EL device according to the exemplary embodiment is not limited except for the above particular description. In general, the thickness preferably ranges from several nanometers to 1 μm because excessively small film thickness is likely to cause defects (e.g. pin holes) and excessively large thickness leads to the necessity of applying high voltage and consequent reduction in efficiency.

Second Exemplary Embodiment

An arrangement of an organic EL device according to a second exemplary embodiment will be described below. In the description of the second exemplary embodiment, the same components as those in the first exemplary embodiment are denoted by the same reference signs and names to simplify or omit an explanation of the components. In the second exemplary embodiment, any materials and compounds that are not specified may be the same as those in the first exemplary embodiment.

The organic EL device according to the second exemplary embodiment is different from the organic EL device according to the first exemplary embodiment in that the emitting layer further includes a fluorescent compound M1. The second exemplary embodiment is the same as the first exemplary embodiment in other respects.

In other words, in the second exemplary embodiment, the emitting layer contains the compound M3 represented by the formula (3), the delayed fluorescent compound M2, and the fluorescent compound M1.

In this arrangement, the compound M1 is preferably a dopant material, the compound M2 is preferably a host material, and the compound M3 is preferably a host material. One of the compound M2 and the compound M3 may be referred to as a first host material, and the other may be referred to as a second host material.

Compound M1

The emitting layer of the exemplary embodiment includes the fluorescent compound M1.

The compound M1 of the exemplary embodiment is not a phosphorescent metal complex. The compound M1 of the exemplary embodiment is preferably not a heavy-metal complex. The compound M1 of the exemplary embodiment is preferably not a metal complex.

A fluorescent material is usable as the compound M1 of the exemplary embodiment. Specific examples of the fluorescent material include a bisarylaminonaphthalene derivative, aryl-substituted naphthalene derivative, bisarylaminoanthracene derivative, aryl-substituted anthracene derivative, bisarylaminopyrene derivative, aryl-substituted pyrene derivative, bisarylamino chrysene derivative, aryl-substituted chrysene derivative, bisarylaminofluoranthene derivative, aryl-substituted fluoranthene derivative, indenoperylene derivative, acenaphthofluoranthene derivative, compound including a boron atom, pyromethene boron complex compound, compound having a pyromethene skeleton, metal complex of the compound having a pyrromethene skeleton, diketopyrrolopyrrole derivative, perylene derivative, and naphthacene derivative.

The compound M1 of the exemplary embodiment is preferably a compound represented by a formula (10) below.

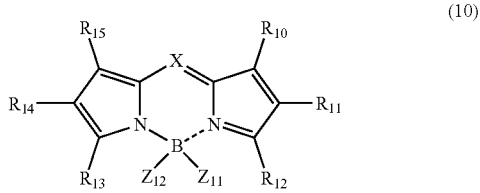

(10)

In the formula (10): X is a nitrogen atom, or a carbon atom bonded to Y; Y is a hydrogen atom or a substituent; $R_{10}$ to $R_{15}$ are each independently a hydrogen atom or a substituent, or at least one pair of a pair of $R_{10}$ and $R_{11}$, a pair of $R_{11}$ and $R_{12}$, a pair of $R_{13}$ and $R_{14}$, or a pair of $R_{14}$ and $R_{15}$ are mutually bonded to form a ring; Y and $R_{10}$ to $R_{15}$ serving as a substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group; $Z_{11}$ and $Z_{12}$ are each independently a substituent, or $Z_{11}$ and $Z_{12}$ are mutually bonded to form a ring; and $Z_{11}$ and $Z_{12}$ serving as a substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

In the formula (10), for instance, when a pair of $R_{14}$ and $R_{15}$ are mutually bonded to form a ring, the compound M1 is represented by a formula (11) below.

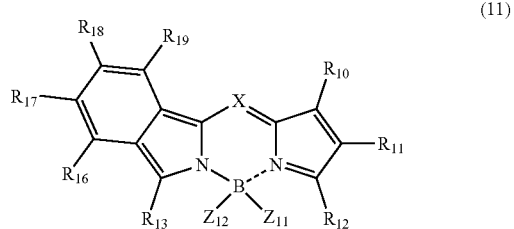

(11)

In the formula (11): X, Y, $R_{10}$ to $R_{13}$, $Z_{11}$ and $Z_{12}$ respectively represent the same as X, Y, $R_{10}$ to $R_{13}$, $Z_{11}$ and $Z_{12}$ in the formula (10); $R_{16}$ to $R_{19}$ are each independently a hydrogen atom or a substituent; and $R_{16}$ to $R_{19}$ serving as a substituent each independently represent the same as $R_{10}$ to $R_{13}$ serving as a substituent.

In the formula (10), when $Z_{11}$ and $Z_{12}$ are mutually bonded to form a ring, the compound M1 is represented by, for instance, a formula (10A) or (10B) below. However, a structure of the compound M1 is not limited to structures below.

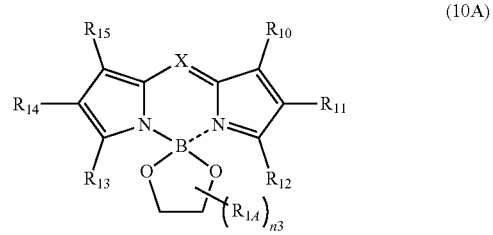

(10A)

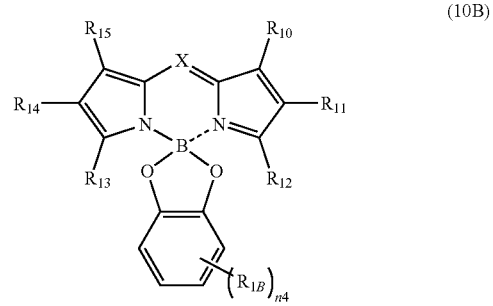

(10B)

In the formula (10A): X, Y and $R_{10}$ to $R_{15}$ respectively represent the same as X, Y and $R_{10}$ to $R_{15}$ in the formula (10); $R_{1A}$ is each independently a hydrogen atom or a substituent; $R_{1A}$ serving as a substituent represents the same as $R_{10}$ to $R_{15}$ serving as a substituent; and n3 is 4.

In the formula (10B): X, Y and $R_{10}$ to $R_{15}$ respectively represent the same as X, Y and $R_{10}$ to $R_{15}$ in the formula (10); $R_{1B}$ is each independently a hydrogen atom or a substituent; $R_{1B}$ serving as a substituent represents the same as $R_{10}$ to $R_{15}$ serving as a substituent; and n4 is 4.

It is preferable that at least one of $Z_{11}$ or $Z_{12}$ (preferably both of $Z_{11}$ and $Z_{12}$) is a group selected from the group consisting of a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

It is more preferable that at least one of $Z_{11}$ or $Z_{12}$ is a group selected from the group consisting of a fluorine-substituted alkoxy group having 1 to 30 carbon atoms, a fluorine-substituted aryloxy group having 6 to 30 ring carbon atoms, and an aryloxy group having 6 to 30 ring carbon atoms and substituted with a fluoroalkyl group having 1 to 30 carbon atoms.

Further preferably, at least one of $Z_{11}$ or $Z_{12}$ is a fluorine-substituted alkoxy group having 1 to 30 carbon atoms. Further more preferably, both of $Z_{11}$ and $Z_{12}$ are a fluorine-substituted alkoxy group having 1 to 30 carbon atoms.

It is also preferable that both of $Z_{11}$ and $Z_{12}$ are the same.

Meanwhile, it is also preferable that at least one of $Z_{11}$ or $Z_{12}$ is a fluorine atom. It is also more preferable that both of $Z_{11}$ and $Z_{12}$ are fluorine atoms.

It is also preferable that at least one of $Z_{11}$ or $Z_{12}$ is a group represented by a formula (10a) below.

(10a)

In the formula (10a), A is a substituted or unsubstituted alkyl group having 1 to 6 carbon atoms, a substituted or unsubstituted alkyl halide group having 1 to 6 carbon atoms, or a substituted or unsubstituted aryl group having 6 to 12 ring carbon atoms, $L_1$ is a substituted or unsubstituted alkylene group having 1 to 6 carbon atoms or a substituted or unsubstituted arylene group having 6 to 12 ring carbon atoms, m is 0, 1, 2, 3, 4, 5, 6, or 7. When m is 2, 3, 4, 5, 6, or 7, a plurality of $L_{12}$ are mutually the same or different, m is preferably 0, 1 or 2. When m is 0, A is directly bonded to O (oxygen atom).

When $Z_{11}$ and $Z_{12}$ in the formula (10) are each a group represented by the formula (10a), the compound M1 is a compound represented by a formula (12) below.

The compound M1 is also preferably a compound represented by the formula (12) below.

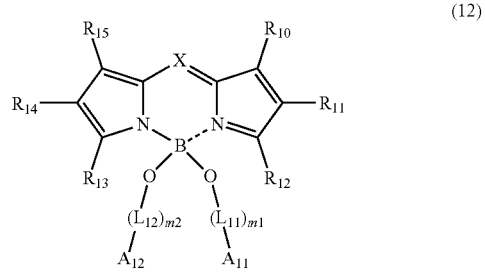

(12)

In the formula (12), X, Y bonded with a carbon atom as X, and $R_{10}$ to $R_{15}$ respectively represent the same as X, Y and $R_{10}$ to $R_{15}$ in the formula (10). $A_{11}$ and $A_{12}$ represent the same as A in the formula (10a) and may be mutually the same or different. $L_{11}$ and $L_{12}$ represent the same as $L_1$ in the formula (10a) and may be mutually the same or different. m1 and m2 are each independently 0, 1, 2, 3, 4, 5, 6 or 7, preferably 0, 1 or 2. When m1 is 2, 3, 4, 5, 6 or 7, a plurality of $L_{11}$ are mutually the same or different. When m2 is 2, 3, 4, 5, 6 or 7, a plurality of $L_{12}$ are mutually the same or different. When m1 is 0, $A_{11}$ is directly bonded to O (oxygen atom). When m2 is 0, $A_{12}$ is directly bonded to O (oxygen atom).

At least one of A or $L_1$ in the formula (10a) is preferably substituted with a halogen atom, more preferably substituted with a fluorine atom.

A in the formula (10a) is more preferably a perfluoroalkyl group having 1 to 6 carbon atoms or a perfluoroaryl group having 6 to 12 ring carbon atoms, further preferably a perfluoroalkyl group having 1 to 6 carbon atoms.

$L_1$ in the formula (10a) is more preferably a perfluoroalkylene group having 1 to 6 carbon atoms or a perfluoroarylene group having 6 to 12 ring carbon atoms, further preferably a perfluoroalkylene group having 1 to 6 carbon atoms.

In other words, the compound M1 is also preferably a compound represented by a formula (12a) below.

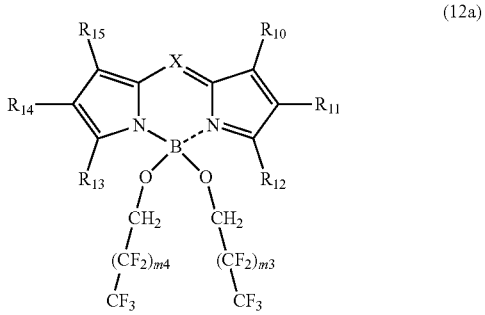

(12a)

In the formula (12a): X represents the same as X in the formula (10); Y bonded with a carbon atom as X represents the same as Y in the formula (10); $R_{10}$ to $R_{15}$ each independently represent the same as $R_{10}$ to $R_{15}$ in the formula (10); m3 is 0, 1, 2, 3 or 4; m4 is 0, 1, 2, 3 or 4; and m3 and m4 are mutually the same or different.

In the formulae (10), (11), (12) and (12a), X is a carbon atom bonded to Y; Y is a hydrogen atom or a substituent; Y serving as a substituent is preferably a substituent selected from the group consisting of a substituted or unsubstituted alkyl group having 1 to 30 carbon atoms, a substituted or unsubstituted alkyl halide group having 1 to 30 carbon atoms and a substituted or unsubstituted aryl group having 6 to 30 ring carbon atoms, more preferably a substituted or unsubstituted aryl group having 6 to 30 ring carbon atoms.

In the formulae (10), (11), (12) and (12a), it is more preferable that: X is a carbon atom bonded to Y; Y is a hydrogen atom or a substituent; Y serving as a substituent is a substituted or unsubstituted aryl group having 6 to 30 ring carbon atoms; and when Y serving as a substituent is an aryl group having 6 to 30 ring carbon atoms having a substituent, the substituent is a substituted or unsubstituted alkyl group having 1 to 30 carbon atoms, a substituted or unsubstituted alkyl halide group having 1 to 30 carbon atoms, a substituted or unsubstituted alkoxy group having 1 to 30 carbon atoms, a substituted or unsubstituted alkoxy halide group having 1 to 30 carbon atoms, or an aryl group having 6 to 30 ring carbon atoms and substituted by an alkyl group having 1 to 30 carbon atoms.

In the compound M1, $Z_{11}$ and $Z_{12}$ may be mutually bonded to form a ring. However, it is preferable that $Z_{11}$ and $Z_{12}$ are not mutually bonded to form no ring.

In the formulae (10), (12) and (12a), at least one of $R_{10}$, $R_{12}$, $R_{13}$ or $R_{15}$ is preferably a substituted or unsubstituted alkyl group having 1 to 30 carbon atoms or a substituted or unsubstituted alkyl halide group having 1 to 30 carbon atoms.

In the formulae (10), (12) and (12a), $R_{10}$, $R_{12}$, $R_{13}$ and $R_{15}$ are more preferably a substituted or unsubstituted alkyl group having 1 to 30 carbon atoms or a substituted or unsubstituted alkyl halide group having 1 to 30 carbon atoms. In this case, $R_{11}$ and $R_{14}$ are preferably hydrogen atoms.

In the formulae (10), (12) and (12a), at least one of $R_{10}$, $R_{12}$, $R_{13}$ or $R_{15}$ is preferably a substituted or unsubstituted aryl group having 6 to 30 ring carbon atoms.

In the formulae (10), (12) and (12a), $R_{10}$, $R_{12}$, $R_{13}$ and $R_{15}$ are more preferably a substituted or unsubstituted aryl group having 6 to 30 ring carbon atoms. In this case, $R_{11}$ and $R_{14}$ are preferably hydrogen atoms.

In the formulae (10), (12) and (12a), it is more preferable that: $R_{10}$, $R_{12}$, $R_{13}$ and $R_{15}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{11}$ and $R_{14}$ are hydrogen atoms.

In the formula (11), at least one of $R_{10}$, $R_{12}$ or $R_{13}$ is preferably a substituted or unsubstituted alkyl group having 1 to 30 carbon atoms or a substituted or unsubstituted alkyl halide group having 1 to 30 carbon atoms.

In the formula (11), $R_{10}$, $R_{12}$ and $R_{13}$ are more preferably a substituted or unsubstituted alkyl group having 1 to 30 carbon atoms or a substituted or unsubstituted alkyl halide group having 1 to 30 carbon atoms. In this case, $R_{11}$ is preferably a hydrogen atom.

In the formula (11), at least one of $R_{10}$, $R_{12}$ or $R_{13}$ is preferably a substituted or unsubstituted aryl group having 6 to 30 ring carbon atoms.

In the formula (11), $R_{10}$, $R_{12}$ and $R_{13}$ are more preferably a substituted or unsubstituted aryl group having 6 to 30 ring carbon atoms. In this case, $R_{11}$ is preferably a hydrogen atom.

In the formula (11), it is more preferable that: $R_{10}$, $R_{12}$ and $R_{13}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{11}$ is a hydrogen atom.

In the compound M1, examples of the fluorine-substituted alkoxy group include 2,2,2-trifluoroethoxy group, 2,2-difluoroethoxy group, 2,2,3,3,3-pentafluoro-1-propoxy group, 2,2,3,3,3-tetrafluoro-1-propoxy group, 1,1,1,3,3,3-hexafluoro-2-propoxy group, 2,2,3,3,4,4,4-heptafluoro-1-butyloxy group, 2,2,3,3,4,4-hexafluoro-1-butyloxy group, nonafluoro-tertiary-butyloxy group, 2,2,3,3,4,4,5,5,5-nonafluoropentanoxy group, 2,2,3,3,4,4,5,5,6,6,6-undecafluorohexanoxy group, 2,3-bis(trifluoromethyl)-2,3-butanedioxy group, 1, 1,2,2-tetra(trifluoromethyl)ethylene glycoxy group, 4,4,5,5,6,6,6-heptafluorohexane-1,2-dioxy group, and 4,4,5,5,6,6,7,7,8,8,9,9,9-tridecafluorononane-1,2-dioxy group.

In the compound M1, examples of the fluorine-substituted aryloxy group or the aryloxy group substituted with a fluoroalkyl group include a pentafluorophenoxy group, 3,4,5-trifluorophenoxy group, 4-trifluoromethylphenoxy group, 3,5-bistrifluoromethylphenoxy group, 3-fluoro-4-trifluoromethylphenoxy group, 2,3,5,6-tetrafluoro-4-trifluoromethylphenoxy group, 4-fluorocatecholato group, 4-trifluoromethylcatecholato group, and 3,5-bistrifluoromethylcatecholato group.

When the compound M1 is a fluorescent compound, the compound M1 preferably emits light having a main peak wavelength in a range from 400 nm to 700 nm.

Herein, the main peak wavelength means a peak wavelength of an emission spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The compound M1 preferably exhibits red or green light emission.

Herein, the red light emission refers to a light emission in which a main peak wavelength of fluorescence spectrum is in a range from 600 nm to 660 nm.

When the compound M1 is a red fluorescent compound, the main peak wavelength of the compound M1 is preferably in a range from 600 nm to 660 nm, more preferably in a range from 600 nm to 640 nm, further preferably in a range from 610 nm to 630 nm.

Herein, the green light emission refers to a light emission in which a main peak wavelength of fluorescence spectrum is in a range from 500 nm to 560 nm.

When the compound M1 is a green fluorescent compound, the main peak wavelength of the compound M1 is preferably in a range from 500 nm to 560 nm, more preferably in a range from 500 nm to 540 nm, further preferably in a range from 510 nm to 540 nm.

Herein, the blue light emission refers to a light emission in which a main peak wavelength of fluorescence spectrum is in a range from 430 nm to 480 nm.

When the compound M1 is a blue fluorescent compound, the main peak wavelength of the compound M1 is preferably in a range from 430 nm to 480 nm, more preferably in a range from 440 nm to 480 nm.

A main peak wavelength of light from an organic EL device is measured as follows.

Voltage is applied on the organic EL devices such that a current density becomes 10 mA/cm², where spectral radiance spectrum is measured by a spectroradiometer CS-2000 (manufactured by Konica Minolta, Inc.).

A peak wavelength of an emission spectrum, at which the luminous intensity of the resultant spectral radiance spectrum is at the maximum, is measured and defined as the main peak wavelength (unit: nm).

Manufacturing Method of Compound M1 According to Exemplary Embodiment The compound M1 can be manufactured by a known method.

Specific examples of the compound M1 according to the exemplary embodiment are shown below. It should however be noted that the invention is not limited to the specific examples of the compound.

A coordinate bond between a boron atom and a nitrogen atom in a pyrromethene skeleton is shown by various means such as a solid line, a broken line, an arrow, and omission. Herein, the coordinate bond is shown by a solid line or a broken line, or the description of the coordinate bond is omitted.

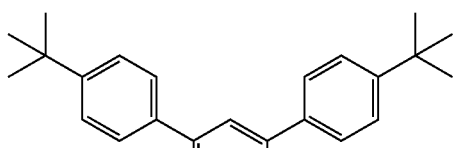

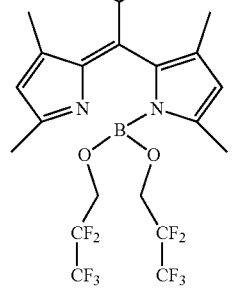

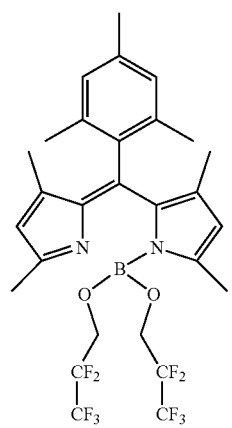

-continued

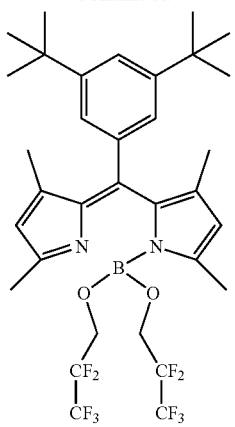

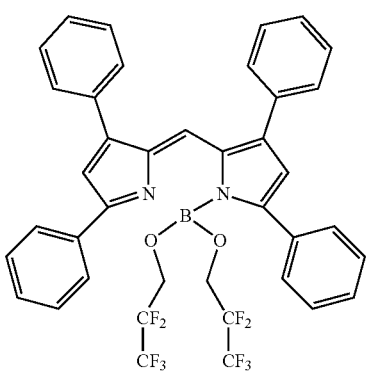

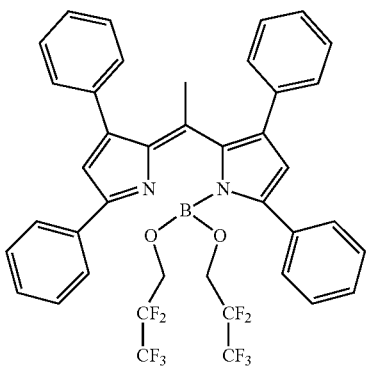

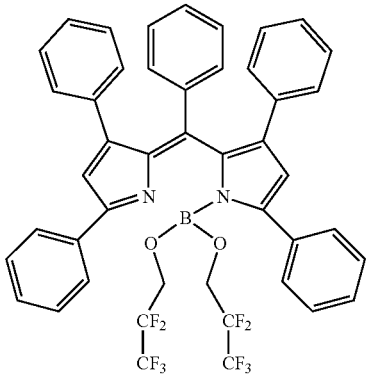

345
-continued
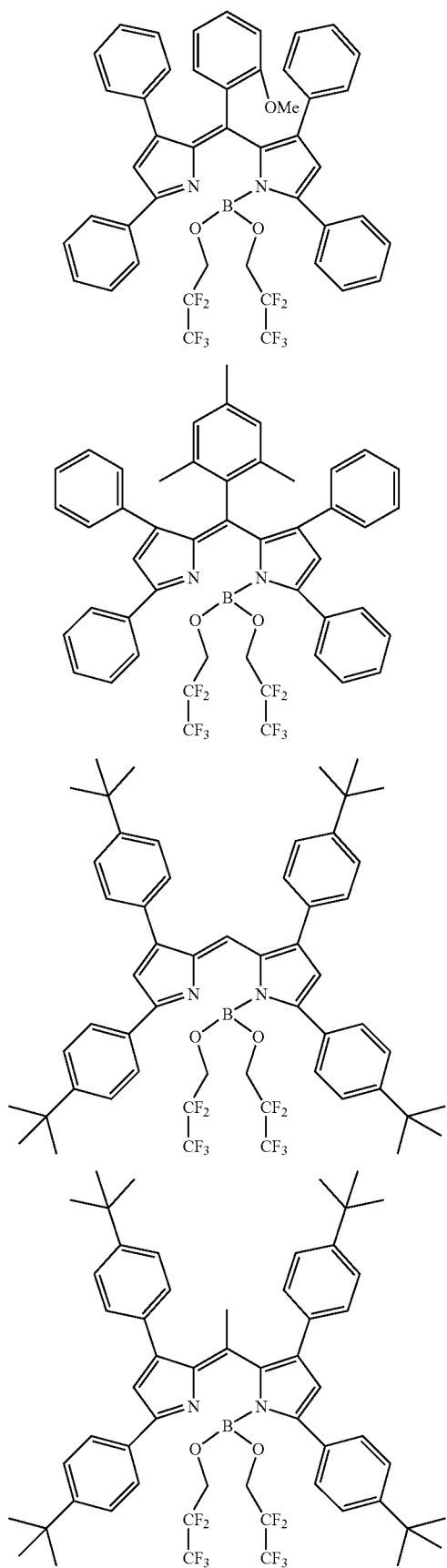
346
-continued
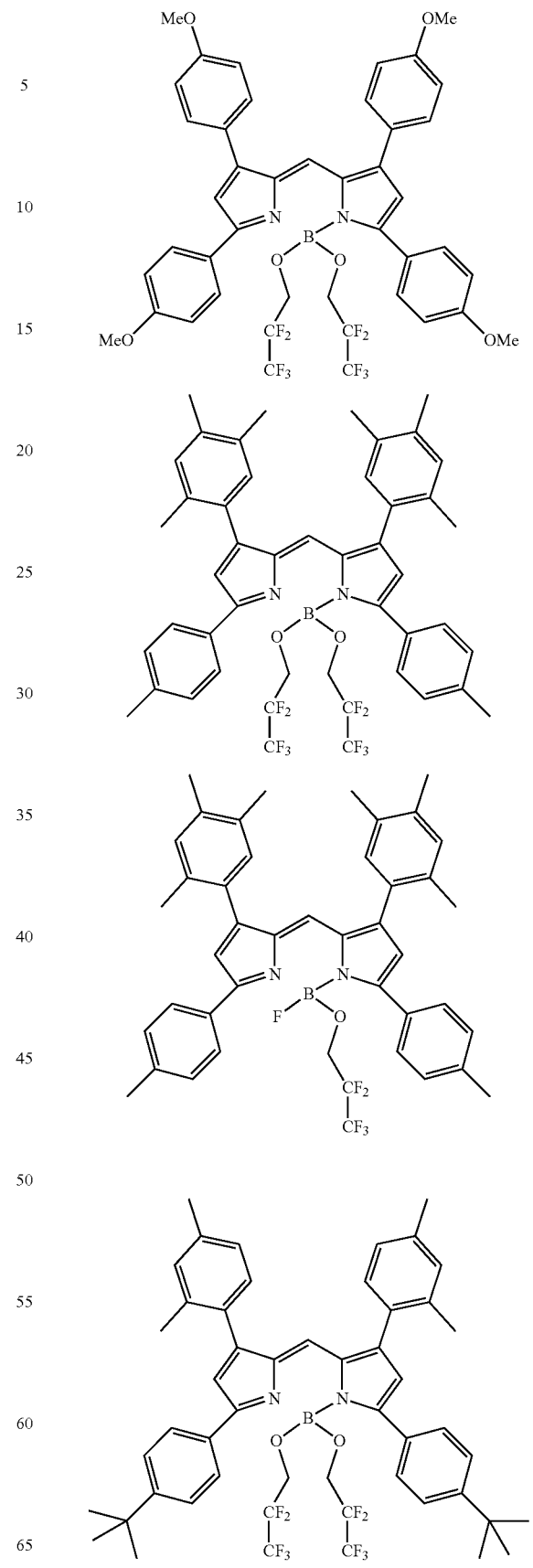

347
-continued
348
-continued
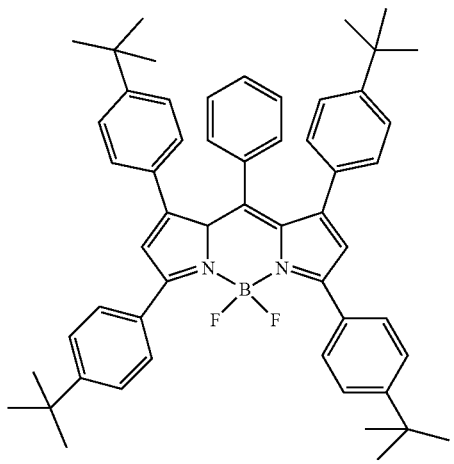
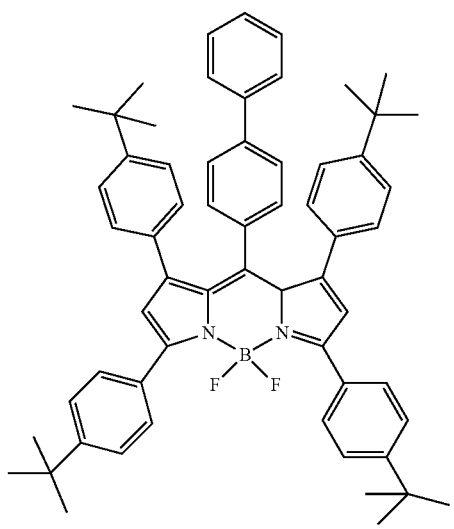
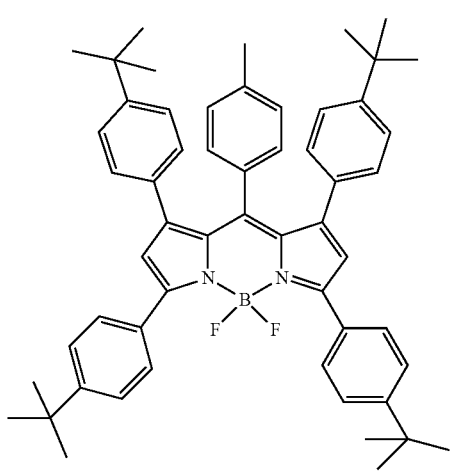
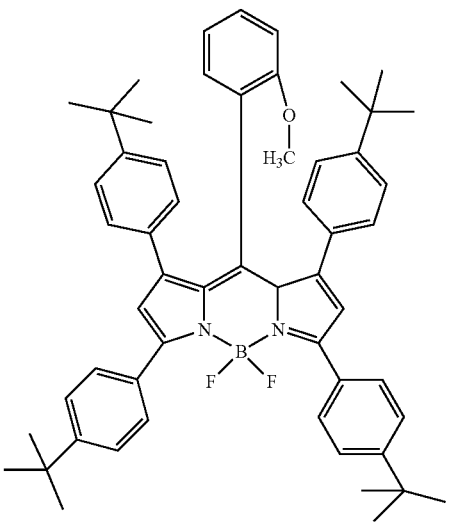
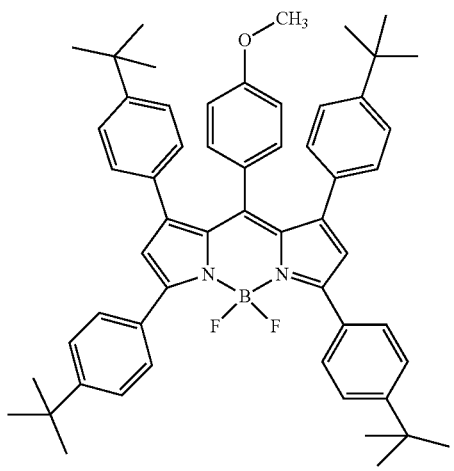
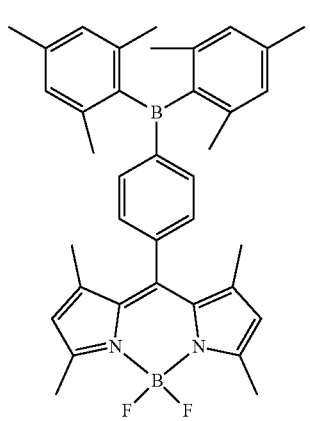

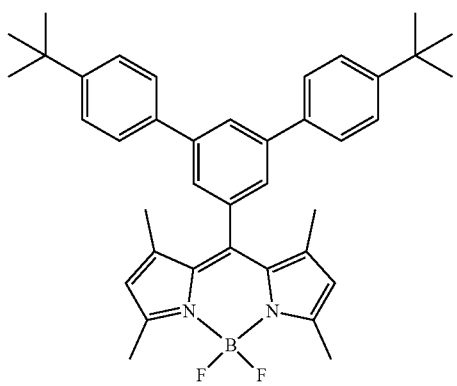
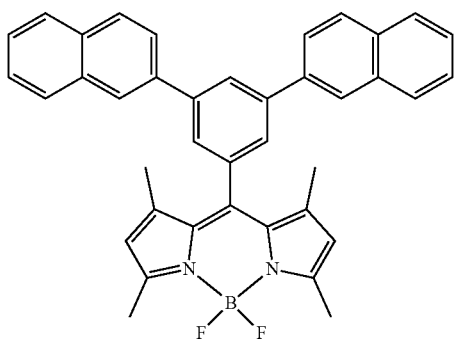
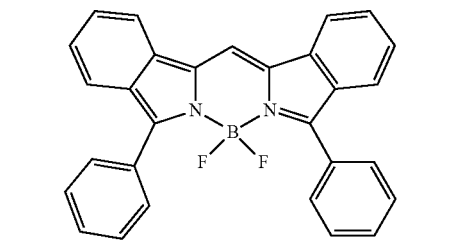
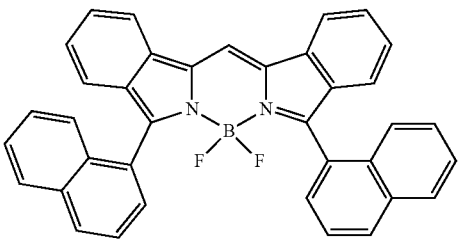
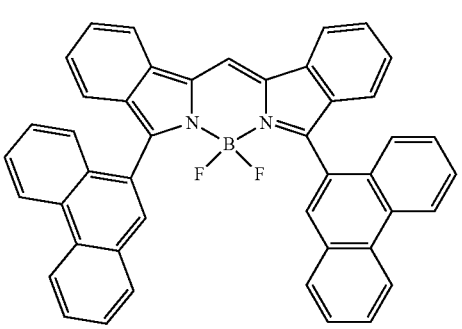
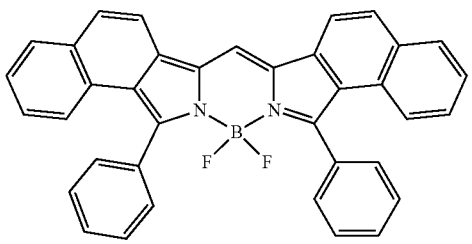
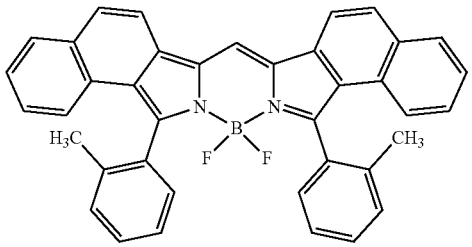
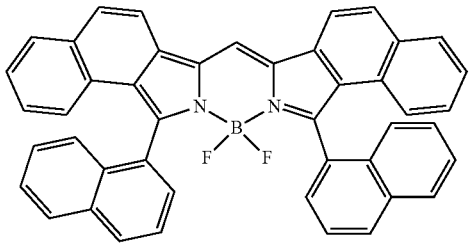
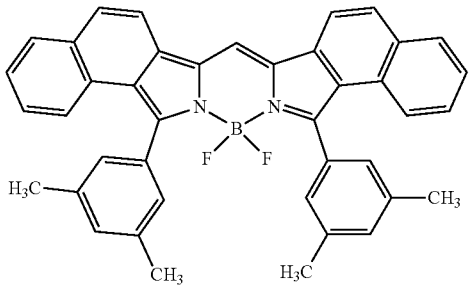
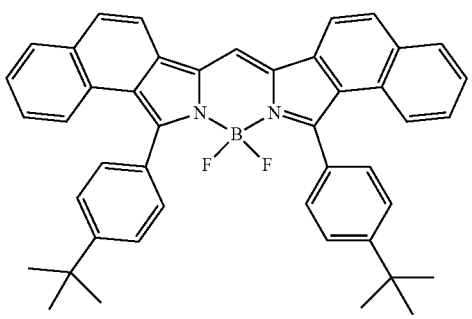
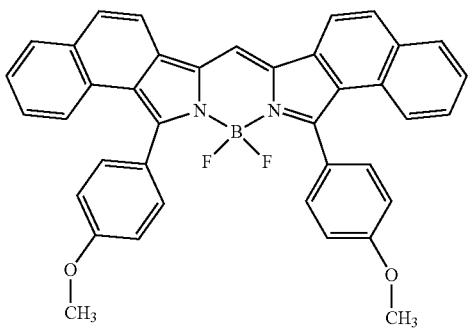

351
-continued
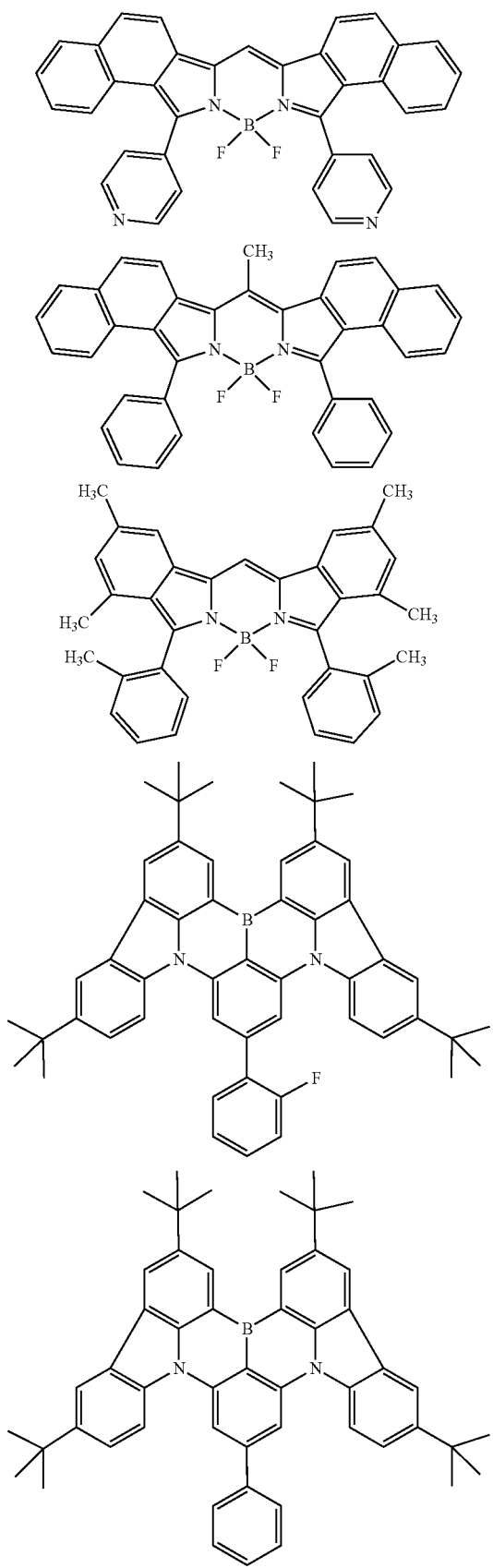
352
-continued
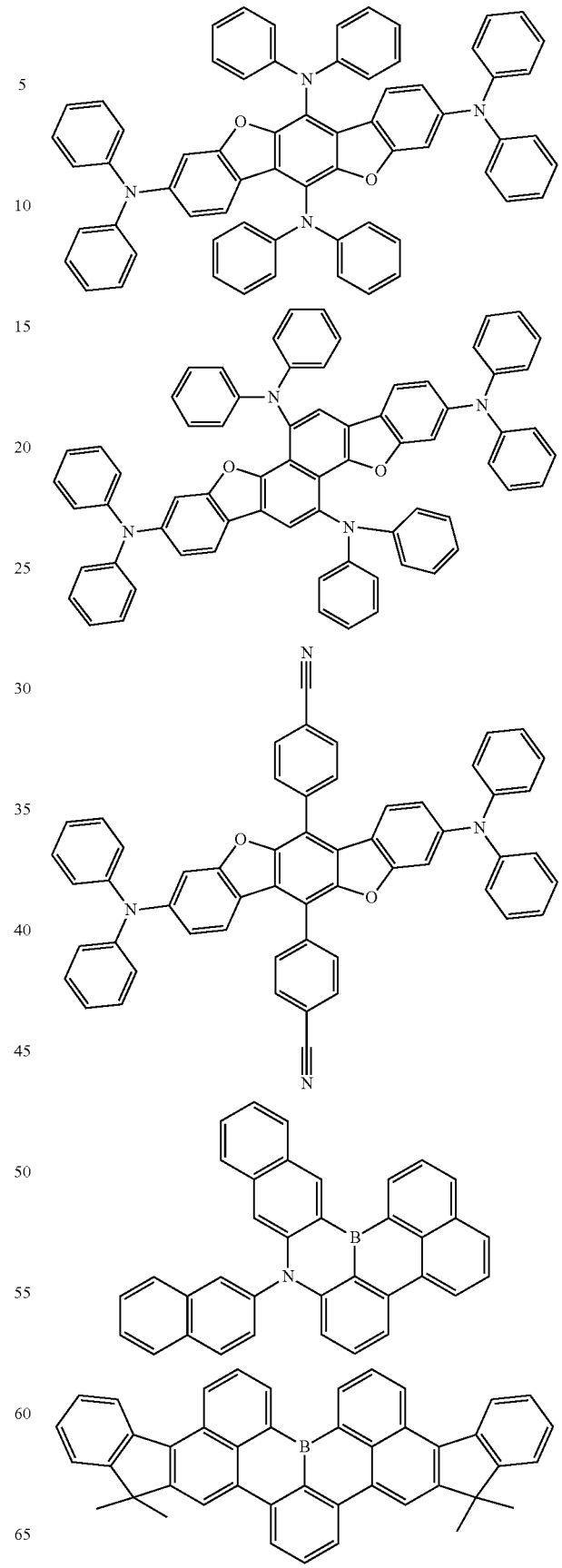

353
-continued
354
-continued
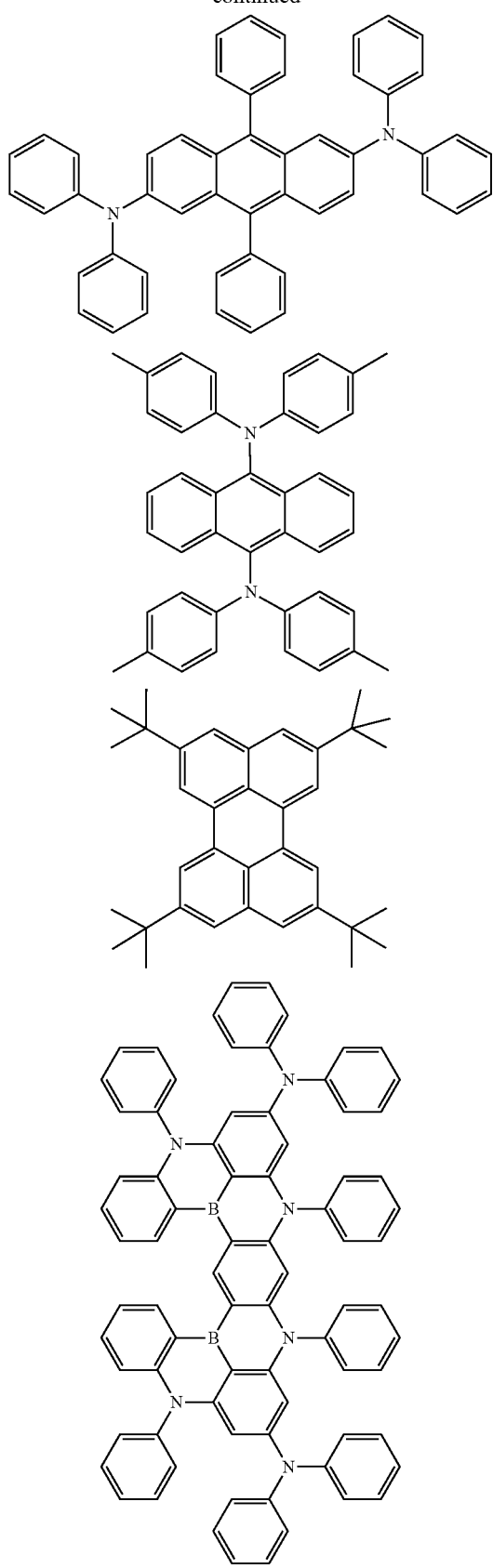
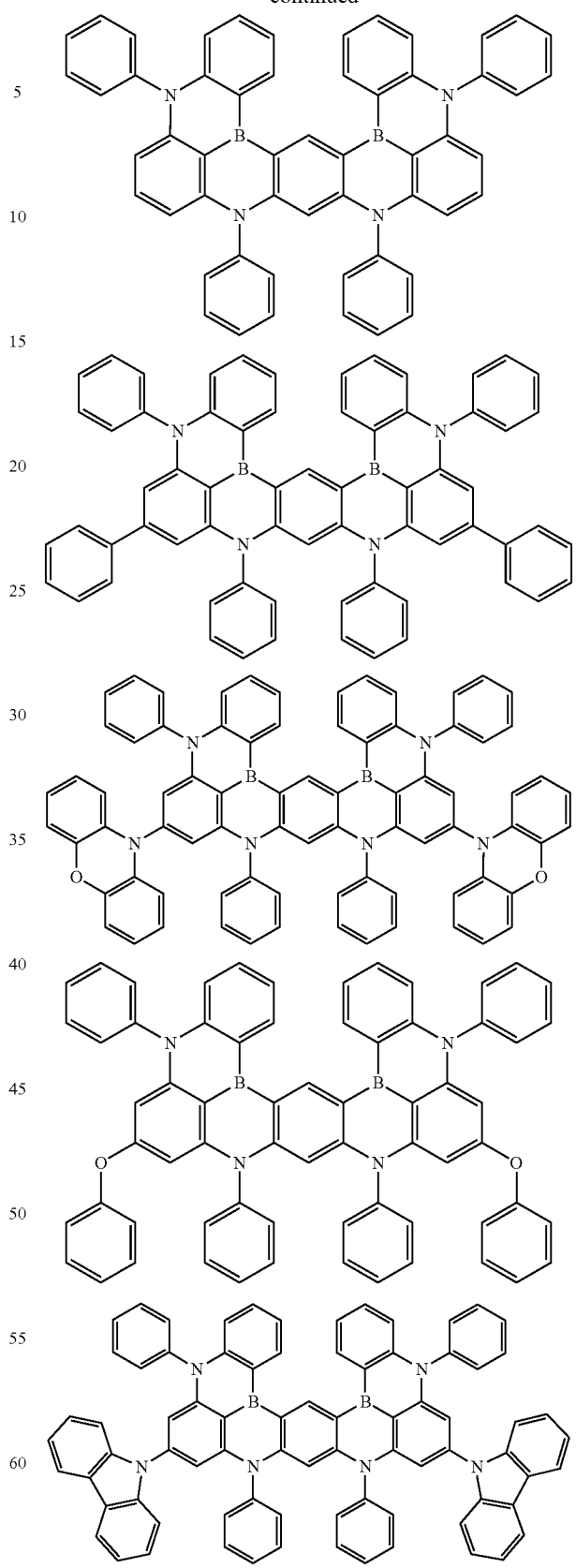

-continued

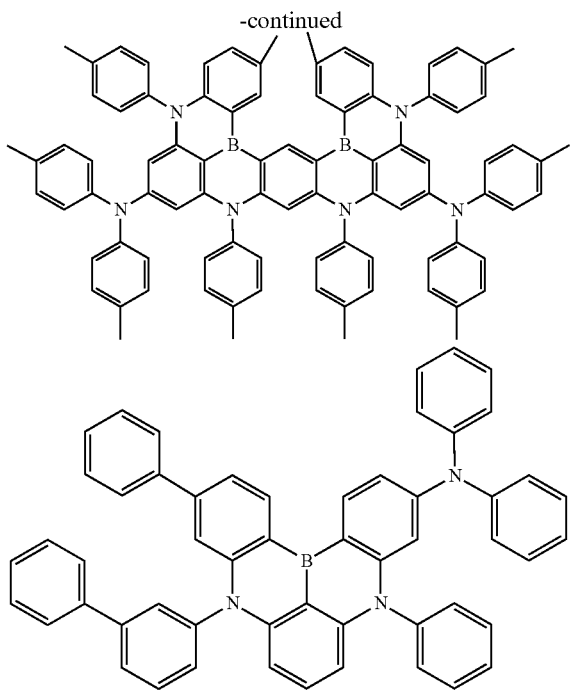

Relationship between Compound M3, Compound M2 and Compound M1 in Emitting Layer

In the organic EL device according to the exemplary embodiment, the singlet energy $S_1(M2)$ of the compound M2 and a singlet energy $S_1(M1)$ of the compound M1 preferably satisfy a relationship of a numerical formula (Numerical Formula 2) below.

$$S_1(M2) > S_1(M1) \quad \text{(Numerical Formula 2)}$$

The singlet energy $S_1(M3)$ of the compound M3 is preferably larger than the singlet energy $S_1(M1)$ of the compound M1.

$$S_1(M3) > S_1(M1) \quad \text{(Numerical Formula 2A)}$$

The singlet energy $S_1(M3)$ of the compound M3, the singlet energy $S_1(M2)$ of the compound M2, and the singlet energy $S_1(M1)$ of the compound M1 preferably satisfy a relationship of a numerical formula (Numerical Formula 2B) below.

$$S_1(M3) > S_1(M2) > S_1(M1) \quad \text{(Numerical Formula 2B)}$$

When the organic EL device according to the exemplary embodiment emits light, it is preferable that the fluorescent compound M1 in the emitting layer mainly emits light.

The organic EL device according to the exemplary embodiment preferably emits red light or green light.

Content Ratios of Compounds in Emitting Layer

Content ratios of the compounds M3, M2 and M1 in the emitting layer are preferably fall within, for instance, the following range.

The content ratio of the compound M3 is preferably in a range from 10 mass % to 80 mass %.

The content ratio of the compound M2 is preferably in a range from 10 mass % to 80 mass %, more preferably in a range from 10 mass % to 60 mass %, further preferably in a range from 20 mass % to 60 mass %.

The content ratio of the compound M1 is preferably in a range from 0.01 mass % to 10 mass %, more preferably in a range from 0.01 mass % to 5 mass %, further preferably in a range from 0.01 mass % to 1 mass %. An upper limit of the total of the respective content ratios of the compounds M3, M2 and M1 in the emitting layer is 100 mass %. It should be noted that the emitting layer of the exemplary embodiment may further contain material(s) other than the compounds M3, M2 and M1.

The emitting layer may include a single type of the compound M3 or may include two or more types of the compound M3. The emitting layer may include a single type of the compound M2 or may include two or more types of the compound M2. The emitting layer may include a single type of the compound M1 or may include two or more types of the compound M1.

FIG. 5 shows an example of a relationship between energy levels of the compounds M3, M2 and M1 in the emitting layer. In FIG. 5, S0 represents a ground state. S1(M1) represents the lowest singlet state of the compound M1. T1(M1) represents the lowest triplet state of the compound M1. S1(M2) represents the lowest singlet state of the compound M2. T1(M2) represents the lowest triplet state of the compound M1. S1(M3) represents the lowest singlet state of the compound M3. T1(M3) represents the lowest triplet state of the compound M3. A dashed arrow directed from S1(M2) to S1(M1) in FIG. 5 represents Förster energy transfer from the lowest singlet state of the compound M2 to the lowest singlet state of the compound M1.

As shown in FIG. 5, when a compound having a small ΔST(M2) is used as the compound M2, inverse intersystem crossing from the lowest triplet state T1(M2) to the lowest singlet state S1(M2) can be caused by a heat energy. Subsequently, Förster energy transfer from the lowest singlet state S1(M2) of the compound M2 to the compound M1 occurs to generate the lowest singlet state S1(M1). Consequently, fluorescence from the lowest singlet state S1(M1) of the compound M1 can be observed. It is inferred that the internal quantum efficiency can be theoretically raised up to 100% also by using delayed fluorescence by the TADF mechanism.

The organic EL device according to the second exemplary embodiment contains the delayed fluorescent compound M2, the compound M3 having the singlet energy larger than that of the compound M2, and the compound M1 having the singlet energy smaller than that of the delayed fluorescent compound M2 in the emitting layer.

According to the second exemplary embodiment, an organic EL device that emits light with a long lifetime can be achieved.

The organic EL device according to the second exemplary embodiment is applicable to an electronic device such as a display device and a light-emitting device.

Third Exemplary Embodiment

Electronic Device

An electronic device according to a third exemplary embodiment is installed with one of the organic EL devices according to the above exemplary embodiments. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Fourth Exemplary Embodiment

Organic-EL-Device Material

An organic-EL-device material according to a fourth exemplary embodiment contains a delayed fluorescent compound M2 and a compound M3 having at least one deuterium atom, in which a singlet energy $S_1(M2)$ of the compound M2 and a singlet energy $S_1(M3)$ of the compound M3 satisfy the relationship of the numerical formula (Numerical Formula 1).

However, the organic-EL-device material according to the fourth exemplary embodiment does not contain a compound having a partial structure represented by the formula (1C) or (2C).

The delayed fluorescent compound M2 contained in the organic-EL-device material according to the fourth exemplary embodiment preferably has at least one deuterium atom.

According to the organic-EL-device material according to the fourth exemplary embodiment, the lifetime of an organic EL device can be extended.

The organic-EL-device material according to the fourth exemplary embodiment may further contain an additional compound. When the organic-EL-device material according to the fourth exemplary embodiment further contains an additional compound, the additional compound may be solid or liquid.

Modification of Exemplary Embodiment(s)

The scope of the invention is not limited to the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiments. For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, excitons or combinations thereof.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

Other Explanations

Herein, numerical ranges represented by "x to y" represents a range whose lower limit is the value (x) recited before "to" and whose upper limit is the value (y) recited after "to."

Rx and Ry are mutually bonded to form a ring, which means herein, for instance, that Rx and Ry contain a carbon atom, a nitrogen atom, an oxygen atom, a sulfur atom or a silicon atom, the atom (a carbon atom, a nitrogen atom, an oxygen atom, a sulfur atom or a silicon atom) contained in Rx and the atom (a carbon atom, a nitrogen atom, an oxygen atom, a sulfur atom or a silicon atom) contained in Ry are mutually bonded via a single bond, a double bond, a triple bond or a divalent linking group to form a ring having 5 or more ring atoms (specifically, a heterocyclic ring or an aromatic hydrocarbon ring). x represents a number, a character or a combination of a number and a character. y represents a number, a character or a combination of a number and a character.

The divalent linking group is not particularly limited and is exemplified by —O—, —CO—, —CO$_2$—, —S—, —SO—, —SO$_2$—, —NH—, —NRa—, and a group obtained by combining two or more linking groups of these linking group.

Specific examples of the heterocyclic ring include a cyclic structure (heterocyclic ring) obtained by removing a bond from a "heteroaryl group Sub$_2$" exemplarily shown in the later-described "Description of Each Substituent in Formula." The heterocyclic ring may have a substituent.

Specific examples of the aromatic hydrocarbon ring include cyclic structures (aromatic hydrocarbon rings) obtained by removing a bond from an "aryl group Sub$_1$" exemplarily shown in the later-described "Description of Each Substituent in Formula." The aromatic hydrocarbon ring may have a substituent.

Examples of Ra include a substituted or unsubstituted alkyl group Sub$_8$ having 1 to 30 carbon atoms, a substituted or unsubstituted aryl group Sub$_1$ having 6 to 40 ring carbon atoms, and a substituted or unsubstituted heteroaryl group Sub$_2$ having 5 to 30 ring atoms, which are exemplarily shown in the later-described "Description of Each Substituent in Formula."

Rx and Ry are mutually bonded to form a ring, which means, for instance, that: an atom contained in Rx$_1$ and an atom contained in Ry$_1$ in a molecular structure represented by a formula (E1) below form a ring (cyclic structure) E represented by a formula (E2); an atom contained in Rx$_1$ and an atom contained in Ry$_1$ in a molecular structure represented by a formula (F1) below form a ring (cyclic structure) F represented by a formula (F2); an atom contained in Rx$_1$ and an atom contained in Ry$_1$ in a molecular structure represented by a formula (G1) below form a ring (cyclic structure) G represented by a formula (G2); an atom contained in $Rx_1$ and an atom contained in $Ry_1$ in a molecular structure represented by a formula (H1) below form a ring (cyclic structure) H represented by a formula (H2); and an atom contained in $Rx_1$ and an atom contained in $Ry_1$ in a molecular structure represented by a formula (I1) below form a ring (cyclic structure) I represented by a formula (I2).

In the formulae (E1) to (I1), * each independently represents a bonding position to another atom in a molecule. Two * in the formula (E1) correspond one-to-one to two * in the formula (E2). Two * in the formula (F1) correspond one-to-one to two * in the formula (F2). Two * in the formula (G1) correspond one-to-one to two * in the formula (G2). Two * in the formula (H1) correspond one-to-one to two * in the formula (H2). Two * in the formula (I1) correspond one-to-one to two * in the formula (I2).

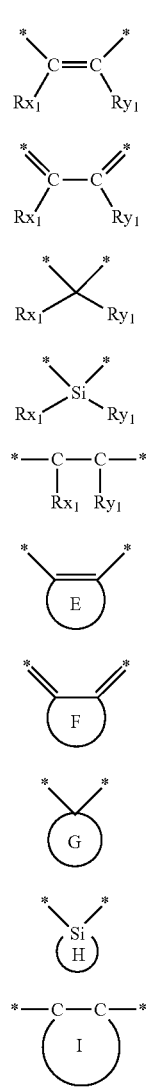

In the molecular structures represented by the respective formulae (E2) to (I2), E to I each represent a cyclic structure (the ring having 5 or more ring atoms). In the formulae (E2) to (I2), * each independently represents a bonding position to another atom in a molecule. Two * in the formula (E2) correspond one-to-one to two * in the formula (E1). Similarly, two * in each of the formulae (F2) to (I2) correspond one-to-one to two * in in each of the formulae (F1) to (I1).

For instance, in the formula (E1), when $Rx_1$ and $Ry_1$ are mutually bonded to form the ring E in the formula (E2) and the ring E is an unsubstituted benzene ring, the molecular structure represented by the formula (E1) is a molecular structure represented by a formula (E3) below. Herein, two * in the formula (E3) correspond one-to-one to two * in each of the formulae (E2) and (E1).

For instance, in the formula (E1), when $Rx_1$ and $Ry_1$ are mutually bonded to form the ring E in the formula (E2) and the ring E is an unsubstituted pyrrole ring, the molecular structure represented by the formula (E1) is a molecular structure represented by a formula (E4) below. Herein, two * in the formula (E4) correspond one-to-one to two * in each of the formulae (E2) and (E1). In the formulae (E3) and (E4), * each independently represents a bonding position to another atom in a molecule.

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the "ring atoms" described later. For instance, a pyridine ring has six ring atoms, a quinazoline ring has ten ring atoms, and a furan ring has five ring atoms.

A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formulae Herein

The aryl group (occasionally referred to as an aromatic hydrocarbon group) herein is exemplified by an aryl group $Sub_1$. Herein, the aryl group $Sub_1$ preferably has 6 to 30 ring carbon atoms, more preferably 6 to 20 ring carbon atoms, further preferably 6 to 14 ring carbon atoms, still further preferably 6 to 12 ring carbon atoms.

The aryl group $Sub_1$ herein is at least one group selected from the group consisting of a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Among the aryl group $Sub_1$, a phenyl group, biphenyl group, naphthyl group, phenanthryl group, terphenyl group and fluorenyl group are preferable.

A carbon atom in a position 9 of each of 1-fluorenyl group, 2-fluorenyl group, 3-fluorenyl group and 4-fluorenyl group is preferably substituted by a substituted or unsubstituted alkyl group Subs or a substituted or unsubstituted aryl group $Sub_1$ described later herein.

The heteroaryl group (occasionally referred to as a heterocyclic group, heteroaromatic ring group or aromatic heterocyclic group) herein is exemplified by a heterocyclic group $Sub_2$. The heterocyclic group $Sub_2$ is a group containing, as a hetero atom(s), at least one atom selected from the group consisting of nitrogen, sulfur, oxygen, silicon, selenium atom and germanium atom. The heterocyclic group $Sub_2$ preferably contains, as a hetero atom(s), at least one atom selected from the group consisting of nitrogen, sulfur and oxygen. The heterocyclic group $Sub_2$ preferably has 5 to 30 ring atoms, more preferably 5 to 20 ring atoms, further preferably 5 to 14 ring atoms.

The heterocyclic group $Sub_2$ herein are, for instance, at least one group selected from the group consisting of a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Among the above heterocyclic group $Sub_2$, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further more preferable. A nitrogen atom in position 9 of 1-carbazolyl group, 2-carbazolyl group, 3-carbazolyl group and 4-carbazolyl group is preferably substituted by the substituted or unsubstituted aryl group $Sub_1$ or the substituted or unsubstituted heterocyclic group $Sub_2$ described herein.

Herein, the heterocyclic group $Sub_2$ may be a group derived from any one of partial structures represented by formulae (XY-1) to (XY-18) below.

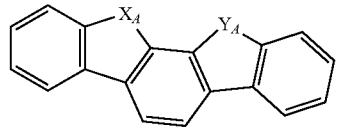

(XY-1)

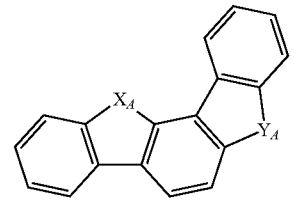

(XY-2)

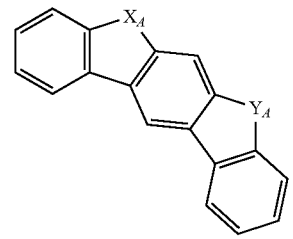

(XY-3)

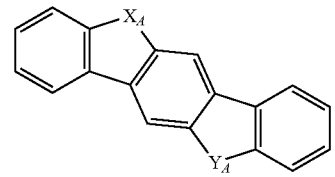

(XY-4)

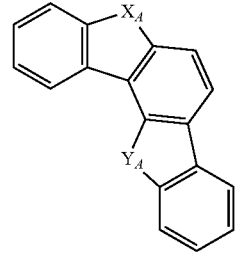

(XY-5)

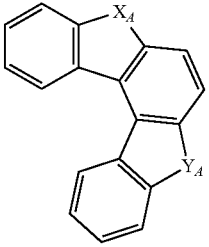

(XY-6)

(XY-7) 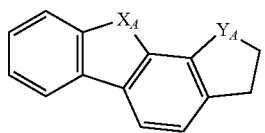

(XY-8) 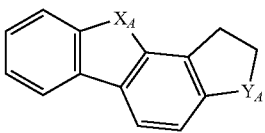

(XY-9) 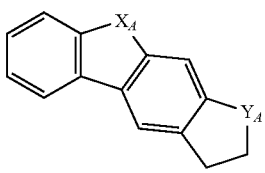

(XY-10) 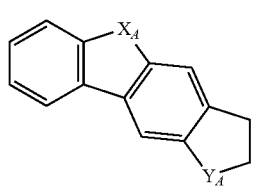

(XY-11) 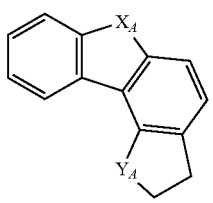

(XY-12) 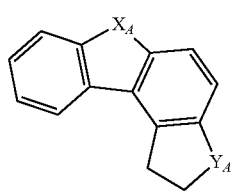

(XY-13) 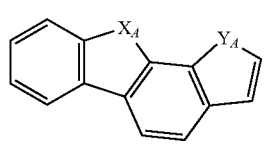

(XY-14) 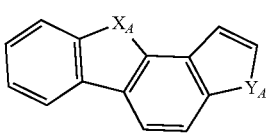

(XY-15) 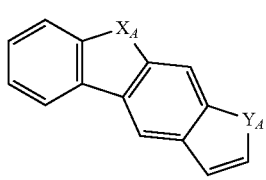

(XY-16) 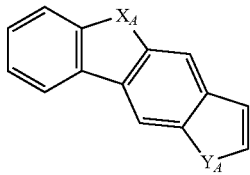

(XY-17) 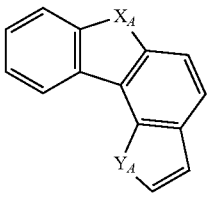

(XY-18) 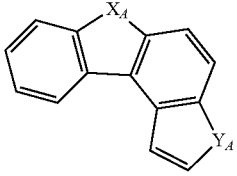

In the formulae (XY-1) to (XY-18), $X_A$ and YA each independently represent a hetero atom, and preferably represent an oxygen atom, sulfur atom, selenium atom, silicon atom or germanium atom. Each of the partial structures represented by the respective formulae (XY-1) to (XY-18) has a bond at any position to provide a heterocyclic group. The heterocyclic group may be substituted.

Herein, the heterocyclic group $Sub_2$ may be a group represented by one of formulae (XY-19) to (XY-22) below. Moreover, the position of the bond may be changed as needed (XY-19) 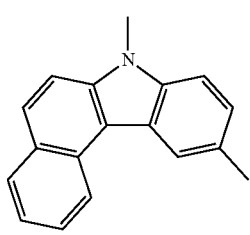

(XY-20) 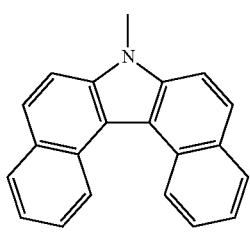

(XY-21) 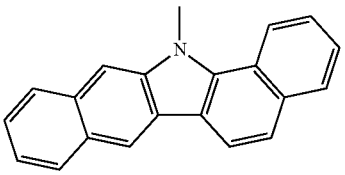

-continued

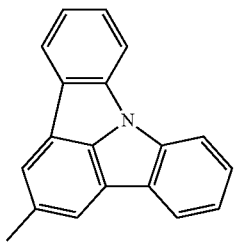

(XY-22)

The alkyl group herein may be any one of a linear alkyl group, branched alkyl group and cyclic alkyl group.

The alkyl group herein is exemplified by an alkyl group $Sub_3$.

The linear alkyl group herein is exemplified by a linear alkyl group $Sub_{31}$.

The branched alkyl group herein is exemplified by a branched alkyl group $Sub_{32}$.

The cyclic alkyl group herein is exemplified by a cyclic alkyl group $Sub_{33}$ (also referred to as a cycloalkyl group $Sub_{33}$).

For instance, the alkyl group Subs is at least one group selected from the group consisting of the linear alkyl group $Sub_{31}$, branched alkyl group $Sub_{32}$, and cyclic alkyl group $Sub_{33}$.

Herein, the linear alkyl group $Sub_{31}$ or branched alkyl group $Sub_{32}$ preferably has 1 to 30 carbon atoms, more preferably 1 to 20 carbon atoms, further preferably 1 to 10 carbon atoms, further more preferably 1 to 6 carbon atoms.

The cycloalkyl group $Sub_{33}$ preferably has 3 to 30 ring carbon atoms, more preferably 3 to 20 ring carbon atoms, further preferably 3 to 10 ring carbon atoms, still further preferably 5 to 8 ring carbon atoms.

The linear alkyl group $Sub_{31}$ or branched alkyl group $Sub_{32}$ is exemplified by at least one group selected from the group consisting of a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear alkyl group $Sub_{31}$ or branched alkyl group $Sub_{32}$ is further more preferably a methyl group, ethyl group, propyl group, isopropyl group, n-butyl group, s-butyl group, isobutyl group, t-butyl group, n-pentyl group, n-hexyl group, amyl group, isoamyl group and neopentyl group.

The cycloalkyl group $Sub_{33}$ herein is exemplified by at least one group selected from the group consisting of a cyclopropyl group, cyclobutyl group, cyclopentyl group, cyclohexyl group, 4-metylcyclohexyl group, adamantyl group and norbornyl group. Among the cycloalkyl group $Sub_{33}$, a cyclopentyl group and a cyclohexyl group are still further preferable.

Herein, an alkyl halide group is exemplified by an alkyl halide group $Sub_4$. The alkyl halide group $Sub_4$ is provided by substituting the alkyl group $Sub_3$ with at least one halogen atom, preferably at least one fluorine atom.

Herein, the alkyl halide group $Sub_4$ is exemplified by at least one group selected from the group consisting of a fluoromethyl group, difluoromethyl group, trifluoromethyl group, fluoroethyl group, trifluoromethylmethyl group, trifluoroethyl group, and pentafluoroethyl group.

Herein, a substituted silyl group is exemplified by a substituted silyl group $Sub_5$. The substituted silyl group Subs is exemplified by at least one group selected from the group consisting of an alkylsilyl group $Sub_{51}$ and an arylsilyl group $Sub_{52}$.

Herein, the alkylsilyl group $Sub_{51}$ is exemplified by a trialkylsilyl group $Sub_{511}$ having the above-described alkyl group $Sub_3$.

The trialkylsilyl group $Sub_{511}$ is exemplified by at least one group selected from the group consisting of a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups Subs in the trialkylsilyl group $Sub_{511}$ may be mutually the same or different.

Herein, the arylsilyl group $Sub_{52}$ is exemplified by at least one group selected from the group consisting of a dialkylarylsilyl group $Sub_{521}$, alkyldiarylsilyl group $Sub_{522}$ and triarylsilyl group $Sub_{523}$.

The dialkylarylsilyl group $Sub_{521}$ is exemplified by a dialkylarylsilyl group including two alkyl groups Subs and one aryl group $Sub_1$. The dialkylarylsilyl group $Sub_{521}$ preferably has 8 to 30 carbon atoms.

The alkyldiarylsilyl group $Sub_{522}$ is exemplified by an alkyldiarylsilyl group including one alkyl group Subs and two aryl groups $Sub_1$. The alkyldiarylsilyl group $Sub_{522}$ preferably has 13 to 30 carbon atoms.

The triarylsilyl group $Sub_{523}$ is exemplified by a triarylsilyl group including three aryl groups $Sub_1$. The triarylsilyl group $Sub_{523}$ preferably has 18 to 30 carbon atoms.

Herein, a substituted or unsubstituted alkyl sulfonyl group is exemplified by an alkyl sulfonyl group $Sub_6$. The alkyl sulfonyl group Subs is represented by $—SO_2Rw$. $R_w$ in $—SO_2R_w$ represents a substituted or unsubstituted alkyl group Subs described above.

Herein, an aralkyl group (occasionally referred to as an arylalkyl group) is exemplified by an aralkyl group $Sub_7$. An aryl group in the aralkyl group $Sub_7$ includes, for instance, at least one of the above-described aryl group $Sub_1$ or the above-described heteroaryl group $Sub_2$.

The aralkyl group $Sub_7$ herein is preferably a group having the aryl group $Sub_1$ and is represented by $—Z_3—Z_4$. $Z_3$ is exemplified by an alkylene group corresponding to the above alkyl group Subs. $Z_4$ is exemplified by the above aryl group $Sub_1$. In this aralkyl group $Sub_7$, an aryl moiety has 6 to 30 carbon atoms (preferably 6 to 20 carbon atoms, more preferably 6 to 12 carbon atoms) and an alkyl moiety has 1 to 30 carbon atoms (preferably 1 to 20 carbon atoms, more preferably 1 to 10 carbon atoms, further preferably 1 to 6 carbon atoms). The aralkyl group $Sub_7$ is exemplified by at least one group selected from the group consisting of a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkoxy group herein is exemplified by an alkoxy group Subs. The alkoxy group Subs is represented by —$OZ_1$. $Z_1$ is exemplified by the above alkyl group Subs. The alkoxy group Subs preferably has 1 to 30 carbon atoms, more preferably 1 to 20 carbon atoms. The alkoxy group Subs is exemplified by at least one group selected from the group consisting of a methoxy group, ethoxy group, propoxy group, butoxy group, pentyloxy group and hexyloxy group.

Herein, an alkoxy halide group is exemplified by an alkoxy halide group $Sub_9$. The alkoxy halide group $Sub_9$ is provided by substituting the alkoxy group Subs with at least one halogen atom, preferably at least one fluorine atom.

Herein, an aryloxy group (occasionally referred to as an arylalkoxy group) is exemplified by an arylalkoxy group $Sub_{10}$. An aryl group in the arylalkoxy group $Sub_{10}$ includes at least one of the aryl group $Sub_1$ or the heteroaryl group $Sub_2$.

The arylalkoxy group $Sub_{10}$ herein is represented by —$OZ_2$. $Z_2$ is exemplified by the aryl group $Sub_1$ or the heteroaryl group $Sub_2$. The arylalkoxy group $Sub_{10}$ preferably has 6 to 30 ring carbon atoms, more preferably 6 to 20 ring carbon atoms. The arylalkoxy group $Sub_{10}$ is exemplified by a phenoxy group.

Herein, a substituted amino group is exemplified by a substituted amino group $Sub_{11}$. The substituted amino group $Sub_{11}$ is exemplified by at least one group selected from the group consisting of an arylamino group $Sub_{111}$ and an alkylamino group $Sub_{112}$.

The arylamino group $Sub_{111}$ is represented by —$NHR_{V1}$ or —$N(R_{V1})_2$. $R_{V1}$ is exemplified by the aryl group $Sub_1$. Two $R_{V1}$ in —$N(R_{V1})_2$ are mutually the same or different.

The alkylamino group $Sub_{112}$ is represented by —$NHR_{V2}$ or —$N(R_{V2})_2$. $R_{V2}$ is exemplified by the alkyl group $Sub_3$. Two $R_{V2}$ in —$N(R_{V2})_2$ are mutually the same or different.

Herein, the alkenyl group is exemplified by an alkenyl group $Sub_{12}$. The alkenyl group $Sub_{12}$, which is linear or branched, is exemplified by at least one group selected from the group consisting of a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

The alkynyl group herein is exemplified by an alkynyl group $Sub_{13}$. The alkynyl group $Sub_{13}$ may be linear or branched, and is exemplified by at least one group selected from the group consisting of an ethynyl group, a propynyl group and a 2-phenylethynyl group.

The alkylthio group herein is exemplified by an alkylthio group $Sub_{14}$.

The alkylthio group $Sub_{14}$ is represented by —$SR_{V3}$. $R_{V3}$ is exemplified by the alkyl group Subs. The alkylthio group $Sub_{14}$ preferably has 1 to 30 carbon atoms, more preferably 1 to 20 carbon atoms.

The arylthio group herein is exemplified by an arylthio group $Sub_{15}$.

The arylthio group $Sub_{15}$ is represented by —$SR_{V4}$. $R_{V4}$ is exemplified by the aryl group $Sub_1$. The arylthio group $Sub_{15}$ preferably has 6 to 30 ring carbon atoms, more preferably 6 to 20 ring carbon atoms.

Herein, examples of the halogen atom include a fluorine atom, a chlorine atom, a bromine atom and an iodine atom, among which a fluorine atom is preferable.

A substituted phosphino group herein is exemplified by a substituted phosphino group $Sub_{16}$. The substituted phosphino group $Sub_{16}$ is exemplified by a phenyl phosphanyl group.

A substituted carbonyl group herein is exemplified by a substituted carbonyl group $Sub_{17}$. The substituted carbonyl group $Sub_{17}$ is represented by —COY'. Y' is exemplified by at least one group selected from the group consisting of the aryl group $Sub_1$, the heteroaryl group $Sub_2$ and the alkyl group $Sub_3$. When-COY' is an arylcarbonyl group, the arylcarbonyl group is exemplified by at least one group selected from the group consisting of a phenyl carbonyl group, diphenyl carbonyl group, naphthyl carbonyl group, and triphenyl carbonyl group.

An acyl group herein is exemplified by an acyl group $Sub_{18}$. The acyl group $Sub_{18}$ is represented by —COR'. R' is exemplified by the alkyl group $Sub_3$. The acyl group $Sub_{18}$ herein is exemplified by at least one group selected from the group consisting of an acetyl group and a propionyl group.

A substituted phosphoryl group herein is exemplified by a substituted phosphoryl group $Sub_{19}$. The substituted phosphoryl group $Sub_{19}$ is represented by a formula (P) below.

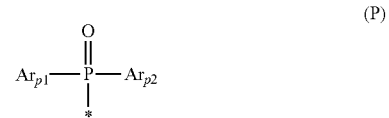

(P)

In the formula (P), $Ar_{P1}$ and $Ar_{P2}$ are any one substituent selected from the group consisting of the above alkyl group Subs and the above aryl group $Sub_1$.

An ester group herein is exemplified by an ester group $Sub_{20}$. The ester group $Sub_{20}$ is exemplified by at least one group selected from the group consisting of an alkyl ester group and an aryl ester group.

An alkyl ester group herein is exemplified by an alkyl ester group $Sub_{201}$. The alkyl ester group $Sub_{201}$ is represented by —C(=O)ORE. RE is exemplified by a substituted or unsubstituted alkyl group Subs described above.

An aryl ester group herein is exemplified by an aryl ester group $Sub_{202}$. The aryl ester group $Sub_{202}$ is represented by —C(=O)$OR^{Ar}$. $R^{Ar}$ is exemplified by a substituted or unsubstituted aryl group $Sub_1$ described above.

A siloxanyl group herein is exemplified by a siloxanyl group $Sub_{21}$. The siloxanyl group $Sub_{21}$ is a silicon compound group through an ether bond. The siloxanyl group $Sub_{21}$ is exemplified by a trimethylsiloxanyl group. A carbamoyl group herein is represented by —$CONH_2$.

A substituted carbamoyl group herein is exemplified by a carbamoyl group $Sub_{22}$. The carbamoyl group $Sub_{22}$ is represented by —CONH—$Ar^C$ or —CONH—$R^C$. $Ar^C$ is exemplified by at least one group selected from the group consisting of the above-described aryl group $Sub_1$ (preferably 6 to 10 ring carbon atoms) and the above-described heteroaryl group $Sub_2$ (preferably 5 to 14 ring atoms). $Ar^C$ may be a group formed by bonding the aryl group $Sub_1$ and the heteroaryl group $Sub_2$.

$R^C$ is exemplified by a substituted or unsubstituted alkyl group Subs described above (preferably having 1 to 6 carbon atoms).

A substituted boryl group herein is exemplified by a substituted boryl group $Sub_{23}$. The substituted boryl group $Sub_{23}$ is represented by a formula (B) below.

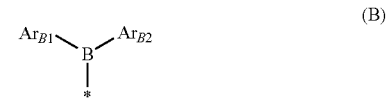

(B)

In the formula (B): $Ar_{B1}$ and $Ar_{B2}$ are each independently a substituent, or a pair of $Ar_{B1}$ and $Ar_{B2}$ are mutually bonded to form a ring; and $Ar_{B1}$ and $Ar_{B2}$ as a substituent are each independently a substituent selected from the group consisting of a halogen atom, the above-described aryl group $Sub_1$, the above-described heteroaryl group $Sub_2$, the above-described alkyl group Subs, the above-described alkyl halide group $Sub_4$, the above-described alkoxy group Subs, the above-described alkoxy halide group $Sub_9$, the above-described aryloxy group $Sub_{10}$, and the above-described arylamino group $Sub_{111}$. $Ar_{B1}$ and $Ar_{B2}$ in the formula (B) are the same or different.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

In chemical formulae herein, unless otherwise specified, it is assumed that a hydrogen atom (i.e., protium, deuterium and tritium) is bonded to each of bondable positions that are not annexed with signs "R" or the like or "D" representing a deuterium.

Hereinafter, an alkyl group Subs means at least one group of a linear alkyl group $Sub_{31}$, a branched alkyl group $Sub_{32}$, or a cyclic alkyl group $Sub_{33}$ described in "Description of Each Substituent."

Similarly, a substituted silyl group Subs means at least one group of an alkylsilyl group $Sub_{51}$ or an arylsilyl group $Sub_{52}$.

Similarly, a substituted amino group $Sub_1$ means at least one group of an arylamino group $Sub_{111}$ or an alkylamino group $Sub_{112}$.

Herein, a substituent for a "substituted or unsubstituted" group is exemplified by a substituent $R_{F1}$. The substituent $R_{F1}$ is at least one group selected from the group consisting of an aryl group $Sub_1$, heteroaryl group $Sub_2$, alkyl group Subs, alkyl halide group $Sub_4$, substituted silyl group $Sub_5$, alkylsulfonyl group $Sub_6$, aralkyl group $Sub_7$, alkoxy group Subs, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, substituted carbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, substituted boryl group $Sub_{23}$, unsubstituted amino group, unsubstituted silyl group, halogen atom, cyano group, hydroxy group, nitro group, and carboxy group.

Specific examples and preferable examples of the substituent $R_{F1}$ are the same as those of the substituents described in "Description of Each Substituent" (e.g., an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group Subs, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, substituted carbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, and substituted boryl group $Sub_{23}$).

The substituent $R_{F1}$ for a "substituted or unsubstituted" group may be further substituted by at least one group (hereinafter, also referred to as a substituent $R_{F2}$) selected from the group consisting of an aryl group $Sub_1$, heteroaryl group $Sub_2$, alkyl group Subs, alkyl halide group $Sub_4$, substituted silyl group $Sub_5$, alkylsulfonyl group $Sub_6$, aralkyl group $Sub_7$, alkoxy group Subs, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, substituted carbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, substituted boryl group $Sub_{23}$, unsubstituted amino group, unsubstituted silyl group, halogen atom, cyano group, hydroxy group, nitro group, and carboxy group. Moreover, a plurality of substituents $R_{F2}$ may be bonded to each other to form a ring.

"Unsubstituted" for a "substituted or unsubstituted" group means that a group is not substituted by the above-described substituent $R_{F1}$ but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of the substituent $R_{F1}$ of the substituted ZZ group.

Herein, "XX to YY atoms" in the description of "substituted or unsubstituted ZZ group having XX to YY atoms" represent atoms of an unsubstituted ZZ group and do not include atoms of the substituent $R_{F1}$ of the substituted ZZ group.

The same description as the above applies to "substituted or unsubstituted" in compounds or partial structures thereof described herein. Herein, when the substituents are bonded to each other to form a ring, the ring is structured to be a saturated ring, an unsaturated ring, an aromatic hydrocarbon ring or a hetero ring.

Herein, examples of the aromatic hydrocarbon group in the linking group include a divalent or multivalent group obtained by eliminating one or more atoms from the above monovalent aryl group $Sub_1$.

Herein, examples of the heterocyclic group in the linking group include a divalent or multivalent group obtained by eliminating one or more atoms from the above monovalent heteroaryl group $Sub_2$.

EXAMPLES

Compounds

Structures of a compound M3a, a compound M3b, a compound M3c, and a compound M3d each serving as the compound M3 and used for manufacturing an organic EL device are shown below.

M3a

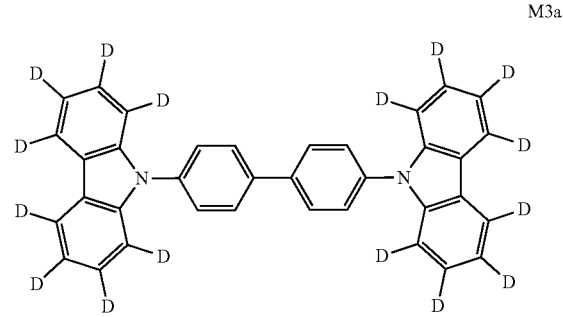

M3b
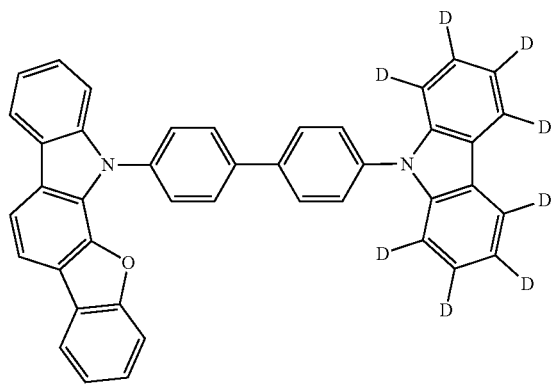
M3c
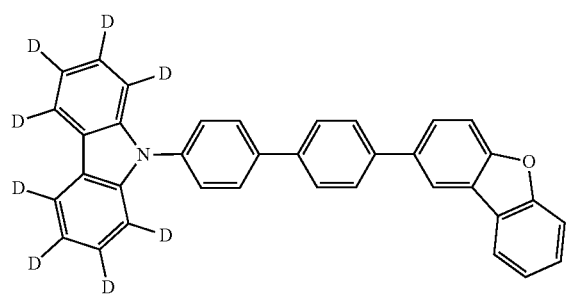
M3d
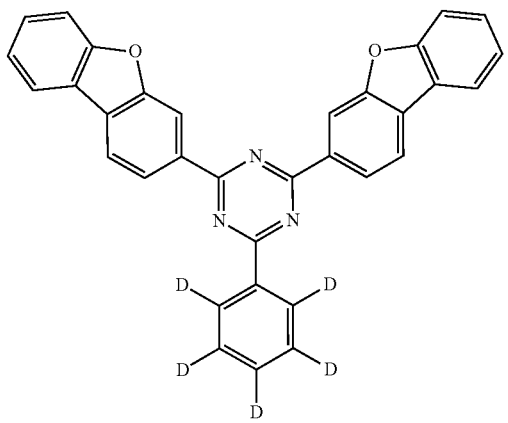
TADF1
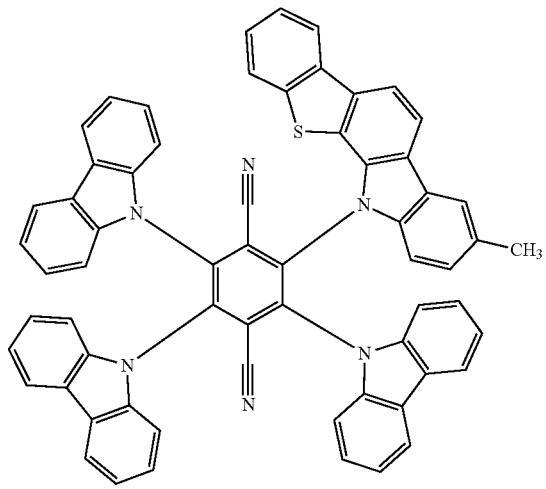
TADF2
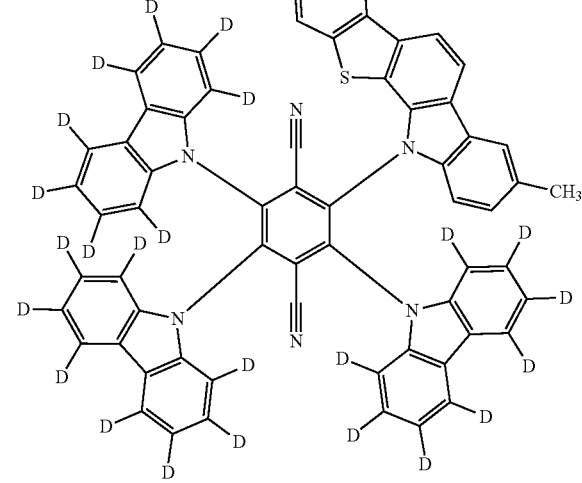
TADF3
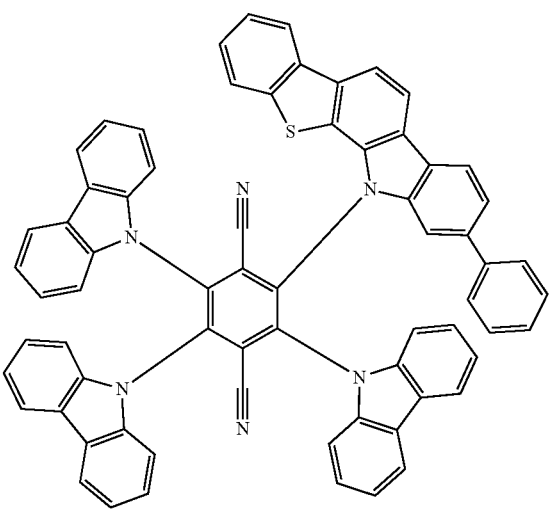
Structures of compounds TADF1 to TADF5 serving as the compound M2 and used for manufacturing the organic EL devices are shown below.

-continued
TADF4
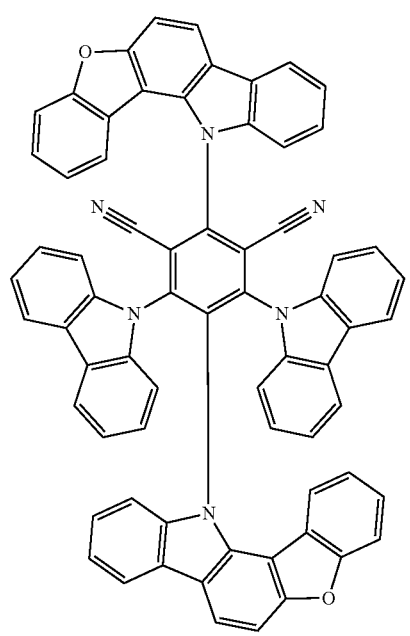
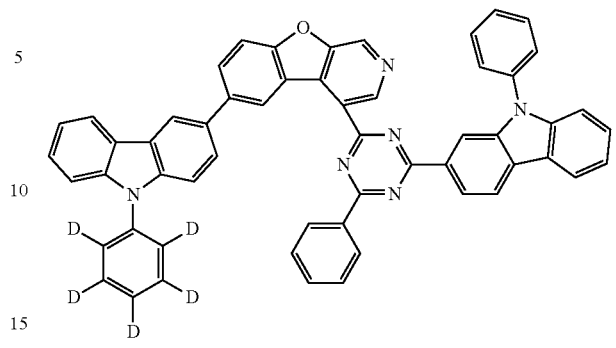
Ref-2
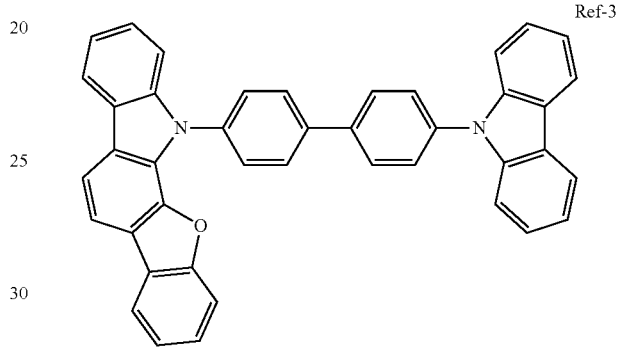
Ref-3
TADF5
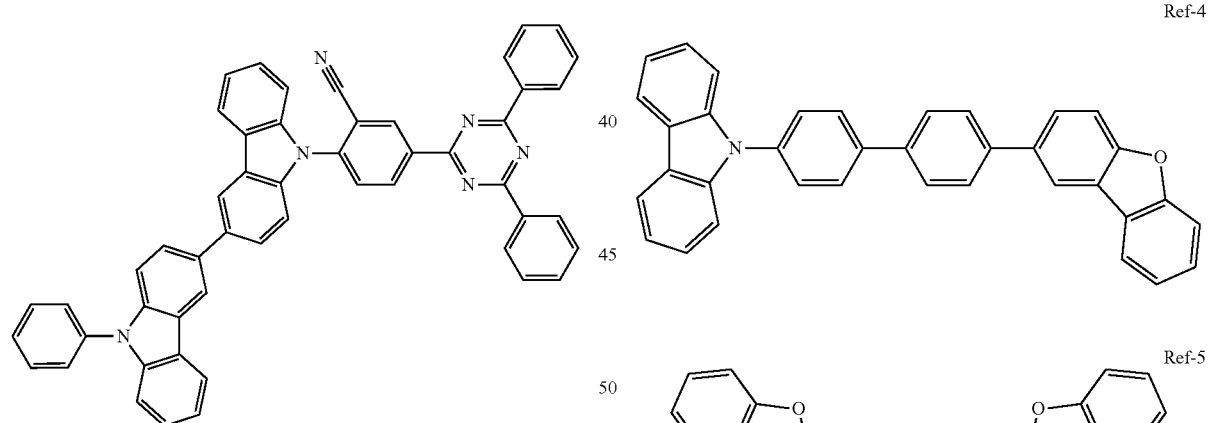
Ref-4
Ref-5
Structures of compounds used for manufacturing organic EL devices in Comparatives are shown below.
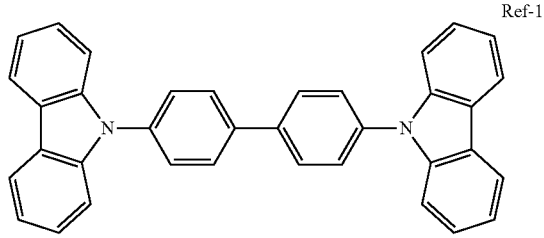
Ref-1
Structures of other compounds used for manufacturing the organic EL devices in Examples and Comparatives are shown below.

HA

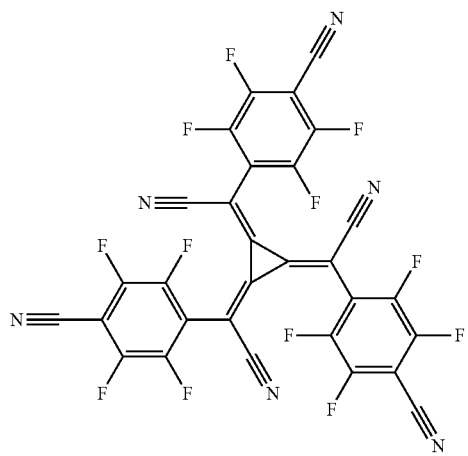

HT

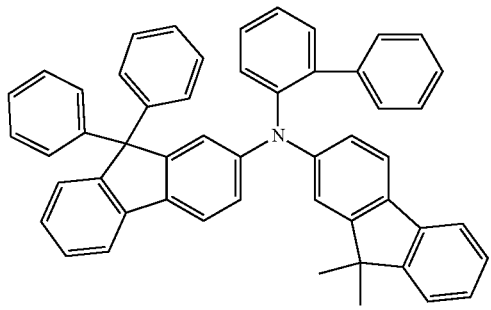

EBL

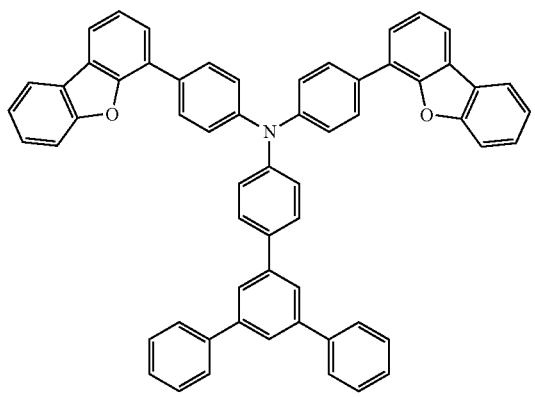

RD

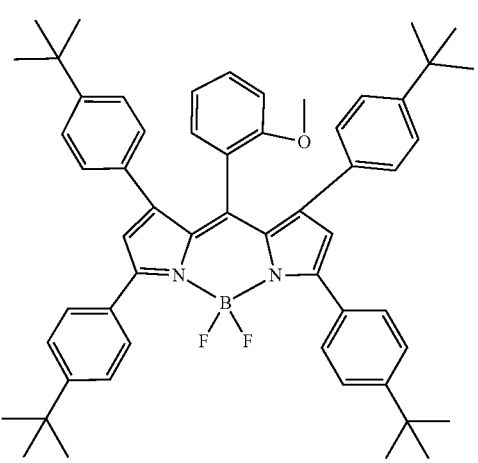

HBL

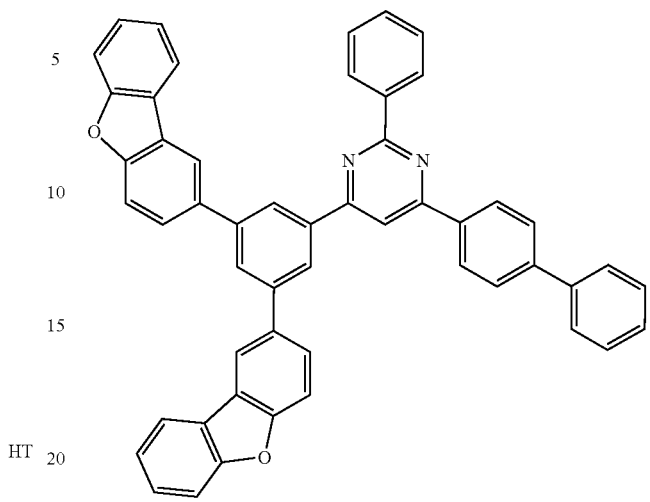

ET

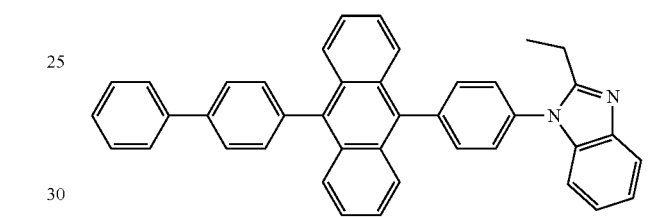

HT2

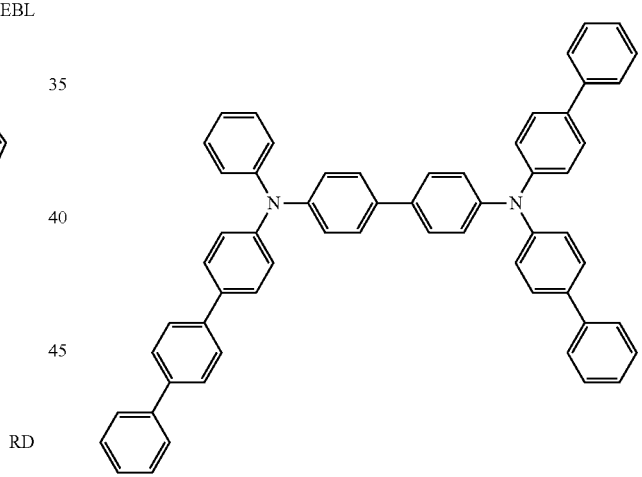

Manufacturing 1 of Organic EL Device

The organic EL devices were manufactured and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, a compound HT and a compound HA were co-deposited on a surface of the glass substrate where the transparent electrode line was provided in a manner to cover the transparent electrode, thereby forming a 10-nm-thick hole injecting layer. The concentrations of the compound HT and the compound HA in the hole injecting layer were 97 mass % and 3 mass %, respectively.

Next, the compound HT was vapor-deposited on the hole injecting layer to form a 200-nm-thick hole transporting layer.

Next, a compound EBL was vapor-deposited on the hole transporting layer to form a 10-nm-thick electron blocking layer.

Next, the compound M3a serving as the compound M3, the compound TADF1 serving as the compound M2, and the compound RD serving as the compound M1 were co-deposited on the electron blocking layer to form a 25-nm-thick emitting layer. The concentrations of the compound M3a, the compound TADF1, and the compound RD in the emitting layer were 74 mass %, 25 mass %, and 1 mass %, respectively.

Next, a compound HBL was vapor-deposited on the emitting layer to form a 10-nm-thick hole blocking layer (first layer).

Next, a compound ET was vapor-deposited on the hole blocking layer to form a 30-nm-thick electron transporting layer.

Lithium fluoride (LiF) was vapor-deposited on the electron transporting layer to form a 1-nm-thick electron injectable electrode (cathode).

Subsequently, metal aluminum (Al) was vapor-deposited on the electron injectable electrode to form an 80-nm-thick metal Al cathode.

A device arrangement of the organic EL device of Example 1 is roughly shown as follows.

ITO (130)/HT:HA (10, 97%:3%)/HT (200)/EBL (10)/M3a:TADF1:RD (25, 74%:25%:1%)/HBL (10)/ET (30)/LiF (1)/Al (80)

Numerals in parentheses represent a film thickness (unit: nm). (97%:3%) represents the proportion (mass %) of the compound HT and the compound HA in the hole injecting layer, and numerals expressed in units of percentage (74%:25%:1%) represent the proportion (mass %) of the compound M3a, the compound TADF1, and the compound RD in the emitting layer.

Example 2

An organic EL device of Example 2 was manufactured as in Example 1 except that the compound TADF1 in the emitting layer of Example 1 was replaced with the compound described in Table 1.

Comparatives 1 and 2

Organic EL devices of Comparatives 1 and 2 were manufactured as in Example 1 except that the compound M3a in the emitting layer of Example 1 was replaced with the compounds described in Table 1.

Evaluation 1 of Organic EL Devices

For the organic EL devices manufactured in Examples 1 and 2 and Comparatives 1 and 2, the following evaluations were performed. The results are shown in Table 1. Although the compounds Ref-1 and Ref-2 used in Comparatives 1 and 2, respectively, do not correspond to the compound M3, Ref-1 and Ref-2 are shown in the same column as the compound M3a in Examples 1 and 2 for convenience.

Main Peak Wavelength ($\lambda p$)

Voltage was applied on the organic EL devices such that a current density of the organic EL device was 10 mA/cm$^2$, where spectral radiance spectrum was measured by a spectroradiometer CS-2000 (manufactured by Konica Minolta, Inc.). The main peak wavelength $\lambda p$ (unit: nm) was calculated based on the obtained spectral-radiance spectra.

External Quantum Efficiency EQE

Voltage was applied on the organic EL devices so that a current density was 10 mA/cm$^2$, where spectral radiance spectrum was measured by a spectroradiometer CS-2000 (manufactured by Konica Minolta, Inc.). The external quantum efficiency EQE (unit: %) was calculated based on the obtained spectral-radiance spectra, assuming that the spectra was provided under a Lambertian radiation.

EQE(%) of Comparative 1 was set to be 100 and EQE(%) of each of Examples and Comparatives was obtained as a "EQE (relative value: %)" using a numerical formula (Numerical Formula 100) below.

EQE (relative value: %) of each of Examples and Comparatives=(EQE(%) of each of Examples and Comparatives/EQE(%) of Comparative 1)×100 (Numerical Formula 100)

Drive Voltage

A voltage (unit: V) was measured when current was applied between the anode and the cathode such that a current density was 10 mA/cm$^2$.

The "drive voltage (V)" of Comparative 1 was set to be 100, and the "drive voltage (V)" of each of Examples and Comparatives was determined as a "drive voltage (relative value: %)" using a numerical formula (Numerical Formula 101) below.

Drive voltage (relative value: %) of each of Examples and Comparatives=(drive voltage (V) of each of Examples and Comparatives/drive voltage (V) of Comparative 1)×100 (Numerical Formula 101)

Lifetime LT95

Voltage was applied to the organic EL devices such that a current density was 50 mA/cm$^2$, and a time (unit: h) elapsed before the luminance intensity was reduced to 95% of the initial luminance intensity was measured using a spectroradiometer CS-200 (manufactured by Konica Minolta, Inc.).

Hereinafter, the time elapsed before the luminance intensity is reduced to 95% of the initial luminance intensity is referred to as "Lifetime LT95 (h)".

"Lifetime LT95 (h)" of Comparative 1 was set to be 100, and "Lifetime LT95 (h)" of each of Examples and Comparatives was determined as a "Lifetime LT95 (relative value: %)" using a numerical formula (Numerical Formula 102) below.

Lifetime LT95 (relative value: %) of each of Examples and Comparatives=(Lifetime LT95 (h) of each of Examples and Comparatives/Lifetime LT95 (h) of Comparative 1)×100 (Numerical Formula 102)

TABLE 1

| | Compound M3 | | Compound M2 | | | Compound M1 | | | Drive voltage | EQE | LT95 |
|---|---|---|---|---|---|---|---|---|---|---|---|
| | Type | $S_1$ [eV] | Type | $S_1$ [eV] | ΔST [eV] | λ [nm] | Type | $S_1$ [eV] | λ [nm] | $\lambda_p$ [nm] | (Relative value: %) | (Relative value: %) | (Relative value: %) |
| Example 1 | M3a | 3.52 | TADF1 | 2.32 | <0.01 | 545 | RD | 2.02 | 609 | 621 | 100 | 100 | 160 |
| Example 2 | M3a | 3.52 | TADF2 | 2.32 | <0.01 | 545 | RD | 2.02 | 609 | 621 | 100 | 100 | 270 |
| Comparative 1 | Ref-1 | 3.41 | TADF1 | 2.32 | <0.01 | 545 | RD | 2.02 | 609 | 621 | 100 | 100 | 100 |
| Comparative 2 | Ref-2 | 2.99 | TADF1 | 2.32 | <0.01 | 545 | RD | 2.02 | 609 | 621 | 100 | 80 | 50 |

Examples 1 and 2 in which the compound M3a having deuterium atoms and the compound TADF1 or TADF2 were contained in the emitting layer had longer lifetimes than Comparative 1 in which the compound M3a in Example 1 was replaced with the "compound Ref-1 having no deuterium atom" and Comparative 2 in which the compound M3a in Example 1 was replaced with the "compound Ref-2 having deuterium atoms but having an aza-dibenzofuran ring".

In particular, Example 2 in which the compound TADF2 having deuterium atoms was contained in the emitting layer together with the compound M3a having deuterium atoms had a significantly longer lifetime than Comparatives 1 and 2.

Furthermore, Examples 1 and 2 had an improved external quantum efficiency EQE compared with Comparative 2.

Manufacture 2 of Organic EL Device

Example 3

An organic EL device of Example 3 was manufactured as in Example 1 except that the compounds M3a and TADF1 in the emitting layer of Example 1 were replaced with the compounds described in Table 2.

Comparatives 3 and 4

Organic EL devices of Comparatives 3 and 4 were manufactured as in Example 1 except that the compounds M3a and TADF1 in the emitting layer of Example 1 were replaced with the compounds described in Table 2.

Evaluation 2 of Organic EL Devices

For the organic EL devices manufactured in Example 3 and Comparatives 3 and 4, the following evaluations were performed. The results are shown in Table 2. Although the compounds Ref-3 and Ref-2 used in Comparatives 3 and 4, respectively, do not correspond to the compound M3, Ref-3 and Ref-2 are shown in the same column as M3b in Example 3 for convenience.

Main Peak Wavelength (λp)

The main peak wavelength λp (unit: nm) was determined by the same method as that used in Example 1.

External Quantum Efficiency EQE

The external quantum efficiency EQE (unit: %) was calculated by the same method as that used in Example 1.

EQE (%) of Comparative 3 was set to be 100, and EQE (%) of each of

Example and Comparatives was determined as an "EQE (relative value: %)" using a numerical formula (Numerical Formula 100A) below.

EQE (relative value: %) of each of Example and Comparatives=(EQE (%) of each of Example and Comparatives/EQE (%) of Comparative 3)×100 (Numerical Formula 100A)

Drive Voltage

The voltage (unit: V) was measured by the same method as that used in Example 1.

The "drive voltage (V)" of Comparative 3 was set to be 100, and the "drive voltage (V)" of each of Example and Comparatives was determined as a "drive voltage (relative value: %)" using a numerical formula (Numerical Formula 101A) below.

Drive voltage (relative value: %) of each of Example and Comparatives=(drive voltage (V) of each of Example and Comparatives/drive voltage (V) of Comparative 3)×100 (Numerical Formula 101A)

Lifetime LT95

The time (unit: h) elapsed before the luminance intensity was reduced to 95% of the initial luminance intensity was measured by the same method as that used in Example 1.

"Lifetime LT95 (h)" of Comparative 3 was set to be 100, and "Lifetime LT95 (h)" of each of Example and Comparatives was determined as a "Lifetime LT95 (relative value: %)" using a numerical formula (Numerical Formula 102A) below.

Lifetime LT95 (relative value: %) of each of Example and Comparatives=(Lifetime LT95 (h) of each of Example and Comparatives/Lifetime LT95 (h) of Comparative 3)×100 (Numerical Formula 102A)

TABLE 2

| | Compound M3 | | Compound M2 | | | Compound M1 | | | Drive voltage | EQE | LT95 |
|---|---|---|---|---|---|---|---|---|---|---|---|
| | Type | $S_1$ [eV] | Type | $S_1$ [eV] | ΔST [eV] | λ [nm] | Type | $S_1$ [eV] | λ [nm] | $\lambda_p$ [nm] | (Relative value: %) | (Relative value: %) | (Relative value: %) |
| Example 3 | M3b | 3.42 | TADF3 | 2.34 | <0.01 | 539 | RD | 2.02 | 609 | 621 | 100 | 100 | 150 |
| Comparative 3 | Ref-3 | 3.42 | TADF3 | 2.34 | <0.01 | 539 | RD | 2.02 | 609 | 621 | 100 | 100 | 100 |
| Comparative 4 | Ref-2 | 2.99 | TADF3 | 2.34 | <0.01 | 539 | RD | 2.02 | 609 | 621 | 105 | 70 | 60 |

Example 3 in which the compound M3b having deuterium atoms and the compound TADF3 were contained in the emitting layer had a longer lifetime than Comparative 3 in which the compound M3b in Example 3 was replaced with the "compound Ref-3 having no deuterium atom" and Comparative 4 in which the compound M3a in Example 3 was replaced with the "compound Ref-2 having deuterium atoms but having an aza-dibenzofuran ring".

Furthermore, Example 3 had a low drive voltage and an improved external quantum efficiency EQE compared with Comparative 4.

Manufacturing 3 of Organic EL Device

The organic EL devices were manufactured and evaluated as follows.

Example 4

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, the compound HT and the compound HA were co-deposited on a surface of the glass substrate where the transparent electrode line was provided in a manner to cover the transparent electrode, thereby forming a 10-nm-thick hole injecting layer. The concentrations of the compound HT and the compound HA in the hole injecting layer were 97 mass % and 3 mass %, respectively.

Next, a compound HT2 was vapor-deposited on the hole injecting layer to form a 110-nm-thick first hole transporting layer on the hole injecting layer.

Next, the compound EBL was vapor-deposited on the first hole transporting layer to form a 5-nm-thick second hole transporting layer.

Next, the compound Ref-1 was vapor-deposited on the second hole transporting layer to form a 5-nm-thick electron blocking layer.

Next, the compound M3c serving as the compound M3 and the compound TADF4 serving as the compound M2 were co-deposited on the electron blocking layer to form a 25-nm-thick emitting layer. The concentrations of the compound M3c and the compound TADF4 in the emitting layer were 50 mass % and 50 mass %, respectively.

Next, the compound HBL was vapor-deposited on the emitting layer to form a 5-nm-thick hole blocking layer (first layer).

Next, the compound ET was vapor-deposited on the hole blocking layer to form a 50-nm-thick electron transporting layer.

Lithium fluoride (LiF) was vapor-deposited on the electron transporting layer to form a 1-nm-thick electron injectable electrode (cathode).

Subsequently, metal aluminum (Al) was vapor-deposited on the electron injectable electrode to form an 80-nm-thick metal Al cathode.

A device arrangement of the organic EL device of Example 4 is roughly shown as follows.

ITO (130)/HT:HA (10, 97%:3%)/HT2 (110)/EBL (5)/Ref-1 (5)/M3c:TADF4 (25, 50%:50%)/HBL (5)/ET (50)/LiF (1)/Al (80)

Numerals in parentheses represent a film thickness (unit: nm). (97%:3%) represents the proportion (mass %) of the compound HT and the compound HA in the hole injecting layer, and numerals expressed in units of percentage (50%:50%) represent the proportion (mass %) of the compound M3c and the compound TADF4 in the emitting layer.

Comparatives 5 and 6

Organic EL devices of Comparatives 5 and 6 were manufactured as in Example 4 except that the compound M3c in the emitting layer of Example 4 was replaced with the compounds described in Table 3.

Evaluation 3 of Organic EL Devices

For the organic EL devices manufactured in Example 4 and Comparatives 5 and 6, the following evaluations were performed. The results are shown in Table 3. Although the compounds Ref-2 and Ref-4 used in Comparatives 5 and 6, respectively, do not correspond to the compound M3, Ref-2 and Ref-4 are shown in the same column as M3c in Example 4 for convenience.

Main Peak Wavelength ($\lambda p$)

The main peak wavelength $\lambda p$ (unit: nm) was determined by the same method as that used in Example 1.

External Quantum Efficiency EQE

The external quantum efficiency EQE (unit: %) was calculated by the same method as that used in Example 1.

EQE (%) of Comparative 6 was set to be 100, and EQE (%) of each of Example and Comparatives was determined as an "EQE (relative value: %)" using a numerical formula in which EQE (%) of Comparative 1 was replaced with EQE (%) of Comparative 6 in the numerical formula (Numerical Formula 100).

Drive Voltage

The voltage (unit: V) was measured by the same method as that used in Example 1.

The drive voltage (V) of Comparative 6 was set to be 100, and the drive voltage (V) of each of Example and Comparatives was determined as a "drive voltage (relative value: %)" using a numerical formula in which the drive voltage (V) of Comparative 1 was replaced with the drive voltage (V) of Comparative 6 in the numerical formula (Numerical Formula 101).

Lifetime LT95

The time (unit: h) elapsed before the luminance intensity was reduced to 95% of the initial luminance intensity was measured by the same method as that used in Example 1.

Lifetime LT95 (h) of Comparative 6 was set to be 100, and Lifetime LT95 (h) of each of Example and Comparatives was determined as a "Lifetime LT95 (relative value: %)" using a numerical formula in which Lifetime LT95 (h) of Comparative 1 was replaced with Lifetime LT95 (h) of Comparative 6 in the numerical formula (Numerical Formula 102).

TABLE 3

| | Compound M3 | | Compound M2 | | | | | Device evaluation results | | |
| | | | | | | | | Drive voltage | EQE | LT95 |
| | Type | $S_1$ [eV] | Type | $S_1$ [eV] | ΔST [eV] | λ [nm] | $λ_p$ [nm] | (Relative value: %) | (Relative value: %) | (Relative value: %) |
|---|---|---|---|---|---|---|---|---|---|---|
| Example 4 | M3c | 3.52 | TADF4 | 2.52 | <0.01 | 511 | 550 | 100 | 100 | 120 |
| Comparative 5 | Ref-2 | 2.99 | TADF4 | 2.52 | <0.01 | 511 | 550 | 100 | 80 | 50 |
| Comparative 6 | Ref-4 | 3.50 | TADF4 | 2.52 | <0.01 | 511 | 550 | 100 | 100 | 100 |

Example 4 in which the compound M3c having deuterium atoms and the compound TADF4 were contained in the emitting layer had a longer lifetime than Comparative 5 in which the compound M3c in Example 4 was replaced with the "compound Ref-2 having deuterium atoms but having an aza-dibenzofuran ring" and Comparative 6 in which the compound M3c in Example 4 was replaced with the "compound Ref-4 having no deuterium atom".

Manufacturing 4 of Organic EL Device

Example 5 and Comparatives 7 and 8

Organic EL devices of Example 5 and Comparatives 7 and 8 were manufactured as in Example 1 except that the compound M3a and the compound TADF1 in the emitting layer of Example 1 were replaced with the compounds described in Table 4.

Evaluation 4 of Organic EL Devices

For the organic EL devices manufactured in Example 5 and Comparatives 7 and 8, the following evaluations were performed. The results are shown in Table 4. Although the compounds Ref-2 and Ref-5 used in Comparatives 7 and 8, respectively, do not correspond to the compound M3, Ref-2 and Ref-5 are shown in the same column as M3d in Example 5 for convenience.

Main Peak Wavelength (λp)

The main peak wavelength λp (unit: nm) was determined by the same method as that used in Example 1.

Lifetime LT95

The time (unit: h) elapsed before the luminance intensity was reduced to 95% of the initial luminance intensity was measured by the same method as that used in Example 1.

Lifetime LT95 (h) of Comparative 8 was set to be 100, and Lifetime LT95 (h) of each of Example and Comparatives was determined as a "Lifetime LT95 (relative value: %)" using a numerical formula in which Lifetime LT95 (h) of Comparative 1 was replaced with Lifetime LT95 (h) of Comparative 8 in the numerical formula (Numerical Formula 102).

Example 5 in which the compound M3d having deuterium atoms and the compound TADF3 were contained in the emitting layer had a longer lifetime than Comparative 7 in which the compound M3d in Example 5 was replaced with the "compound Ref-2 having deuterium atoms but having an aza-dibenzofuran ring" and Comparative 8 in which the compound M3d in Example 5 was replaced with the "compound Ref-5 having no deuterium atom".

Manufacturing 5 of Organic EL Device

The organic EL devices were manufactured and evaluated as follows.

Example 6

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, the compound HT and the compound HA were co-deposited on a surface of the glass substrate where the transparent electrode line was provided in a manner to cover the transparent electrode, thereby forming a 10-nm-thick hole injecting layer. The concentrations of the compound HT and the compound HA in the hole injecting layer were 97 mass % and 3 mass %, respectively.

Next, the compound HT2 was vapor-deposited on the hole injecting layer to form a 110-nm-thick first hole transporting layer on the hole injecting layer.

Next, the compound EBL was vapor-deposited on the first hole transporting layer to form a 5-nm-thick second hole transporting layer.

Next, the compound Ref-1 was vapor-deposited on the second hole transporting layer to form a 5-nm-thick electron blocking layer.

Next, the compound M3b serving as the compound M3 and the compound TADF5 serving as the compound M2 were co-deposited on the electron blocking layer to form a

TABLE 4

| | Compound M3 | | Compound M2 | | | | Compound M1 | | | Device evaluation results |
| | | | | | | | | | | LT95 |
| | Type | $S_1$ [eV] | Type | $S_1$ [eV] | ΔST [eV] | λ [nm] | Type | $S_1$ [eV] | λ [nm] | $λ_p$ [nm] | (Relative value: %) |
|---|---|---|---|---|---|---|---|---|---|---|---|
| Example 5 | M3d | 3.48 | TADF3 | 2.34 | <0.01 | 539 | RD | 2.02 | 609 | 621 | 120 |
| Comparative 7 | Ref-2 | 2.99 | TADF3 | 2.34 | <0.01 | 539 | RD | 2.02 | 609 | 621 | 60 |
| Comparative 8 | Ref-5 | 3.48 | TADF3 | 2.34 | <0.01 | 539 | RD | 2.02 | 609 | 621 | 100 |

25-nm-thick emitting layer. The concentrations of the compound M3b and the compound TADF5 in the emitting layer were 75 mass % and 25 mass %, respectively.

Next, the compound Ref-5 was vapor-deposited on the emitting layer to form a 5-nm-thick hole blocking layer (first layer).

Next, a compound ET was vapor-deposited on the hole blocking layer to form a 50-nm-thick electron transporting layer.

Lithium fluoride (LiF) was vapor-deposited on the electron transporting layer to form a 1-nm-thick electron injectable electrode (cathode).

Subsequently, metal aluminum (Al) was vapor-deposited on the electron injectable electrode to form an 80-nm-thick metal Al cathode.

A device arrangement of the organic EL device of Example 6 is roughly shown as follows.

ITO (130)/HT:HA (10, 97%:3%)/HT2 (110)/EBL (5)/Ref-1 (5)/M3b:TADF5 (25, 75%:25%)/Ref-5 (5)/ET (50)/LiF (1)/Al (80)

Numerals in parentheses represent a film thickness (unit: nm). (97%:3%) represents the proportion (mass %) of the compound HT and the compound HA in the hole injecting layer, and numerals expressed in units of percentage (75%:25%) represent the proportion (mass %) of the compound M3b and the compound TADF5 in the emitting layer.

Comparatives 9 and 10

Organic EL devices of Comparatives 9 and 10 were manufactured as in Example 6 except that the compound M3b in the emitting layer of Example 6 was replaced with the compounds described in Table 5.
Evaluation 5 of Organic EL Devices For the organic EL devices manufactured in Example 6 and Comparatives 9 and 10, the following evaluations were performed. The results are shown in Table 5. Although the compounds Ref-2 and Ref-3 used in Comparatives 9 and 10, respectively, do not correspond to the compound M3, Ref-2 and Ref-3 are shown in the same column as M3b in Example 6 for convenience.
Main Peak Wavelength ($\lambda_p$)

The main peak wavelength $\lambda_p$ (unit: nm) was determined by the same method as that used in Example 1.
Lifetime LT95

The time (unit: h) elapsed before the luminance intensity was reduced to 95% of the initial luminance intensity was measured by the same method as that used in Example 1.

Lifetime LT95 (h) of Comparative 10 was set to be 100, and Lifetime LT95 (h) of each of Example and Comparatives was determined as a "Lifetime LT95 (relative value: %)" using a numerical formula in which Lifetime LT95 (h) of Comparative 1 was replaced with Lifetime LT95 (h) of Comparative 10 in the numerical formula (Numerical Formula 102).

TABLE 5

| Compound | | | | | | | Device evaluation results |
|---|---|---|---|---|---|---|---|
| M3 | | Compound M2 | | | | | LT95 |
| Type | $S_1$ [eV] | Type | $S_1$ [eV] | $\Delta ST$ [eV] | $\lambda$ [nm] | $\lambda_p$ [nm] | (Relative value: %) |
| Example 6 M3b | 3.42 | TADF5 | 2.79 | 0.03 | 503 | 519 | 125 |
| Comparative 9 Ref-2 | 2.99 | TADF5 | 2.79 | 0.03 | 503 | 519 | 50 |

TABLE 5-continued

| Compound | | | | | | | Device evaluation results |
|---|---|---|---|---|---|---|---|
| M3 | | Compound M2 | | | | | LT95 |
| Type | $S_1$ [eV] | Type | $S_1$ [eV] | $\Delta ST$ [eV] | $\lambda$ [nm] | $\lambda_p$ [nm] | (Relative value: %) |
| Comparative 10 | Ref-3 3.42 | TADF5 | 2.79 | 0.03 | 503 | 519 | 100 |

Example 6 in which the compound M3b having deuterium atoms and the compound TADF5 were contained in the emitting layer had a longer lifetime than Comparative 9 in which the compound M3b in Example 6 was replaced with the "compound Ref-2 having deuterium atoms but having an aza-dibenzofuran ring" and Comparative 10 in which the compound M3b in Example 6 was replaced with the "compound Ref-3 having no deuterium atom".
Evaluation of Compounds Physical properties of the compounds described in Tables 1 to 5 and Synthesis Examples described later were measured by the following methods.
Thermally Activated Delayed Fluorescence
Delayed Fluorescence of Compound TADF1

Thermally activated delayed fluorescence was checked by measuring transient photoluminescence (PL) using a device shown in FIG. 2. The compound TADF1 was dissolved in toluene to prepare a dilute solution with an absorbance of 0.05 or less at the excitation wavelength to eliminate the contribution of self-absorption. In order to prevent quenching due to oxygen, the sample solution was frozen and degassed and then sealed in a cell with a lid under an argon atmosphere to obtain an oxygen-free sample solution saturated with argon.

The fluorescence spectrum of the above sample solution was measured with a spectrofluorometer FP-8600 (manufactured by JASCO Corporation), and the fluorescence spectrum of a 9,10-diphenylanthracene ethanol solution was measured under the same conditions. Using the fluorescence are intensities of both spectra, the total fluorescence quantum yield was calculated by an equation (1) in Morris et al. J. Phys. Chem. 80 (1976) 969.

Prompt emission is observed promptly when the excited state is achieved by exciting the compound TADF1 with a pulse beam (i.e., a beam emitted from a pulse laser) having a wavelength to be absorbed by the compound TADF1, and Delay emission is observed not promptly when the excited state is achieved but after the excited state is achieved. The delayed fluorescence in Examples means that an amount of Delay Emission is 5% or more with respect to an amount of Prompt Emission. Specifically, provided that the amount of Prompt emission is denoted by $X_P$ and the amount of Delay emission is denoted by $X_D$, the delayed fluorescence means that a value of $X_D/X_P$ is 0.05 or more.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

It was found that the amount of Delay emission was 5% or more with respect to the amount of Prompt emission in the compound TADF1.

Specifically, the value of $X_D/X_P$ in the compound TADF1 was 0.05 or more. Delayed Fluorescence of Compounds TADF2 to TADF5

Delayed fluorescence of each of the compounds TADF2 to TADF5 was checked in the same manner except that each of the compounds TADF2 to TADF5 was used instead of the compound TADF1.

It was found that the value of $X_D/X_P$ in each of the compounds TADF2 to TADF5 was 0.05 or more.

Singlet Energy $S_1$

A singlet energy $S_1$ of each of the compounds M3a, M3b, M3c, and M3d, the compounds TADF1 to TADF5, the compound RD, and the comparative compounds Ref-1 to Ref-5 was measured by the solution method described above. The results are shown in Tables 1 to 5.

Energy Gap at 77K

An energy gap $T_{77K}$ at 77K of each of the compounds M3a, M3b, M3c, and M3d, the compounds TADF1 to TADF5, and the comparative compounds Ref-1 to Ref-5 was measured by the method for measuring the energy gap $T_{77K}$ described in the "Relationship between Triplet Energy and Energy Gap at 77K". ΔST ΔST was calculated based on the measured singlet energy $S_1$ and energy gap $T_{77K}$ at 77K.

The ΔST of each of the compounds TADF1 to TADF4 was less than 0.01 eV.

The ΔST of the compound TADF5 was 0.03 eV.

Energy Gap $T_{77K}$

The $T_{77K}$ of the compound M3a was 2.80 eV.

The $T_{77K}$ of the compound M3b was 2.97 eV.

The $T_{77K}$ of the compound M3c was 2.74 eV.

The $T_{77K}$ of the compound M3d was 2.71 eV.

The $T_{77K}$ of the comparative compound Ref-1 was 2.69 eV.

The $T_{77K}$ of the comparative compound Ref-2 was 2.68 eV.

The $T_{77K}$ of the comparative compound Ref-3 was 2.89 eV.

The $T_{77K}$ of the comparative compound Ref-4 was 2.74 eV.

The $T_{77K}$ of the comparative compound Ref-5 was 2.71 eV.

Main Peak Wavelength λ of Compound

A main peak wavelength λ of a compound was measured by the following method.

A toluene solution of a measurement target compound at a concentration of 5 μmol/L was prepared and put in a quartz cell. An emission spectrum (ordinate axis: luminous intensity, abscissa axis: wavelength) of the thus-obtained sample was measured at a normal temperature (300K). In Examples, the emission spectrum was measured using a spectrophotometer manufactured by Hitachi, Ltd. (device name: F-7000). It should be noted that the machine for measuring the emission spectrum is not limited to the machine used herein. A peak wavelength of the emission spectrum exhibiting the maximum luminous intensity was defined as a main peak wavelength A.

Synthesis of Compounds

Synthesis Example 1: Synthesis of Compound M3a

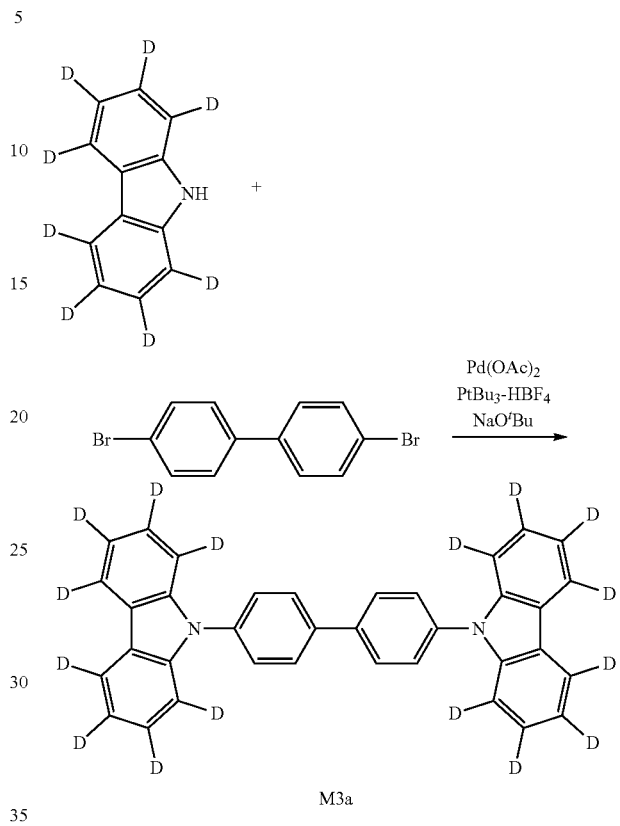

M3a

Under nitrogen atmosphere, xylene (50 mL) was added to a mixture of 9H-carbazole-1,2,3,4,5,6,7,8-d8 (1.58 g, 9.00 mmol), 4,4'-dibromo-1,1'-biphenyl (1.40 g, 4.50 mmol), palladium acetate (101.0 mg, 0.45 mmol), tri-tert-butylphosphonium tetrafluoroborate (261.1 mg, 0.90 mmol), and sodium tert-butoxide (2.59 g, 27.0 mmol), and the resulting mixture was stirred at 130 degrees C. for seven hours. After completion of the reaction, the solid was filtered out and recrystallized with toluene to obtain a compound M3a (1.54 g, a yield of 68%). The obtained compound was identified as the compound M3a by analysis according to LC-MS (Liquid chromatography mass spectrometry).

(2) Synthesis Example 2: Synthesis of Compound M3b (2-1) Synthesis of Intermediate 1

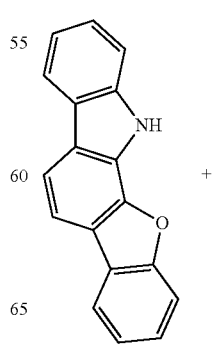

-continued

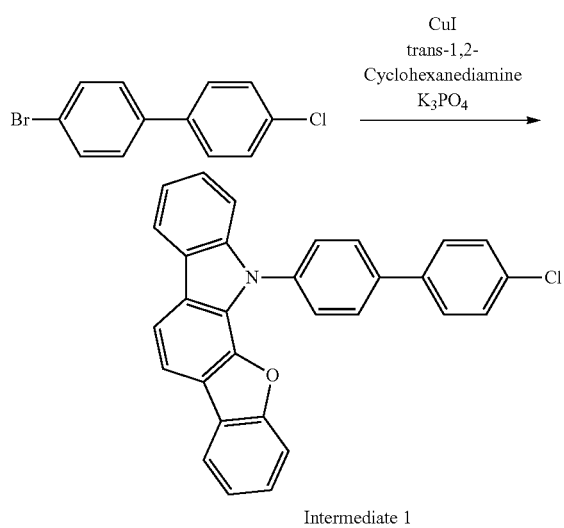

Intermediate 1

Under nitrogen atmosphere, 1,4-dioxane (70 mL) was added to a mixture of 12H-benzofuro[2,3-a]carbazole (3.60 g, 14.0 mmol), 4-bromo-4'-chloro-1,1'-biphenyl (4.49 g, 16.8 mmol), copper(I) iodide (2.67 g, 14.0 mmol), trans-1, 2-cyclohexanediamine (3.20 g, 3.37 mL, 28.0 mmol), and potassium phosphate (8.92 g, 42.0 mmol), and the resulting mixture was stirred at 100 degrees C. for eight hours. After completion of the reaction, the solid was removed by filtration using a Celite pad, the solvent was distilled off, and recrystallization was then performed with toluene to obtain an intermediate 1 (5.96 g, a yield of 96%). The obtained compound was identified as the intermediate 1 by analysis of LC-MS.

(2-2) Synthesis of Compound M3b

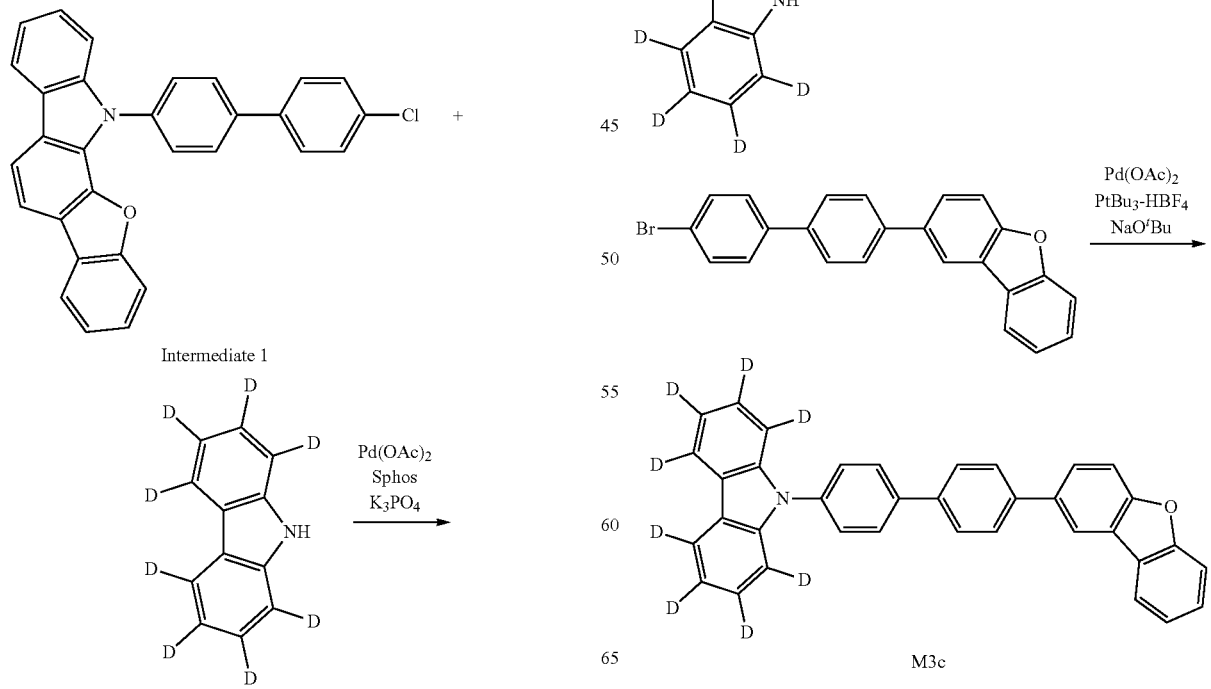

-continued

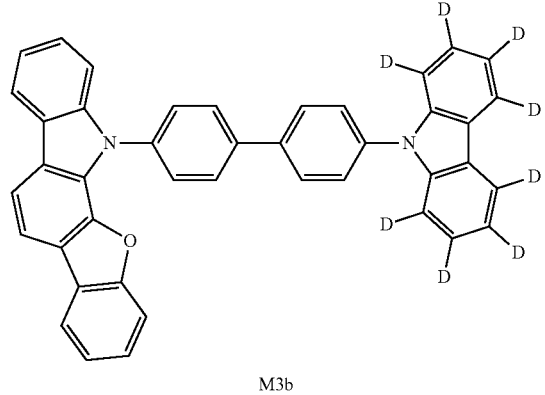

M3b

Under nitrogen atmosphere, xylene (40 mL) was added to a mixture of the intermediate 1 (3.11 g, 7.00 mmol), 9H-carbazole-1,2,3,4,5,6,7,8-d8 (1.23 g, 7.00 mmol), palladium acetate (157.2 mg, 0.70 mmol), SPhos (574.8 mg, 0.14 mmol), and potassium phosphate (4.46 g, 21.0 mmol), and the resulting mixture was stirred at 130 degrees C. for 12 hours. After completion of the reaction, the solid was filtered out and recrystallized with toluene to obtain a compound M3b (3.62 g, a yield of 75%). The obtained compound was identified as the compound M3b by analysis of LC-MS.

(3) Synthesis Example 3: Synthesis of Compound M3c

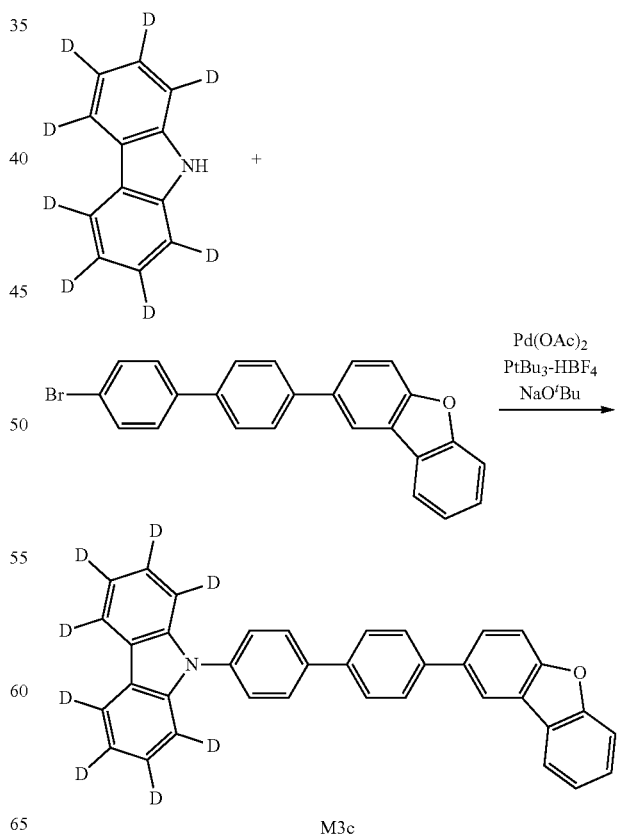

M3c

Under nitrogen atmosphere, xylene (40 mL) was added to a mixture of 9H-carbazole-1,2,3,4,5,6,7,8-d8 (1.40 g, 8.00 mmol), 2-(4'-bromo-[1,1'-biphenyl]-4-yl)dibenzo[b,d]furan (3.19 g, 8.00 mmol), palladium acetate (35.9 mg, 0.16 mmol), tri-tert-butylphosphonium tetrafluoroborate (92.8 mg, 0.32 mmol), and sodium tert-butoxide (2.31 g, 24.0 mmol), and the resulting mixture was stirred at 130 degrees C. for four hours. After completion of the reaction, the solid was filtered out and recrystallized with toluene to obtain a compound M3c (2.70 g, a yield of 68%). The obtained compound was identified as the compound M3c by analysis of LC-MS.

(4) Synthesis Example 4: Synthesis of Compound TADF1

(4-1) Synthesis of Intermediates A1 and A2

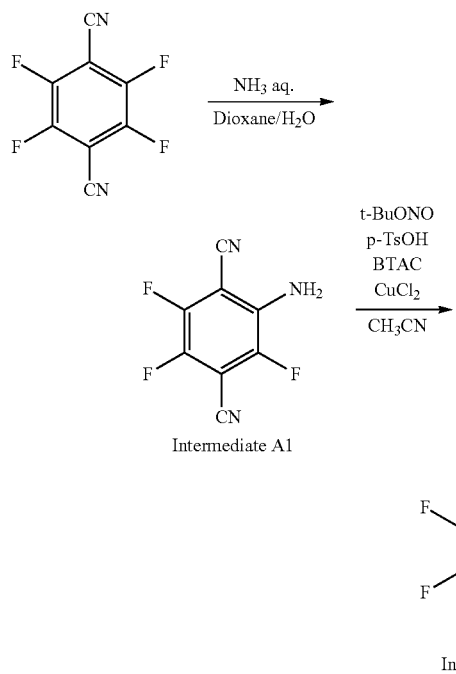

Intermediate A1

Intermediate A2

Under nitrogen atmosphere, into a 2000-mL three-necked flask, tetrafluoroterephthalonitrile (25 g, 125 mmol), 1,4-dioxane (625 mL) and water (400 mL) were put. Next, 30 mass % ammonia water (13 mL) was put into the mixture and heated at 80 degrees C. for ten hours with stirring and then returned to room temperature (25 degrees C.). The solvent was distilled off with an evaporator, and the resulting solid was purified by silica-gel column chromatography. A white solid (24 g) was obtained. The obtained solid was identified as an intermediate A1 (a yield of 98%) by GC-MS (Gas Chromatograph Mass Spectrometry).

Under nitrogen atmosphere, into a 2000-mL three-necked flask, the intermediate A1 (24 g, 122 mmol), p-toluenesulfonic acid (p-TsOH) (25 g, 146 mmol), benzyltrimethylammonium chloride (BTAC) (45.3 g, 244 mmol), copper(II) chloride (0.16 g, 1.22 mmol) and acetonitrile (400 mL) were put. Next, tert-Butyl nitrite (t-BuONO) (15 g, 146 mmol) was put into the mixture and stirred at 25 degrees C. for six hours. The solvent was distilled off with an evaporator, and the resulting solid was purified by silica-gel column chromatography. A white solid (17 g) was obtained. The obtained solid was identified as an intermediate A2 (a yield of 65%) by GC-MS.

(4-2) Synthesis of Intermediate A3

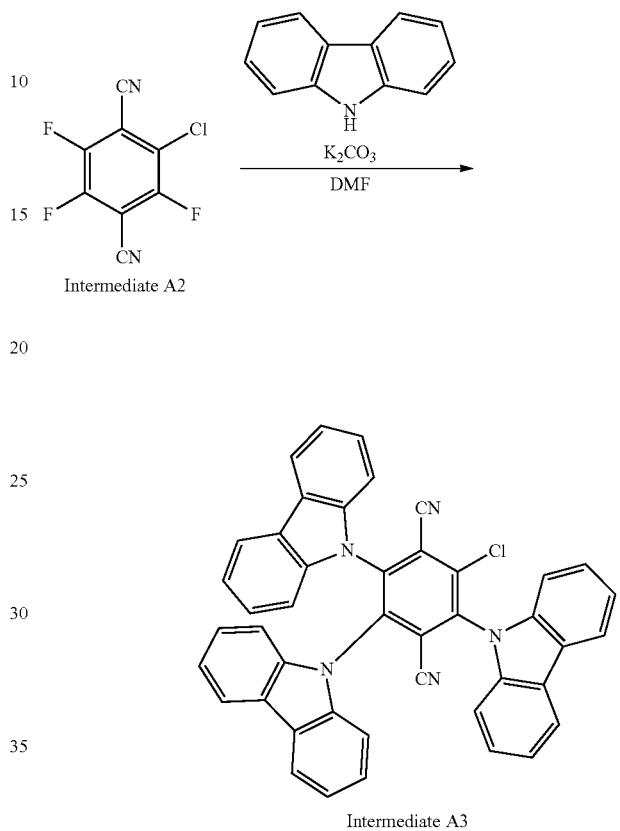

Intermediate A2

Intermediate A3

Under nitrogen atmosphere, into a 1000-mL three-necked flask, the intermediate A2 (10 g, 46 mmol), carbazole (23 g, 138 mmol), potassium carbonate (19 g, 138 mmol) and DMF (450 mL) were put and stirred at 0 degrees C. for 24 hours. 300 mL of a saturated aqueous solution of ammonium chloride was added to the reaction mixture. The deposited solid was purified by silica-gel column chromatography to obtain a yellow solid (26 g). The obtained solid was identified as an intermediate A3 (a yield of 85%) by anlysis of ASAP-MS (Atmospheric Pressure Solid Analysis Probe Mass Spectrometry).

(4-3) Synthesis of Intermediates C2 and D2

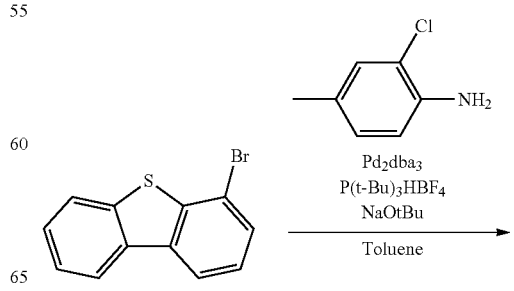

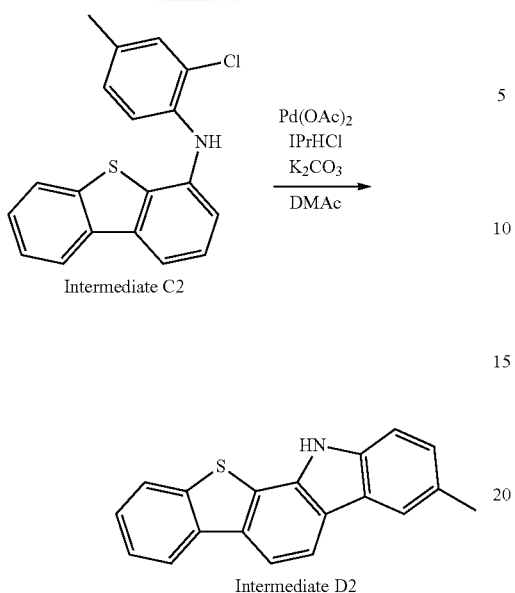

Intermediate C2

Intermediate D2

Under nitrogen atmosphere, to a 1-L three-necked flask, 4-bromodibenzothiophene (26.0 g, 100 mmol), 2-chloro-4-methylaniline (17 g, 120 mmol), tris(dibenzylideneacetone)dipalladium(0) (Pd$_2$dba$_3$) (0.9 g, 1 mmol), tri-tert-butylphosphonium tetrafluoroborate (P(t-Bu)$_3$HBF$_4$) (2.3 g, 8 mmol), sodium tert-butoxide (NaOtBu) (11.5 g, 120 mmol) and toluene (350 mL) were added, heated at 60 degrees C. for seven hours with stirring, and subsequently cooled to room temperature (25 degrees C.). The reaction solution was purified by silica-gel column chromatography to obtain a white solid (26 g). The obtained solid was identified as an intermediate C2 (a yield of 80%) by GC-MS.

Under nitrogen atmosphere, to a 1-L three-necked flask, an intermediate C (26.0 g, 80 mmol), 1,3-bis(2,6-diisopropylphenyl)imidazolium chloride (IPrHCl) (1.4 g, 3.2 mmol), palladium(II) acetate (Pd(OAc)$_2$) (0.36 g, 1.6 mmol), potassium carbonate (22.0 g, 160 mmol), and N,N-dimethylacetamide (DMAc) (400 mL) were added, stirred at 130 degrees C. for seven hours, and subsequently cooled to room temperature (25 degrees C.). The reaction solution was purified by silica-gel column chromatography to obtain a white solid (21 g). The obtained solid was identified as an intermediate D2 (a yield of 91%) by GC-MS.

(4-4) Synthesis of Compound TADF1

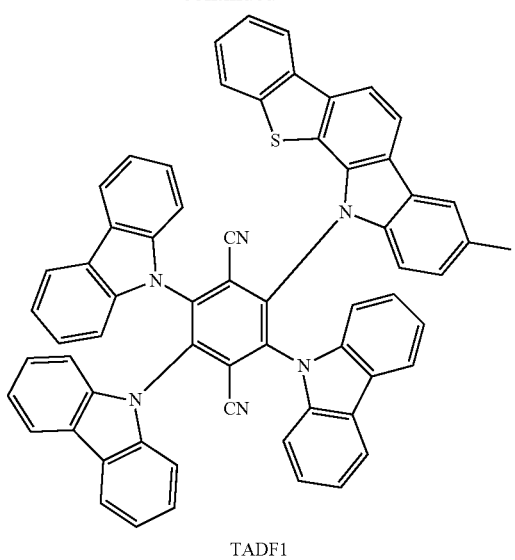

TADF1

Under nitrogen atmosphere, into a 100-mL three-necked flask, an intermediate A3 (2 g, 3.0 mmol), the intermediate D2 (1.0 g, 3.6 mmol), potassium carbonate (0.6 g, 4.5 mmol) and DMF (30 mL) were put and stirred at 70 degrees C. for eight hours. 50 mL of a saturated aqueous solution of ammonium chloride was added to the reaction mixture. The deposited solid was purified by silica-gel column chromatography to obtain a red solid (1.8 g). The obtained solid was identified as TADF1 (a yield of 66%) by analysis of ASAP-MS.

(5) Synthesis Example 5: Synthesis of Compound TADF2

(5-1) Synthesis of Intermediate P2

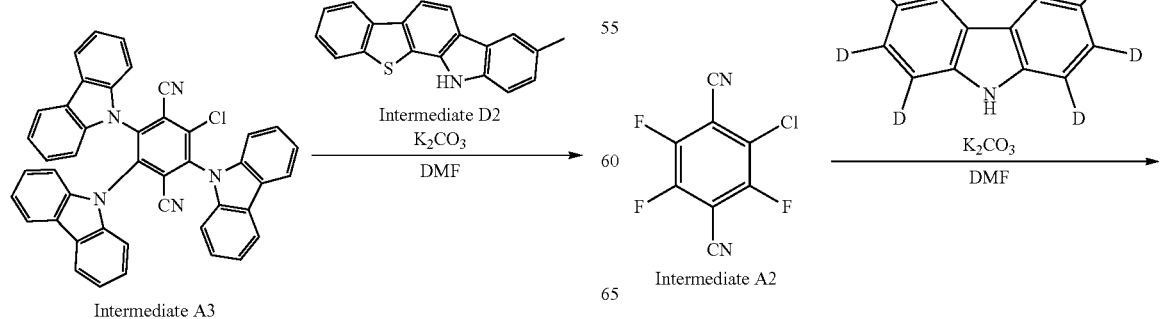

Intermediate A3

Intermediate A2

-continued

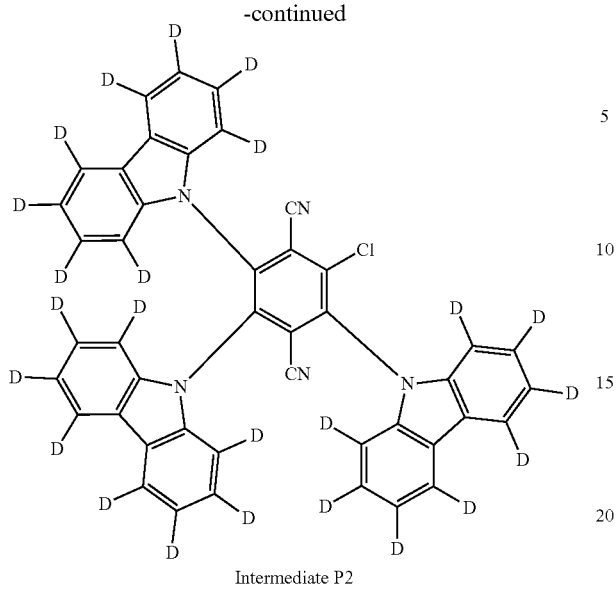
Intermediate P2

Under nitrogen atmosphere, into a 1000-mL three-necked flask, an intermediate A2 (1.16 g, 5.35 mmol), carbazole-1,2,3,4,5,6,7,8-d8 (with a deuteration ratio of 98% was used) (3 g, 17.1 mmol), potassium carbonate (3.5 g, 25.7 mmol), and DMF (30 mL) were put and stirred at 0 degrees C. for nine hours. The reaction mixture was added to a saturated aqueous solution (30 mL) of ammonium chloride. The deposited solid was purified by silica-gel column chromatography to obtain a yellow solid (3.0 g). The obtained solid was identified as an intermediate P2 (a yield of 82%) by analysis of ASAP-MS.

(5-2) Synthesis of TADF2

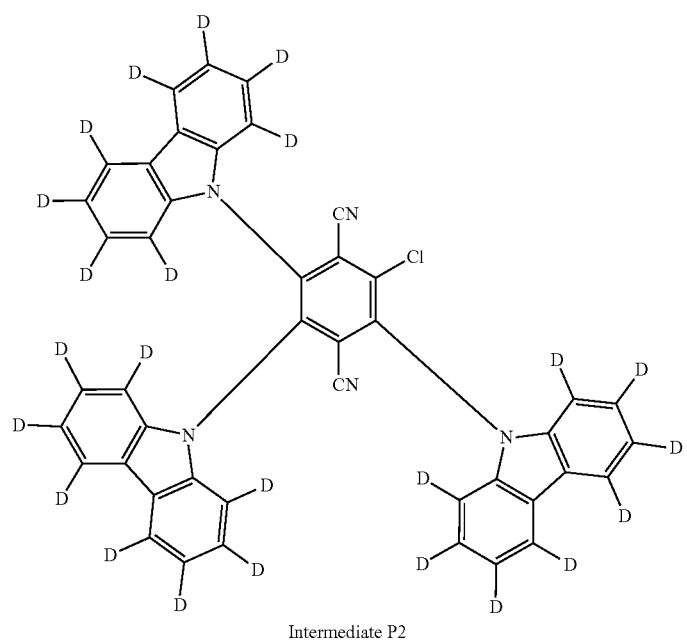
Intermediate P2

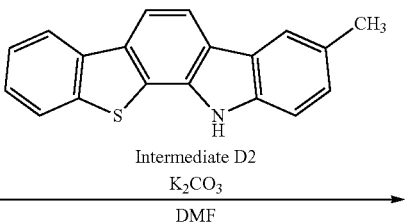
Intermediate D2
K₂CO₃
DMF

-continued

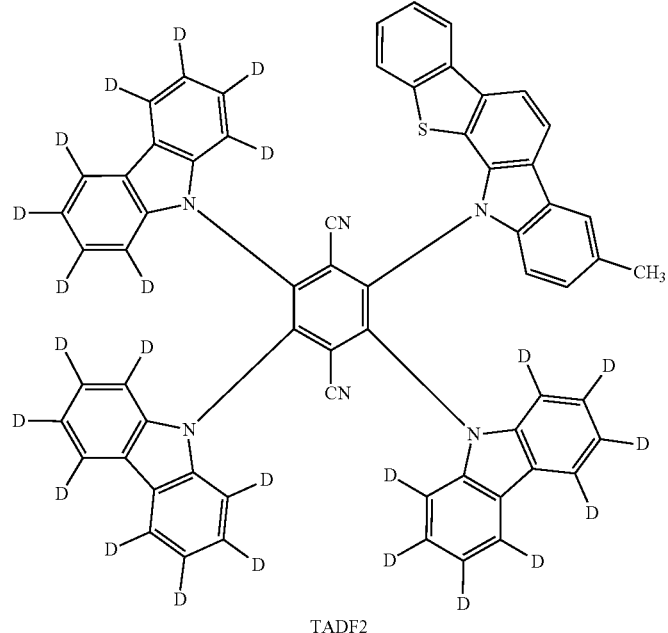

TADF2

Under nitrogen atmosphere, into a 100-mL three-necked flask, the intermediate P2 (2.6 g, 3.8 mmol), an intermediate D2 (1.6 g, 5.7 mmol), potassium carbonate (1.2 g, 8.9 mmol), and DMF (30 mL) were put and stirred at 115 degrees C. for six hours. To the reaction mixture, a saturated aqueous solution (50 mL) of ammonium chloride was added. The deposited solid was purified by silica-gel column chromatography to obtain a red solid (2.5 g). The obtained solid was identified as TADF2 (a yield of 70%) by analysis of ASAP-MS.

(6) Synthesis Example 6: Synthesis of Compound TADF3

(6-1) Synthesis of Intermediates E1, E2, and E3

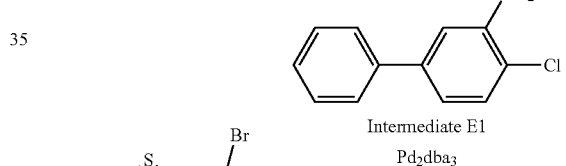

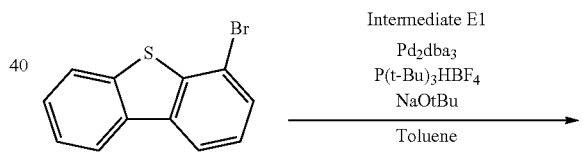

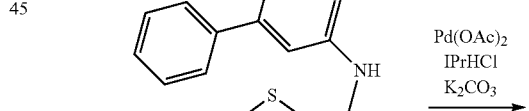

Intermediate E1

Under nitrogen atmosphere, into a 500-mL three-necked flask, 5-bromo-2-chloro-aniline (50 g, 242 mmol), phenylboronic acid (32.5 g, 266 mmol), palladium acetate (1.4 g, 6.2 mmol), sodium carbonate (50 g, 484 mmol), and methanol (250 mL) were put and stirred at 80 degrees C. for six hours. To the reaction mixture, 100 mL of ion-exchange water was added. The deposited solid was purified by silica-gel column chromatography to obtain a white solid (39.5 g). The obtained solid was identified as an intermediate E1 (a yield of 80%) by analysis of GC-MS.

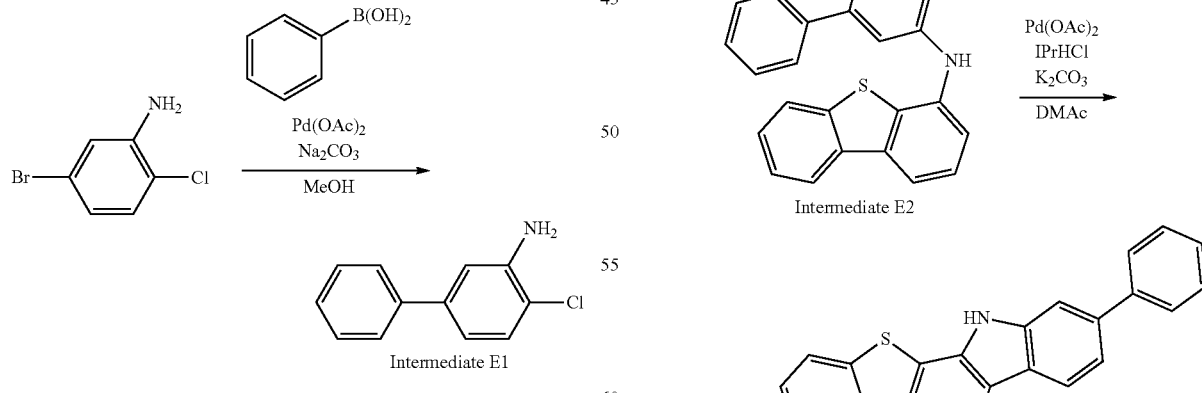

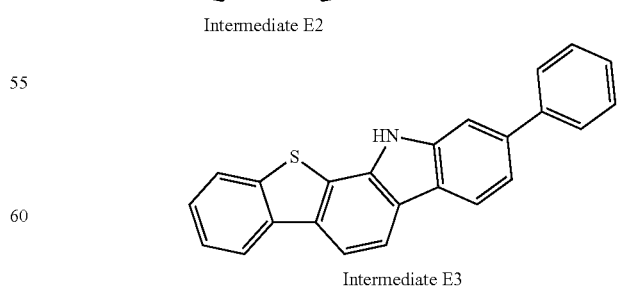

Intermediate E3

Under nitrogen atmosphere, to a 200-mL three-necked flask, 4-bromodibenzothiophene (12.9 g 49.1 mmol), the intermediate E1 (10 g, 49.1 mmol), tris(dibenzylideneacetone)dipalladium(0) (Pd$_2$dba$_3$) (0.67 g, 0.74 mmol), tri-tert-butylphosphonium tetrafluoroborate (P(t-Bu)$_3$HBF$_4$) (0.85 g, 2.95 mmol), sodium tert-butoxide (NaOtBu) (7.1 g, 73.7 mmol), and toluene (130 mL) were added, heated at 60 degrees C. for seven hours with stirring, and subsequently cooled to room temperature (25 degrees C.). The reaction solution was purified by silica-gel column chromatography to obtain a white solid (18 g). The obtained solid was identified as an intermediate E2 (a yield of 93%) by analysis of GC-MS.

Under nitrogen atmosphere, to a 200-mL three-necked flask, the intermediate E2 (10 g, 26 mmol), 1,3-bis(2,6-diisopropylphenyl)imidazolium chloride (IPrHCl) (0.22 g, 0.52 mmol), palladium(II) acetate (Pd(OAc)$_2$) (58 mg, 0.26 mmol), potassium carbonate (7.1 g, 52 mmol), and N,N-dimethylacetamide (DMAc) (90 mL) were added, stirred at 160 degrees C. for three hours, and subsequently cooled to room temperature (25 degrees C.). The reaction solution was purified by silica-gel column chromatography to obtain a white solid (7.9 g). The obtained solid was identified as an intermediate E3 (a yield of 87%) by analysis of GC-MS.

(6-2) Synthesis of TADF3

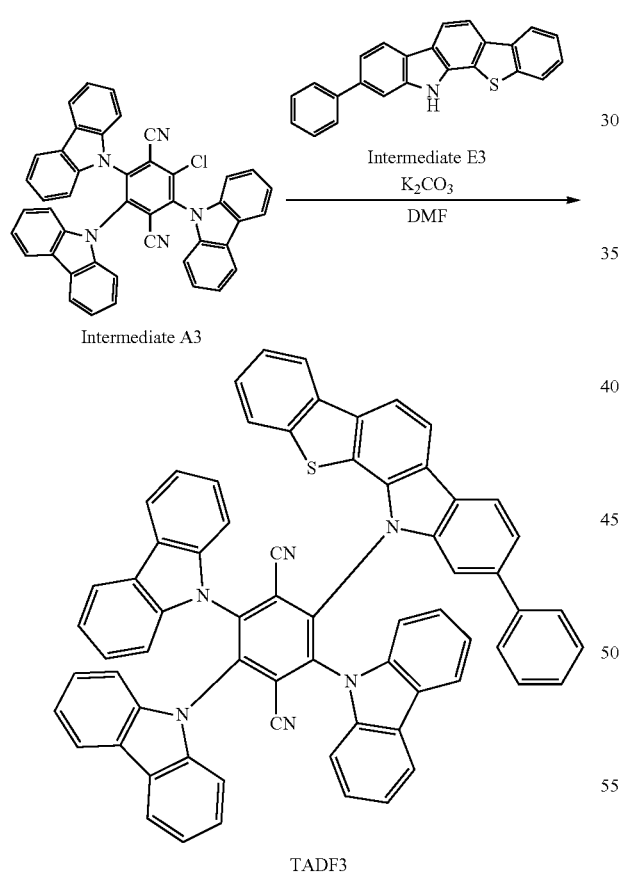

Under nitrogen atmosphere, into a 50-mL three-necked flask, the intermediate A3 (3.0 g, 4.6 mmol), the intermedium E3 (1.9 g, 5.5 mmol), potassium carbonate (1.1 g, 8.2 mmol), and DMF (11 mL) were put and stirred at 120 degrees C. for four hours. To the reaction mixture, a saturated aqueous solution (10 mL) of ammonium chloride was added. The deposited solid was purified by silica-gel column chromatography to obtain a red solid (2.3 g). The obtained solid was identified as TADF3 (a yield of 52%) by analysis of ASAP-MS.

(7) Synthesis Example 7: Synthesis of Compound M3d

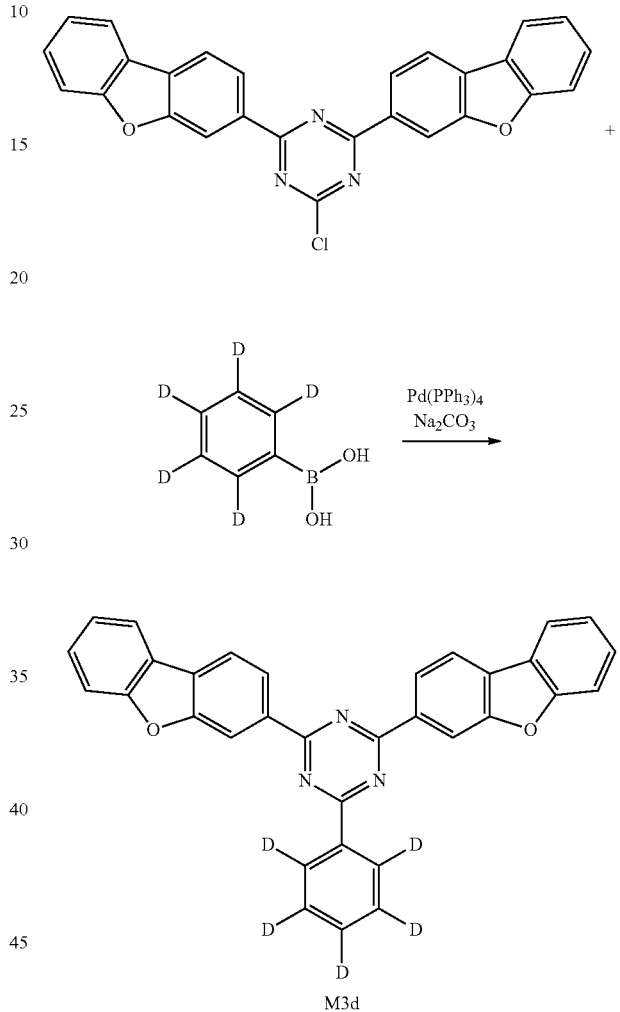

Under nitrogen atmosphere, 1,2-dimethoxyethane (70 mL) and water (35 mL) were added to a mixture of 2-chloro-4,6-bis(dibenzo[b,d]furan-3-yl)-1,3,5-triazine (4.48 g, 10.0 mmol), (phenyl-d5) boronic acid (1.65 g, 13.0 mmol), tetrakis(triphenylphosphine)palladium (577.8 mg, 0.500 mmol), and sodium carbonate (3.18 g, 30.0 mmol), and the resulting mixture was stirred at 80 degrees C. for six hours. After completion of the reaction, the solid was filtered out and recrystallized with toluene to obtain a compound M3d (3.60 g, a yield of 73%). The obtained compound was identified as the compound M3d by analysis of LC-MS.

The invention claimed is:

1. A compound, comprising:
a partial structure of formula (3-1A), a partial structure of formula (32h), and a partial structure of formula (3-11B) in one molecule,

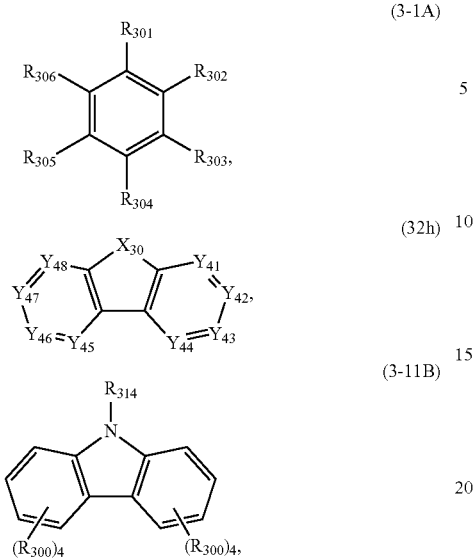

(3-1A)

(32h)

(3-11B)

wherein, in the formula (3-1A):
$R_{301}$ to $R_{306}$ are each independently a hydrogen atom or a substituent, or at least one pair of a pair of adjacent $R_{301}$ and $R_{302}$, a pair of adjacent $R_{302}$ and $R_{303}$, a pair of adjacent $R_{303}$ and $R_{304}$, a pair of adjacent $R_{304}$ and $R_{305}$, a pair of adjacent $R_{305}$ and $R_{306}$, and a pair of adjacent $R_{306}$ and $R_{301}$ are mutually bonded to form a ring, or $R_{301}$ to $R_{306}$ are each independently a single bond bonded to another atom or another structure in the molecule of the compound,
at least one of $R_{301}$ to $R_{306}$ is a single bond bonded to another atom or another structure in the molecule of the compound, and
one of $R_{301}$ to $R_{306}$ is a single bond bonded to the partial structure of formula (32h),
wherein, in the formula (32h):
$X_{30}$ is a nitrogen atom bonded to the partial structure of formula (3-1A),
$Y_{41}$ to $Y_{48}$ are each independently $CR_{32}$, or a carbon atom bonded to another atom or another structure in the molecule of the compound,
at least one of $Y_{41}$ to $Y_{48}$ is a carbon atom bonded to the partial structure of formula (3-11B),
$R_{32}$ are each independently a hydrogen atom or a substituent, or at least one pair of pairs of adjacent ones of $R_{32}$ are mutually bonded to form a ring, or $R_{32}$ are each independently a single bond bonded to another atom or another structure in the molecule of the compound,
at least one of $R_{32}$ is a single bond bonded to another atom or another structure in the molecule of the compound,
in the formula (3-11B):
$R_{300}$ are each independently a hydrogen atom or a substituent, or at least one pair of pairs of adjacent ones of $R_{300}$ are mutually bonded to form a ring, or $R_{300}$ are each independently a single bond bonded to another atom or another structure in the molecule of the compound,
at least one of $R_{300}$ or $R_{314}$ is a single bond bonded to another atom or another structure in the molecule of the compound,
$R_{314}$ is a single bond bonded to the partial structure of formula (32h), and
a plurality of $R_{300}$ are mutually the same or different, in the formulae (3-1A), (32h), and (3-11B):
$R_{301}$ to $R_{306}$, $R_{32}$, and $R_{300}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, a substituted or unsubstituted arylthio group having 6 to 30 ring carbon atoms, a substituted or unsubstituted aralkyl group having 7 to 30 carbon atoms, a substituted germanium group, a substituted phosphine oxide group, a nitro group, a substituted or unsubstituted carbonyl group, or a substituted boryl group, and
at least one of a plurality of $R_{32}$ or a plurality of $R_{300}$ is a deuterium atom.

2. The compound of claim 1, wherein the compound is not a compound comprising a partial structure of formula (1C) and formula (2C):

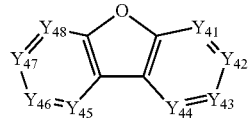

(1C)

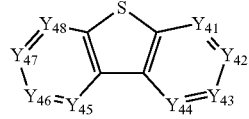

(2C)

wherein, in the formulae (1C) and (2C):
$Y_{41}$ to $Y_{48}$ are each independently a nitrogen atom, CR, or a carbon atom bonded to another atom or another structure, with at least one of $Y_{41}$ to $Y_{48}$ being a nitrogen atom and at least one of $Y_{41}$ to $Y_{48}$ being a carbon atom bonded to another atom or another structure, R are each independently a hydrogen atom or a substituent, and a plurality of R are mutually the same or different.

3. The compound of claim 1, wherein at least one of $R_{301}$ to $R_{306}$ is a substituent, and $R_{301}$ to $R_{306}$ as the substituent are each independently a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted cycloalkyl group having 3 to 30 ring carbon atoms, a substituted or unsubstituted alkylsilyl group having 3 to 30 carbon atoms, or a substituted or unsubstituted arylsilyl group having 6 to 60 ring carbon atoms.

4. The compound of claim 1, wherein $R_{301}$ to $R_{306}$ not being the single bond bonded to another atom or another structure in the molecule of the compound are each a hydrogen atom.

5. The compound of claim 1, wherein $R_{301}$ to $R_{306}$ not being the single bond bonded to another atom or another structure in the molecule of the compound are each a deuterium atom.

6. The compound of claim 1, wherein
$Y_{43}$ or $Y_{46}$ in the formula (32h) is a carbon atom bonded to the partial structure of formula (3-11B), and
$R_{314}$ in the formula (3-11B) is a single bond bonded to $Y_{43}$ or $Y_{46}$ in the formula (32h).

7. The compound of claim 1, wherein at least one of $R_{32}$ is a substituent, and each $R_{32}$ as the substituent is independently a substituted or unsubstituted aryl group having 6 to 30 ring carbon atoms, a substituted or unsubstituted alkyl group having 1 to 30 carbon atoms, a substituted or unsubstituted cycloalkyl group having 3 to 30 ring carbon atoms, or a substituted or unsubstituted arylsilyl group having 6 to 60 ring carbon atoms.

8. The compound of claim 1, wherein $R_{32}$ not being the single bond bonded to another atom or another structure in the molecule of the compound is a hydrogen atom.

9. The compound of claim 1, wherein $R_{32}$ not being the single bond bonded to another atom or another structure in the molecule of the compound is a deuterium atom.

10. The compound of claim 1, wherein at least one of $R_{300}$ is a substituent, and each $R_{300}$ as the substituent is independently a substituted or unsubstituted aryl group having 6 to 30 ring carbon atoms, a substituted or unsubstituted alkyl group having 1 to 30 carbon atoms, a substituted or unsubstituted cycloalkyl group having 3 to 30 ring carbon atoms, or a substituted or unsubstituted arylsilyl group having 6 to 60 ring carbon atoms.

11. The compound of claim 1, wherein $R_{300}$ is a hydrogen atom.

12. The compound of claim 1, wherein $R_{300}$ is a deuterium atom.

13. The compound of claim 1, wherein the partial structure of formula (32h) is a partial structure of formula (3-10):

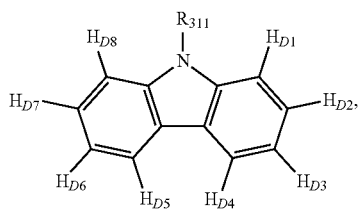

(3-10)

wherein, in the formula (3-10):
$H_{D1}$ to $H_{D8}$ are each independently a hydrogen atom or a single bond bonded to another atom or another structure in the molecule of the compound, at least one of $H_{D1}$ to $H_{D8}$ is a deuterium atom, and
at least one of $H_{D1}$ to $H_{D8}$ is a single bond bonded to the partial structure of formula (3-11B), and $R_{314}$ in the formula (3-11B) is a single bond bonded to one of $H_{D1}$ to $H_{D8}$ in the formula (3-10), and $R_{311}$ is a single bond bonded to the partial structure of formula (3-1A).

14. The compound of claim 1, wherein the partial structure of formula (32h) is a partial structure of formula (3-100):

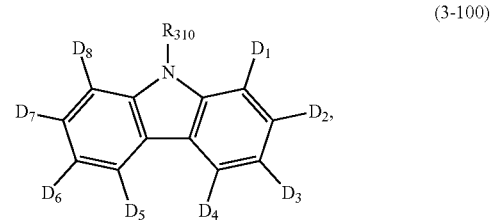

(3-100)

wherein, in the formula (3-100):
$D_1$ to $D_8$ are each independently a deuterium atom or a single bond bonded to another atom or another structure in the molecule of the compound,
at least one of $D_1$ to $D_8$ is a single bond bonded to the partial structure of formula (3-11B), and $R_{314}$ in the formula (3-11B) is a single bond bonded to one of $D_1$ to $D_8$ in the formula (3-100), and
$R_{310}$ is a single bond bonded to the partial structure of formula (3-1A).

15. The compound of claim 1, wherein the partial structure of formula (3-11B) is a partial structure of formula (3-10):

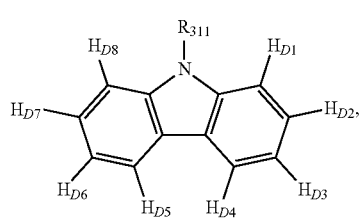

(3-10)

wherein, in the formula (3-10):
$H_{D1}$ to $H_{D8}$ are each independently a hydrogen atom or a single bond bonded to another atom or another structure in the molecule of the compound, at least one of $H_{D1}$ to $H_{D8}$ is a deuterium atom, and $R_{311}$ is a single bond bonded to the partial structure of formula (32h).

16. The compound of claim 15, wherein
$Y_{43}$ or $Y_{46}$ in the formula (32h) is a carbon atom bonded to the partial structure of formula (3-10), and
$R_{311}$ in the formula (3-10) is a single bond bonded to $Y_{43}$ or $Y_{46}$ in the formula (32h).

17. The compound of claim 15, wherein
the compound comprises two partial structures each of formula (3-10) in one molecule,
$Y_{43}$ and $Y_{46}$ in the formula (32h) are each a carbon atom bonded to the partial structure of formula (3-10), and
$R_{311}$ in one of the two partial structures each of formula (3-10) is a single bond bonded to $Y_{43}$ in the formula (32h) and $R_{311}$ in the other of the two partial structures each of formula (3-10) is a single bond bonded to $Y_{46}$ in the formula (32h).

18. The compound of claim 1, wherein the partial structure of formula (3-11B) is a partial structure of formula (3-100):

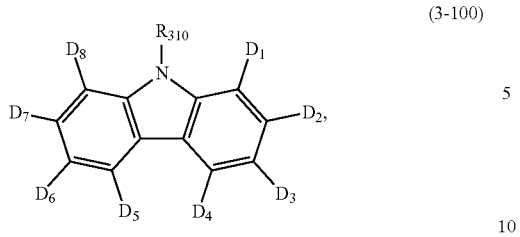

(3-100)

wherein, in the formula (3-100):

$D_1$ to $D_8$ are each independently a deuterium atom or a single bond bonded to another atom or another structure in the molecule of the compound, and $R_{310}$ is a single bond bonded to the partial structure of formula (32h).

19. The compound of claim 18, wherein
$Y_{43}$ or $Y_{46}$ in the formula (32h) is a carbon atom bonded to the partial structure of formula (3-100), and
$R_{310}$ in the formula (3-100) is a single bond bonded to $Y_{43}$ or $Y_{46}$ in the formula (32h).

20. The compound of claim 18, wherein
the compound comprises two partial structures each of formula (3-100) in one molecule,
$Y_{43}$ and $Y_{46}$ in the formula (32h) are each a carbon atom bonded to the partial structure of formula (3-100), and
$R_{310}$ in one of the two partial structures each of formula (3-100) is a single bond bonded to $Y_{43}$ in the formula (32h) and $R_{310}$ in the other of the two partial structures each of formula (3-100) is a single bond bonded to $Y_{46}$ in the formula (32h).

* * * * *